United States Patent
Rai et al.

(10) Patent No.: US 12,187,732 B2
(45) Date of Patent: *Jan. 7, 2025

(54) INHIBITORS OF THE MYST FAMILY OF LYSINE ACETYL TRANSFERASES

(71) Applicant: Isosterix, Inc., San Carlos, CA (US)

(72) Inventors: Roopa Rai, San Carlos, CA (US); Mark Bures, Zionsville, IN (US)

(73) Assignee: Isosterix, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/190,224

(22) Filed: Mar. 27, 2023

(65) Prior Publication Data

US 2023/0303580 A1    Sep. 28, 2023

Related U.S. Application Data

(60) Provisional application No. 63/476,826, filed on Dec. 22, 2022, provisional application No. 63/324,624,
(Continued)

(51) Int. Cl.
| | | |
|---|---|---|
| *C07D 487/04* | (2006.01) | |
| *A61P 35/00* | (2006.01) | |

(Continued)

(52) U.S. Cl.
CPC ............ *C07D 487/04* (2013.01); *A61P 35/00* (2018.01); *C07D 213/56* (2013.01);
(Continued)

(58) Field of Classification Search
CPC .. C07D 487/04; C07D 213/56; C07D 307/85; C07D 401/04; C07D 405/12;
(Continued)

(56) References Cited

U.S. PATENT DOCUMENTS

| | | | |
|---|---|---|---|
| 11,492,346 B2 | 11/2022 | Bozikis et al. | |
| 2020/0399258 A1* | 12/2020 | Bozikis | A61P 35/04 |

FOREIGN PATENT DOCUMENTS

| | | |
|---|---|---|
| CN | 115073392 A | 9/2022 |
| CN | 115594695 A | 1/2023 |

(Continued)

OTHER PUBLICATIONS

Fleming FF, Yao L, Ravikumar PC, Funk L, Shook BC. Nitrile-containing pharmaceuticals: efficacious roles of the nitrile pharmacophore. J Med Chem. Nov. 25, 2010;53(22):7902-17. doi: 10.1021/jm100762r. Epub Aug. 30, 2010. PMID: 20804202; PMCID: PMC2988972. (Year: 2010).*

(Continued)

*Primary Examiner* — Bruck Kifle
*Assistant Examiner* — Kevin S Martin
(74) *Attorney, Agent, or Firm* — Rimon, P.C.; Dale L. Rieger

(57) ABSTRACT

Provided herein are compounds of Formula (I). Methods for the preparation of the compounds of Formula (I) and intermediates useful in the preparation of the compounds of Formula (I) are described herein. The compounds of Formula (I) may be useful as inhibitors of the MYST family of lysine acetyltransferases (KATs) for the treatment of and/or prophylaxis of hyperproliferative diseases, disorders or conditions such as cancer. In particular, the compounds of Formula (I) are useful for the inhibition of KAT6A and KAT6B which are enzymes frequently mutated, overexpressed, amplified and/or translocated in cancer altering their normal expression, activity and function. The use of the compounds of Formula (I) in the manufacture of pharmaceutical compositions or for treating cancers is further described, including for treating cancer in combination with other anti-cancer agents.

55 Claims, 1 Drawing Sheet

Specification includes a Sequence Listing.

Related U.S. Application Data filed on Mar. 28, 2022, provisional application No. 63/324,619, filed on Mar. 28, 2022.

(51) Int. Cl.

| | | |
|---|---|---|
| *C07D 213/56* | (2006.01) | |
| *C07D 307/85* | (2006.01) | |
| *C07D 401/04* | (2006.01) | |
| *C07D 405/12* | (2006.01) | |
| *C07D 413/04* | (2006.01) | |
| *C07D 413/06* | (2006.01) | |
| *C07D 413/12* | (2006.01) | |
| *C07D 213/46* | (2006.01) | |
| *C07D 231/12* | (2006.01) | |
| *C07D 231/38* | (2006.01) | |
| *C07D 413/08* | (2006.01) | |
| *C07D 413/10* | (2006.01) | |
| *C07D 413/14* | (2006.01) | |
| *C07D 471/04* | (2006.01) | |
| *C07D 519/00* | (2006.01) | |

(52) U.S. Cl.
CPC ......... *C07D 307/85* (2013.01); *C07D 401/04* (2013.01); *C07D 405/12* (2013.01); *C07D 413/04* (2013.01); *C07D 413/06* (2013.01); *C07D 413/12* (2013.01)

(58) Field of Classification Search
CPC .. C07D 413/04; C07D 413/06; C07D 413/12; C07D 213/46; C07D 231/12; C07D 231/38; C07D 413/08; C07D 413/10; C07D 413/14; C07D 471/04; C07D 519/00; A61P 35/00
See application file for complete search history.

(56) References Cited

FOREIGN PATENT DOCUMENTS

| CN | 115611877 A | 1/2023 |
|---|---|---|
| WO | 2019243491 A1 | 12/2019 |
| WO | 2020002587 A1 | 1/2020 |
| WO | 2020254946 A1 | 12/2020 |
| WO | 2020254989 A1 | 12/2020 |
| WO | 2022013369 A1 | 1/2022 |
| WO | 2022081807 A1 | 4/2022 |
| WO | 2022081842 A1 | 4/2022 |
| WO | 2022243983 A1 | 11/2022 |
| WO | 2023280182 A1 | 1/2023 |
| WO | 2023016484 A1 | 2/2023 |
| WO | 2023088233 A1 | 5/2023 |
| WO | 202314867 A1 | 6/2023 |
| WO | 2023114710 A1 | 6/2023 |

OTHER PUBLICATIONS

Bishop, et al. Nat. Chem Biol. 2023, doi.org/10.1038/s41589-023-01320-7.
Yang, et al. J. Am. Chem. Soc. 2010, 132, 656-666.
Allis and Jenuwein. "The Molecular Hallmarks of Epigenetic Control". Nature Reviews Genetics 2016, vol. 17, pp. 487-500.
Vernarecci, et al. "Tuning Acetylated Chromatin with HAT Inhibitors: A Novel Tool for Therapy". Epigentics, vol. 5(2): pp. 105-111, 2009.
Wiesel-Motiuk, et al. "The Key Roles of the Lysine Acetyltransferases KAT6A and KAT6B in Physiology and Pathology". Drug Resistance Updates, 2020, vol. 53, 100729.
Wapenaar and Dekker. "Histone Acetyltransferases: Challenges in Targeting Bi-Substrate Enzymes". Clinical Epigenetics, vol. 8(59) pp. 1-11 (2016) (DOI 10.1186/s13148-016-0225-2).
Carrozza, et al., Trends in Genetics 2003, vol. 19, pp. 321-329.
Trisciuoglio, et al. "Emerging Role of Histone Acetyltransferase in Stem Cells and Cancer". Stem Cells Int., vol. 2018, Article ID 8908751 (https://doi.org/10.1155/2018/8908751).
Huang, et al. "Regulation of KAT6 Acetyltransferases and Their Roles in Cell Cycle Progression, Stem Cell Maintenance, and Human Disease". Molecular and Cellular Biology 2016, vol. 63, pp. 1900-1907.
Zack, et al. "Pan-Cancer Patterns of Somatic Copy Number Alteration". Nature Genetics, vol. 45(10), pp. 1134-1140, 2013.
Sheikh, et al. "MOZ Regulates B-Cell Progenitors and, Consequently, MOZ Haploinsufficiency Dramatically Retards MYC-Induced Lymphoma Development". Blood, vol. 125(12), pp. 1910-1921 (2015).
Glozak, et al. "Acetylation and Deacetylation of Non-Histone Proteins". Gene, vol. 363, pp. 15-23 (2005).
Das and Kundu. "Transcriptional Regulation by the Acetylation of Nonhistone Proteins in Humans—A New Target for Therapeutics". IUBMB Life, vol. 57(3), pp. 137-148, 2005.
Priebbenow, et al. "Discovery of Acylsulfonohydrazide-Derived Inhibitors of the Lysine Acetyltransferase, KAT6A, as Potent Senescence-Inducing Anti-Cancer Agents". J. Med. Chem., vol. 63(9): 4655-4684, 2020.
Singh, et al. "The Resurgence of Covalent Drugs". Nature Reviews, Drug Discovery, vol. 10., pp. 307-317, Apr. 2011.
Sutanto, et al. "Covalent Inhibitors: A Rational Approach to Drug Discovery". RSC Med. Chem., 11: 876-884 (2020).
Sharma, et al. AACR-2021 Poster. First-in-class KAT6A/KAT6B Inhibitor CTx-648 (PF-9363) Demonstrates Potent Anti-tumor Activity in ER+ Breast Cancer with KAT6A Dysregulation (Apr. 10-15, 2021).

\* cited by examiner

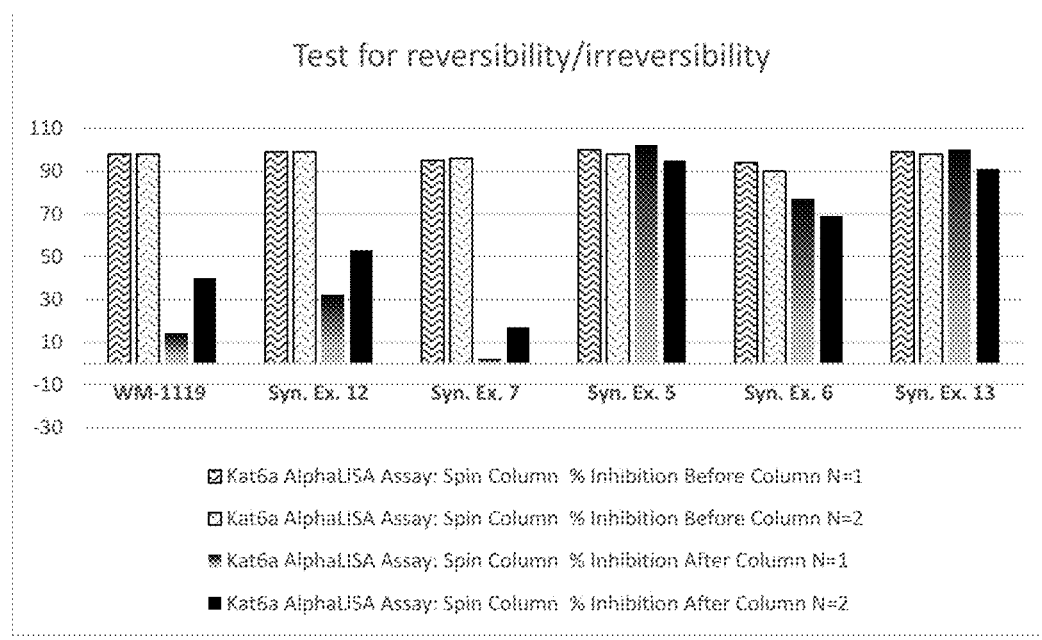

INHIBITORS OF THE MYST FAMILY OF LYSINE ACETYL TRANSFERASES

RELATED APPLICATIONS

This application claims priority to U.S. Provisional Patent Applications 63/324,619, filed Mar. 28, 2022, 63/324,624, filed Mar. 28, 2022, and 63/476,826, filed Dec. 22, 2022. The disclosures of each of the above-referenced applications is incorporated by referenced herein in their entirety.

SEQUENCE LISTING

This application contains a Sequence Listing XML, which is being submitted herewith as an XML filed named "ISTX102US_SL.xml", created on Sep. 27, 2023, size 5413 bytes, which is incorporated by reference herein in its entirety.

FIELD

Provided herein are compounds of Formula (I). Methods for the preparation of the compounds of Formula (I) and intermediates useful in the preparation of the compounds of Formula (I) are described herein. The compounds of Formula (I) may be useful as inhibitors of the MYST family of lysine acetyltransferases (KATs) for the treatment of and/or prophylaxis of hyperproliferative diseases, disorders or conditions such as cancer. In particular, the compounds of Formula (I) are useful for the inhibition of KAT6A and KAT6B which are enzymes frequently mutated, overexpressed, amplified and/or translocated in cancer, altering their normal expression, activity and function. The use of the compounds of Formula (I) in the manufacture of pharmaceutical compositions or for treating cancers is further described, including for treating cancer in combination with other anti-cancer agents.

BACKGROUND

Epigenetic regulation is a complex dynamic process that is critically important to cellular physiology and controls of gene expression, cell-cycle progression, cellular proliferation rates and stem cell maintenance and differentiation (Allis and Jenuwein, *Nature Reviews Genetics* 2016, Vol 17, pp. 487-500). Lysine acetyl transferases (KATs) and histone deacetylases (HDACs) play key roles in epigenetic regulation. KATs are a multi-family of enzymes that acetylate both histone and non-histone proteins. Histones are key components of chromatin-DNA complex and their acetylation state is critical to their function (Vernarecci, et al., *Epigentics* 2009, Vol. 5, pp. 105-111). KATs catalyze the post translational modification of histones through acetylation of the epsilon amino group of lysine on histone proteins. This acetylation confers an open conformation to the chromatin and typically promotes gene transcription.

One key family of KAT enzymes are known as the MYST family. This family consists of five members including KAT6A (also known as, MOZ or MYST3), KAT6B (also known as MORF or MYST4), KAT5 (also known as, Tip60), KAT7 (also known as, HBO1 or MYST2) and Kat8 (also known as, MOF or MYST1) (Wiesel-Motiuk and Assaraf, *Drug Resistance Updates* 2020, Vol 53, 100729; Wapenaar and Dekker, *Clinical Epigenetics* 2016, 8:59, 1 (DOI 10.1186/s13148-016-0225-2), "Wapenaar et al., 2016"). The MYST family of KATs is particularly important in regulation of the cell cycle (Carrozza, et al., *Trends in Genetics* 2003, Vol 19, pp. 321-329).

Dysregulation of the expression of KAT6 proteins supports tumor progression (Trisciuoglio et al., Emerging role of histone acetyltransferase in stem cells and Cancer. *Stem Cells Int.* Volume 2018, Article ID 8908751 (https://doi.org/10.1155/2018/8908751). Dysregulation through gene amplification, overexpression or mutation of KAT6A has been documented in multiple cancer types including breast, lung adenocarcinoma, ovarian, colon and rectal adenocarcinoma, and uterine cervix (Huang, et al., *Molecular and Cellular Biology* 2016, Vol 63, pp. 1900-1907; Zack, et al., *Nature Genetics* 2013, Vol 45, pp. 1134-1140). It is reported that the locus that contains the gene for KAT6A (8p11-p12 amplicon) is the 12$^{th}$ most commonly amplified region of the genome across all cancer types (Zack, et al., 2013). In acute myeloid leukemia (AML), recurrent oncogenic fusions of KAT6A have been documented that can drive transformation to a malignant state (Sheikh, et al., *Blood* 2015, Vol 125, pp. 1910-1921). Translocation of KAT6A and fusion to a partner such as CBP, p300, TIF2 and NCOA3 are known to lead to aggressive forms of AML (Sheikh, et al., 2015).

A key aspect of the catalytic mechanism of the KAT family of enzymes is the acetylation of lysine residues using the cofactor Ac-CoA as an acetyl donor. One possible catalytic mechanism is the stepwise transfer of the acetyl group from acetyl co-enzyme A (Ac-CoA) to transiently form an acetyl-enzyme intermediate. This acetyl-enzyme intermediate subsequently is the source of the acetyl group that is transferred to the substrate, typically a lysine on a histone (Wapenaar et al., 2016). In the MYST family of KATs there is a conserved cysteine that is acylated transiently as part of the catalytic cycle, as indicated with the arrow below.

Amino Acid Sequence Alignment Near the Ac-CoA Binding Site

Of the MYST Family of KATs

| KAT5 | ESTEDYNVACILTLPPYQRR | (SEQ ID NO: 1) |
| KAT8 | ESPDGNNVACILTLPPYQRR | (SEQ ID NO: 2) |
| KAT7 | NSFLNYNVSCILTMPQYMRQ | (SEQ ID NO: 3) |
| KAT6A | HCQQKYNVSCIMILPQYQRK | (SEQ ID NO: 4) |
| KAT6B | LCQQKYNVSCIMIMPQHQRQ | (SEQ ID NO: 5) |

In one embodiment, the present disclosure provides compounds that may covalently bind to this conserved cysteine.

Enzyme inhibitors that covalently interact with conserved cysteines at or near the active site of an enzyme are an important therapeutic modality. Therapeutics which covalently and specifically react to form a covalent adduct with an active site cysteine offer potential advantages in potency, possible lower dose, and increased target engagement duration resulting in reduced dosing frequency.

In addition to the role that KATs play in epigenetic regulation, KATs also acetylate non-histone proteins (Glozak, et al., 2005; Das and Kundu, 2008). Through modification of the acetylation state of non-histone proteins, KATs are involved modulating protein function and stability, protein-protein and protein-DNA interactions, and regulation of enzyme activity (Glozak, et al., Gene 2005, Vol 363, pp. 15-23; Das and Kundu, *IUBMB Life* 2005, Vol 57, pp. 137-148).

Provided herein are compounds of Formula (I) which may inhibit the MYST family of lysine acetyl transferases. The compounds described in the present disclosure inhibit MYST family members, including KAT6A. In some embodiments, the inhibition is through covalent modification of a cysteine residue at the Ac-CoA binding site. The compounds described herein are useful for the treatment of cancer including breast cancer, lung cancer, ovarian cancer, colon cancer, prostate cancer, uterine/cervical cancer and leukemia. The compounds of Formula I can be used as single agents or in combination with a standard of care treatment for a particular cancer.

SUMMARY

Provided herein are compounds, pharmaceutical compositions comprising the compounds, and methods of using the compounds and compositions in treating a condition, disease, or disorder by inhibiting MYST family of lysine acetyl transferases, including KAT6A and KAT6B, including hyperproliferative disorders and cancer.

In one aspect, provided is a compound of Formula (I):

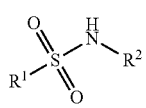

(I)

where $R^1$ is $C_3$-$C_8$-cycloalkyl optionally substituted with 1, 2, or 3 $R^{1a}$; $C_3$-$C_8$-cycloalkyl-$C_1$-$C_6$alkyl where the $C_3$-$C_8$-cycloalkyl is optionally substituted with 1, 2, or 3 $R^{1a}$; phenyl optionally substituted with 1, 2, or 3 $R^{1b}$; phenyl-$C_1$-$C_6$alkyl optionally substituted with 1, 2, or 3 $R^{1b}$; naphthyl optionally substituted with 1, 2, or 3 $R^{1b}$; or 5- or 6-membered monocyclic heteroaryl optionally substituted with 1, 2, or 3 $R^{1b}$; 8- to 10-membered bicyclic heteroaryl optionally substituted with 1, 2, or 3 $R^{1b}$;

each $R^{1a}$ is independently selected from hydrogen, halo, $C_1$-$C_6$alkoxy, and $C_3$-$C_8$-cycloalkyloxy;

each $R^{1b}$ is independently selected from hydrogen, halo, $C_1$-$C_6$alkyl, $C_1$-$C_6$alkoxy, hydroxyalkyloxy, —O-alkylene-$NR^{1b1}R^{1b4}$, —O-alkylene-C(O)$OR^{1b1}$, —O-alkylene-O-alkylene-$NR^{1b1}R^{1b4}$,

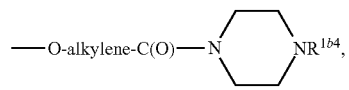

cyano, —$(CH_2)_{0-2}$C(O)—$OR^{1b1}$, —$(CH_2)_{0-2}$C(O)$NR^{1b1}R^{1b2}$, —$(CH_2)_{0-2}NR^{1b1}$C(O)$R^{1b3}$, —$(CH_2)_{0-2}$OH, and $C_3$-$C_8$-cycloalkyloxy;

$R^{1b1}$ is hydrogen or $C_1$-$C_6$alkyl; $R^{1b2}$ is hydrogen or $C_1$-$C_6$alkyl; $R^{1b3}$ is hydrogen or $C_1$-$C_6$alkyl; and $R^{1b4}$ is hydrogen,

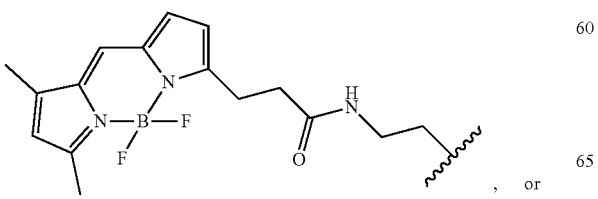

, or

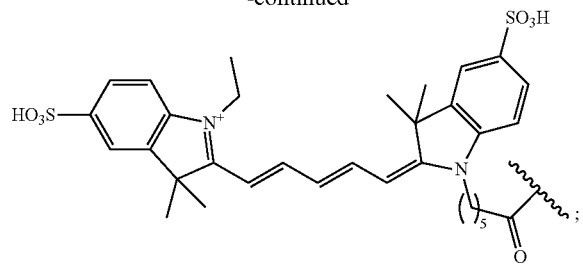

;

$R^2$ is selected from the group consisting of

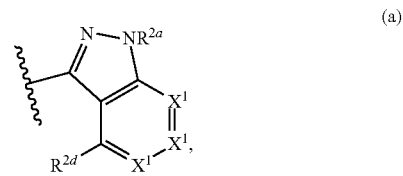

(a)

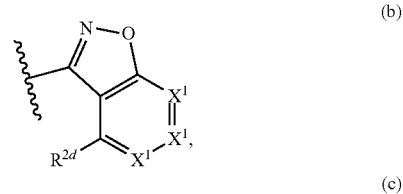

(b)

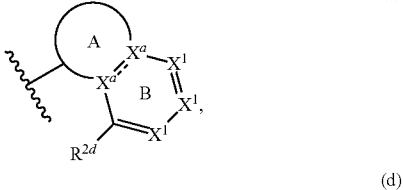

(c)

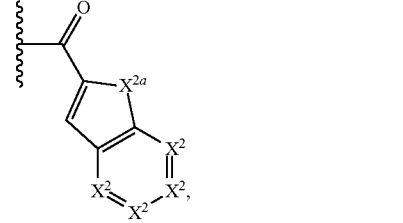

(d)

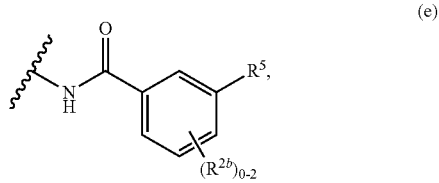

(e)

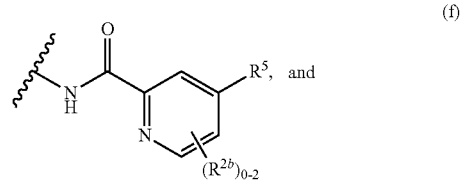

(f)

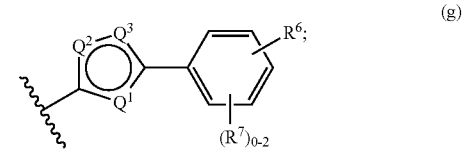

(g)

$R^{2a}$ is hydrogen or $C_1$-$C_6$alkyl;

each $R^{2b}$ is independently hydrogen, halo, —$(CH_2)_{0-2}$OH, $C_1$-$C_3$alkyl, cyclopropyl, cyano, —$CHF_2$, —$CF_3$, $C_1$-$C_4$alkoxy, —$OCHF_2$, —$OCF_3$, or $C_3$-$C_8$cycloalkyloxy;

each $R^{2e}$ is independently hydrogen, —OH, halo, $C_1$-$C_6$alkyl, halo-$C_1$-$C_6$alkyl, $C_3$-$C_8$cycloalkyl, $C_1$-$C_6$alkoxy, halo-$C_1$-$C_6$alkoxy, or $C_3$-$C_8$cycloalkyloxy;

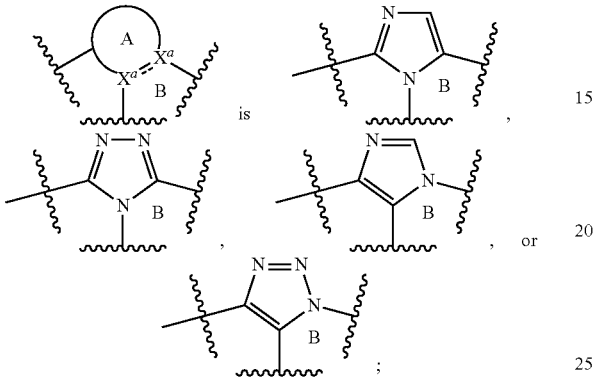

is wherein, for rings (a), (b), and (c)
one $X^1$ is $CR^3$ and the other $X^1$ are independently selected from N and $CR^{2b}$;
$R^{2d}$ is hydrogen, halo, $C_1$-$C_6$alkyl, $C_1$-$C_6$cycloalkyl, $C_1$-$C_6$alkoxy, or $C_3$-$C_8$-cycloalkyloxy;
$R^3$ is —$(CH_2)_{0-2}$Y or —$(CH_2)_{0-2}$-L-Y;
L is -$L^1$-$L^2$-$L^3$-, where $L^1$, $L^2$ and $L^3$ are each independently a bond, —CRR—, O, $S(O)_{0-2}$, C(O) or NR, where each R is independently H or alkyl;
Y is a 5-membered monocyclic heteroaryl substituted with $R^Y$ and optionally substituted with $R^{2e}$; Y is a 6-membered monocyclic aryl or heteroaryl substituted with $R^Y$ and optionally substituted with 1 or 2 $R^{2e}$; Y is an 8-membered bicyclic heteroaryl substituted with $R^Y$ and optionally substituted with 1 or 2 $R^{2e}$; Y is a 9-membered bicyclic heteroaryl substituted with $R^Y$ and optionally substituted with 1, 2, or 3 $R^{2e}$; Y is a 10-membered bicyclic heteroaryl substituted with $R^Y$ and optionally substituted with 1, 2, or 3 $R^{2e}$; Y is a 8- or 9-membered bicyclic heterocyclic substituted with $R^Y$ and optionally substituted with 1 or 2 $R^{2e}$; Y is a 4-9-membered monocyclic or bicyclic heterocycloalkyl substituted with $R^Y$ and optionally substituted with 1 or 2 $R^{2e}$; Y is

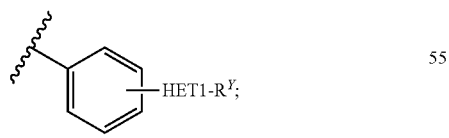

Y is —$(CH_2)_{0-3}NR^{3b}R^Y$; or Y is —$(CH_2)_{0-3}NR^{3b}C(O)R^Y$;
$R^Y$ is —$(CH_2)_{0-3}NR^{3b}C(O)R^{3a}$, —$(CH_2)_{0-2}NR^{3b}S(O)_2R^{3a}$, —$C(O)R^{3a}$, —$S(O)_2R^{3a}$, —$C(O)NR^{3b}R^{3a}$, $C_3$-$C_8$heterocycloalkyl substituted with —$C(O)R^{3a}$; —$(CH_2)_{0-3}NR^{3b}(C_1$-$C_6$alkylene) $NR^{3b1}C(O)R^{3a}$, —$(CH_2)_{0-3}NR^{3b}(C_1$-$C_6$alkylene) $NR^{3b1}S(O)_2R^{3a}$, —$(CH_2)_{0-3}NR^{3b}C(O)(C_1$-

$C_6$alkylene)$NR^{3b1}C(O)R^{3a}$, or —$(CH_2)_{0-3}NR^{3b}C(O)(C_1$-$C_6$alkylene)$NR^{3b1}S(O)_2R^{3a}$,
$R^{3a}$, $R^{3b}$ and $R^{3b1}$ are selected from (i), (ii) or (iii):
(i) one of $R^{3a}$, $R^{3b}$ and $R^{3b1}$ is selected from group a):
$C_1$-$C_6$alkyl substituted with 1 or 2 halo which are independently selected; $C_1$-$C_6$alkyl substituted with cyano; $C_1$-$C_6$alkyl substituted with fluoroalkoxy; $C_1$-$C_6$alkyl substituted with aryloxy or heteroaryloxy, each of which is optionally substituted with 1-3 substituents each independently selected from halo, $C_{1-6}$alkyl, $C_{2-6}$alkenyl, $C_{1-6}$alkoxy, cyano, $C_{3-8}$cycloalkyl or $C_{3-8}$heterocycloalkyl; $C_2$-$C_6$alkenyl; $C_2$-$C_6$alkenyl substituted with cyano; $C_2$-$C_6$alkenyl substituted with halo; —CH=CH—$CH_2$—$NR^{3c}R^{3d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH≡CH—$CH_2$—$NR^{3c}R^{3d}$; CH≡CH—$CH_2$—OH; —CH≡CH—$CH_2$—O—$C_1$-$C_6$alkyl; spirocycloalkyl substituted with cyano; chloropyridyl; fluoropyridyl; chloropyrazinyl; fluoropyrazinyl; chloropyrimidinyl; fluoropyrimidinyl; pentafluorophenyl; tetrafluorophenyl; trifluorophenyl; difluorophenyl; and monofluorophenyl; and the others of $R^{3a}$, $R^{3b}$ and $R^{3b1}$ are selected from group b): hydrogen, and $C_1$-$C_6$alkyl; or
(ii) one of $R^{3a}$, $R^{3b}$ and $R^{3b1}$ is selected from group a): hydrogen; $C_1$-$C_6$alkyl; $C_1$-$C_6$alkyl substituted with aryloxy or heteroaryloxy, each of which is optionally substituted with 1-3 substituents each independently selected from $C_{1-6}$alkyl, $C_{2-6}$alkenyl, $C_{1-6}$alkoxy, cyano, $C_{3-8}$cycloalkyl or $C_{3-8}$heterocycloalkyl; $C_2$-$C_6$alkenyl; $C_3$-$C_8$cycloalkenyl; —C(O)—$C_3$-$C_8$cycloalkyl; $C_2$-$C_6$alkynyl; spirocycloalkyl; pyridyl; pyrimidinyl; and phenyl; and the others of $R^{3a}$, $R^{3b}$ and $R^{3b1}$ are selected from group b): hydrogen, and $C_1$-$C_6$alkyl; or
(iii) $R^{3a}$, $R^{3b}$ and $R^{3b1}$ are each independently hydrogen or $C_1$-$C_6$alkyl;
$R^{3c}$ is hydrogen, or $C_1$-$C_6$alkyl, and $R^{3d}$ is hydrogen, or $C_1$-$C_6$alkyl; or $R^{3c}$ and $R^{3d}$ together with the nitrogen to which they are attached form a 3-8 membered, saturated ring where the other 2-7 ring members are carbon; and
HET1 is $C_3$-$C_8$heterocycloalkyl;
wherein, for ring (d),
$X^{2a}$ is O or S;
one $X^2$ is $CR^4$ and the other $X^2$ are independently selected from N and $CR^{2b}$; $R^4$ is —$(CH_2)_{0-3}NR^{4b}C(O)R^{4a}$, —$(CH_2)_{0-2}NR^{4b}S(O)_2R^{4a}$, —$C(O)R^{4a}$, —$C(O)NR^{4b}R^{4a}$, —$NR^{4b}(C_1$-$C_6$alkylene)$NR^{4b1}C(O)R^{4a}$, —$(CH_2)_{0-3}NR^{4b}C(O)(C_1$-$C_6$alkylene) $NR^{4b1}C(O)R^{4a}$, —$C(O)NR^{4b}(C_1$-$C_6$alkylene) $NR^{4b1}C(O)R^{4a}$, —C(O)—HET1-C(O)$R^{4a}$, —C(O)—HET1-$NR^4$OC(O)$R^{4a}$, —$(CH_2)_{0-3}NR^{4b}C(O)$-HET1-C(O)$R^{4a}$, $C_3$-$C_8$heterocycloalkyl substituted with —C(O)$R^{4a}$ (preferably where the $C_3$-$C_8$heterocycloalkyl is attached to ring (d) through a carbon in the $C_3$-$C_8$heterocycloalkyl ring); or —$(CH_2)_{0-2}$HET2-C(O)$R^{4a}$;
$R^{4a}$, $R^{4b}$ and $R^{4b1}$ is selected from (i), (ii) and (iii):
(i) one of $R^{4a}$, $R^{4b}$ and $R^{4b1}$ is selected from group a): alkyl substituted with 1 or 2 halo which are independently selected; $C_1$-$C_6$alkyl substituted with cyano; $C_2$-$C_6$alkenyl; $C_2$-$C_6$alkenyl substituted with cyano; $C_2$-$C_6$alkenyl substituted with halo; —CH=CH—$CH_2$—$NR^{4c}R^{4d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH=CH—$CH_2$—$NR^{4c}R^{4d}$; CH=CH—$CH_2$—OH; CH=CH—$CH_2$—O—$C_1$-$C_6$alkyl; spirocycloalkyl substituted with cyano; chloropyridyl, fluoropyridyl, chloropyrazinyl, fluoropyrazinyl, chloropyrimidinyl, fluoropyrimidinyl, pentafluorophenyl; tetraflurophenyl; trifluorophenyl; difluorophenyl; and monofluorophenyl; and the others of $R^{4a}$, $R^{4b}$ and $R^{4b1}$ are selected from group b): hydrogen, and $C_1$-$C_6$alkyl;

(ii) one of $R^{4a}$, $R^{4b}$ and $R^{4b1}$ is selected from group a): hydrogen; alkyl; $C_2$-$C_6$alkenyl; $C_3$-$C_8$cycloalkenyl; —C(O)—$C_3$-$C_8$cycloalkyl; $C_2$-$C_6$alkynyl; spirocycloalkyl; pyridyl; pyrazinyl; pyrimidinyl; and phenyl; and the others of $R^{4a}$, $R^{4b}$ and $R^{4b1}$ are selected from group b): hydrogen, and $C_1$-$C_6$alkyl; or (iii) $R^{4a}$, $R^{4b}$ and $R^{4b1}$ are each independently hydrogen or $C_1$-$C_6$alkyl;

$R^{4c}$ is hydrogen, or $C_1$-$C_6$alkyl, and $R^{4d}$ is hydrogen, or $C_1$-$C_6$alkyl; or $R^{4c}$ and $R^{4d}$ together with the nitrogen to which they are attached form a 3-8 membered, saturated ring where the other 2-7 ring members are carbon;

HET1 is $C_3$-$C_8$heterocycloalkyl; and

HET2 is a 8-, 9- or 10-membered bicyclic heterocyclic optionally substituted with 1 or 2 $R^{2e}$;

wherein, for ring (e) and (f), $R^5$ is a 5-membered monocyclic heteroaryl substituted with Z and optionally substituted with $R^{2e}$; $R^5$ is a 6-membered monocyclic heteroaryl substituted with Z and optionally substituted with $R^{2e}$; $R^5$ is —C(O)N($R^{5b}$)Z; $R^5$ is heterocycloalkyl substituted with Z and optionally substituted with $R^{2e}$; $R^5$ is —$(CH_2)_{0-20}$-HET1-Z; $R^5$ is —$(CH_2)_{0-2}$O—Z;

Z is —$(CH_2)_{0-3}NR^{5b}C(O)R^{5a}$, —$(CH_2)_{0-2}NR^{5b}S(O)_2R^{5a}$, —C(O)$R^{5a}$, —S(O)$_2R^{5a}$, —$(CH_2)_{0-3}$—C(O)$NR^{5b}R^{5a}$, —$(CH_2)_{0-3}NR^{5b}(C_1$-$C_6$alkylene)$NR^{5b1}C(O)R^{5a}$, $C_3$-$C_8$heterocycloalkyl substituted with —$NR^{5b}C(O)R^{5a}$, $C_3$-$C_8$heterocycloalkyl substituted with —S(O)$_2R^{5a}$, or $C_3$-$C_8$heterocycloalkyl substituted with —C(O)$R^{5a}$;

$R^{5a}$, $R^{5b}$ and $R^{5b1}$ are selected from (i), (ii) or (iii):

(i) one of $R^{5a}$, $R^{5b}$ and $R^{5b1}$ is selected from group a): $C_1$-$C_6$alkyl substituted with 1 or 2 halo which are independently selected; $C_1$-$C_6$alkyl substituted with cyano; $C_2$-$C_6$alkenyl; $C_2$-$C_6$alkenyl substituted with cyano; $C_2$-$C_6$alkenyl substituted with halo; —CH=CH—$CH_2$—$NR^{5c}R^{5d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH=CH—$CH_2$—$NR^{5c}R^{5d}$; CH=CH—$CH_2$—OH; CH—CH—$CH_2$—O—$C_1$-$C_6$alkyl; spirocycloalkyl substituted with cyano; chloropyridyl, fluoropyridyl, chloropyrazinyl, fluoropyrazinyl, chloropyrimidinyl, fluoropyrimidinyl, pentafluorophenyl; tetraflurophenyl; trifluorophenyl; difluorophenyl; and monofluorophenyl and the other of $R^{5a}$, $R^{5b}$ and $R^{5b1}$ are selected from group b): hydrogen, and $C_1$-$C_6$alkyl;

(ii) one of $R^{5a}$, $R^{5b}$ and $R^{5b1}$ is selected from group a): hydrogen; $C_1$-$C_6$alkyl; $C_2$-$C_6$alkenyl; $C_3$-$C_8$cycloalkenyl; —C(O)—$C_3$-$C_8$cycloalkyl; $C_2$-$C_6$alkynyl; spirocycloalkyl; pyridyl; pyrazinyl; pyrimidinyl; and phenyl; and the other of $R^{5a}$, $R^{5b}$ and $R^{5b1}$ are selected from group b): hydrogen, and $C_1$-$C_6$alkyl; or (iii) $R^{5a}$, $R^{5b}$ and $R^{5b1}$ are each independently hydrogen or $C_1$-$C_6$alkyl;

each $R^{5c}$ is independently hydrogen, or $C_1$-$C_6$alkyl and $R^{5d}$ is hydrogen, or $C_1$-$C_6$alkyl; or $R^{5c}$ and $R^{5d}$ together with the nitrogen to which they are attached form a 3-8 membered saturated ring where the other 2-7 ring members are carbon; HET1 is $C_3$-$C_8$heterocycloalkyl;

wherein, for ring (g), $Q^1$ is $CR^{Q1}$, $Q^2$ is N, and $Q^3$ is O; or $Q^1$ is $CR^{Q1}$, $Q^2$ is O, and $Q^3$ is N; or $Q^1$ is S, $Q^2$ is N, and $Q^3$ is N; or $Q^1$ is N, $Q^2$ is N, and $Q^3$ is O; or $Q^1$ is O, $Q^2$ is N, and $Q^3$ is N; where $R^{Q1}$ is hydrogen, C(O)$C_1$-$C_6$alkyl, or $C_1$;

$R^6$ is a 5- or 6-membered monocyclic heteroaryl substituted with Q and optionally substituted with $R^{2e}$; or $R^6$ is Q;

Q is —$(CH_2)_{0-3}NR^{6b}C(O)R^{6a}$, —$(CH_2)_{0-2}NR^{6b}S(O)_2R^{6a}$, —C(O)$R^{6a}$, —C(O)$NR^{6b}R^{6a}$, or $C_3$-$C_8$heterocycloalkyl substituted with —C(O)$R^{6a}$, $R^{6a}$ and $R^{6b}$ are selected from (i), (ii) or (iii):

(i) one of $R^{6a}$ and $R^{6b}$ is selected from group a): $C_1$-$C_6$alkyl substituted with 1 or 2 halo which are independently selected; $C_1$-$C_6$alkyl substituted with cyano; $C_2$-$C_6$alkenyl; $C_2$-$C_6$alkenyl substituted with cyano; $C_2$-$C_6$alkenyl substituted with halo; —CH=CH—$CH_2$—$NR^{6c}R^{6d}$; —CH=CH—$CH_2$—O—$C_1$-$C_6$alkyl; $C_3$-$C_8$cycloalkenyl; —C(O)cycloalkyl; alkynyl; —CH=CH—$CH_2$—$NR^{6c}R^{6d}$; CH=CH—$CH_2$—OH; CH=CH—$CH_2$—O—$C_1$-$C_6$alkyl; spirocycloalkyl substituted with cyano; chloropyridyl, fluoropyridyl, chloropyrazinyl, fluoropyrazinyl, chloropyrimidinyl, fluoropyrimidinyl, pentafluorophenyl; tetraflurophenyl; trifluorophenyl; difluorophenyl; and monofluorophenyl; and the other of $R^{6a}$ and $R^{6b}$ is selected from group b): hydrogen, and $C_1$-$C_6$alkyl;

(ii) one of $R^{6a}$ and $R^{6b}$ is selected from group a): $C_1$-$C_6$alkyl; $C_2$-$C_6$alkenyl; $C_3$-$C_8$cycloalkenyl; —C(O)cycloalkyl; alkynyl; spirocycloalkyl; pyridyl; pyrazinyl; pyrimidinyl; and phenyl; and the other of $R^{6a}$ and $R^{6b}$ is selected from group b): hydrogen, and $C_1$-$C_6$alkyl; or (iii) $R^{6a}$ and $R^{6b}$ are each independently hydrogen, and $C_1$-$C_6$alkyl;

$R^{6c}$ is hydrogen, or $C_1$-$C_6$alkyl and $R^{6d}$ is hydrogen, or $C_1$-$C_6$alkyl; or $R^{6c}$ and $R^{6d}$ together with the nitrogen to which they are attached form a 3-8 membered saturated ring where the other 2-7 ring members are carbon; and each $R^7$ is independently hydrogen, $C_1$-$C_6$alkyl, $C_1$-$C_6$alkoxy, or $C_3$-$C_8$cycloalkyl;

or a pharmaceutically acceptable salt or salts thereof; and/or a stereoisomer or mixture of stereoisomers thereof.

In one aspect, provided is a compound of Formula (I):

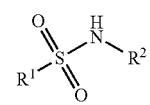

(I)

where $R^1$ is $C_3$-$C_8$-cycloalkyl optionally substituted with 1, 2, or 3 $R^{1a}$; $C_3$-$C_8$-cycloalkyl-$C_1$-$C_6$alkyl where the $C_3$-$C_8$-cycloalkyl is optionally substituted with 1, 2, or 3 $R^{1a}$; phenyl optionally substituted with 1, 2, or 3 $R^{1b}$; phenyl-$C_1$-$C_6$alkyl optionally substituted with 1, 2, or 3 $R^{1b}$; naphthyl optionally substituted with 1, 2, or 3 $R^{1b}$; or 5- or 6-membered monocyclic heteroaryl optionally substituted with 1, 2, or 3 $R^{1b}$; 8- to 10-membered bicyclic heteroaryl optionally substituted with 1, 2, or 3 $R^{1b}$;

each $R^{1a}$ is independently selected from hydrogen, halo, $C_1$-$C_6$alkoxy, and $C_3$-$C_8$-cycloalkyloxy;

each $R^{1b}$ is independently selected from hydrogen, halo, $C_1$-$C_6$alkyl, $C_1$-$C_6$alkoxy, hydroxyalkyloxy, —O-alkylene-$NR^{1b1}R^{1b4}$, —O-alkylene-C(O)$OR^{1b1}$, —O-alkylene-O-alkylene-$NR^{1b1}R^{1b4}$,

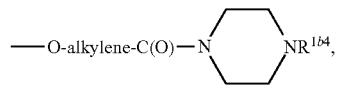

cyano, —$(CH_2)_{0-2}$C(O)—$OR^{1b1}$, —$(CH_2)_{0-2}$C(O)$NR^{1b1}R^{1b2}$, —$(CH_2)_{0-2}$$NR^{1b1}$C(O)$R^{1b3}$, —$(CH_2)_{0-2}$OH, and $C_3$-$C_8$-cycloalkyloxy;

$R^{1b1}$ is hydrogen or $C_1$-$C_6$alkyl; $R^{1b2}$ is hydrogen or $C_1$-$C_6$alkyl; $R^{1b3}$ is hydrogen or $C_1$-$C_6$alkyl; and $R^{1b4}$ is hydrogen,

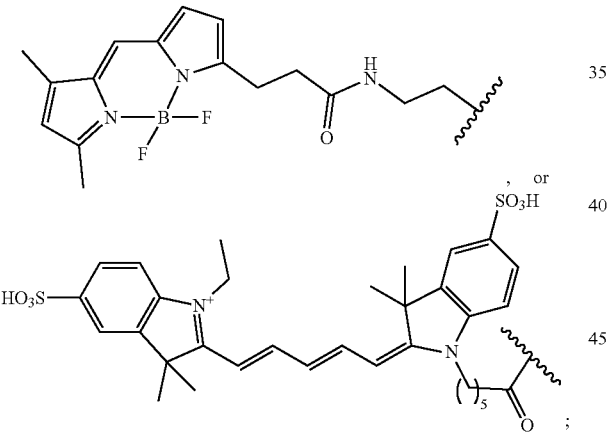

$R^2$ is selected from the group consisting of:

(a)
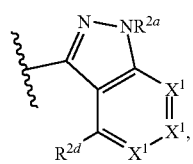

(b)
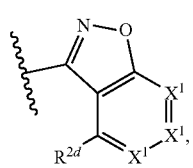

(c)
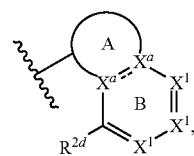

(d)
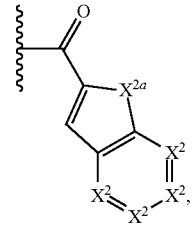

(e)
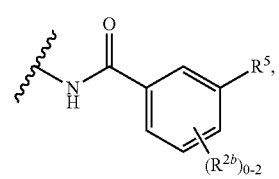

(f)
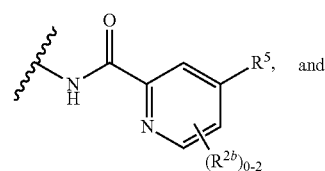
and (g)
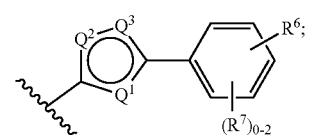

$R^{2a}$ is hydrogen or $C_1$-$C_6$alkyl;

each $R^{2b}$ is independently hydrogen, halo, —$(CH_2)_{0-2}$OH, $C_1$-$C_3$alkyl, cyclopropyl, cyano, —$CHF_2$, —$CF_3$, $C_1$-$C_4$alkoxy, —$OCHF_2$, —$OCF_3$, or $C_3$-$C_8$cycloalkyloxy;

each $R^{2c}$ is independently hydrogen, —OH, halo, $C_1$-$C_6$alkyl, halo-$C_1$-$C_6$alkyl, $C_3$-$C_8$cycloalkyl, $C_1$-$C_6$alkoxy, halo-$C_1$-$C_6$alkoxy, or $C_3$-$C_8$cycloalkyloxy;

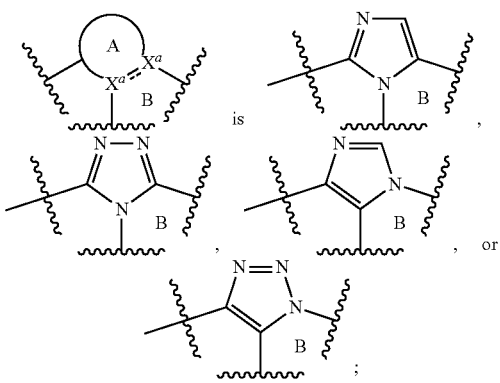

wherein, for rings (a), (b), and (c) one $X^1$ is $CR^3$ and the other $X^1$ are independently selected from N and $CR^{2b}$;

$R^{2d}$ is hydrogen, halo, $C_1$-$C_6$alkyl, $C_1$-$C_6$cycloalkyl, $C_1$-$C_6$alkoxy, or $C_3$-$C_8$-cycloalkyloxy;

$R^3$ is —$(CH_2)_{0-2}$Y;

Y is a 5-membered monocyclic heteroaryl substituted with $R^Y$ and optionally substituted with $R^{2e}$; Y is a 6-membered monocyclic aryl or heteroaryl substituted with $R^Y$ and optionally substituted with 1 or 2 $R^{2e}$; Y is an 8-membered bicyclic heteroaryl substituted with $R^Y$ and optionally substituted with 1 or 2 $R^{2e}$; Y is a 9-membered bicyclic heteroaryl substituted with $R^Y$ and optionally substituted with 1, 2, or 3 $R^{2e}$; Y is a 10-membered bicyclic heteroaryl substituted with $R^Y$ and optionally substituted with 1, 2, or 3 $R^{2e}$; Y is a 8- or 9-membered bicyclic heterocyclic substituted with $R^Y$ and optionally substituted with 1 or 2 $R^{2e}$; Y is a 4-9-membered monocyclic or bicyclic heterocycloalkyl substituted with $R^Y$ and optionally substituted with 1 or 2 $R^{2e}$; Y is

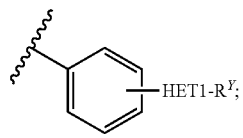

Y is —$(CH_2)_{0-3}NR^{3b}R^Y$; or Y is —$(CH_2)_{0-3}NR^{3b}C(O)R^Y$; $R^Y$ is —$(CH_2)_{0-3}NR^{3b}C(O)R^{3a}$, —$(CH_2)_{0-2}NR^{3b}S(O)_2R^{3a}$, —$C(O)R^{3a}$, —$S(O)_2R^{3a}$, —$C(O)NR^{3b}R^{3a}$, $C_3$-$C_8$heterocycloalkyl substituted with —$C(O)R^{3a}$; —$(CH_2)_{0-3}NR^{3b}(C_1$-$C_6$alkylene)$NR^{3b1}C(O)R^{3a}$, —$(CH_2)_{0-3}NR^{3b}(C_1$-$C_6$alkylene)$NR^{3b1}S(O)_2R^{3a}$, —$(CH_2)_{0-3}NR^{3b}C(O)(C_1$-$C_6$alkylene)$NR^{3b1}C(O)R^{3a}$, or —$(CH_2)_{0-3}NR^{3b}C(O)(C_1$-$C_6$alkylene)$NR^{3b1}S(O)_2R^{3a}$, one of $R^{3a}$, $R^{3b}$ and $R^{3b1}$ is selected from group a): $C_1$-$C_6$alkyl substituted with 1 or 2 halo which are independently selected; $C_1$-$C_6$alkyl substituted with cyano; $C_1$-$C_6$alkyl substituted with fluoroalkoxy; $C_1$-$C_6$alkyl substituted with aryloxy or heteroaryloxy, each of which is optionally substituted with 1-3 substituents each independently selected from halo, $C_{1-6}$alkyl, $C_{2-6}$alkenyl, $C_{1-6}$alkoxy, cyano, $C_{3-8}$cycloalkyl or $C_{3-8}$heterocycloalkyl; $C_2$-$C_6$alkenyl; $C_2$-$C_6$alkenyl substituted with cyano; $C_2$-$C_6$alkenyl substituted with halo; —CH=CH—$CH_2$—$NR^{3c}R^{3d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH≡CH—$CH_2$—$NR^{3c}R^{3d}$; CH≡CH—$CH_2$—OH; —CH≡CH—$CH_2$—O—$C_1$-$C_6$alkyl; spirocycloalkyl substituted with cyano; chloropyridyl; fluoropyridyl; chloropyrazinyl; fluoropyrazinyl; chloropyrimidinyl; fluoropyrimidinyl; pentafluorophenyl; tetraflurophenyl, trifluorophenyl, difluorophenyl; and monofluorophenyl; and the others of $R^{3a}$, $R^{3b}$ and $R^{3b1}$ are selected from group b): hydrogen, and $C_1$-$C_6$alkyl; $R^{3c}$ is hydrogen, or $C_1$-$C_6$alkyl, and $R^{3d}$ is hydrogen, or $C_1$-$C_6$alkyl; or $R^{3c}$ and $R^{3d}$ together with the nitrogen to which they are attached form a 3-8 membered, saturated ring where the other 2-7 ring members are carbon; and HET1 is $C_3$-$C_8$heterocycloalkyl;

wherein, for ring (d), $X^{2a}$ is O or S;

one $X^2$ is $CR^4$ and the other $X^2$ are independently selected from N and $CR^{2b}$;

$R^4$ is —$(CH_2)_{0-3}NR^{4b}C(O)R^{4a}$, —$(CH_2)_{0-2}NR^{4b}S(O)_2R^{4a}$, —$C(O)R^{4a}$, —$C(O)NR^{4b}R^{4a}$, —$NR^{4b}(C_1$-$C_6$alkylene)$NR^{4b1}C(O)R^{4a}$, —$(CH_2)_{0-3}NR^{4b}C(O)(C_1$-$C_6$alkylene)$NR^{4b1}C(O)R^{4a}$, —$C(O)NR^{4b}(C_1$-$C_6$alkylene)$NR^{4b1}C(O)R^{4a}$, —C(O)—HET1-$C(O)R^{4a}$, —C(O)—HET1-$NR^4OC(O)R^{4a}$, —$(CH_2)_{0-3}NR^{4b}C(O)$-HET1-$C(O)R^{4a}$, $C_3$-$C_8$heterocycloalkyl substituted with —$C(O)R^{4a}$ (preferably where the $C_3$-$C_8$heterocycloalkyl is attached to ring (d) through a carbon in the $C_3$-$C_8$heterocycloalkyl ring); or —$(CH_2)_{0-2}$HET2-$C(O)R^{4a}$;

one of $R^{4a}$, $R^{4b}$ and $R^{4b1}$ is selected from group a): alkyl substituted with 1 or 2 halo which are independently selected; $C_1$-$C_6$alkyl substituted with cyano; $C_2$-$C_6$alkenyl; $C_2$-$C_6$alkenyl substituted with cyano; $C_2$-$C_6$alkenyl substituted with halo; —CH=CH—$CH_2$—$NR^{4c}R^{4d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH≡CH—$CH_2$—$NR^{4c}R^{4d}$; CH≡CH—$CH_2$—OH; CH≡CH—$CH_2$—O—$C_1$-$C_6$alkyl; spirocycloalkyl substituted with cyano; chloropyridyl, fluoropyridyl, chloropyrazinyl, fluoropyrazinyl, chloropyrimidinyl, fluoropyrimidinyl, pentafluorophenyl; tetraflurophenyl; trifluorophenyl; difluorophenyl; and monofluorophenyl; and the other of $R^{4a}$, $R^{4b}$ and $R^{4b1}$ are selected from group b): hydrogen, and $C_1$-$C_6$alkyl;

$R^{4c}$ is hydrogen, or $C_1$-$C_6$alkyl, and $R^{4d}$ is hydrogen, or $C_1$-$C_6$alkyl; or $R^{4c}$ and $R^{4d}$ together with the nitrogen to which they are attached form a 3-8 membered, saturated ring where the other 2-7 ring members are carbon;

HET1 is $C_3$-$C_8$heterocycloalkyl; and

HET2 is a 8-, 9- or 10-membered bicyclic heterocyclic optionally substituted with 1 or 2 $R^{2e}$;

wherein, for ring (e) and (f), $R^5$ is a 5-membered monocyclic heteroaryl substituted with Z and optionally substituted with $R^{2e}$; $R^5$ is a 6-membered monocyclic heteroaryl substituted with Z and optionally substituted with $R^{2e}$; $R^5$ is —$C(O)N(R^{5b})Z$; $R^5$ is heterocycloalkyl substituted with Z and optionally substituted with $R^{2e}$; $R^5$ is —$(CH_2)_{0-20}$-HET1-Z; $R^5$ is —$(CH_2)_{0-2}$O—Z;

Z is —$(CH_2)_{0-3}NR^{5b}C(O)R^{5a}$, —$(CH_2)_{0-2}NR^{5b}S(O)_2R^{5a}$, —$C(O)R^{5a}$, —$S(O)_2R^{5a}$, —$(CH_2)_{0-3}$—$C(O)NR^{5b}R^{5a}$, —$(CH_2)_{0-3}NR^{5b}(C_1$-$C_6$alkylene)$NR^{5b1}C(O)R^{5a}$, $C_3$-$C_8$heterocycloalkyl substituted with —$NR^{5b}C(O)R^{5a}$, $C_3$-$C_8$heterocycloalkyl substituted with —$S(O)_2R^{5a}$, or $C_3$-$C_8$heterocycloalkyl substituted with —$C(O)R^{5a}$;

one of $R^5$, $R^{5b}$ and $R^{5b1}$ is selected from group a): $C_1$-$C_6$alkyl substituted with 1 or 2 halo which are independently selected; $C_1$-$C_6$alkyl substituted with cyano; $C_2$-$C_6$alkenyl; $C_2$-$C_6$alkenyl substituted with cyano; $C_2$-$C_6$alkenyl substituted with halo; —CH=CH—$CH_2$—$NR^{5c}R^{5d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH≡CH—$CH_2$—$NR^{5c}R^{5d}$; CH≡CH—$CH_2$—OH; CH—CH—$CH_2$—O—$C_1$-$C_6$alkyl; spirocycloalkyl substituted with cyano; chloropyridyl, fluoropyridyl, chloropyrazinyl, fluoropyrazinyl, chloropyrimidinyl, fluoropyrimidinyl, pentafluorophenyl; tetraflurophenyl; trifluorophenyl; difluorophenyl; and monofluorophenyl and the other of $R^5$, $R^{5b}$ and $R^{5b1}$ are selected from group b): hydrogen, and $C_1$-$C_6$alkyl;

each $R^{5c}$ is independently hydrogen, or $C_1$-$C_6$alkyl and $R^{5d}$ is hydrogen, or $C_1$-$C_6$alkyl; or $R^{5c}$ and $R^{5d}$ together with the nitrogen to which they are attached form a 3-8 membered saturated ring where the other 2-7 ring members are carbon;

HET1 is $C_3$-$C_8$heterocycloalkyl;

wherein, for ring (g),
$Q^1$ is $CR^{Q1}$, $Q^2$ is N, and $Q^3$ is O; or $Q^1$ is $CR^{Q1}$, $Q^2$ is O, and $Q^3$ is N; or $Q^1$ is S, $Q^2$ is N, and $Q^3$ is N; or $Q^1$ is N, $Q^2$ is N, and $Q^3$ is O; or $Q^1$ is O, $Q^2$ is N, and $Q^3$ is N; where $R^{Q1}$ is hydrogen, $C(O)C_1$-$C_6$alkyl, or $C_1$;

$R^6$ is a 5- or 6-membered monocyclic heteroaryl substituted with Q and optionally substituted with $R^{2e}$; or $R^6$ is Q;

Q is —$(CH_2)_{0-3}NR^{6b}C(O)R^{6a}$, —$(CH_2)_{0-2}NR^{6b}S(O)_2R^{6a}$, —$C(O)R^{6a}$, —$C(O)NR^{6b}R^{6a}$, or $C_3$-$C_8$heterocycloalkyl substituted with —$C(O)R^{6a}$;

one of $R^{6a}$ and $R^{6b}$ is selected from group a): is $C_1$-$C_6$alkyl substituted with 1 or 2 halo which are independently selected; $C_1$-$C_6$alkyl substituted with cyano; $C_2$-$C_6$alkenyl; $C_2$-$C_6$alkenyl substituted with cyano; $C_2$-$C_6$alkenyl substituted with halo; —CH=CH—$CH_2$—$NR^{6c}R^{6d}$; —CH=CH—$CH_2$—O—$C_1$-$C_6$alkyl; $C_3$-$C_8$cycloalkenyl; —C(O)cycloalkyl; alkynyl; —CH≡CH—$CH_2$—$NR^{6c}R^{6d}$; CH≡CH—$CH_2$—OH; CH≡CH—$CH_2$—O—$C_1$-$C_6$alkyl; spirocycloalkyl substituted with cyano; chloropyridyl, fluoropyridyl, chloropyrazinyl, fluoropyrazinyl, chloropyrimidinyl, fluoropyrimidinyl, pentafluorophenyl; tetraflurophenyl; trifluorophenyl; difluorophenyl; and monofluorophenyl; and the other of $R^{6a}$ and $R^{6b}$ is selected from group b): hydrogen, and $C_1$-$C_6$alkyl;

$R^{6c}$ is hydrogen, or $C_1$-$C_6$alkyl and $R^{6d}$ is hydrogen, or $C_1$-$C_6$alkyl; or $R^{6c}$ and $R^{6d}$ together with the nitrogen to which they are attached form a 3-8 membered saturated ring where the other 2-7 ring members are carbon; and each $R^7$ is independently hydrogen, $C_1$-$C_6$alkyl, $C_1$-$C_6$alkoxy, or $C_3$-$C_8$cycloalkyl;

or a pharmaceutically acceptable salt or salts thereof; and/or a stereoisomer or mixture of stereoisomers thereof.

In another aspect provided is a compound comprising an alkenyl-containing or alkynyl-containing electrophilic group capable of binding to KAT6A or KAT6B irreversibly and/or covalently. Also included are other electrophilic groups like nitrile and halomethyl ketone.

In one aspect, provided is a compound of Formula (I):

(I)

where $R^1$ is $C_3$-$C_8$-cycloalkyl optionally substituted with 1, 2, or 3 $R^{1a}$; $C_3$-$C_8$-cycloalkylalkyl where the $C_3$-$C_8$-cycloalkyl is optionally substituted with 1, 2, or 3 $R^{1a}$; phenyl optionally substituted with 1, 2, or 3 $R^{1b}$; naphthyl optionally substituted with 1, 2, or 3 $R^{1b}$; 5- or 6-membered monocyclic heteroaryl optionally substituted with 1, 2, or 3 $R^{1b}$; or 8-10-membered bicyclic heteroaryl optionally substituted with 1, 2, or 3 $R^{1b}$;

each $R^{1a}$ is independently selected from H, halo, $C_1$-$C_6$alkoxy, and $C_3$-$C_8$-cycloalkyloxy;

each $R^{1b}$ is independently selected from H, halo, $C_1$-$C_6$alkoxy, cyano, and $C_3$-$C_8$-cycloalkyloxy;

$R^2$ is selected from the group consisting of:

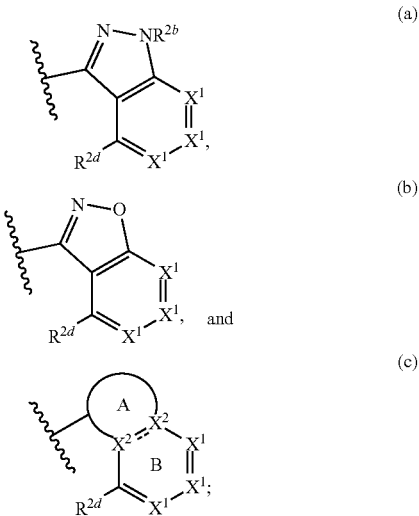

wherein, for ring (a),
$R^{2b}$ is hydrogen or $C_1$-$C_6$alkyl;
one $X^1$ is $C(CH_2R^{2c})$, and the other two $X^1$ are independently selected from N and $CR^{2e}$;
$R^{2c}$ is a 5-membered monocyclic heteroaryl optionally substituted with 1 or 2 $R^{2c1}$; $R^{2c}$ is a 8- or 9-membered bicyclic heterocyclic optionally substituted with 1 or 2 $R^{2c1}$; $R^{2c}$ is a 6-membered monocyclic heteroaryl optionally substituted with 1, 2, or 3 $R^{2c1}$; $R^{2c}$ is a 9-membered bicyclic heteroaryl optionally substituted with 1, 2, or 3 $R^{2c1}$; or $R^{2c}$ is a 10-membered bicyclic heteroaryl optionally substituted with 1, 2, or 3 $R^{2c1}$; and
each $R^{2c1}$ is independently H, halo, $C_1$-$C_6$alkyl, $C_1$-$C_6$alkylcarbonyl, —CN, $C_1$-$C_6$alkoxy, $C_3$-$C_8$cycloalkyloxy, —$(CH_2)_{0-1}NH_2$, —$NH(C_1$-$C_6$alkyl), —$N(C_1$-$C_6$alkyl$)_2$, —$(CH_2)_{0-1}NHC(O)R^{2f}$, —$(CH_2)_{0-1}NHC(O)OR^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

wherein, for ring (b),
one $X^1$ is $C(CH_2R^{2c})$, and the other two $X^1$ are independently selected from N and $CR^{2e}$;
$R^{2c}$ is a 5-membered monocyclic heteroaryl substituted with $R^{2c2}$ and optionally substituted with $R^{2c3}$; $R^{2c}$ is a 8- or 9-membered bicyclic heterocyclic optionally substituted with 1 or 2 $R^{2c1}$; $R^2$ is a 8- or 9-membered bicyclic heterocyclic substituted with $R^{2c2}$ and optionally substituted with $R^{2c3}$; $R^{2c}$ is a 6-membered monocyclic heteroaryl substituted with $R^{2c2}$ and optionally substituted with 1 or 2 $R^{2c3}$; $R^{2c}$ is a 9-membered bicyclic heteroaryl substituted with $R^{2c2}$ and optionally substituted with 1 or 2 $R^{2c3}$; or $R^{2c}$ is a 10-membered bicyclic heteroaryl optionally substituted with 1, 2, or 3 $R^{2c1}$;

$R^{2c2}$ is hydrogen, $C_1$-$C_6$alkylcarbonyl, —CN, —CH$_2$NH$_2$, $C_1$-$C_6$alkoxy, —NH($C_1$-$C_6$alkyl), —N($C_1$-$C_6$alkyl)$_2$, —CH$_2$NHC(O)R$^{2f}$, —(CH$_2$)$_{0-1}$NHC(O)OR$^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

$R^{2c3}$ is independently H, halo, $C_1$-$C_6$alkyl, $C_1$-$C_6$alkoxy, or $C_3$-$C_8$cycloalkyloxy; and each $R^{2c1}$ is independently H, halo, $C_1$-$C_6$alkyl, $C_1$-$C_6$alkylcarbonyl, $C_1$-$C_6$alkoxy, $C_3$-$C_8$cycloalkyloxy, —CN, —CH$_2$NH$_2$, —NH($C_1$-$C_6$alkyl), —N($C_1$-$C_6$alkyl)$_2$, —CH$_2$NHC(O)R$^{2f}$, —(CH$_2$)$_{0-1}$NHC(O)OR$^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

wherein, for ring (c), one $X^1$ is C(CH$_2$R$^{2c}$), and the other two $X^1$ are independently selected from N and CR$^{2e}$;

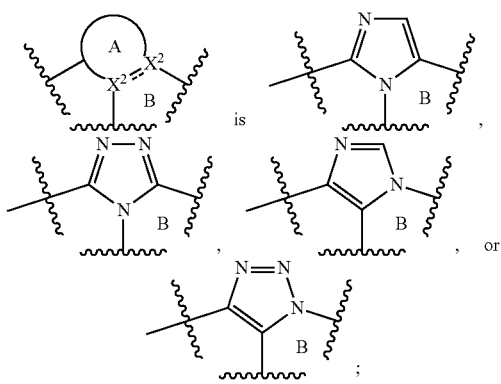

is $R^{2c}$ is a 5-membered monocyclic heteroaryl optionally substituted with 1 or 2 $R^{2c1}$; $R^{2c}$ is a 8- or 9-membered bicyclic heterocyclic optionally substituted with 1 or 2 $R^{2c1}$; $R^{2c}$ is a 6-membered monocyclic heteroaryl optionally substituted with 1, 2, or 3 $R^{2c1}$; $R^{2c}$ is a 9-membered bicyclic heteroaryl optionally substituted with 1, 2, or 3 $R^{2c1}$; or $R^2$, is a 10-membered bicyclic heteroaryl optionally substituted with 1, 2, or 3 $R^{2c1}$; and each $R^{2c1}$ is independently H, halo, $C_1$-$C_6$alkyl, $C_1$-$C_6$alkylcarbonyl, —CN, $C_1$-$C_6$alkoxy, $C_3$-$C_8$cycloalkyloxy, —CH$_2$NH$_2$, —NH($C_1$-$C_6$alkyl), —N($C_1$-$C_6$alkyl)$_2$, —CH$_2$NHC(O)R$^{2f}$, —(CH$_2$)$_{0-1}$NHC(O)OR$^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

$R^{2d}$ is halo, $C_1$-$C_6$alkyl, $C_1$-$C_6$alkoxy, or $C_3$-$C_8$-cycloalkyloxy; and each $R^{2e}$ is independently hydrogen, halo, $C_1$-$C_3$alkyl, cyclopropyl, —CHF$_2$, —CF$_3$, $C_1$-$C_4$alkoxy, —OCHF$_2$, or —OCF$_3$;

or a pharmaceutically acceptable salt or salts thereof; and/or a stereoisomer or mixture of stereoisomers thereof.

In another aspect, provided herein is a compound of $R^2$NH$_2$ (Formula A), where $R^2$ is selected from the group consisting of:

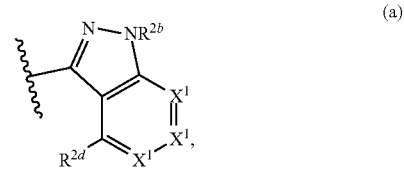

(a)

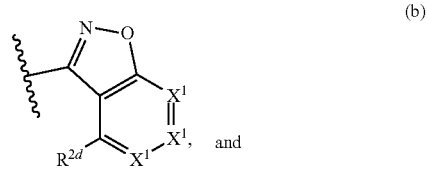

(b)

and

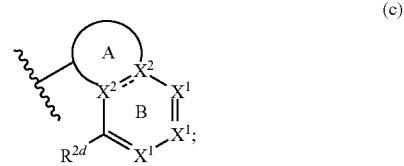

(c)

wherein, for ring (a), $R^{2b}$ is hydrogen or $C_1$-$C_6$alkyl;

one $X^1$ is C(CH$_2$R$^{2c}$), and the other two $X^1$ are independently selected from N and CR$^{2e}$;

$R^{2c}$ is a 5-membered monocyclic heteroaryl optionally substituted with 1 or 2 $R^{2c1}$; $R^{2C}$ is a 8- or 9-membered bicyclic heterocyclic optionally substituted with 1 or 2 $R^{2c1}$; $R^{2c}$ is a 6-membered monocyclic heteroaryl optionally substituted with 1, 2, or 3 $R^{2c1}$; $R^{2c}$ is a 9-membered bicyclic heteroaryl optionally substituted with 1, 2, or 3 $R^{2c1}$; or $R^{2c}$ is a 10-membered bicyclic heteroaryl optionally substituted with 1, 2, or 3 $R^{2c1}$; and each $R^{2c1}$ is independently H, halo, $C_1$-$C_6$alkyl, $C_1$-$C_6$alkylcarbonyl, —CN, $C_1$-$C_6$alkoxy, $C_3$-$C_8$cycloalkyloxy, —(CH$_2$)$_{0-1}$NH$_2$, —NH($C_1$-$C_6$alkyl), —N($C_1$-$C_6$alkyl)$_2$, —(CH$_2$)$_{0-1}$NHC(O)R$^{2f}$, —(CH$_2$)$_{0-1}$NHC(O)OR$^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

wherein, for ring (b), one $X^1$ is C(CH$_2$R$^{2c}$), and the other two $X^1$ are independently selected from N and CR$^{2e}$;

$R^{2c}$ is a 5-membered monocyclic heteroaryl substituted with $R^{2c2}$ and optionally substituted with $R^{2c3}$; $R^{2c}$ is a 8- or 9-membered bicyclic heterocyclic optionally substituted with 1 or 2 $R^{2c1}$; $R^{2c}$ is a 6-membered monocyclic heteroaryl substituted with $R^{2c2}$ and optionally substituted with 1 or 2 $R^{2c3}$; $R^{2c}$ is a 9-membered bicyclic heteroaryl substituted with $R^{2c2}$ and optionally substituted with 1 or 2 $R^{2c3}$; or $R^{2c}$ is a 10-membered bicyclic heteroaryl optionally substituted with 1, 2, or 3 $R^{2c1}$;

$R^{2c2}$ is $C_1$-$C_6$alkylcarbonyl, —CN, —(CH$_2$)$_{0-1}$NH$_2$, $C_1$-$C_6$alkoxy, —NH($C_1$-$C_6$alkyl), —N($C_1$-$C_6$alkyl)$_2$, —(CH$_2$)$_{0-1}$NHC(O)R$^{2f}$, —(CH$_2$)$_{0-1}$NHC(O)OR$^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

$R^{2c3}$ is independently H, halo, $C_1$-$C_6$alkyl, $C_1$-$C_6$alkoxy, or $C_3$-$C_8$cycloalkyloxy; and each $R^{2c1}$ is independently H, halo, $C_1$-$C_6$alkyl, $C_1$-$C_6$alkylcarbonyl, $C_1$-$C_6$alkoxy, $C_3$-$C_8$cycloalkyloxy, —CN, —$(CH_2)_{0-1}NH_2$, —$NH(C_1$-$C_6$alkyl), —$N(C_1$-$C_6$alkyl)$_2$, —$(CH_2)_{0-1}NHC(O)R^{2f}$, —$(CH_2)_{0-1}NHC(O)OR^{2f}$, 5 or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

wherein, for ring (c),
one $X^1$ is $C(CH_2R^{2c})$, and the other two $X^1$ are independently selected from N and $CR^{2e}$;

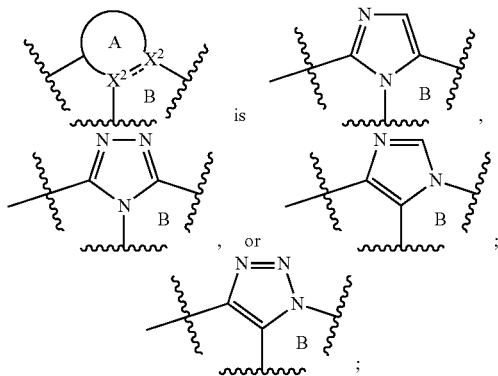

$R^{2c}$ is a 5-membered monocyclic heteroaryl optionally substituted with 1 or 2 $R^{2c1}$; $R^{2c}$ is a 8- or 9-membered bicyclic heterocyclic optionally substituted with 1 or 2 $R^{2c1}$; $R^{2c}$ is a 6-membered monocyclic heteroaryl optionally substituted with 1, 2, or 3 $R^{2c1}$; $R^{2c}$ is a 9-membered bicyclic heteroaryl optionally substituted with 1, 2, or 3 $R^{2c1}$; or $R^{2c}$ is a 10-membered bicyclic heteroaryl optionally substituted with 1, 2, or 3 $R^{2c1}$; and each $R^{2c1}$ is independently H, halo, $C_1$-$C_6$alkyl, $C_1$-$C_6$alkylcarbonyl, —CN, $C_1$-$C_6$alkoxy, $C_3$-$C_8$cycloalkyloxy, —$(CH_2)_{0-1}NH_2$, —$NH(C_1$-$C_6$alkyl), —$N(C_1$-$C_6$alkyl)$_2$, —$(CH_2)_{0-1}NHC(O)R^{2f}$, —$(CH_2)_{0-1}NHC(O)OR^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

$R^{2d}$ is halo, $C_1$-$C_6$alkyl, $C_1$-$C_6$alkoxy, or $C_3$-$C_8$-cycloalkyloxy; and each $R^{2e}$ is independently hydrogen, halo, $C_1$-$C_3$alkyl, cyclopropyl, $CHF_2$, $CF_3$, $C_1$-$C_4$alkoxy, —$OCHF_2$, or —$OCF_3$;

or a pharmaceutically acceptable salt or salts thereof; and/or a stereoisomer or mixture of stereoisomers thereof.

In another aspect, provided herein are pharmaceutical compositions, single unit dosage forms, and kits suitable for use in treating disorders by inhibiting MYST family of lysine acetyl transferases, including KAT6A and KAT6B, which comprise a therapeutically effective amount of a compound provided herein, e.g., of some or any of the embodiments, of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), and specific compounds, and a pharmaceutically acceptable carrier thereof.

In another aspect, provided herein is a method of treating a condition, disease, or disorder by inhibiting MYST family of lysine acetyl transferases, including KAT6A and KAT6B, comprising a) administering a therapeutically effective amount of a compound provided herein, e.g., of some or any of the embodiments, of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), and specific compounds or a stereoisomer, a mixture of stereoisomers, and/or a pharmaceutically acceptable salt thereof or b) administering a therapeutically effective amount of a composition comprising a compound provided herein, e.g., of some or any of the embodiments, of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), and specific compounds or a stereoisomer, a mixture of stereoisomers, and/or a pharmaceutically acceptable salt thereof and a pharmaceutically acceptable carrier thereof.

In another aspect, provided herein is a method of preparing a compound of Formula (I), and specific compounds or a stereoisomer, a mixture of stereoisomers, and/or a pharmaceutically acceptable salt thereof comprising treating

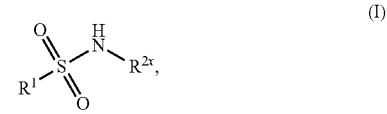

(I)

or a salt thereof, where
$R^1$ is $C_3$-$C_8$-cycloalkyl optionally substituted with 1, 2, or 3 $R^{1a}$; $C_3$-$C_8$-cycloalkyl-$C_1$-$C_6$alkyl where the $C_3$-$C_8$-cycloalkyl is optionally substituted with 1, 2, or 3 $R^{1a}$; phenyl optionally substituted with 1, 2, or 3 $R^{1b}$; naphthyl optionally substituted with 1, 2, or 3 $R^{1b}$; or 5- or 6-membered monocyclic heteroaryl optionally substituted with 1, 2, or 3 $R^{1b}$; 8- to 10-membered bicyclic heteroaryl optionally substituted with 1, 2, or 3 $R^{1b}$;

each $R^{1a}$ is independently selected from hydrogen, halo, $C_1$-$C_6$alkoxy, and $C_3$-$C_8$-cycloalkyloxy;

each $R^{1b}$ is independently selected from hydrogen, halo, $C_1$-$C_6$alkyl, $C_1$-$C_6$alkoxy, hydroxyalkyloxy, —O-alkylene-$NR^{1b1}R^{1b4}$, —O-alkylene-C(O)$OR^{1b1}$, —O-alkylene-O-alkylene-$NR^{1b1}R^{1b4}$,

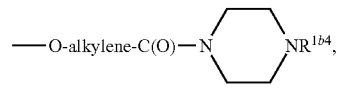

cyano, —$(CH_2)_{0-2}C(O)OR^{1b1}$, —$(CH_2)_{0-2}C(O)NR^{1b2}R^{1b3}$, —$(CH_2)_{0-2}NRC(O)R$, —$(CH_2)_{0-2}OH$, and $C_3$-$C_8$-cycloalkyloxy;

$R^{1b1}$ is hydrogen or $C_1$-$C_6$alkyl; $R^{1b2}$ is hydrogen or $C_1$-$C_6$alkyl; $R^{1b3}$ is hydrogen or $C_1$-$C_6$alkyl; and $R^{1b4}$ is hydrogen,

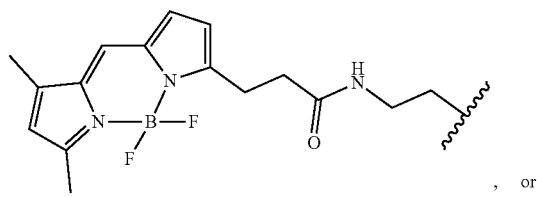

, or

-continued

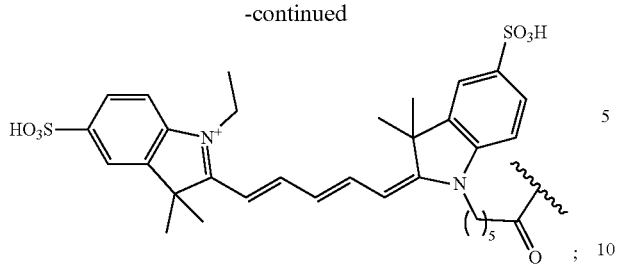

a) where $R^{2x}$ is

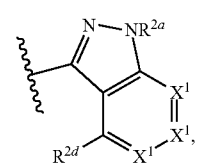
(ax)

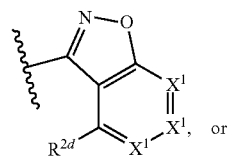
(bx)

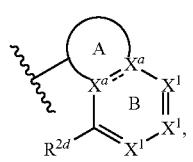
(cx)

and
$R^{2a}$ is hydrogen or $C_1$-$C_6$alkyl;
each $R^{2b}$ is independently hydrogen, halo, $C_1$-$C_3$alkyl, —(CH$_2$)$_{0-2}$OH, cyclopropyl, cyano, —CHF$_2$, —CF$_3$, $C_1$-$C_4$alkoxy, —OCHF$_2$, —OCF$_3$, or $C_3$-$C_8$cycloalkyloxy;
each $R^{2e}$ is independently hydrogen, —OH, halo, $C_1$-$C_6$alkyl, halo-$C_1$-$C_6$alkyl, $C_3$-$C_8$cycloalkyl, $C_1$-$C_6$alkoxy, halo-$C_1$-$C_6$alkoxy, or $C_3$-$C_8$cycloalkyloxy;

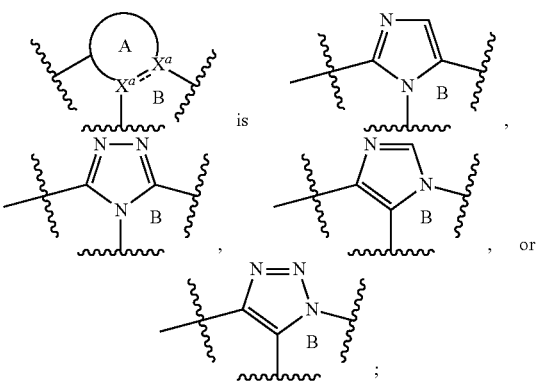

one $X^1$ is $CR^3$ and the other $X^1$ are independently selected from N and $CR^{2b}$;
$R^{2d}$ is hydrogen, halo, $C_1$-$_6$alkyl, $C_1$-$_6$cycloalkyl, $C_1$-$C_6$alkoxy, or $C_3$-$C_8$-cycloalkyloxy;

$R^3$ is —(CH$_2$)$_{0-2}$Y$^x$ or —(CH$_2$)$_{0-2}$-L-Y$^x$;
L is -L$^1$-L$^2$-L$^3$-, where L$^1$, L$^2$ and L$^3$ are each independently a bond, —CRR—, O, S(O)$_{0-2}$, C(O) or NR, where each R is independently H or alkyl; and
$Y^x$ is a 5-membered monocyclic heteroaryl optionally substituted with $R^{2e}$; $Y^x$ is an 8-membered bicyclic heteroaryl optionally substituted with 1 or 2 $R^{2e}$; $Y^x$ is a 9-membered bicyclic heteroaryl optionally substituted with 1, 2, or 3 $R^{2e}$; $Y^x$ is a 10-membered bicyclic heteroaryl optionally substituted with 1, 2, or 3 $R^{2e}$; $Y^x$ is a 8- or 9-membered bicyclic heterocyclic optionally substituted with 1 or 2 $R^{2e}$; $Y^x$ is a 4-9-membered monocyclic or bicyclic heterocycloalkyl optionally substituted with 1 or 2 $R^{2e}$; or $Y^x$ is

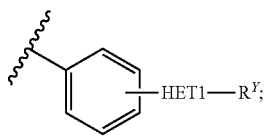

a1) wherein Y has a substitutable nitrogen comprised as a ring atom in the 5-membered monocyclic heteroaryl, 8-membered bicyclic heteroaryl, 9-membered bicyclic heteroaryl, 10-membered bicyclic heteroaryl, and 8- or 9-membered bicyclic heterocyclic; or
a2) wherein Y is substituted with —(CH$_2$)$_{0-2}$—NH$_2$, or —(CH$_2$)$_{0-2}$—NH—(C$_1$-C$_6$alkylene)NH$_2$;
wherein the group in a1) is treated with an intermediate of formula LG-C(O)R$^{3a}$; or
wherein the group in a2) is treated with an intermediate of formula LG-C(O)R$^{3a}$, LG-S(O)$_2$R$^{3a}$; LG-C(O)(C$_1$-C$_6$alkylene)NR$^{3b}$C(O)R$^{3a}$, LG-C(O)(C$_1$-C$_6$alkylene) NR$^{3b}$S(O)$_2$R$^{3a}$, where
LG is a leaving group such as halo or OH activated with a reagent such as HATU, HBTU, T3P, EDCI/HOBt or other agents known to those skilled in the art;
one of $R^{3a}$ and $R^{3b}$ is selected from group a): $C_1$-$C_6$alkyl substituted with 1 or 2 halo which are independently selected; $C_1$-$C_6$alkyl substituted with cyano; $C_1$-$C_6$alkyl substituted with fluoroalkoxy; $C_1$-$C_6$alkyl substituted with aryloxy or heteroaryloxy, each of which may be further substituted with 1-3 substituents each independently selected from halo, $C_{1-6}$alkyl, $C_{2-6}$alkenyl, $C_{1-6}$alkoxy, cyano, $C_3$-8cycloalkyl or $C_{3-8}$heterocycloalkyl; $C_2$-$C_6$alkenyl; $C_2$-$C_6$alkenyl substituted with cyano; $C_2$-$C_6$alkenyl substituted with halo; —CH=CH—CH$_2$—NR$^{3c}$R$^{3d}$; —CH=CH—CH$_2$—O—C$_1$-C$_6$alkyl; $C_3$-$C_8$cycloalkenyl; —C(O)—C$_3$-C$_8$cycloalkyl; $C_2$-$C_6$alkynyl; —CH≡CH—CH$_2$—NR$^{3c}$R$^{3d}$; —CH≡CH—CH$_2$—O—C$_1$-C$_6$alkyl; —CH≡CH—CH$_2$—O—C$_1$-C$_6$alkyl; chloropyridyl, fluoropyridyl, chloropyrazinyl, fluoropyrazinyl, chloropyrimidinyl, fluoropyrimidinyl, pentafluorophenyl; tetraflurophenyl; trifluorophenyl; difluorophenyl; and monofluorophenyl; and
the other of $R^{3a}$ and $R^{3b}$ is selected from group b): hydrogen, and $C_1$-$C_6$alkyl;
$R^{3c}$ is hydrogen, or $C_1$-$C_6$alkyl, and $R^{3d}$ is hydrogen, or $C_1$-$C_6$alkyl; or $R^{3c}$ and $R^{3d}$ together with the nitrogen to which they are attached form a 3-8 membered, saturated ring where the other 2-7 ring members are carbon; or b) where $R^{2x}$ is

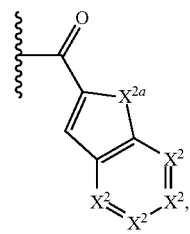

and each $R^{2b}$ is independently hydrogen, halo, $C_1$-$C_3$alkyl, —$(CH_2)_{0-2}$OH, cyclopropyl, cyano, —$CHF_2$, —$CF_3$, $C_1$-$C_4$alkoxy, —$OCHF_2$, —$OCF_3$, or $C_3$-$C_8$cycloalkyloxy;

each $R^{2e}$ is independently hydrogen, halo, —OH, $C_1$-$C_6$alkyl, halo-$C_1$-$C_6$alkyl, $C_3$-$C_8$cycloalkyl, $C_1$-$C_6$alkoxy, halo-$C_1$-$C_6$alkoxy, or $C_3$-$C_8$cycloalkyloxy; $X^{2a}$ is O or S;

one $X^2$ is $CR^{4x}$ and the other $X^2$ are independently selected from N and $CR^{2b}$; and b1) $R^{4x}$ is —$(CH_2)_{0-2}$HET2; $R^{4x}$ is —C(O)—HET1; $R^{4x}$ is —$(CH_2)_{0-3}$$NR^{4b}$C(O)-HET1; or $R^{4x}$ is $C_3$-$C_8$heterocycloalkyl; and wherein HET2 is a 8-, 9- or 10-membered bicyclic heterocyclic optionally substituted with 1 or 2 $R^{2e}$ and has a substitutable nitrogen comprised as a ring atom and HET1 is $C_3$-$C_8$heterocycloalkyl and comprises a substitutable nitrogen as a ring atom in HET1;

b2) $R^{4x}$ is —$(CH_2)_{0-2}$$NH_2$; $R^{4x}$ is —$NR^{4b}$($C_1$-$C_6$alkylene)$NH_2$; $R^{4x}$ is —$(CH_2)_{0-3}$$NR^{4b}$C(O)($C_1$-$C_6$alkylene)$NH_2$; $R^{4x}$ is —C(O)$NR^{4b}$($C_1$-$C_6$alkylene)$NH_2$; or $R^{4x}$ is —C(O)—HET1-$NH_2$;

wherein the group in b1) is treated with an intermediate of formula LG-C(O)$R^{4a}$; or wherein the group in b2) is treated with an intermediate of formula LG-C(O)$R^{4a}$ or LG-S(O)$_2$$R^{4a}$; and where LG is a leaving group such as halo or OH activated with a reagent such as HATU, HBTU, T3P, EDCI/HOBt or other agents known to those skilled in the art;

$R^{4a}$ is alkyl substituted with 1 or 2 halo which are independently selected; $C_1$-$C_6$alkyl substituted with cyano; $C_2$-$C_6$alkenyl; $C_2$-$C_6$alkenyl substituted with cyano; $C_2$-$C_6$alkenyl substituted with halo; —CH=CH—$CH_2$—$NR^{4c}R^{4d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH≡CH—$CH_2$—$NR^{4c}R^{4d}$; CH≡CH—$CH_2$—OH; CH≡CH—$CH_2$—O—$C_1$-$C_6$alkyl; chloropyridyl, fluoropyridyl, chloropyrazinyl, fluoropyrazinyl, chloropyrimidinyl, fluoropyrimidinyl, pentafluorophenyl; tetraflurophenyl; trifluorophenyl; difluorophenyl; or monofluorophenyl;

$R^{4b}$ is hydrogen, or $C_1$-$C_6$alkyl;

$R^{4c}$ is hydrogen, or $C_1$-$C_6$alkyl, and $R^{4d}$ is hydrogen, or $C_1$-$C_6$alkyl; or $R^{4c}$ and $R^{4d}$ together with the nitrogen to which they are attached form a 3-8 membered, saturated ring where the other 2-7 ring members are carbon;

c) where $R^{2x}$ is

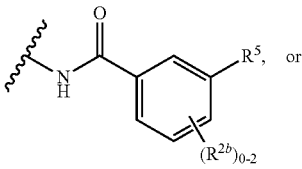

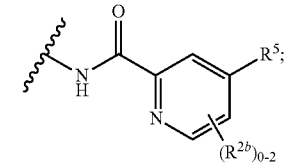

and each $R^{2b}$ is independently hydrogen, halo, $C_1$-$C_3$alkyl, —$(CH_2)_{0-2}$OH, cyclopropyl, cyano, —$CHF_2$, —$CF_3$, $C_1$-$C_4$alkoxy, —$OCHF_2$, —$OCF_3$, or $C_3$-$C_8$cycloalkyloxy;

$R^{5x}$ is a 5-membered monocyclic heteroaryl substituted with $Z^x$ and optionally substituted with $R^{2e}$; $R^{5x}$ is a 6-membered monocyclic heteroaryl substituted with $Z^x$ and optionally substituted with $R^{2e}$; $R^{5x}$ is —C(O)$LG^1$; $R^{5x}$ is —$(CH_2)_{0-20}$-HET1; or $R^{5x}$ is —$(CH_2)_{0-3}$O—$(CH_2)_{0-3}$$NH_2$; where $LG^1$ is a leaving group such as halo or OH activated with a reagent such as HATU, HBTU, T3P, EDCI/HOBt or other agents known to those skilled in the art;

c1) $Z^x$ is —$(CH_2)_{0-3}$$NH_2$; or $Z^x$ is —$(CH_2)_{0-3}$$NR^{5b}$($C_1$-$C_6$alkylene)$NH_2$;

c2) $Z^x$ is $C_3$-$C_8$heterocycloalkyl and comprises a substitutable nitrogen as a ring atom;

wherein the group in c1) is treated with an intermediate of formula $LG^2$-C(O)$R^{5a}$ or $LG^2$-S(O)$_2$$R^{5a}$;

wherein the group in c2) is treated with an intermediate of formula $LG^2$-C(O)$R^{5a}$; and where $LG^2$ is a leaving group such as halo or OH activated with a reagent such as HATU, HBTU, T3P, EDCI/HOBt or other agents known to those skilled in the art $R^{5a}$ is $C_1$-$C_6$alkyl substituted with 1 or 2 halo which are independently selected; $C_1$-$C_6$alkyl substituted with cyano; $C_2$-$C_6$alkenyl; $C_2$-$C_6$alkenyl substituted with cyano; $C_2$-$C_6$alkenyl substituted with halo; —CH=CH—$CH_2$—$NR^{5c}R^{5d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH≡CH—$CH_2$—$NR^{5c}R^{5d}$; CH≡CH—$CH_2$—OH; CH≡CH—$CH_2$—O—$C_1$-$C_6$alkyl; chloropyridyl; fluoropyridyl; chloropyrazinyl, fluoropyrazinyl, chloropyrimidinyl, fluoropyrimidinyl, pentafluorophenyl; tetraflurophenyl; trifluorophenyl; difluorophenyl; or monofluorophenyl; and $R^{5b}$ is hydrogen, or $C_1$-$C_6$alkyl;

each $R^{5'}$ is independently hydrogen, or $C_1$-$C_6$alkyl and $R^{5d}$ is hydrogen, or $C_1$-$C_6$alkyl; or $R^{5'}$ and $R^{5d}$ together with the nitrogen to which they are attached form a 3-8 membered saturated ring where the other 2-7 ring members are carbon;

to yield a Compound of Formula (I) and specific compounds; or a stereoisomer, a mixture of stereoisomers, and/or a pharmaceutically acceptable salt thereof.

In another aspect, provided herein is a method of preparing a compound of Formula (I), (Ih), (Ii) and (Ij), and specific compounds or a stereoisomer, a mixture of stereoisomers, and/or a pharmaceutically acceptable salt thereof comprising treating R²NH₂ (Formula A) with R'S(O)₂X where X is halo, preferably chloro using coupling conditions described herein or known to one of ordinary skill in the art. In some or any embodiments, halo is bromo.

BRIEF DESCRIPTION OF THE DRAWINGS

FIG. 1 shows results of a test for reversibility/irreversibility for compounds provided herein (see, Biological Example 2).

DESCRIPTION OF EXEMPLARY EMBODIMENTS

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise. Unless specified otherwise, where a term is defined as being unsubstituted or substituted, the groups in the list of substituents are themselves unsubstituted. For example, a substituted alkyl group can be substituted, for example, with a cycloalkyl group, and the cycloalkyl group is not further substituted unless specified otherwise.

Reference to "about" a value or parameter herein includes (and describes) variations that are directed to that value or parameter per se. For example, description referring to "about X" includes description of "X".

As used herein, and unless otherwise specified, the terms "about" and "approximately," when used in connection with temperatures, doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, within 10%, within 5%, within 4%, within 3%, within 2%, within 1%, or within 0.5% of the specified dose, amount, or weight percent.

The terms "a" or "an," as used in herein means one or more, unless context clearly dictates otherwise.

"Alkyl" means a linear or branched hydrocarbon group having one to eight carbon atoms. "Lower alkyl" or "$C_1$-$C_6$alkyl" means an alkyl group having one to six carbon atoms. In some embodiments, lower alkyl includes methyl, ethyl, propyl, isopropyl, butyl, s-butyl, t-butyl, isobutyl, pentyl, hexyl and the like. A "$C_0$" alkyl (as in "$C_0$-$C_6$-alkyl") is a covalent bond. "$C_6$ alkyl" refers to, for example, n-hexyl, iso-hexyl, and the like.

"Alkoxy" means an —OR group where R is an alkyl group as defined herein. In some embodiments, R is $C_1$-$C_6$alkyl.

"Alkyloxyalkyl" means an alkyl group, as defined herein, substituted with one alkoxy, as defined herein. In some embodiments, alkyloxyalkyl is —CH₂OCH₃.

"Alkenyl" means a straight or branched hydrocarbon radical having from 2 to 8 carbon atoms and at least one double bond and includes ethenyl, propen-1-yl, propen-2-yl, 1-but-3-enyl, 1-pent-3-enyl, 1-hex-5-enyl and the like. "Lower alkenyl" means an alkenyl group having two to six carbon atoms.

"Alkynyl" means a straight or branched hydrocarbon radical having from 2 to 8 carbon atoms and at least one triple bond and includes ethynyl, propynyl, butynyl, pentyn-2-yl and the like. "Lower alkynyl" means an alkynyl group having two to six carbon atoms.

"Cycloalkyl" means a monocyclic or polycyclic hydrocarbon radical having three to thirteen carbon atoms. The cycloalkyl can be saturated or partially unsaturated, but cannot contain an aromatic ring. In some embodiments, cycloalkyl is $C_3$-$C_8$cycloalkyl. In some embodiments, cycloalkyl is $C_3$-$C_6$cycloalkyl. In some embodiments, cycloalkyl includes fused, bridged, and spiro ring systems. In some embodiments, cycloalkyl is cyclopropyl, cyclobutyl, cyclopentyl or cyclohexyl.

"Cycloalkylalkyl" means alkyl group substituted with one or two cycloalkyl group(s), as defined herein. In some embodiments, cycloalkylalkyl includes cyclopropylmethyl, 2-cyclobutyl-ethyl, and the like.

"Spirocycloalkyl substituted with cyano" means

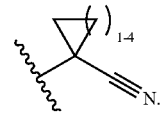

In some embodiments, spirocycloalkyl substituted with cyano is

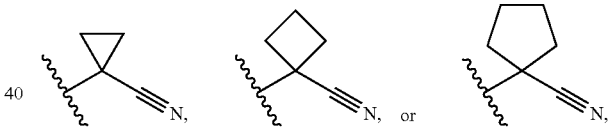

In some embodiments, spirocycloalkyl substituted with cyano is

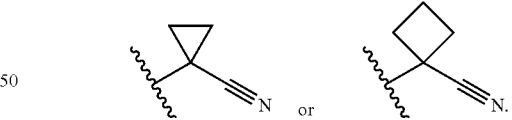

In some embodiments, spirocycloalkyl substituted with cyano is

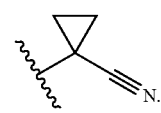

"Cycloalkyloxy" means an —OR group where R is cycloalkyl, as defined herein.

"Cycloalkenyl" means a cycloalkyl, as defined herein, which comprises at least one double bond, but wherein the ring is not aromatic.

"Haloalkyl" means an alkyl group, as defined herein, substituted with one or more halogens, for example one, two, three, four, or five halo atoms. Representative examples includes 2,2-difluoroethyl, trifluoromethyl, and 2-chloro-1-fluoroethyl, and the like.

"Haloalkoxy" means an —OR' group where R' is haloalkyl as defined herein, in some embodiments, haloalkoxy is trifluoromethoxy or 2,2,2-trifluoroethoxy, and the like.

"Heteroaryl" means a monocyclic or bicyclic, monovalent aromatic radical of 5-10 ring atoms containing one or more heteroatoms, for example one, two, or three ring heteroatoms, independently selected from oxygen, nitrogen, and sulfur and the remaining ring atoms being carbon. Unless stated otherwise, the point of attachment may be located on any atom of any ring of the heteroaryl group, valency rules permitting. In some embodiments, the term heteroaryl includes, but is not limited to, 1,2,4-triazolyl, 1,3,5-triazolyl, pyrrolyl, imidazolyl, thienyl, furanyl, tetrazoyl, pyridinyl, pyrazolyl, pyrazinyl, pyrimidinyl, pyridazinyl, oxazolyl, isooxazolyl, oxadiazolyl, thiazolyl, isothiazolyl, thiadiazolyl, indolyl, isoindolyl, benzothiazolyl, benzoxazolyl, quinolinyl, isoquinolinyl, tetrazolyl, and the like, and an N-oxide thereof. When the heteroaryl ring contains 5 or 6 ring atoms, it is also referred to herein as 5- or 6-membered heteroaryl. "Heteroaryl" also includes "8-10-membered bicyclic heteroaryl," as used herein.

"Heterocycloalkyl," as used herein, means a saturated or partially unsaturated (but not aromatic) monovalent monocyclic group of 3 to 9 ring atoms or a saturated or partially unsaturated (but not aromatic) monovalent fused bicyclic group of 5 to 12 ring atoms in which one or more heteroatoms, for example one, two, three, or four ring heteroatoms, independently selected from —O—, —S(O)$_n$— (n is 0, 1, or 2), —N═, —N(R$^y$)— (where R$^y$ is a substituent as provided in any embodiment for a heterocycloalkyl, including for example —C(O)R$^{4a}$ and similar groups), the remaining ring atoms being carbon. One or two ring carbon atoms may be replaced by a —C(O)—, —C(S)—, or —C(═NH)— group. Fused bicyclic radical includes bridged ring systems and spirocyclic ring systems. Unless otherwise stated, the point of attachment of the group may be located on any atom of any ring within the radical, valency rules permitting. In particular, when the point of attachment is located on a nitrogen atom, R$^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, octahydropyrrolo[3,4-c]pyrrolyl, (3aR,6aS)-hexahydro-1H-5λ$^2$-pyrrolo[3,4-c]pyrrolyl, and tetrahydropyranyl, and an N-oxide thereof.

"Bicyclic heterocyclic," as used herein, and unless otherwise specified, refers to a bicyclic ring system that contains one non-aromatic ring and one aromatic ring; wherein one or more (in some or any embodiments, 1, 2, 3, or 4) of any of the ring atoms in the bicyclic ring system is a heteroatom(s) independently selected from O, S(O)$_{0-2}$, and N, and the remaining ring atoms are carbon, and wherein the bicyclic heterocyclic contains 8-12 ring atoms (in some embodiments, 8, 9, or 10 ring atoms). The term "bicyclic heterocyclic" does not include a fully aromatic bicyclic ring, i.e. does not include benzisoxazole, indazole, and the like. In some or any embodiments, the bicyclic heterocyclic group has 8 ring atoms. In some or any embodiments, the bicyclic heterocyclic group has 9 ring atoms. In some or any embodiments, the bicyclic heterocyclic ring comprises one, two, or three heteroatom(s) which are independently selected from nitrogen and oxygen. In some or any embodiments, the bicyclic heterocyclic ring comprises one or two heteroatom(s) which are oxygen. In some or any embodiments, the bicyclic heterocyclic ring comprises one, two, or three heteroatom(s) which are nitrogen (where the nitrogen can be substituted as described in any aspect or embodiment described herein). In some or any embodiments, the bicyclic heterocyclic comprises one heteroatom in the non-aromatic ring, or comprises one or two heteroatoms in the aromatic ring, or comprises two heteroatoms in the aromatic ring, or comprises two heteroatoms where one is in an aromatic ring and the other is in a non-aromatic ring or comprises two heteroatoms in the aromatic ring and one heteroatom in the nonaromatic ring. In some or any embodiments, the bicyclic heterocyclic group may be a bridged or non-bridged, and/or fused or not fused bicyclic group. One or more of the nitrogen and sulfur atoms may be optionally oxidized, one or more of the nitrogen atoms may be optionally quaternized, one or more of the carbon atoms may be optionally replaced with

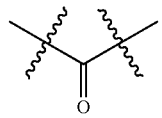

The bicyclic heterocyclic may be attached to the main structure at any heteroatom or carbon atom which results in a stable compound. The bicyclic heterocyclic may be attached to the main structure through any of its rings, including any aromatic or nonaromatic ring, regardless of whether the ring contains a heteroatom. In some or any embodiments, the bicyclic heterocyclic includes a 5-membered heteroaryl group, preferably pyrazolyl, fused to a nonaromatic ring, preferably comprising a nitrogen ring atom, e.g. 2,4,5,6-tetrahydropyrrolo[3,4-c]pyrazolyl, 4,5,6,7-tetrahydro-2H-pyrazolo[3,4-c]pyridinyl, or 4,5,6,7-tetrahydro-2H-pyrazolo[4,3-c]pyridinyl; in some or any embodiments, the rest of the Compound of Formula (I) is attached to the 5-membered heteroaryl group (preferably pyrazolyl), fused to a nonaromatic ring (preferably comprising a nitrogen ring atom), through the 5-membered heteroaryl portion, e.g. 2,4,5,6-tetrahydropyrrolo[3,4-c]pyrazol-1-yl, 2,4,5,6-tetrahydropyrrolo[3,4-c]pyrazol-2-yl, 4,5,6,7-tetrahydro-2H-pyrazolo[3,4-c]pyridin-1-yl, 4,5,6,7-tetrahydro-2H-pyrazolo[3,4-c]pyridin-2-yl, 4,5,6,7-tetrahydro-2H-pyrazolo[4,3-c]pyridin-1-yl, or 4,5,6,7-tetrahydro-2H-pyrazolo[4,3-c]pyridin-2-yl. When the bicyclic heterocyclic is substituted, it can be substituted on any ring, i.e. on any aromatic or nonaromatic ring comprised by the bicyclic heterocyclic. In some or any embodiments, the bicyclic heterocyclic includes, but is not limited to, 2,4,5,6-tetrahydropyrrolo[3,4-c]pyrazolyl, benzodioxolyl, 1,3-dihydroisobenzofuranyl, benzofuranonyl, dihydrobenzofuranyl, benzotetrahydrothienyl, 2,2-dioxo-1,3-dihydrobenzo[c]thienyl, dihydrofuryl, dihydroisoindolyl, indolinyl, 2-oxo-indolinyl, isobenzotetrahydrofuranyl, isobenzotetrahydrothienyl, isoindolinyl, 1-oxo-isoindolinyl, 1,3-dioxo-isoindolinyl; each of which is optionally substituted with 1, 2, 3, or 4 groups as defined throughout the specification.

"Hydroxyalkyl," as used herein, and unless otherwise specified, refers to an alkyl group, as defined herein, substituted with 1, 2, or 3 hydroxy groups (provided that more than one hydroxy group is not on the same carbon). In some embodiments, hydroxyalkyl is hydroxyC$_{1-6}$-alkyl. In some embodiments, hydroxyalkyl is hydroxyethyl.

"Hydroxyalkyloxy," as used herein, and unless otherwise specified, refers to an —OR group where R is hydroxylalkyl, as defined herein. In some embodiments, hydroxyalkyloxy is hydroxyethyloxy.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, PA, 1985, which is incorporated herein by reference or S. M. Berge, et al., "Pharmaceutical Salts," J. Pharm. Sci., 1977; 66:1-19 both of which are incorporated herein by reference. It is also understood that the compound can have one or more pharmaceutically acceptable salts associated with it.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

The term "substantially free of" or "substantially in the absence of" stereoisomers with respect to a composition refers to a composition that includes at least 85 or 90% by weight, in certain embodiments 95%, 98%, 99% or 100% by weight, of a designated stereoisomer of a compound in the composition. In certain embodiments, in the methods and compounds provided herein, the compounds are substantially free of stereoisomers.

Similarly, the term "isolated" with respect to a composition refers to a composition that includes at least 85, 90%, 95%, 98%, 99% to 100% by weight, of a specified compound, the remainder comprising other chemical species or stereoisomers.

The term "solvate," as used herein, and unless otherwise specified, refers to a compound provided herein or a salt thereof, that further includes a stoichiometric or non-stoichiometric amount of solvent bound by non-covalent intermolecular forces. Where the solvent is water, the solvate is a hydrate.

The term "isotopic composition," as used herein, and unless otherwise specified, refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopic enrichment," as used herein, and unless otherwise specified, refers to the percentage of incorporation of an amount of a specific isotope at a given atom in a molecule in the place of that atom's natural isotopic abundance. In certain embodiments, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

The term "isotopically enriched," as used herein, and unless otherwise specified, refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," and "heterocycloalkyl" groups optionally comprise deuterium at one or more positions where hydrogen atoms are present, and wherein the deuterium composition of the atom or atoms is other than the natural isotopic composition.

Also as used herein, "alkyl," "cycloalkyl," and "heterocycloalkyl" groups optionally comprise carbon-13 at an amount other than the natural isotopic composition.

As used herein, and unless otherwise specified, the term "IC$_{50}$" refers to an amount, concentration or dosage of a particular test compound that achieves a 50% inhibition of a maximal response in an assay that measures such response.

As used herein, the terms "subject" and "patient" are used interchangeably. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and in certain embodiments, a human. In certain embodiments, the subject is a farm animal (e.g., a horse, a cow, a pig, etc.) or a pet (e.g., a dog or a cat). In certain embodiments, the subject is a human.

"Administration" and variants thereof (in some embodiments, "administering" a compound) in reference to a compound of the invention means introducing the compound or a prodrug of the compound into the system of the animal in need of treatment. When a compound of the invention or prodrug thereof is provided in combination with one or more other active agents (in some embodiments, surgery, radiation, and chemotherapy, etc.), "administration" and its variants are each understood to include concurrent and sequential introduction of the compound or prodrug thereof and other agents.

"Therapeutically effective amount" is an amount of a compound or composition, that when administered to a patient, is sufficient to effect such treatment for the condition, disease, or disorder, e.g. to ameliorate a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development (stable disease); and (iii) relieving the disease, disorder, or syndrome, e.g. relieving or reducing a symptom thereof, and/or causing regression of the disease, disorder, or syndrome. As is known in the art, adjustments for systemic versus localized delivery, age, body weight, general health, sex, diet, time of administration, drug interaction and the severity of the condition, disease, or disorder may be necessary, and will be ascertainable with routine experimentation by one of ordinary skill in the art. "Treating" or "treatment" of any condition, disease, or disorder refers, in certain embodiments, to ameliorating a condition, disease, or disorder that exists in a subject. In another embodiment, "treating" or "treatment" includes ameliorating at least one physical parameter, which may be indiscernible by the subject. In yet another embodiment, "treating" or "treatment" includes modulating the condition, disease, or disorder, either physically (e.g., stabilization of a discernible symptom) or physiologically (e.g., stabilization of a physical parameter) or both. In yet another embodiment, "treating" or "treatment" includes delaying the onset of the condition, disease, or disorder.

The terms "inhibiting" and "reducing," or any variation of these terms includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of the activity compared to normal.

As used herein, the terms "prophylactic agent" and "prophylactic agents" refer to any agent(s) which can be used in the prevention of a condition, disease, or disorder or one or more symptoms thereof. In certain embodiments, the term "prophylactic agent" includes a compound provided herein. In certain other embodiments, the term "prophylactic agent" does not refer a compound provided herein. In certain embodiments, a prophylactic agent can be an agent which is known to be useful for, or has been or is currently being used to prevent or impede the onset, development, progression and/or severity of a condition, disease, or disorder.

As used herein, the phrase "prophylactically effective amount" refers to the amount of a therapy (e.g., prophylactic agent) which is sufficient to result in the prevention or reduction of the development, recurrence or onset of one or more symptoms associated with a condition, disease, or disorder, or to enhance or improve the prophylactic effect(s) of another therapy (e.g., another prophylactic agent).

Compounds

The embodiments described herein include the recited compounds as well as a pharmaceutically acceptable salt or salts, hydrate, solvate, stereoisomer, tautomer, or mixture thereof.

In some or any embodiments, the compound is according to Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1). In some or any embodiments, the pharmaceutical composition comprises a compound according to Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1). In some or any embodiments, the method of treating comprises administering a compound according to Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1).

Embodiment A: In some or any embodiments, the Compound is that wherein $R^1$ is $C_3$-$C_8$-cycloalkyl-$C_1$-$C_6$alkyl; or phenyl optionally substituted with 1, 2, or 3 $R^{1b}$;
each $R^{1b}$ is independently selected from hydrogen, alkyl, —C(O)OH, —C(O)O($C_{1-3}$alkyl), halo, and $C_1$-$C_6$alkoxy;
$R^2$ is selected from the group consisting of:

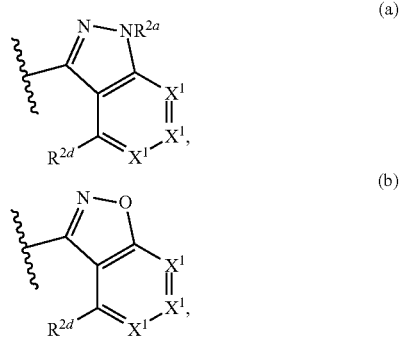

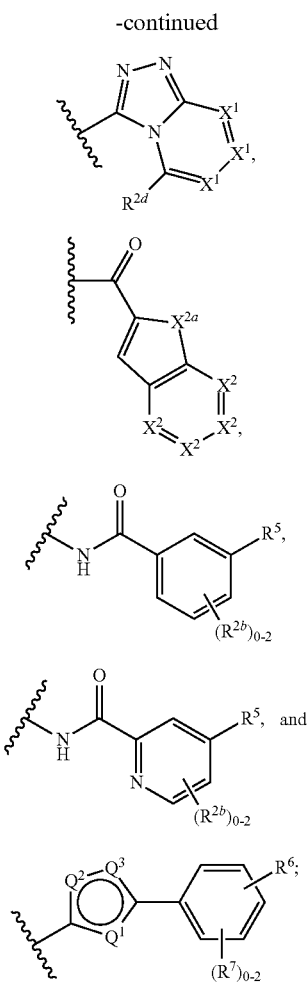

R$^{2a}$ is hydrogen;
each R$^{2b}$ is independently hydrogen, C$_1$-C$_3$alkyl or —(CH$_2$)$_{0-2}$OH;
each R$^{2e}$ is hydrogen;
wherein, for rings (a) and (b)
  one X$^1$ is CR$^3$ and the other X$^1$ are each CH;
  R$^{2d}$ is C$_1$-C$_3$alkoxy;
  R$^3$ is —(CH$_2$)$_{0-2}$Y or —(CH$_2$)$_{0-2}$-L-Y;
  L is -L$^1$-L$^2$-L$^3$-, where L$^1$, L$^2$ and L$^3$ are each independently a bond, —CRR—, O, S(O)$_{0-2}$, C(O) or NR, where each R is independently H or alkyl;
  Y is a 5-membered monocyclic heteroaryl substituted with R$^Y$; Y is a 8- or 9-membered bicyclic heterocyclic substituted with R$^Y$; or Y is a 4-9-membered monocyclic or bicyclic heterocycloalkyl substituted with R$^Y$ and optionally substituted with 1 or 2 R$^{2e}$.
  R$^Y$ is —(CH$_2$)$_{0-3}$NR$^{3b}$C(O)R$^{3a}$, —(CH$_2$)$_{0-2}$NR$^{3b}$S(O)$_2$R$^{3a}$, —C(O)R$^{3a}$, —S(O)$_2$R$^{3a}$, —C(O)NR$^{3b}$R$^{3a}$, or C$_3$-C$_8$heterocycloalkyl substituted with —C(O)R$^{3a}$;
  R$^{3a}$ is C$_1$-C$_6$alkyl substituted with 1 or 2 halo; C$_1$-C$_6$alkyl substituted with fluoroalkoxy; C$_1$-C$_6$alkyl substituted with aryloxy or heteroaryloxy, each of which may be further substituted with 1-3 substituents each independently selected from halo, C$_{1-6}$alkyl, C$_2$-6alkenyl, C$_{1-6}$alkoxy, cyano, C$_{3-8}$cycloalkyl or C$_{3-8}$heterocycloalkyl; C$_2$-C$_6$alkenyl; C$_2$-C$_6$alkenyl substituted with cyano; C$_2$-C$_6$alkenyl substituted with halo; —CH=CH—CH$_2$—NR$^{3c}$R$^{3d}$; —CH=CH—CH$_2$—O—C$_1$-C$_6$alkyl; tetrafluorophenyl; trifluorophenyl; C$_2$-C$_6$alkynyl; or —CH≡CH—CH$_2$—NR$^{3c}$R$^{3d}$;
  R$^{3b}$ and R$^{3b1}$ are each independently hydrogen or C$_1$-C$_6$alkyl; and
  R$^{3c}$ is hydrogen or C$_1$-C$_6$alkyl, and R$^{3d}$ is hydrogen or C$_1$-C$_6$alkyl;
wherein, for ring (d),
  X$^{2a}$ is O;
  one X$^2$ is CR$^4$ and the other X$^2$ are each CH;
  R$^4$ is —(CH$_2$)$_{0-3}$NR$^{4b}$C(O)R$^{4a}$, —NR$^{4b}$(C$_1$-C$_6$alkylene)NR$^{4b1}$C(O)R$^{4a}$, —(CH$_2$)$_{0-3}$NR$^{4b}$C(O)(C$_1$-C$_6$alkylene)NR$^{4b}$C(O)R$^{4a}$, —C(O)NR$^{4b}$(C$_1$-C$_6$alkylene)NR$^{4b}$C(O)R$^{4a}$, —C(O)—HET1-C(O)R$^{4a}$, —C(O)—HET1-NR$^{4b}$C(O)R$^{4a}$, —(CH$_2$)$_{0-3}$NR$^{4b}$C(O)-HET1-C(O)R$^{4a}$, C$_3$-C$_8$heterocycloalkyl substituted with —C(O)R$^{4a}$ (preferably where the C$_3$-C$_8$heterocycloalkyl is attached to ring (d) through a carbon in the C$_3$-C$_8$heterocycloalkyl ring); or —(CH$_2$)$_{0-2}$HET2-C(O)R$^{4a}$;
  R$^{4a}$ is C$_2$-C$_6$alkenyl or C$_2$-C$_6$alkynyl;
  R$^{4b}$ and R$^{4b1}$ are each hydrogen;
  HET1 is C$_3$-C$_8$heterocycloalkyl comprising at least one nitrogen; and
  HET2 is an 8-, 9- or 10-membered bicyclic heterocyclic comprising at least one nitrogen ring atom and —C(O)R$^{4a}$ is to attached to HET2 through the at least one nitrogen ring atom in the HET2 ring;
wherein, for ring (e) and (f),
  R$^5$ is a 5-membered monocyclic heteroaryl substituted with Z and; or R$^5$ is a 6-membered monocyclic heteroaryl substituted with Z;
  Z is —(CH$_2$)$_{0-3}$NR$^{5b}$C(O)R$^{5a}$, —(CH$_2$)$_{0-3}$NR$^{5b}$(C$_1$-C$_6$alkylene)NR$^{5}$b1C(O)R$^{5a}$, C$_3$-C$_8$heterocycloalkyl substituted with —S(O)$_2$R$^{5a}$, or C$_3$-C$_8$heterocycloalkyl substituted with C(O)R$^{5a}$;
  R$^{5a}$ is C$_2$-C$_6$alkenyl or C$_2$-C$_6$alkynyl;
  R$^{5b}$ and R$^{5b1}$ are each hydrogen;
wherein, for ring (g),
  Q$^1$ is CH, Q$^2$ is N, and Q$^3$ is O;
  R$^6$ is a 5-membered monocyclic heteroaryl substituted with Q; or R$^6$ is Q;
  Q is —(CH$_2$)$_{0-3}$NR$^6$C(O)R$^{6a}$;
  R$^{6a}$ is C$_2$-C$_6$alkenyl;
  R$^{6b}$ is hydrogen; and
  each R$^7$ is independently hydrogen, C$_1$-C$_6$alkyl, C$_1$-C$_6$alkoxy, or C$_3$-C$_8$cycloalkyl; or a pharmaceutically acceptable salt or salts thereof; and/or a stereoisomer or mixture of stereoisomers thereof.

Embodiment 1: Provided is a compound according to Formula (I), wherein R$^1$ is C$_3$-C$_8$-cycloalkylalkyl where the C$_3$-C$_8$-cycloalkylalkyl is optionally substituted with 1, 2, or 3 R$^{1a}$, or phenyl optionally substituted with 1, 2, or 3 R$^{1b}$; and all other groups are as defined in the Summary or in some or any embodiment provided herein.

Embodiment 2: Provided is a compound according to Formula (I), wherein R$^1$ is C$_3$-C$_8$-cycloalkylalkyl where the C$_3$-C$_8$-cycloalkylalkyl is optionally substituted with 1, 2, or 3 R$^{1a}$; and all other groups are as defined in the Summary or in some or any embodiment provided herein.

Embodiment 3: Provided is a compound according to Formula (I), wherein R$^1$ is C$_3$-C$_8$-cycloalkyl optionally substituted with 1, 2, or 3 R$^{1a}$; and all other groups are as defined in the Summary or in some or any embodiment provided herein.

Embodiment 4: Provided is a compound according to Formula (I), wherein each R$^{1a}$ is independently hydrogen;

and all other groups are as defined in the Summary or in some or any embodiment provided herein, including any one of Embodiments 1-3.

Embodiment 5: Provided is a compound according to Formula (I), wherein $R^1$ is phenyl optionally substituted with 1, 2, or 3 $R^{1b}$; and all other groups are as defined in the Summary or in some or any embodiment provided herein, including Embodiment 1.

Embodiment 6: Provided is a compound according to Formula (I), wherein $R^1$ is phenyl-$C_1$-$C_6$alkyl optionally substituted with 1, 2, or 3 $R^{1b}$; and all other groups are as defined in the Summary or in some or any embodiment provided herein.

Embodiment 7: Provided is a compound according to Formula (I), wherein $R^1$ is naphthyl optionally substituted with 1, 2, or 3 $R^{1b}$; and all other groups are as defined in the Summary or in some or any embodiment provided herein.

Embodiment 8: Provided is a compound according to Formula (I), wherein $R^1$ is 5- or 6-membered monocyclic heteroaryl optionally substituted with 1, 2, or 3 $R^{1b}$; and all other groups are as defined in the Summary or in some or any embodiment provided herein.

Embodiment 9: Provided is a compound according to Formula (I), (wherein $R^1$ is 8-10-membered bicyclic heteroaryl; and all other groups are as defined in the Summary or in some or any embodiment provided herein.

Embodiment 10: Provided is a compound according to Formula (I), wherein each $R^{1b}$ is independently selected from hydrogen, halo, $C_1$-$C_6$alkyl, $C_1$-$C_6$alkoxy, hydroxy$C_{1-6}$-alkyloxy, —O-alkylene-$NR^{1b1}R^{1b4}$, —O-alkylene-O-alkylene-$NR^{1b1}R^{1b4}$,

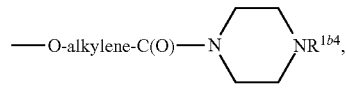

—$(CH_2)_{0-2}C(O)OR^{1b1}$, —$(CH_2)_{0-2}C(O)NR^{1b2}R^{1b3}$, and —$(CH_2)_{0-2}NR^{1b1}C(O)R^{1b3}$; and all other groups are as defined in the Summary or in some or any embodiment provided herein, including any one of Embodiments 1 and 5-9. In a subembodiment of embodiment 10, provided is compound of Formula (I), wherein each $R^{1b}$ is independently selected from hydrogen, halo, $C_1$-$C_3$alkyl, $C_1$-$C_3$alkoxy, hydroxy$C_{1-4}$-alkyloxy, —$C(O)OR^{1b1}$, —$C(O)NHR^{1b3}$, and —$NHC(O)R^{1b3}$. In a subembodiment of embodiment 10, provided is compound of Formula (I), wherein each $R^{1b}$ is independently selected from hydrogen, fluoro, ethyl, methoxy, hydroxyethyloxy, —C(O)OH, —C(O)O $CH_3$, and —C(O)NH$CH_3$. In a subembodiment of embodiment 10 and subembodiments thereof, provided is compound of (I), wherein one or two $R^{1b}$ are present. In a subembodiment of embodiment 10 and subembodiments thereof, provided is a compound according to Formula (I), wherein one $R^{1b}$ are present. In a subembodiment of embodiment 10 and subembodiments thereof, provided is compound of Formula (I), wherein two $R^{1b}$ are present.

Embodiment 11. Provided is a compound of Formula (I) according to Formula (Ia):

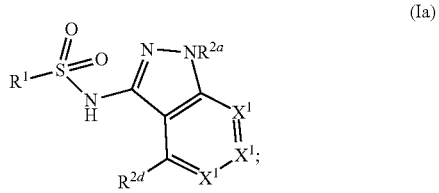

where $R^1$, $R^{2a}$, $R^{2d}$, and $X^1$ and all other groups are as defined in the Summary or in some or any embodiment provided herein, including any one of Embodiments 1-10; or a pharmaceutically acceptable salt or salts thereof; and/or a stereoisomer or mixture of stereoisomers thereof. In some or any embodiments of Embodiment 1, $R^{2a}$ is hydrogen or methyl. In some or any embodiments, provided is a compound of Formula (I) according to Formula (Ia-1):

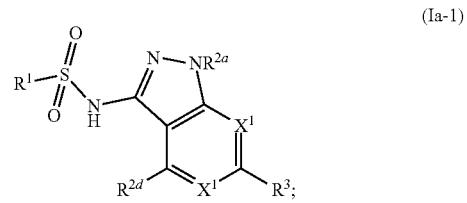

where $R^1$, $R^{2a}$, $R^{2d}$, $R^3$, and $X^1$ and all other groups are as defined in the Summary or in some or any embodiment provided herein, including any one of Embodiments 1-10; or a pharmaceutically acceptable salt or salts thereof; and/or a stereoisomer or mixture of stereoisomers thereof. In some or any embodiments of Embodiment 11, provided is a compound of Formula (Ia) or (Ia-1), wherein $R^{2a}$ is hydrogen or $C_1$-$C_3$alkyl. In some or any embodiments of Embodiment 11, provided is a compound of Formula (Ia) or (Ia-1), wherein $R^{2a}$ is hydrogen or methyl. In some or any embodiments of Embodiment 11, provided is a compound of Formula (Ia) or (Ia-1), wherein $R^{2a}$ is hydrogen. In some or any embodiments of Embodiment 11, provided is a compound of Formula (Ia) or (Ia-1), wherein $R^{2a}$ is $C_1$-$C_6$alkyl. In some or any embodiments of Embodiment 11, provided is a compound of Formula (Ia) or (Ia-1), wherein $R^{2a}$ is $C_1$-$C_3$alkyl. In some or any embodiments of Embodiment 11, provided is a compound of Formula (Ia) or (Ia-1), wherein $R^{2a}$ is methyl.

Embodiment 12. Provided is a compound of Formula (I) according to Formula (Ib):

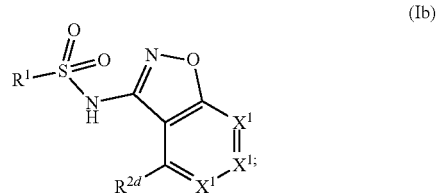

where $R^1$, $R^{2d}$, and $X^1$ and all other groups are as defined in the Summary or in some or any embodiment provided herein, including any one of Embodiments 1-10; or a pharmaceutically acceptable salt or salts thereof; and/or a stereoisomer or mixture of stereoisomers thereof. In some or any embodiments, provided is a compound of Formula (I) according to Formula (Ib-1):

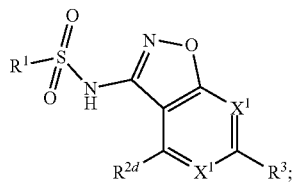
(Ib-1)

where $R^1$, $R^{2d}$, $R^3$, and $X^1$ and other groups are as defined in the Summary or in some or any embodiment provided herein, including any one of Embodiments 1-10; or a pharmaceutically acceptable salt or salts thereof; and/or a stereoisomer or mixture of stereoisomers thereof.

Embodiment 13. Provided is a compound of Formula (I) according to Formula (Ic):

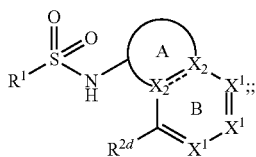
(Ic)

where $R^1$, $R^{2d}$, $X^1$,

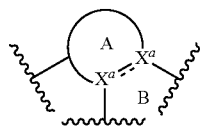

and all other groups are as defined in the Summary or in some or any embodiment provided herein, including any one of Embodiments 1-10; or a pharmaceutically acceptable salt or salts thereof; and/or a stereoisomer or mixture of stereoisomers thereof. In some or any embodiments, provided is a compound of Formula (I) according to Formula (Ic-1):

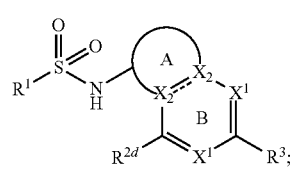
(Ic-1)

where $R^1$, $R^{2d}$, $R^3$, $X^1$,

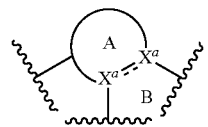

and all other groups are as defined in the Summary or in some or any embodiment provided herein, including any one of Embodiments 1-10; or a pharmaceutically acceptable salt or salts thereof; and/or a stereoisomer or mixture of stereoisomers thereof. In some or any embodiments, provided is a compound of Formula (I) according to Formula (Ic-2):

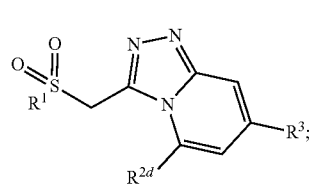
(Ic-2)

where $R^1$, $R^{2d}$, $R^3$, $X^1$, and all other groups are as defined in the Summary or in some or any embodiment provided herein, including any one of Embodiments 1-10; or a pharmaceutically acceptable salt or salts thereof, and/or a stereoisomer or mixture of stereoisomers thereof.

Embodiment 14. Provided is a compound of Formula (I), (Ia), (Ib), (Ic), (Ia-1), (Ib-1), (Ic-1), or (Ic-2), wherein $R^{2d}$ is hydrogen, halo, $C_1$-$C_6$alkyl, $C_{1-6}$cycloalkyl, $C_1$-$C_3$alkoxy, or $C_3$-$C_6$-cycloalkyloxy and all other groups are as defined in the Summary or in some or any embodiment provided herein, including any one of Embodiments 1-13. In some or any embodiments, the compound of Formula (I), (Ia), (Ib), (Ic), (Ia-1), (Ib-1), (Ic-1), or (Ic-2) is that wherein $R^{2d}$ is halo, methyl, methoxy, isopropoxy, or cyclopropyloxy. In some or any embodiments, the compound of Formula (I), (Ia), (Ib), (Ic), (Ia-1), (Ib-1), (Ic-1), or (Ic-2) is that wherein $R^{2d}$ is $C_1$-$C_6$alkoxy, $C_1$-$C_3$alkoxy, or methoxy.

Embodiment 15. Provided is a compound of Formula (I), (Ia), (Ib), (Ic), (Ia-1), (Ib-1), (Ic-1), or (Ic-2), wherein each $R^{2b}$ is hydrogen and all other groups are as defined in the Summary or in some or any embodiment provided herein, including any one of Embodiments 1-14. Provided is a compound of Formula (I), (Ia), (Ib), (Ic), (Ia-1), (Ib-1), (Ic-1), or (Ic-2), wherein one $R^{2b}$ is halo, $C_1$-$C_3$alkyl, —$(CH_2)_{0-2}OH$, cyclopropyl, cyano, —$CHF_2$, —$CF_3$, $C_1$-$C_4$alkoxy, —$OCHF_2$, —$OCF_3$, or $C_3$-$C_8$cycloalkyloxy and the other $R^{2b}$ are each hydrogen and all other groups are as defined in the Summary or in some or any embodiment provided herein, including any one of Embodiments 1-14.

Embodiment 16: Provided is a compound of Formula (I), (Ia), (Ib), (Ic), (Ia-1), (Ib-1), (Ic-1), or (Ic-2), wherein one $X^1$ is $CR^3$ (optionally in the meta position with respect to $R^{2d}$), one $X^1$ is N, and the other $X^1$ are $CR^{2b}$; or wherein one $X^1$ is $CR^3$ (optionally in the meta position with respect to $R^{2d}$) and the other $X^1$ are $CR^{2b}$ (optionally CH); and all other groups are as defined in the Summary or in some or any embodiment provided herein, including any one of Embodiments 1-15.

Embodiment 16a. Provided is a compound of Formula (I), (Ia), (Ib), (Ic), (Ia-1), (Ib-1), (Ic-1), or (Ic-2), wherein one $X^1$ is $CR^3$ (optionally in the meta position with respect to $R^{2d}$), one $X^1$ is N, and the other $X^1$ are $CR^{2b}$; and all other groups are as defined in the Summary or in some or any embodiment provided herein, including any one of Embodiments 1-15. In some or any embodiments, one $X^1$ is $CR^3$ (optionally in the meta position with respect to $R^{2d}$), one $X^1$ is N, and the other $X^1$ are CH.

Embodiment 16b. Provided is a compound of Formula (I), (Ia), (Ib), (Ic), (Ia-1), (Ib-1), (Ic-1), or (Ic-2), wherein one $X^1$ is $CR^3$ (optionally in the meta position with respect to $R^{2d}$) and the other $X^1$ are $CR^{2b}$; and all other groups are as defined in the Summary or in some or any embodiment provided herein, including any one of Embodiments 1-15. In some or any embodiments, one $X^1$ is $CR^3$ (optionally in the meta position with respect to $R^{2d}$) and the other $X^1$ are CH.

Embodiment 17. Provided is a compound of Formula (I), (Ia), (Ib), (Ic), (Ia-1), (Ib-1), (Ic-1), or (Ic-2), wherein $R^3$ is —(CH$_2$)—Y; and all other groups are as defined in the Summary or in some or any embodiment provided herein, including any one of Embodiments 1-16b.

Embodiment 17a. Provided is a compound of Formula (I), (Ia), (Ib), (Ic), (Ia-1), (Ib-1), (Ic-1), or (Ic-2), wherein $R^3$ is —(CH$_2$)-L-Y; and all other groups are as defined in the Summary or in some or any embodiment provided herein, including any one of Embodiments 1-16b.

Embodiment 17b. Provided is a compound of Formula (Ib) or (Ib-1), wherein $R^3$ is —(CH$_2$)-L-Y; and all other groups are as defined in the Summary or in some or any embodiment provided herein, including any one of Embodiments 1-16b.

Embodiment 17c. Provided is a compound of Formula (Ib) or (Ib-1), wherein $R^3$ is —(CH$_2$)-L-Y; L is -L$^1$-L$^2$-; and all other groups are as defined in the Summary or in some or any embodiment provided herein, including any one of Embodiments 1-16b.

Embodiment 17d. Provided is a compound of Formula (Ib) or (Ib-1), wherein $R^3$ is —(CH$_2$)-L-Y; L is —CH$_2$—O— or —O—CH$_2$—; and all other groups are as defined in the Summary or in some or any embodiment provided herein, including any one of Embodiments 1-16b.

Embodiment 18. Provided is a compound of Formula (I), (Ia), (Ib), (Ic), (Ia-1), (Ib-1), (Ic-1), or (Ic-2), wherein Y is a 5-membered monocyclic heteroaryl (in some embodiments, pyrazolyl) substituted with $R^Y$ and optionally substituted with $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 6-membered monocyclic aryl substituted with $R^Y$ and optionally substituted with 1 or 2 $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 6-membered monocyclic heteroaryl substituted with $R^Y$ and optionally substituted with 1 or 2 $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 8-membered bicyclic heteroaryl substituted with $R^Y$ and optionally substituted with 1 or 2 $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 9-membered bicyclic heteroaryl substituted with $R^Y$ and optionally substituted with 1, 2, or 3 $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 10-membered bicyclic heteroaryl substituted with $R^Y$ and optionally substituted with 1, 2, or 3 $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 8- or 9-membered bicyclic heterocyclic (in some embodiments,

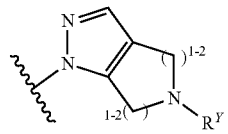

(where $R^Y$ is —C(O)$R^{3a}$ where $R^{3a}$ is selected from group a)) substituted with $R^Y$ and optionally substituted with 1 or 2 $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 8- or 9-membered bicyclic heterocyclic (in some embodiments,

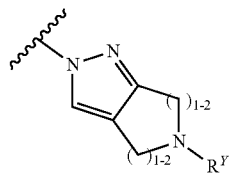

(where $R^Y$ is —C(O)$R^{3a}$ where $R^{3a}$ is selected from group a)) substituted with $R^Y$ and optionally substituted with 1 or 2 $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 8- or 9-membered bicyclic heterocyclic (in some embodiments,

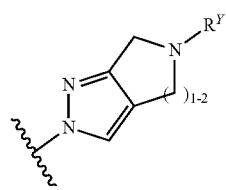

(where $R^Y$ is —C(O)$R^{3a}$ where $R^{3a}$ is selected from group a)) substituted with $R^Y$ and optionally substituted with 1 or 2 $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 4-9-membered monocyclic or bicyclic heterocycloalkyl substituted with $R^Y$ and optionally substituted with 1 or 2 $R^{2e}$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is

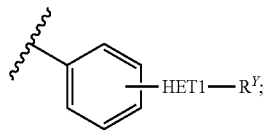

and all other groups are as defined in the Summary or in some or any embodiment provided herein, including any one of Embodiments 1-17.

Embodiment 18a. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; Y is

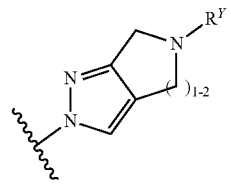

and $R^Y$ is —S(O)$_2$R$^{3a}$ or —C(O)R$^{3a}$, where R$^{3a}$ is selected from group a); or Y is 4-9-membered monocyclic or bicyclic heterocycloalkyl substituted with $R^Y$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; Y is

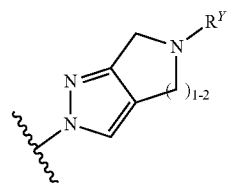

and $R^Y$ is —C(O)R$^{3a}$ where R$^{3a}$ is selected from group a); or Y is 4-9-membered monocyclic or bicyclic heterocycloalkyl substituted with $R^Y$; and all other groups are as defined in the Summary or in some or any embodiment provided herein, including any one of Embodiments 1-17.

Embodiment 18b. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; or Y is

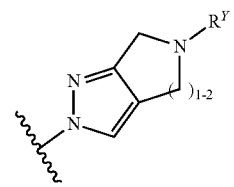

and $R^Y$ is —S(O)$_2$R$^{3a}$ or —C(O)R$^{3a}$, where R$^{3a}$ is selected from group a); and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; or Y is and $R^Y$ is —C(O)R$^{3a}$, where R$^{3a}$ is selected from group a); and all other groups are as defined in the Summary or in some or any embodiment provided herein, including any one of Embodiments 1-17.

Embodiment 18c. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; Y is

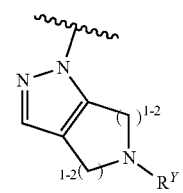

and $R^Y$ is —S(O)$_2$R$^{3a}$ or —C(O)R$^{3a}$, where R$^{3a}$ is selected from group a); or Y is 4-9-membered monocyclic or bicyclic heterocycloalkyl substituted with $R^Y$; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with R; Y is

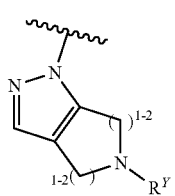

and $R^Y$ is —C(O)$R^{3a}$, where $R^{3a}$ is selected from group a); or Y is 4-9-membered monocyclic or bicyclic heterocycloalkyl substituted with $R^Y$; and all other groups are as defined in the Summary or in some or any embodiment provided herein, including any one of Embodiments 1-17.

Embodiment 18d. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; or Y is

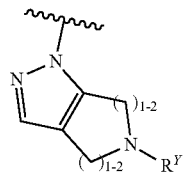

and $R^Y$ is —S(O)$_2R^{3a}$ or —C(O)$R^{3a}$, where $R^{3a}$ is selected from group a); and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; or Y is

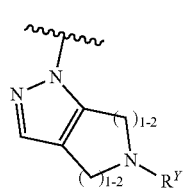

and $R^Y$ is —C(O)$R^{3a}$, where $R^{3a}$ is selected from group a); and all other groups are as defined in the Summary or in some or any embodiment provided herein, including any one of Embodiments 1-17.

Embodiment 18e. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; or Y is

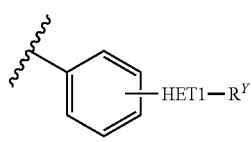

and $R^Y$ is —S(O)$_2R^{3a}$ or —C(O)$R^{3a}$, where $R^{3a}$ is selected from group a); and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; or Y is

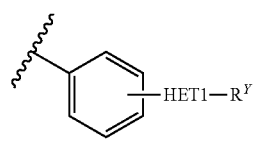

and $R^Y$ is —C(O)$R^{3a}$, where $R^{3a}$ is selected from group a); and all other groups are as defined in the Summary or in some or any embodiment provided herein, including any one of Embodiments 1-17.

Embodiment 18f. Provided is a compound of Formula (I), (Ia), (Ib), (Ic), (Ia-1), (Ib-1), (Ic-1), or (Ic-2), wherein Y is

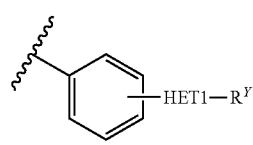

and $R^Y$ is —S(O)$_2R^{3a}$ or —C(O)$R^{3a}$, where $R^{3a}$ is selected from group a); HET1 is a 5- to 7-membered heterocycloalkyl; and all other groups are as defined in the Summary or in some or any embodiment provided herein, including any one of Embodiments 1-17. Provided is a compound of Formula (I), (Ia), (Ib), (Ic), (Ia-1), (Ib-1), (Ic-1), or (Ic-2), wherein Y is

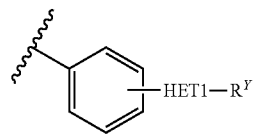

and $R^Y$ is —S(O)$_2R^{3a}$ or —C(O)$R^{3a}$, where $R^{3a}$ is selected from group a); HET1 is a 5- to 7-membered heterocycloalkyl containing 1 or 2 nitrogen atoms in the ring; and all other groups are as defined in the Summary or in some or any embodiment provided herein, including any one of Embodiments 1-17.

Embodiment 19. Provided is a compound of Formula (I), (Ia), (Ib), (Ic), (Ia-1), (Ib-1), (Ic-1), or (Ic-2), wherein $R^{3b}$ and $R^{3b1}$ are each hydrogen; and all other groups are as defined in the Summary or in some or any embodiment provided herein, including any one of Embodiments 1-18a.

Embodiment 20. Provided is a compound of Formula (I), (Ia), (Ib), (Ic), (Ia-1), (Ib-1), (Ic-1), or (Ic-2), wherein $R^Y$ is —(CH$_2$)$_{0-3}$NHC(O)$R^{3a}$, —(CH$_2$)$_{0-2}$NHS(O)$_2R^{3a}$, —C(O)$R^{3a}$, —S(O)$_2R^{3a}$, —(CH$_2$)$_{0-3}$NR$^{3b}$(C$_1$-C$_6$alkylene)NR$^{3b1}$C(O)$R^{3a}$, —(CH$_2$)$_{0-3}$NR$^{3b}$(C$_1$-C$_6$alkylene)NR$^{3b1}$S(O)$_2R^{3a}$, —(CH$_2$)$_{0-3}$NR$^{3b}$C(O)(C$_1$-C$_6$alkylene)NR$^{3b1}$C(O)$R^{3a}$, —(CH$_2$)$_{0-3}$NR$^{3b}$C(O)(C$_1$-C$_6$alkylene)NR$^{3b1}$S(O)$_2R^{3a}$, or C$_3$-C$_8$heterocycloalkyl substituted with —C(O)$R^{3a}$; where $R^{3a}$ is selected from group a); and all other groups are as defined in the Summary or in some or any embodiment provided herein, including any one of Embodiments 1-19.

Embodiment 21. Provided is a compound of Formula (I), (Ia), (Ib), (Ic), (Ia-1), (Ib-1), (Ic-1), or (Ic-2), wherein $R^{3a}$ is —$CH_2$(halo); —$(CH_2)_{1-2}CN$; —$CH_2OCH(CF_3)_2$; —$CH_2O$(trifluorophenyl); —$CH_2O$(tetrafluorophenyl); —$CH_2O$(isoxazolyl, optionally substituted with 1-3 substituents each independently selected from halo, $C_{1-6}$alkyl, $C_{2-6}$alkenyl, $C_1$-6alkoxy, cyano, $C_{3-8}$cycloalkyl or $C_{3-8}$heterocycloalkyl); —$CH_2O$(pyrimidinyl, optionally substituted with 1-3 substituents each independently selected from halo, $C_{1-6}$alkyl, $C_2$-6alkenyl, $C_{1-6}$alkoxy, cyano, $C_{3-8}$cycloalkyl or $C_{3-8}$heterocycloalkyl); —$CH_2O$(pyridyl, optionally substituted with 1-3 substituents each independently selected from halo, $C_{1-6}$alkyl, $C_{2-6}$alkenyl, $C_{1-6}$alkoxy, cyano, $C_{3-8}$cycloalkyl or $C_{3-8}$heterocycloalkyl); $C_2$-$C_6$alkenyl; $C_2$-$C_4$alkenyl substituted with cyano (in some embodiments, —C(CN)(=$CH_2$)); $C_2$-$C_4$alkenyl substituted with halo (in some embodiments, $C_2$-$C_4$alkenyl substituted with fluoro); —CH=CH—$CH_2$—$NR^{3c}R^{3d}$; —CH=CH—$CH_2$—O—$C_1$-$C_6$alkyl; trifluorophenyl; tetrafluorophenyl; $C_2$-$C_6$alkynyl; —CH≡CH—$CH_2$—$NR^{3c}R^{3d}$; or —CH≡CH—$CH_2$—O—$C_1$-$C_6$alkyl; and all other groups are as defined in the Summary or in some or any embodiment provided herein, including any one of Embodiments 1-20.

Embodiment 21a. Provided is a compound of Formula (Ib) or (Ib-1), wherein $R^{3a}$ is $C_1$-$C_6$alkyl substituted with 1 or 2 halo which are independently selected; $C_1$-$C_6$alkyl substituted with cyano; $C_2$-$C_6$alkenyl substituted with cyano (in some embodiments, —C(CN)(=$CH_2$)); $C_2$-$C_6$alkenyl substituted with halo (in some embodiments, $C_2$-$C_4$alkenyl substituted with fluoro); —CH=CH—$CH_2$—$NR^{3c}R^{3d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH≡CH—$CH_2$—$NR^{3c}R^{3d}$; CH≡CH—$CH_2$—OH; —CH≡CH—$CH_2$—O—$C_1$-$C_6$alkyl; spirocycloalkyl substituted with cyano; pentafluorophenyl; tetraflurophenyl; trifluorophenyl; difluorophenyl; or monofluorophenyl; and all other groups are as defined in the Summary or in some or any embodiment provided herein, including any one of Embodiments 1-20.

Embodiment 22. Provided is a compound of Formula (I), (Ia), (Ib), (Ic), (Ia-1), (Ib-1), (Ic-1), or (Ic-2), wherein $R^Y$ is

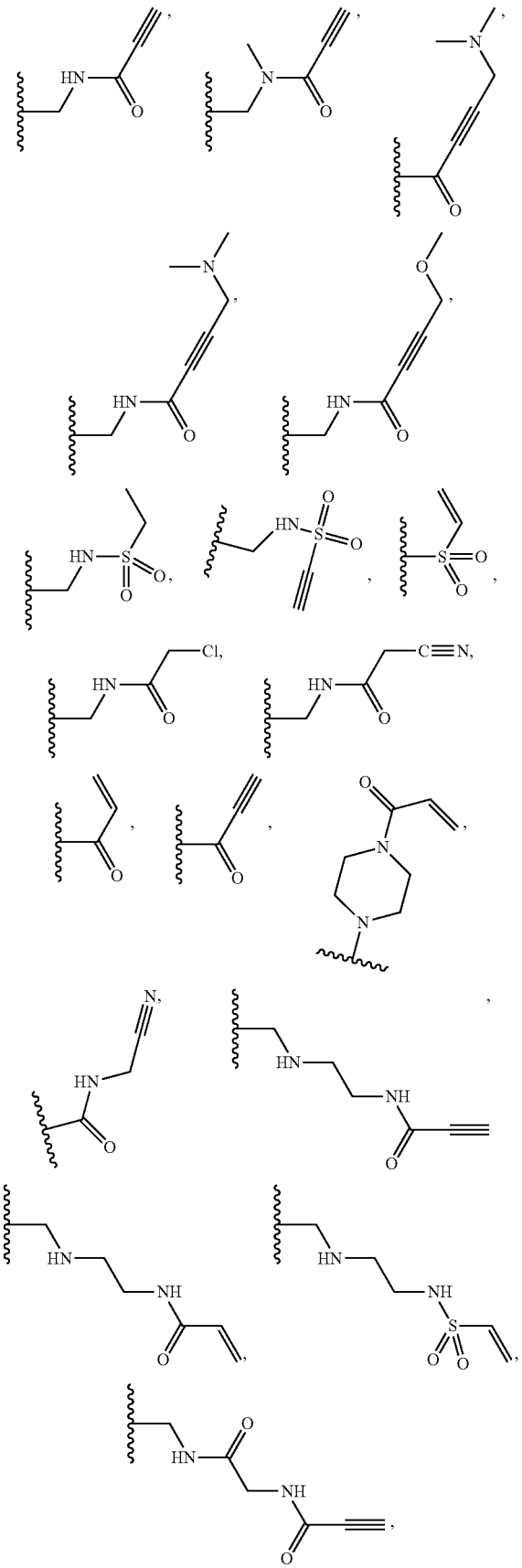

-continued
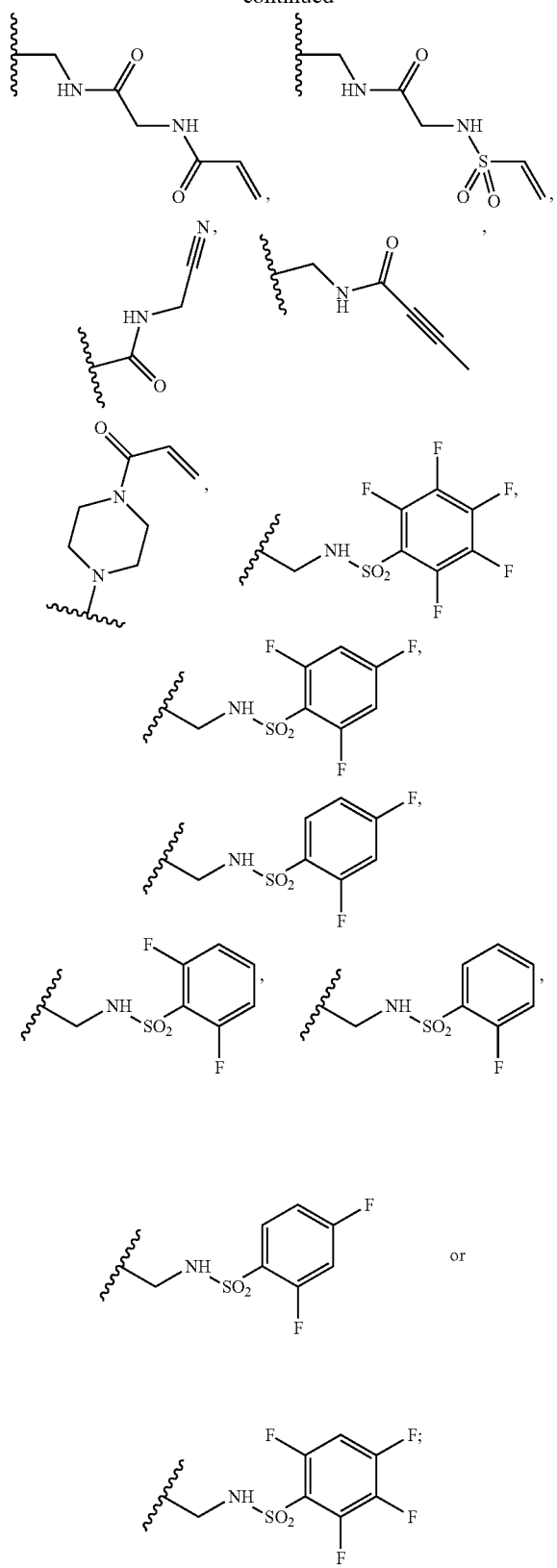
and all other groups are as defined in the Summary or in some or any embodiment provided herein, including any one of Embodiments 1-19.
Embodiment 22a. Provided is a compound of Formula (I), (Ia), (Ib), (Ic), (Ia-1), (Ib-1), (Ic-1), or (Ic-2), wherein $R^Y$ is
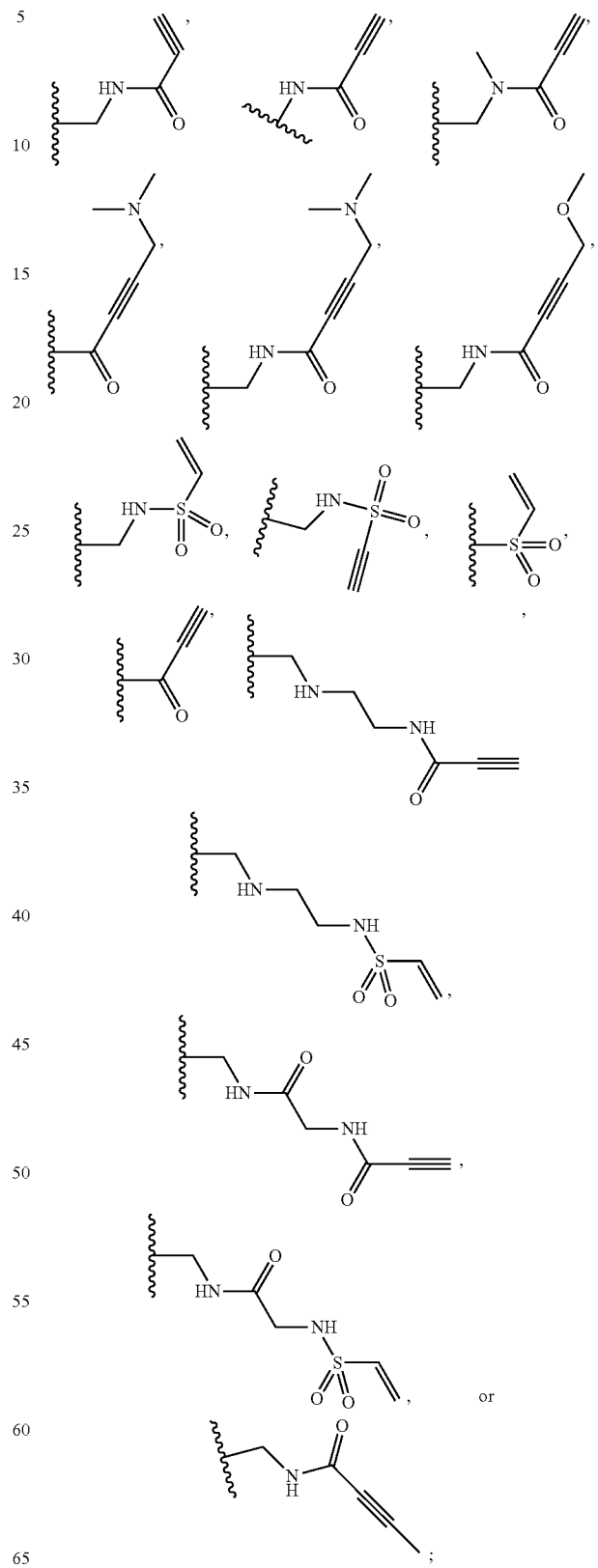

and all other groups are as defined in the Summary or in some or any embodiment provided herein, including any one of Embodiments 1-19.

Embodiment 23. Provided is a compound of Formula (I), (Ia), (Ib), (Ic), (Ia-1), (Ib-1), (Ic-1), or (Ic-2), wherein one $R^{2b}$ is fluoro, $C_1$-$C_3$alkyl, —(CH$_2$)$_{0-2}$OH, cyclopropyl, —CHF$_2$, —CF$_3$, $C_1$-$C_4$alkoxy, —OCHF$_2$, or —OCF$_3$ and the other are hydrogen; and all other groups are as defined in the Summary or in some or any embodiment provided herein, including any one of Embodiments 1-22. Provided is a compound of Formula (I), (Ia), (Ib), (Ic), (Ia-1), (Ib-1), (Ic-1), or (Ic-2), wherein each $R^{2e}$ is hydrogen or —OH; and all other groups are as defined in the Summary or in some or any embodiment provided herein, including any one of Embodiments 1-22.

Embodiment 24. Provided is a compound of Formula (I) according to Formula (Id):

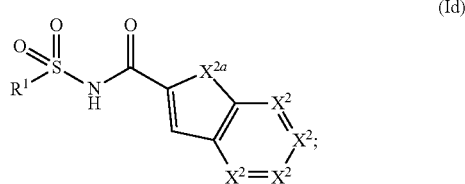

(Id)

where $R^1$, $X^{2a}$, $X^2$, and all other groups are as defined in the Summary or in some or any embodiment provided herein, including any one of Embodiments 1-10; or a pharmaceutically acceptable salt or salts thereof; and/or a stereoisomer or mixture of stereoisomers thereof. In some or any embodiments, provided is a compound of Formula (I) according to Formula (Id-1):

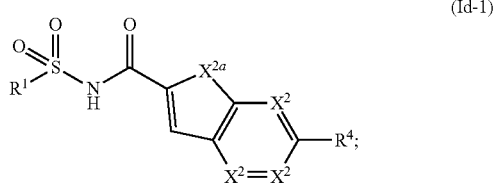

(Id-1)

where $R^1$, $X^{2a}$, $R^4$, and $X^2$ and other groups are as defined in the Summary or in some or any embodiment provided herein, including any one of Embodiments 1-10; or a pharmaceutically acceptable salt or salts thereof, and/or a stereoisomer or mixture of stereoisomers thereof.

Embodiment 25. Provided is a compound of Formula (I), (Id), or (Id-1), wherein each $R^{2b}$ is hydrogen; and all other groups are as defined in the Summary or in some or any embodiment provided herein, including any one of Embodiments 1-10 and 24. Provided is a compound of Formula (I), (Id), or (Id-1), wherein one $R^{2b}$ is halo, $C_1$-$C_3$alkyl, —(CH$_2$)$_{0-2}$OH, cyclopropyl, cyano, —CHF$_2$, —CF$_3$, $C_1$-$C_4$alkoxy, —OCHF$_2$, —OCF$_3$, or $C_3$-$C_8$cycloalkyloxy and the other $R^{2b}$ are each hydrogen and all other groups are as defined in the Summary or in some or any embodiment provided herein, including any one of Embodiments 1-9 and 24.

Embodiment 26: In some or any embodiments, one $X^1$ is $CR^3$ (optionally in the meta position with respect to $R^{2d}$), one $X^1$ is N, and the other $X^1$ are $CR^{2b}$; or wherein one $X^1$ is $CR^3$ (optionally in the meta position with respect to $R^{2d}$) and the other $X^1$ are $CR^{2b}$(optionally CH) and all other groups are as defined in the Summary or in some or any embodiment provided herein, including any one of Embodiments 1-10, 24, and 25. In some or any embodiments, one $X^1$ is $CR^3$ (optionally in the meta position with respect to $R^{2d}$), one $X^1$ is N, and the other $X^1$ are $CR^{2b}$ and all other groups are as defined in the Summary or in some or any embodiment provided herein, including any one of Embodiments 1-10, 24, and 25. In some or any embodiments, one $X^1$ is $CR^3$ (optionally in the meta position with respect to $R^{2d}$), one $X^1$ is $CR^3$ (optionally in the meta position with respect to $R^{2d}$) and the other $X^1$ are $CR^{2b}$ (optionally CH) and all other groups are as defined in the Summary or in some or any embodiment provided herein, including any one of Embodiments 1-10, 24, and 25.

Embodiment 26. Provided is a compound of Formula (I), (Id), or (Id-1), wherein one $X^2$ is $CR^4$ and the other $X^2$ are $CR^{2b}$; and all other groups are as defined in the Summary or in some or any embodiment provided herein, including any one of Embodiments 1-10, 24, and 25. In some or any embodiments, one $X^2$ is $CR^4$ and the other $X^2$ are CH.

Embodiment 27. Provided is a compound of Formula (I), (Id), or (Id-1), wherein $X^{2a}$ is O; and all other groups are as defined in the Summary or in some or any embodiment provided herein, including any one of Embodiments 1-10, and 24-26. Provided is a compound of Formula (I), (Id), or (Id-1), wherein $X^{2a}$ is S; and all other groups are as defined in the Summary or in some or any embodiment provided herein, including any one of Embodiments 1-10, and 24-26.

Embodiment 28. Provided is a compound of Formula (I), (Id), or (Id-1), wherein $R^{4b}$ and $R^{4b1}$ are each hydrogen; and all other groups are as defined in the Summary or in some or any embodiment provided herein, including any one of Embodiments 1-10, and 24-27.

Embodiment 29. Provided is a compound of Formula (I), (Id), or (Id-1), wherein $R^4$ is —(CH$_2$)$_{0-3}$NR$^{4b}$C(O)R$^{4a}$, —(CH$_2$)$_{0-2}$NR$^{4b}$S(O)$_2$R$^{4a}$, —C(O)R$^{4a}$, —C(O)NR$^{4b}$R$^{4a}$, —NR$^{4b}$(C$_1$-C$_6$alkylene)NR$^{4b1}$C(O)R$^{4a}$, —(CH$_2$)$_{0-3}$NR$^{4b}$C(O)(C$_1$-C$_6$alkylene)NR$^{4b1}$C(O)R$^{4a}$, —C(O)NR$^{4b}$(C$_1$-C$_6$alkylene)NR$^{4b1}$C(O)R$^{4a}$, —C(O)—HET1-C(O)R$^{4a}$, —C(O)—HET1-NR$^{4b}$C(O)R$^{4a}$, —(CH$_2$)$_{0-3}$NR$^{4b}$C(O)-HET1-C(O)R$^{4a}$, C$_3$-C$_8$heterocycloalkyl substituted with —C(O)R$^{4a}$ (preferably where the C$_3$-C$_8$heterocycloalkyl is attached to ring (d) through a carbon in the C$_3$-C$_8$heterocycloalkyl ring); or —(CH$_2$)$_{0-2}$HET2-C(O)R$^{4a}$; where R$^{4a}$ is selected from group a); and all other groups are as defined in the Summary or in some or any embodiment provided herein, including any one of Embodiments 1-10, and 24-28.

Embodiment 29a. Provided is a compound of Formula (I), (Id), or (Id-1), wherein $R^4$ is
 —(CH$_2$)$_{0-2}$NHC(O)R$^{4a}$;
 —NH(C$_2$-C$_4$-alkylene)NHC(O)R$^{4a}$;
 C$_3$-C$_8$heterocycloalkyl substituted with —C(O)R$^{4a}$ on a nitrogen ring atom in the C$_3$-C$_8$heterocycloalkyl (preferably where the C$_3$-C$_8$heterocycloalkyl is attached to ring (d) through a carbon in the C$_3$-C$_8$heterocycloalkyl ring);
 —C(O)—HET1-C(O)R$^{4a}$ where —C(O)R$^{4a}$ is attached to a nitrogen ring atom in HET1;
 —C(O)—HET1-NHC(O)R$^{4a}$ where —C(O)— is attached to a nitrogen ring atom in HET1;
 —C(O)NH(C$_1$-C$_6$alkylene)NHC(O)R$^{4a}$;
 —(CH$_2$)$_{0-2}$HET2-C(O)R$^{4a}$ where HET2 is a 5-membered monocyclic heteroaryl or is a 8- or 9-membered bicyclic heterocyclic and where the —C(O)R$^{4a}$ is to attached to HET2 through a nitrogen ring atom in HET2;
—(CH$_2$)$_{0-3}$NHC(O)(C$_1$-C$_6$alkylene)NHC(O)R$^{4a}$; or
—(CH$_2$)$_{0-3}$NHC(O)-HET1-C(O)R$^{4a}$;
where R$^{4a}$ is selected from group a); and all other groups are as defined in the Summary or in some or any embodiment provided herein, including any one of Embodiments 1-10, and 24-28.

Embodiment 30. Provided is a compound of Formula (I), (Id), or (Id-1), wherein R$^{4a}$ is —CH$_2$(halo); —(CH$_2$)$_{1-2}$CN; C$_2$-C$_6$alkenyl; C$_2$-C$_4$alkenyl substituted with cyano; C$_2$-C$_4$alkenyl substituted with halo; —CH═CH—CH$_2$—NR$^{4c}$R$^{4d}$; —CH═CH—CH$_2$—O—C$_1$-C$_6$alkyl; C$_2$-C$_6$alkynyl; —CH≡CH—CH$_2$—NR$^{4c}$R$^{4d}$; or —CH≡CH—CH$_2$—O—C$_1$-C$_6$alkyl; and all other groups are as defined in the Summary or in some or any embodiment provided herein, including any one of Embodiments 1-10, and 24-29a.

Embodiment 30a. Provided is a compound of Formula (I), (Id), or (Id-1), wherein R$^{4a}$ is C$_1$-C$_6$alkyl substituted with 1 or 2 halo which are independently selected; C$_1$-C$_6$alkyl substituted with cyano; C$_2$-C$_6$alkenyl substituted with cyano (in some embodiments, —C(CN)(═CH$_2$)); C$_2$-C$_6$alkenyl substituted with halo (in some embodiments, C$_2$-C$_4$alkenyl substituted with fluoro); —CH═CH—CH$_2$—NR$^{4c}$R$^{4d}$; —CH═CH—CH$_2$—O—C$_1$-C$_6$alkyl; C$_3$-C$_8$cycloalkenyl; —C(O)—C$_3$-C$_8$cycloalkyl; C$_2$-C$_6$alkynyl; —CH≡CH—CH$_2$—NR$^{4c}$R$^{4d}$; CH—CH—CH$_2$—OH; —CH≡CH—CH$_2$—O—C$_1$-C$_6$alkyl; spirocycloalkyl substituted with cyano; pentafluorophenyl; tetraflurophenyl; trifluorophenyl; difluorophenyl; or monofluorophenyl; and all other groups are as defined in the Summary or in some or any embodiment provided herein, including any one of Embodiments 1-10, and 24-29a.

Embodiment 31. Provided is a compound of Formula (I), (Id), or (Id-1), wherein HET1-C(O)R$^{4a}$ is

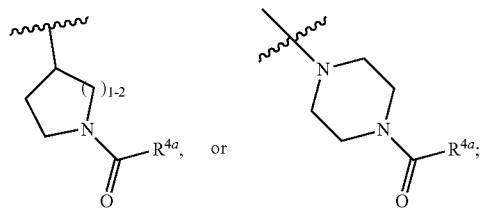

HET1-NHC(O)R$^{4a}$ is H R$^{4a}$;

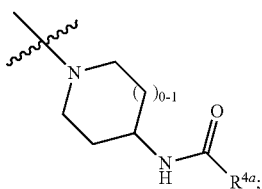

and HET2-C(O)R$^{4a}$ is

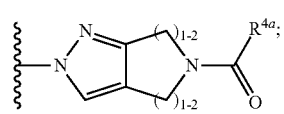

where R$^{4a}$ is selected from group a); and all other groups are as defined in the Summary or in some or any embodiment provided herein, including any one of Embodiments 1-10, and 24-30.

Embodiment 32. Provided is a compound of Formula (I), (Id), or (Id-1), wherein R$^4$ is

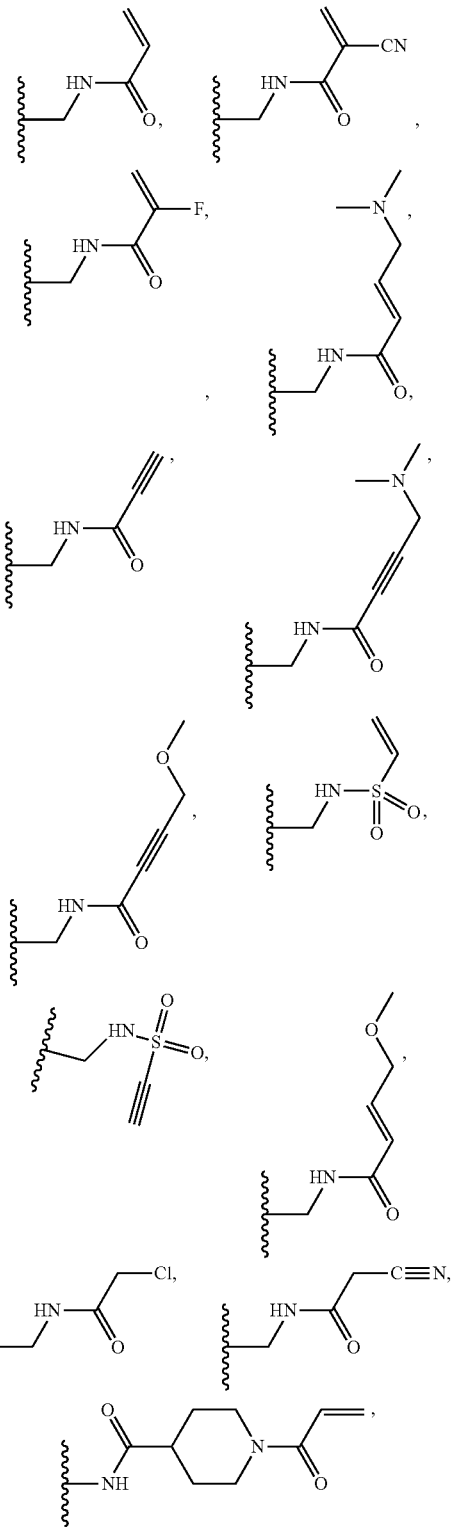

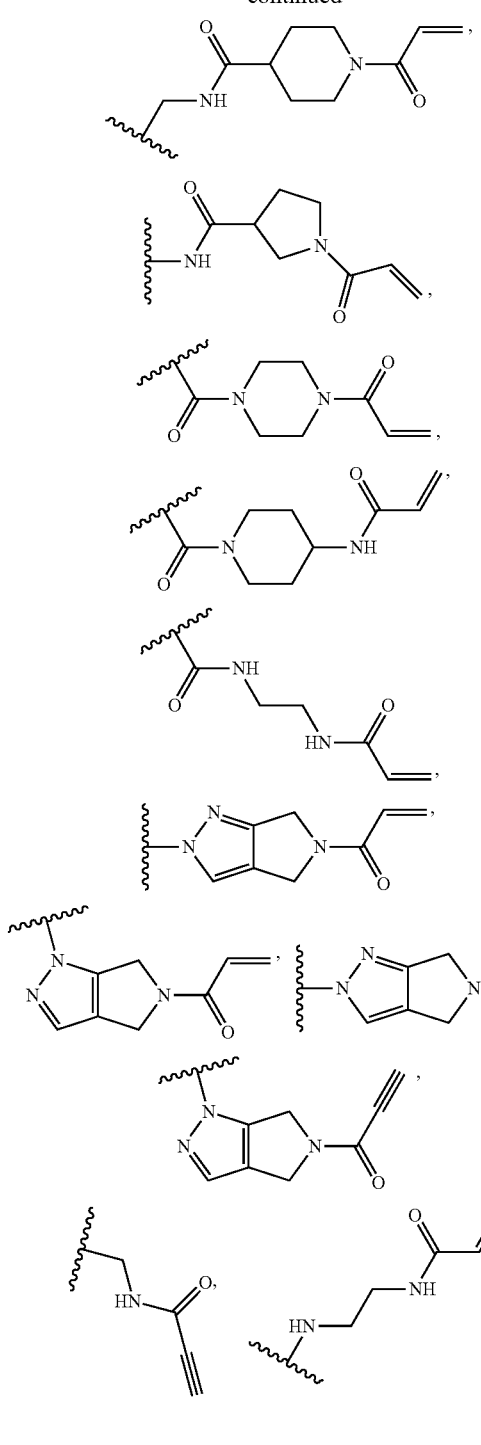
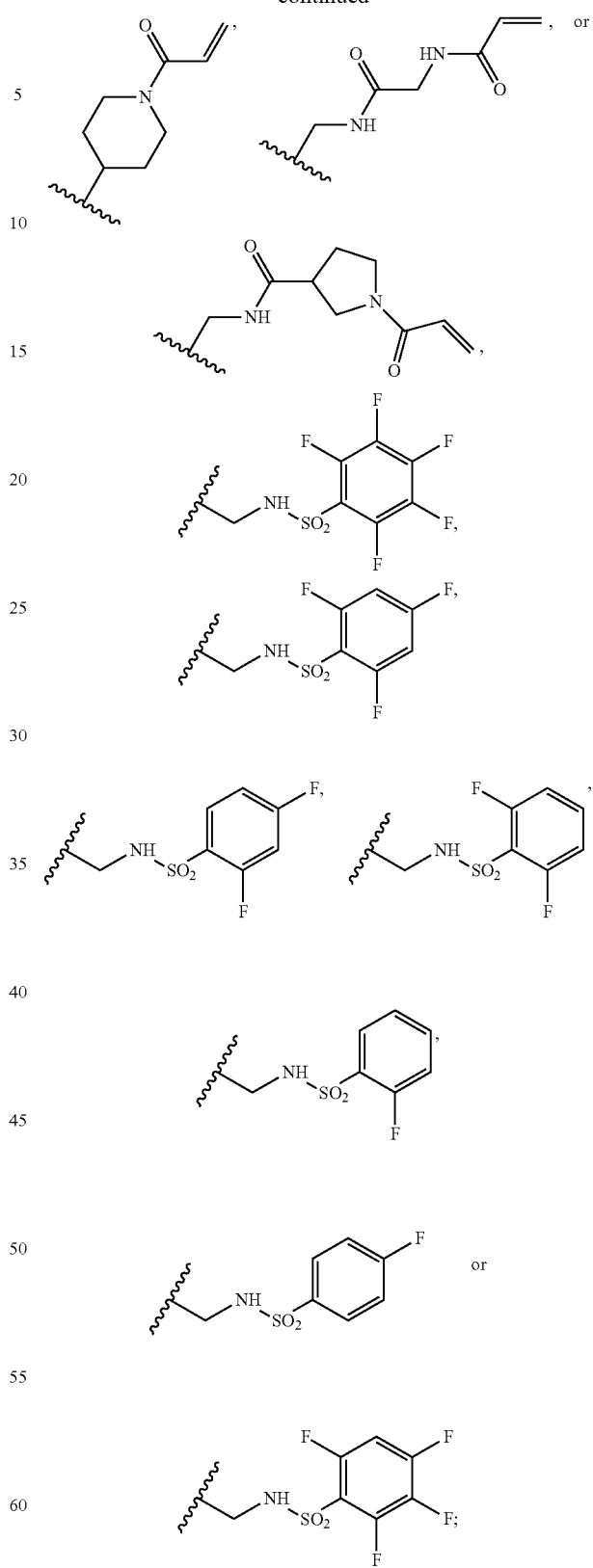
and all other groups are as defined in the Summary or in some or any embodiment provided herein, including any one of Embodiments 1-10, and 24-28.

Embodiment 32a. Provided is a compound of Formula (I), (Id), or (Id-1), wherein $R^4$ is

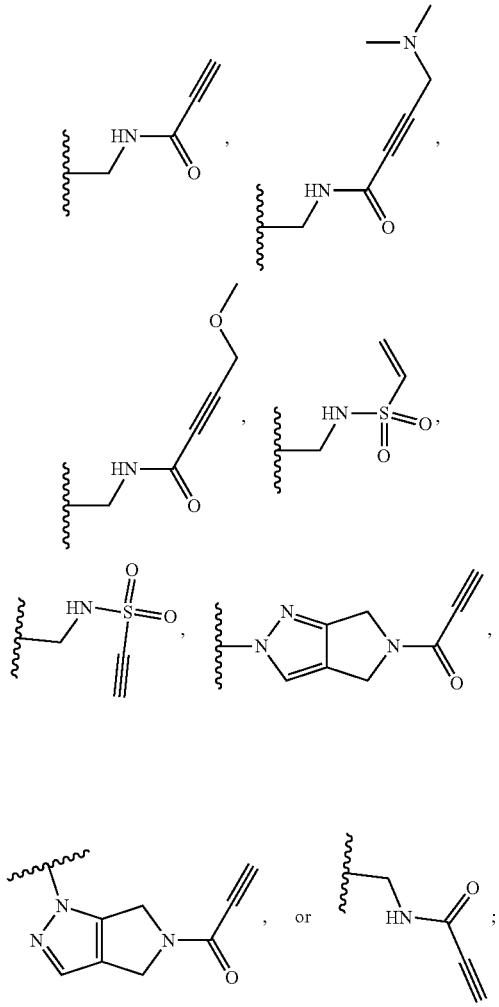

and all other groups are as defined in the Summary or in some or any embodiment provided herein, including any one of Embodiments 1-10, and 24-28.

Embodiment 33. Provided is a compound of Formula (I) according to Formula (Ie):

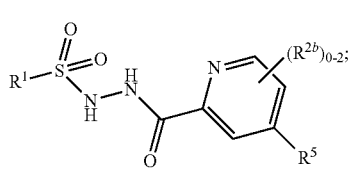

(Ie)

where $R^1$, $R^{2b}$, $R^5$, and all other groups are as defined in the Summary or in some or any embodiment provided herein, including any one of Embodiments 1-10; or a pharmaceutically acceptable salt or salts thereof; and/or a stereoisomer or mixture of stereoisomers thereof. In some or any embodiments, provided is a compound of Formula (I) according to Formula (Ie-1):

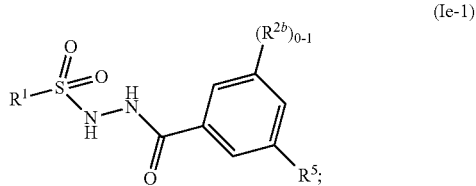

(Ie-1)

where $R^1$, $R^{2b}$, $R^5$, and other groups are as defined in the Summary or in some or any embodiment provided herein, including any one of Embodiments 1-10; or a pharmaceutically acceptable salt or salts thereof, and/or a stereoisomer or mixture of stereoisomers thereof.

Embodiment 34. Provided is a compound of Formula (I) according to Formula (If):

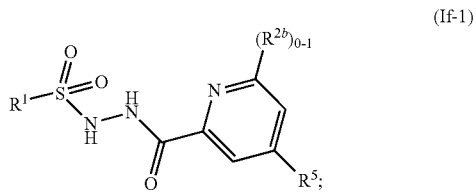

(If)

where $R^1$, $R^{2b}$, $R^5$, and all other groups are as defined in the Summary or in some or any embodiment provided herein, including any one of Embodiments 1-10; or a pharmaceutically acceptable salt or salts thereof; and/or a stereoisomer or mixture of stereoisomers thereof. In some or any embodiments, provided is a compound of Formula (I) according to Formula (If-1):

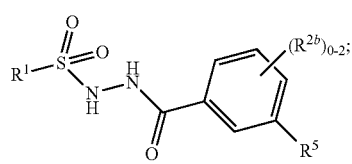

(If-1)

where $R^1$, $R^{2b}$, $R^5$, and all other groups are as defined in the Summary or in some or any embodiment provided herein, including any one of Embodiments 1-10; or a pharmaceutically acceptable salt or salts thereof, and/or a stereoisomer or mixture of stereoisomers thereof.

Embodiment 35. Provided is a compound of Formula (I), (Ie), (If), (Ie-1), or (If-1), wherein each $R^{2b}$ is independently hydrogen or $C_1$-$C_3$alkyl; and all other groups are as defined in the Summary or in some or any embodiment provided herein, including any one of Embodiments 1-10 and 34. In some or any embodiments, each $R^{2b}$ is independently hydrogen or methyl.

Embodiment 36. Provided is a compound of Formula (I), (Ie), (If), (Ie-1), or (If-1), wherein $R^5$ is pyridinyl, pyrazolyl, or imidazolyl; each of which is substituted with Z and optionally substituted with $R^{2e}$; and all other groups are as defined in the Summary or in some or any embodiment provided herein, including any one of Embodiments 1-10, 34, and 35.

Embodiment 36a. Provided is a compound of Formula (I), (Ie), (If), (Ie-1), or (If-1), wherein $R^5$ is —C(O)N($R^{5b}$)Z where $R^{5b}$ is selected from group b); and all other groups are as defined in the Summary or in some or any embodiment provided herein, including any one of Embodiments 1-10, 34, and 35. In a subembodiment of Embodiment 36a, provided is a compound of Formula (I), (Ie), (If), (Ie-1), or (If-1), wherein $R^5$ is —C(O)NHZ; and all other groups are as defined in the Summary or in some or any embodiment provided herein, including any one of Embodiments 1-10, 34, and 35.

Embodiment 36b. Provided is a compound of Formula (I), (Ie), (If), (Ie-1), or (If-1), wherein $R^5$ is heterocycloalkyl (in some embodiments, pyrrolidinyl) substituted with Z and optionally substituted with $R^{2e}$; and all other groups are as defined in the Summary or in some or any embodiment provided herein, including any one of Embodiments 1-10, 34, and 35.

Embodiment 36c. Provided is a compound of Formula (I), (Ie), (If), (Ie-1), or (If-1), wherein $R^5$ is —$(CH_2)_{0-20}$-HET1-Z; and all other groups are as defined in the Summary or in some or any embodiment provided herein, including any one of Embodiments 1-10, 34, and 35.

Embodiment 36d. Provided is a compound of Formula (I), (Ie), (If), (Ie-1), or (If-1), wherein $R^5$ is —$(CH_2)_{0-2}$O—Z; and all other groups are as defined in the Summary or in some or any embodiment provided herein, including any one of Embodiments 1-10, 34, and 35.

Embodiment 37. Provided is a compound of Formula (I), (Ie), (If), (Ie-1), or (If-1), wherein $R^{5a}$ is —$CH_2$(halo); —$(CH_2)_{1-2}$CN; $C_2$-$C_6$alkenyl; $C_2$-$C_4$alkenyl substituted with cyano; $C_2$-$C_4$alkenyl substituted with halo; —CH=CH—$CH_2$—$NR^{5c}R^{5d}$; —CH=CH—$CH_2$—O—$C_1$-$C_6$alkyl; $C_2$-$C_6$alkynyl; —CH≡CH—$CH_2$—$NR^{5c}R^{5d}$; CH≡CH—$CH_2$—OH; —CH≡CH—$CH_2$—O—$C_1$-$C_6$alkyl; spirocycloalkyl substituted with cyano; pentafluorophenyl; tetraflurophenyl; trifluorophenyl; difluorophenyl; or monofluorophenyl; and all other groups are as defined in the Summary or in some or any embodiment provided herein, including any one of Embodiments 1-10 and 34-36.

Embodiment 38. Provided is a compound of Formula (I), (Ie), (If), (Ie-1), or (If-1), wherein each $R^{5b}$ and $R^{5b1}$ are each hydrogen; and all other groups are as defined in the Summary or in some or any embodiment provided herein, including any one of Embodiments 1-10, and 34-37.

Embodiment 39. Provided is a compound of Formula (I), (Ie), (If), (Ie-1), or (If-1), wherein Z is —$(CH_2)_{0-3}$NHC(O)$R^{5a}$, —$(CH_2)_{0-2}$NHS(O)$_2R^{5a}$, —C(O)$R^{5a}$, —S(O)$_2R^{5a}$, —$(CH_2)_{0-3}$—C(O)NH$R^{5a}$, —$(CH_2)_{0-3}$NH($C_1$-$C_6$alkylene)NHC(O)$R^{5a}$, $C_3$-$C_8$heterocycloalkyl substituted with —NHC(O)$R^{5a}$, $C_3$-$C_8$heterocycloalkyl substituted with —S(O)$_2R^{5a}$, or $C_3$-$C_8$heterocycloalkyl substituted with —C(O)$R^{5a}$; where $R^{5a}$ is selected from group a); and all other groups are as defined in the Summary or in some or any embodiment provided herein, including any one of Embodiments 1-10 and 34-38.

Embodiment 40. Provided is a compound of Formula (I), (Ie), (If), (Ie-1), or (If-1), wherein Z is

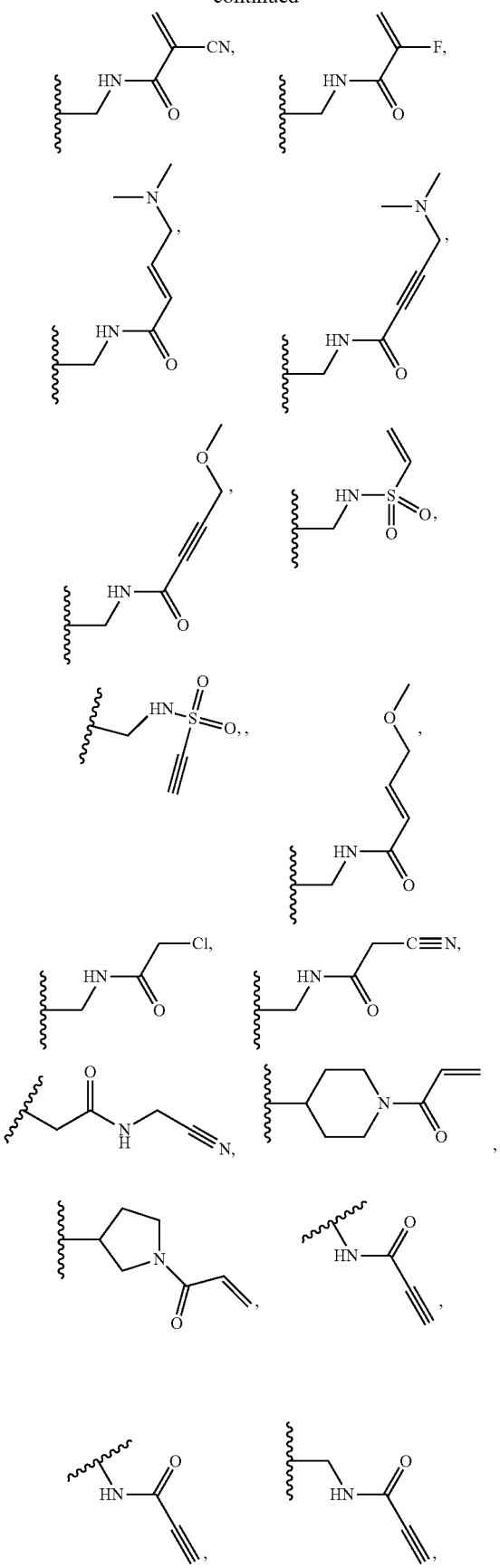

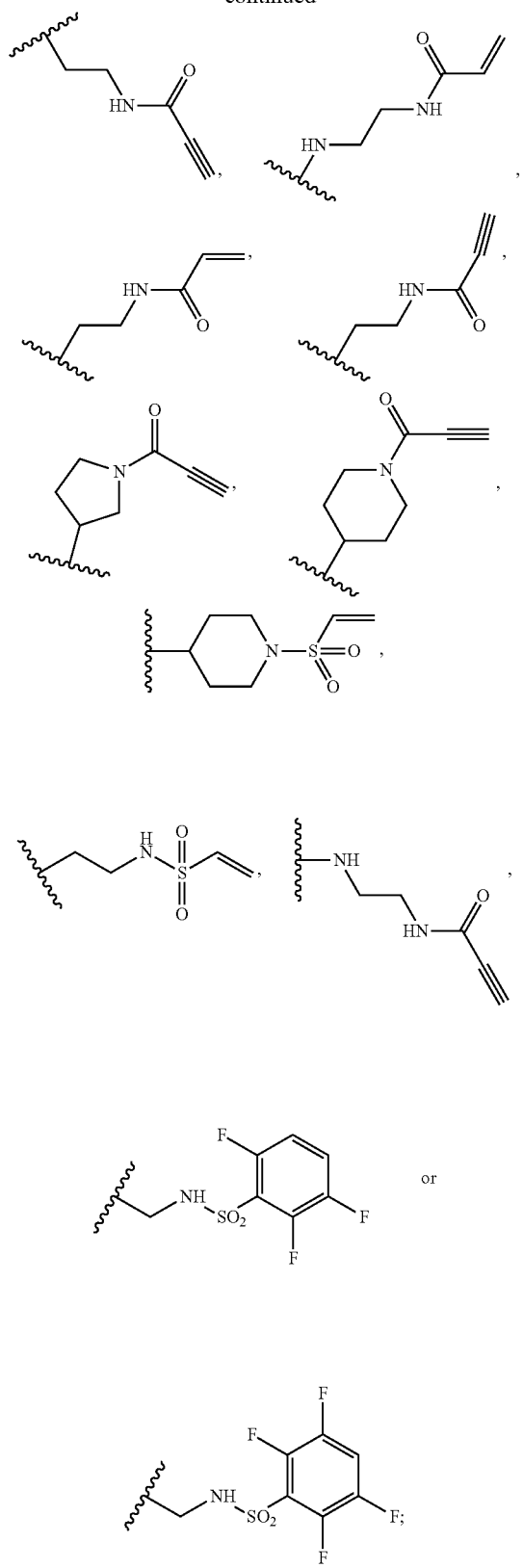
Embodiment 40. Provided is a compound of Formula (I), (Ie), (If), (Ie-1), or (If-1), wherein Z is
and all other groups are as defined in the Summary or in some or any embodiment provided herein, including any one of Embodiments 1-10, and 34-36.

Embodiment 41. Provided is a compound of Formula (I) according to Formula (Ig):

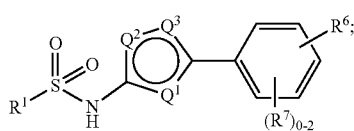

where $R^1$, $Q^1$, $Q^2$, $Q^3$, $R^6$, $R^7$, and all other groups are as defined in the Summary or in some or any embodiment provided herein, including any one of Embodiments 1-10; or a pharmaceutically acceptable salt or salts thereof; and/or a stereoisomer or mixture of stereoisomers thereof. In some or any embodiments, provided is a compound of Formula (I) according to Formula (Ig-1):

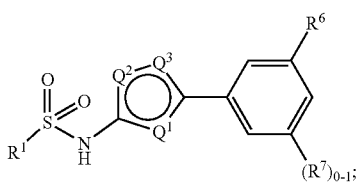

where $R^1$, $Q^1$, $Q^2$, $Q^3$, $R^6$, $R^7$, and all other groups are as defined in the Summary or in some or any embodiment provided herein, including any one of Embodiments 1-10; or a pharmaceutically acceptable salt or salts thereof; and/or a stereoisomer or mixture of stereoisomers thereof.

Embodiment 42. Provided is a compound of Formula (I), (Ig), or (Ig-1), wherein $Q^1$ is $CR^{Q1}$, $Q^2$ is O, and $Q^3$ is N; and all other groups are as defined in the Summary or in some or any embodiment provided herein, including any one of Embodiments 1-10 and 41. Provided is a compound of Formula (I), (Ig), or (Ig-1), wherein $Q^1$ is S, $Q^2$ is N, and $Q^3$ is N; and all other groups are as defined in the Summary or in some or any embodiment provided herein, including any one of Embodiments 1-10 and 41. Provided is a compound of Formula (I), (Ig), or (Ig-1), wherein $Q^1$ is N, $Q^2$ is N, and $Q^3$ is O; and all other groups are as defined in the Summary or in some or any embodiment provided herein, including any one of Embodiments 1-10 and 41. Provided is a compound of Formula (I), (Ig), or (Ig-1), wherein $Q^1$ is O, $Q^2$ is N, and $Q^3$ is N; and all other groups are as defined in the Summary or in some or any embodiment provided herein, including any one of Embodiments 1-10 and 41. Provided is a compound of Formula (I), (Ig), or (Ig-1), wherein $Q^1$ is $CR^{Q1}$ (optionally wherein $R^{Q1}$ is hydrogen), $Q^2$ is N, and $Q^3$ is O; and all other groups are as defined in the Summary or in some or any embodiment provided herein, including any one of Embodiments 1-10 and 41. In some or any embodiments, $R^{Q1}$ is hydrogen, $C(O)CH_3$, or Cl. In some or any embodiments, $R^{Q1}$ is hydrogen.

Embodiment 43. Provided is a compound of Formula (I), (Ig), or (Ig-1), wherein $R^6$ is a pyrazolyl substituted with Q and optionally substituted with $R^{2e}$; or $R^6$ is $-(CH_2)_{0-3}NHC(O)R^{6a}$; where $R^{6a}$ is selected from group a); and all other groups are as defined in the Summary or in some or any embodiment provided herein, including any one of Embodiments 1-10 and 42.

Embodiment 44. Provided is a compound of Formula (I), (Ig), or (Ig-1), wherein $R^{6a}$ is $-CH_2(halo)$; $-(CH_2)_{1-2}CN$; $C_2$-$C_6$alkenyl; $C_2$-$C_4$alkenyl substituted with cyano; $C_2$-$C_4$alkenyl substituted with halo; $-CH=CH-CH_2-NR^{3c}R^{3d}$; $-CH=CH-CH_2-O-C_1$-$C_6$alkyl; tetrafluorophenyl; trifluorophenyl; $C_2$-$C_6$alkynyl; $-CH\equiv CH-CH_2-NR^{3c}R^{3d}$; or $-CH\equiv CH-CH_2-O-C_1$-$C_6$alkyl; and all other groups are as defined in the Summary or in some or any embodiment provided herein, including any one of Embodiments 1-10 and 43.

Embodiment 44a. Provided is a compound of Formula (I), (Ig), or (Ig-1), wherein $R^{6a}$ is $C_1$-$C_6$alkyl substituted with 1 or 2 halo which are independently selected; $C_1$-$C_6$alkyl substituted with cyano; $C_2$-$C_6$alkenyl substituted with cyano (in some embodiments, $-C(CN)(=CH_2)$); $C_2$-$C_6$alkenyl substituted with halo (in some embodiments, $C_2$-$C_4$alkenyl substituted with fluoro); $-CH=CH-CH_2-NR^{6c}R^{6d}$; $-CH=CH-CH_2-O-C_1$-$C_6$alkyl; $C_3$-$C_8$cycloalkenyl; $-C(O)-C_3$-$C_8$cycloalkyl; tetrafluorophenyl; trifluorophenyl; $C_2$-$C_6$alkynyl; $-CH\equiv CH-CH_2-NR^{6c}R^{6d}$; $CH\equiv CH-CH_2-OH$; $-CH\equiv CH-CH_2-O-C_1$-$C_6$alkyl; spirocycloalkyl substituted with cyano; and all other groups are as defined in the Summary or in some or any embodiment provided herein, including any one of Embodiments 1-10 and 43.

Embodiment 45. Provided is a compound of Formula (I), (Ig), or (Ig-1), wherein $R^{6b}$ is hydrogen; and all other groups are as defined in the Summary or in some or any embodiment provided herein, including any one of Embodiments 1-10 and 42.

Embodiment 46. Provided is a compound of Formula (I), (Ig), or (Ig-1), wherein one $R^7$ is $C_1$-$C_6$alkyl, $C_1$-$C_6$alkoxy, or $C_3$-$C_8$cycloalkyl; and all other groups are as defined in the Summary or in some or any embodiment provided herein, including any one of Embodiments 1-10 and 45.

Embodiment 47. Provided is a compound of Formula (I), (Ia), (Ib), (Ic), (Id), (Ie), (If), (Ig), (Ia-1), (Ib-1), (Ic-1), (Ic-2), (Id-1), (Ie-1), (If-1), or (Ig-1), wherein $R^{3c}$, $R^{3d}$, $R^{4a}$, $R^{4d}$, $R^{5c}$, $R^{5d}$, $R^{6c}$, and $R^{6d}$ are each independently hydrogen or $C_1$-$C_3$alkyl; or where each pair of $R^{3c}$ and $R^{3d}$, $R^{4c}$ and $R^{4d}$, $R^{5c}$ and $R^{5d}$, and $R^{6c}$ and $R^{6d}$, together with the nitrogen to which they are attached, form a pyrrolidinyl or piperidinyl; and all other groups are as defined in the Summary or in some or any embodiment provided herein, including any one of preceding embodiments.

Embodiment 47a. Provided is a compound of Formula (I), (Ia), (Ib), (Ic), (Id), (Ie), (If), (Ig), (Ia-1), (Ib-1), (Ic-1), (Ic-2), (Id-1), (Ie-1), (If-1), or (Ig-1), wherein $R^{3a}$, $R^{4a}$, $R^{5a}$, and $R^a$ are $-CH_2(halo)$; $-(CH_2)_{1-2}CN$; $C_2$-$C_6$alkenyl; $C_2$-$C_4$alkenyl substituted with cyano; $C_2$-$C_4$alkenyl substituted with halo; $-CH=CH-CH_2-NR^{3c}R^{3d}$; $-CH=CH-CH_2-O-C_1$-$C_6$alkyl; tetrafluorophenyl; trifluorophenyl; $C_2$-$C_6$alkynyl; $-CH\equiv CH-CH_2-NR^{3c}R^{3d}$; or $-CH\equiv CH-CH_2-O-C_1$-$C_6$alkyl; and all other groups are as defined in the Summary or in some or any embodiment provided herein, including any one of preceding embodiments.

Embodiment 47b. Provided is a compound of Formula (I), (Ia), (Ib), (Ic), (Id), (Ie), (If), (Ig), (Ia-1), (Ib-1), (Ic-1), (Ic-2), (Id-1), (Ie-1), (If-1), or (Ig-1), wherein
$R^Y$ is
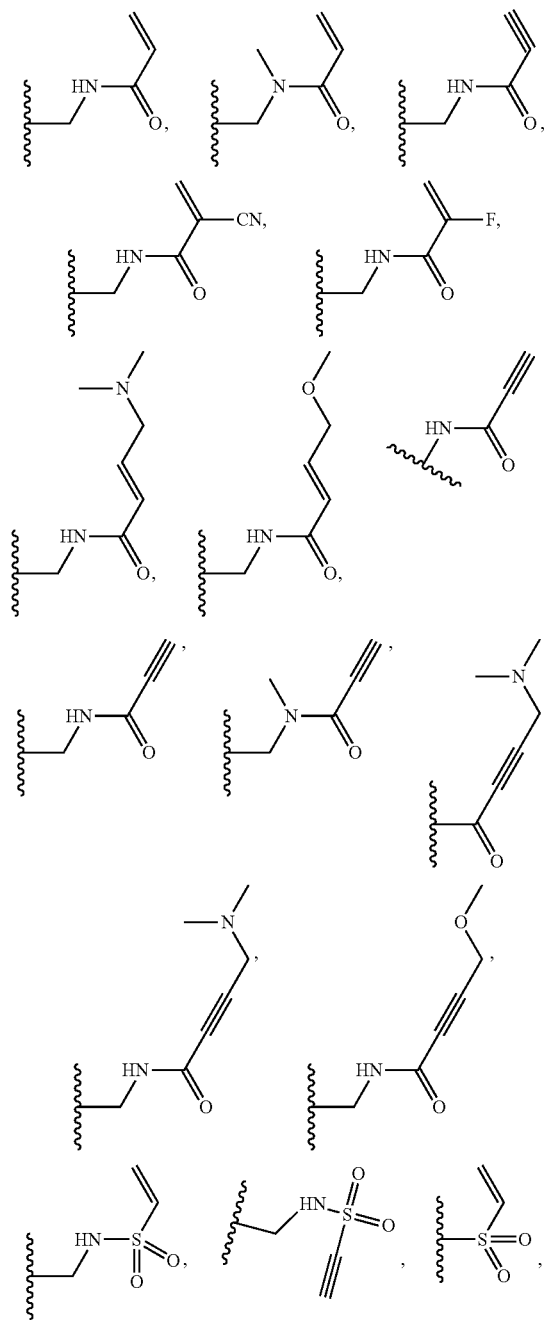
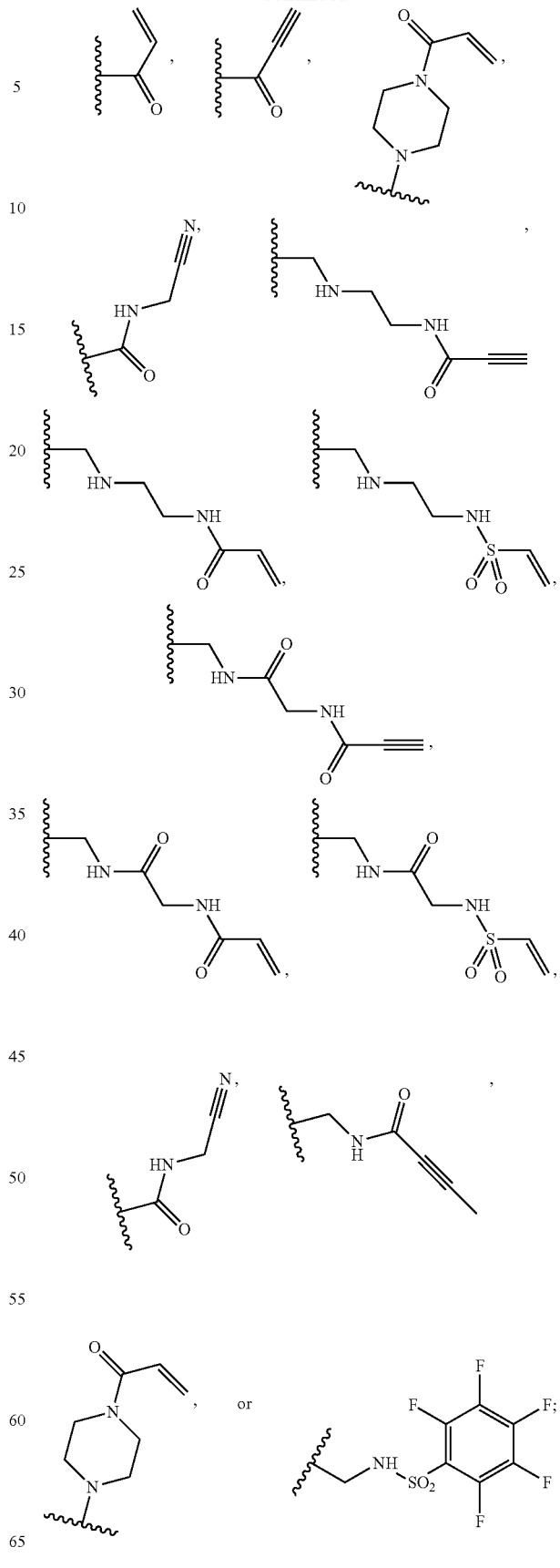

$R^4$ is
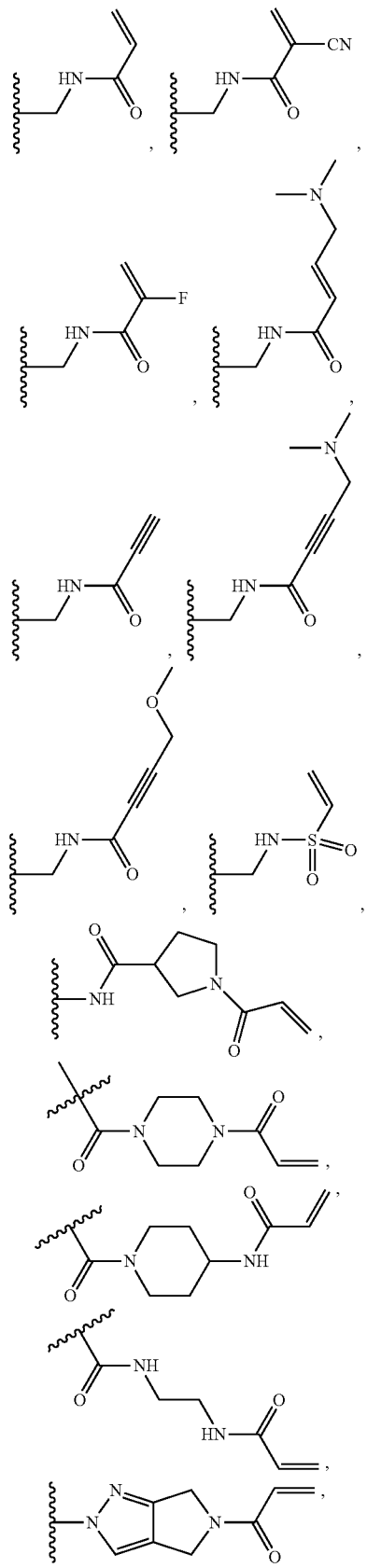
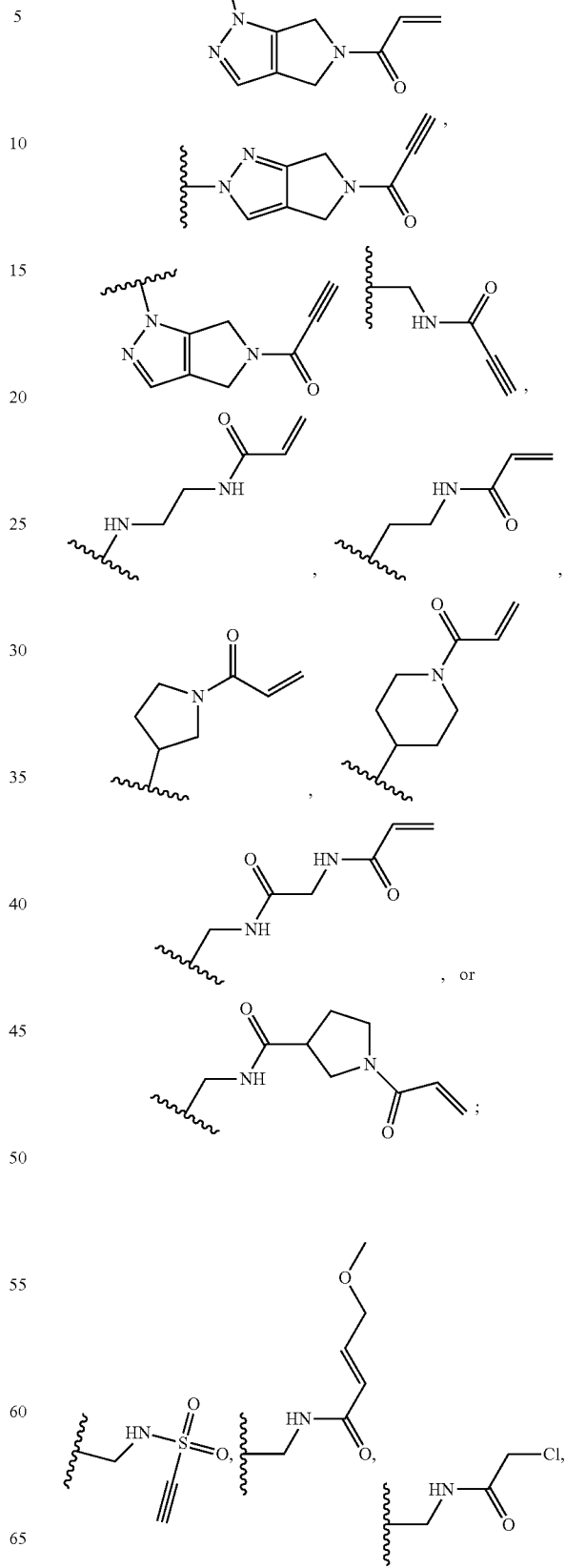

and
Z is

67
-continued
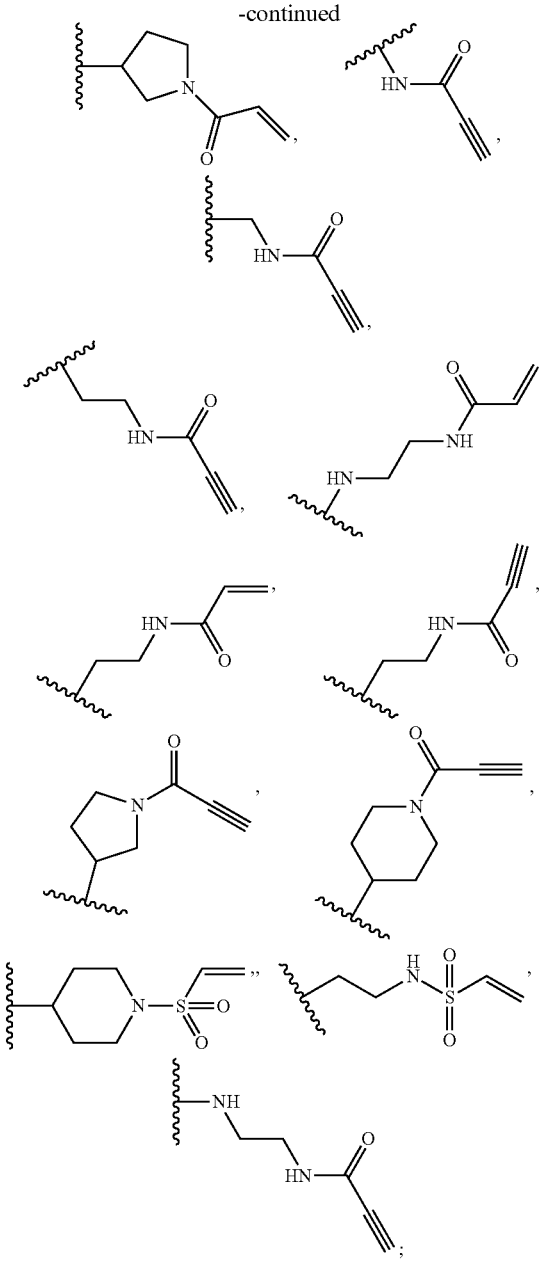
68
-continued
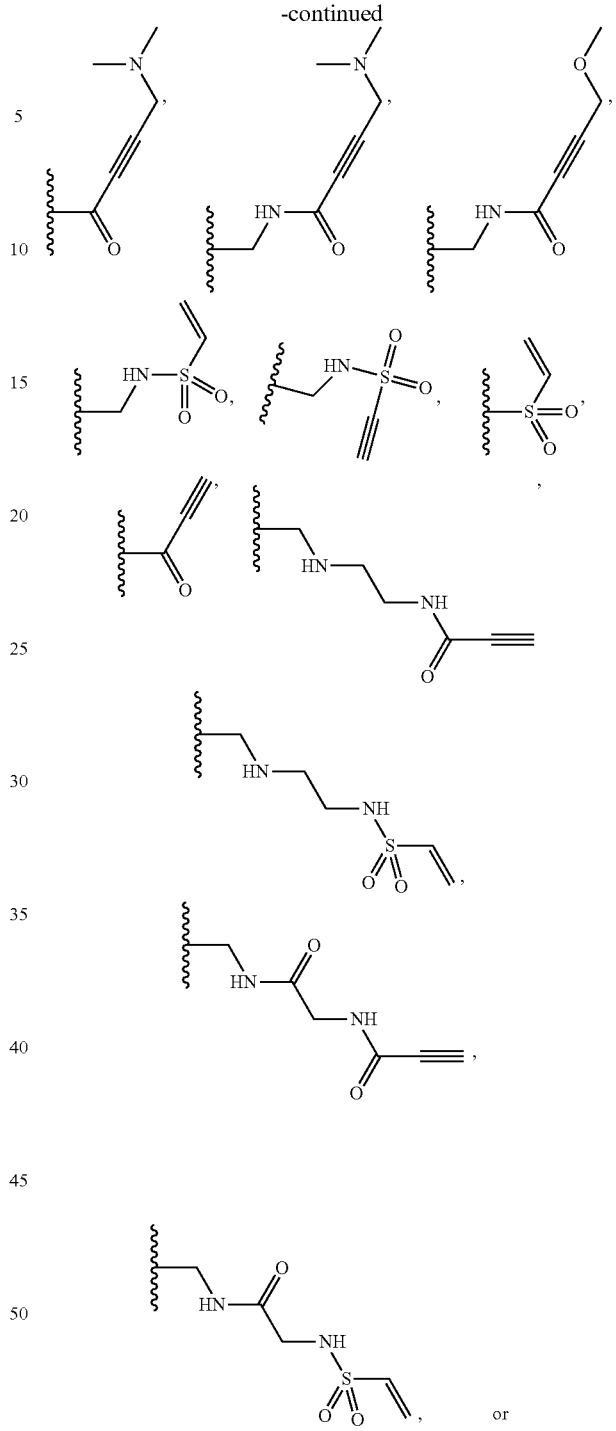
and all other groups are as defined in the Summary or in some or any embodiment provided herein, including any one of preceding embodiments.
Embodiment 47c. Provided is a compound of Formula (I), (Ia), (Ib), (Ic), (Id), (Ie), (If), (Ig), (Ia-1), (Ib-1), (Ic-1), (Ic-2), (Id-1), (Ie-1), (If-1), or (Ig-1), wherein
$R^Y$ is
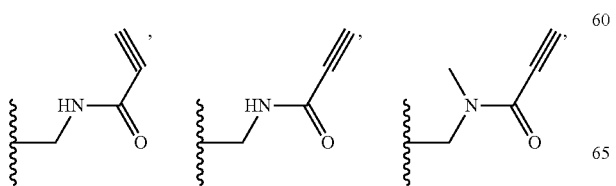
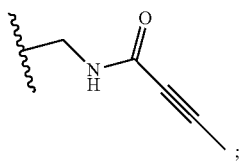

$R^4$ is

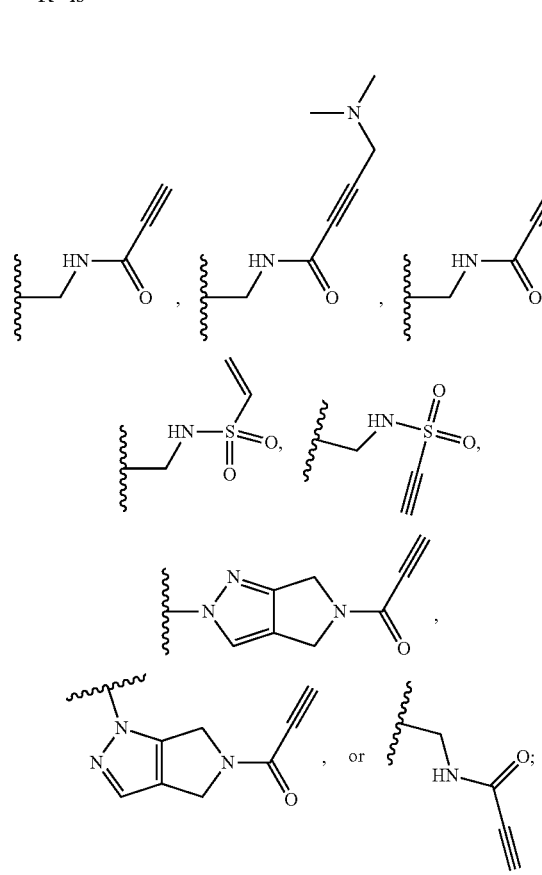

and

Z is

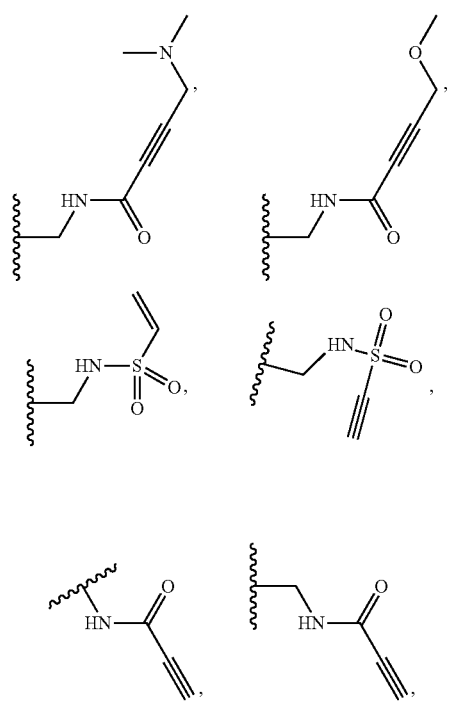

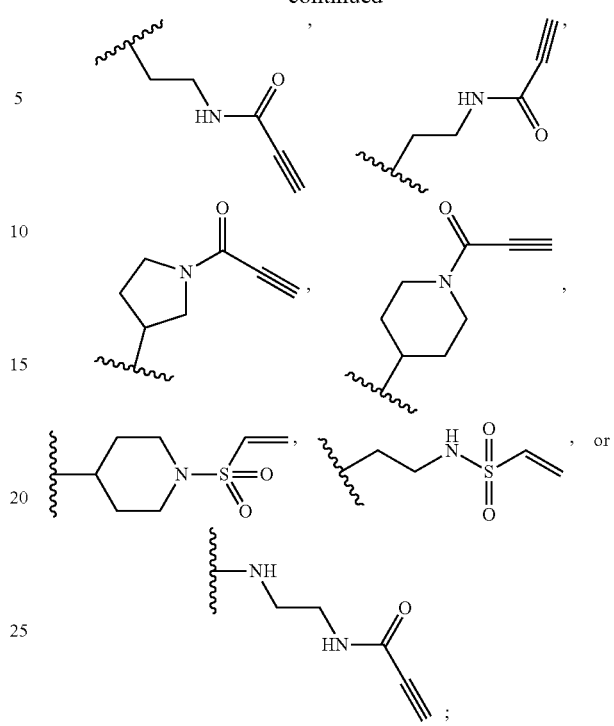

and all other groups are as defined in the Summary or in some or any embodiment provided herein, including any one of preceding embodiments.

Embodiment 48: Provided is a compound where the 8- or 9-membered bicyclic heterocyclic (optionally substituted as provided herein) is a 5-membered heteroaryl group, preferably a pyrazolyl, fused to a nonaromatic cyclic group, preferably forming an 8-membered bicyclic heterocyclic, which is optionally substituted as provided herein. In an embodiment of Embodiment 48, provided is a compound where the 8- or 9-membered bicyclic heterocyclic (optionally substituted as provided herein) is a 5-membered heteroaryl group, preferably a pyrazolyl, fused to a nonaromatic cyclic group, preferably forming an 8-membered bicyclic heterocyclic group, which is optionally substituted as provided herein; and where the rest of the molecule is attached to the 5-membered heteroaryl group fused to the nonaromatic cyclic group through the 5-membered heteroaryl portion. In an embodiment of Embodiment 48, provided is a compound where the nonaromatic portion of the 8- or 9-membered bicyclic heterocyclic (optionally substituted as provided herein) comprises a heteroatom in the ring, preferably nitrogen.

Embodiment 49: Provided is a pharmaceutical composition comprising a Compound of any one of Embodiments 1-48 or a stereoisomer, a mixture of stereoisomers, and/or a pharmaceutically acceptable salt thereof; and a pharmaceutically acceptable carrier.

Embodiment 50: Provided is a method of treating a condition, disease, or disorder by inhibiting MYST family of lysine acetyl transferases, including KAT6A and KAT6B, comprising administering to a patient in need thereof a therapeutically effective amount of the Compound of any one of Embodiments 1-48 or a stereoisomer, a mixture of stereoisomers, and/or a pharmaceutically acceptable salt thereof or a therapeutically effective amount of the composition of Embodiment 4.

Embodiment 51: Provided is the method of embodiment 50 where the condition, disease, or disorder is a hyperproliferative disease, such as cancer. In some or any embodiments, the cancer is a particular type selected from: lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, and sarcoma (e.g. angiosarcoma, chondrosarcoma, osteosarcoma). In some or any embodiments, the cancer may be a MYST overexpressing cancer; the cancer may over-express MYST protein relative to non-cancerous tissue; the cancer may overproduce MYST mRNA relative to non-cancerous tissue; the cancer may be a MYST overexpressing cancer where the overexpressed MYST protein or MYST mRNA may be any one of KATs of the MYST family, e.g. KAT6A. In some or any embodiments, the cancer is selected from one or more of the following leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, breast ductal carcinoma, colon and rectal cancer, colon cancer, squamous cell carcinoma, gastric cancer, adrenocortical cancer, anal cancer, bladder cancer, blood cancer, bone cancer, brain tumor, cancer of the female genital system, cancer of the male genital system (including testicular cancer and penile cancer), central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, testicular cancer, thyroid cancer, urinary system cancer, uterine cancer, uterine sarcoma, vaginal cancer, endocrine, neoplasms of the central nervous system (CNS), primary CNS lymphoma, spinal axis tumors, glioblastoma, brain stem glioma, pituitary adenoma, vascular system, Waldenstrom's macroglobulinemia and/or Wilms' tumor. In some or any embodiments, the cancer is breast cancer, including ER positive breast cancer, non-small cell lung cancer, prostate cancer, pancreatic cancer, ovarian cancer, or blood cancer (including a leukemia or lymphoma).

Embodiment B: In one embodiment is a compound of Formula (I) where
- $R^1$ is unsubstituted $C_{3-8}$cycloalkylalkyl, preferably cyclohexylmethyl, or phenyl where the phenyl is optionally substituted with one or two groups independently selected from halo, preferably fluoro, and $C_{1-3}$alkoxy, preferably methoxy;
- $R^2$ is ring (a) or ring (b); where one $X^1$ is $C(CH_2R^{2c})$, and the other two $X^1$ are each CH; preferably, the $C(CH_2R^{2c})$ is in the meta-position with respect to $R^{2d}$; $R^{2b}$ is hydrogen or $C_1$-$C_6$alkyl, preferably hydrogen or methyl;
- $R^{2c}$ is a 5-membered heteroaryl, preferably pyrazol-1-yl, optionally substituted with cyano or —$CH_2NHC(O)CH_3$; or $R^{2c}$ is 2,4,5,6-tetrahydropyrrolo[3,4-c]pyrazol-2-yl optionally substituted with $C_{1-6}$alkylcarbonyl; or $R^{2c}$ is a 6-membered heteroaryl, preferably pyridin-2-yl; $R^{2d}$ is $C_{1-3}$alkoxy; or
- a pharmaceutically acceptable salt or salts thereof; and/or a stereoisomer or mixture of stereoisomers thereof.

Embodiment 52. Provided is a compound of Formula (I) according to Formula (Ih):

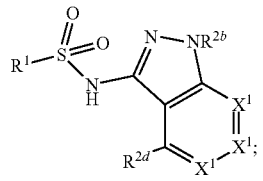

(Ih)

where $R^1$, $R^{2b}$, $R^{2d}$, and $X^1$ and all other groups are as defined in the Summary or in some or any embodiment provided herein; or a pharmaceutically acceptable salt or salts thereof; and/or a stereoisomer or mixture of stereoisomers thereof. In some or any embodiments of Embodiment 52, $R^{2b}$ is hydrogen or methyl.

Embodiment 53. Provided is a compound of Formula (I) according to Formula (Ii):

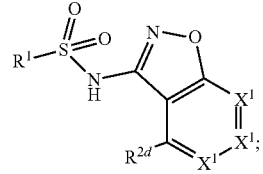

(Ii)

where $R^1$, $R^{2d}$, and $X^1$ and all other groups are as defined in the Summary or in some or any embodiment provided herein; or a pharmaceutically acceptable salt or salts thereof; and/or a stereoisomer or mixture of stereoisomers thereof.

Embodiment 54. Provided is a compound of Formula (I) according to Formula (Ij):

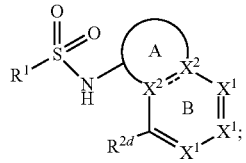

(Ij)

where $R^1$, $R^{2d}$, $X^1$, and $X^2$ and all other groups are as defined in the Summary or in some or any embodiment provided herein; or a pharmaceutically acceptable salt or salts thereof; and/or a stereoisomer or mixture of stereoisomers thereof.

Embodiment 55: Provided is a compound according to Formula (I), (Ih), (Ii), or (Ij), wherein $R^1$ is $C_3$-$C_8$-cycloalkylalkyl where the $C_3$-$C_8$-cycloalkylalkyl is optionally substituted with 1, 2, or 3 $R^{1a}$, or phenyl optionally substituted with 1, 2, or 3 $R^{1b}$; and all other groups are as defined in the Summary or in some or any embodiment provided herein, including any one of Embodiments 52-54.

Embodiment 56: Provided is a compound according to Formula (I), (Ih), (Ii), or (Ij), wherein $R^1$ is $C_3$-$C_8$-cycloalkylalkyl where the $C_3$-$C_8$-cycloalkylalkyl is optionally substituted with 1, 2, or 3 $R^{1a}$; and all other groups are as defined in the Summary or in some or any embodiment provided herein, including any one of Embodiments 52-54.

Embodiment 57: Provided is a compound according to Formula (I), (Ih), (Ii), or (Ij), wherein each $R^{1a}$ is independently H; and all other groups are as defined in the Summary or in some or any embodiment provided herein, including any one of Embodiments 52-56.

Embodiment 58: Provided is a compound according to Formula (I), (Ih), (Ii), or (IIc), wherein $R^1$ is phenyl optionally substituted with 1, 2, or 3 $R^{1b}$; and all other groups are as defined in the Summary or in some or any embodiment provided herein, including any one of Embodiments 52-55.

Embodiment 59: Provided is a compound according to Formula (I), (Ih), (Ii), or (Ij), wherein $R^1$ is naphthyl optionally substituted with 1, 2, or 3 $R^{1b}$; and all other groups are as defined in the Summary or in some or any embodiment provided herein, including any one of Embodiments 52-54.

Embodiment 60: Provided is a compound according to Formula (I), (Ih), (Ii), or (Ij), wherein $R^1$ is 5- or 6-membered monocyclic heteroaryl optionally substituted with 1, 2, or 3 $R^{1b}$; and all other groups are as defined in the Summary or in some or any embodiment provided herein, including any one of Embodiments 52-54.

Embodiment 60a: Provided is a compound according to Formula (I), (Ih), (Ii), or (Ij), wherein $R^1$ is 8-10-membered bicyclic heteroaryl; and all other groups are as defined in the Summary or in some or any embodiment provided herein, including any one of Embodiments 52-54.

Embodiment 61: Provided is a compound according to Formula (I), (Ih), (Ii), or (Ij), wherein each $R^{1b}$ is independently selected from H, halo, and $C_1$-$C_6$alkoxy; and all other groups are as defined in the Summary or in some or any embodiment provided herein, including any one of Embodiments 52-55 and 58-60. In a subembodiment of embodiment 61, provided is compound of Formula (I), (Ih), (Ii), or (Ij) wherein each $R^{1b}$ is independently selected from H, halo, and $C_1$-$C_3$alkoxy. In a subembodiment of embodiment 61, provided is compound of Formula (I), (Ih), (Ii), or (Ij) wherein each $R^{1b}$ is independently selected from H, fluoro, and methoxy. In a subembodiment of embodiment 61 and subembodiments thereof, provided is compound of Formula (I), (Ih), (Ii), or (Ij) wherein one or two $R^{1b}$ are present. In a subembodiment of embodiment 61 and subembodiments thereof, provided is compound of Formula (I), (Ih), (Ii), or (Ij) wherein one $R^{1b}$ are present. In a subembodiment of embodiment 61 and subembodiments thereof, provided is compound of Formula (I), (Ih), (Ii), or (Ij) wherein two $R^{1b}$ are present.

Embodiment 62: Provided is a compound according to Formula (I), (Ih), (Ii), or (Ij), wherein $R^{2d}$ is halo, $C_1$-$C_3$alkyl, $C_1$-$C_3$alkoxy, or $C_3$-cycloalkyloxy; and all other groups are as defined in the Summary or in some or any embodiment provided herein, including any one of Embodiments 52-61. In a subembodiment of embodiment 62, provided is compound of Formula (I), (Ih), (Ii), or (Ij) wherein $R^{2d}$ is $C_1$-$C_6$alkoxy, preferably $C_1$-$C_3$alkoxy, preferably methoxy. In a subembodiment of embodiment 62, provided is compound of Formula (I), (Ih), (Ii), or (Ij) wherein $R^{2d}$ is methoxy, isopropoxy, or cyclopropyloxy.

Embodiment 63: Provided is a compound according to Formula (I), (Ih), (Ii), or (Ij), wherein each $R^{2e}$ is independently hydrogen, fluoro, $C_1$-$C_3$alkyl, cyclopropyl, —$CHF_2$, —$CF_3$, $C_1$-$C_4$alkoxy, —$OCHF_2$, or —$OCF_3$; and all other groups are as defined in the Summary or in some or any embodiment provided herein, including any one of Embodiments 52-61. In a subembodiment of embodiment 63, provided is compound of Formula (I), (Ih), (Ii), or (Ij) wherein each $R^{2e}$ is hydrogen.

Embodiment 64: Provided is a compound according to Formula (I) or (Ih), wherein
  $R^{2c}$ is a 5-membered monocyclic heteroaryl optionally substituted with 1 or 2 $R^{2c1}$; $R^{2c}$ is a 8- or 9-membered bicyclic heterocyclic optionally substituted with 1 or 2 $R^{2c1}$; $R^{2c}$ is a 6-membered monocyclic heteroaryl optionally substituted with 1, 2, or 3 $R^{2c1}$; and
  each $R^{2c1}$ is independently H, halo, $C_1$-$C_6$alkyl, $C_1$-$C_6$alkylcarbonyl, —CN, $C_1$-$C_6$alkoxy, $C_3$-$C_8$cycloalkyloxy, —$(CH_2)_{0-1}NH_2$, —$(CH_2)_{0-1}NHC(O)R^{2f}$, —$(CH_2)_{0-1}NHC(O)OR^{2f}$, —$NH(C_1$-$C_6$alkyl), —$N(C_1$-$C_6$alkyl)$_2$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;
and all other groups are as defined in the Summary or in some or any embodiment provided herein, including any one of Embodiments 55-63. In a subembodiment of Embodiment 64, provided is a compound where $R^{2c}$ is a 5-membered monocyclic heteroaryl optionally substituted with 1 or 2 $R^{2c1}$; $R^{2c}$ is a 8-membered bicyclic heterocyclic optionally substituted with 1 or 2 $R^{2c1}$; or $R^{2c}$ is a 6-membered monocyclic heteroaryl optionally substituted with 1, 2, or 3 $R^{2c1}$.

Embodiment 64a: In an embodiment of Embodiment 64, provided is a compound where each $R^{2c1}$ is hydrogen (i.e. $R^{2c}$ is not substituted); and all other groups are as defined in the Summary or in some or any embodiment provided herein, including any one of Embodiments 55-63. In a subembodiment of Embodiment 64, provided is a compound where one $R^{2c1}$ is hydrogen and the other $R^{2c1}$ is selected from $C_1$-$C_6$alkylcarbonyl, —CN, —$(CH_2)_{0-1}NH_2$, and —$(CH_2)_{0-1}NHC(O)R^{2f}$, —$(CH_2)_{0-1}NHC(O)OR^{2f}$; wherein $R^{2f}$ is $C_1$-$C_6$alkyl, $C_3$-$C_6$cycloalkyl, or $C_3$-$C_6$cycloalkyl$C_1$-$C_3$alkyl; and all other groups are as defined in the Summary or in some or any embodiment provided herein, including any one of Embodiments 55-63. In a subembodiment of Embodiment 64, provided is a compound where one $R^{2c1}$ is hydrogen and the other $R^{2c1}$ is —CN; and all other groups are as defined in the Summary or in some or any embodiment provided herein, including any one of Embodiments 55-63.

Embodiment 64b: In a subembodiment of Embodiment 64 or 64a, provided is a compound where $R^{2c}$ is pyrazolyl, pyridinyl, or 2,4,5,6-tetrahydropyrrolo[3,4-c]pyrazolyl, each of which is optionally substituted with 1 or 2 $R^{2c1}$. In a subembodiment of Embodiment 64 or 64a, provided is a compound where $R^{2c}$ is a 5-membered monocyclic heteroaryl optionally substituted with 1 or 2 $R^{2c1}$. In a subembodiment of Embodiment 64 or 64a, provided is a compound where $R^{2c}$ is a 8-membered bicyclic heterocyclic optionally substituted with 1 or 2 $R^{2c1}$. In a subembodiment of Embodiment 64 or 64a, provided is a compound where $R^{2c}$ is a 6-membered monocyclic heteroaryl optionally substituted with 1, 2, or 3 $R^{2c1}$.

Embodiment 64c: In an embodiment of Embodiment 64, provided is a compound where $R^{2c}$ is pyrazolyl, preferably pyrazol-2-yl, and is unsubstituted (i.e. both $R^{2c1}$ are hydrogen) or is substituted with one $R^{2c1}$ which is preferably cyano (i.e. the other $R^{2c1}$ is hydrogen); and all other groups are as defined in the Summary or in some or any embodiment provided herein, including any one of Embodiments 55-63. In an embodiment of Embodiment 64, provided is a compound where $R^{2c}$ is pyridinyl, preferably pyridin-2-yl, and is unsubstituted (i.e. both $R^{2c1}$ are hydrogen) or is substituted with one $R^{2c1}$ which is cyano (i.e. the other $R^{2c1}$ is hydrogen); and all other groups are as defined in the Summary or in some or any embodiment provided herein, including any one of Embodiments 55-63. In an embodiment of Embodiment 64, provided is a compound where $R^{2c}$ is 2,4,5,6-tetrahydropyrrolo[3,4-c]pyrazolyl, preferably 2,4,5,6-tetrahydropyrrolo[3,4-c]pyrazol-2-yl, and is unsubstituted (i.e. both $R^{2c1}$ are hydrogen) or is substituted with one $R^{2c1}$ (i.e. the other $R^{2c1}$ is hydrogen) where the one $R^{2c1}$ is alkylcarbonyl, preferably, methylcarbonyl or ethylcarbonyl; and all other groups are as defined in the Summary or in some or any embodiment provided herein, including any one of Embodiments 55-63.

Embodiment 64d: In an embodiment of Embodiment 64 or 64a, provided is a compound where $R^{2c}$ is a 8- or 9-membered bicyclic heterocyclic optionally substituted with 1 or 2 $R^{2c1}$; and all other groups are as defined in the Summary or in some or any embodiment provided herein, including any one of Embodiments 55-63.

Embodiment 64d-1: In a sub-embodiment of Embodiment 64d, provided is a compound where the 8- or 9-membered bicyclic heterocyclic (optionally substituted with 1 or 2 $R^{2c1}$) is a 5-membered heteroaryl group, preferably a pyrazolyl, fused to a nonaromatic cyclic group, preferably forming an 8-membered bicyclic heterocyclic, which is optionally substituted with 1 or 2 $R^{2c1}$.

Embodiment 64d-2: In a sub-embodiment of Embodiment 64d, provided is a compound where the 8- or 9-membered bicyclic heterocyclic (optionally substituted with 1 or 2 $R^{2c1}$) is a 5-membered heteroaryl group, preferably a pyrazolyl, fused to a nonaromatic cyclic group, preferably forming an 8-membered bicyclic heterocyclic group, which is optionally substituted with 1 or 2 $R^{2c1}$; and where the rest of the molecule is attached to the 5-membered heteroaryl group fused to the nonaromatic cyclic group through the 5-membered heteroaryl portion.

Embodiment 64d-3: In a sub-embodiment of any one of Embodiments 64d, 64d-1, and 64d-2, provided is a compound where the nonaromatic portion of the 8- or 9-membered bicyclic heterocyclic (optionally substituted with 1 or 2 $R^{2c1}$) comprises a heteroatom in the ring, preferably nitrogen.

Embodiment 64d-4: In a sub-embodiment of any one of Embodiments 64d, 64d-1, 64d-2, and 64d-3, provided is a compound where the 8- or 9-membered bicyclic heterocyclic is substituted with one $R^{2c1}$ which is hydrogen and a second $R^{2c1}$ which is selected from hydrogen and $C_1$-$C_6$alkylcarbonyl, preferably methylcarbonyl or ethylcarbonyl.

Embodiment 65: Provided is a compound according to Formula (I) or (Ii), wherein
$R^{2c}$ is a 5-membered monocyclic heteroaryl substituted with $R^{2c2}$ and optionally substituted with $R^{2c3}$; $R^{2c}$ is a 8- or 9-membered bicyclic heterocyclic optionally substituted with 1 or 2 $R^{2c1}$; $R^{2c}$ is a 8- or 9-membered bicyclic heterocyclic substituted with $R^{2c2}$ and optionally substituted with $R^{2c3}$; $R^{2c}$ is a 6-membered monocyclic heteroaryl substituted with $R^{2c2}$ and optionally substituted with 1 or 2 $R^{2c3}$; and
$R^{2c2}$ is $C_1$-$C_6$alkylcarbonyl, —CN, —$(CH_2)_{0-1}NH_2$, $C_1$-$C_6$alkoxy, —NH($C_1$-$C_6$alkyl), —N($C_1$-$C_6$alkyl)$_2$, —$(CH_2)_{0-1}NHC(O)R^{2f}$, —$(CH_2)_{0-1}NHC(O)OR^{21}$ 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl; and
$R^{2c3}$ is independently H, halo, $C_1$-$C_6$alkyl, $C_1$-$C_6$alkoxy, or $C_3$-$C_8$cycloalkyloxy;
each $R^{2c1}$ is independently H, halo, $C_1$-$C_6$alkyl, $C_1$-$C_6$alkylcarbonyl, $C_1$-$C_6$alkoxy, $C_3$-$C_8$cycloalkyloxy, —CN, —$(CH_2)_{0-1}NH_2$, —NH($C_1$-$C_6$alkyl), —N($C_1$-$C_6$alkyl)$_2$, —$(CH_2)_{0-1}NHC(O)R^{2f}$, —$(CH_2)_{0-1}NHC(O)OR^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;
and all other groups are as defined in the Summary or in some or any embodiment provided herein, including any one of Embodiments 55-63. In a subembodiment of Embodiment 65, provided is a compound where $R^{2c}$ is a 5-membered monocyclic heteroaryl substituted with $R^{2c2}$ and optionally substituted with $R^{2c3}$; 8-membered bicyclic heterocyclic optionally substituted with 1 or 2 $R^{2c1}$; $R^{2c}$ is a 8-membered bicyclic heterocyclic substituted with $R^{2c2}$ and optionally substituted with $R^{2c3}$; or $R^{2c}$ is a 6-membered monocyclic heteroaryl substituted with $R^{2c2}$ and optionally substituted with 1 or 2 $R^{2c3}$.

Embodiment 65a: In an embodiment of Embodiment 65, provided is a compound where each $R^{2c1}$ is hydrogen (i.e. $R^{2c}$ is not substituted); and all other groups are as defined in the Summary or in some or any embodiment provided herein, including any one of Embodiments 55-63. In a subembodiment of Embodiment 65, provided is a compound where one $R^{2c1}$ is hydrogen and the other $R^{2c1}$ is selected from $C_1$-$C_6$alkylcarbonyl, —CN, —$(CH_2)_{0-1}NH_2$, and —$(CH_2)_{0-1}NHC(O)R^{2f}$, —$(CH_2)_{0-1}NHC(O)OR^{2f}$; wherein $R^{2f}$ is $C_1$-$C_6$alkyl, $C_3$-$C_6$cycloalkyl, or $C_3$-$C_6$cycloalkyl$C_1$-$C_3$alkyl; and all other groups are as defined in the Summary or in some or any embodiment provided herein, including any one of Embodiments 55-63. In a subembodiment of Embodiment 65, provided is a compound where one $R^{2c1}$ is hydrogen and the other $R^{2c1}$ is —CN; and all other groups are as defined in the Summary or in some or any embodiment provided herein, including any one of Embodiments 55-63.

Embodiment 65b: In an embodiment of Embodiment 65, provided is a compound where $R^{2c2}$ is $C_1$-$C_6$alkylcarbonyl, —CN, —$(CH_2)_{0-1}NH_2$, or —$(CH_2)_{0-1}NHC(O)R^{2f}$, —$(CH_2)_{0-1}NHC(O)OR^{2f}$; wherein $R^{2f}$ is $C_1$-$C_6$alkyl, $C_3$-$C_6$cycloalkyl, or $C_3$-$C_6$cycloalkyl$C_1$-$C_3$alkyl; and all other groups are as defined in the Summary or in some or any embodiment provided herein, including any one of Embodiments 55-63.

Embodiment 65c: In an embodiment of Embodiment 65 or 65b, provided is a compound where each $R^{2c3}$ is hydrogen; and all other groups are as defined in the Summary or in some or any embodiment provided herein, including any one of Embodiments 55-63.

Embodiment 65d: In a subembodiment of Embodiment 65, 65b, or 65c, provided is a compound where $R^{2c}$ is pyrazolyl, pyridinyl, or 2,4,5,6-tetrahydropyrrolo[3,4-c]pyrazolyl, each of which is substituted with $R^{2c2}$ and optionally substituted with $R^{2c3}$; and all other groups are as defined in the Summary or in some or any embodiment provided herein, including any one of Embodiments 55-63. In a subembodiment of Embodiment 65, 65b, or 65c, provided is a compound where $R^{2c}$ is a 5-membered monocyclic heteroaryl substituted with $R^{2c2}$ and optionally substituted with $R^{2c3}$. In a subembodiment of Embodiment 65, 65b, or 65c, provided is a compound where $R^{2c}$ is a 8-membered bicyclic heterocyclic substituted with $R^{2c2}$ and optionally substituted with $R^{2c3}$. In a subembodiment of Embodiment 65, 65b, or 65c, provided is a compound where $R^{2c}$ is a 6-membered monocyclic heteroaryl substituted with $R^{2c2}$ and optionally substituted with $R^{2c3}$.

Embodiment 65e: In an embodiment of Embodiment 65, provided is a compound where $R^{2c}$ is pyrazolyl, preferably pyrazol-2-yl, substituted $R^{2c2}$ which is cyano and $R^{2c3}$ is hydrogen; and all other groups are as defined in the Summary or in some or any embodiment provided herein, including any one of Embodiments 55-63. In an embodiment of Embodiment 65, provided is a compound where $R^{2c}$ is pyridinyl, preferably pyridin-2-yl, substituted with $R^{2c2}$ which is cyano and $R^{2c3}$ is hydrogen; and all other groups are as defined in the Summary or in some or any embodiment provided herein, including any one of Embodiments 55-63. In an embodiment of Embodiment 65, provided is a compound where $R^{2c}$ is 2,4,5,6-tetrahydropyrrolo[3,4-c]pyrazolyl, preferably 2,4,5,6-tetrahydropyrrolo[3,4-c]pyrazol-2-yl, substituted with $R^{2c2}$ where $R^{2c2}$ is alkylcarbonyl, preferably, methylcarbonyl or ethylcarbonyl and where $R^{2c3}$ is hydrogen; and all other groups are as defined in the Summary or in some or any embodiment provided herein, including any one of Embodiments 55-63.

Embodiment 65f: In an embodiment of Embodiment 65, provided is a compound where $R^{2c}$ is a 8- or 9-membered bicyclic heterocyclic optionally substituted with 1 or 2 $R^{2c1}$; and all other groups are as defined in the Summary or in some or any embodiment provided herein, including any one of Embodiments 55-63.

Embodiment 65f-1: In a sub-embodiment of Embodiment 65f, provided is a compound where the 8- or 9-membered bicyclic heterocyclic (optionally substituted with 1 or 2 $R^{2c1}$) is a 5-membered heteroaryl group, preferably a pyrazolyl, fused to a nonaromatic cyclic group, preferably forming an 8-membered bicyclic heterocyclic, which is optionally substituted with 1 or 2 $R^{2c1}$.

Embodiment 65f-2: In a sub-embodiment of Embodiment 65f, provided is a compound where the 8- or 9-membered bicyclic heterocyclic (optionally substituted with 1 or 2 $R^{2c1}$) is a 5-membered heteroaryl group, preferably a pyrazolyl, fused to a nonaromatic cyclic group, preferably forming an 8-membered bicyclic heterocyclic group, which is optionally substituted with 1 or 2 $R^{2c1}$; and where the rest of the molecule is attached to the 5-membered heteroaryl group fused to the nonaromatic cyclic group through the 5-membered heteroaryl portion.

Embodiment 65f-3: In a sub-embodiment of any one of Embodiments 65f, 65f-1, and 65f-2, provided is a compound where the nonaromatic portion of the 8- or 9-membered bicyclic heterocyclic (optionally substituted with 1 or 2 $R^{2c1}$) comprises a heteroatom in the ring, preferably nitrogen.

Embodiment 65f-4: In a sub-embodiment of any one of Embodiments 65f, 65f-1, 65f-2, and 65f-3, provided is a compound where the 8- or 9-membered bicyclic heterocyclic is substituted with one $R^{2c1}$ which is hydrogen and a second $R^{2c1}$ which is selected from hydrogen and $C_1$-$C_6$alkylcarbonyl, preferably methylcarbonyl or ethylcarbonyl.

Embodiment 65g: In an embodiment of Embodiment 65, provided is a compound where $R^2$, is a 8- or 9-membered bicyclic heterocyclic substituted with $R^{2c2}$ and optionally substituted with $R^{2c3}$; and all other groups are as defined in the Summary or in some or any embodiment provided herein, including any one of Embodiments 55-63.

Embodiment 65g-1: In a sub-embodiment of Embodiment 65g, provided is a compound where the 8- or 9-membered bicyclic heterocyclic (substituted with $R^{2c2}$ and optionally substituted with $R^{2c3}$) is a 5-membered heteroaryl group, preferably a pyrazolyl, fused to a nonaromatic cyclic group, preferably forming an 8-membered bicyclic heterocyclic, which is substituted with $R^{2c2}$ and optionally substituted with $R^{2c3}$.

Embodiment 65g-2: In a sub-embodiment of Embodiment 65g, provided is a compound where the 8- or 9-membered bicyclic heterocyclic (substituted with $R^{2c2}$ and optionally substituted with $R^{2c3}$) is a 5-membered heteroaryl group, preferably a pyrazolyl, fused to a nonaromatic cyclic group, preferably forming an 8-membered bicyclic heterocyclic group, which is substituted with $R^{2c2}$ and optionally substituted with $R^{2c3}$; and where the rest of the molecule is attached to the 5-membered heteroaryl group fused to the nonaromatic cyclic group through the 5-membered heteroaryl portion.

Embodiment 65g-3: In a sub-embodiment of any one of Embodiments 65g, 65g-1, and 65g-2, provided is a compound where the nonaromatic portion of the 8- or 9-membered bicyclic heterocyclic (substituted with $R^{2c2}$ and optionally substituted with $R^{2c3}$) comprises a heteroatom in the ring, preferably nitrogen.

Embodiment 65g-4: In a sub-embodiment of any one of Embodiments 65g, 65g-1, 65g-2, and 65g-3, provided is a compound where the 8- or 9-membered bicyclic heterocyclic is substituted with $C_1$-$C_6$alkylcarbonyl, preferably methylcarbonyl or ethylcarbonyl, and $R^{2c3}$ is hydrogen.

Embodiment 66: Provided is a compound according to Formula (I) or (Ij), wherein
$R^{2c}$ is a 5-membered monocyclic heteroaryl optionally substituted with 1 or 2 $R^{2c1}$; a 8- or 9-membered bicyclic heterocyclic optionally substituted with 1 or 2 $R^{2c1}$; or a 6-membered monocyclic heteroaryl optionally substituted with 1, 2, or 3 $R^{2c1}$; and
each $R^{2c1}$ is independently H, halo, $C_1$-$C_6$alkyl, $C_1$-$C_6$alkylcarbonyl, —CN, $C_1$-$C_6$alkoxy, $C_3$-$C_8$cycloalkyloxy, —$(CH_2)_{0-1}NH_2$, —$NH(C_1$-$C_6$alkyl), —$N(C_1$-$C_6$alkyl)$_2$, —$(CH_2)_{0-1}NHC(O)R^2$, —$(CH_2)_{0-1}NHC(O)OR^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

and all other groups are as defined in the Summary or in some or any embodiment provided herein, including any one of Embodiments 55-63. In a subembodiment of Embodiment 66, provided is a compound where $R^{2c}$ is a 5-membered monocyclic heteroaryl optionally substituted with 1 or 2 $R^{2c1}$; $R^{2c}$ is a 8-membered bicyclic heterocyclic optionally substituted with 1 or 2 $R^{2c1}$; or $R^{2c}$ is a 6-membered monocyclic heteroaryl optionally substituted with 1, 2, or 3 $R^{2c1}$.

Embodiment 66a: In an embodiment of Embodiment 66, provided is a compound where each $R^{2c1}$ is hydrogen (i.e. $R^{2c}$ is not substituted); and all other groups are as defined in the Summary or in some or any embodiment provided herein, including any one of Embodiments 55-63. In a subembodiment of Embodiment 66, provided is a compound where one $R^{2c1}$ is hydrogen and the other $R^{2c1}$ is selected from $C_1$-$C_6$alkylcarbonyl, —CN, —$(CH_2)_{0-1}NH_2$, and —$(CH_2)_{0-1}NHC(O)R^{21}$, —$(CH_2)_{0-1}NHC(O)OR^{2f}$; wherein $R^{2f}$ is $C_1$-$C_6$alkyl, $C_3$-$C_6$cycloalkyl, or $C_3$-$C_6$cycloalkyl$C_1$-$C_3$alkyl; and all other groups are as defined in the Summary or in some or any embodiment provided herein, including any one of Embodiments 55-63. In a subembodiment of Embodiment 66, provided is a compound where one $R^{2c1}$ is hydrogen and the other $R^{2c1}$ is —CN; and all other groups are as defined in the Summary or in some or any embodiment provided herein, including any one of Embodiments 55-63.

Embodiment 66b: In a subembodiment of Embodiment 66 or 66a, provided is a compound where $R^{2c}$ is pyrazolyl, pyridinyl, or 2,4,5,6-tetrahydropyrrolo[3,4-c]pyrazolyl, each of which is optionally substituted with 1 or 2 $R^{2c1}$. In a subembodiment of Embodiment 66 or 66a, provided is a compound where $R^{2c}$ is a 5-membered monocyclic heteroaryl optionally substituted with 1 or 2 $R^{2c1}$. In a subembodiment of Embodiment 66 or 66a, provided is a compound where $R^{2c}$ is a 8-membered bicyclic heterocyclic optionally substituted with 1 or 2 $R^{2c1}$. In a subembodiment of Embodiment 66 or 66a, provided is a compound where $R^{2c}$ is a 6-membered monocyclic heteroaryl optionally substituted with 1, 2, or 3 $R^{2c1}$.

Embodiment 66c: In an embodiment of Embodiment 66, provided is a compound where $R^{2c}$ is pyrazolyl, preferably pyrazol-2-yl, and is unsubstituted (i.e. both $R^{2c1}$ are hydrogen) or is substituted with one $R^{2c1}$ which is preferably cyano (i.e. the other $R^{2c1}$ is hydrogen); and all other groups are as defined in the Summary or in some or any embodiment provided herein, including any one of Embodiments 55-63. In an embodiment of Embodiment 66, provided is a compound where $R^{2c}$ is pyridinyl, preferably pyridin-2-yl, and is unsubstituted (i.e. both $R^{2c1}$ are hydrogen) or is substituted with one $R^{2c1}$ which is cyano (i.e. the other $R^{2c1}$ is hydrogen); and all other groups are as defined in the Summary or in some or any embodiment provided herein, including any one of Embodiments 55-63. In an embodiment of Embodiment 66, provided is a compound where $R^{2c}$ is 2,4,5,6-tetrahydropyrrolo[3,4-c]pyrazolyl, preferably 2,4,5,6-tetrahydropyrrolo[3,4-c]pyrazol-2-yl, and is unsubstituted (i.e. both $R^{2c1}$ are hydrogen) or is substituted with one $R^{2c1}$ (i.e. the other $R^{2c1}$ is hydrogen) where the one $R^{2c1}$ is alkylcarbonyl, preferably, methylcarbonyl or ethylcarbonyl; and all other groups are as defined in the Summary or in some or any embodiment provided herein, including any one of Embodiments 55063.

Embodiment 66d: In an embodiment of Embodiment 66 or 66a, provided is a compound where $R^{2c}$ is a 8- or 9-membered bicyclic heterocyclic optionally substituted with 1 or 2 $R^{2c1}$; and all other groups are as defined in the Summary or in some or any embodiment provided herein, including any one of Embodiments 55-63.

Embodiment 66d-1: In a sub-embodiment of Embodiment 66d, provided is a compound where the 8- or 9-membered bicyclic heterocyclic (optionally substituted with 1 or 2 $R^{2c1}$) is a 5-membered heteroaryl group, preferably a pyrazolyl, fused to a nonaromatic cyclic group, preferably forming an 8-membered bicyclic heterocyclic, which is optionally substituted with 1 or 2 $R^{2c1}$.

Embodiment 66d-2: In a sub-embodiment of Embodiment 66d, provided is a compound where the 8- or 9-membered bicyclic heterocyclic (optionally substituted with 1 or 2 $R^{2c1}$) is a 5-membered heteroaryl group, preferably a pyrazolyl, fused to a nonaromatic cyclic group, preferably forming an 8-membered bicyclic heterocyclic group, which is optionally substituted with 1 or 2 $R^{2c1}$; and where the rest of the molecule is attached to the 5-membered heteroaryl group fused to the nonaromatic cyclic group through the 5-membered heteroaryl portion.

Embodiment 66d-3: In a sub-embodiment of any one of Embodiments 66d, 66d-1, and 66d-2, provided is a compound where the nonaromatic portion of the 8- or 9-membered bicyclic heterocyclic (optionally substituted with 1 or 2 $R^{2c1}$) comprises a heteroatom in the ring, preferably nitrogen.

Embodiment 66d-4: In a sub-embodiment of any one of Embodiments 66d, 66d-1, 66d-2, and 66d-3, provided is a compound where the 8- or 9-membered bicyclic heterocyclic is substituted with one $R^{2c1}$ which is hydrogen and a second $R^{2c1}$ which is selected from hydrogen and $C_1$-$C_6$alkylcarbonyl, preferably methylcarbonyl or ethylcarbonyl.

Embodiment 67: Provided is a compound according to Formula (I), (Ih), (Ii), or (Ij), wherein one $X^1$ is $C(CH_2R^{2c})$, and the other two $X^1$ are each $CR^{2e}$; and all other groups are as defined in the Summary or in some or any embodiment provided herein, including any one of Embodiments 52 to 66d-4. In a sub-embodiment, each $CR^{2e}$ is CH. In a sub-embodiment, $C(CH_2R^{2c})$ is in the meta-position with respect to $R^{2d}$.

Embodiment 68: Provided is a compound according to Formula (I), (Ih), (Ii), or (Ij), wherein one $X^1$ is $C(CH_2R^{2c})$, the second $X^1$ is N, and the third $X^1$ is $CR^{2e}$; and all other groups are as defined in the Summary or in some or any embodiment provided herein, including any one of Embodiments 52 to 66d-4. In a sub-embodiment, $CR^{2e}$ is CH. In a sub-embodiment, $C(CH_2R^{2c})$ is in the meta-position with respect to $R^{2d}$.

Embodiment 69: Provided is a compound according to Formula (I), (Ih), (Ii), or (Ij), wherein one $X^1$ is $C(CH_2R^{2c})$, and the other two $X^1$ are each N; and all other groups are as defined in the Summary or in some or any embodiment provided herein, including any one of Embodiments 52 to 66d-4. In a sub-embodiment, $C(CH_2R^{2c})$ is in the meta-position with respect to $R^{2d}$.

Embodiment 70: Provided is a pharmaceutical composition comprising a Compound of any one of Embodiments 52-69 or a stereoisomer, a mixture of stereoisomers, and/or a pharmaceutically acceptable salt thereof; and a pharmaceutically acceptable carrier.

Embodiment 71: Provided is a method of treating a condition, disease, or disorder by inhibiting MYST family of lysine acetyl transferases, including Kat6a and Kat6b, comprising administering to a patient in need thereof a therapeutically effective amount of the Compound of any one of Embodiments 52-69 or a stereoisomer, a mixture of stereoisomers, and/or a pharmaceutically acceptable salt thereof or a therapeutically effective amount of the composition of Embodiment 70.

Embodiment 72: Provided is the method of embodiment 71 where the condition, disease, or disorder is a hyperproliferative disease, such as cancer. In some or any embodiments, the cancer is a particular type selected from: lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, and sarcoma (e.g. angiosarcoma, chondrosarcoma, osteosarcoma). In some or any embodiments, the cancer may be a MYST overexpressing cancer; the cancer may over-express MYST protein relative to non-cancerous tissue; the cancer may overproduce MYST mRNA relative to non-cancerous tissue; the cancer may be a MYST overexpressing cancer where the overexpressed MYST protein or MYST mRNA may be any one of KATs of the MYST family, e.g. KAT6A. In some or any embodiments, the cancer is selected from one or more of the following leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, breast ductal carcinoma, colon and rectal cancer, colon cancer, squamous cell carcinoma, gastric cancer, adrenocortical cancer, anal cancer, bladder cancer, blood cancer, bone cancer, brain tumor, cancer of the female genital system, cancer of the male genital system (including testicular cancer and penile cancer), central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, testicular cancer, thyroid cancer, urinary system cancer, uterine cancer, uterine sarcoma, vaginal cancer, endocrine, neoplasms of the central nervous system (CNS), primary CNS lymphoma, spinal axis tumors, glioblastoma, brain stem glioma, pituitary adenoma, vascular system, Waldenstrom's macroglobulinemia and/or Wilms' tumor. In some or any embodiments, the cancer is breast cancer, including ER positive breast cancer, non-small cell lung cancer, prostate cancer, pancreatic cancer, ovarian cancer, or blood cancer (including a leukemia or lymphoma).

In some embodiments, provided herein are:
(a) compounds as described herein, e.g., of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), Embodiments A, B and 1-72, and pharmaceutically acceptable salts and compositions thereof;
(b) compounds as described herein, e.g., of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), Embodiments A, B and 1-72, and pharmaceutically acceptable salts and compositions thereof for use in the treatment of a condition, disease, or disorder by inhibiting MYST family of lysine acetyl transferases, including KAT6A and KAT6B;
(c) processes for the preparation of compounds as described herein, e.g., of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), Embodiments A, B and 1-72, as described in more detail elsewhere herein;
(d) pharmaceutical formulations comprising a compound as described herein, e.g., of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), Embodiments A, B and 1-72, or a stereoisomer, a mixture of stereoisomers, and/or a pharmaceutically acceptable salt thereof together with a pharmaceutically acceptable carrier;
(e) a method for the treatment of a condition, disease, or disorder by inhibiting MYST family of lysine acetyl transferases, including KAT6A and KAT6B, in a subject that includes the administration of an effective treatment amount of a compound as described herein, e.g., of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), Embodiments A, B and 1-72, its pharmaceutically acceptable salt or composition;
(f) pharmaceutical formulations comprising a compound as described herein, e.g., of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), Embodiments A, B and 1-72, or a stereoisomer, a mixture of stereoisomers, and/or a pharmaceutically acceptable salt thereof together with one or more other effective agents for treating a condition, disease, or disorder by inhibiting MYST family of lysine acetyl transferases, including KAT6A and KAT6B, optionally in a pharmaceutically acceptable carrier; or
(g) a method for the treatment of a condition, disease, or disorder by inhibiting MYST family of lysine acetyl transferases, including KAT6A and KAT6B, in a subject that includes the administration of an effective treatment amount of a compound as described herein, e.g., of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), Embodiments A, B and 1-72, its pharmaceutically acceptable salt or composition in combination and/or alternation with one or more agent for the treatment of a condition, disease, or disorder by inhibiting MYST family of lysine acetyl transferases, including KAT6A and KAT6B.

Optically Active Compounds

It is appreciated that compounds provided herein have several chiral centers and may exist in and be isolated in optically active and racemic forms. It is to be understood that any racemic, optically-active, diastereomeric, tautomeric, or stereoisomeric form, or mixtures thereof, of a compound provided herein, which possess the useful properties described herein is within the scope of the invention. It being well known in the art how to prepare optically active forms (in certain embodiments, by resolution of the racemic form by recrystallization techniques, by synthesis from optically-active starting materials, by chiral synthesis, or by chromatographic separation using a chiral stationary phase).

In some or any embodiments, the term "stereoisomers" includes diastereomers, enantiomers, rotamers, atropisomers, regioisomers, and geometric isomers; and mixtures thereof.

In certain embodiments, methods to obtain optically active materials are known in the art, and include at least the following.

i) physical separation of crystals—a technique whereby macroscopic crystals of the individual stereoisomers are manually separated. This technique can be used if crystals of the separate stereoisomers exist, i.e., the material is a conglomerate, and the crystals are visually distinct;

ii) simultaneous crystallization—a technique whereby the individual stereoisomers are separately crystallized from a solution of the racemate, possible only if the latter is a conglomerate in the solid state;

iii) enzymatic resolutions—a technique whereby partial or complete separation of a racemate by virtue of differing rates of reaction for the stereoisomers with an enzyme;

iv) enzymatic asymmetric synthesis—a synthetic technique whereby at least one step of the synthesis uses an enzymatic reaction to obtain an stereoisomerically pure or enriched synthetic precursor of the desired stereoisomer;

v) chemical asymmetric synthesis—a synthetic technique whereby the desired stereoisomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the stereoisomers with a chiral, non-racemic reagent or catalyst under kinetic conditions;

ix) stereospecific synthesis from non-racemic precursors—a synthetic technique whereby the desired stereoisomer is obtained from non-chiral starting materials and where the stereochemical integrity is not or is only minimally compromised over the course of the synthesis;

x) chiral liquid chromatography—a technique whereby the stereoisomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and stereoisomers are separated by virtue of their differing interactions in the gaseous mobile phase with a column containing a fixed non-racemic chiral adsorbent phase;

xii) extraction with chiral solvents—a technique whereby the stereoisomers are separated by virtue of preferential dissolution of one stereoisomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one stereoisomer of the racemate to pass through.

Isotopically Enriched Compounds

Also provided herein are isotopically enriched compounds, including but not limited to isotopically enriched di-substituted pyrazoles.

Isotopic enrichment (in certain embodiments, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, in certain embodiments, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster et al., Adv. Drug Res., vol. 14, pp. 1-36 (1985); Kushner et al., Can. J. Physiol. Pharmacol., vol. 77, pp. 79-88 (1999).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as T20. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. In certain embodiments, such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Pharmaceutical Compositions and Methods of Administration

The compounds provided herein can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), Embodiments A, B and 1-72, if appropriate in a salt form, either used alone or in the form of a combination with one or more compatible and pharmaceutically acceptable carriers, such as diluents or adjuvants, or with another agent for the treatment of a condition, disease, or disorder by inhibiting MYST family of lysine acetyl transferases, including KAT6A and KAT6B.

In certain embodiments, the second agent can be formulated or packaged with the compound provided herein. The second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in certain embodiments, wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, in certain embodiments, ethyl oleate. These compositions can also contain adjuvants, in particular wetting, isotonizing, emulsifying, dispersing and stabilizing agents. Sterilization can be carried out in several ways, in certain embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, in certain embodiments, dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Any embodiment described for "excipient". Such pharmaceutical carriers can be sterile liquids, such as water and oils, including those of petroleum, animal, vegetable or synthetic origin, such as peanut oil, soybean oil, mineral oil, sesame oil and the like.

Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in certain embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in certain embodiments, in the U.S. Pharmacopeia (USP 36-NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In certain embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, in certain embodiments, an animal subject, such as a mammalian subject, in certain embodiments, a human subject.

A pharmaceutical composition is formulated to be compatible with its intended route of administration. In certain embodiments, routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

In certain embodiments, dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In certain embodiments, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art.

See, e.g., Remington: The Science and Practice of Pharmacy; Pharmaceutical Press; 22 edition (Sep. 15, 2012).

Generally, the ingredients of compositions are supplied either separately or mixed together in unit dosage form, in certain embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In certain embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In certain embodiments, excipients suitable for use in oral liquid or aerosol dosage forms include, but are not limited to, water, glycols, oils, alcohols, flavoring agents, preservatives, and coloring agents. In certain embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In certain embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In certain embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In certain embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, PA), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in certain embodiments, a syloid silica gel (AEROSIL 200, manufactured by W.R. Grace Co. of Baltimore, MD), a coagulated aerosol of synthetic silica (marketed by Degussa Co. of Plano, TX), CAB O SIL (a pyrogenic silicon dioxide product sold by Cabot Co. of Boston, MA), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. In certain embodiments, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in certain embodiments, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition, disease, or disorder in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intra-arterial. Because their administration typically bypasses subjects' natural defenses against contaminants, parenteral dosage forms are typically, sterile or capable of being sterilized prior to administration to a subject. In certain embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In certain embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In certain embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating a condition, disease, or disorder by inhibiting MYST family of lysine acetyl transferases, including KAT6A and KAT6B, in a subject by administering, to a subject in need thereof, an effective amount of a compound provided herein, or a stereoisomer, a mixture of stereoisomers, and/or a pharmaceutically acceptable salt thereof. The amount of the compound or composition which will be effective in the treatment of a disorder or one or more symptoms thereof will vary with the nature and severity of the condition, disease, or disorder, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the condition, disease, or disorder described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day, in further embodiments, between about 100 and about 300 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different conditions, diseases, or disorders, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. In certain embodiments, the dosage administered to the subject may be increased to improve the prophylactic or therapeutic effect of the composition or it may be decreased to reduce one or more side effects that a particular subject is experiencing.

In certain embodiments, the daily dosage of the composition provided herein, based on weight of the active compound, administered to prevent, treat, manage, or ameliorate a condition, disorder, disease, or one or more symptoms thereof in a subject is about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, about 225 mg/kg, about 250 mg/kg, about 275 mg/kg, about 300 mg/kg, about 325 mg/kg, bout 350 mg/kg, about 375 mg/kg, about 400 mg/kg, about 425 mg/kg, about 450 mg/kg, about 475 mg/kg, about 500 mg/kg, or about 600 mg/kg. In certain embodiments, the daily dosage of the composition provided herein, based on weight of the active compound, administered to prevent, treat, manage, or ameliorate a condition, disorder, disease, or one or more symptoms thereof in a subject is between (inclusive) about 1-10 mg/kg, about 10 mg/kg, about 25-50 mg/kg, about 50-100 mg/kg, about 50-150 mg/kg, about 100-150 mg/kg, about 100-200 mg/kg, about 150-200 mg/kg, about 150-250 mg/kg, about 250-300 mg/kg, about 300-350 mg.kg, about 300-400 mg/kg, about 200-400 mg/kg, about 100-300 mg/kg, or about 400-500 mg/kg.

In certain embodiment, the twice daily dosage of the composition provided herein, based on weight of the active compound, administered to prevent, treat, manage, or ameliorate a condition, disorder, disease, or one or more symptoms thereof in a subject is about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, about 225 mg/kg, about 250 mg/kg, about 275 mg/kg, or about 300 mg/kg. In certain embodiments, the twice daily dosage of the composition provided herein, based on weight of the active compound, administered to prevent, treat, manage, or ameliorate a condition, disorder, disease, or one or more symptoms thereof in a subject is between (inclusive) about 1-10 mg/kg, about 10 mg/kg, about 25-50 mg/kg, about 50-100 mg/kg, about 50-150 mg/kg, about 100-150 mg/kg, about 100-200 mg/kg, about 150-200 mg/kg, or about 150-250 mg/kg In certain embodiments, administration of the same composition may be repeated and the administrations may be separated by at least 2 hours, 4 hours, 6 hours, 8 hours, 12 hours, 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 4 hours, 6 hours, 8 hours, 12 hours, 1 day, 2 days, 3 days, 5 days, 10 days, 15 days, 30 days, 45 days, 2 months, 75 days, 3 months, or 6 months.

In certain aspects, provided herein are unit dosages comprising a compound, or a stereoisomer, a mixture of stereoisomers, and/or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

In certain embodiments, dosages of the second agents to be used in a combination therapy are provided herein. In certain embodiments, dosages lower than those which have been or are currently being used to treat a condition, disease, or disorder by inhibiting MYST family of lysine acetyl transferases, including KAT6A and KAT6B, are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics 9$^{th}$ Ed, Mc-Graw-Hill, New York; Physician's Desk Reference (PDR) 57$^{th}$ Ed., 2003, Medical Economics Co., Inc., Montvale, NJ; which are incorporated herein by reference in their entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, in certain embodiments, a mammal, such as a human, in a sequence and within a time interval such that the compound provided herein can act together with the other agent to provide an increased benefit than if they were administered otherwise. In certain embodiments, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. In certain embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a condition, disease, or disorder by inhibiting MYST family of lysine acetyl transferases, including KAT6A and KAT6B. The kits can include a compound or composition provided herein, a second agent or composition, and instructions providing information to a health care provider regarding usage for treating a condition, disease, or disorder by inhibiting MYST family of lysine acetyl transferases, including KAT6A and KAT6B. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 day. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Inhibitors of post-translational lysine acetylation mediated by KATs of the MYST family are considered to be promising anti-neoplastic agents and therefore may be useful therapeutic agents, e.g. for use in the treatment of cancer. Such agents may also be useful as therapeutic agents for the treatment of cancers which exhibit overexpression of MYST proteins.

Provided herein is a method for treating a condition, disease, or disorder by inhibiting MYST family of lysine acetyl transferases, including KAT6A and KAT6B, in a subject, which comprises contacting the subject with a therapeutically effective amount of a compound disclosed herein, e.g., a compound of Formula (I), (Ia), (Ib), (Ic), (Id), (Ie), (If), (Ig), (Ih), (Ii), (Ij), (Ia-1), (Ib-1), (Ic-1), (Ic-2), (Id-1), (Ie-1), (If-1), or (Ig-1), Embodiments A, B and 1-72, including a single enantiomer, a mixture of an enantiomeric pair, an individual diastereomer, a mixture of diastereomers, an individual stereoisomer, a mixture of stereoisomers, an individual geometric isomer, a mixture of geometric isomers, or a tautomeric form thereof; or a pharmaceutically acceptable salt, solvate, prodrug, phosphate, or active metabolite thereof.

In certain embodiments, provided herein are methods for treating a condition, disease, or disorder by inhibiting MYST family of lysine acetyl transferases, including KAT6A and KAT6B, in a subject. In certain embodiments, the methods encompass the step of administering to the subject in need thereof an amount of a compound effective for the treatment of a condition, disease, or disorder by inhibiting MYST family of lysine acetyl transferases, including KAT6A and KAT6B, in combination with a second agent. The compound can be any compound as described herein, and the second agent can be any second agent described in the art or herein. In certain embodiments, the compound is in the form of a pharmaceutical composition or dosage form, as described elsewhere herein.

Diseases which can be treated with the Compound according to any of the Formulas described herein, including Compounds in Embodiments A, B and 1-72, include leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, breast ductal carcinoma, colon and rectal cancer, colon cancer, squamous cell carcinoma, gastric cancer, adrenocortical cancer, anal cancer, bladder cancer, blood cancer, bone cancer, brain tumor, cancer of the female genital system, cancer of the male genital system (including testicular cancer and penile cancer), central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, testicular cancer, thyroid cancer, urinary system cancer, uterine cancer, uterine sarcoma, vaginal cancer, endocrine, neoplasms of the central nervous system (CNS), primary CNS lymphoma, spinal axis tumors, glioblastoma, brain stem glioma, pituitary adenoma, vascular system, Waldenstrom's macroglobulinemia and/or Wilms' tumor.

Assay Methods

Compounds can be assayed for efficacy in treating a condition, disease, or disorder by inhibiting MYST family of lysine acetyl transferases, including KAT6A and KAT6B, according to any assay known to those of skill in the art. Exemplary assay methods are provided elsewhere herein.

Second Therapeutic Agents

In certain embodiments, the compounds and compositions provided herein are useful in methods of treatment of a condition, disease, or disorder by inhibiting MYST family of lysine acetyl transferases, including KAT6A and KAT6B, that comprise further administration of a second agent. The second agent can be any agent known to those of skill in the art to be effective for the treatment of a condition, disease, or disorder by inhibiting MYST family of lysine acetyl transferases, including KAT6A and KAT6B, including those currently approved by the United States Food and Drug Administration, or other similar body of a country foreign to the United States.

In some embodiments, the disease is cancer and the second agent is a cancer treatment. In some embodiments, the disease is cancer and the second agent is the standard of care treatment for the particular cancer to be treated. In some embodiments, the disease is cancer and the second agent is a chemotherapeutic agent. In some embodiments, the second agent is selected from an alkylating agent (e.g. cyclophosphamide, mechlorethamine, chlorambucil, melphalan, dacarbazine (DTIC), a nitrosoureas, temozolomide (oral dacarbazine); an anthracycline (e.g. daunorubicin, doxorubicin, liposomal doxorubicin, epirubicin, idarubicin, mitoxantrone, and valrubicin); a cytoskeletal disruptor (a taxane, e.g. paclitaxel, Albumin-bound paclitaxel and docetaxel); epothilone; an Histone Deacetylase inhibitor (e.g. vorinostat and romidepsin); an inhibitor of Topoisomerase I (e.g. irinotecan and topotecan); an inhibitor of Topoisomerase II (e.g. etoposide, teniposide, and tafluposide); a kinase inhibitor (e.g. sorafenib, cobimetinib, cabozantanib, lapatinib, bortezomib, erlotinib, gefitinib, imatinib, vemurafenib, and vismodegib); a nucleotide analog and precursor analog (e.g. azacitidine, azathioprine, capecitabine, cytarabine, doxifluridine, fluorouracil, gemcitabine, hydroxyurea, mercaptopurine, methotrexate, and tioguanine); a peptide antibiotic (e.g. bleomycin and actinomycin); a platinum agent (e.g. carboplatin, cisplatin, and oxaliplatin); a retinoid (e.g. tretinoin, alitretinoin, and bexarotene); a *vinca* alkaloid or derivative (e.g. Capecitabine, vinblastine, vincristine, vindesine, and vinorelbine); eribulin; ixabepilone; radiation; bevacizumab; olaparib; an aromatase inhibitor (e.g. letrozole, anastrozole, and exemestane); rituximab; ibritumomab; prednisone; a kinase inhibitor e.g. sorafenib, cobimetinib, cabozantanib, lapatinib, bortezomib, erlotinib, gefitinib, imatinib, vemurafenib, and vismodegib; a CDK1, 4, and/or 6 inhibitor, such as palbociclib, Kisqali or Verzenio; immunotherapy, such as a checkpoint inhibitor (e.g. pembrolizumab, nivolumab and atezolizumab; and enzalutamide.

In some embodiments, the disease is cancer and the second agent is a CDK1, 4, and/or 6 inhibitor. In some embodiments, the disease is cancer and the second agent is palbociclib, ribociclib, or abemaciclib.

In some embodiments, the disease is cancer and the second agent is immunotherapy, such as a checkpoint inhibitor (e.g. pembrolizumab, nivolumab and atezolizumab.

In some embodiments, the disease is breast cancer and the second agent is fulvestrant.

In some embodiments, the disease is breast cancer (e.g. post-menopausal breast carcinoma) and the second agent is radiation, docetaxel, paclitaxel, platinum agents (cisplatin, carboplatin), vinorelbine, capecitabine, liposomal doxorubicin, gemcitabine, mitoxantrone, ixabepilone, albumin-bound paclitaxel, eribulin, trastuzumab, pertuzimab, ado-trastuzumab, lapatinib, bevacizumab, olaparib, radiation, an aromatase inhibitor (e.g. letrozole, anastrozole, and exemestane), or tamoxifen.

In some embodiments, the disease is liver cancer (e.g. hepatocellular carcinoma, hepatocellular carcinoma not amenable to surgical or locoregional therapy) and the second agent is sorafenib.

In some embodiments, the disease is prostate cancer and the second agent is radiation, abiraterone, or enzalutamide.

In some embodiments, the disease is pancreatic adenocarcinoma and the second agent is radiation.

In some embodiments, the disease is ovarian cancer and the second agent is bevacizumab, olaparib, radiation, an aromatase inhibitor (e.g. letrozole, anastrozole, and exemestane), or tamoxifen.

In some embodiments, the disease is B cell lymphoma and the second agent is rituximab, radiation, ibritumomab, cyclophosphamide, doxorubicin, vincristine, or prednisone.

In certain embodiments, a compound provided herein is administered in combination with one second agent. In further embodiments, a compound provided herein is administered in combination with two second agents. In still further embodiments, a compound provided herein is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an agent effective in the treatment of a condition, disease, or disorder by inhibiting MYST family of lysine acetyl transferases, including KAT6A and KAT6B. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition, disease, or disorder to be treated. It is to be further understood that for any particular subject, specific dosage regimens and schedules should be adjusted over time according to the individual need and the professional judgment of the person administering or supervising the administration of the compositions.

Preparation of Compounds

The compounds provided herein can be prepared, isolated or obtained by any method apparent to those of skill in the art. Compounds provided herein can be prepared according to the Exemplary Preparation Schemes provided below. Reaction conditions, steps, and reactants not provided in the Exemplary Preparation Schemes would be apparent to, and known by, those skilled in the art.

Additional steps and reagents not provided in the Exemplary Preparation Schemes would be known to those of skill in the art. Exemplary methods of preparation are described in detail in the Examples herein.

GENERAL SCHEME 1

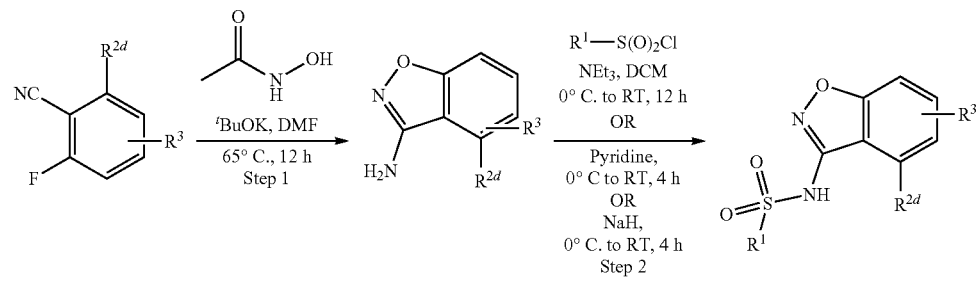

(A)

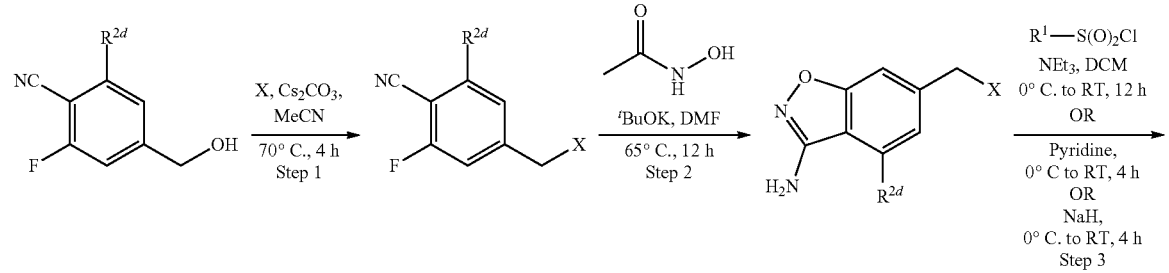

(B)

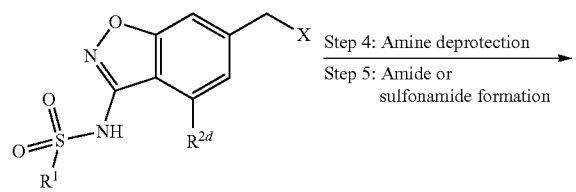

-continued

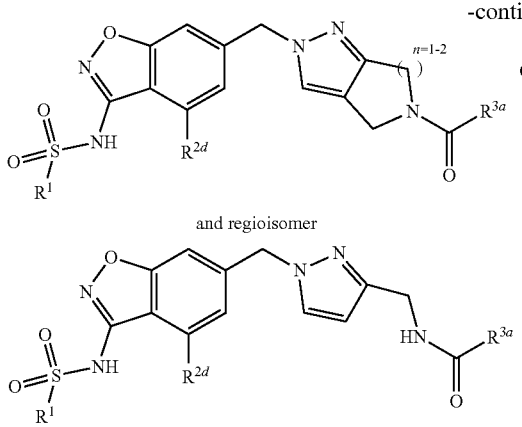

and regioisomer

OR

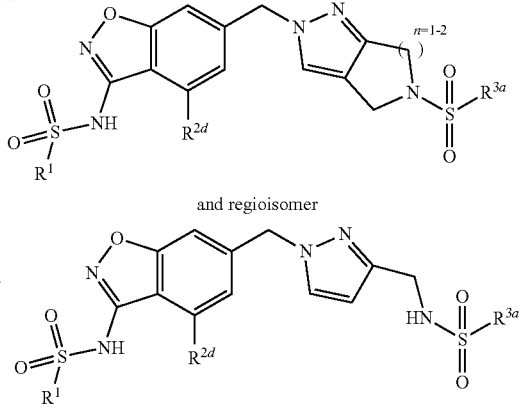

and regioisomer

General Scheme 1A describes the preparation of a Compound of Formula (I) where $R^2$ is ring (b); one $X^1$ is $CR^3$, and the other two are CH; and all other groups are as defined in the Summary or in any embodiments described herein. General Scheme 1B describes the preparation of a Compound of Formula (I) where $R^2$ is ring (b); one $X^1$ is $CR^3$, and the other two are CH; $R^3$ is —(CH$_2$)Y; Y is

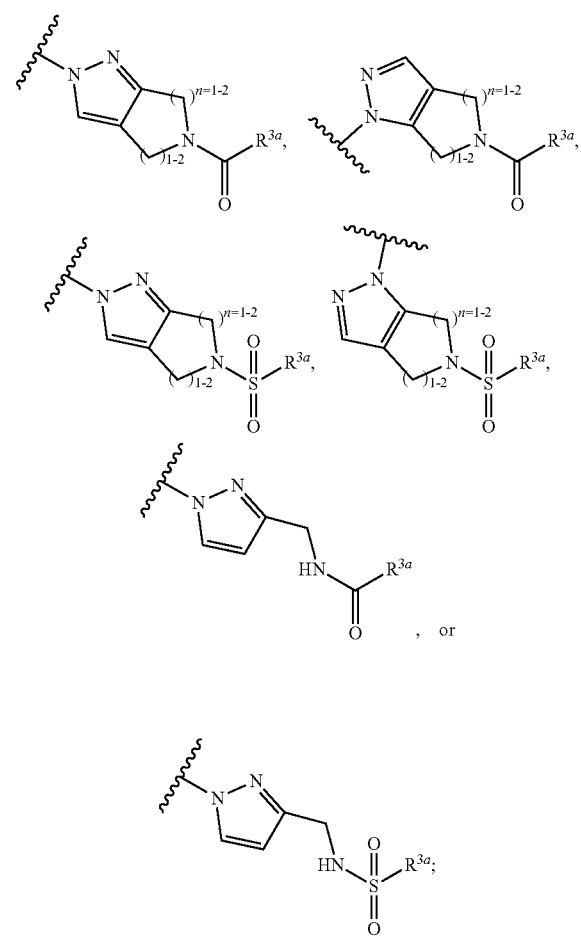

, or and all other groups are as defined in the Summary or in any embodiments described herein.

General Scheme 1 describes the preparation of a Compound of Formula (I)

Scheme (A) describes a way to prepare the appropriately substituted benzo[d]isoxazole compounds where in Step 1, a 2-fluorobenzonitrile can be converted to a benzo[d]isoxazol-3-amine scaffold by reacting with N-hydroxyacetamide in presence of a base like potassium t-butoxide. In Step 2, the free amine is reacted with $R^1S(O)_2Cl$ in presence of a base such as triethylamine, pyridine or sodium hydride.

Scheme (B) describes a synthesis of compounds where $R^3$ is —(CH$_2$)Y and Y is an appropriately substituted 5-membered heteroaryl such as a pyrazole. This synthesis can be extended to other heteroaryls, including C-linked heteroaryls by those skilled in the art.

The synthesis of the benzo[d]isoxazole compounds can be started with an appropriately substituted 2-fluoro-4-(hydroxymethyl)benzonitrile. The hydroxy group can be converted to a substituted pyrazole moiety by reacting with a compound of formula Ms-X (where Ms-X is

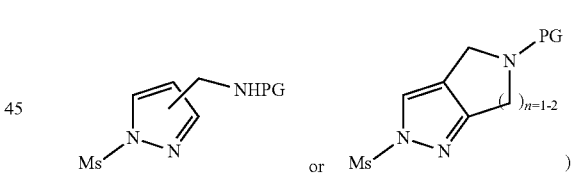

in presence of a base such as CsCO$_3$ as shown in Step 1 above. The fluorobenzonitrile can be converted to the benzo[d]isoxazol-3-amine scaffold by its reaction with N-hydroxyacetamide in presence of a base like potassium t-butoxide (Step 2 above). In the next step (Step 3), the free amine is reacted with $R^1S(O)_2Cl$ in presence of a base such as triethylamine, pyridine or sodium hydride. The final steps involve deprotection of the amine (Step 4) followed by amide formation (either via a reaction with $R^{3a}C(O)Cl$, where $R^{3a}$ is selected from group a), or via activation of $R^{3a}C(O)OH$, where $R^{3a}$ is selected from group a), using a coupling agent such as HATU, HBTU, T3P, EDCI/HOBt or other agents known to those skilled in the art) or sulfonamide formation with a sulfonyl chloride ($R^{3a}S(O)_2Cl$, where $R^{3a}$ is selected from group a)) in the presence of a base such as triethyl amine in Step 5.

GENERAL SCHEME 2
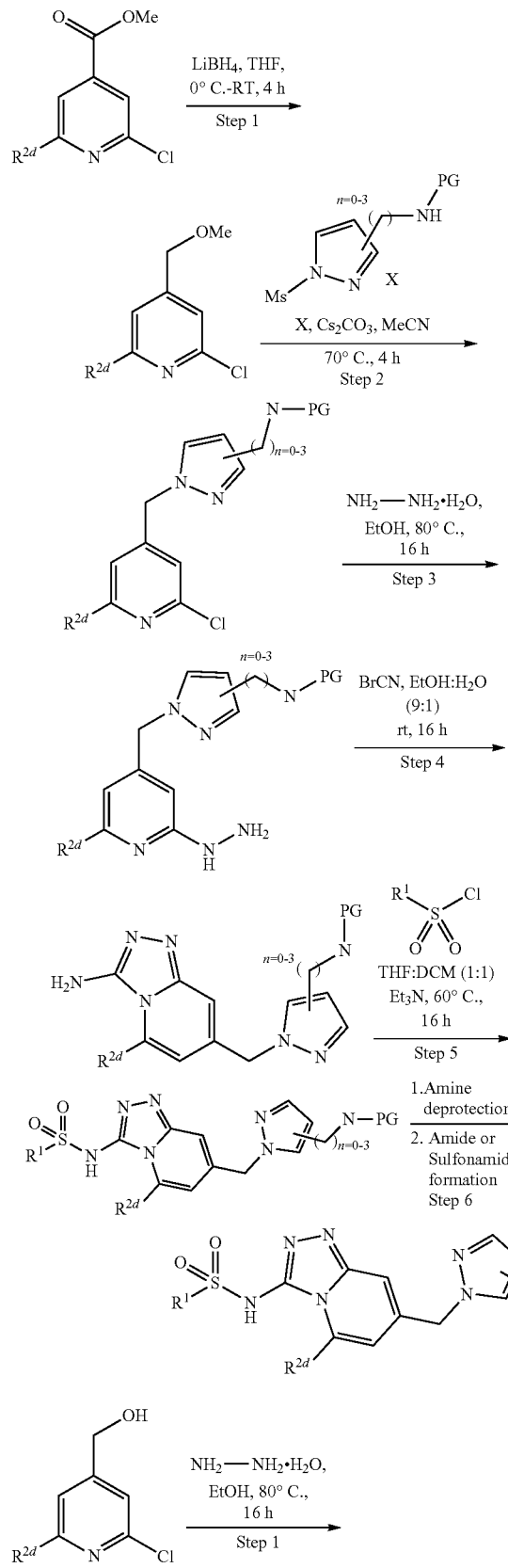
(A)
(B)
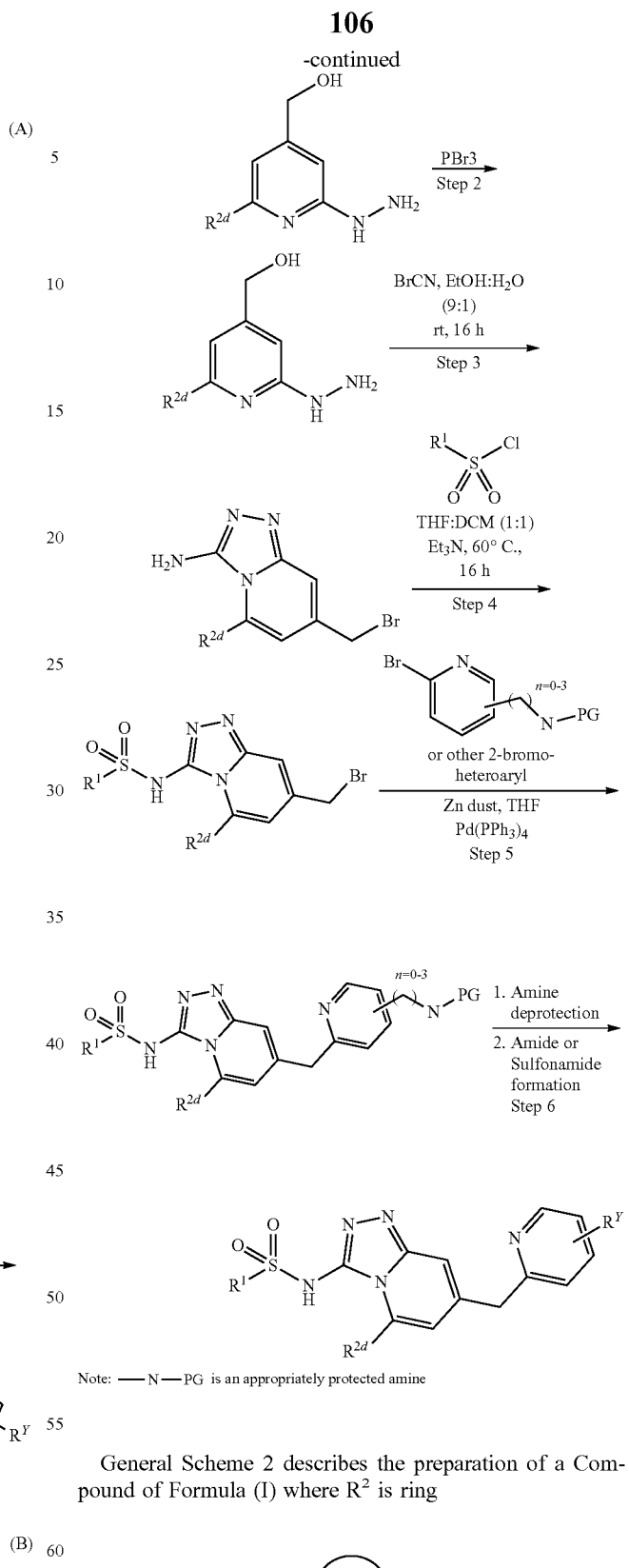
Note: —N—PG is an appropriately protected amine
General Scheme 2 describes the preparation of a Compound of Formula (I) where $R^2$ is ring
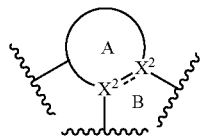

is

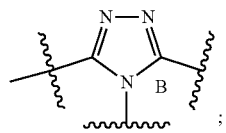

$R^3$ is —$(CH_2)Y$ and Y is pyrazolyl or pyridinyl, each of which is substituted with $R^Y$; and all other groups are as defined in the Summary or in any embodiments described herein.

The [1,2,4]triazolo[4,3-a]pyridine compounds can be prepared by starting with an appropriately substituted methyl-2-chloroisonicotinate. In Scheme (A) above, with a reducing agent like LiBH4, the ester can be reduced to an alcohol (Step 1 above). The hydroxy group can be converted to a substituted pyrazole moiety by reacting with a 1-(methylsulfonyl)-1H-pyrazole of formula X in presence of a base such as $CsCO_3$ as shown in Step 2 above. The resulting 2-chloropyridine can be converted to the corresponding 2-hydrazinopyridine by heating in presence of hydrazine hydrate (Step 3). In Step 4, reaction with cyanogen bromide can lead to the assembly of the [1,2,4]triazolo[4,3-a]pyridin-3-amine scaffold. Reaction with $R^1S(O)_2Cl$ in the presence of a base such as triethyl amine, pyridine or sodium hydride can lead to the N-linked pyrazole substituted compounds. The final steps involve deprotection of the amine (Step 4) followed by amide formation (either via a reaction with $R^{3a}C(O)Cl$, where $R^{3a}$ is selected from group a), or via activation of $R^{3a}C(O)OH$, where $R^{3a}$ is selected from group a), using a coupling agent such as HATU, HBTU, T3P, EDCI/HOBt or other agents known to those skilled in the art) or sulfonamide formation with a sulfonyl chloride ($R^{3a}S(O)_2Cl$, where $R^{3a}$ is selected from group a)) in the presence of a base such as triethyl amine in Step 6.

For the C-linked heteroaryl substituted final compounds, a slightly altered Scheme (B) can be used. In this case, the main difference is that the hydroxymethyl pyridine can be converted to a bromomethyl group using phosphorus tribromide (Step 2). Eventually, this bromomethyl group can be subjected to Negishi coupling conditions with a 2-bromo-hetero aryl compound (2-bromopyridine in Scheme (B)), through the mediation of zinc dust followed by a palladium catalyst such as tetrakis(triphenylphosphine)palladium. Such a method can be applied to other heteroaryl analogs as well.

General Scheme 3

General Scheme 3 describes the preparation of a Compound of Formula (I) where $R^2$ is ring (c);

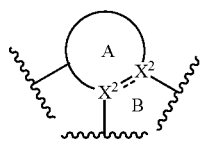

is

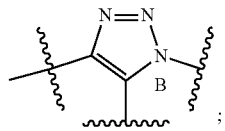

$R^3$ is —$(CH_2)Y$ and Y is pyrazolyl substituted with $R^Y$ and optionally substituted with $R^{2e}$; and all other groups are as defined in the Summary or in any embodiments described herein.

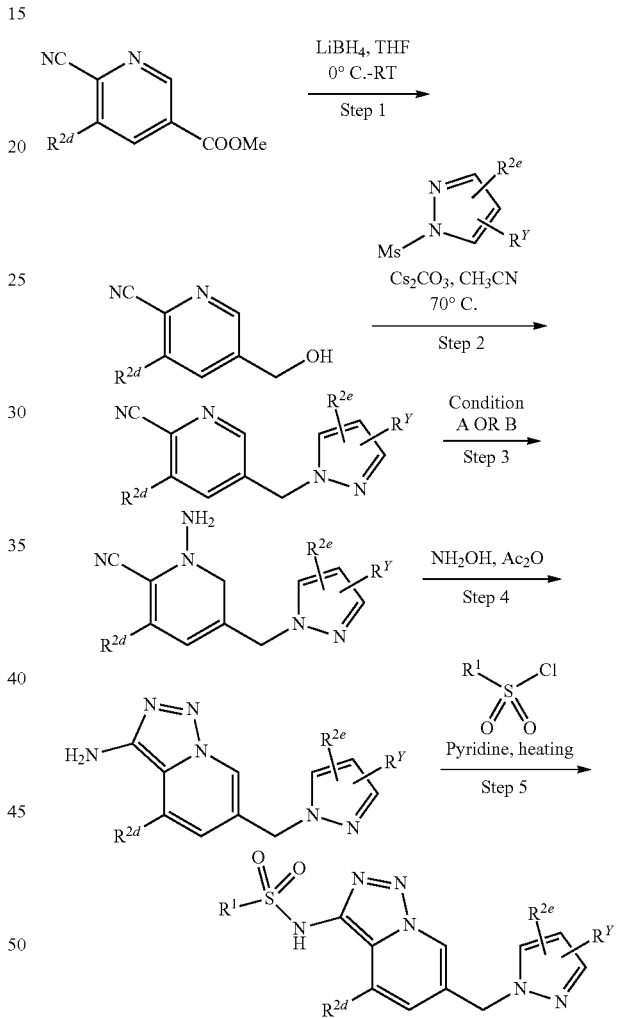

Condition A: O-Mesitylenesulfonylhydroxylamine in 10-40% $H_2O$, DCM, 0° C., 3 h
Condition B: $NH_2OSO_3H$, $K_2CO_3$, HI, $H_2O$, 90° C., 3 h The [1,2,3]triazolo[1,5-a]pyridine compounds can be synthesized using a substituted 2-cyanopyridine compound. The introduction of the N-linked pyrazole moiety (Steps 1 and 2) can use procedures described above for the [1,2,4]triazolo [4,3-a]pyridine compounds. The assembly of the core scaffold is described in Steps 3 and 4 above. The 2-cyano pyridine can be converted to a 1-amino 2-cyano pyridine by reacting with a sulfonylated hydroxyl amine (Step 3), followed by cyclization in the presence of hydroxylamine and acetic anhydride. In the final step (Step 5), the free amine can be reacted with $R^1S(O)_2Cl$ in presence of a base such as triethyl amine, pyridine or sodium hydride. In this Scheme, $R^Y$ can be a group that harbors an amine with an appropriate protecting group. After scaffold assembly in Step 5, the final steps can involve deprotection of the amine followed by amide formation (either via a reaction with $R^{3a}C(O)Cl$, where $R^{3a}$ is selected from group a), or via activation of $R^{3a}C(O)OH$, where $R^{3a}$ is selected from group a), using a coupling agent such as HATU, HBTU, T3P, EDCI/HOBt or other agents known to those skilled in the art) or sulfonamide formation with a sulfonyl chloride ($R^{3a}S(O)_2Cl$, where $R^{3a}$ is selected from group a)) in the presence of a base such as triethyl amine.

heteroaryl with a substituent $R^Y$ that harbors an amine with an appropriate protecting group. After scaffold assembly in Step 6, the final steps can involve deprotection of the amine followed by amide formation (either via a reaction with $R^{3a}C(O)Cl$, where $R^{3a}$ is selected from group a), or via activation of $R^{3a}C(O)OH$, where $R^{3a}$ is selected from group a), using a coupling agent such as HATU, HBTU, T3P, EDCI/HOBt or other agents known to those skilled in the art) or sulfonamide formation with a sulfonyl chloride ($R^{3a}S(O)_2Cl$, where R3a is selected from group a)) in the presence of a base such as triethyl amine.

GENERAL SCHEME 4

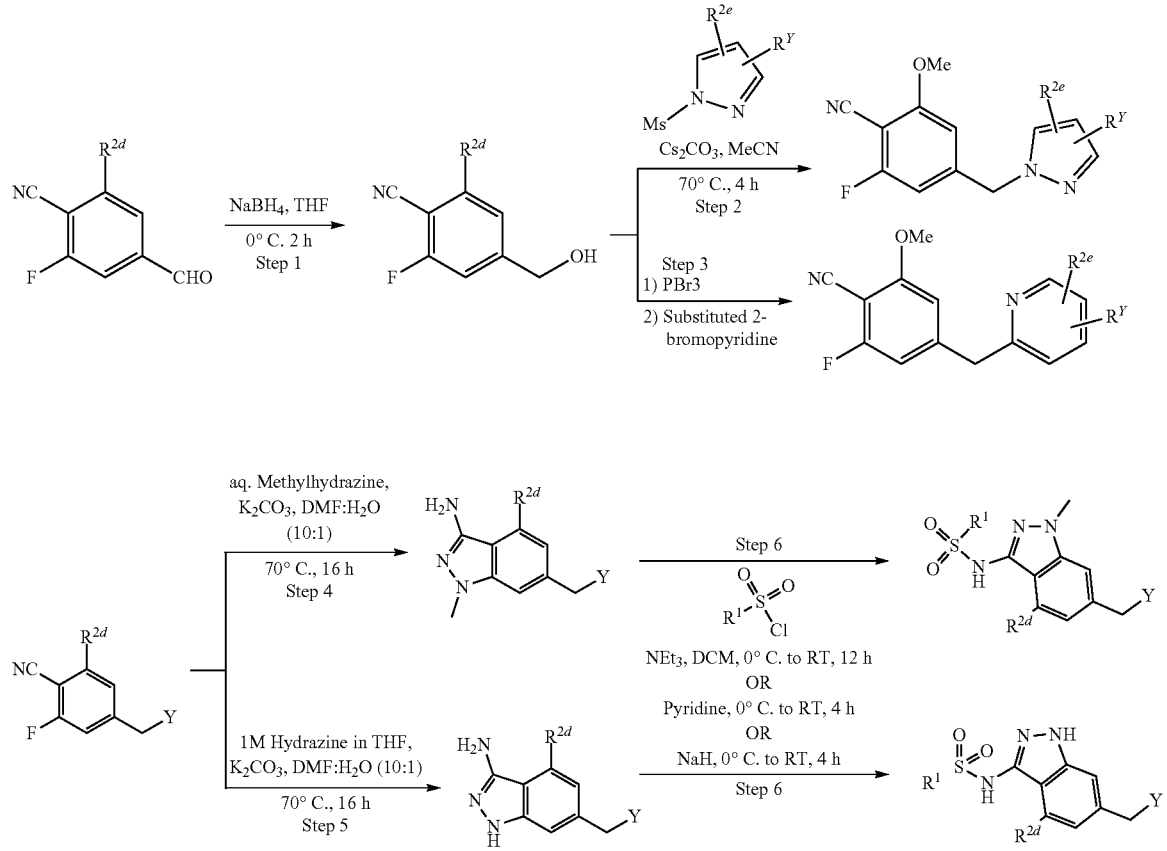

General Scheme 4 describes the preparation of a Compound of Formula (I) where $R^2$ is ring (a) and $R^3$ is —(CH$_2$)Y; and all other groups are as defined in the Summary or in any embodiments described herein.

The benzopyrazole compounds can be synthesized by using an appropriately substituted 2-fluorobenzonitrile as starting material. Steps 1, 2 and 3 can be done as described previously in General Schemes 2 and 3 above. The fluoro benzonitrile intermediate can be converted to the N-methyl benzopyrazole (Step 4, using methyl hydrazine) or unsubstituted benzopyrazole (Step 5, using hydrazine) as shown above. In Step 6, the free amine can be reacted with $R^1S(O)_2Cl$ in presence of a base such as triethyl amine, pyridine or sodium hydride. In this Scheme, Y can be a

GENERAL SCHEME 5

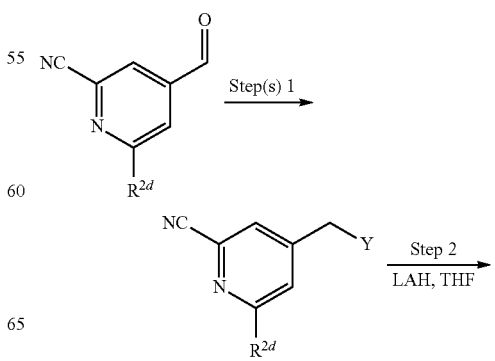

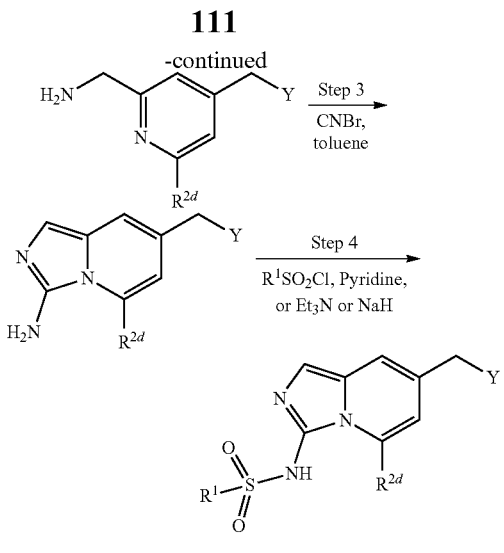

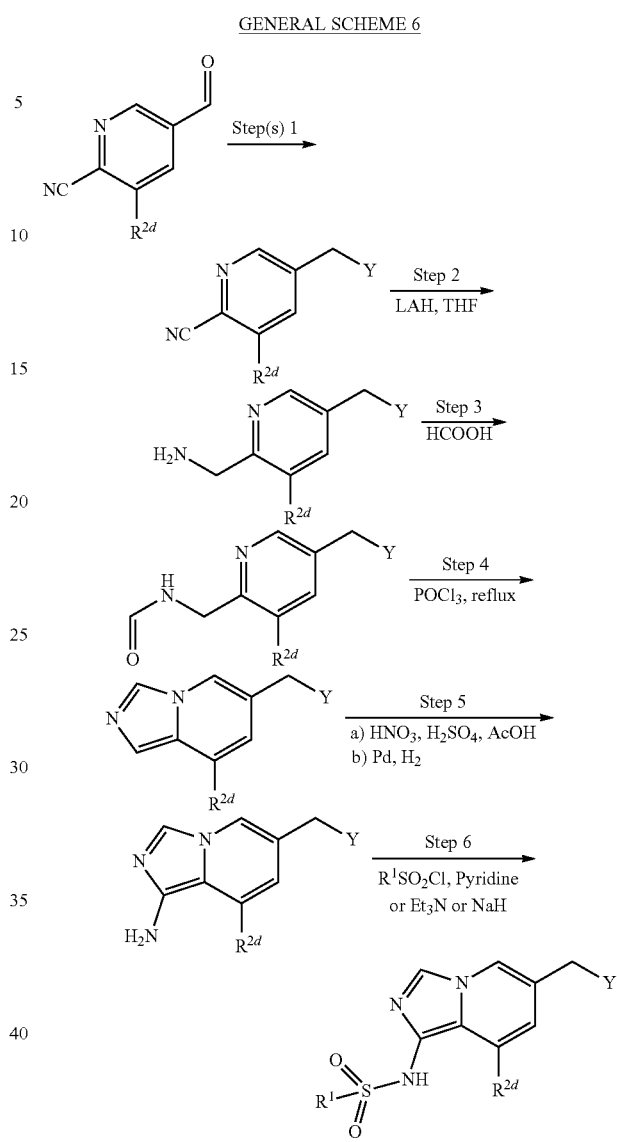

GENERAL SCHEME 6

General Scheme 5 describes the preparation of a Compound of Formula (I) where $R^2$ is ring (c);

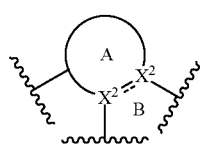

is

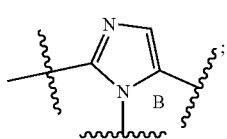

$R^3$ is —$(CH_2)Y$; and all other groups are as defined in the Summary or in any embodiments described herein.

By starting with an appropriately substituted 2-cyano-4-formyl pyridine. Step(s) 1 constitute reduction of the aldehyde with $NaBH_4$ to the alcohol followed by substitution with leaving group, such as methylsulfonyl or a halide, and can be done as described previously in Steps 2 and 3 of General Scheme 4. Reduction in Step 2 can be accomplished by treating the picolinonitrile with LAH in THF. Treatment of the 2-aminomethyl pyridine intermediate with cyanogen bromide in toluene (Step 3) can afford the imidazo[1,5-a]pyridin-3-amine intermediate which can be converted to the desired Compound of Formula I with $R^1S(O)_2Cl$ and a base such as pyridine, triethylamine or sodium hydride as shown in Step 2 and described in General Scheme 1(A). In this Scheme, Y can be a heteroaryl with a substituent $R^Y$ that harbors an amine with an appropriate protecting group. After scaffold assembly in Step 4, the final steps can involve deprotection of the amine followed by amide formation (either via a reaction with $R^{3a}C(O)Cl$, where $R^{3a}$ is selected from group a), or via activation of $R^{3a}C(O)OH$, where $R^{3a}$ is selected from group a), using a coupling agent such as HATU, HBTU, T3P, EDCI/HOBt or other agents known to those skilled in the art) or sulfonamide formation with a sulfonyl chloride ($R^{3a}S(O)_2Cl$, where R3a is selected from group a)) in the presence of a base such as triethyl amine.

General Scheme 6 describes the preparation of a Compound of Formula (I) where $R^2$ is ring (c);

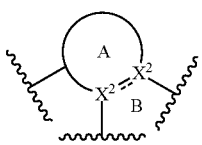

is

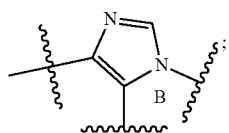

$R^3$ is —$(CH_2)Y$; and all other groups are as defined in the Summary or in any embodiments described herein.

An appropriately substituted 2-cyano-5-formyl pyridine can be subjected to steps 1 and 2 following methods described in Scheme 5 above. Steps 3 and 4 involve N-formylation followed by refluxing in phosphorus oxychloride to construct the imidazo[1,5-a]pyridine ring. Nitration and reduction with the reagents in Step 5 can lead to the substituted imidazo[1,5-a]pyridin-1-amine. The final sulfonamide products can result by reacting this amine with $R^1S(O)_2Cl$ and a base such as pyridine, triethylamine or sodium hydride as shown in Step 6 and described in General Scheme 1. In this Scheme, Y can be a heteroaryl with a substituent $R^Y$ that harbors an amine with an appropriate protecting group. After scaffold assembly in Step 6, the final steps can involve deprotection of the amine followed by amide formation (either via a reaction with $R^{3a}C(O)Cl$, where $R^{3a}$ is selected from group a), or via activation of $R^{3a}C(O)OH$, where $R^{3a}$ is selected from group a), using a coupling agent such as HATU, HBTU, T3P, EDCI/HOBt or other agents known to those skilled in the art) or sulfonamide formation with a sulfonyl chloride ($R^{3a}S(O)_2Cl$, where $R^{3a}$ is selected from group a)) in the presence of a base such as triethyl amine.

an appropriately substituted acid using a coupling agent such as HBTU or with an appropriately substituted acid chloride or sulfonyl chloride in the presence of a base such as triethyl amine. In this Scheme, $R^4$ can be a linker that harbors an amine with an appropriate protecting group. After scaffold assembly in Step 3, the final steps can involve deprotection of the amine followed by amide formation (either via a reaction with $R^{3a}C(O)Cl$, where $R^{3a}$ is selected from group a), or via activation of $R^{3a}C(O)OH$, where $R^{3a}$ is selected from group a), using a coupling agent such as HATU, HBTU, T3P, EDCI/HOBt or other agents known to those skilled in the art) or sulfonamide formation with a sulfonyl chloride ($R^{3a}S(O)_2Cl$, where $R^{3a}$ is selected from group a)) in the presence of a base such as triethyl amine.

GENERAL SCHEME 7

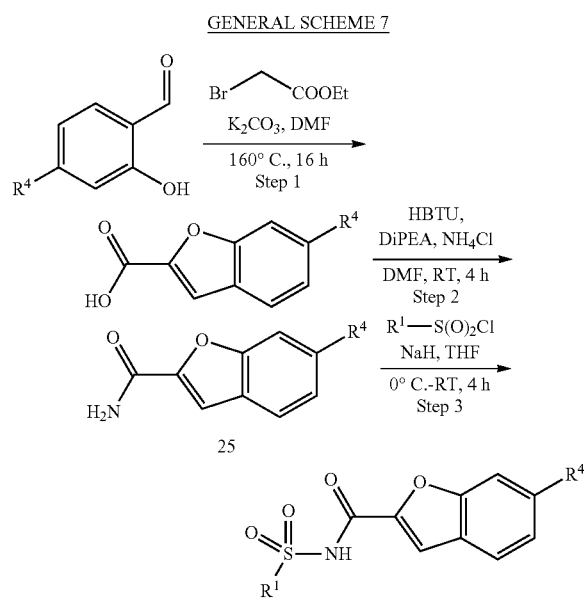

GENERAL SCHEME 8

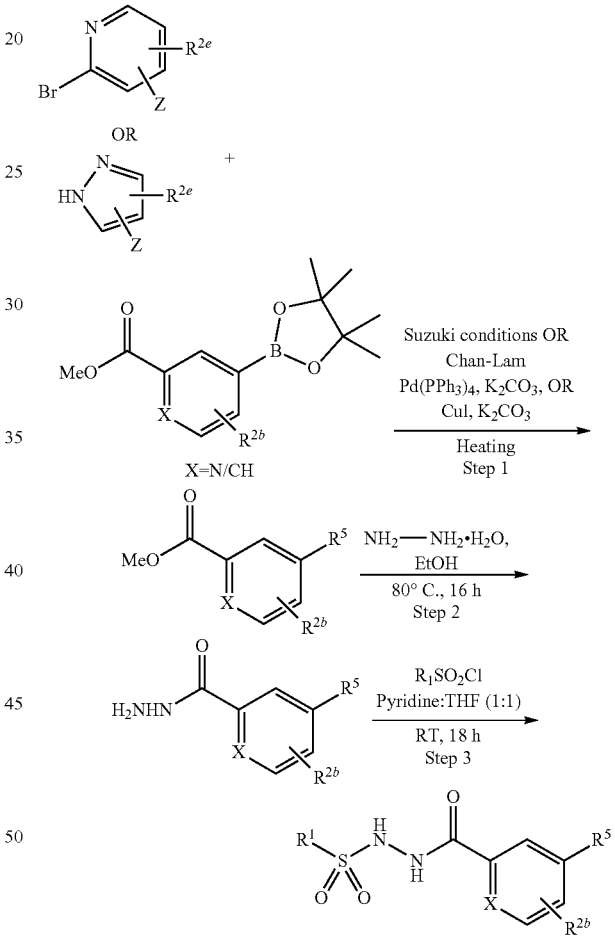

General Scheme 7 describes the preparation of a Compound of Formula (I) where $R^2$ is ring (d); $X^{2a}$ is O; one $X^2$ is $CR^4$ and the other $X^2$ are each CH; and all other groups are as defined in the Summary or in any embodiments described herein.

The synthesis of the benzofuran compounds can be started with an appropriately substituted 2-hydroxybenzaldehyde compound. Cyclization to the benzofuran compound (Step 1) occurs by heating with ethyl bromoacetate in presence of a base such as K2CO3. The resulting acid can be converted to the corresponding primary amide (Step 2) using ammonium chloride and an amide coupling agent such as HATU, HBTU, T3P, EDCI/HOBt or other agents known to those skilled in the art, in presence of a base. The synthesis of the acyl sulfonamide in Step 3 can be accomplished by deprotonating the primary amide with a base like NaH and then reacting with an appropriately substituted sulfonyl chloride. Step 4 constitutes deprotection of the amine protecting group followed by Step 5 where the amine is coupled with General Scheme 8 describes the preparation of a Compound of Formula (I) where $R^2$ is ring (e) or ring (f); and all other groups are as defined in the Summary or in any embodiments described herein.

The synthesis of the N'-benzoyl sulfonyl hydrazide compounds of Formula (I) can be started with a Suzuki coupling of an appropriately substituted 2-bromoheteroaryl or a Chan-Lam coupling of an appropriately substituted pyrazole (for example) with methyl or ethyl 3-carboxyphenyl boronic acid/ester (Step 1). In Step 2, the ester can be reacted with hydrazine hydrate under heating to convert to the corresponding hydrazide. The hydrazide can be converted to the sulfonyl hydrazide by reacting with an appropriately substituted sulfonyl chloride in the presence of a base like pyridine. In this general Scheme, $R^5$ can be a 5- or 6-membered monocyclic heteroaryl substituted with Z and optionally substituted with $R^{2e}$.

Z harbors an amine with an appropriate protecting group. After scaffold assembly in Step 3, the final steps can involve deprotection of the amine followed by amide formation (either via a reaction with $R^{3a}C(O)Cl$, where $R^{3a}$ is selected from group a), or via activation of $R^{3a}C(O)OH$, where $R^{3a}$ is selected from group a), using a coupling agent such as HATU, HBTU, T3P, EDCI/HOBt or other agents known to those skilled in the art) or sulfonamide formation with a sulfonyl chloride ($R^{3a}S(O)_2Cl$, where $R^{3a}$ is selected from group a)) in the presence of a base such as triethyl amine.

GENERAL SCHEME 9

(A) Scaffold Assembly

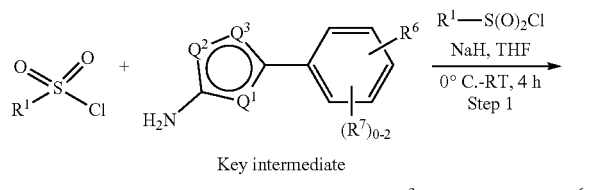

Key intermediate (B) Synthesis of key intermediate (1)

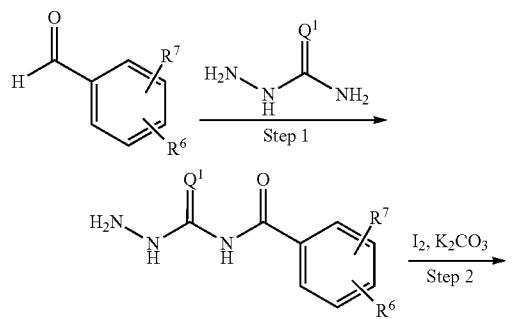

(2)

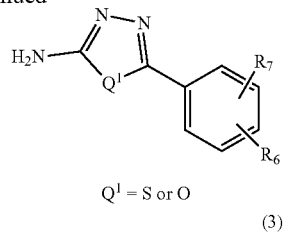

$Q^1$ = S or O (3)

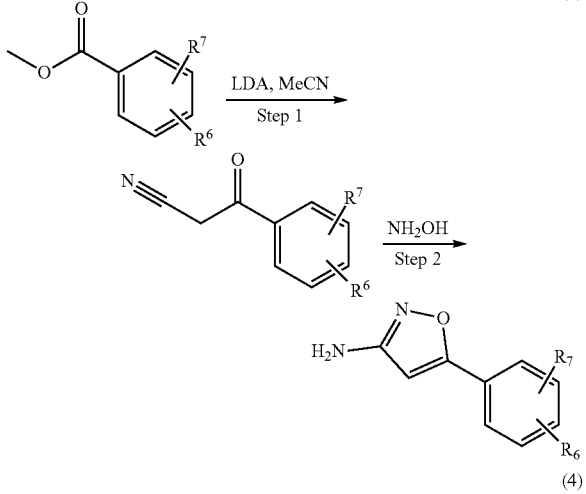

(4)

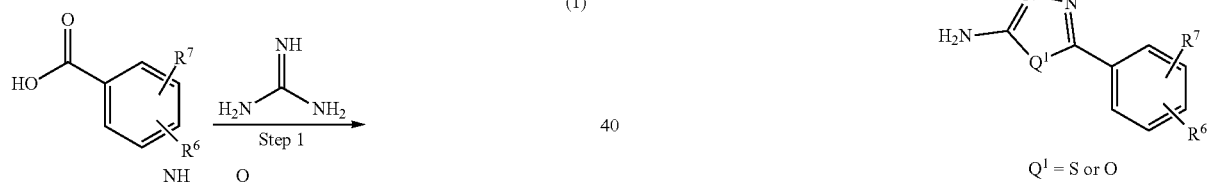

$Q^1$ = S or O

General Scheme 9 describes the preparation of a Compound of Formula (I) where $R^2$ is ring (g), where $Q^1$ and $Q^2$ are each N and $Q^3$ is O; or $Q^2$ and $Q^3$ are each N and $Q^1$ is S or O; or $Q^1$ is CH, $Q^2$ is N, and $Q^3$ is O.

Ring (g) can be assembled by reaction of an appropriately substituted phenyl-heteroaryl amine with $R^1S(O)_2Cl$ in presence of a base such as triethyl amine, pyridine or sodium hydride. In ring (g), $R^6$ is a monocyclic heteroaryl substituted with Q and optionally substituted with $R^{2e}$; or $R^6$ is Q. Q initially harbors an amine with an appropriate protecting group. After scaffold assembly in Step 1, the final steps can involve deprotection of the amine followed by amide formation (either via a reaction with $R^{3a}C(O)Cl$, where $R^{3a}$ is selected from group a), or via activation of $R^{3a}C(O)OH$, where $R^{3a}$ is selected from group a), using a coupling agent such as HATU, HBTU, T3P, EDCI/HOBt or other agents known to those skilled in the art) or sulfonamide formation with a sulfonyl chloride ($R^{3a}S(O)_2Cl$, where $R^{3a}$ is selected from group a)) in the presence of a base such as triethyl amine.

The assembly of the key intermediate (phenyl-heteroaryl amine) shown in Step 1(A) can be done through various means, as known to persons skilled in the art. Some examples are drawn in the Scheme 9(B). In row (1), an appropriately substituted benzoic acid can be activated using a coupling agent such as HATU, HBTU, T3P, EDCI/HOBt or other agents known to those skilled in the art, then reacting with guanidine. The cyclization to the aminoheteroaryl intermediate can accomplished through the mediation of iodobenzene diacetate. In row (2), an appropriately substituted benzaldehyde can be condensed with semicarbazide/thiosemicarbazide in the presence, but not limited to NaOAc. The oxidative cyclization to the key aminoheteroaryl intermediate can be accomplished in the presence of iodine and a base such as $K_2CO_3$ or $Cs_2CO_3$. In another instance (Row 3), an appropriately substituted methylbenzoate ester can be converted to the corresponding 3-oxo-3-phenylpropanenitrile using a base such as LDA and reacting with acetonitrile. Cyclization to the amino isoxazole compound occurs in the presence of hydroxyl amine. Row 4 illustrates another general method to assemble this key intermediate. A protected 2-amino 5-bromo substituted heteroaryl compound can undergo Suzuki coupling (or other coupling conditions known to those skilled in the art) with an appropriately substituted phenyl boronic acid (or boronic ester). Subsequent deprotection of the amine can afford the desired key intermediate.

$C(CH_2R^{2c})$, and the other two $X^1$ are $CR^{2e}$; and $R^{2c}$ is pyrazol-1-yl substituted with two $R^{2c1}$; and all other groups are as defined in the Summary or in any embodiments described herein.

The synthesis of the benzo[d]isoxazole compounds can be started with an appropriately substituted 2-fluoro-4-(hydroxymethyl)benzonitrile. The hydroxy group can be converted to a substituted pyrazole moiety by reacting with a 1-(methylsulfonyl)-1H-pyrazole of formula X in presence of a base such as $CsCO_3$ as shown in Step 1 above. The fluorobenzonitrile can be converted to the benzo[d]isoxazol-3-amine scaffold by its reaction with N-hydroxyacetamide in presence of a base like potassium t-butoxide (Step 2 above). In the final step (Step 3), the free amine can be reacted with $R^1S(O)_2Cl$ in presence of a base such as triethylamine, pyridine or sodium hydride.

GENERAL SCHEME 11

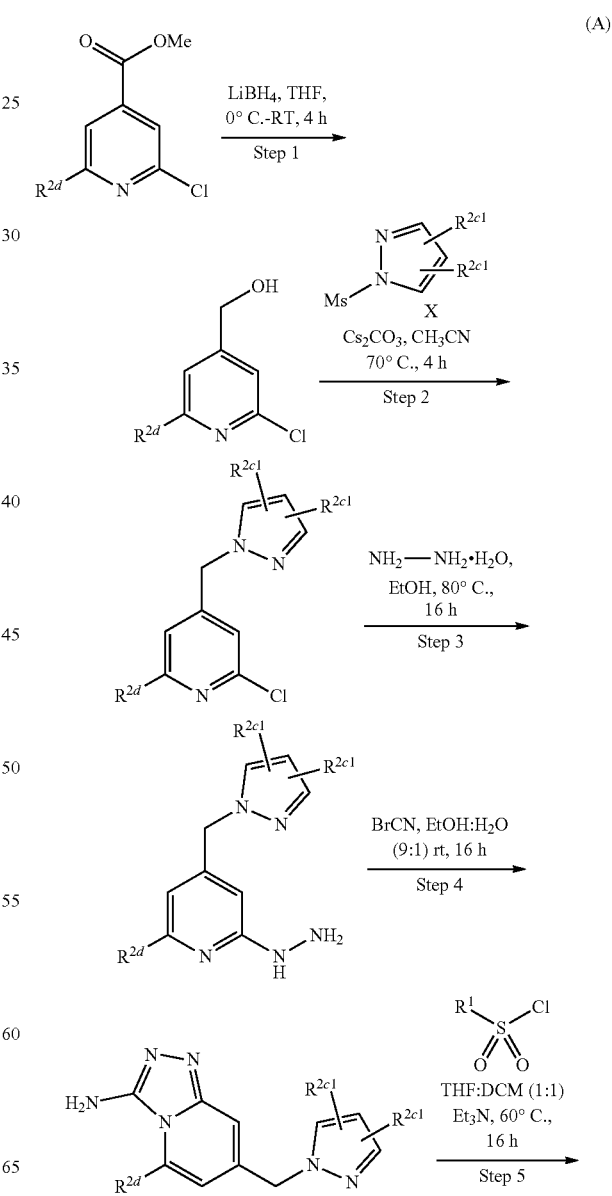

GENERAL SCHEME 10

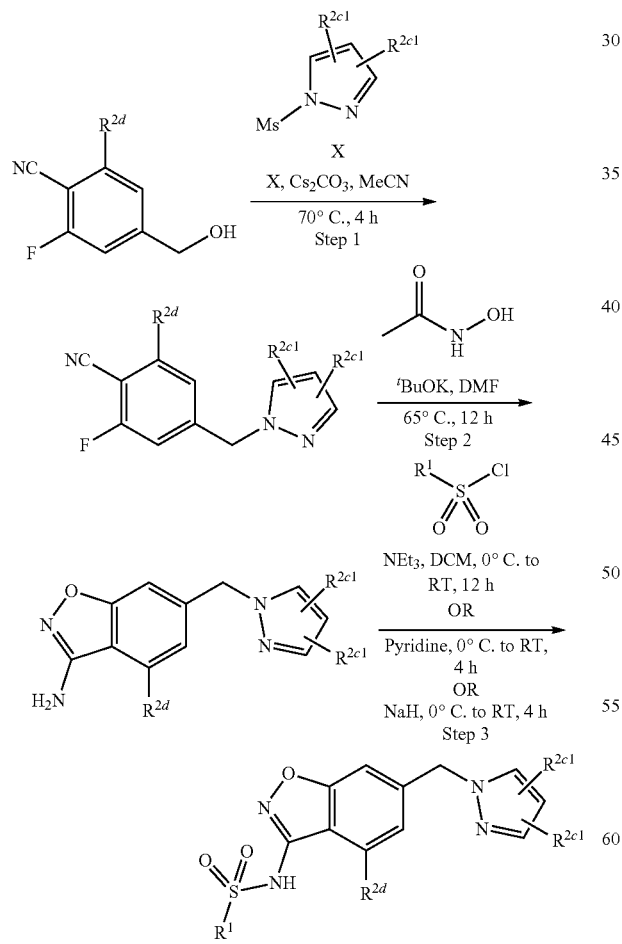

General Scheme 10 describes the preparation of a Compound of Formula (I) where $R^2$ is ring (b); one $X^1$ is -continued

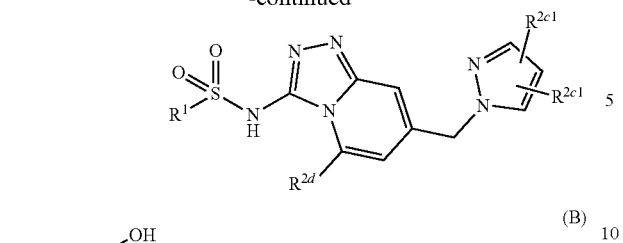

(B)

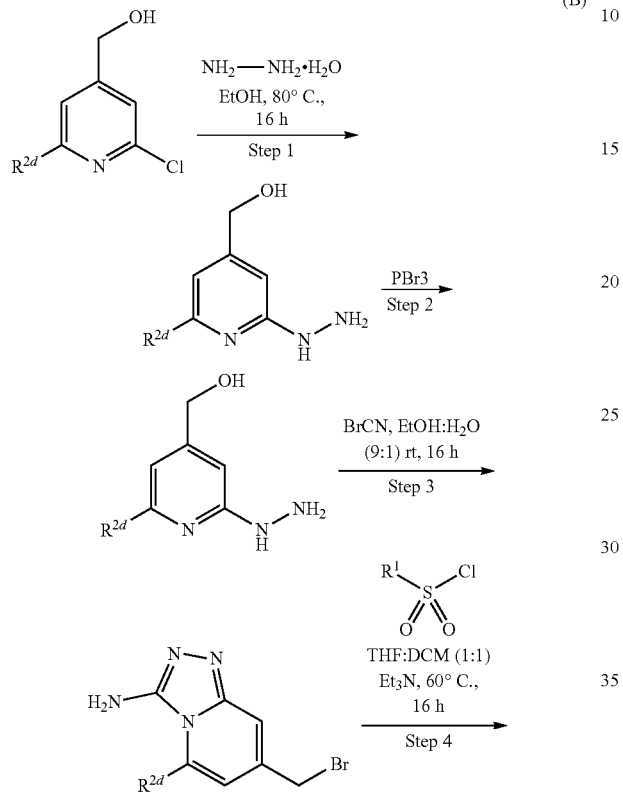

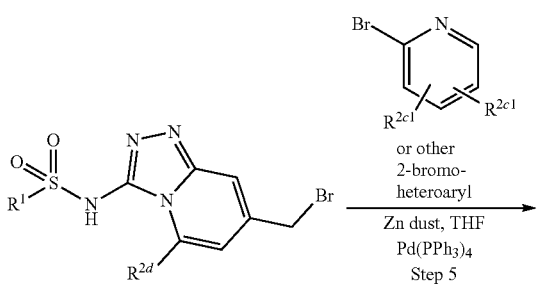

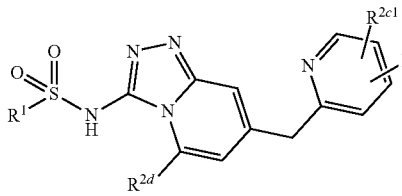

General Scheme 11 describes the preparation of a Compound of Formula (I) where $R^2$ is ring (c);

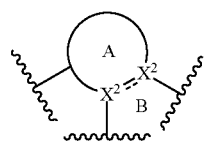

is

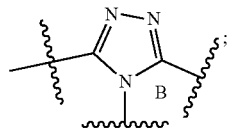

one $X^1$ is $C(CH_2R^{2c})$, and the other two $X^1$ are $CR^{2e}$; and $R^{2c}$ is pyrazol-1-yl substituted with two $R^{2c1}$; and all other groups are as defined in the Summary or in any embodiments described herein.

The [1,2,4]triazolo[4,3-a]pyridine compounds can be prepared by starting with an appropriately substituted methyl-2-chloroisonicotinate. In Scheme (A) above, with a reducing agent like LiBH4, the ester can be reduced to an alcohol (Step 1 above). The hydroxy group can be converted to a substituted pyrazole moiety by reacting with a 1-(methylsulfonyl)-1H-pyrazole of formula X in presence of a base such as $CsCO_3$ as shown in Step 2 above. The resulting 2-chloropyridine can be converted to the corresponding 2-hydrazinopyridine by heating in presence of hydrazine hydrate (Step 3). In Step 4, reaction with cyanogen bromide can lead to the assembly of the [1,2,4]triazolo[4,3-a]pyridin-3-amine scaffold. Reaction with $R^1S(O)_2Cl$ in the presence of a base such as triethyl amine, pyridine or sodium hydride can lead to the N-linked pyrazole substituted final compounds.

For the C-linked heteroaryl substituted final compounds, a slightly altered Scheme (B) can be used. In this case, the main difference is that the hydroxymethyl pyridine can be converted to a bromomethyl group using phosphorus tribromide (Step 2). Eventually, this bromomethyl group can be subjected to Negishi coupling conditions through the mediation of zinc dust followed by a palladium catalyst such as tetrakis(triphenylphosphine)palladium. Such a method can be applied to other heteroaryl analogs as well.

GENERAL SCHEME 12

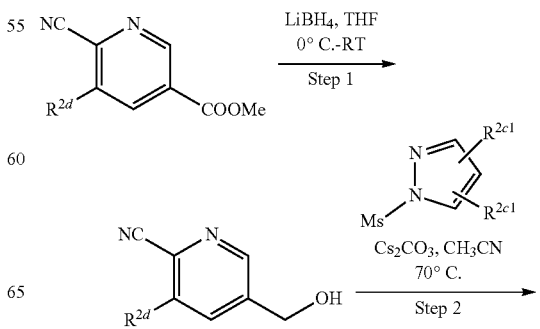

-continued

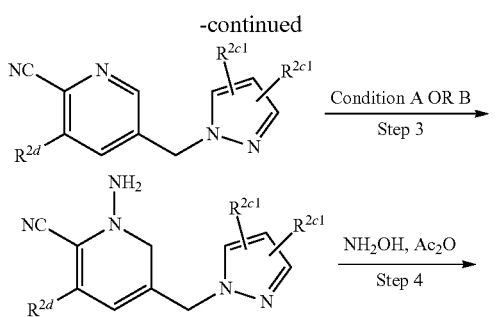

General Scheme 12 describes the preparation of a Compound of Formula (I) where $R^2$ is ring (c);

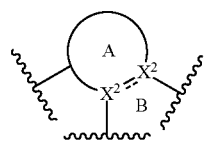

is

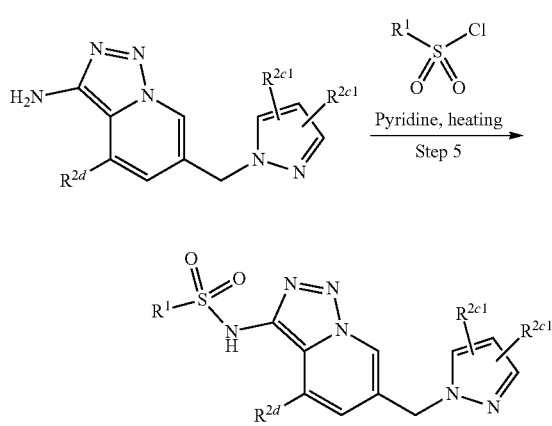

one $X^1$ is $C(CH_2R^{2c})$ and the other two $X^1$ are $CR^{2e}$; and $R^{2e}$ is pyrazol-1-yl substituted with two $R^{2c1}$; and all other groups are as defined in the Summary or in any embodiments described herein.

The [1,2,3]triazolo[1,5-a]pyridine compounds can be synthesized using a substituted 2-cyanopyridine compound. The introduction of the N-linked pyrazole moiety (Steps 1 and 2) can use procedures described above for the [1,2,4]triazolo[4,3-a]pyridine compounds. The assembly of the core scaffold is described in Steps 3 and 4 above. The 2-cyano pyridine can be converted to a 1-amino 2-cyano pyridine by reacting with a sulfonylated hydroxyl amine (Step 3), followed by cyclization in the presence of hydroxylamine and acetic anhydride. In the final step (Step 5), the free amine can be reacted with $R^1S(O)_2Cl$ in presence of a base such as triethyl amine, pyridine or sodium hydride.

GENERAL SCHEME 13

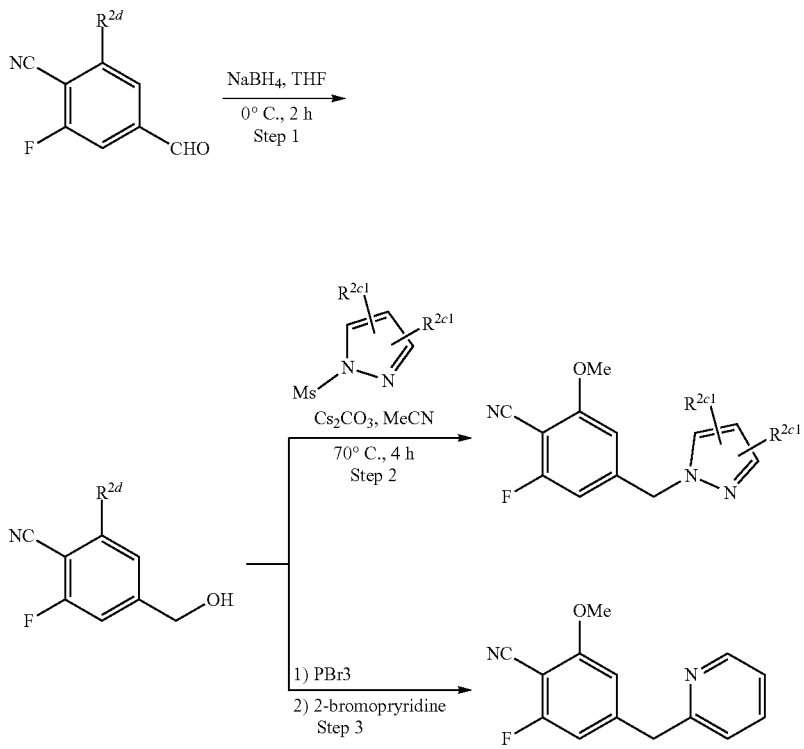

123

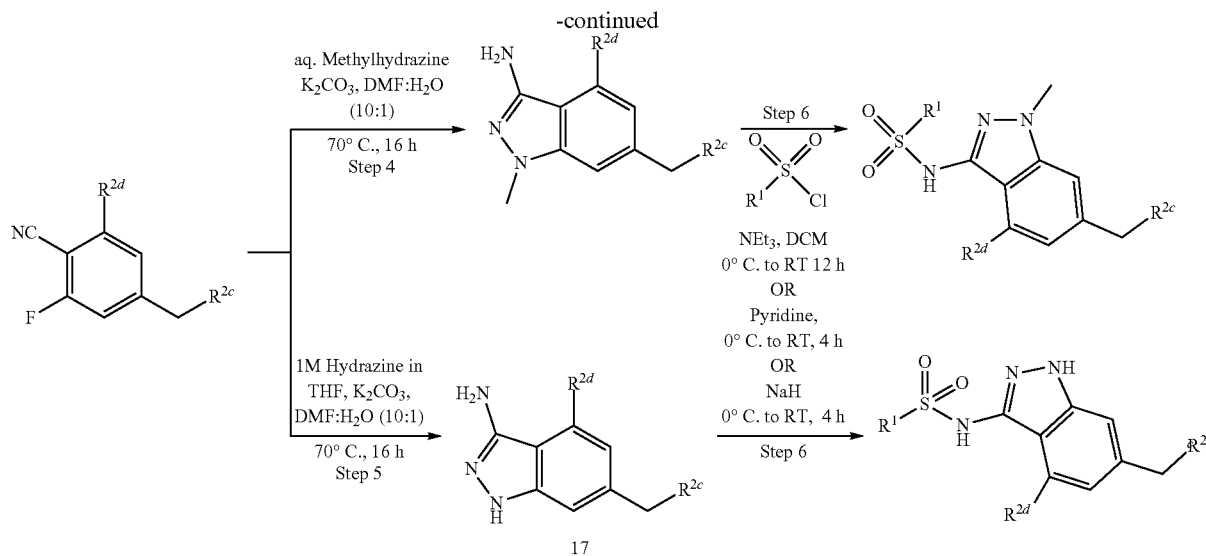

General Scheme 13 describes the preparation of a Compound of Formula (I) where $R^2$ is ring (a); one $X^1$ is $C(CH_2R^{2c})$, and the other two $X^1$ are $CR^{2e}$; and $R^{2c}$ is pyrazol-1-yl substituted with two $R^{2c1}$; and all other groups are as defined in the Summary or in any embodiments described herein.

The benzopyrazole compounds can be synthesized by using an appropriately substituted 2-fluorobenzonitrile as starting material. Steps 1, 2 and 3 can be done as described previously in the synthesis of the [1,2,4]triazolo[4,3-a]pyridine compounds (General Schemes 2 and 3 above). The fluoro benzonitrile intermediate can be converted to the N-methyl benzopyrazole (Step 4, using methyl hydrazine) or unsubstituted benzopyrazole (Step 5, using hydrazine) as shown above. In the final step (Step 6), the free amine can be reacted with $R^1S(O)_2Cl$ in presence of a base such as triethyl amine, pyridine or sodium hydride.

GENERAL SCHEME 14

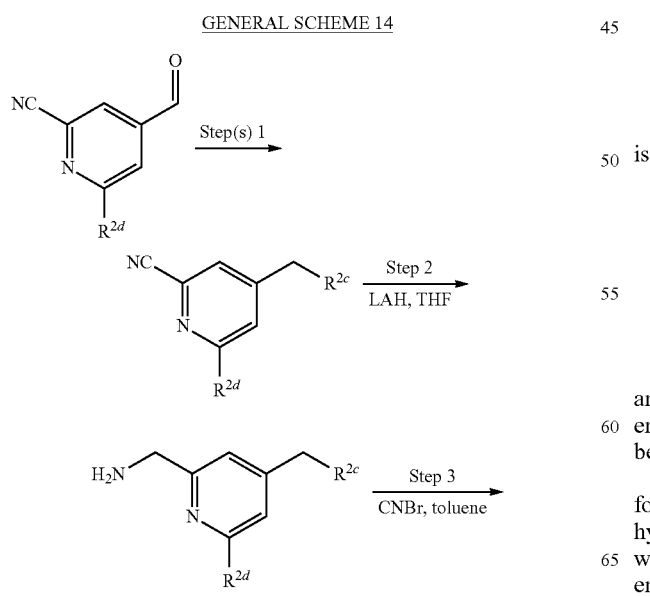

124

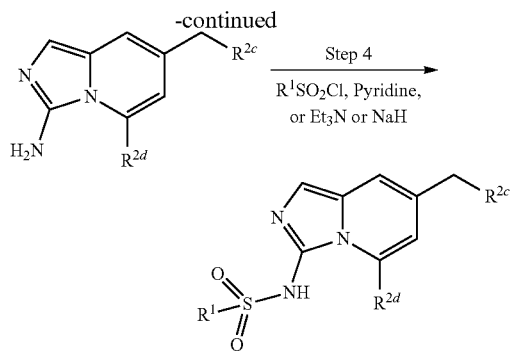

General Scheme 14 describes the preparation of a Compound of Formula (I) where $R^2$ is ring (c);

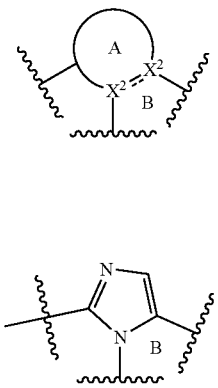

is and all other groups are as defined in the Summary or in any embodiments described herein, can be prepared as shown below:

By starting with an appropriately substituted 2-cyano-4-formyl pyridine. Step(s) 1 constitute reduction of the aldehyde with $NaBH_4$ to the alcohol followed by substitution with $R^{2c}$-LG, where $R^{2c}$ is as defined in any aspect or embodiment provided herein, and LG is a leaving group, such as methylsulfonyl or a halide, and can be done as described previously in Steps 2 and 3 of General Scheme 13. Reduction in Step 2 can be accomplished by treating the picolinonitrile with LAH in THF. Treatment of the 2-aminomethyl pyridine intermediate with cyanogen bromide in toluene (Step 3) can afford the imidazo[1,5-a]pyridin-3-amine intermediate which can be converted to the desired Compound of Formula II with $R^1S(O)_2Cl$ and a base such as pyridine, triethylamine or sodium hydride as shown in Step 4 and described in General Scheme 10.

GENERAL SCHEME 15

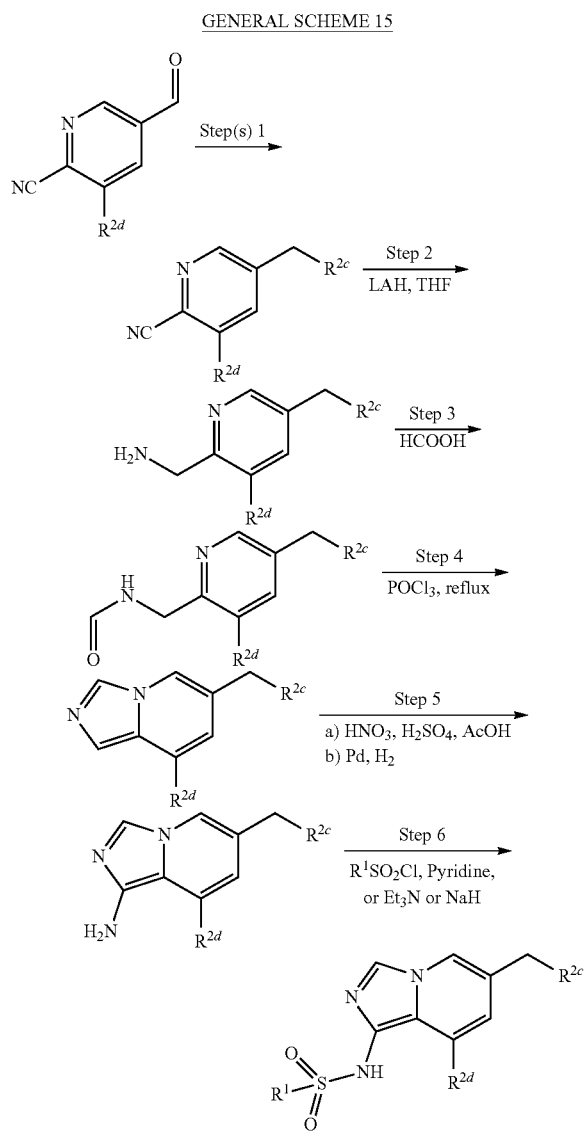

General Scheme 15 describes the preparation of a Compound of Formula (I) where $R^2$ is ring (c);

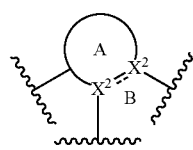

is

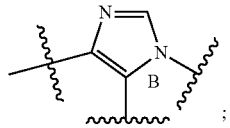

and all other groups are as defined in the Summary or in any embodiments described herein, can be prepared as shown below:

An appropriately substituted 2-cyano-5-formyl pyridine can be subjected to steps 1 and 2 following methods described in Scheme A above. Steps 3 and 4 involve N-formylation followed by refluxing in phosphorus oxychloride to construct the imidazo[1,5-a]pyridine ring. Nitration and reduction with the reagents in Step 5 can lead to the substituted imidazo[1,5-a]pyridin-1-amine. The final sulfonamide products can result by reacting this amine with $R^1S(O)_2Cl$ and a base such as pyridine, triethylamine or sodium hydride as shown in Step 6 and described in General Scheme 10.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); M (micromolar); Hz (Hertz); MHz (megahertz); mmol (millimoles); h, hr or hrs (hours); min (minutes); MS (mass spectrometry); ESI (electrospray ionization); rt (room temperature); Rf (retention factor); TLC (thin-layer chromatography); LCMS (liquid chromatography-mass spectrometry); HPLC (high performance liquid chromatography); AcOH (acetic acid); n-BuLi (n-Butyl lithium); ᵗBuOK (potassium tert-butoxide); CDCl₃ (Chloroform-d); CH₃CN (acetonitrile); Cs₂CO₃ (cesium carbonate); DMF (N,N-Dimethylformamide); DCM (dichloromethane); DEA (diethylamine); DIPEA (diisopropyl ethylamine); DMSO (dimethylsulfoxide); DMSO-d₆ (dimethyl sulfoxide-d₆); EtOAc or EA (ethyl acetate); Et₃N (triethylamine); EtOH (ethanol); HCl (hydrochloric acid); H₂SO₄ (sulphuric acid); K₂CO₃ (potassium carbonate); LiOH (lithium hydroxide); MsCl (methane sulphonyl chloride); MeI (methyl iodide); MeOH (Methanol); MeOH-d₄ (Methanol-d₄); NaBH₄ (sodium borohydride); NaH (sodium hydride); NaHCO₃ (sodium bicarbonate); NaNO₂ (sodium nitrite); NaOH (sodium hydroxide); NaOMe (sodium methoxide); Na₂SO₄ (sodium sulphate); Pd(PPh₃)₄ (tetrakis(triphenylphosphine)palladium(0)); SO₂ (sulphur dioxide); SO₂Cl₂ (sulfuryl chloride); T3P (propanephosphonic acid anhydride); THF (tetrahydrofuran); TMEDA (1,2-bis(dimethylamino)ethane); Zn (zinc); ZnCN₂ (zinc cyanide).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Synthetic Intermediate Examples

Scheme 1: Synthesis of cyclohexylmethanesulfonyl chloride (3)

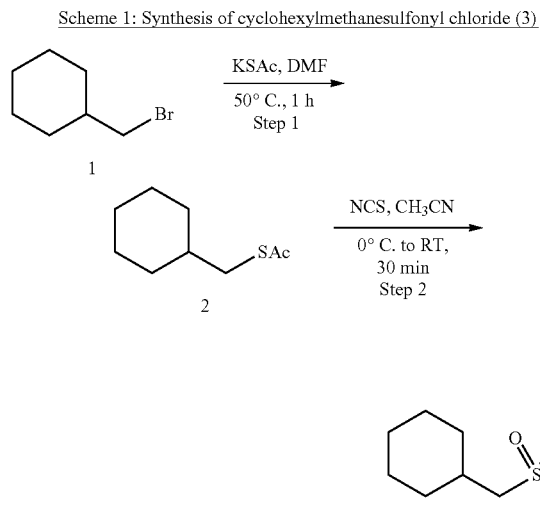

Step 1: Synthesis of S-(cyclohexylmethyl) ethanethioate (2)

To a stirred solution of compound 1 (2 g, 11.3 mmol) in DMF (20 mL) was added potassium thioacetate (1.93 g, 17 mmol) in portion-wise manner at the room temperature. The reaction mixture was stirred at 50° C. for 1 h. The progress of the reaction was monitored by TLC. After completion, the reaction mixture was diluted with ice water and extracted with ethyl acetate. The organic layer was collected, washed with brine, dried over anhydrous $Na_2SO_4$ and concentrated under reduced pressure to afford the title compound 2 (1.8 g, 92.61%) as a dark brown liquid. TLC: Heptane ($R_f$ 0.7) $^1$H NMR (400 MHz, $CDCl_3$): δ 2.79 (d, J=6.8 Hz, 2H), 2.33 (s, 3H), 1.79-1.61 (m, 5H), 1.49-1.38 (m, 1H), 1.27-1.12 (m, 3H), 1.05-0.89 (m, 2H).

Step 2: Synthesis of cyclohexyl methane sulfonyl chloride (3)

To a stirred solution of N-chlorosuccinimide (2.7 g, 20.3 mmol) in 2N HCl (1.7 mL) at 0° C. was added a pre-dissolved solution of compound 2 (1 g, 0.58 mmol) in acetonitrile (10 mL). The reaction mixture was stirred at room temperature for 30 min. The progress of the reaction was monitored by TLC. After completion, the reaction mixture was concentrated in vacuo and the residue was extracted with diethyl ether. The organic layer was collected, washed with brine, dried over anhydrous $Na_2SO_4$ and concentrated under reduced pressure. The crude compound was purified by silica gel (100-200 mesh) column chromatography using a gradient method of 0-5% EtOAc/Heptane to afford the title compound 3 (0.81 g, 71%) as a yellow liquid. TLC: 10% EtOAc/Heptane ($R_f$ 0.25) $^1$H NMR (400 MHz, $CDCl_3$): δ 3.63 (d, J=6.4 Hz, 2H), 2.24-2.18 (m, 1H), 2.01-1.96 (m, 2H), 1.80-1.66 (m, 3H), 1.40-1.29 (m, 2H), 1.25-1.11 (m, 3H).

Scheme 2: Synthesis of 2,6-Dimethoxybenzenesulfonyl chloride (5)

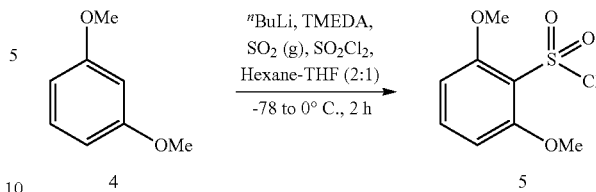

To a stirred solution of 1,3-dimethoxybenzene 4 (2 g, 14.4 mmol) and TMEDA (2.4 mL, 15.9 mmol) in THF (20 mL) at 0° C. under Nitrogen atmosphere was added $^n$BuLi [2.5 M solution in hexanes] (6.3 mL, 15.9 mmol) in drop-wise manner while keeping the internal reaction temperature below 5° C. The contents were stirred at the same temperature for 30 min, then cooled to −78° C. and bubbled with $SO_2$ gas for 30 min. The reaction mixture was then allowed to warm slowly to 10° C. and the resulting precipitate was collected by filtration and washed with dry diethyl ether. The solid was suspended in hexane (20 ml), cooled to 0° C. and a solution of $SO_2Cl_2$ (2.2 mL, 28.8 mmol) in hexane (20 mL) was added drop wise manner while keeping the internal temperature below 3° C. The reaction mixture was then stirred at 0° C. for 1 h and the solids were collected by filtration and washed with cold hexane. The solids were partitioned between diethyl ether and water, the layers were separated; the aqueous layer was further extracted with diethyl ether. The combined organic extracts were dried over anhydrous $Na_2SO_4$, filtered and concentrated under reduced pressure to give the title compound 5 (1 g, 29.23%) as a white solid. TLC: 10% EtOAc/Heptane ($R_f$ 0.3) $^1$H NMR (400 MHz, DMSO-$d_6$): δ 7.27 (t, J=8.0 Hz, 1H), 6.64 (d, J=8.8 Hz, 2H), 3.72 (s, 6H).

Scheme 3: Synthesis of tert-butyl ((1-methylsulfonyl)-1H-pyrazol-4-yl)methyl)-carbamate (7)

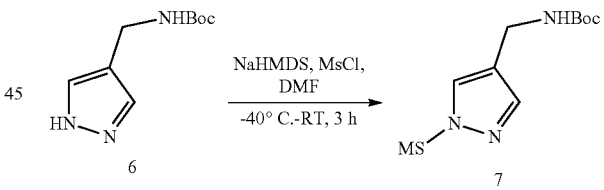

To a stirred solution of compound 6 (0.1 g, 0.5 mmol) in DMF (2 mL) at −40° C. was added NaHMDS (0.5 mL, 0.5 mmol) followed by methane sulfonyl chloride (0.04 mL, 0.55 mmol) and the resulting reaction mixture was allowed to stir at the room temperature for 3 h. After completion of the reaction (monitored by TLC), the reaction mixture was quenched with saturated $NH_4Cl$ solution and extracted with ethyl acetate. The organic layer was collected, washed with brine, dried over anhydrous $Na_2SO_4$, filtered and concentrated under reduced pressure to afford the title compound 7 (0.06 g, 42.98%) as a white gummy solid. TLC: 50% EtOAc/Heptane ($R_f$ 0.4). $^1$H NMR (400 MHz, DMSO-$d_6$): δ 8.08 (s, 1H), 7.84 (s, 1H), 7.29 (broad s, 1H), 4.02 (broad s, 2H), 3.50 (s, 3H), 1.39 (s, 9H). LCMS Calculated for $C_{10}H_{17}N_3O_4S$: 275.32; Found: 299.90 (M+23).

Scheme 4: Synthesis of tert-butyl ((1-methylsulfonyl)-1H-pyrazol-3-yl)methyl)-carbamate (10)

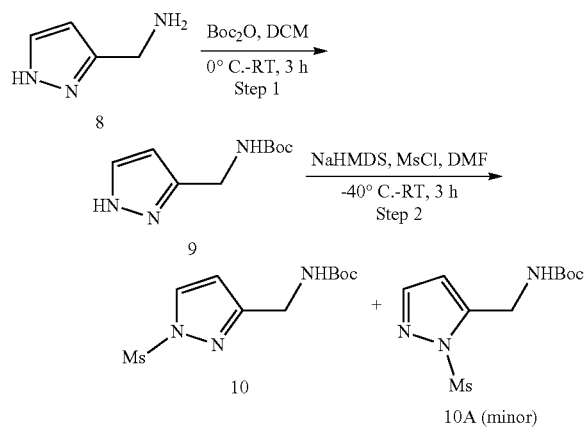

Step 1: Synthesis of tert-butyl ((1H-pyrazol-3-yl)methyl)carbamate (9)

To a stirred solution of compound 8 (1 g, 10.30 mmol) in DCM (50 mL) at 0° C. was added (Boc)$_2$O (2.12 mL, 9.27 mmol) and the reaction mixture was allowed to stir at the room temperature for 3 h. After completion of the reaction (monitored by TLC), the reaction mixture was quenched with water and extracted with DCM. The organic layer was collected, washed with brine, dried over anhydrous Na$_2$SO$_4$ and concentrated under reduced pressure to afford the title compound 9 (1.7 g, 83.7%) as a white solid. TLC: 70% EtOAc/Heptane (R$_f$: 0.3). LCMS Calculated for C$_9$H$_{15}$N$_3$O$_2$: 197.24; Found: 198.2 (M+1).

Step 2: Synthesis of tert-butyl ((1-(methylsulfonyl)-1H-pyrazol-3-yl)methyl)carbamate (10) and tert-butyl ((1-(methylsulfonyl)-1H-pyrazol-5-yl)methyl)carbamate (10A)

To a stirred solution of compound 9 (1.7 g, 8.62 mmol) in DMF (25 mL) at −40° C. was added NaHMDS (8.6 mL, 8.62 mmol) followed by methane sulfonyl chloride (0.72 mL, 9.40 mmol) and the resulting reaction mixture was allowed to stir at the room temperature for 3 h. After completion of the reaction (monitored by TLC), the reaction mixture was quenched with saturated NH$_4$Cl solution and extracted with ethyl acetate. The organic layer was collected, washed with brine, dried over anhydrous Na$_2$SO$_4$ and concentrated under reduced pressure to afford the title compound 10 (0.9 g, 38.1%) as a white gummy solid. TLC: 50% EtOAc/Heptane (R$_f$: 0.4). $^1$H NMR (400 MHz, DMSO-d$_6$): δ 8.18 (d, J=2.4 Hz, 1H), 7.41 (t, J=6.0 Hz, 1H), 6.43 (d, J=2.4 Hz, 1H), 4.15 (d, J=6.4 Hz, 2H), 3.50 (s, 3H), 1.40 (s, 9H). $^1$H NMR indicates 10 as the major isomer. LCMS Calculated for C$_{10}$H$_{17}$N$_3$O$_4$S: 275.32; Found: 273.95 (M−1) and 10A is minor isomer and found to be less pure and was discarded.

Scheme 5: Synthesis of tert-buyl 2-(methylsulfonyl)-2,6-dihydropyrrolo[3,4-c]pyrazole-5(4H)-carboxylate (7)

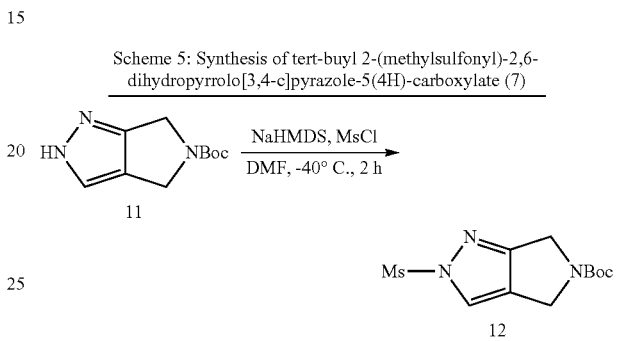

To a stirred solution of compound 11 (2.0 g, 9.56 mmol) in DMF (20 mL) at 0° C. was added NaHMDS (9.5 mL, 9.56 mmol) followed by methane sulfonyl chloride (0.85 mL, 10.51 mmol) and the resulting reaction mixture was allowed to stir at −40° C. for 2 h. After completion of the reaction (monitored by TLC), the reaction mixture was concentrated under reduced pressure, water was added to the residue and extracted with ethyl acetate. The organic layer was collected, washed with saturated NaHCO$_3$ solution followed by brine, dried over anhydrous Na$_2$SO$_4$ and concentrated under reduced pressure to afford the title compound 12 (1.2 g, 43.69%) as a pale yellow liquid. TLC: 50% EtOAc/Heptane (R$_f$: 0.4). $^1$H NMR (400 MHz, DMSO-d$_6$): δ 8.00-8.10 (m, 1H), 4.50-4.52 (m, 2H), 4.33-4.31 (m, 2H), 3.53 (s, 3H), 1.45 (s, 9H). VT NMR at 80° C. indicates a 1:1 mixture of rotamers.

Synthesis of Compounds of Formula (I)

Scheme 6: Scheme for the synthesis of N-(6-((5-acryloyl-5,6-dihydropyrrolo[3,4-c]pyrazol-2(4H)-yl)methyl)-4-methoxybenzo[d]isoxazol-3-yl)-1-cyclohexylmethanesulfonamide, 1-cyclohexyl-N-(4-methoxy-6-((5-propioloyl-5,6-dihydropyrrolo[3,4-c]pyrazol-2(4H)-yl)methyl)benzo[d]isoxazol-3-yl) methanesulfonamide and 1-cyclohexyl-N-(6-((5-(4-(dimethylamino)but-2-ynoyl)-5,6-dihydropyrrrolo[3,4-c]pyrazol-2(4H)-yl)methyl)-4-methoxybenzo[d]isoxazol-3-yl)methanesulfonamide

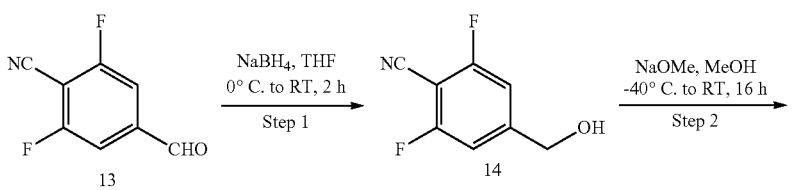

-continued
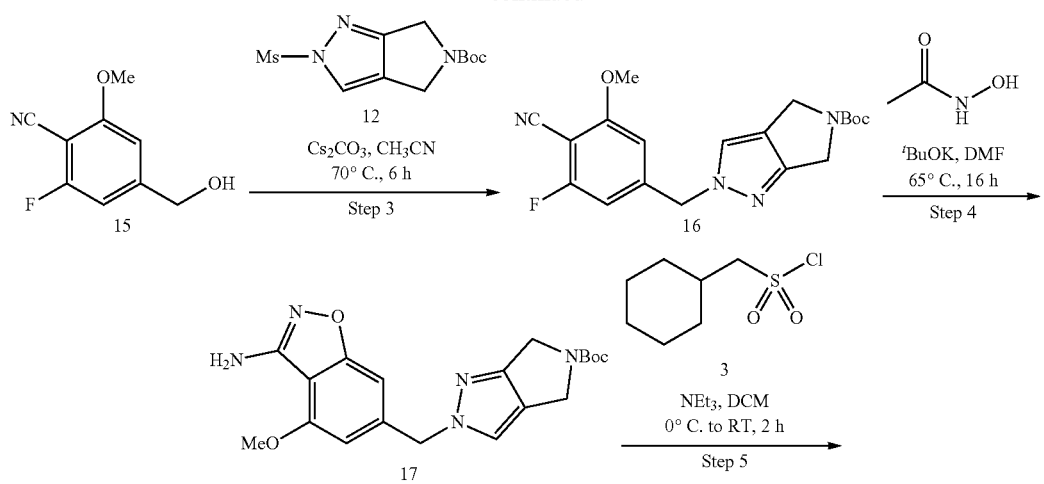
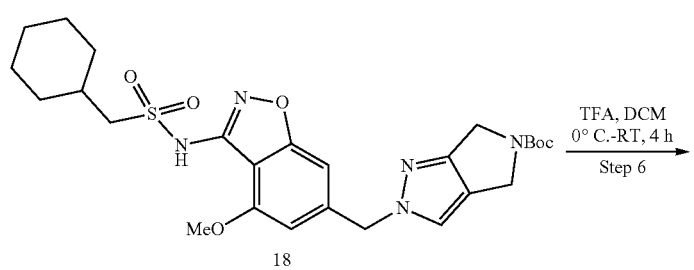
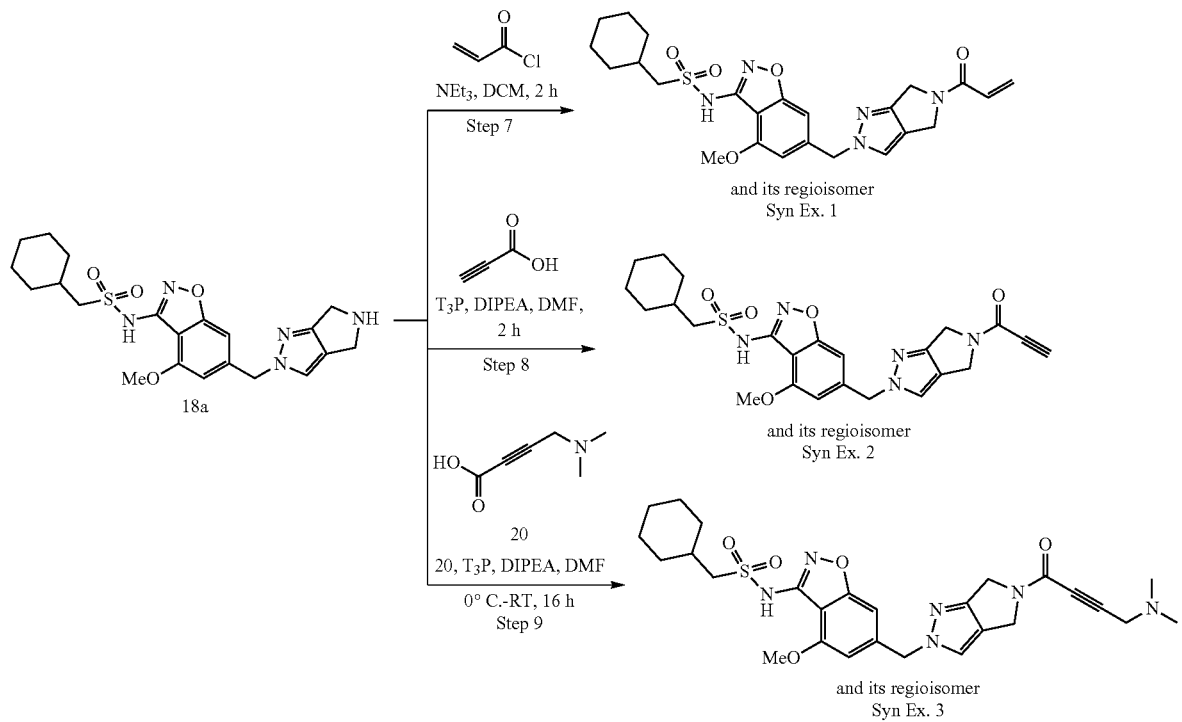

(Note that only one regioisomer of compounds for 16, 17, 18, and 18a are depicted in the above scheme and throughout examples 1-3; however, both are present in the reaction mixtures.)

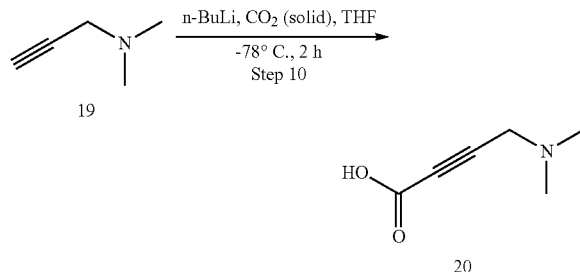

Synthesis of 2,6-difluoro-4-(hydroxymethyl)benzonitrile (14)

To a stirred solution of compound 13 (5 g, 29.00 mmol) in THF (50 mL) at 0° C. was added NaBH$_4$ (1.6 g, 44.00 mmol) and the resulting reaction mixture was stirred at the same temperature for 2 h. After completion of the reaction (monitored by TLC), the reaction mixture was neutralized with 1N HCl and extracted with ethyl acetate. The organic layer was collected, washed with brine, dried over anhydrous Na$_2$SO$_4$ and concentrated under reduced pressure to afford the title compound 14 (4.5 g, 88.93%) as a yellow solid. TLC: 30% EtOAc/Heptane (R$_f$ 0.35). $^1$H NMR (400 MHz, DMSO-d$_6$): δ 7.35-7.32 (m, 2H), 5.69 (t, J=6.0 Hz, 1H), 4.60 (d, J=6.0 Hz, 2H).

Synthesis of 2-fluoro-4-(hydroxymethyl)-6-methoxybenzonitrile (15)

To a stirred solution of compound 14 (4 g, 23.12 mmol) in MeOH (60 mL) at −40° C. was added NaOMe (5.1 g, 94.00 mmol) and the reaction mixture was allowed to stir at the room temperature for 16 h. After completion of the reaction (monitored by TLC), the solvent was concentrated under high vacuum. Water was added to the residue and extracted with ethyl acetate. The organic layer was collected, washed with brine, dried over anhydrous Na$_2$SO$_4$ and concentrated under reduced pressure to afford the title compound 15 (3.5 g, 81.69%) as a yellow solid. TLC: 50% EtOAc/Heptane (R$_f$ 0.25). $^1$H NMR (400 MHz, CDCl$_3$): δ 6.81-6.78 (m, 2H), 4.75 (s, 2H), 3.96 (s, 3H). OH proton not observed.

Synthesis of tert-butyl 2-(4-cyano-3-fluoro-5-methoxybenzyl)-2,6-dihydropyrrolo[3,4-c]pyrazole-5(4H)-carboxylate (16)

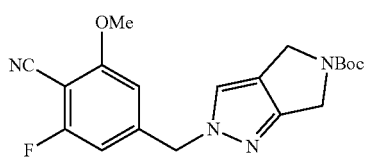

16

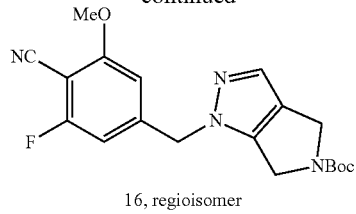

16, regioisomer

To a stirred solution of compound 15 (1.0 g, 5.5 mmol) in acetonitrile (5 mL) was added Cs$_2$CO$_3$ (3.22 g, 9.90 mmol) followed by compound 12 (1.74 g, 6.07 mmol) and the resulting reaction mixture was heated at 70° C. for 6 h. After completion of the reaction (monitored by TLC), the reaction mixture was cooled to room temperature, water was added and extracted with ethyl acetate. The organic layer was collected, washed with brine, dried over anhydrous Na$_2$SO$_4$ and concentrated under reduced pressure. The crude compound obtained was purified by silica gel (100-200 mesh) column chromatography using a gradient method of 0-50% EtOAc/Heptane to afford the title compound 16 (1.0 g, 48.65%, isolated as inseparable regioisomeric mixture) as a yellow solid. TLC: 80% EtOAc/Heptane (R$_f$ 0.45). LCMS Calculated for C$_{19}$H$_{21}$FN$_4$O$_3$: 372.40; Found: 373.85 (M+1). $^1$H NMR is complicated and indicates an isomeric mixture. This was taken on as a mixture for the synthesis of final compounds, where a single regioisomer is drawn.

Synthesis of tert-butyl 2-((3-amino-4-methoxybenzo[d]isoxazol-6-yl)methyl)-2,6-dihydropyrrolo[3,4-c]pyrazole-5(4H)-carboxylate (17)

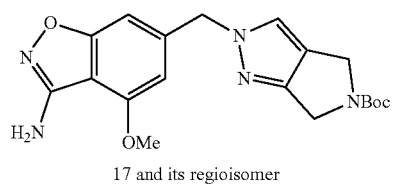 [SMILES: COc1cc(Cn2cc3c(n2)CN(C(=O)OC(C)(C)C)C3)cc2onc(N)c12]

17 and its regioisomer

To a stirred solution of compound 16 (0.50 g, 1.34 mmol) in DMF (7 mL) was added acetohydroxamic acid (0.31 g, 4.02 mmol) followed by $^t$BuOK (0.45 g, 4.02 mmol) and the reaction mixture was allowed to stir at 65° C. for 16 h. After completion of the reaction (monitored by TLC), the reaction mixture was cooled to room temperature, quenched with ice water and extracted with ethyl acetate. The organic layer was collected, washed with brine, dried over anhydrous Na$_2$SO$_4$ and concentrated under reduced pressure. The crude compound obtained was purified by silica gel (100-200 mesh) column chromatography using a gradient method of 0-50% EtOAc/Heptane to afford the title compound 17 (0.20 g, 38.64%, isolated as inseparable regioisomeric mixture) as an off-white solid. TLC: 70% EtOAc/Heptane (R$_f$ 0.40). LCMS Calculated for C$_{19}$H$_{23}$N$_5$O$_4$: 385.42; Found: 386.00 (M+1). $^1$H NMR is complicated and indicates a regioisomeric mixture.

Synthesis of tert-butyl 2-((3-((cyclohexylmethyl)sulfonamido)-4-methoxybenzo[d]isoxazol-6-yl)methyl)-2,6-dihydropyrrolo[3,4-c]pyrazole-5(4H)-carboxylate (18)

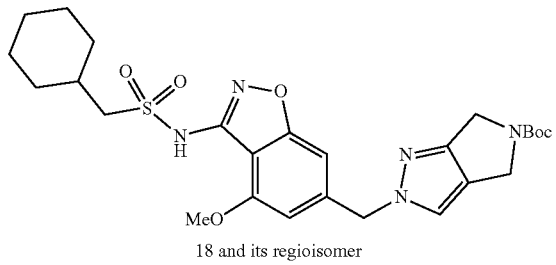 [SMILES: COc1cc(Cn2cc3c(n2)CN(C(=O)OC(C)(C)C)C3)cc2onc(NS(=O)(=O)CC3CCCCC3)c12]

18 and its regioisomer

To a stirred solution of compound 17 (0.160 g, 0.42 mmol) in DCM (3 mL) was added Et$_3$N (0.15 mL, 1.14 mmol) followed by cyclohexylmethanesulfonyl chloride (3, 0.11 g, 0.58 mmol) at 0° C. and the resulting reaction mixture was allowed to stir at room temperature for 2 h. After completion of the reaction (monitored by TLC), the reaction mixture was again cooled to room temperature, diluted with DCM and extracted. The organic layer was collected, washed with brine, dried over anhydrous Na$_2$SO$_4$ and concentrated under reduced pressure. The crude compound was purified by silica gel (100-200 mesh) column chromatography using a gradient method of 0-60% EtOAc/Heptane to afford the title compound 18 (0.18 g, 79.60%, isolated as inseparable regioisomeric mixture) as an off-white solid. TLC: 80% EtOAc/Heptane (R$_f$, 0.35). LCMS Calculated for C$_{26}$H$_{35}$N$_5$O$_6$S: 545.66; Found: 544.40 (M−1). $^1$H NMR is complicated and indicates a regioisomeric mixture.

Synthesis of 1-cyclohexyl-N-(6-((5,6-dihydropyrrolo[3,4-c]pyrazol-2(4H)-yl)methyl)-4-methoxybenzo[d]isoxazol-3-yl)methanesulfonamide

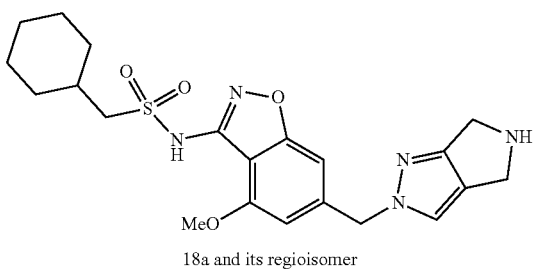 [SMILES: COc1cc(Cn2cc3c(n2)CNC3)cc2onc(NS(=O)(=O)CC3CCCCC3)c12]

18a and its regioisomer

To a stirred solution of compound 18 (180 mg, 0.33 mmol) in DCM (3 mL) was added TFA (0.13 mL, 1.73 mmol) at 0° C. and the reaction was allowed to stir at room temperature for 4 h. After completion of the reaction (monitored by TLC), reaction mixture was again cooled to room temperature, basified with sat. NaHCO$_3$ solution and extracted with DCM. The organic layer was collected, washed with brine, dried over anhydrous Na$_2$SO$_4$ and concentrated under reduced pressure to obtain crude residue which was triturated with di-ethyl ether/pentane to afford the title compound (100 mg, 67.10%, isolated as inseparable regioisomeric mixture) as a white solid which was used in the next reaction without further purification. LCMS Calculated for C$_{21}$H$_{27}$N$_5$O$_4$S: 445.54; Found: 446.50 (M+1). $^1$H NMR is complicated and indicates a regioisomeric mixture.

Synthetic Example 1

Synthesis of Mixture of N-(6-((5-acryloyl-5,6-dihydropyrrolo[3,4-c]pyrazol-2(4H)-yl)methyl)-4-methoxybenzo[d]isoxazol-3-yl)-1-cyclohexylmethanesulfonamide and its Regioisomer

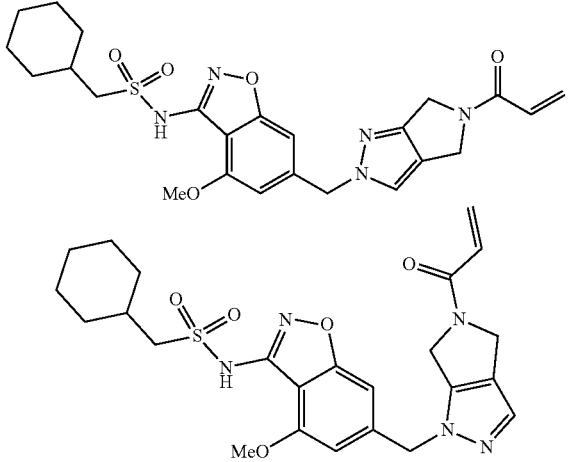

To a stirred solution of 18a (0.050 g, 0.11 mmol) in DCM (3 mL) at 0° C. was added Et$_3$N (0.045 mL, 0.63 mmol) followed by acryloyl chloride (0.01 g, 0.11 mmol). The reaction mixture was stirred at the room temperature for 2 h. After completion of the reaction (monitored by TLC), the reaction mixture was concentrated under reduced pressure and diluted with water and extracted with 5% MeOH/DCM. The organic layer was collected, washed with brine, dried over anhydrous Na$_2$SO$_4$ and concentrated under reduced pressure. The crude compound was purified by using reverse phase HPLC to afford the title compound (7 mg, 9.9%, isolated as inseparable regioisomeric mixture) as an off-white solid. TLC: 5% MeOH/DCM (R$_f$, 0.5). (See analytical data in Table 1).

Synthetic Example 2

Synthesis of a Mixture of 1-cyclohexyl-N-(4-methoxy-6-((5-propioloyl-5,6-dihydropyrrolo[3,4-c]pyrazol-2(4H)-yl)methyl)benzo[d]isoxazol-3-yl)methanesulfonamide and its Regioisomer

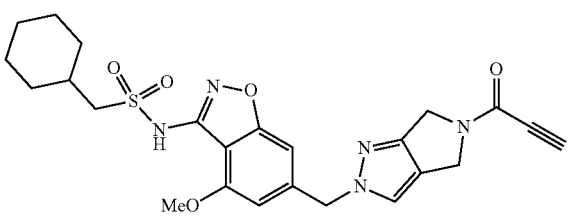

137

-continued

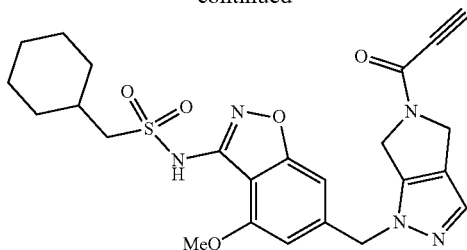

To a stirred solution of 18a (0.050 g, 0.11 mmol) in DMF (2 mL) at 0° C. was added DIPEA (0.06 mL, 0.39 mmol), followed by T3P (0.06 mL, 0.22 mmol). The reaction was allowed to stir at the room temperature for 20 min. A pre-dissolved solution of propiolic acid (8 mg, 0.12 mmol) in DMF (0.5 mL) was added in a drop-wise manner and the reaction mixture was stirred at room temperature for 2 h. After completion (monitored by TLC), the solvent was concentrated under high vacuum. The residue was quenched with water and extracted with DCM. The organic layer was collected, washed with brine, dried over anhydrous $Na_2SO_4$ and concentrated under reduced pressure. The crude compound was purified by using reverse phase HPLC to afford the title compound (6.1 mg, 11%, isolated as inseparable regioisomeric mixture) as an off-white solid. TLC: 5% MeOH/DCM ($R_f$, 0.5). (See analytical data in Table 1).

Synthesis of 4-(dimethylamino)but-2-ynoic acid (20)

To a stirred solution of compound 19 (2.0 g, 0.24 mmol) in THF (20 mL) at −78° C. under inert atmosphere was added n-BuLi (15 mL, 0.24 mmol, 1.6M in Hexane). The mixture was stirred at −78° C. for 1 h, then added to another flask containing crushed $CO_2$ (11.5 g, 0.241 mmol) and the resulting reaction mixture was allowed to stir at the same temperature for 30 min. The progress of the reaction was monitored by TLC. After completion, the reaction mixture was poured in to ice water and washed with ethyl acetate. The aqueous layer was collected and concentrated under reduced pressure to afford the residue, which was diluted with MeOH and filtered. The filtrate was concentrated under reduced pressure to get the title compound 20 (1.4 g, 45.74%) as a pale brown solid. TLC: 10% MeOH/DCM ($R_f$,

138

0.3). $^1$H NMR (400 MHz, DMSO-$d_6$): δ 3.15 (s, 2H), 2.14 (s, 6H). LCMS Calculated for $C_6H_9NO_2$: 127.14; Found: 128.2 (M+1).

Synthetic Example 3

Synthesis of 1-cyclohexyl-N-(6-((5-(4-(dimethylamino)but-2-ynoyl)-5,6-dihydropyrrolo[3,4-c]pyrazol-2(4H)-yl)methyl)-4-methoxybenzo[d]isoxazol-3-yl)methanesulfonamide

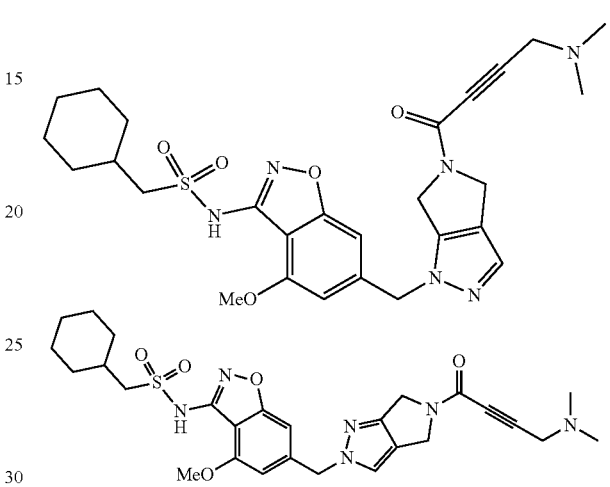

To a stirred solution of compound 18a (70 mg, 0.16 mmol) in DMF (1 mL) at 0° C. was added DIPEA (0.09 mL, 0.51 mmol), followed by compound 20 (18 mg, 0.14 mmol). The resultant mixture was allowed to stir at 0° C. for 5 min. After that, T3P (0.06 mL, 0.19 mmol) was added and the reaction was allowed to stir at the room temperature for 16 h. After completion (monitored by TLC), the reaction was quenched with water and extracted with ethyl acetate. The organic layer was collected, washed with brine, dried over anhydrous $Na_2SO_4$ and concentrated under reduced pressure. The crude compound was purified by using prep. HPLC to afford the title compounds as a mixture of regioisomers (7 mg, 8%) as an off-white solid. TLC: 10% MeOH/DCM ($R_f$, 0.5). (See analytical data for Table 1).

Synthetic Examples 4-6

Scheme 7: Scheme for the synthesis of N-(6-((4-(aminomethyl)-1H-pyrazol-1-yl)methyl)-4-methoxybenzo[d]isoxazol-3-yl)-1-cyclohexylmethanesulfonamide, N-((1-((3-((cyclohexylmethyl)sulfonamido)-4-methoxybenzo[d]isoxazol-6-yl)methyl)-1H-pyrazol-4-yl)methyl)acrylamide, N-((1-((3-((cyclohexylmethyl)sulfonamido-4-methoxybenzo[d]isoxazol-6-yl)methyl)-1H-pyrazol-4-yl)methyl)propiolamide and N-((1-((3-((cyclohexylmethyl)sulfonamide)-4-methoxybenzo[d]isoxazol-6-yl)methyl)-1H-pyrazol-4-yl)methyl)ethenesulfonamide

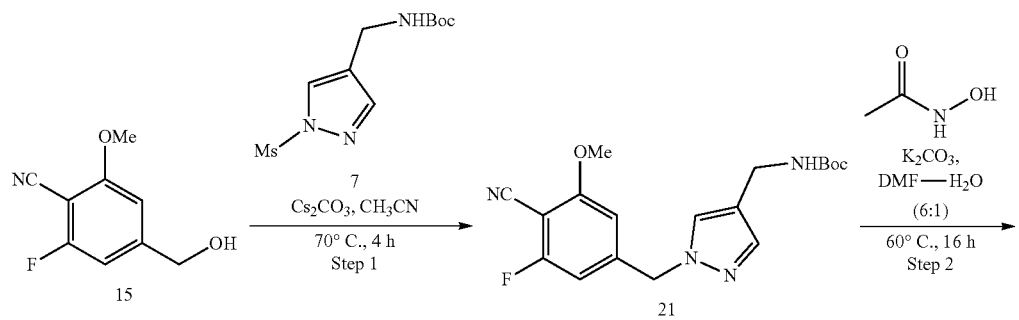

-continued
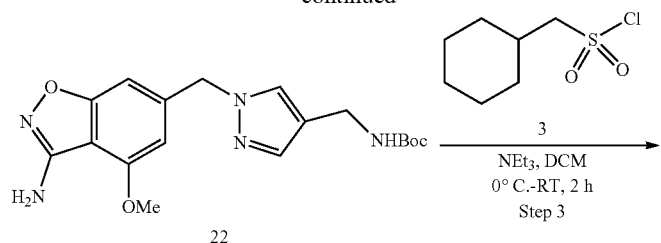
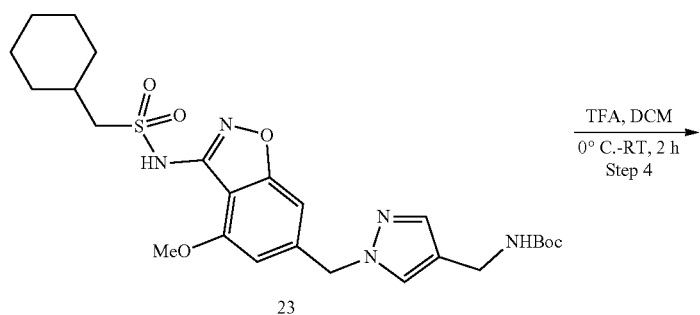
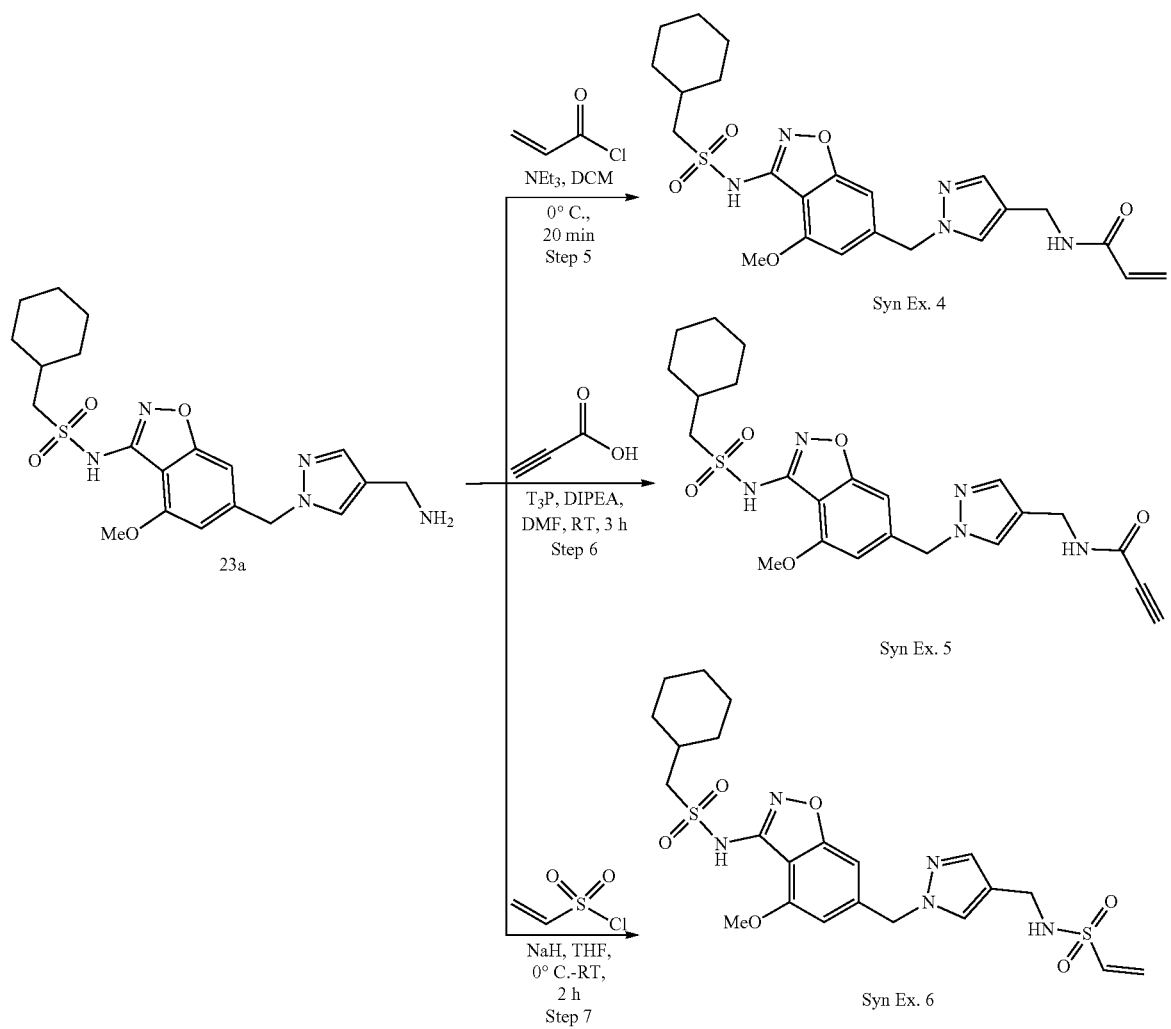

Synthesis of tert-butyl ((1-(4-cyano-3-fluoro-5-methoxybenzyl)-1H-pyrazol-4-yl)methyl)carbamate (21)

To a stirred solution of compound 15 (0.5 g, 2.76 mmol) in acetonitrile (10 mL) at the room temperature was added $Cs_2CO_3$ (2.7 g, 8.28 mmol) followed by compound 7 (1.13 g, 4.14 mmol) and the resulting reaction mixture was heated at 70° C. for 4 h. After completion of the reaction (monitored by TLC), the reaction mixture was cooled to room temperature, water added and extracted with ethyl acetate. The organic layer was collected, washed with brine, dried over anhydrous $Na_2SO_4$ and concentrated under reduced pressure. The crude compound was purified by Combi-flash chromatography using a gradient method of 40-70% EtOAc/Heptane to afford the title compound 21 (0.400 g, 40.22%) as a brown semi-solid. TLC: 80% EtOAc/Heptane ($R_f$ 0.45). $^1$H NMR (400 MHz, DMSO-$d_6$): δ 7.72 (s, 1H), 7.39 (s, 1H), 7.18-7.12 (m, 1H), 7.00 (s, 1H), 6.69 (d, J=9.6 Hz, 1H), 5.37 (s, 2H), 3.96 (d, J=5.6 Hz, 2H), 3.91 (s, 3H), 1.37 (s, 9H). LCMS Calculated for $C_{18}H_{21}FN_4O_3$: 360.39; Found: 361.00 (M+1).

Synthesis of tert-butyl ((1-((3-amino-4-methoxybenzo[d]isoxazol-6-yl)methyl)-1H-pyrazol-4-yl)methyl)carbamate (22)

To a stirred solution of compound 21 (0.2 g, 0.55 mmol) in a 6:1 mixture of $DMF:H_2O$ (7 mL) at the room temperature was added acetohydroxamic acid (0.112 g, 1.50 mmol) followed by $K_2CO_3$ (0.414 g, 3.0 mmol). The reaction mixture was allowed to stir at 60° C. for 16 h. After completion of the reaction (monitored by TLC), the reaction mixture was cooled to room temperature, ice water added and extracted with ethyl acetate. The organic layer was collected, washed with brine, dried over anhydrous $Na_2SO_4$ and concentrated under reduced pressure. The crude compound was purified by Combi flash chromatography using a gradient method of 40-60% EtOAc/Heptane to afford the title compound 22 (0.1 g, 48.25%) as a brown semi-solid. TLC: 80% EtOAc/Heptane ($R_f$ 0.40). $^1$H NMR (400 MHz, DMSO-$d_6$): δ 7.67 (s, 1H), 7.35 (s, 1H), 7.18-7.12 (m, 1H), 6.69 (s, 1H), 6.63 (s, 1H), 5.93 (s, 2H), 5.34 (s, 2H), 3.95 (d, J=6.0 Hz, 2H), 3.86 (s, 3H), 1.36 (s, 9H). LCMS Calculated for $C_{18}H_{23}N_5O_4$: 373.41; Found: 374.05 (M+1).

Synthesis of tert-butyl ((1-((3-((cyclohexylmethyl)sulfonamido)-4-methoxybenzo[d]isoxazol-6-yl)methyl)-1H-pyrazol-4-yl)methyl)carbamate (23)

To a stirred solution of compound 22 (0.1 g, 0.26 mmol) in DCM (3 mL) at 0° C. was added $Et_3N$ (0.11 mL, 0.80 mmol) followed by cyclohexylmethanesulfonyl chloride (3, 0.057 g, 0.29 mmol) and the reaction was allowed to stir at the room temperature for 2 h. After completion of the reaction (monitored by TLC), the reaction mixture was diluted with DCM, water added and extracted. The organic layer was collected, washed with brine, dried over anhydrous $Na_2SO_4$ and concentrated under reduced pressure. The crude compound was purified by Combi flash column chromatography using a gradient method of 40-60% EtOAc/Heptane to afford the title compound 23 (0.070 g, 48.98%) as an off-white solid. TLC: 80% EtOAc/Heptane ($R_f$ 0.35). LCMS Calculated for $C_{25}H_{35}N_5O_6S$: 533.64; Found: 532.43 (M−1).

Synthesis of N-(6-((4-(aminomethyl)-1H-pyrazol-1-yl)methyl)-4-methoxybenzo[d]isoxazol-3-yl)-1-cyclohexylmethanesulfonamide To a stirred solution of compound 23 (70 mg, 0.13 mmol) in DCM (2 mL) at 0° C., TFA (0.1 mL, 1.31 mmol) was added, and the reaction was allowed to stir at the room temperature for 2 h. After completion of the reaction (monitored by TLC), it was concentrated under reduced pressure and the crude compound was purified by reverse phase HPLC to afford the title compound (4 mg, 7%) as an off-white solid. TLC: 5% MeOH/DCM ($R_f$ 0.5). $^1$H NMR (400 MHz, DMSO-$d_6$): δ 10.41 (broad s, 1H), 7.95 (broad s, 2H), 7.91 (s, 1H), 7.58 (s, 1H), 6.92 (s, 1H), 6.83 (s, 1H), 5.48 (s, 2H), 3.91 (merged s, 5H), 3.37 (merged d, J=5.6 Hz, 2H), 2.04-1.91 (m, 1H), 1.86 (d, J=12.4 Hz, 2H), 1.61 (d, J=12.4 Hz, 2H), 1.59-1.51 (m, 1H), 1.29-1.04 (m, 5H); LCMS Calculated for $C_{20}H_{27}N_5O_4S$: 433.53; Found: 434.15 (M+1).

Synthetic Example 4

Synthesis of N-((1-((3-((cyclohexylmethyl)sulfonamido)-4-methoxybenzo[d]isoxazol-6-yl)methyl)-1H-pyrazol-4-yl)methyl)acrylamide To a stirred solution of compound 23a (60 mg, 0.13 mmol) in DCM (5 mL) at 0° C. was added $Et_3N$ (0.09 mL, 0.65 mmol) followed by acryloyl chloride (0.008 mL, 0.11 mmol) and the reaction was allowed to stir at the same temperature for 20 min. After completion of the reaction (monitored by TLC), the reaction mixture was concentrated under reduced pressure, water added and extracted with 5% MeOH/DCM. The organic layer was collected, washed with brine, dried over anhydrous $Na_2SO_4$ and concentrated under reduced pressure. The crude compound was purified by prep HPLC to afford the title compound (2.5 mg, 7.9%) as an off-white solid. TLC: 5% MeOH/DCM ($R_f$ 0.5). (See Table 1 for analytical data).

Synthetic Example 5

Synthesis of N-((1-((3-((cyclohexylmethyl)sulfonamido)-4-methoxybenzo[d]isoxazol-6-yl)methyl)-1H-pyrazol-4-yl)methyl)propiolamide To a stirred solution of compound 23a (60 mg, 0.13 mmol) in DMF (1 mL) at 0° C. was added DIPEA (0.07 mL, 0.41 mmol), followed by T3P (0.08 mL, 0.27 mmol). The reaction was allowed to stir at the room temperature for 20 min. After that, a pre-dissolved solution of propionic acid (11 mg, 0.16 mmol) in DMF (0.5 mL) was added in drop-wise manner and the reaction was allowed to stir at the room temperature for 16 h. After completion (monitored by TLC), the reaction mixture was quenched with water and extracted with ethyl acetate. The organic layer was collected, washed with brine, dried over anhydrous $Na_2SO_4$ and concentrated under reduced pressure. The crude compound was purified by using prep. HPLC to afford the title compound (6.5 mg, 10%) as an off-white solid. TLC: 100% EtOAc ($R_f$ 0.5). (See Table 1 for analytical data).

Synthetic Example 6

Synthesis of N-((1-((3-((cyclohexylmethyl)sulfonamido)-4-methoxybenzo[d]isoxazol-6-yl)methyl)-1H-pyrazol-4-yl)methyl)ethenesulfonamide To a stirred solution of compound 23a (70 mg, 0.16 mmol) in THF (1 mL) was added NaH [60% dispersion in mineral oil] (12.8 mg, 0.32 mmol) at 0° C. followed by ethenesulfonyl chloride (22 mg, 0.17 mmol) and the resulting reaction mixture was allowed to stir at room temperature for 2 h. After completion of the reaction (monitored by TLC), diluted with ethyl acetate and extracted. The organic layer was collected, washed with brine, dried over anhydrous Na₂SO₄ and concentrated under reduced pressure. The crude compound was purified by using prep HPLC to afford the title compound (3.5 mg, 4.0%) as an off-white solid. TLC: 80% EtOAc/Heptane (R$_f$ 0.35). (See Table 1 for analytical data).

Synthetic Examples 7-9

Scheme 8: Synthesis of N-(6-((3-(aminomethyl)-1H-pyrazol-1-yl)methyl)-4-methoxybenzo[d]isoxazol-3-yl)-1-cyclohexylmethanesulfonamide, N-((1-((3-((cyclohexylmethyl)sulfonamido)-4-methoxybenzo[d]isoxazol-6-yl)methyl)-1H-pyrazol-3-yl)methyl)acrylamide, N-((1-((3-((cyclohexylmethyl)sulfonamido-4-methoxybenzo[d]isoxazol-6-yl-)methyl)-1H-pyrazol-3-yl)methyl)propiolamide and N-((1-((3-((cyclohexymethyl)sulfonamido)-4-methoxybenzo[d]isoxazol-6-yl)methyl)-1H-pyrazol-3-yl)methyl)propionamide

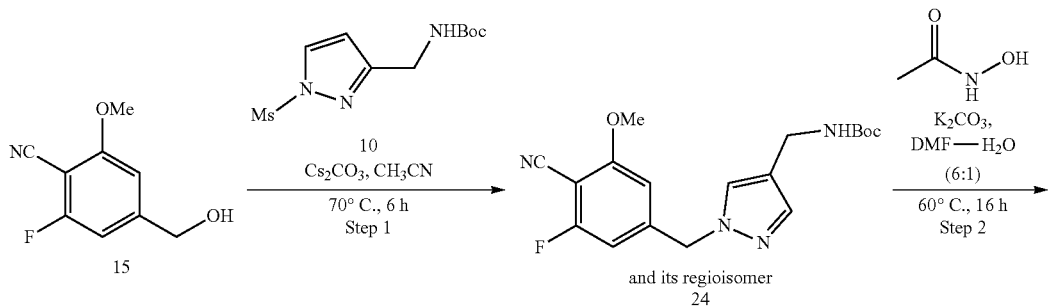

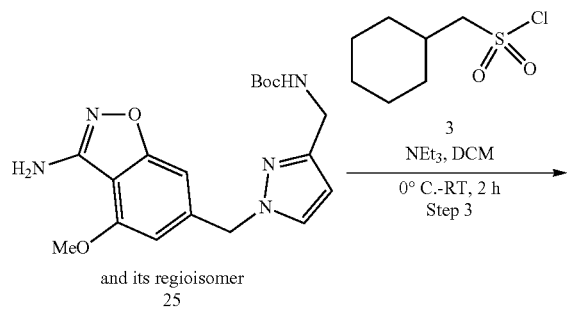

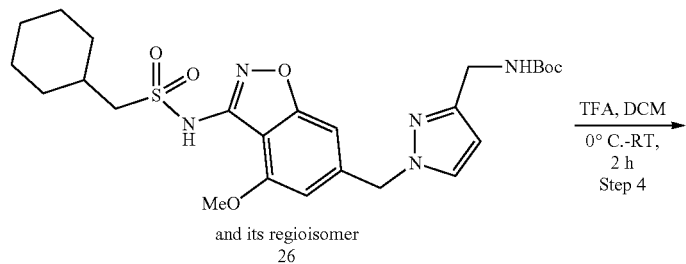

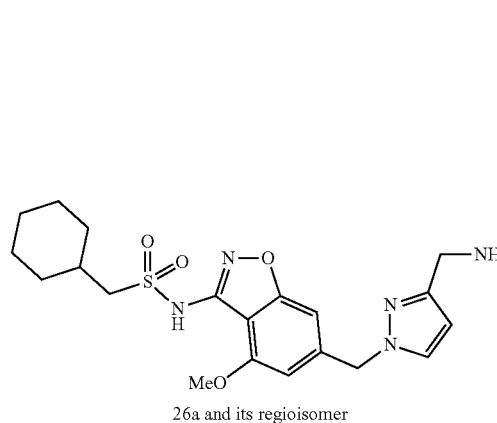

26a and its regioisomer

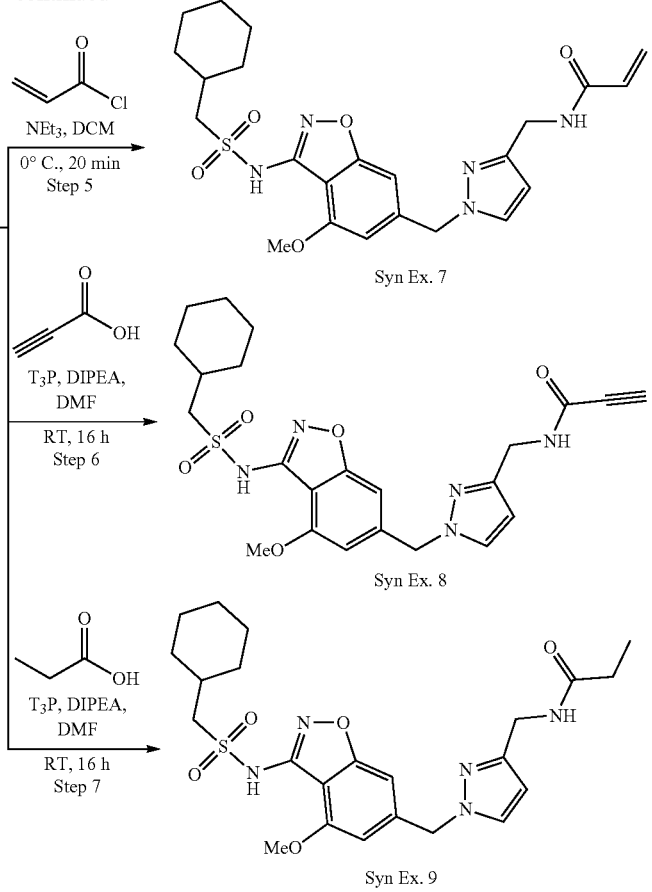

Syn Ex. 7

Syn Ex. 8

Syn Ex. 9

Note that for the final compounds (Syn Ex. 7-9), the other regioisomer was removed by purification and the isomer as drawn was obtained.

Synthesis of tert-butyl ((1-(4-cyano-3-fluoro-5-methoxybenzyl)-1H-pyrazol-3-yl)methyl)carbamate (24 and its Regioisomer)

To a stirred solution of compound 15 (0.2 g, 1.10 mmol) in acetonitrile (5 mL) at the room temperature was added Cs$_2$CO$_3$ (1.07 g, 3.30 mmol) followed by compound 10 (0.440 g, 1.60 mmol) and the resulting reaction mixture was heated at 70° C. for 6 h. After completion of the reaction (monitored by TLC), the mixture was cooled to room temperature, water added and extracted with ethyl acetate. The organic layer was collected, washed with brine, dried over anhydrous Na$_2$SO$_4$ and concentrated under reduced pressure. The crude compound was purified by Combi-flash chromatography using a gradient method of 40-70% EtOAc/Heptane to afford the title compound 24 (0.180 g, 45.4%, isolated as inseparable mixture) as a brown semi-solid. TLC: 80% EtOAc/Heptane (R$_f$ 0.45). $^1$H NMR (400 MHz, DMSO-d$_6$): δ 7.78 (s, 1H), 7.24-7.18 (m, 1H), 6.97 (s, 1H), 6.71 (d, J=9.6 Hz, 1H), 6.15 (d, J=2.0 Hz, 1H), 5.35 (s, 2H), 4.05 (d, J=5.6 Hz, 2H), 3.91 (s, 3H), 1.37 (s, 9H). $^1$H NMR indicates presence of minor regioisomer as well; LCMS Calculated for C$_{18}$H$_{21}$FN$_4$O$_3$: 360.39; Found: 359.0 (M−1).

Synthesis of tert-butyl ((1-((3-amino-4-methoxy-benzo[d]isoxazol-6-yl)methyl)-1H-pyrazol-3-yl)methyl)carbamate (25 and its Regioisomer)

To a stirred solution of compound 24 (0.18 g, 0.5 mmol) in a 6:1 mixture of DMF:H$_2$O (7 mL) at room temperature was added N-hydroxyacetamide (0.112 g, 1.50 mmol) followed by K$_2$CO$_3$ (0.414 g, 3.0 mmol). The reaction mixture was allowed to stir at 60° C. for 16 h. After completion of the reaction (monitored by TLC), the reaction mixture was cooled to room temperature, ice water added and extracted with ethyl acetate. The organic layer was collected, washed with brine, dried over anhydrous Na$_2$SO$_4$ and concentrated under reduced pressure. The crude compound was purified by Combi flash chromatography using a gradient method of 40-60% EtOAc/Heptane to afford the title compound 25 (0.130 g, 69.7%, isolated as inseparable mixture) as a brown semi-solid. TLC: 80% EtOAc/Heptane (R$_f$ 0.40). 1H NMR (400 MHz, DMSO-d$_6$): δ 7.78 (broad s, 1H), 7.24-7.18 (m, 1H), 6.97 (s, 1H), 6.71 (d, J=10 Hz, 1H), 6.16 (s, 1H), 5.35 (s, 2H), 4.05 (d, J=5.6 Hz, 2H), 3.94 (s, 3H), 1.37 (s, 9H). $^1$H NMR indicates presence of minor regioisomer as well and NH$_2$ protons not observed; LCMS Calculated for C$_{18}$H$_{23}$N$_5$O$_4$: 373.41; Found: 374.02 (M+1).

Synthesis of tert-butyl ((1-((3-((cyclohexylmethyl)sulfonamido)-4-methoxybenzo[d]isoxazol-6-yl)methyl)-1H-pyrazol-3-yl)methyl)carbamate (26 and its regioisomer)

To a stirred solution of compound 25 (0.130 g, 0.34 mmol) in DCM (3 mL) at 0° C. was added Et$_3$N (0.14 mL, 1.00 mmol) followed by cyclohexylmethanesulfonyl chloride (3, 0.081 g, 0.41 mmol) and the reaction was allowed to stir at the room temperature for 2 h. After completion of the reaction (monitored by TLC), the mixture was diluted with DCM, water added and extracted. The organic layer was collected, washed with brine, dried over anhydrous $Na_2SO_4$ and concentrated under reduced pressure. The crude compound was purified by Combi flash column chromatography using a gradient method of 40-60% EtOAc/Heptane to afford the title compound 26 (0.065 g, 34.99%, isolated as inseparable mixture) as a brown gummy solid. TLC: 80% EtOAc/Heptane ($R_f$ 0.35). LCMS Calculated for $C_{25}H_{35}N_5O_6S$: 533.64; Found: 532.03 (M−1). $^1H$ NMR is complicated and indicates presence of minor regioisomer as a mixture with the desired product.

Synthesis of N-(6-((3-(aminomethyl)-1H-pyrazol-1-yl)methyl)-4-methoxybenzo[d]isoxazol-3-yl)-1-cyclohexylmethanesulfonamide To a stirred solution of compound 26 (65 mg, 0.12 mmol) in DCM (2 mL) at 0° C., TFA (0.1 mL, 1.2 mmol) was added and the reaction was allowed to stir at the room temperature for 2 h. After completion of the reaction (monitored by TLC), it was concentrated under reduced pressure and the crude compound was purified by reverse phase HPLC to afford the title compound (6 mg, 11.36%) as an off-white solid. TLC: 5% MeOH/DCM ($R_f$ 0.5). $^1H$ NMR (400 MHz, DMSO-$d_6$): δ 8.36 (broad s, 2H), 7.92 (d, J=2.0 Hz, 1H), 6.66 (s, 1H), 6.54 (s, 1H), 6.37 (d, J=2.4 Hz, 1H), 5.37 (s, 2H), 4.01 (s, 2H), 3.79 (s, 3H), 2.94 (d, J=6.0 Hz, 2H), 1.86 (d, J=12.4 Hz, 2H), 1.79-1.76 (m, 1H), 1.61-1.53 (m, 3H), 1.24-1.05 (m, 3H), 0.94 (q, J=11.2 Hz, 2H). LCMS Calculated for $C_{20}H_{27}N_5O_4S$: 433.53; Found: 434.55 (M+1).

Synthetic Example 7

Synthesis of Mixture of N-((1-((3-((cyclohexylmethyl)sulfonamido)-4-methoxybenzo[d]isoxazol-6-yl)methyl)-1H-pyrazol-3-yl)methyl)acrylamide and its regioisomer

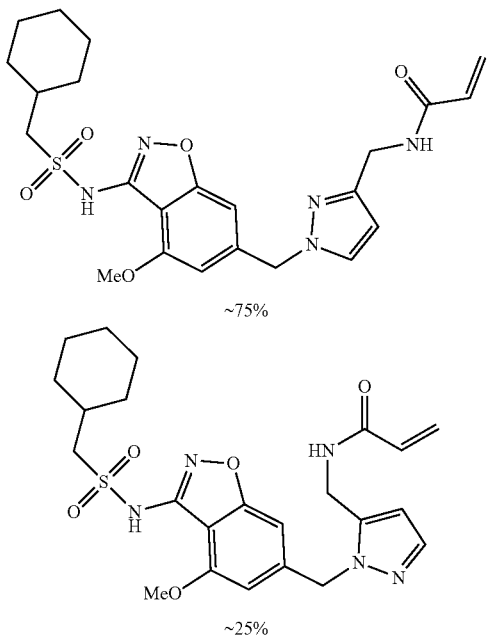

~75%

~25%

To a stirred solution of 26a (60 mg, 0.13 mmol) in DCM (5 mL) at 0° C., was added $Et_3N$ (0.09 mL, 0.65 mmol) followed by acryloyl chloride (0.008 mL, 0.11 mmol) and the reaction was allowed to stir at the same temperature for 20 min. After completion of the reaction (monitored by TLC), reaction mixture was concentrated under reduced pressure, added water and extracted with 5% MeOH/DCM. The organic layer was collected, washed with brine, dried over anhydrous $Na_2SO_4$ and concentrated under reduced pressure. The crude compound was purified by prep HPLC to afford the title compound (5 mg, 7.4%, isolated as inseparable regioisomeric mixture, ~75% regioisomer as drawn) as an off-white solid. TLC: 5% MeOH/DCM ($R_f$ 0.5). (See analytical data in Table 1).

Synthetic Example 8

Synthesis of N-((1-((3-((cyclohexylmethyl)sulfonamido)-4-methoxybenzo[d]isoxazol-6-yl)methyl)-1H-pyrazol-3-yl)methyl)propiolamide To a stirred solution of compound 26a (80 mg, 0.18 mmol) in DMF (2.5 mL) at 0° C. was added DIPEA (0.12 mL, 0.72 mmol), followed by T3P (0.17 mL, 0.27 mmol). The reaction was allowed to stir at the room temperature for 20 min. After that, a pre-dissolved solution of propiolic acid (12 mg, 0.18 mmol) in DMF (0.5 mL) was added in drop-wise manner and the reaction was allowed to stir at the room temperature for 16 h. After completion (monitored by TLC), solvent was concentrated under high vacuum. The residue was quenched with water and extracted with ethyl acetate. The organic layer was collected, washed with brine, dried over anhydrous $Na_2SO_4$ and concentrated under reduced pressure to afford crude compound which was purified by using prep-HPLC to obtain inseparable mixture of isomers. The isomers were further separated by using Chiral HPLC (Method: Chiral-Met-B 30%_1.0 ml. Icm; Mobile phase: A; 0.1% DEA in n-Hexane; B; DCM:MeOH (50:50) A:B, 70:30; Injection volume: 10 μL; Flow rate: 1.0 mL/min; Column: CHIRAL PAK IG (250*4.6 mm, 5 μm); Duration up to 25 min.) to afford the title compound (27 mg, 31%) as a white solid. TLC: 100% EtOAc ($R_f$ 0.5). (See Table 1 for analytical data). Minor isomer was not isolated in enough quantity due to merged impurities.

Synthetic Example 9

Synthesis of N-((1-((3-((cyclohexylmethyl)sulfonamido)-4-methoxybenzo[d]isoxazol-6-yl)methyl)-1H-pyrazol-3-yl)methyl)propionamide To a stirred solution of compound 26a (80 mg, 0.18 mmol) in DMF (2.5 mL) at 0° C. was added DIPEA (0.12 mL, 0.72 mmol), followed by T3P (0.17 mL, 0.27 mmol). The reaction was allowed to stir at the room temperature for 20 min. After that, a pre-dissolved solution of propionic acid (13 mg, 0.18 mmol) in DMF (0.5 mL) was added in drop-wise manner and the reaction was allowed to stir at the room temperature for 16 h. After completion (monitored by TLC), solvent was concentrated under high vacuum. The residue was quenched with water and extracted with ethyl acetate. The organic layer was collected, washed with brine, dried over anhydrous $Na_2SO_4$ and concentrated under reduced pressure to afford crude compound which was purified by using prep-HPLC to obtain inseparable mixture of isomers. The isomers were further separated by using Chiral HPLC (Method: Chiral-Met-B 30% 1.0 ml. Icm;

Mobile phase: A; 0.1% DEA in n-Hexane; B; DCM:MEOH (50:50) A:B, 70:30; Injection volume: 5 μL; Flow rate: 1.0 mL/min; Column: CHIRAL PAK IG (250*4.6 mm, 5 μm); Duration up to 25 min.) to afford the title compound (18 mg, 20%) as an off-white solid. TLC: 100% EtOAc ($R_f$ 0.5). (See Table 1 for analytical data). Minor isomer was not isolated in enough quantity due to merged impurities.

ethyl acetate. The combined organic layer was washed with water, dried over anhydrous $Na_2SO_4$, filtered and concentrated under reduced pressure to afford the title compound 28 (5.2 g, 43.33%) as a brown solid. This compound was used in the next step without further purification. TLC: 80% EtOAc/heptane ($R_f$ 0.5). $^1$H NMR (400 MHz, DMSO-$d_6$): δ 13.5 (broad s, 1H), 8.05 (s, 1H), 7.95 (s, 1H), 7.74 (d, J=8.8

Scheme 9: Synthesis of 6-(acrylamidomethyl)-N-((2-fluorophenyl)sulfonyl)benzofuran-2-carboxamide and N-((2-fluorophenyl)sulfonyl)-6-(propiolamidomethyl)benzofuran-2-carboxamide

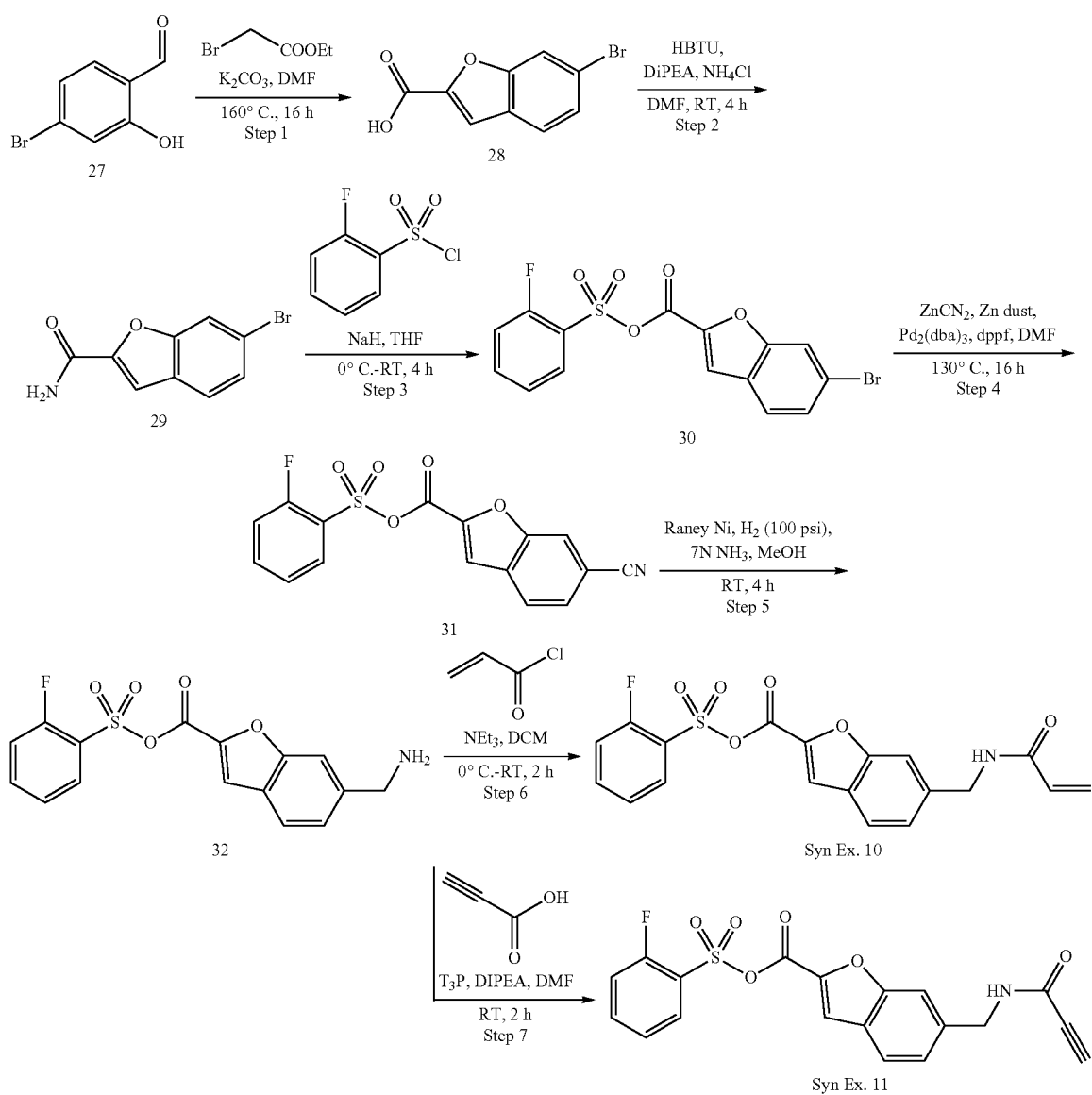

Hz, 1H), 7.53 (dd, J=8.4, 1.2 Hz, 1H). LCMS calculated for $C_9H_5BrO_3$: 241.04; Found: 239.12 (M-2).

Synthesis of 6-bromobenzofuran-2-carboxylic acid (28)

To a stirred solution of compound 27 (10 g, 49.75 mmol) in DMF (100 mL) was added $K_2CO_3$ (20.6 g, 149.250 mmol) followed by ethyl 2-bromoacetate (11 mL, 99.50 mmol). The reaction mixture was allowed to stir at 160° C. for 16 h. After completion of the reaction (monitored by TLC), the reaction mixture was cooled to room temperature, acidified with 1N HCl (up to pH~4-5) and extracted with Synthesis of 6-bromobenzofuran-2-carboxamide (29)

To a stirred solution of compound 28 (1.5 g, 6.22 mmol) in DMF (15 mL) was added DIPEA (3.25 mL, 18.66 mmol) followed by HBTU (2.83 g, 7.46 mmol) and $NH_4Cl$ (1 g, 18.66 mmol). The reaction was stirred at the room temperature for 4 h. The progress of the reaction was monitored by TLC. After completion, water was added and extracted with ethyl acetate. The combined organic layer was washed with water, dried over anhydrous $Na_2SO_4$, filtered and concentrated under reduced pressure to afford the title compound 29 (0.654 g, 43.78%) as a brown solid. This compound was used in the next step without further purification. TLC: 80% EtOAc/heptane ($R_f$ 0.6); $^1$H NMR (400 MHz, DMSO-$d_6$): 8.15 (broad s, 1H), 7.93 (s, 1H), 7.73 (d, J=8.4 Hz, 2H), 7.56 (s, 1H), 7.50 (dd, J=8.8, 1.6 Hz, 1H). LCMS Calculated for $C_9H_6BrNO_2$: 240.06; Found: 241.75 (M+1).

Synthesis of 6-bromo-N-((2-fluorophenyl)sulfonyl)benzofuran-2-carboxamide (30)

To a stirred solution of compound 29 (1.5 g, 6.30 mmol) in THF (20 mL) at 0° C. was added NaH [60% dispersion in mineral oil] (0.378 g, 9.45 mmol) and the contents were stirred for 15 min. 2-Fluorobenzenesulfonyl chloride (1.34 g, 6.93 mmol) was added and the reaction was allowed to stir at the room temperature for 4 h. After completion of the reaction (monitored by TLC), the reaction mixture was cooled to 0° C., quenched with ice water and extracted with ethyl acetate. The combined organic layer was dried over anhydrous $Na_2SO_4$, filtered and concentrated under reduced pressure. The crude compound was purified by silica gel [100-200 mesh] column chromatography to afford the title compound 30 (2.01 g, 80.72%) as a white solid. TLC: 5% MeOH/DCM ($R_f$ 0.2); $^1$H NMR (400 MHz, DMSO-$d_6$): δ 7.89 (s, 1H), 7.83 (t, J=8.0 Hz, 1H), 7.63 (d, J=8.4 Hz, 1H), 7.46 (q, J=5.2 Hz, 1H), 7.41 (d, J=7.6 Hz, 1H), 7.27-7.11 (m, 3H). NH proton not observed; LCMS Calculated for $C_{15}H_9BrFNO_4S$: 398.20; Found: 400.15 (M+2).

Synthesis of 6-cyano-N-((2-fluorophenyl) sulfonyl) benzofuran-2-carboxamide (31)

To an argon purged solution of 30 (200 mg, 50 mmol) in DMF (5 mL) was added $Zn(CN)_2$ (73 mg, 0.63 mmol) followed by Zn dust (32 mg, 50 mmol) and purged again with argon for 15 min. $Pd_2(dba)_3$ (23 mg, 2.5 mmol) and dppf (37 mg, 5 mmol) were added to the resulting mixture. The reaction was allowed to stir at 130° C. for 16 h. The progress of the reaction was monitored by TLC. After completion, the reaction mixture was filtered through a pad of Celite which was washed with ethyl acetate. The filtrate was concentrated under reduced pressure. The crude compound was purified by prep-HPLC to afford the title compound 31 (0.348 g, 80.18%) as an off-white solid. TLC: 5% MeOH/DCM ($R_f$ 0.4); $^1$H NMR (400 MHz, DMSO-$d_6$): δ 8.34 (s, 1H), 8.05-7.96 (m, 3H), 7.78-7.72 (m, 2H), 7.48-7.41 (m, 2H). NH proton not observed; LCMS Calculated for $C_{16}H_9FN_2O_4S$: 344.32; Found: 345.05 (M+1).

Synthesis of 6-(aminomethyl)-N-((2-fluorophenyl) sulfonyl)benzofuran-2-carboxamide (32)

An autoclave was charged with a solution of 31 (400 mg 1.16 mmol) in MeOH (10 mL) and the mixture was purged with nitrogen for 5 min. A pre-dissolved solution of Raney Ni (w/w of SM) in 7N $NH_3$/MeOH (5 mL) was added under nitrogen atmosphere. The reaction mixture was then purged with hydrogen and was allowed to stir under hydrogen atmosphere (100 psi) at the room temperature for 4 h. The progress of the reaction was monitored by TLC. After completion, the reaction mixture was filtered through a pad of Celite which was washed with MeOH. The filtrate was concentrated under reduced pressure to dryness. The crude product was purified by Combi flash chromatography (using a gradient method of 5% MeOH/DCM) to afford the desired title compound 32 (0.314 g, 78.5%) as a yellow solid. TLC: 5% MeOH/DCM ($R_f$ 0.5); $^1$H NMR (400 MHz, DMSO-$d_6$): δ 8.14 (broad s, 3H), 7.84 (t, J=7.2 Hz, 1H), 7.73 (s, 1H), 7.70 (d, J=2.8 Hz, 1H), 7.51-7.42 (m, 1H), 7.33 (d, J=7.6 Hz, 1H), 7.27-7.14 (m, 3H), 4.16 (d, J=3.6 Hz, 2H). LCMS Calculated for $C_{16}H_{13}FN_2O_4S$: 348.35; Found: 347.10 (M−1).

Synthetic Example 10

Synthesis of 6-(acrylamidomethyl)-N-((2-fluorophenyl)sulfonyl)benzofuran-2-carboxamide To a stirred solution of 32 (100 mg, 0.28 mmol) in DCM (5 mL) at 0° C. was added $Et_3N$ (0.12 mL, 0.84 mmol), followed by acryloyl chloride (22.6 mg, 0.28 mmol) and the reaction was allowed to stir at the room temperature for 2 h. After completion of the reaction (monitored by TLC), the reaction mixture was concentrated under reduced pressure, water added and extracted with 5% MeOH/DCM. The organic layer was collected, washed with brine, dried over anhydrous $Na_2SO_4$ and concentrated under reduced pressure. The crude compound was purified by using reverse phase HPLC to afford the title compound (5 mg, 4.3%) as an off-white solid. TLC: 5% MeOH/DCM ($R_f$ 0.5). (See analytical data in Table 1).

Synthetic Example 11

Synthesis of N-((2-fluorophenyl)sulfonyl)-6-(propiolamidomethyl)benzofuran-2-carboxamide To a stirred solution of 32 (150 mg, 0.43 mmol) in DMF (2 mL) at 0° C. was added DIPEA (0.22 mL, 1.29 mmol), followed by $T_3P$ (205 μL, 0.64 mmol). The reaction was allowed to stir at the room temperature for 20 min. After that, a pre-dissolved solution of propiolic acid (30 mg, 0.43 mmol) in DMF (0.5 mL) was added in a drop-wise manner and the reaction was allowed to stir at the room temperature for 2 h. After completion (monitored by TLC), the solvent was concentrated under high vacuum. The residue was quenched with water and extracted with DCM. The organic layer was collected, washed with brine, dried over anhydrous $Na_2SO_4$ and concentrated under reduced pressure. The crude compound was purified by using reverse phase HPLC to afford the title compound (7 mg, 4%) as an off-white solid. TLC: 10% MeOH/DCM ($R_f$ 0.5). (See analytical data in Table 1).

Scheme 10: Synthesis of N-((2-(3-(2-((2-fluorophenyl)sulfonyl)hydrazine-1-carbonyl)-5-methylphenyl)pyridin-4-yl)methyl)acrylamide & N-((2-(3-(2-((2-fluorophenyl)sulfonyl)hyrazine-1-carbonyl)-5-methylphenyl)pyridin-4-yl)methyl)propiolamide
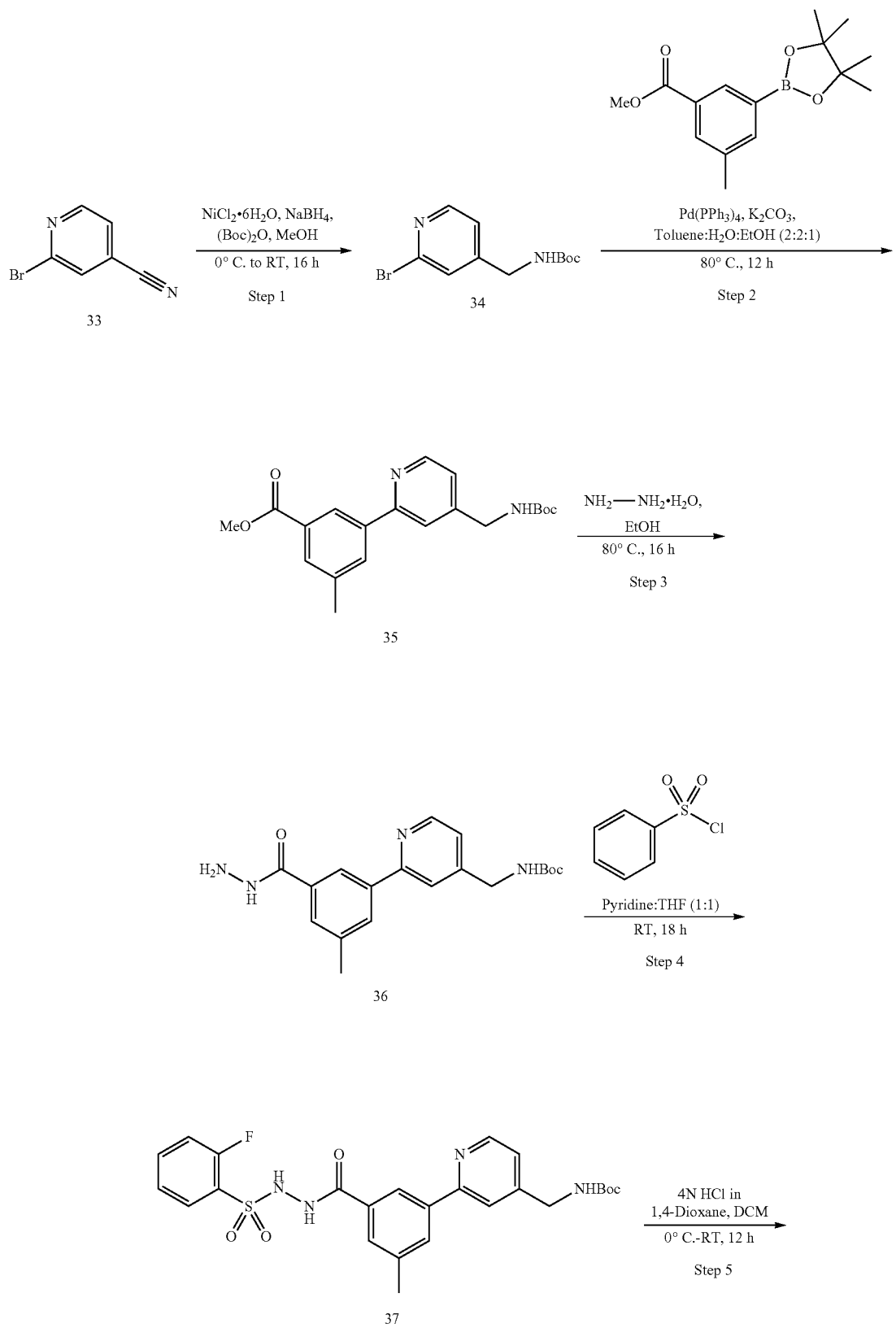

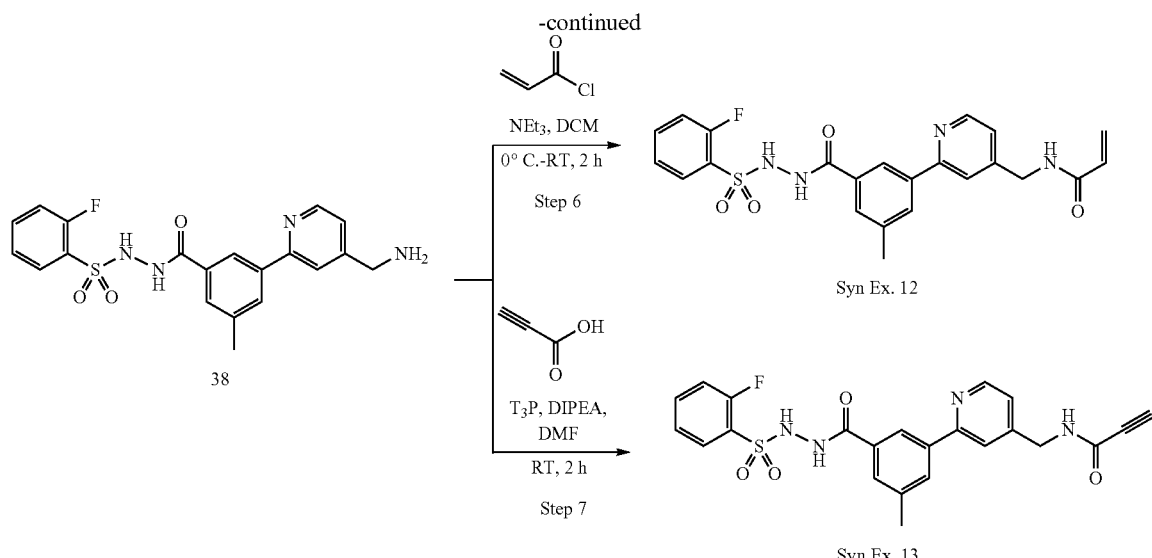

Syn Ex. 12

Syn Ex. 13

Synthesis of tert-butyl ((2-bromopyridin-4-yl)methyl)carbamate (34)

To a stirred solution of compound 33 (2 g, 10.92 mmol) in MeOH (30 mL) at 0° C. was added (Boc)$_2$O (2.5 mL, 10.92 mmol) followed by NiCl$_2$·6H$_2$O (0.490 g, 2.06 mmol). After few minutes of stirring, the resulting mixture at the same temperature, was added NaBH$_4$ (1.24 g, 32.70 mmol) and the reaction was allowed to warm to room temperature and stirred for 16 h. After completion of the reaction (monitored by TLC), water was added to the reaction mixture and extracted with ethyl acetate. The combined organic layer was collected, washed with saturated NaHCO$_3$ solution, brine, dried over anhydrous Na$_2$SO$_4$ and concentrated under reduced pressure. The crude compound was purified by combi flash chromatography (using a gradient method of 0-15% EtOAc/Heptane) to afford the title compound 34 (1.0 g, 32.0%) as a yellow solid. TLC: 30% EtOAc/Heptane (R$_f$ 0.35); $^1$H NMR (400 MHz, DMSO-d$_6$): δ 8.29 (d, J=5.2 Hz, 1H), 7.52 (t, J=5.6 Hz, 1H), 7.44 (s, 1H), 7.27 (d, J=4.8 Hz, 1H), 4.14 (d, J=6.0 Hz, 2H), 1.34 (s, 9H); LCMS Calculated for C$_{11}$H$_{15}$BrN$_2$O$_2$: 287.16; Found: 286.89 (M−1).

Synthesis of methyl 3-(4-(((tert-butoxycarbonyl)amino)methyl)pyridin-2-yl)-5-methylbenzoate (35)

To a stirred solution of compound 34 (1.73 g, 6.03 mmol) in a 2:2:1 mixture of Toluene:H$_2$O:EtOH (37 mL), was added K$_2$CO$_3$ (2.89 g, 20.90 mmol) followed by Pd(PPh$_3$)$_4$ (0.231 g, 0.2 mmol) and methyl 3-methyl-5-(4,4,5,5-tetramethyl-1,3,2-dioxaborolan-2-yl)benzoate (1.2 g, 4.19 mmol). The resulting reaction mixture was stirred at 80° C. for 12 h. After completion (monitored by TLC), the reaction mixture was cooled to room temperature, water added and extracted with ethyl acetate. The organic layer was collected, washed with brine, dried over anhydrous Na$_2$SO$_4$ and concentrated under reduced pressure. The crude compound was purified by combi flash chromatography (using a gradient method of 0-50% EtOAc/Heptane) to afford the title compound 35 (0.9 g, 60.46%) as an off-white solid. TLC: 80% EtOAc/Heptane (R$_f$ 0.25). $^1$H NMR (400 MHz, DMSO-d$_6$): δ 8.61 (d, J=4.4 Hz, 1H), 8.44 (s, 1H), 8.15 (s, 1H), 7.85 (s, 2H), 7.59-7.54 (m, 1H), 7.24 (d, J=3.6 Hz, 1H), 4.24 (d, J=6.0 Hz, 2H), 3.89 (s, 3H), 2.46 (s, 3H), 1.42 (s, 9H); LCMS Calculated for C$_{20}$H$_{24}$N$_2$O$_4$: 356.42; Found: 357.2 (M+1).

Synthesis of tert-butyl ((2-(3-(hydrazinecarbonyl)-5-methylphenyl)pyridin-4-yl)methyl)carbamate (34)

To a stirred solution of Compound 35 (1.5 g, 4.21 mmol) in EtOH (10 mL) was added hydrazine hydrate (5 mL) and the reaction was allowed to stir at 80° C. for 16 h. After completion (monitored by TLC), water was added to the reaction mixture and extracted with ethyl acetate. The combined organic layer was collected, washed with brine, dried over anhydrous Na$_2$SO$_4$ and concentrated under reduced pressure to afford the title compound 36 (1.4 g, 93.33%) as an off-white solid. TLC: 10% MeOH/DCM (R$_f$ 0.3). $^1$H NMR (400 MHz, DMSO-d$_6$): δ 9.83 (broad s, 1H), 8.60 (d, J=4.8 Hz, 1H), 8.28 (s, 1H), 8.02 (s, 1H), 7.85 (s, 1H), 7.70 (s, 1H), 7.56 (t, J=5.6 Hz, 1H), 7.22 (d, J=4.4 Hz, 1H), 4.51 (s, 2H), 4.24 (d, J=5.6 Hz, 2H), 2.43 (s, 3H), 1.41 (s, 9H); LCMS Calculated for C$_{19}$H$_{24}$N$_4$O$_3$: 356.43; Found: 355.13 (M−1).

Synthesis of tert-butyl ((2-(3-(2-((2-fluorophenyl)sulfonyl)hydrazine-1-carbonyl)-5-methylphenyl)pyridin-4-yl)methyl)carbamate (37)

To a stirred solution of compound 36 (100 mg, 0.28 mmol) in a 1:1 mixture of pyridine and THF (3 mL) was added 2-fluorobenzenesulfonyl chloride (60 mg, 0.30 mmol). The reaction was allowed to stir at room temperature for 18 h. After completion (monitored by TLC), the reaction mixture was concentrated under high vacuum. The residue was diluted with ethyl acetate, quenched with water and extracted. The combined organic layer was collected, washed with brine, dried over anhydrous Na$_2$SO$_4$ and concentrated under reduced pressure to afford the title compound 37 (110 mg, 76.18%) as an off-white solid. TLC: 10% MeOH/DCM (R$_f$ 0.6); $^1$H NMR (400 MHz, DMSO-d$_6$): δ 10.82 (s, 1H), 10.33 (d, J=2.0 Hz, 1H), 8.91 (d, J=4.8 Hz, 1H), 8.65 (d, J=5.2 Hz, 1H), 8.58-8.52 (m, 1H), 8.16 (s, 1H), 8.03 (t, J=7.6 Hz, 1H), 7.91 (s, 1H), 7.81 (t, J=7.6 Hz, 1H), 7.69-7.54 (m, 1H), 7.42-7.28 (m, 2H), 7.11 (d, J=7.6 Hz, 1H), 4.28 (d, J=6.0 Hz, 2H), 2.41 (s, 3H), 1.41 (s, 9H); LCMS Calculated for $C_{25}H_{27}FN_4O_5S$: 514.57; Found: 514.89 (M+1).

Synthesis of N-(3-(4-(aminomethyl)pyridin-2-yl)-5-methylbenzoyl)-2-fluorobenzenesulfonohydrazide (38)

To a stirred solution of compound 37 (100 mg, 0.19 mmol) in DCM (2 mL) at 0° C., 4N HCl in 1,4-dioxane (0.2 mL) was added and the reaction was allowed to stir at the room temperature for 12 h. After completion (monitored by TLC), the reaction mixture was quenched with sat. $NaHCO_3$ solution and extracted with DCM. The combined organic layer was collected, washed with brine, dried over anhydrous $Na_2SO_4$ and concentrated under reduced pressure, to afford the title compound 38 (80 mg, 91%) as a white solid. TLC: 10% MeOH/DCM ($R_f$ 0.3); $^1$H NMR (400 MHz, DMSO-$d_6$): δ 10.81 (s, 1H), 10.32 (d, J=2.0 Hz, 1H), 8.91 (d, J=5.2 Hz, 1H), 8.72 (d, J=4.8 Hz, 1H), 8.56 (t, J=7.2 Hz, 1H), 8.25 (s, 1H), 8.09 (s, 1H), 8.04 (t, J=6.8 Hz, 1H), 7.85-7.79 (m, 1H), 7.72-7.62 (m, 1H), 7.50 (d, J=4.8 Hz, 1H), 7.40 (t, J=9.2 Hz, 1H), 7.30 (t, J=7.6 Hz, 1H), 7.10 (d, J=7.6 Hz, 1H), 4.16 (q, J=5.6 Hz, 2H), 2.42 (s, 3H); LCMS Calculated for: $C_{20}H_{19}FN_4O_3S$: 414.46; Found: 415.84 (M+1).

Synthetic Example 12

Synthesis of N-((2-(3-(2-((2-fluorophenyl)sulfonyl)hydrazine-1-carbonyl)-5-methylphenyl)pyridin-4-yl)methyl)acrylamide To a stirred solution of compound 38 (100 mg, 0.24 mmol) in DCM (4 mL) at 0° C. was added $Et_3N$ (0.067 mL, 0.48 mmol) followed by a pre-dissolved solution of acryloyl chloride (20 mg, 0.21 mmol) in DCM (1 mL) and the reaction was allowed to stir at the room temperature for 2 h. After completion of the reaction (monitored by TLC), the mixture was concentrated under reduced pressure, diluted with ethyl acetate, water added and extracted. The organic layer was collected, washed with brine, dried over anhydrous $Na_2SO_4$ and concentrated under reduced pressure. The crude compound was purified by using prep HPLC to afford the title compound (12 mg, 10.6%) as an off-white solid. TLC: 10% MeOH/DCM ($R_f$ 0.4). (See analytical data in Table 1).

Synthetic Example 13

Synthesis of N-((2-(3-(2-((2-fluorophenyl)sulfonyl)hydrazine-1-carbonyl)-5-methylphenyl)pyridin-4-yl)methyl)propiolamide To a stirred solution of compound 38 (100 mg, 0.22 mmol) in DMF (2 mL) at 0° C. was added DIPEA (0.11 mL, 0.66 mmol), followed by $T_3P$ (0.31 mL, 0.44 mmol). The reaction was allowed to stir at the room temperature for 20 min. After, a pre-dissolved solution of propiolic acid (14 mg, 0.22 mmol) in DMF (0.5 mL) was added in drop-wise manner and the reaction mixture was stirred at room temperature for 2 h. After completion (monitored by TLC), the solvent was concentrated under high vacuum. The residue was quenched with water and extracted with DCM. The organic layer was collected, washed with brine, dried over anhydrous $Na_2SO_4$ and concentrated under reduced pressure. The crude compound was purified by using prep. HPLC to afford the title compound (5 mg, 4.4%) as an off-white solid. TLC: 5% MeOH/DCM ($R_f$ 0.5); (See Table 1 for analytical data).

Synthetic Example 14

Scheme 11: Synthesis of 1-acryloyl-N-((2-((2-fluorophenyl)sulfonyl)carbamoyl)benzofuran-6-yl)methyl)piperidine-4-carboxamide

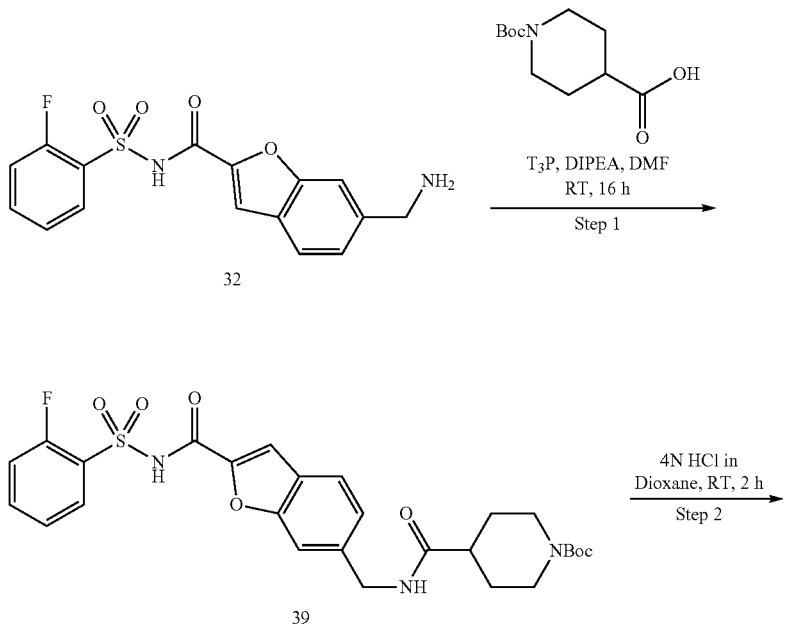

-continued

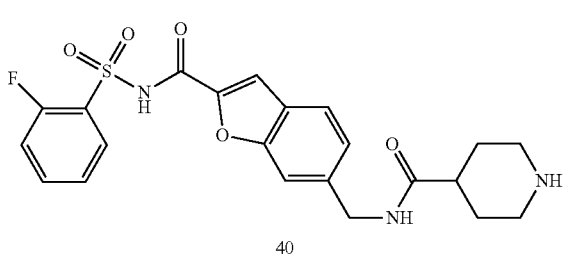
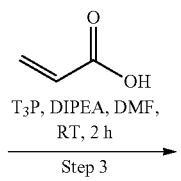

T₃P, DIPEA, DMF, RT, 2 h
Step 3

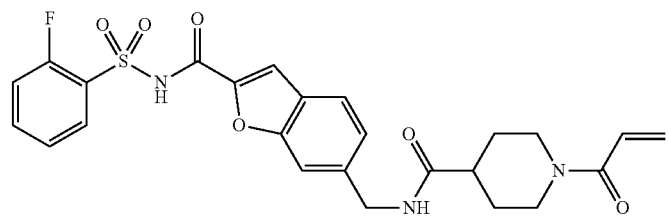

Syn. Ex. 14

Synthesis of tert-butyl 4-(((2-(((2-fluorophenyl)sulfonyl)carbamoyl)benzofuran-6-yl)methyl)carbamoyl)piperidine-1-carboxylate (37)

To a stirred solution of 1-(tert-butoxycarbonyl)piperidine-4-carboxylic (100 mg, 0.43 mmol) in DMF (2 mL) at 0° C. was added DIPEA (221 µL, 0.61 mmol), followed by T₃P (201 mg, 1.29 mmol), and 32 (150 mg, 0.43 mmol) was added. The reaction was allowed to stir at the room temperature for 16 h. After completion (monitored by TLC), the reaction mixture was quenched with water and extracted with ethyl acetate. The organic layer was collected, washed with brine, dried over anhydrous Na₂SO₄ and concentrated under reduced pressure. The crude compound was purified by using trituration with DCM and n-Pentaneto afford compound 39 (134 mg, 56) as a yellow solid. TLC: 5%% MeOH/DCM (Rf: 0.5). 1H NMR (400 MHz, DMSO-d₆): δ 8.42 (s, 1H), 7.95 (d, J=8.0 Hz, 1H), 7.67 (d, J=8.0 Hz, 1H), 7.43 (s, 1H), 7.36-7.14 (i, 1H), 7.25 (s, 1H), 7.20 (d, J=7.6 Hz, 1H), 6.76 (s, 1H), 7.38 (d, J=5.2 Hz, 1H), 3.93 (d, J=11.2 Hz, 2H), 2.88 (s, 1H), 2.72 (m, 2H), 2.23 (t, J=11.2 Hz, 1H), 1.67 (m, 2H), 1.38 (s, 9H), 1.25 (in, 2H); 2 protons not observed; LCMS Calculated for C₂₇H₃₀FN₃O₇S: 559.61; Found: 558.93 (M−1).

Synthesis of N-((2-(((2-fluorophenyl)sulfonyl)carbamoyl)benzofuran-6-yl)methyl)piperidine-4-carboxamide (40)

To a stirred solution of compound 39 (130 mg, 0.23 mmol) in DCM (2 mL) at 0° C., 4N HCl in 1, 4-dioxane (2 mL) was added and the reaction mixture was allowed to stir at the room temperature for 2 h. After completion of the reaction (monitored by TLC), the volatiles were removed under vacuo, the residue obtained was triturated with DCM/Heptane to afford compound 40 (100 mg, 93%) as an off-white solid. TLC: 500 MeOH/DCM (R$_f$: 0.3). ¹H NMR (400 MHz, DMSO-d₆): δ 9.02 (brs, 1H), 8.63 (d, J=6.0 Hz, 2H), 8.01 (t, J=7.2 Hz, 1H), 7.96 (s, 1H), 7.77 (d, J=8.4 Hz, 1H), 7.48 (d, J=8.0 Hz, 2H), 7.37 (s, 1H), 7.26 (d, J=8.0 Hz, 1H), 6.89 (s, 1H), 4.40 (d, J=6.0 Hz, 1H), 3.56 (s, 1H), 3.24 (m, 2H), 2.88 (m, 2H), 2.33 (m, 1H), 1.86 (m, 2H), 1.74 (m, 2H); LCMS Calculated for C₂₂H₂₂FN₃O₅S: 459.49; Found: 458.63 (M−1).

Synthesis of 1-acryloyl-N-((2-(((2-fluorophenyl)sulfonyl)carbamoyl)benzofuran-6-yl)methyl)piperidine-4-carboxamide To a stirred solution of acrylic acid (20 mg, 0.26 mmol) in DMF (2 mL) at 0° C. was added DIPEA (187 µL, 1.08 mmol), followed by T3P (104 mg, 0.32 mmol) and reaction mixture was allowed to stir for 30 min. To the above reaction mixture was added compound 40 (100 mg, 0.21 mmol) and stirring was continued at room temperature for 2 h. After completion (monitored by TLC), the reaction mixture was concentrated under reduced pressure and the crude compound obtained was purified by using prep HPLC to afford the (14 mg, 12.6%) as a white solid. TLC: 10% MeOH/DCM (R$_f$: 0.5). (See analytical data in Table 1).

Synthetic Examples 15-16

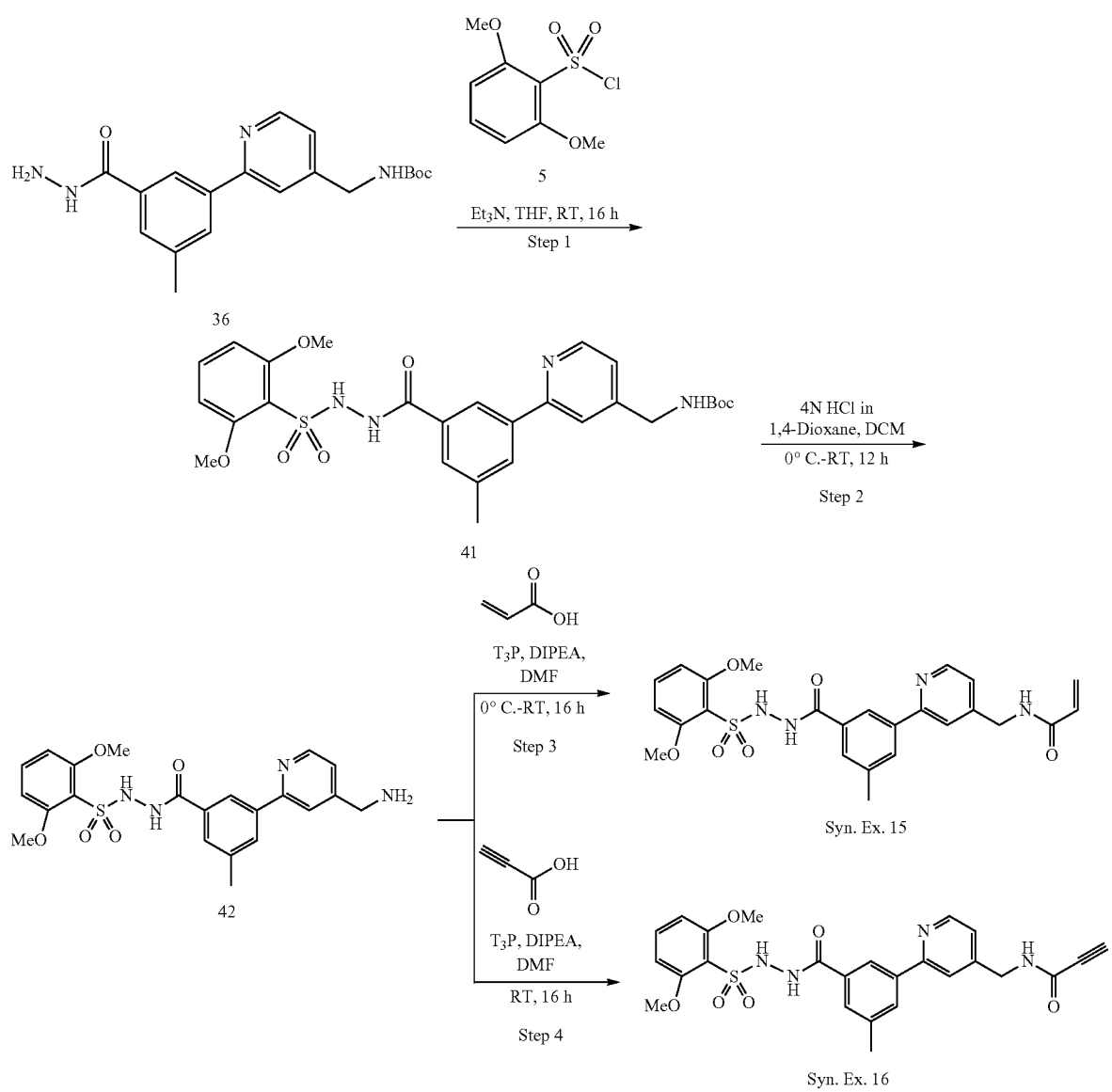

Scheme 12: Synthesis of N-((2-(3-(2-((2,6-dimethoxyphenyl)sulfonyl)hydrazine-1-carbonyl)-5-methylphenyl)pyridin-4-yl)methyl)acrylamide & N-((2-(3-(2-((2,6-dimethoxyphenyl)sulfonyl)hyrazine-1-carbonyl)-5-methylphenyl)pyridin-4-yl)methyl)propiolamide Synthesis of tert-butyl ((2-(3-(2-((2,6-dimethoxyphenyl)sulfonyl)hydrazine-1-carbonyl)-5-methylphenyl)pyridin-4-yl)methyl)carbamate (41)

To a stirred solution of compound 36 (450 mg, 1.26 mmol) in THF (10 mL) was added compound 5 (298 mg, 1.26 mmol), followed by Et₃N (0.88 mL, 6.32 mmol) and the resulting reaction mixture was allowed to stir at room temperature for 16 h. After completion (monitored by TLC), the reaction mixture was concentrated under vacuo, crude compound obtained was triturated with DCM/pentane to afford the title compound 41 (350 mg, 50%) as pale yellow solid. LCMS Calculated for C27H32N4O7S: 556.63; Found: 557.89 (M+1).

Synthesis of N'-(3-(4-(aminomethyl)pyridin-2-yl)-5-methylbenzoyl)-2,6-dimethoxybenzenesulfonohydrazide (42)

To a stirred solution of compound 41 (400 mg, 0.71 mmol) in DCM (2 mL) at 0° C., 4N HCl in 1,4-dioxane (0.2 mL) was added and the reaction was allowed to stir at the room temperature for 12 h. After completion (monitored by TLC), the reaction mixture was neutralised using sat. NaHCO₃ solution and extracted with DCM. The combined organic layer was collected, washed with brine, dried over anhydrous Na$_2$SO$_4$ and concentrated under reduced pressure to afford the title compound 42 (250 mg, 78.12%) as a white solid. TLC: 10% MeOH/DCM (R$_f$, 0.3); LCMS Calculated for: C$_{22}$H$_{24}$N$_4$O$_5$S: 456.52; Found: 457.01 (M+1).

Synthetic Example 15

Synthesis of N-((2-(3-(2-((2,6-dimethoxyphenyl) sulfonyl)hydrazine-1-carbonyl)-5-methylphenyl) pyridin-4-yl)methyl)acrylamide To a stirred solution of acrylic acid (15.15 mg, 0.17 mmol) in DMF (0.8 mL) at 0° C. was added DIPEA (0.09 mL, 0.52 mmol) and T$_3$P (111 mg, 0.35 mmol) followed by compound 42 (80 mg, 0.17 mmol) and the reaction was allowed to stir at the room temperature for 16 h. After completion of the reaction (monitored by TLC), the mixture was concentrated under reduced pressure, diluted with ethyl acetate, water added and extracted. The organic layer was collected, washed with brine, dried over anhydrous Na$_2$SO$_4$ and concentrated under reduced pressure. The crude compound was purified by using prep HPLC to afford the title compound (12 mg, 13.4%) as a white solid. TLC: 10% MeOH/DCM (R$_f$, 0.6). (See analytical data in Table 1).

Synthetic Example 16

Synthesis of N-((2-(3-(2-((2,6-dimethoxyphenyl) sulfonyl)hydrazine-1-carbonyl)-5-methylphenyl) pyridin-4-yl)methyl)propiolamide To a stirred solution of propiolic acid (16.5 mg, 0.23 mmol) in DMF (2 mL) at 0° C. was added DIPEA (0.11 mL, 0.59 mmol), followed by T$_3$P (125 mg, 0.39 mmol) and the reaction mixture was allowed to stir at the room temperature for 10 min. To the above reaction mixture compound 42 (90 mg, 0.22 mmol) was added and the mixture allowed to stir at room temperature for 16 h. After completion (monitored by TLC), the reaction mixture was concentrated under vacuo and the residue obtained was dissolved in DCM and then extracted. The combined organic layer was collected, washed with brine, dried over anhydrous Na$_2$SO$_4$ and concentrated under reduced pressure to afford the crude compound which was purified by using prep. HPLC to give title compound (10 mg, 10%) as a white solid. TLC: 10% MeOH/DCM (R$_f$, 0.6); (See analytical data for Table 1).

Synthetic Examples 17-19

Scheme 13: Synthesis of 2-fluoro-N-(4-methoxy-6-((3-(vinylfulfonamidomethyl)-1H-pyrazol-1-yl)methyl)benzo[d]isoxazol-3-yl)benzenesulfonamide, N-((1-((3-((2-fluorophenyl)sulfonamido)-4-methoxybenzo[d]isoxazol-6-yl)methyl)-1H-pyrazol-3-yl)methyl)acrylamide and 2,6-dimethoxy-N-(4-methoxy-6-((3-(vinysulfonamidomethyl)-1H-pyrazol-1-yl)methyl)benzo[d]isoxazol-3-yl)benzenesulfonamide

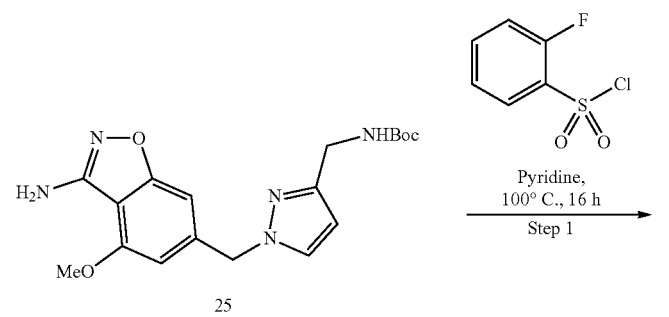

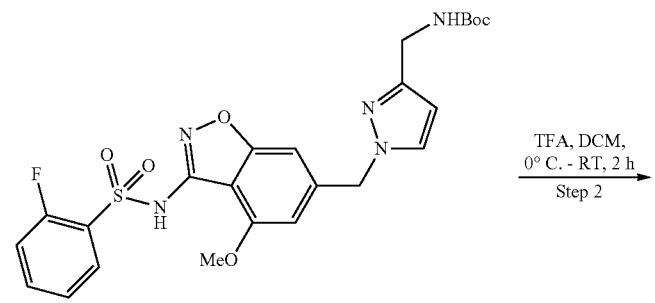

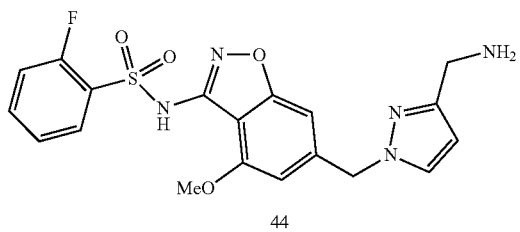

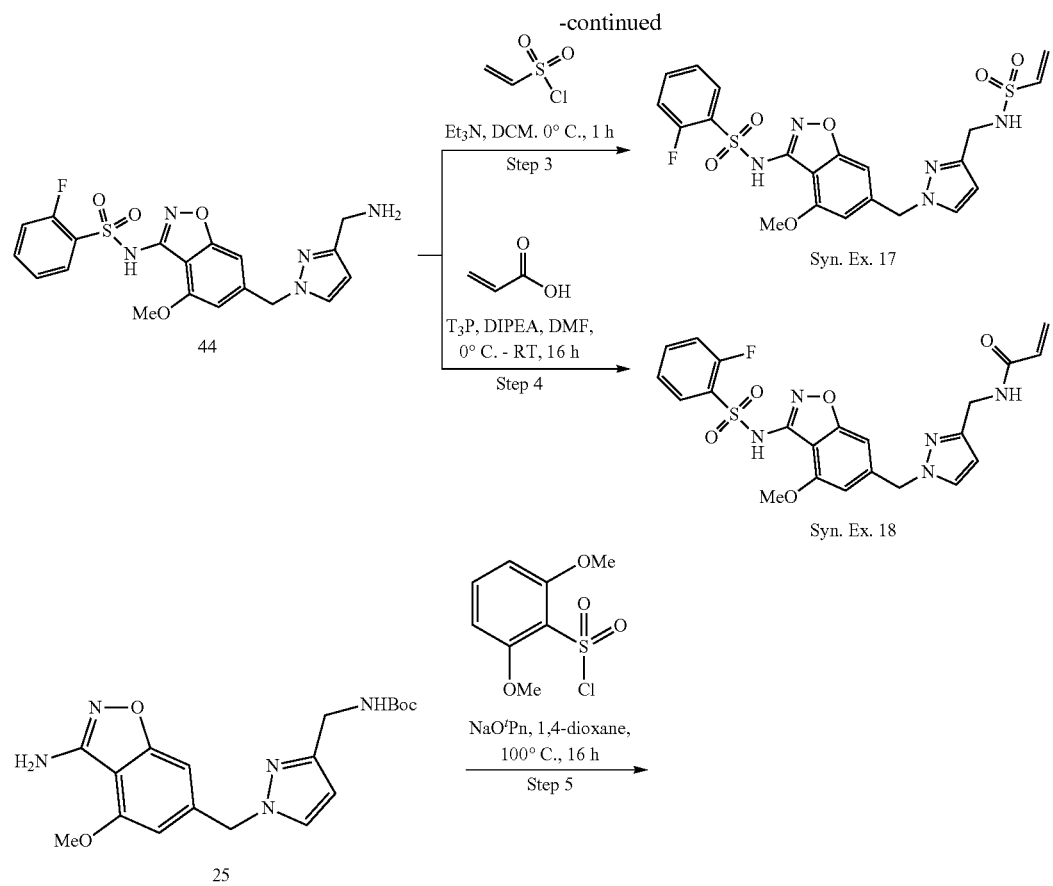
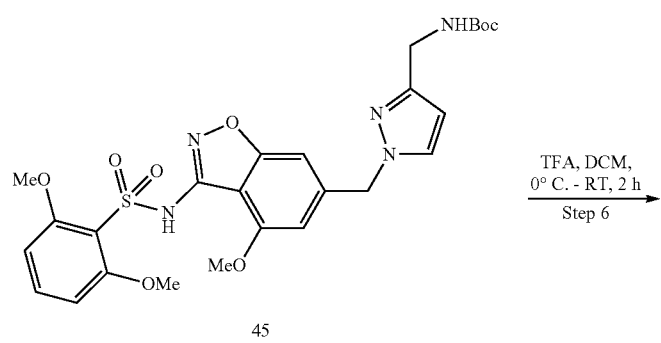
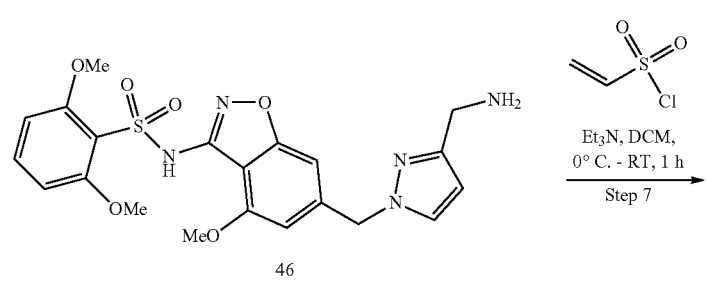

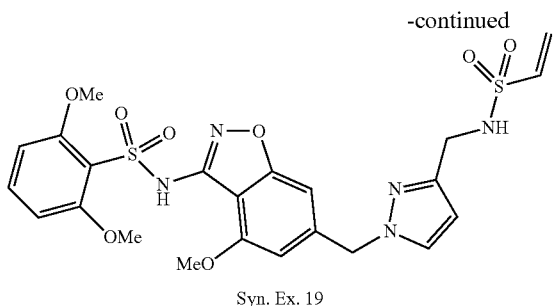

Syn. Ex. 19

Synthesis of tert-butyl ((1-((3-((2-fluorophenyl) sulfonamido)-4-methoxybenzo[d]isoxazol-6-yl) methyl)-1H-pyrazol-3-yl)methyl)carbamate (43)

To a stirred solution of compound 25 (0.3 g, 0.80 mmol) in Pyridine (3 mL) at room temperature was added 2-fluorobenzenesulfonyl chloride (0.186 g, 0.96 mmol) and the reaction was allowed to stir at 100° C. for 16 h. After completion (reaction monitored by TLC), the reaction mixture was quenched with 1N HCl, water added and extracted with ethyl acetate. The organic layer was collected, washed with brine, dried over anhydrous $Na_2SO_4$, and concentrated under reduced pressure. The crude compound was purified by Combi flash column chromatography using a gradient method of 40-80% EtOAc/Heptane to afford the title compound 43 (0.220 g, 51.52%) as a brown gummy solid. TLC: 80% EtOAc/Heptane ($R_f$ 0.35); LCMS Calculated for $C_{24}H_{26}FN_5O_6S$: 531.56; Found: 530.01 (M−1).

Synthesis of N-(6-((3-(aminomethyl)-1H-pyrazol-1-yl)methyl)-4-methoxybenzo[d]isoxazol-3-yl)-2-fluorobenzenesulfonamide (44)

To a stirred solution of compound 43 (0.22 g, 0.41 mmol) in DCM (3 mL) at 0° C., TFA (0.31 mL, 4.14 mmol) was added, and the reaction was allowed to stir at room temperature for 2 h. After completion (reaction monitored by TLC), the reaction mixture was concentrated under reduced pressure to afford the title compound 44 (0.19 g, quant.) as a brown gummy solid. TLC: 10% MeOH/DCM ($R_f$ 0.3); LCMS Calculated for $C_{19}H_{18}FN_5O_4S$: 431.44; Found: 432.00 (M+1).

Synthetic Example 17

Synthesis of 2-fluoro-N-(4-methoxy-6-((3-(vinylsulfonamidomethyl)-1H-pyrazol-1-yl)methyl) benzo[d]isoxazol-3-yl)benzenesulfonamide To a stirred solution of compound 44 (160 mg, 0.37 mmol) in DCM (5 mL) was added TEA (0.15 mL, 1.07 mmol) at 0° C. followed by ethene sulfonyl chloride (42 mg, 0.33 mmol) and the resulting reaction mixture was allowed to stir at 0° C. for 1 h. After completion (reaction monitored by TLC), the reaction mixture was quenched with ice water and extracted with ethyl acetate. The organic layer was collected, washed with brine, dried over anhydrous $Na_2SO_4$, and concentrated under reduced pressure. The crude compound was purified by prep HPLC to afford the title compound (3.8 mg, 2.03%) as an off-white solid. TLC: 10% MeOH/DCM ($R_f$ 0.5). (Analytical data in Table 1)

Synthetic Example 18

Synthesis of N-((1-((3-((2-fluorophenyl)sulfonamido)-4-methoxybenzo[d]isoxazol-6-yl)methyl)-1H-pyrazol-3-yl)methyl)acrylamide To a stirred solution of acrylic acid (16 mg, 0.22 mmol) in DMF (0.8 mL) at 0° C. was added DIPEA (0.09 mL, 0.52 mmol) and $T_3P$ (86 mg, 0.27 mmol) followed by compound 44 (85 mg, 0.18 mmol), the reaction was allowed to stir at room temperature for 16 h. After completion (reaction monitored by TLC), the reaction mixture was concentrated under reduced pressure, diluted with ethyl acetate, water added and extracted. The organic layer was collected, washed with brine, dried over anhydrous $Na_2SO_4$, and concentrated under reduced pressure. The crude compound was purified by using Chiral HPLC to afford the title compound (18 mg, 19%) as a white solid. TLC: 10% MeOH/DCM ($R_f$ 0.6). (Analytical data in Table 1).

Synthesis of tert-butyl ((1-((3-((2,6-dimethoxyphenyl)sulfonamido)-4-methoxybenzo[d]isoxazol-6-yl) methyl)-1H-pyrazol-3-yl)methyl)carbamate (45)

To a stirred solution of compound 25 (0.3 g, 0.80 mmol) in 1,4-dioxane (5 mL) was added compound 2,6-dimethoxybenzenesulfonyl chloride (0.379 g, 1.60 mmol), followed by NaO$^t$Pn (0.264 g, 2.40 mmol) and the resulting reaction mixture was allowed to stir at 100° C. for 16 h. After completion (reaction monitored by TLC), the reaction mixture was quenched with ice water and extracted with ethyl acetate. The organic layer was collected, washed with brine, dried over anhydrous $Na_2SO_4$, and concentrated under reduced pressure. The crude compound was purified by using combi flash gradient 70-80% ethyl acetate. to afford the title compound 45 (80 mg, 17.46%) as a brown solid. TLC: 10% MeOH/DCM ($R_f$ 0.6). LCMS Calculated for $C_{26}H_{31}N_5O_8S$: 573.62; Found: 572.06 (M−1).

Synthesis of N-(6-((3-(aminomethyl)-1H-pyrazol-1-yl)methyl)4methoxybenzo[d]isoxazol-3-yl)-2,6-dimethoxybenzenesulfonamide (46)

To a stirred solution of compound 45 (0.15 g, 0.26 mmol) in DCM (3 mL) at 0° C., TFA (0.20 mL, 2.61 mmol) was added, and the reaction was allowed to stir at room temperature for 2 h. After completion (reaction monitored by TLC), the reaction mixture was concentrated under reduced pressure to afford the title compound 46 (0.13 g, quant.) as a brown gummy solid. TLC: 5% MeOH/DCM ($R_f$ 0.3). LCMS Calculated for $C_{21}H_{23}N_5O_6S$: 473.50; Found: N.A.

Synthetic Example 19

Synthesis of 2,6-dimethoxy-N-(4-methoxy-6-((3-(vinylsulfonamidomethyl)-1H-pyrazol-1-yl)methyl)benzo[d]isoxazol-3-yl)benzenesulfonamide To a stirred solution of compound 46 (110 mg, 0.23 mmol) in DCM (6 mL) was added TEA (0.088 mL, 0.63 mmol) at 0° C., followed by ethene sulfonyl chloride (26 mg, 0.20 mmol) and the resulting reaction mixture was allowed to stir at room temperature for 1 h. After completion (reaction monitored by TLC), the reaction mixture was quenched with ice water and extracted with ethyl acetate. The organic layer was collected, washed with brine, dried over anhydrous $Na_2SO_4$, and concentrated under reduced pressure. The crude compound was purified by using prep HPLC to afford the title compound (3 mg, 2.54%) as an off-white solid. TLC: 5% MeOH/DCM ($R_f$. 0.5). (Analytical data in Table1).

Synthetic Examples 20-21

Scheme 14: Synthesis of N-((1-((4-methoxy-3-((phenylmethyl)sulfonamido)benzo[d]isoxazol-6-yl)methyl)-1H-pyrazol-3-yl)methyl)acrylamide and N-((1-((4-methoxy-3-((phenylmethyl)sulfonamido)benzo[d]isoxazol-6-yl)methyl)-1H-pyrazol-3-yl)methyl)ethenesulfonamide

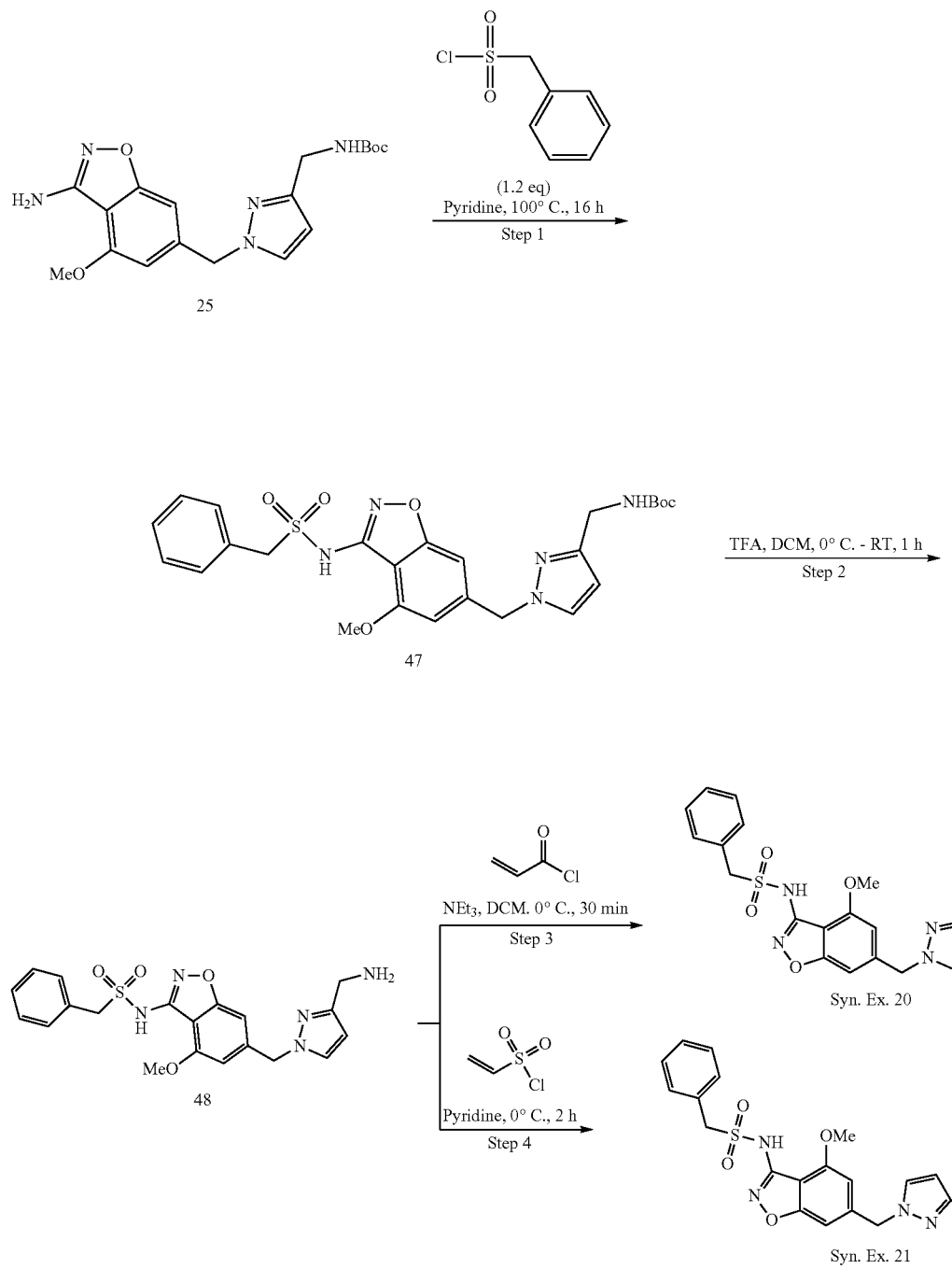

Synthesis of tert-butyl ((1-((4-methoxy-3-((phenyl-methyl)sulfonamido)benzo[d]isoxazol-6-yl)methyl)-1H-pyrazol-3-yl)methyl)carbamate (47)

To a stirred solution of compound 25 (0.3 g, 0.80 mmol) in Pyridine (3 mL) at room temperature, was added phenylmethanesulfonyl chloride (0.18 g, 0.96 mmol) and the reaction was allowed to stir at 100° C. for 16 h. After completion (reaction monitored by TLC), the reaction mixture was cooled to room temperature, quenched with 1N HCl, and extracted with ethyl acetate. The organic layer was collected, washed with brine, dried over anhydrous $Na_2SO_4$, and concentrated under reduced pressure. The crude compound was purified by Combi flash column chromatography using a gradient method of 40-80% EtOAc/Heptane to afford the title compound 47 (0.220 g, 51.52%) as a brown gummy solid. TLC: 80% EtOAc/Heptane ($R_f$ 0.35). LCMS Calculated for $C_{25}H_{29}N_5O_6S$: 527.60; Found: 428.84 (M-Boc+1).

Synthesis of N-(4-methoxy-6-((3-(((2,2,2-trifluoro-acetyl)-14-azaneyl)methyl)-1H-pyrazol-1-yl)methyl)benzo[d]isoxazol-3-yl)-1-phenylmethanesulfonamide (48)

To a stirred solution of compound 47 (0.22 g, 0.51 mmol) in DCM (3 mL) at 0° C., TFA (0.39 mL, 5.14 mmol) was added, and the reaction was allowed to stir at room temperature for 1 h. After completion of the reaction (monitored by TLC), concentrated under reduced pressure to afford the title compound 48 (0.18 g, quant.) as a brown gummy solid. A part of it was purified by prep HPLC to afford the title compound (6 mg, 11.36%) as an off-white solid. TLC: 5% MeOH/DCM ($R_f$ 0.5). This was the pure regioisomer, as drawn. TLC: 10% MeOH/DCM ($R_f$ 0.5). LCMS Calculated for $C_{20}H_{21}N_5O_4S$: 427.48: Found: 428.2 (M+1).

Synthetic Example 20

Synthesis of N-((1-((4-methoxy-3-((phenylmethyl)sulfonamido)benzo[d]isoxazol-6-yl)methyl)-1H-pyrazol-3-yl)methyl)acrylamide To a stirred solution of compound 48 (120 mg, 0.28 mmol) in DCM (5 mL) at 0° C. was added TEA (0.12 mL, 0.84 mmol) followed by acryloyl chloride (25 mg, 0.28 mmol) and the resulting reaction mixture was allowed to stir at the same temperature for 30 min. After completion (reaction monitored by TLC), the reaction mixture was quenched with ice water and extracted with ethyl acetate. The organic layer was collected, washed with brine, dried over anhydrous $Na_2SO_4$, and concentrated under reduced pressure. The crude compound was purified by prep HPLC to afford the title compound (12 mg, 8.8%) as an off-white solid. TLC: 10% MeOH/DCM ($R_f$ 0.5). (See analytical data for Table 1)

Synthetic Example 21

Synthesis of N-((1-((4-methoxy-3-((phenylmethyl)sulfonamido)benzo[d]isoxazol-6-yl)methyl)-1H-pyrazol-3-yl)methyl)ethenesulfonamide To a stirred solution of compound 48 (120 mg, 0.28 mmol) in DCM (3 mL) at 0° C. was added TEA (0.12 mL, 0.84 mmol) followed by ethene sulfonyl chloride (42 mg, 0.33 mmol) and the reaction mixture was allowed to stir at the same temperature for 2 h. After completion (reaction monitored by TLC), the reaction mixture was quenched with ice water and extracted with ethyl acetate. The organic layer was collected, washed with brine, dried over anhydrous $Na_2SO_4$, and concentrated under reduced pressure. The crude compound was purified by prep HPLC to afford the title compound (5 mg, 3.4%) as an off-white solid. TLC: 10% MeOH/DCM ($R_f$ 0.5). (Analytical data in Table1).

Synthetic Example 22

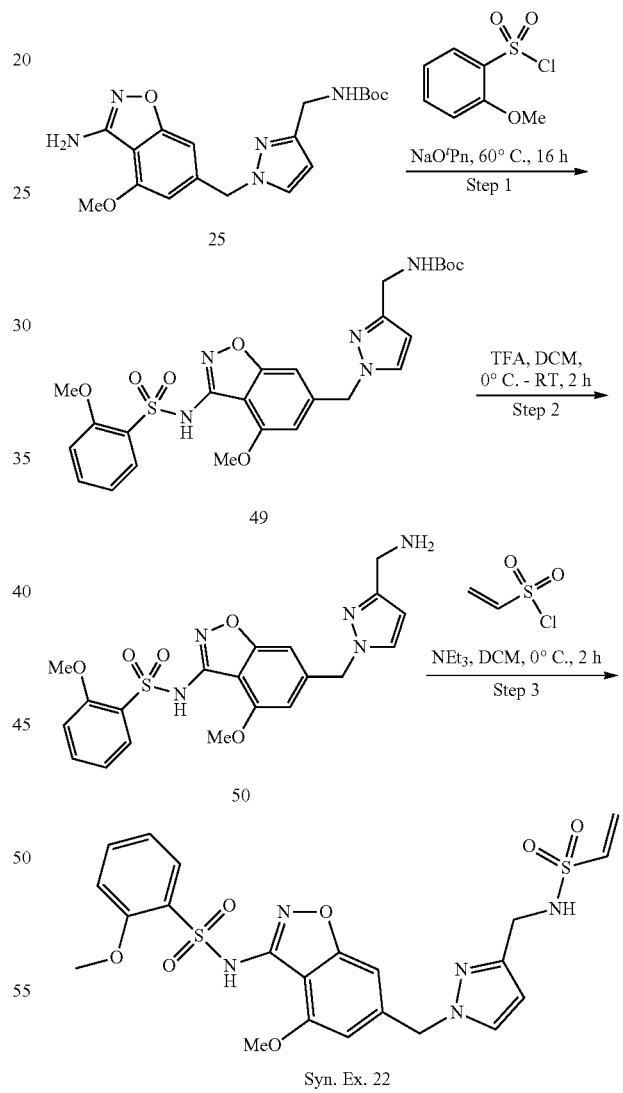

Scheme 15: Synthesis of 2-methoxy-N-(4-methoxy-6-((3-(vinylsulfonamidomethyl)-1H-pyrazol-1-yl)methyl)benzo[d]isoxazol-3-yl)benzenesulfonamide Syn. Ex. 22

Synthesis of tert-butyl ((1-((4methoxy3((2methoxyphenyl)sulfonamido)benzo[d]isoxazol-6-yl)methyl)-1H-pyrazol-3-yl)methyl)carbamate (49)

To a stirred solution of compound 25 (0.45 g, 1.20 mmol) in THF (5 mL) was added 2-methoxybenzenesulfonyl chloride (0.49 g, 2.41 mmol), followed by NaO'Pn (0.396 g, 3.60 mmol) and the resulting reaction mixture was allowed to stir at 60° C. for 16 h. After completion (reaction monitored by TLC), the reaction mixture was quenched with ice water and extracted with ethyl acetate. The organic layer was collected, washed with brine, dried over anhydrous Na$_2$SO$_4$, and concentrated under reduced pressure. The crude compound was purified Combi flash chromatography using a gradient method of 60-80% ethyl acetate/Heptane to afford the title compound 49 (0.130 g, 19.9%) as a brown gummy solid. TLC: 5% MeOH/DCM (R$_f$. 0.6). LCMS Calculated for C$_{25}$H$_{29}$N$_5$O$_7$S: 543.60; Found: 542.1 (M−1).

Synthesis of 2-methoxy-N-(4-methoxy-6-((3-(((2,2, 2-trifluoroacetyl)-14-azaneyl)methyl)-1H-pyrazol-1-yl)methyl)benzo[d]isoxazol-3-yl)benzenesulfonamide (50)

To a stirred solution of compound 49 (0.13 g, 0.23 mmol) in DCM (3 mL) at 0° C., TFA (0.18 mL, 2.39 mmol) was added, and the reaction was allowed to stir at room temperature for 2 h. After completion (reaction monitored by TLC), reaction mixture was concentrated under reduced pressure to afford the title compound 50 (0.1 g, 94.3%) as a brown semi solid. TLC: 10% MeOH/DCM (R$_f$. 0.5). LCMS Calculated for C$_{20}$H$_{21}$N$_5$O$_5$S: 443.48: Found: 442.4 (M−1).

Synthesis of 2-methoxy-N-(4-methoxy-6-((3-(vinylsulfonamidomethyl)-1H-pyrazol-1-yl)methyl) benzo[d]isoxazol-3-yl)benzenesulfonamide To a stirred solution of compound 50 (0.1 g, 0.22 mmol) in DCM (3 mL) was added TEA (0.1 mL, 0.66 mmol) at 0° C. followed by ethene sulfonyl chloride (27.85 mg, 0.22 mmol) and the resulting reaction mixture was allowed to stir at the same temperature for 2 h. After completion (reaction monitored by TLC), reaction mixture was quenched with ice water and extracted with ethyl acetate. The organic layer was collected, washed with brine, dried over anhydrous Na$_2$SO$_4$, and concentrated under reduced pressure. The crude compound was purified by prep HPLC to afford the title compound (6 mg, 5%) as an off-white solid. TLC: 10% MeOH/DCM (R$_f$. 0.5). (Analytical data in Table1).

Synthetic Examples 23-24

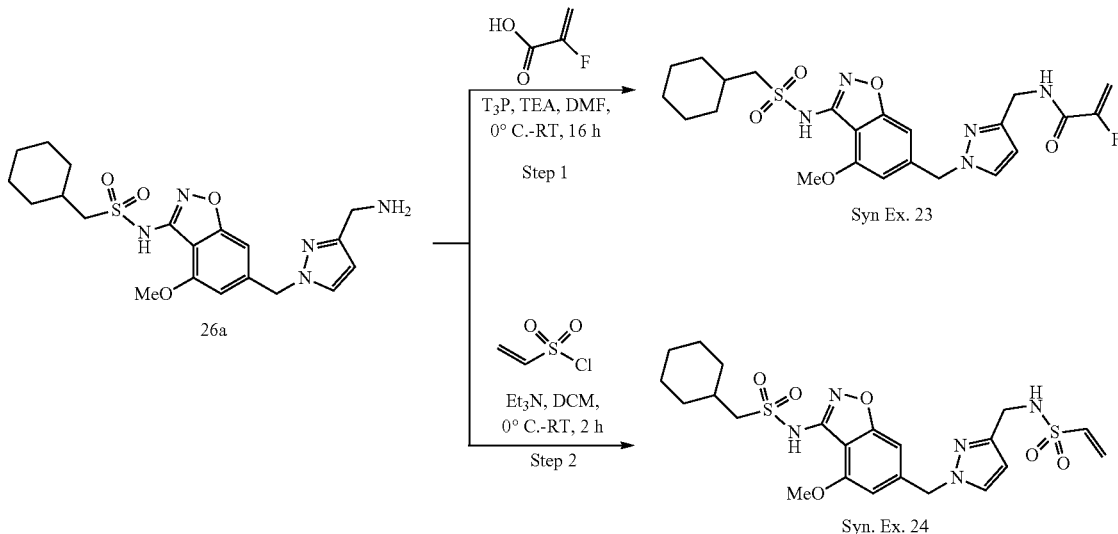

Scheme 16: Synthesis of N-((1-((3-(((cyclohexylmethyl)sulfonamido)-4-methoxybenzo[d]isoxazol-6-yl) methyl)-1-H-pyrazol-3-yl)methyl)-2-fluoroacrylamide and N-((1-((3-((cyclohexylmethyl) sulfonamido)-4-methoxybenzo[d]isoxazol-6-yl)methyl)-1H-pyrazol-3-yl)methyl)ethenesulfonamide Synthetic Example 23

Synthesis of N-((1-((3-((cyclohexylmethyl)sulfonamido)-4-methoxybenzo[d]isoxazol-6-yl)methyl)-1H-pyrazol-3-yl)methyl)-2-fluoroacrylamide To a stirred solution of Compound 26a (150 mg, 0.34 mmol) in DMF (3 mL) at 0° C. was added TEA (0.14 mL, 1.03 mmol) and T$_3$P (162 mg, 0.51 mmol), followed by 2-fluoroacrylic acid (30.6 mg, 0.34 mmol). The reaction was allowed to stir at room temperature for 16 h. After completion (reaction monitored by TLC), the reaction mixture was concentrated under reduced pressure, diluted with ethyl acetate, water added and extracted. The organic layer was collected, washed with brine, dried over anhydrous Na$_2$SO$_4$, and concentrated under reduced pressure. The crude compound was purified by using prep HPLC to afford the title compound (8.0 mg, 4.5%) as an off-white solid. TLC: 10% MeOH/DCM (R$_f$. 0.6). (Analytical data in Table1).

Synthetic Example 24

Synthesis of N-((1-((3-((cyclohexylmethyl)sulfonamido)-4-methoxybenzo[d]isoxazol-6-yl)methyl)-1H-pyrazol-3-yl)methyl)ethenesulfonamide To a stirred solution of compound 26a (15 mg, 0.35 mmol) in DCM (3 mL) was added TEA (0.01 mL, 0.103 mmol) at 0° C. followed by ethene sulfonyl chloride (44 mg, 0.35 mmol) and the reaction mixture was allowed to stir at room temperature for 2 h. After completion of the reaction (monitored by TLC), the reaction mixture was concentrated under reduced pressure and the crude compound was purified by prep HPLC to afford the title compound (5.8 mg, 32%) as an off-white solid. TLC: 80% EtOAc/Heptane (R$_f$ 0.5). (Analytical data in Table1).

Synthetic Examples 25A and 25B, 26A and 26B, and 27A and 27B

Scheme 17: Synthesis of 2,6-dimethoxy-N-(4-methoxy-6-((5-propioloyl-5,6-dihydropyrrolo[3,4-c]pyrazol-1(4H)-yl)methyl)benzo[d]isoxazol-3-yl)benzenesulfonamide, 2,6-dimethoxy-N-(4-methoxy-6-((5-propioloyl-5,6-dihydropyrrolo[3,4-c]pyrazol-2(4H)-yl)methyl)benzo[d]isoxazol-3-yl)benzenesulfonamide, 2-methoxy-N-(4-methoxy-6-((5-propioloyl-5,6-dihydropyrrolo[3,4-c]pyrazol-1(4H)-yl)methyl)benzo[d]isoxazol-3-yl)benzenesulfonamide, 2-methoxy-N-(4-methoxy-6-((5-propioloyl-5,6-dihydropyrrolo[3,4-c]pyrazol-2(4H)-yl)methyl)benzo[d]isoxazol-3-yl)benzenesulfonamide, 2-methoxy-N-(4-methoxy-6-((5-(vinylsulfonyl)-5,6-dihydropyrorolo[3,4-c]pyrazol-2(4H)-yl)methyl)benzo[d]isoxazol-3-yl)benzenesulfonamide and 2-methoxy-N-(4-methoxy-6-((5-(vinylsulfonyl)-5,6-dihydropyrrolo[3,4-c]pyrazol-1(4H)-yl)methyl)benzo[d]isoxazol-3-yl)benzenesulfonamide

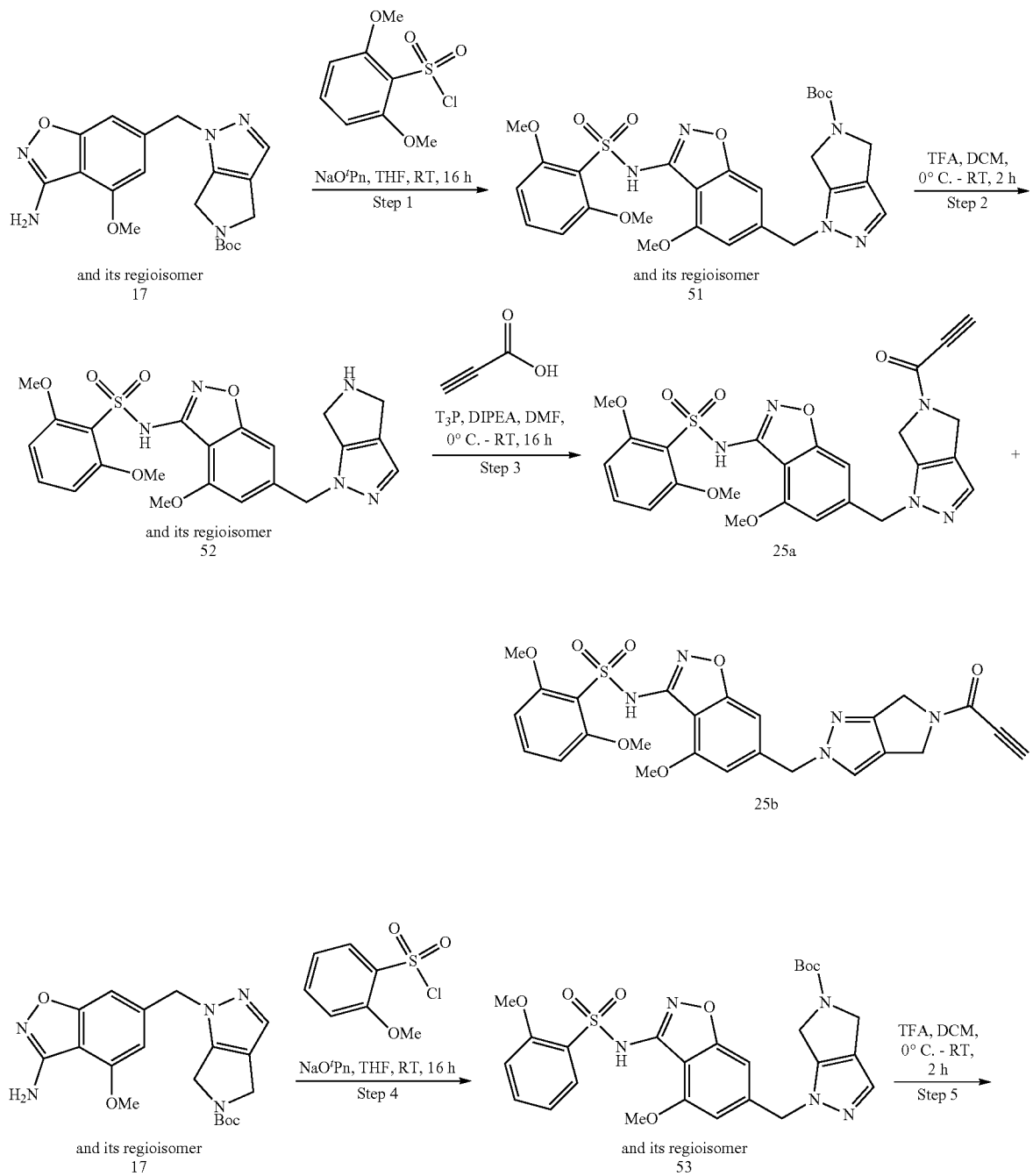

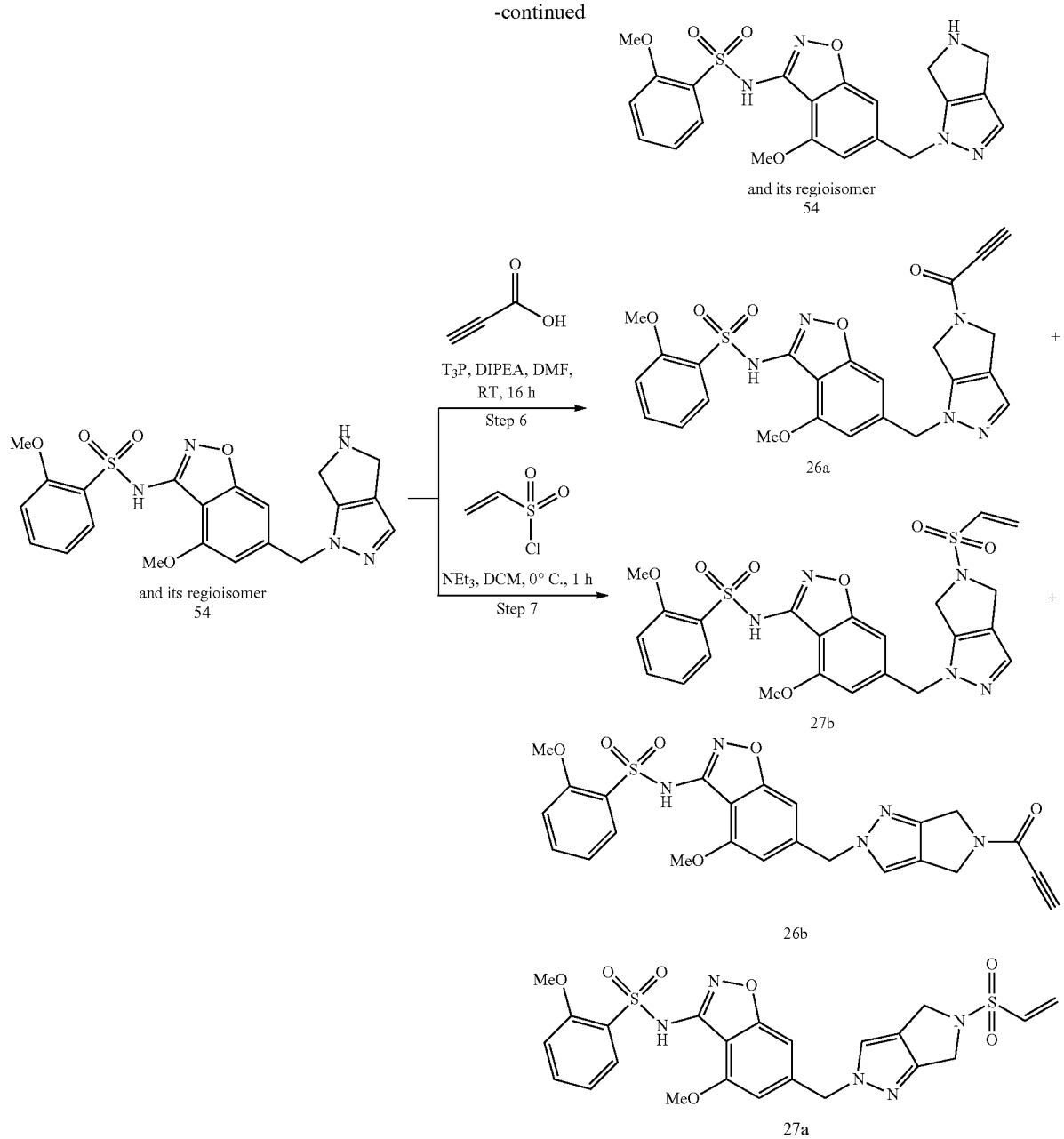

Synthesis of tert-butyl1-((3-((2,6-dimethoxyphenyl)sulfonamido)-4methoxybenzo[d]isoxazol-6-yl)methyl)-4,6-dihydropyrrolo[3,4-c]pyrazole-5(1H)-carboxylate (51 and its Regioisomer)

To a stirred solution of compound 17 (0.22 g, 0.57 mmol) in THF (5 mL) was added NaO$^t$Pn (0.377 g, 3.42 mmol) followed by 2,6-dimethoxybenzenesulfonyl chloride (0.405 g, 1.71 mmol) and the reaction mixture was allowed to stir at room temperature for 16 h. After completion (reaction monitored by TLC), the reaction mixture was quenched with ice water and extracted with ethyl acetate. The organic layer was collected, washed with brine, dried over anhydrous Na$_2$SO$_4$, and concentrated under reduced pressure. The crude compound was purified by combi flash chromatography using gradient method of 50-80% ethyl acetate/Heptane to afford the title compound 51 (91 mg, 27.22%, isolated as inseparable regio-isomeric mixture) as a gummy brown solid. TLC: 5% MeOH/DCM (R$_f$, 0.6). LCMS Calculated for C$_{27}$H$_{31}$N$_5$O$_8$S: 585.63; Found: 586.2 (M+1). $^1$H NMR is complicated and indicates a regio-isomeric mixture.

Synthesis of 2,6-dimethoxy-N-(4-methoxy-6-((5-(2,2,2-trifluoroacetyl)-5,6-dihydro-514-pyrrolo[3,4-c]pyrazol-1(4H)-yl)methyl)benzo[d]isoxazol-3-yl)benzenesulfonamide (52 and its Regioisomer)

To a stirred solution of compound 51 (0.1 g, 0.17 mmol) in DCM (1 mL) at 0° C., TFA (0.13 mL, 1.70 mmol) was added, and the reaction was allowed to stir at room temperature for 2 h. After completion (reaction monitored by TLC), the reaction mixture was concentrated under reduced pressure to afford the residue was triturated with ether and dried under vacuum to afford the title mixture of isomers compound 52 (120 mg, crude, isolated as inseparable regio-isomeric mixture) as a brown oil. TLC: 5% MeOH/DCM ($R_f$ 0.3). LCMS Calculated for $C_{22}H_{23}N_5O_6S$: 485.52: Found: 486.50 (M+1). $^1$H NMR is complicated and indicates a regio-isomeric mixture.

Synthetic Examples 25a and 25B

Synthesis of 2,6-dimethoxy-N-(4-methoxy-6-((5-propioloyl-5,6-dihydropyrrolo[3,4-c]pyrazol-1(4H)-yl)methyl)benzo[d]isoxazol-3-yl)benzenesulfonamide and 2,6-dimethoxy-N-(4-methoxy-6-((5-propioloyl-5,6-dihydropyrrolo[3,4-c]pyrazol-2(4H)-yl)methyl)benzo[d]isoxazol-3-yl) benzenesulfonamide To a stirred solution of compound 52 (0.13 g, 0.26 mmol) in DMF (1.5 mL) at 0° C. was added DIPEA (0.16 mL, 0.937 mmol) and $T_3P$ (0.166 g, 0.52 mmol) followed by propiolic acid (21 mg, 0.309 mmol) and the reaction was allowed to stir at room temperature for 16 h. After completion (reaction monitored by TLC), the reaction mixture was concentrated under reduced pressure, quenched with ice water and extracted with ethyl acetate. The organic layer was collected, washed with brine, dried over anhydrous $Na_2SO_4$, and concentrated under reduced pressure. The crude compound was purified by using chiral HPLC to afford the title compound 2,6-dimethoxy-N-(4-methoxy-6-((5-propioloyl-5,6-dihydropyrrolo[3,4-c]pyrazol-1(4H)-yl)methyl)benzo[d]isoxazol-3-yl)benzenesulfonamide (7 mg, 5%) as an off white solid and 2,6-dimethoxy-N-(4-methoxy-6-((5-propioloyl-5,6-dihydropyrrolo[3,4-c]pyrazol-2(4H)-yl)methyl) benzo[d]isoxazol-3-yl)benzenesulfonamide (8 mg, 5.5%) as an off-white solid. TLC: 5% MeOH/DCM ($R_f$ 0.6). (Analytical data in Table1).

Synthesis of tert-butyl 1-((4-methoxy-3-((2-methoxyphenyl)sulfonamido)benzo[d]isoxazol-6-yl) methyl)-4,6-dihydropyrrolo[3,4-c]pyrazole-5(1H)-carboxylate (53 and its Regioisomer)

To a stirred solution of compound 17 (0.3 g, 0.77 mmol) in THF (5 mL) was added 2-methoxybenzenesulfonyl chloride (0.320 g, 1.55 mmol), followed by NaO$^t$Pn (0.428 g, 3.89 mmol) and the resulting reaction mixture was allowed to stir at room temperature for 16 h. After completion (reaction monitored by TLC), the reaction was quenched with ice water and extracted with ethyl acetate. The organic layer was collected, washed with brine, dried over anhydrous $Na_2SO_4$, and concentrated under reduced pressure. The crude compound was purified by combi flash chromatography using a gradient method of 70-80% ethyl acetate/Heptane to afford the title compound 53 (310 mg, 71.75%, isolated as inseparable regio-isomeric mixture) as brown solid. TLC: 5% MeOH/DCM ($R_f$ 0.6). LCMS Calculated for $C_{26}H_{29}N_5O_7S$: 555.61; Found: 556.2 (M+1). $^1$H NMR is complicated and indicates a regio-isomeric mixture.

Synthesis of 2-methoxy-N-(4-methoxy-6-((5-(2,2,2-trifluoroacetyl)-5,6-dihydro-514-pyrrolo[3,4-c]pyrazol-1(4H)-yl)methyl)benzo[d]isoxazol-3-yl)benzenesulfonamide (54 and its Regioisomer)

To a stirred solution of compound 53 (0.4 g, 0.72 mmol) in DCM (4 mL) at 0° C., TFA (0.54 mL, 7.2 mmol) was added, and the reaction was allowed to stir at room temperature for 2 h. After completion (reaction monitored by TLC), the reaction mixture was concentrated under reduced pressure to obtain the residue, which was triturated with ether and dried under vacuum to afford the title compound 54 (410 mg, crude, isolated as inseparable regio-isomeric mixture) as a brown solid. TLC: 10% MeOH/DCM ($R_f$ 0.5). LCMS Calculated for $C_{21}H_{21}N_5O_5S$: 455.49: Found: 454.3 (M−1). $^1$H NMR is complicated and indicates a regio-isomeric mixture.

Synthetic Examples 26A and 26B

Synthesis of 2-methoxy-N-(4-methoxy-6-((5-propioloyl-5,6-dihydropyrrolo[3,4-c]pyrazol-1(4H)-yl) methyl)benzo[d]isoxazol-3-yl)benzenesulfonamide and 2-methoxy-N-(4-methoxy-6-((5-propioloyl-5,6-dihydropyrrolo[3,4-c]pyrazol-2(4H)-yl)methyl) benzo[d]isoxazol-3-yl)benzenesulfonamide To a stirred solution of compound 54 (0.2 g, 0.43 mmol) in DMF (3 mL) at 0° C. was added DIPEA (0.22 mL, 1.3 mmol) and $T_3P$ (0.27 g, 0.86 mmol), followed by propiolic acid (30 mg, 0.43 mmol). The reaction was allowed to stir at room temperature for 16 h. After completion (reaction monitored by TLC), the reaction mixture was concentrated under reduced pressure, quenched with ice water and extracted with ethyl acetate. The organic layer was collected, washed with brine, dried over anhydrous $Na_2SO_4$, and concentrated under reduced pressure. The crude compound was purified by using chiral HPLC to afford the title compounds 2-methoxy-N-(4-methoxy-6-((5-propioloyl-5,6-dihydropyrrolo[3,4-c]pyrazol-1(4H)-yl)methyl)benzo[d] isoxazol-3-yl)benzenesulfonamide (17 mg, 7.6%) as an off white solid and 2-methoxy-N-(4-methoxy-6-((5-propioloyl-5,6-dihydropyrrolo[3,4-c]pyrazol-2(4H)-yl)methyl)benzo [d]isoxazol-3-yl)benzenesulfonamide (19 mg, 8.55%) as an off-white solid. TLC: 5% MeOH/DCM ($R_f$ 0.6). (Analytical data in Table1).

Synthetic Examples 27B and 27A

Synthesis of 2-methoxy-N-(4-methoxy-6-((5-(vinylsulfonyl)-5,6-dihydropyrrolo[3,4-c]pyrazol-2 (4H)-yl)methyl)benzo[d]isoxazol-3-yl)benzenesulfonamide and 2-methoxy-N-(4-methoxy-6-((5-(vinylsulfonyl)-5,6-dihydropyrrolo[3,4-c]pyrazol-1 (4H)-yl)methyl)benzo[d]isoxazol-3-yl) benzenesulfonamide To a stirred solution of compound 54 (0.5 g, 1.09 mmol) in DCM (4 mL) was added TEA (0.65 mL, 4.52 mmol) at 0° C. followed by ethenesulfonyl chloride (343 mg, 2.71 mmol) and the resulting reaction mixture was allowed to stir at the same temperature for 1 h. After completion of the reaction (monitored by TLC), reaction mixture was quench with ice water and extracted with ethyl acetate. The organic layer was collected, washed with brine, dried over anhydrous $Na_2SO_4$ and concentrated under reduced pressure. The crude compound was purified by using chiral HPLC to afford the title compound 27b (12 mg, 2.02%) as an off white solid and 27a (9 mg, 1.51%) as an off-white solid. TLC: 5% MeOH/DCM ($R_f$ 0.6). (Analytical data in Table1).

Synthetic Examples 28A, 28B, 29A, 29B, 30A and 30B

Scheme 18: Synthesis of 1-cyclohexyl-N-(6-((5,6-dihydropyrrolo[3,4-c]pyrazol-1(4H)-yl)methyl)-4-methoxybenzo[d]isoxazol-3-yl)methanesulfonamide, 1-cyclohexyl-N-(6-((5,6-dihydropyrrolo[3,4-c]pyrazol-2(4H)-yl)methyl)-4-methoxybenzo[d]isoxazol-3-yl)methanesulfonamide, N-(6-((5-acryloyl-5,6-dihydropyrrolo[3,4-c]pyrazol-1(4H)-yl)methyl)-4-methoxybenzo[d]isoxazol-3-yl)-1-cyclohexylmethanesulfonamide, N-(6-((5-acryloyl-5,6-dihydropyrrolo[3,4-c]pyrazol-2(4H)-yl)methyl)-4-methoxybenzo[d]isoxazol-3-yl)-1-cyclohexylmethanesulfonamide, 1-cyclohexyl-N-(4-methoxy-6-((5-propioloyl-5,6-dihydropyrrolo[3,4-c]pyrazol-1(4H)-yl)methyl)benzo[d]isoxazol-3-yl)methanesulfonamide and 1-cyclohexyl-N-(4-methoxy-6-((5-propioloyl-5,6-dihydropyrrolo[3,4-c]pyrazol-2(4H)-yl)methyl)benzo[d]isoxazol-3-yl)methanesulfonamide

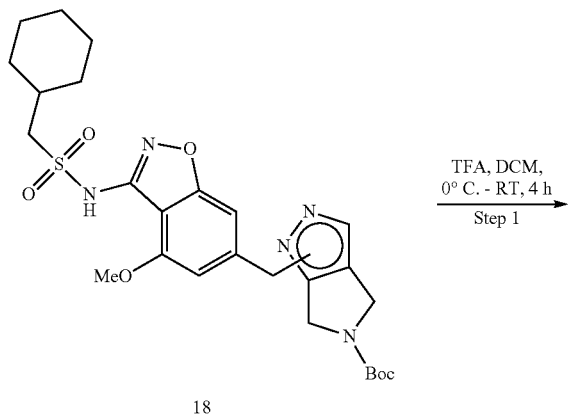

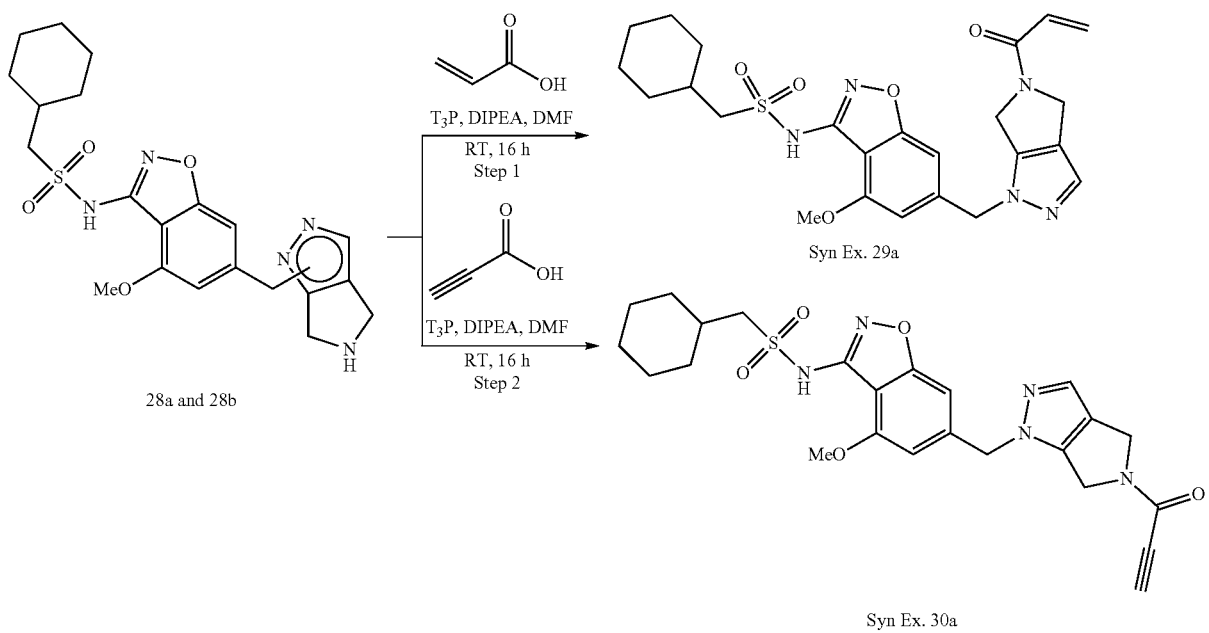

-continued

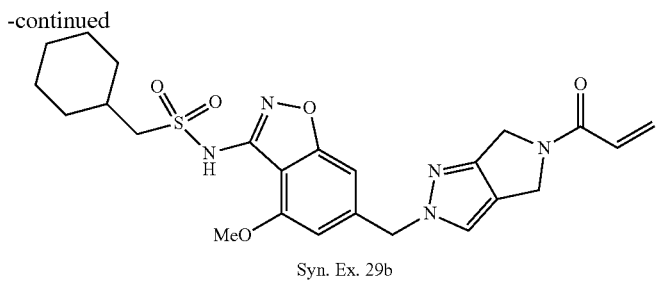

Syn. Ex. 29b

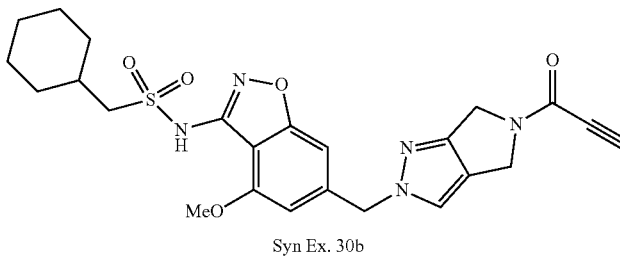

Syn Ex. 30b

Synthetic Examples 28A and 28B

Synthesis of Synthesis of 1-cyclohexyl-N-(6-((5,6-dihydropyrrolo[3,4-c]pyrazol-1(4H)-yl)methyl)-4-methoxybenzo[d]isoxazol-3-yl)methanesulfonamide and 1-cyclohexyl-N-(6-((5,6-dihydropyrrolo[3,4-c]pyrazol-2(4H)-yl)methyl)-4-methoxybenzo[d]isoxazol-3-yl)methanesulfonamide To a stirred solution of compound 18 (180 mg, 0.33 mmol) in DCM (3 mL) was added TFA (0.13 mL, 1.73 mmol) at 0° C. and the reaction was allowed to stir at room temperature for 4 h. After completion of the reaction (monitored by TLC), the reaction mixture was basified with sat. NaHCO$_3$ solution and extracted with DCM. The organic layer was collected, washed with brine, dried over anhydrous Na$_2$SO$_4$ and concentrated under reduced pressure to obtain crude residue, which was triturated with di-ethyl ether/pentane to afford (100 mg, 67.10%, isolated as inseparable regioisomeric mixture) as a white solid which was purified using chiral HPLC to get the title compounds 28a: (6.5 mg, 4.42%) as a white solid and 28b: (12 mg, 8.16%) as a white solid. LCMS Calculated for C$_{21}$H$_{27}$N$_5$O$_4$S: 445.54; Found: 446.50 (M+1). (Analytical data in Table1).

Synthetic Examples 29A and 29B

Synthesis of N-(6-((5-acryloyl-5,6-dihydropyrrolo[3,4-c]pyrazol-1(4H)-yl)methyl)-4-methoxybenzo[d]isoxazol-3-yl)-1-cyclohexylmethanesulfonamide and N-(6-((5-acryloyl-5,6-dihydropyrrolo[3,4-c]pyrazol-2(4H)-yl)methyl)-4-methoxybenzo[d]isoxazol-3-yl)-1-cyclohexylmethanesulfonamide To a stirred solution of compound 18a (150 mg, 0.33 mmol) in DMF (1.5 mL) at 0° C. was added DIPEA (0.17 mL, 0.96 mmol), followed by T$_3$P (175 mg, 0.55 mmol) and the contents were allowed to stir at room temperature for 20 min. After, a pre-dissolved solution of acrylic acid (22 mg, 0.31 mmol) in DMF (0.5 mL) was added in a drop-wise manner and the reaction mixture was stirred at room temperature for 16 h. After completion (reaction monitored by TLC), the reaction mixture was concentrated under reduced pressure, water added and extracted with ethyl acetate. The organic layer was collected, washed with brine, dried over anhydrous Na$_2$SO$_4$ and concentrated under reduced pressure. The crude compound was purified by using chiral HPLC to afford the title compounds N-(6-((5-acryloyl-5,6-dihydropyrrolo[3,4-c]pyrazol-1(4H)-yl)methyl)-4-methoxybenzo[d]isoxazol-3-yl)-1-cyclohexylmethanesulfonamide (4 mg, 2.4%) as an off-white solid and N-(6-((5-acryloyl-5,6-dihydropyrrolo[3,4-c]pyrazol-2(4H)-yl)methyl)-4-methoxybenzo[d]isoxazol-3-yl)-1-cyclohexylmethanesulfonamide (6 mg, 3.6%) as an off-white solid. TLC: 5% MeOH/DCM (R$_f$ 0.5). (Analytical data in Table1).

Synthetic Examples 30A and 30B

Synthesis of 1-cyclohexyl-N-(4-methoxy-6-((5-propioloyl-5,6-dihydropyrrolo[3,4-c]pyrazol-1(4H)-yl)methyl)benzo[d]isoxazol-3-yl)methanesulfonamide and 1-cyclohexyl-N-(4-methoxy-6-((5-propioloyl-5,6-dihydropyrrolo[3,4-c]pyrazol-2(4H)-yl)methyl)benzo[d]isoxazol-3-yl)methanesulfonamide To a stirred solution of 1-cyclohexyl-N-(6-((5,6-dihydropyrrolo[3,4-c]pyrazol-1(4H)-yl)methyl)-4-methoxybenzo[d]isoxazol-3-yl)methanesulfonamide 1-cyclohexyl-N-(6-((5,6-dihydropyrrolo[3,4-c]pyrazol-2(4H)-yl)methyl)-4-methoxybenzo[d]isoxazol-3-yl)methanesulfonamide (130 mg, 0.29 mmol) in DMF (1 mL) at 0° C. was added DIPEA (0.15 mL, 0.87 mmol), followed by T$_3$P (138 mg, 0.43 mmol) and the contents were allowed to stir at room temperature for 20 min. After, a pre-dissolved solution of propiolic acid (20 mg, 0.29 mmol) in DMF (0.5 mL) was added in a drop-wise manner and the reaction mixture was stirred at room temperature for 2 h. After completion (reaction monitored by TLC), the reaction mixture was concentrated under high vacuum. The residue was quenched with water and extracted with DCM. The organic layer was collected, washed with brine, dried over anhydrous Na$_2$SO$_4$ and concentrated under reduced pressure. The crude compound was purified by using reverse phase HPLC to obtain (16.5 mg, 11.36%, isolated as inseparable regio-isomeric mixture) as an off-white solid. TLC: 5% MeOH/DCM (R$_f$ 0.5). The regio-isomeric mixture was again purified by chiral HPLC to afford the tile compounds as 30a (8 mg, 5.5%) as an off-white solid and 30b (8.5 mg, 5.8%) as an off-white solid (Analytical data in Table1).

Synthetic Examples 31-35

Scheme 19: Synthesis of N-((1-((4-methoxy-3-((2-methoxyphenyl) sulfonamido) benzo[d]isoxazol-6yl) methyl)-1H-pyrazol-4-yl) methyl) propiolamide, 2-methoxy-N-(4-methoxy-6-((4-(vinylsulfonamidomethyl)-1H-pyrazol-1-yl) methyl)benzo[d]isoxazol-3-yl)benzenesulfonamide, 2,6-dimethoxy-N-(4-methoxy-6-((4-(vinylsulfonamidomethyl)-1H-pyrazol-1-yl)methyl)benzo[d]isoxazol-3-yl)benzenesulfonamide, N-((1-((3-((2,6-dimethoxyphenyl) sulfonamido)-4-methoxybenzo[d]isoxazol-6-yl)methyl)-1H-pyrazol-4-yl)methyl)propiolamide and N-((1-((4-methoxy-3-((3-methoxyphenyl) sulfonamido)-benzo[d]isoxazol-6-yl)methyl)-1H-pyrazol-4-yl)methyl)propioladmide

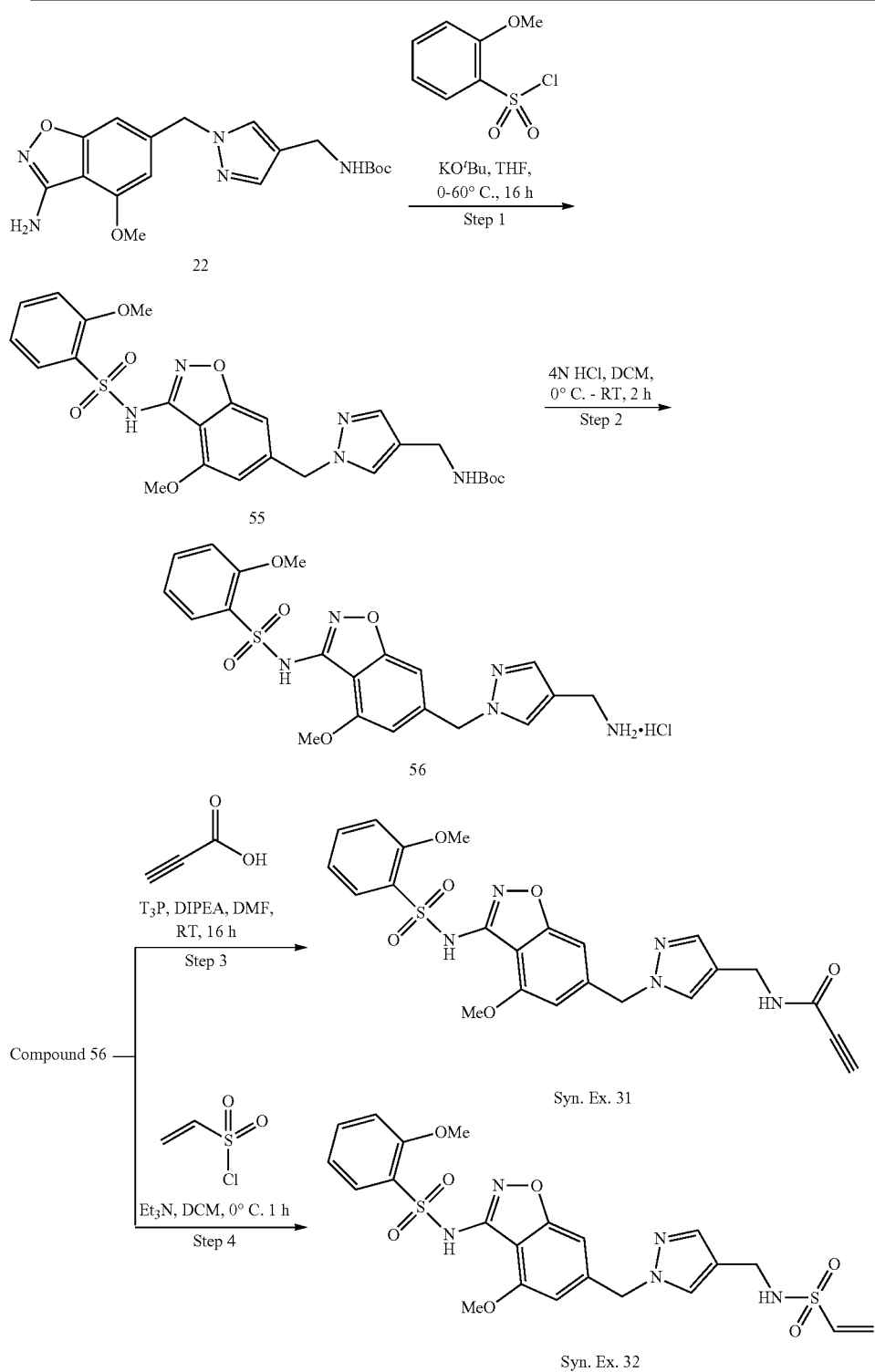

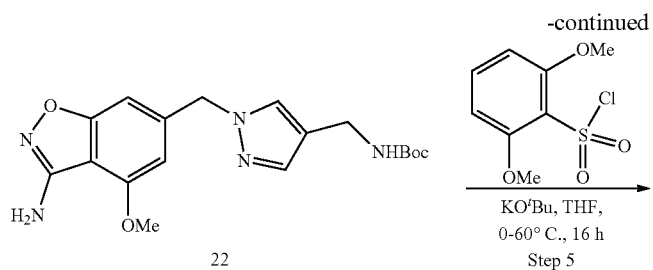
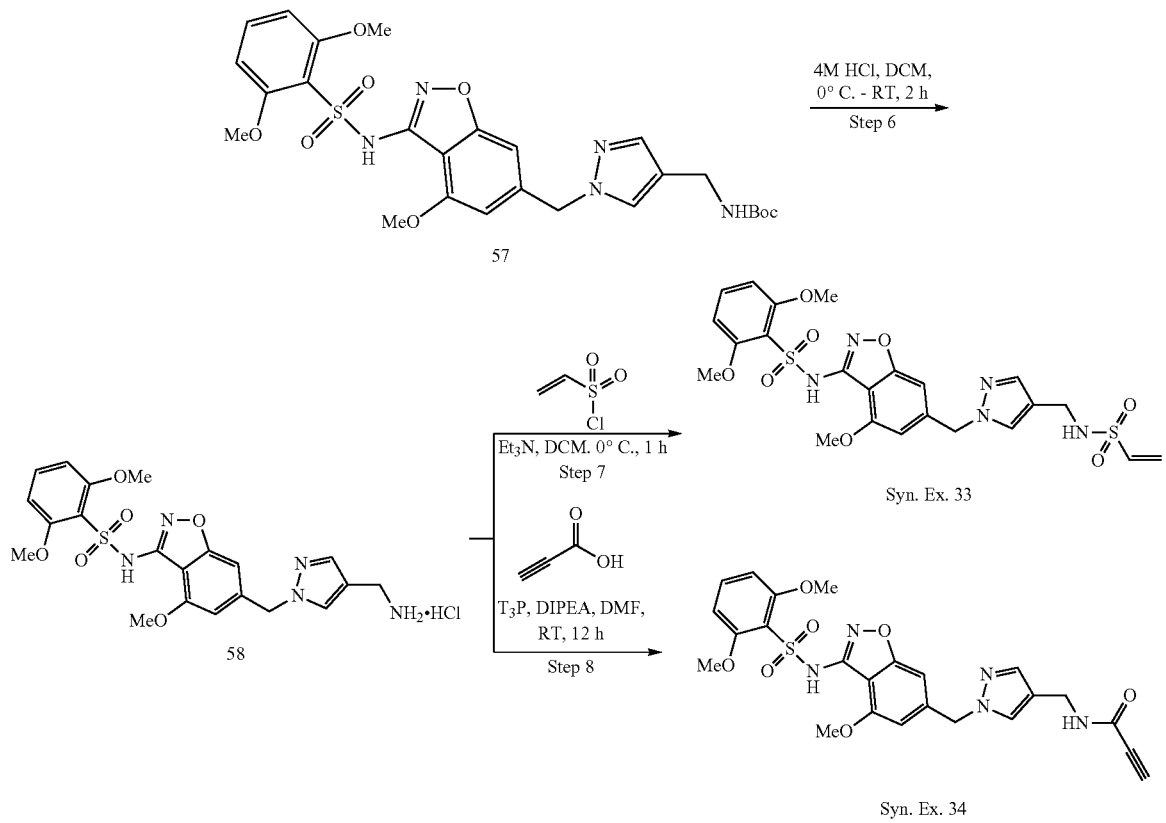
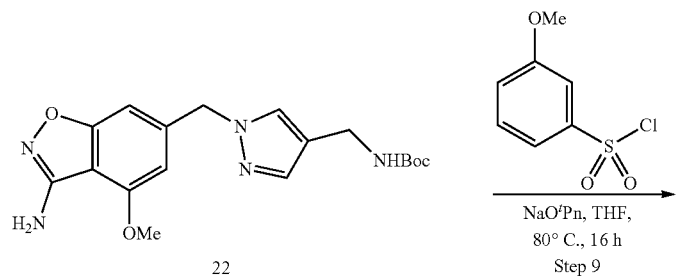
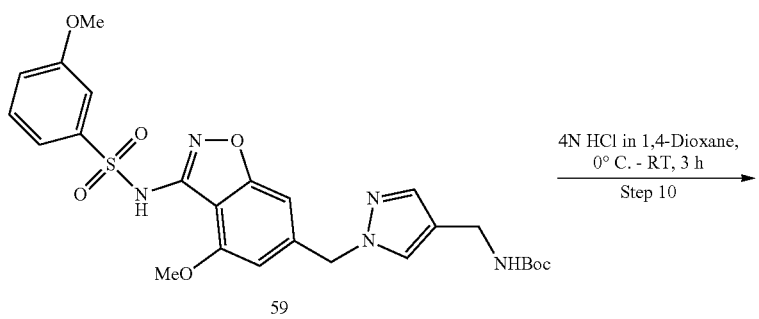

-continued

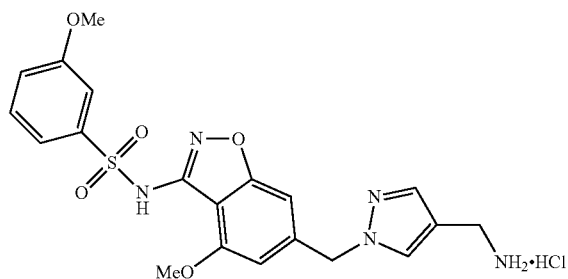
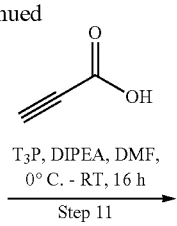

T₃P, DIPEA, DMF,
0° C. - RT, 16 h
Step 11

Syn. Ex. 35

Synthesis of tert-butyl ((1-((4-methoxy-3-((2-methoxyphenyl)sulfonamido)benzo[d]isoxazol-6-yl) methyl)-1H-pyrazol-4-yl)methyl)carbamate (55)

To a stirred solution of compound 22 (0.250 g, 0.66 mmol) in THF (4 mL) at 0° C. was added KO'Bu (0.225 g, 2.01 mmol), followed by 2-methoxybenzenesulfonyl chloride (0.166 g, 0.80 mmol) and the reaction was allowed to stir at 60° C. for 16 h. After completion of the reaction (monitored by TLC), the reaction mixture was diluted with DCM, water added and extracted. The organic layer was collected, washed with brine, dried over anhydrous $Na_2SO_4$, and concentrated under reduced pressure. The crude compound was purified by Combi flash column chromatography using a gradient method of 40-60% EtOAc/Heptane to afford the title compound 55 (0.081 g, 22.3%) as a white solid. TLC: 100% EtOAc ($R_f$ 0.35). ¹H NMR (400 MHz, DMSO-$d_6$): δ 10.10 (s, 1H), 7.79 (dd, J=8.0, 1.6 Hz, 1H), 7.67 (s, 1H), 7.63 (t, J=8.0 Hz, 1H), 7.35 (s, 1H), 7.20 (d, J=8.0 Hz, 1H), 7.10 (t, J=8.0 Hz, 1H), 6.82 (s, 1H), 6.74 (s, 1H), 5.37 (s, 2H), 3.95 (d, J=5.6 Hz, 2H), 3.98 (s, 3H), 3.78 (s, 3H), 1.36 (s, 9H); LCMS Calculated for $C_{25}H_{29}N_5O_7S$: 543.60; Found: 545.2 (M+2).

Synthesis of N-(6-((4-(aminomethyl)-1H-pyrazol-1-yl)methyl)4methoxybenzo[d]isoxazol-3-yl)-2-methoxybenzenesulfonamide hydrochloride (56)

To a stirred solution of compound 55 (80 mg, 0.147 mmol) in DCM (2 mL) at 0° C., 4M HCl in 1,4-dioxane (0.15 mL, 0.589 mmol) was added, and the reaction was allowed to stir at room temperature for 2 h. After completion (reaction monitored by TLC), the reaction mixture was concentrated under reduced pressure to afford the title compound 56 (70 mg, 98%, HCl salt) as an off-white solid. TLC: 10% MeOH/DCM ($R_f$ 0.5). ¹H NMR (400 MHz, DMSO-$d_6$): δ10.17 (s, 1H), 8.02 (broad s, 2H), 7.91 (s, 1H), 7.80 (d, J=7.6 Hz, 2H), 7.65 (t, J=8.4 Hz, 1H), 7.57 (s, 1H), 7.21 (d, J=8.4 Hz, 1H), 7.11 (t, J=7.6 Hz, 1H), 6.85 (s, 1H), 6.80 (s, 1H), 5.44 (s, 2H), 3.89 (d, J=5.6 Hz, 2H), 3.84 (s, 3H), 3.79 (s, 3H); LCMS Calculated for $C_{20}H_{22}ClN_5O_5S$: 479.94; Found: 444.08 (M+1). The salt was taken forward to the next step without any further purification.

Synthetic Example 31

Synthesis of N-((1-((4-methoxy-3-((2-methoxyphenyl) sulfonamido) benzo[d]isoxazol-6-yl) methyl)-1H-pyrazol-4-yl) methyl) propiolamide To a stirred solution of compound 56 (70 mg, 0.145 mmol) in DMF (2 mL) at 0° C. was added DIPEA (0.08 mL, 0.437 mmol), followed by $T_3P$ (69 mg, 0.217 mmol) and the contents were allowed to stir at room temperature for 20 min. After that, a pre-dissolved solution of propiolic acid (15.2 mg, 0.217 mmol) in DMF (0.5 mL) was added in drop-wise manner and the reaction was stirred at room temperature for 16 h. After completion (monitored by TLC), the reaction mixture was quenched with water and extracted with ethyl acetate. The organic layer was collected, washed with brine, dried over anhydrous $Na_2SO_4$, and concentrated under reduced pressure. The crude compound was purified by prep. HPLC to afford the title compound (27 mg, 37.3%) as an off-white solid. TLC: 5% MeOH/DCM ($R_f$ 0.5). (Analytical data in Table1).

Synthetic Example 32

Synthesis of 2-methoxy-N-(4-methoxy-6-((4-(vinylsulfonamidomethyl)-1H-pyrazol-1-yl)methyl) benzo[d]isoxazol-3-yl)benzenesulfonamide To a stirred solution of compound 56 (70 mg, 0.145 mmol) in DCM (4 mL) at 0° C. was added TEA (0.06 mL, 0.435 mmol) followed by ethenesulfonyl chloride (19 mg, 0.15 mmol) and the resulting reaction mixture was allowed to stir at the same temperature for 1 h. After completion (reaction monitored by TLC), the reaction mixture was quenched with ice water and extracted with ethyl acetate. The organic layer was collected, washed with brine, dried over anhydrous $Na_2SO_4$, and concentrated under reduced pressure. The crude compound was purified by prep HPLC to afford the title compound (1 mg, 1.2%) as a white solid. TLC: 100% E. A. ($R_f$ 0.5). (Analytical data in Table1).

Synthetic Example 33

Synthesis of tert-butyl ((1-((3-((2,6-dimethoxyphenyl)sulfonamido)-4-methoxybenzo[d]isoxazol-6-yl)methyl)-1H-pyrazol-4-yl)methyl)carbamate (57)

To a stirred solution of compound 22 (1 g, 2.67 mmol) in THF (20 mL) was added KOtBu (8.0 mL, 8.03 mmol) followed by 2,6-dimethoxybenzenesulfonyl chloride (950 mg, 4.02 mmol) and the reaction mixture was allowed to stir at the room temperature for 16 h. After completion (monitored by TLC), the reaction mixture was quenched with ice water and extracted with ethyl acetate. The organic layer was dried over anhydrous $Na_2SO_4$ and concentrated under reduced pressure. The crude compound was purified by combi flash chromatography (neutral alumina) to afford compound 57 (650 mg, 42.310%) as an off-white solid. TLC: 100 EtOAc (Rf: 0.6). LCMS Calculated for C26H31N5O8S: 573.19; Found: 573.30 (M+).

Synthesis of N-(6-((4-(aminomethyl)-1H-pyrazol-1-yl)methyl)-4-methoxybenzo[d]isoxazol-3-yl)-2,6-dimethoxybenzenesulfonamide hydrochloride (58)

To a stirred solution of compound 57 (0.65 g, 1.13 mmol) in DCM (3 mL) at 0° C. was added 4M HCl in 1,4-Dioxane (1.4 mL, 5.66 mmol). The reaction was allowed to stir at room temperature for 2 h. After completion (reaction monitored by TLC), the reaction mixture was concentrated under reduced pressure. The crude was washed with $Et_2O$ to afford the title compound 58 (500 mg, 87.0%) as an off-white solid. TLC: 10% MeOH/DCM (Rf: 0.1). LCMS Calculated for C21H23N5O6S: 473.14; Found: 474.30 (M+1).

Synthesis of 2,6-dimethoxy-N-(4-methoxy-6-((4-(vinylsulfonamidomethyl)-1H-pyrazol-1-yl)methyl)benzo[d]isoxazol-3-yl)benzenesulfonamide To a stirred solution of compound 58 (70 mg, 0.137 mmol) in DCM (4 mL) at 0° C. was added TEA (0.06 mL, 0.411 mmol), followed by ethene sulfonyl chloride (19 mg, 0.15 mmol) and the reaction mixture was allowed to stir at 0° C. for 1 h. After completion (reaction monitored by TLC), the reaction mixture was quenched with ice water and extracted with ethyl acetate. The organic layer was collected, washed with brine, dried over anhydrous $Na_2SO_4$, and concentrated under reduced pressure. The crude compound was purified by prep HPLC to afford the title compound (7.6 mg, 9.87%) as a white solid. TLC: 100% E.A. ($R_f$ 0.5). (Analytical data in Table1).

Synthetic Example 34

Synthesis of N-((1-((3-((2,6-dimethoxyphenyl)sulfonamido)-4-methoxybenzo[d]isoxazol-6-yl)methyl)-1H-pyrazol-4-yl)methyl)propiolamide To a stirred solution of compound 58 (60 mg, 0.117 mmol) in DMF (2 mL) at 0° C. was added DIPEA (0.063 mL, 0.353 mmol), followed by $T_3P$ (44.5 mg, 0.140 mmol) and the contents were stirred at room temperature for 5 min. After that, a pre-dissolved solution of propiolic acid (12.2 mg, 0.175 mmol) in DMF (0.5 mL) was added in a dropwise manner and the reaction was allowed to stir at room temperature for 12 h. After completion (monitored by TLC), the reaction mixture concentrated under reduced pressure. The crude compound was purified by using prep HPLC to afford the title compound (7 mg, 11.3%) as a white solid. TLC: 10% MeOH/DCM ($R_f$ 0.5). (Analytical data in Table1).

Synthetic Example 35

Synthesis of tert-butyl ((1-((4methoxy-3-((3-methoxyphenyl)sulfonamido) benzo[d]isoxazol-6-yl)methyl)-1H-pyrazol-4-yl)methyl)carbamate (59)

To a stirred solution of compound 22 (0.400 g, 1.07 mmol) in THF (4 mL) at room temperature was added NaO$^t$Pn (0.353 g, 3.21 mmol) and the contents were stirred for 15 min. 3-Methoxybenzenesulfonyl chloride (0.33 g, 1.60 mmol) was added at room temperature and the reaction was allowed to stir at 80° C. for 16 h. After completion of the reaction (monitored by TLC), the reaction mixture was cooled to 0° C., quenched with ice water and extracted with ethyl acetate. The combined organic layer was dried over anhydrous $Na_2SO_4$, filtered and concentrated under reduced pressure. The crude compound was purified by using combi flash chromatography using a gradient of 70-80% ethyl acetate/Heptane to afford the title compound 59 (248 mg, 42.6%) as a white solid. TLC: 50% EtOAc/Heptane ($R_f$ 0.2); LCMS Calculated for $C_{25}H_{29}N_5O_7S$: 543.60: Found: 544.2 (M+1).

Synthesis of N-(6-((4-(aminomethyl)-1H-pyrazol-1-yl)methyl)4methoxybenzo[d]isoxazol-3-yl)-3-methoxybenzenesulfonamide (60)

To a stirred solution of compound 59 (0.4 g, 0.76 mmol) in 1,4-Dioxane (1 mL) at 0° C., a 4M HCl in 1,4-Dioxane (0.4 mL) was added and the reaction was allowed to stir at room temperature for 3 h. After completion (reaction monitored by TLC), the reaction mixture was concentrated under reduced pressure and washed with Diethyl Ether/Heptane to afford the title compound 60 (250 mg, 70.8%) as pale brown solid. TLC: 10% MeOH/DCM ($R_f$ 0.5). $^1$H NMR (400 MHz, DMSO-$d_6$): δ 10.17 (s, 1H), 8.10 (br s, 3H), 7.92 (s, 2H), 7.59-7.50 (m, 4H), 7.25 (d, J=6.8 Hz, 1H), 6.87 (s, 1H), 6.81 (s, 1H), 5.45 (s, 2H), 3.86 (s, 3H), 3.80 (s, 3H); LCMS Calculated for $C_{20}H_{22}ClN_5O_5S$: 540.49; Found: 444.08 (Freebase+1).

Synthesis of N-((1-((4-methoxy-3-((3-methoxyphenyl)sulfonamido)benzo[d]isoxazol-6-yl)methyl)-1H-pyrazol-4-yl)methyl)propiolamide To a stirred solution of compound 60 (125 mg, 0.260 mmol) in DMF (2 mL) at 0° C. was added DIPEA (0.14 mL, 0.84 mmol), followed by T₃P (270 mg, 0.846 mmol) and the reaction was allowed to stir at room temperature for 5 min. After that, a pre-dissolved solution of propiolic acid (39.5 mg, 0.56 mmol) in DMF (0.5 mL) was added in drop-wise manner and the reaction was allowed to stir at room temperature for 16 h. After completion (reaction monitored by TLC), the reaction mixture was quenched with ice-water and extracted with ethyl acetate. The organic layer was collected, washed with brine, dried over anhydrous Na₂SO₄, and concentrated under reduced pressure. The crude compound was purified by prep. HPLC to afford the title compound (14.2 mg, 11.02%) as a white solid. TLC: 10% MeOH/DCM (R_f 0.5). (Analytical data in Table1).

Synthetic Examples 36-38

Scheme 20: Synthesis of methyl 2-(N-(4-methoxy-6-((4-(propiolamidomethyl)-1H-pyrazol-1-yl)methyl)benzo[d]isoxazol-3yl)sulfamoyl)benzoate, 2-(N-(4-methoxy-6-((4-(propiolamidomethyl)-1H-pyrazol-1yl)methyl)benzo[d]isoxazol-3yl)sulfamoyl)benzoic acid and methyl 4-(N-(4-methoxy-6-((4-(propiolamidomethyl)-1H-pyrazol-1-yl)methyl)benzo[d]isoxazol-3yl)sulfamoyl)benzoate

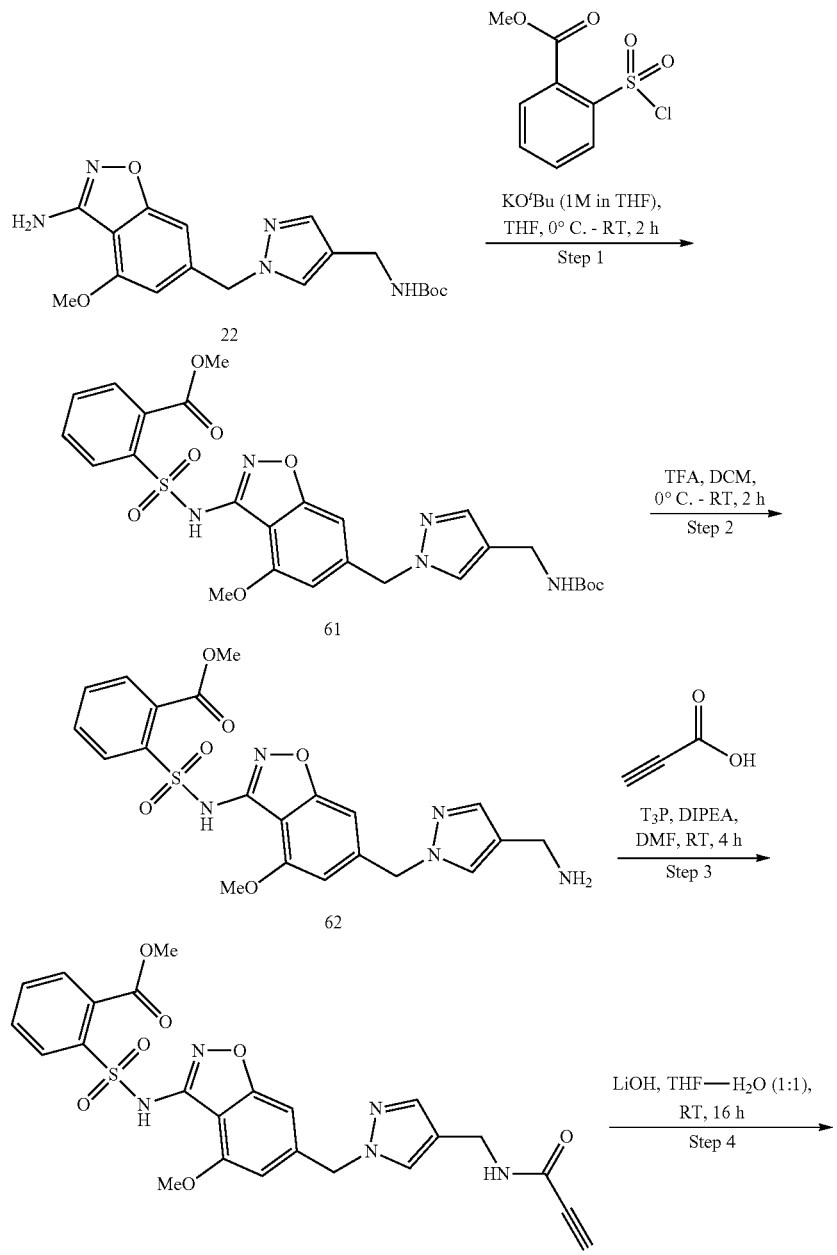

Syn. Ex. 36

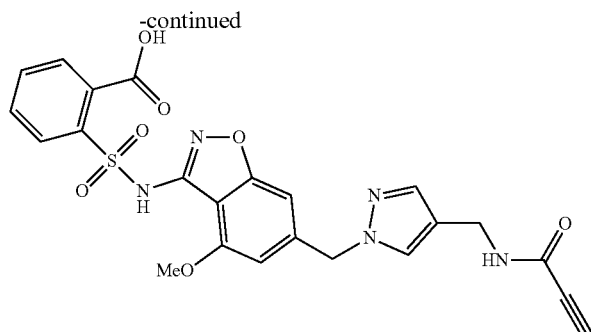

Syn. Ex. 37

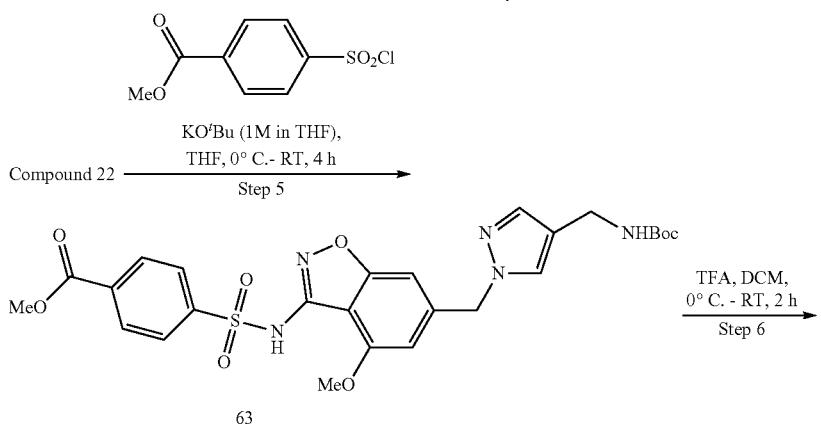

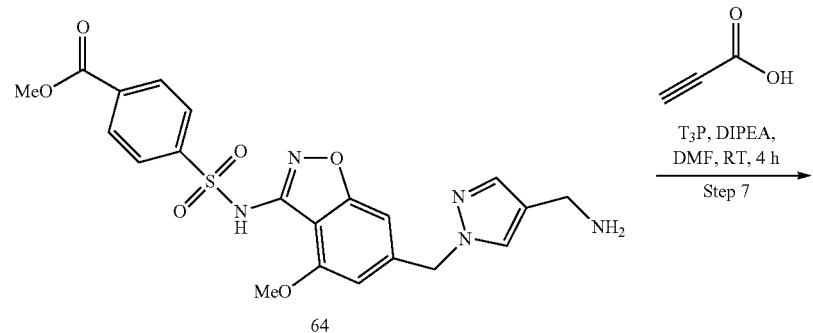

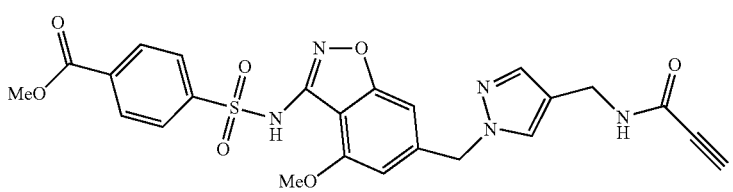

Syn. Ex. 38

Synthesis of methyl 2-(N-(6-((4-(((tert-butoxycarbonyl)amino)methyl)-1H-pyrazol-1-yl)methyl)-4-methoxybenzo[d]isoxazol-3-yl)sulfamoyl)benzoate (61)

To a stirred solution of compound 22 (1 g, 2.67 mmol) in THF (10 mL) at 0° C. was added a 1M solution of KO$^t$Bu in THF (8 mL, 8.03 mmol), followed by methyl methyl-2-(chlorosulfonyl)benzoate (1.25 g, 5.34 mmol) and the reaction was allowed to stir at the same temperature for 2 h. After completion of the reaction (monitored by TLC), the reaction mixture was diluted with ethyl acetate, water added and extracted. The organic layer was collected, washed with brine, dried over anhydrous $Na_2SO_4$, and concentrated under reduced pressure. The crude compound was purified by Combi flash column chromatography using a gradient method of 40-50% EtOAc/Heptane to afford the title compound 61 (0.065 g, 43.9%) as a brown solid. TLC: 70% EtOAc ($R_f$, 0.35). $^1$H NMR (400 MHz, DMSO-$d_6$): δ 10.36 (br s, 1H), 8.06-8.04 (m, 1H), 7.76-7.67 (m, 4H), 7.35 (s, 1H), 7.11 (s, 1H), 6.88 (d, J=8.4 Hz, 1H), 6.72 (t, J=7.2 Hz, 1H), 5.36 (s, 2H), 3.95 (t, J=5.6 Hz, 2H), 3.80 (s, 6H, merged), 1.35 (s, 9H); LCMS Calculated for $C_{26}H_{29}N_5O_8S$: 571.61; Found: 572.20 (M+1).

Synthesis of methyl 2-(N-(6-((4-(aminomethyl)-1H-pyrazol-1-yl)methyl)-4-methoxybenzo[d]isoxazol-3-yl)sulfamoyl)benzoate (62)

To a stirred solution of compound 61 (100 mg, 1.75 mmol) in DCM (3 mL) at 0° C., TFA (1.32 mL, 17.51 mmol) was added and the reaction was allowed to stir at room temperature for 2 h. After completion (reaction monitored by TLC), reaction mixture was concentrated under reduced pressure to afford the title compound 62 (75 mg, 90.90%) as a brown gummy solid. TLC: 10% MeOH/DCM ($R_f$ 0.5). LCMS Calculated for $C_{21}H_{21}N_5O_6S$: 471.50; Found: 472.3 (M+1).

Synthetic Example 36

Synthesis of methyl 2-(N-(4-methoxy-6-((4-(propiolamidomethyl)-1H-pyrazol-1-yl)methyl)benzo[d]isoxazol-3-yl)sulfamoyl)benzoate To a stirred solution of compound 62 (100 mg, 0.21 mmol) in DMF (2 mL) at 0° C. was added DIPEA (0.11 mL, 0.63 mmol), followed by $T_3P$ (87 mg, 0.27 mmol) and the contents were allowed to stir at room temperature for 20 min. After, a pre-dissolved solution of propiolic acid (14.7 mg, 0.211 mmol) in DMF (0.3 mL) was added in drop-wise manner and the reaction was stirred at room temperature for 4 h. After completion (reaction monitored by TLC), the reaction mixture was quenched with water and extracted with ethyl acetate. The organic layer was collected, washed with brine, dried over anhydrous $Na_2SO_4$, and concentrated under reduced pressure. The crude compound was purified by prep. HPLC to afford the title compound (8.5 mg, 7.7%) as an off white solid. TLC: 10% MeOH/DCM ($R_f$ 0.5). (Analytical data in Table1).

Synthetic Example 37

Synthesis of 2-(N-(4-methoxy-6-((4-(propiolamidomethyl)-1H-pyrazol-1-yl)methyl)benzo[d]isoxazol-3-yl)sulfamoyl)benzoic acid To a stirred solution of methyl 2-(N-(4-methoxy-6-((4-(propiolamidomethyl)-1H-pyrazol-1-yl)methyl)benzo[d]isoxazol-3-yl)sulfamoyl)benzoate (100 mg, 0.19 mmol) in a 1:1 mixture of THF-$H_2O$ (2 mL), LiOH (13 mg, 0.57 mmol) was added and the reaction mixture was stirred at room temperature for 16 h. The progress of the reaction was monitored by TLC. After completion, the reaction mixture was concentrated under reduced pressure. The residue was neutralized with 1N HCl and extracted with ethyl acetate. The organic layer was collected, washed with brine, dried over anhydrous $Na_2SO_4$ and concentrated under reduced pressure to afford the title compound (6 mg, 6.16%) as an off white solid. TLC: 100% EtOAc/Heptane ($R_f$ 0.2) (Analytical data in Table1).

Synthesis of methyl 4-(N-(6-((4-(((tert-butoxycarbonyl) amino)methyl)-1H-pyrazol-1-yl)methyl)-4-methoxybenzo[d]isoxazol-3-yl)sulfamoyl)benzoate (63)

To a stirred solution of compound 22 (0.50 g, 1.33 mmol) in THF (4 mL) at 0° C. was added a 1M solution of KO$^t$Bu in THF (4 mL, 4.01 mmol), followed by methyl 4-(chlorosulfonyl) benzoate (0.63 g, 2.67 mmol) and the reaction was allowed to stir at room temperature for 4 h. After completion (reaction monitored by TLC), the reaction mixture was diluted with ethyl acetate, water added and extracted. The organic layer was collected, washed with brine, dried over anhydrous $Na_2SO_4$ and concentrated under reduced pressure. The crude compound was purified by Combi flash column chromatography using a gradient method of 40-60% EtOAc/Heptane to afford the title compound 63 (0.090 g, 11.71%) as a white solid. TLC: 100% EtOAc ($R_f$ 0.35). $^1$H NMR (400 MHz, DMSO-$d_6$): δ 10.10 (s, 1H), 7.81-7.79 (dd, J=7.6, 2.0 Hz, 1H), 7.67 (s, 1H), 7.63 (t, J=8.0 Hz, 1H), 7.35 (s, 1H), 7.20 (d, J=8.0 Hz, 1H), 7.10 (t, J=8.0 Hz, 1H), 6.82 (s, 1H), 6.74 (s, 1H), 5.37 (s, 1H), 3.95 (d, J=5.6 Hz, 2H), 3.78 (s, 3H), 3.28 (s, 3H), 1.36 (s, 9H), 1.25 (m, 2H); LCMS Calculated for $C_{26}H_{29}N_5O_8S$: 571.61; Found: 572.2 (M+1).

Synthesis of methyl 4-(N-(6-((4-(aminomethyl)-1H-pyrazol-1-yl) methyl)-4-methoxybenzo[d]isoxazol-3-yl)sulfamoyl)benzoate (64)

To a stirred solution of compound 63 (0.2 g, 0.35 mmol) in DCM (3 mL) at 0° C., TFA (0.4 mL, 3.49 mmol) was added, and the reaction was allowed to stir at room temperature for 2 h. After completion (reaction monitored by TLC), the reaction mixture was concentrated under reduced pressure to afford the title compound 64 (150 mg, 90.9%) as a brown gummy solid. TLC: 10% MeOH/DCM ($R_f$ 0.5). LCMS Calculated for $C_{21}H_{21}N_5O_6S$: 471.49; Found: 472.2 (M+1).

Synthetic Example 38

Synthesis of methyl 4-(N-(4-methoxy-6-((4-(propiolamidomethyl)-1H-pyrazol-1-yl)methyl)benzo[d]isoxazol-3-yl)sulfamoyl)benzoate To a stirred solution of compound 64 (100 mg, 0.21 mmol) in DMF (1 mL) at 0° C. was added DIPEA (0.1 mL, 0.53 mmol), followed by $T_3P$ (100 mg, 0.31 mmol) and the contents were allowed to stir at room temperature for 20 min. After that, a pre-dissolved solution of propiolic acid (15 mg, 0.217 mmol) in DMF (0.5 mL) was added in drop-wise manner and the reaction was stirred at room temperature for 4 h. After completion (reaction monitored by TLC), the reaction mixture was quenched with water and extracted with ethyl acetate. The organic layer was collected, washed with brine, dried over anhydrous $Na_2SO_4$, and concentrated under reduced pressure. The crude compound was purified by using prep. HPLC to afford the title compound (2.5 mg, 2.71%) as an off white solid. TLC: 5% MeOH/DCM ($R_f$ 0.5). (Analytical data in Table1).

Synthetic Example 39

Scheme 21: Synthesis of 6-((2-acrylamidoacetamido) methyl)-N-((2-fluorophenyl) sulfonyl) benzofuran-2-carboxamide

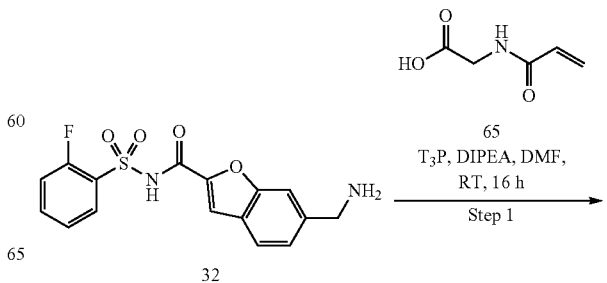

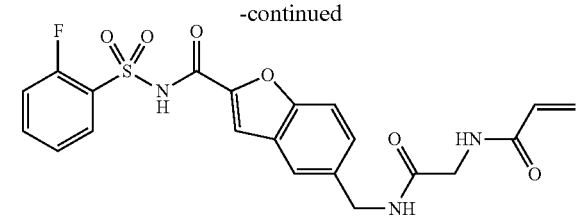

Syn. Ex. 39

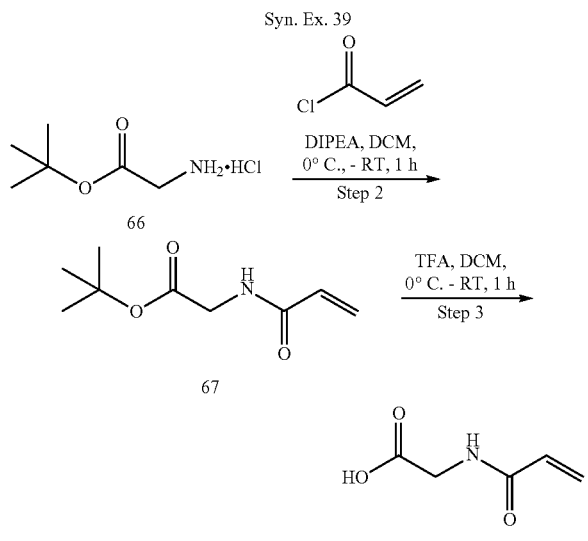

Synthesis of tert-butyl acryloylglycinate (67)

To a stirred solution of 66 (0.500 g, 2.99 mmol) in DCM (10 mL) at 0° C. was added DIPEA (1.55 mL, 8.97 mmol) followed by acryloyl chloride (0.4 g, 4.49 mmol). The reaction mixture was stirred at room temperature for 1 h. After completion (reaction monitored by TLC), water was added and extracted with DCM. The organic layer was dried over anhydrous $Na_2SO_4$ and concentrated under reduced pressure to afford the title compound 67 (581 mg, quant.) as a yellow liquid, which was used in the next reaction without further purification. TLC: 5% MeOH/DCM ($R_f$, 0.5). $^1$H NMR (400 MHz, DMSO-$d_6$): δ 8.40 (brs, 1H), 6.25 (q, J=10.0 Hz, 1H), 6.10 (dd, J=16.0, 2.0 Hz, 1H), 5.62 (d, J=2.4 Hz, 1H), 3.79 (d, J=6.4 Hz, 2H), 1.39 (s, 9H); LCMS Calculated for $C_9H_{15}NO_3$: 185.22; Found: 187.20 (M+2).

Synthesis of acryloylglycine (65)

To a stirred solution of compound 67 (560 mg, 3.02 mmol) in DCM (5 mL) at 0° C. was added TFA (0.47 mL, 6.05 mmol) and the reaction was allowed to stir at room temperature for 1 h. After completion of the reaction (monitored by TLC), reaction mixture was concentrated under reduced pressure to obtain a residue which was triturated with di-ethyl ether/pentane to afford 65 (420 mg, quant.) as a yellow solid which was used in the next reaction without further purification. TLC: 10% MeOH/DCM ($R_f$, 0.6). $^1$H NMR (400 MHz, DMSO-$d_6$): δ 8.41 (brs, 1H), 6.28 (q, J=10.0 Hz, 1H), 6.12 (d, J=16.8 Hz, 1H), 5.62 (d, J=10.0 Hz, 1H), 3.83 (d, J=5.2 Hz, 2H). $^1$H-NMR didn't hint acid proton. LCMS Calculated for $C_5H_7NO_3$: 129.12; Found: 257.05 (2M-1).

Synthesis of 6-((2-acrylamidoacetamido)methyl)-N-((2-fluorophenyl)sulfonyl)benzofuran-2-carboxamide To a stirred solution of 32 (200 mg, 0.57 mmol) in DMF (5 mL) at 0° C. was added DIPEA (0.294 mL, 1.71 mmol), followed by $T_3P$ (0.273 mg, 0.86 mmol) and the contents were allowed to stir at room temperature for 20 min. After, Compound 65 (112 mg, 0.86 mmol) was added and the reaction mixture was stirred at room temperature for 16 h. After completion (reaction monitored by TLC), the reaction mixture was quenched with water and extracted with 25% IPA/DCM. The organic layer was dried over anhydrous $Na_2SO_4$ and concentrated under reduced pressure. The crude compound was purified by using prep HPLC to afford the title compound (2.5 mg, 1%) as an off-white solid. TLC: 10% MeOH/DCM ($R_f$, 0.5). (Analytical data in Table1).

Synthetic Example 40

Scheme 22: Synthesis of 1-acryloyl-N-((2-(((2-fluorophenyl)sulfonyl)carbamoyl)benzofuran-6-yl)methyl)pyrrolidine-3-carboxamide

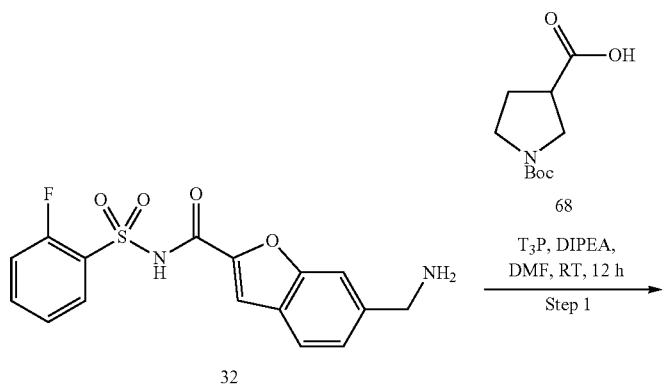

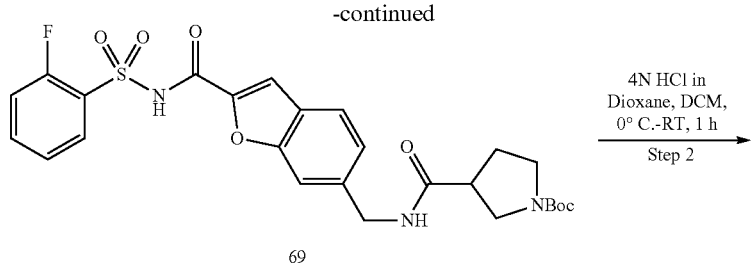

69

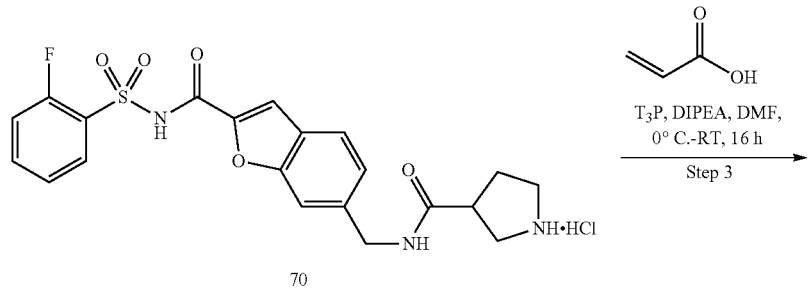

70

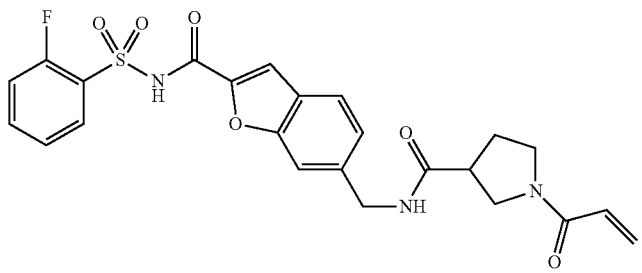

Syn. Ex. 40

Synthesis of tert-butyl 3-(((2-(((2-fluorophenyl)sulfonyl)carbamoyl)benzofuran-6-yl)methyl)carbamoyl)pyrrolidine-1-carboxylate (69)

To a stirred solution of Compound 68 (203 mg, 0.94 mmol) in DMF (4 mL) at 0° C. was added DIPEA (0.443 mL, 2.58 mmol), followed by T$_3$P (410 mg, 1.29 mmol). The contents were allowed to stir at room temperature for 20 min. After, a pre-dissolved solution of Compound 32 (300 mg, 0.86 mmol) in DMF (0.5 mL) was added and the reaction mixture was stirred at room temperature for 12 h. After completion (reaction monitored by TLC), the reaction mixture was quenched with water and extracted with 10% MeOH/DCM. The organic layer was dried over anhydrous Na$_2$SO$_4$ and concentrated under reduced pressure to obtain the residue which was triturated with di-ethyl ether/pentane to afford the title compound 69 (220 mg, 47%) as an off-white solid. TLC: 10% MeOH/DCM (R$_f$ 0.5); LCMS Calculated for C$_{26}$H$_{28}$FN$_3$O$_7$S: 545.58; Found: 547.01 (M+1).

Synthesis of N((2(((2fluorophenyl) sulfonyl) carbamoyl) benzofuran6yl) methyl) pyrrolidine-3-carboxamide hydrochloride (70)

To a stirred solution of compound 69 (200 mg, 0.36 mmol) in DCM (2 mL) at 0° C., 4N HCl in 1,4-dioxane (1 mL) was added and the reaction was allowed to stir at room temperature for 1 h. After completion (reaction monitored by TLC), the reaction mixture was concentrated under reduced pressure to obtain the residue, which was triturated with DCM/n-Heptane to afford the title compound 70 (170 mg, HCl salt, 96%) as an off-white solid. TLC: 10% MeOH/DCM (R$_f$ 0.3); LCMS Calculated for C$_{21}$H$_{20}$ClFN$_3$O$_5$S: 481.92; Found: 446.29 (Freebase M+1).

Synthesis of 1-acryloyl-N-((2-(((2-fluorophenyl)sulfonyl)carbamoyl)benzofuran-6-yl)methyl)pyrrolidine-3-carboxamide To a stirred solution of Compound 70 (120 mg, 0.25 mmol) in DMF (2 mL) at 0° C. was added DIPEA (0.13 mL, 0.76 mmol) and followed by T$_3$P (120 mg, 0.39 mmol), acrylic acid (21 mg, 0.28 mmol). The reaction mixture was stirred at room temperature for 16 h. After completion (reaction monitored by TLC), the reaction mixture was quenched with cool water and extracted with 10% IPA/DCM. The organic layer was dried over anhydrous Na$_2$SO$_4$ and concentrated under reduced pressure to obtain the residue, which was purified by using prep HPLC to afford the title compound (4.7 mg, 4%) as a brown solid. TLC: 10% MeOH/DCM (R$_f$ 0.5). (Analytical data in Table1).

Synthetic Examples 41 and 42
Scheme 23: Synthesis of N'-(3-(4-(1-acryloylpiperidin-4-yl) pyridin-2-yl)-5-methylbenzoyl)-2-fluorobenzenesulfonohydrazide and 2-fluoro-N'-(3-methyl-5-(4-(1-vinysulfonyl)piperidin-4-yl)pyridin-2-yl)benzoyl)benzenesulfonohydrazide
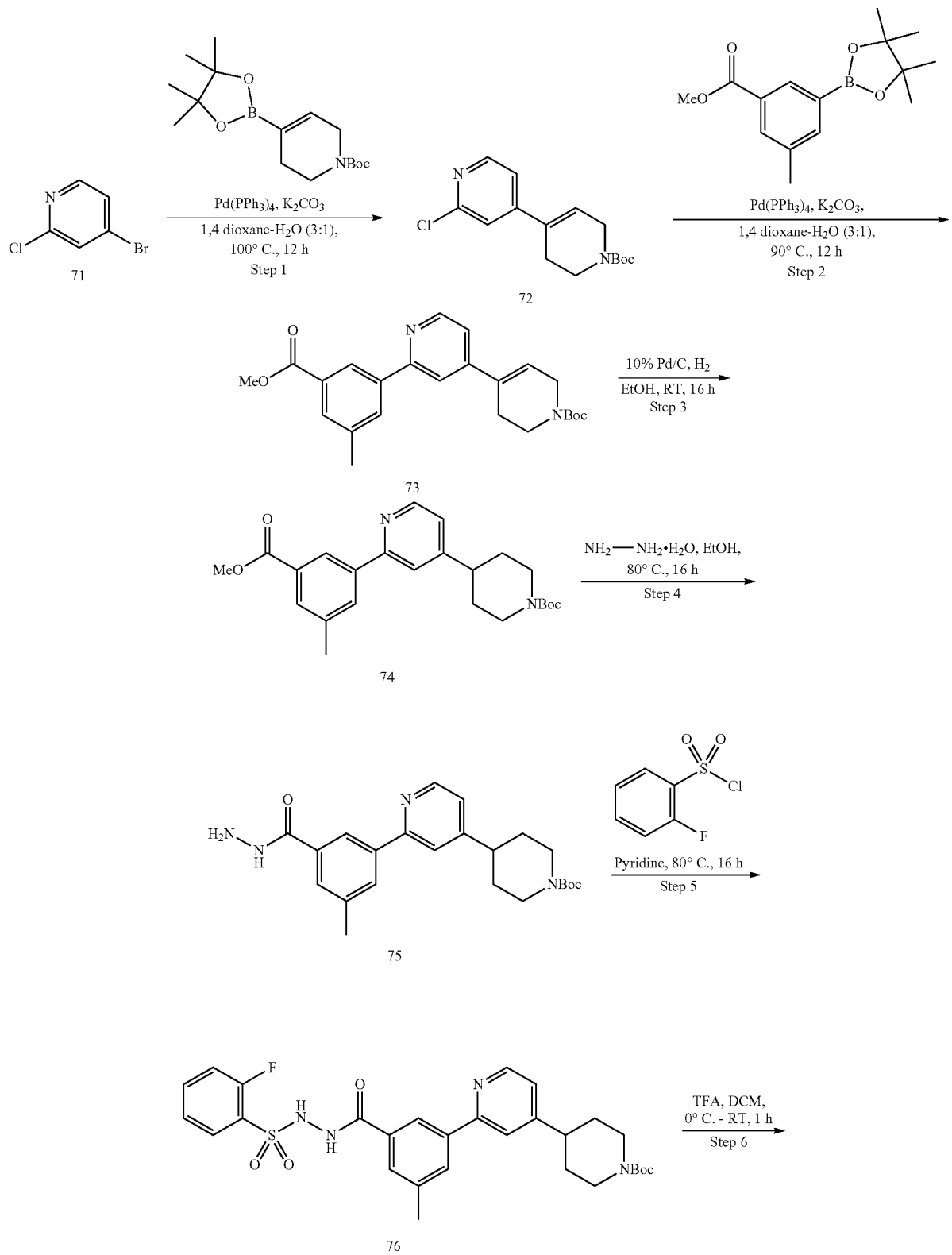

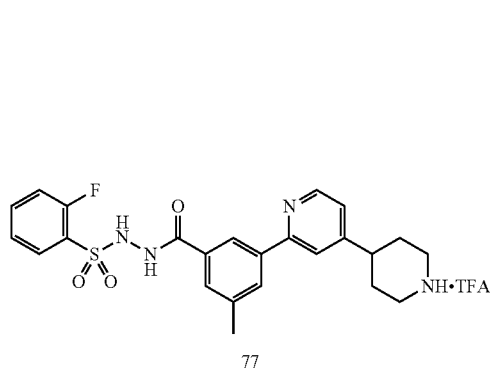
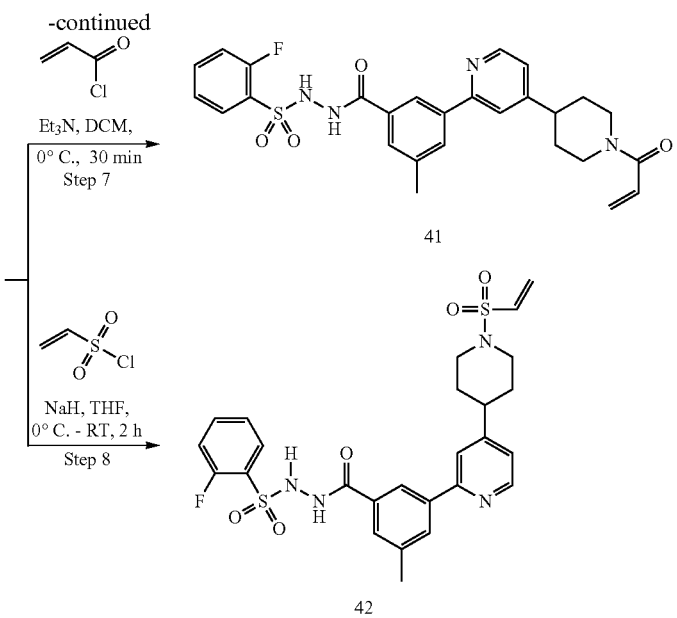

Synthesis of tert-butyl 2'-chloro-3,6-dihydro-[4,4'-bipyridine]-1(2H)-carboxylate (72)

To a stirred solution of 4-bromo-2-chloropyridine 71 (3 g, 15.58 mmol) in 3:1 mixture of 1,4 dioxane:water (80 mL), was added $K_2CO_3$ (10.77 g, 77.94 mmol) followed by $Pd(PPh_3)_4$ (0.9 g, 0.779 mmol) and tert-butyl 4-(4,4,5,5-tetramethyl-1,3,2-dioxaborolan-2-yl)-3,6-dihydropyridine-1(2H)-carboxylate (5.78 g, 18.69 mmol). The resulting reaction mixture was stirred at 100° C. for 12 h. After completion (monitored by TLC), the reaction mixture was cooled to room temperature, added water and extracted with ethyl acetate. The organic layer was collected, washed with brine, dried over anhydrous $Na_2SO_4$ and concentrated under reduced pressure. The crude compound was purified by combi flash chromatography using a gradient method of 0-30% EtOAc/Heptane to afford the title compound 72 (2.8 g, 61%) as a yellow solid. TLC: 50% EtOAc/Heptane ($R_f$ 0.5). $^1$H NMR (400 MHz, DMSO-$d_6$): δ 8.35 (d, J=4.8 Hz, 1H), 7.52 (s, 1H), 7.47 (d, J=5.2 Hz, 1H), 6.56 (brs, 1H), 4.03 (s, 2H), 3.54 (t, J=5.6 Hz, 2H), 2.46 (s, 2H), 1.42 (s, 9H); LCMS Calculated for $C_{15}H_{19}ClN_2O_2$: 294.78; Found: 294.97 (M+1).

Synthesis of tert-butyl 2'-(3-(methoxycarbonyl)-5-methylphenyl)-3,6-dihydro-[4,4'-bipyridine]-1(2H)-carboxylate (73)

To a stirred solution of compound 72 (1 g, 3.40 mmol) in a 3:1 mixture of 1,4 dioxane:water (40 mL), was added $K_2CO_3$ (2.34 g, 17.00 mmol) followed by $Pd(PPh_3)_4$ (196 mg, 0.17 mmol) and methyl 3-methyl-5-(4,4,5,5-tetramethyl-1,3,2-dioxaborolan-2-yl)benzoate (1.12 g, 4.08 mmol). The reaction mixture was stirred at 90° C. for 12 h. After completion (reaction monitored by TLC), the reaction mixture was cooled to room temperature, added water and extracted with ethyl acetate. The organic layer was collected, washed with brine, dried over anhydrous $Na_2SO_4$ and concentrated under reduced pressure. The crude compound was purified by combi flash chromatography using a gradient method of 0-30% EtOAc/Heptane to afford the title compound 73 (1.0 g, 72%) as a pale yellow solid. TLC: 50% EtOAc/Heptane ($R_f$ 0.5). $^1$H NMR (400 MHz, DMSO-$d_6$): δ 8.63 (d, J=4.8 Hz, 1H), 8.53 (s, 1H), 8.25 (s, 1H), 8.00 (s, 1H), 7.84 (s, 1H), 7.43 (q, J=2.1 Hz, 1H), 6.60 (brs, 1H), 4.07 (s, 2H), 3.89 (s, 3H), 3.57 (t, J=5.2 Hz, 2H), 2.57-2.52 (m, 2H), 2.47 (s, 3H), 1.40 (s, 9H); LCMS Calculated for $C_{24}H_{28}N_2O_4$: 408.50; Found: 409.0 (M+1).

Synthesis of tert-butyl 4-(2-(3-(methoxycarbonyl)-5-methylphenyl)pyridin-4-yl)piperidine-1-carboxylate (74)

An autoclave was charged with a suspension of Compound 73 (700 mg, 1.7 mmol) in EtOH (15 mL) and the mixture was purged with nitrogen for 5 min. After, 10% Pd/C (350 mg) was added under nitrogen atmosphere. The reaction mixture was purged with hydrogen gas and was allowed to stir under hydrogen atmosphere (100 psi) at room temperature for 16 h. The progress of the reaction was monitored by TLC. After completion, the reaction mixture was filtered through a pad of Celite, and which was washed with MeOH. The filtrate was concentrated under reduced pressure to the dryness. The crude product was purified by Combi flash chromatography using a gradient method of 0-5% MeOH/DCM to afford the desired title compound 74 (600 mg, 85%) as white solid. TLC: 50% EtOAc/Heptane ($R_f$ 0.6). LCMS Calculated for $C_{24}H_{30}N_2O_4$: 410.51; Found: 411.08 (M+1).

Synthesis of tert-butyl4-(2-(3-(hydrazinecarbonyl)-5-methylphenyl) pyridin-4-yl)piperidine-1-carboxylate (75)

To a stirred solution of Compound 74 (1.0 g, 2.43 mmol) in EtOH (20 mL) was added hydrazine hydrate (6 mL) and the reaction was allowed to stir at 80° C. for 16 h. After completion (monitored by TLC), the reaction mixture was concentrated under reduced pressure to obtain the residue which was triturated with DCM/n-Heptane and concentrated under reduced pressure to afford the title compound 75 (600 mg, 60%) as a pale-yellow solid. TLC: 5% MeOH/DCM ($R_f$ 0.3). $^1$H NMR (400 MHz, DMSO-d$_6$): δ 9.08 (s, 1H), 8.55 (d, J=5.2 Hz, 1H), 8.28 (s, 1H), 8.08 (s, 1H), 7.89 (s, 1H), 7.68 (s, 1H), 7.26 (d, J=4.8 Hz, 1H), 4.49 (s, 2H), 3.10 (s, 1H), 2.82-2.79 (m, 2H), 2.41 (s, 3H), 1.84-1.82 (m, 2H), 1.81 (s, 2H), 1.62-1.58 (m, 2H), 1.43 (s, 9H); LCMS Calculated for C$_{23}$H$_{30}$N$_4$O$_3$: 410.52; Found: 409.01 (M-1).

Synthesis of tert-butyl 4-(2-(3-(2-((2-fluorophenyl) sulfonyl)hydrazine-1-carbonyl)-5-methylphenyl) pyridin-4-yl)piperidine-1-carboxylate (76)

To a stirred solution of compound 75 (300 mg, 0.73 mmol) in Pyridine (3 mL) was added 2-fluorobenzenesulfonyl chloride (142 mg, 0.73 mmol) and the reaction was allowed to stir at 80° C. for 16 h. After completion (reaction monitored by TLC), the reaction mixture was neutralized with 1N HCl and extracted with ethyl acetate. The organic layer was collected, washed with brine, dried over anhydrous Na$_2$SO$_4$ and concentrated under reduced pressure to afford the title compound 76 (230 mg, Crude) as a brown solid. TLC: 5% MeOH/DCM (R$_f$ 0.6); LCMS Calculated for C$_{29}$H$_{33}$FN$_4$O$_5$S: 568.66; Found: 569.86 (M+1).

Synthesis of 2-fluoro-N'-(3-methyl-5-(4-(piperidin-4-yl)pyridin2yl)benzoyl) benzenesulfonohydrazide (77)

To a stirred solution of compound 76 (230 mg, 0.40 mmol) in DCM (3 mL) at 0° C., TFA (0.3 mL, 4.04 mmol) was added, and the reaction was allowed to stir at room temperature for 1 h. After completion (reaction monitored by TLC), the reaction mixture was concentrated under reduced pressure to afford the title compound 77 (180 mg, TFA salt) as a brown solid. TLC: 5% MeOH/DCM (R$_f$ 0.5). LCMS Calculated for C$_{26}$H$_{25}$F$_4$N$_4$O$_4$S: 565.56; Found: 469.15 (Free base M+1).

Synthetic Example 41

Synthesis of N-(3-(4-(1-acryloylpiperidin-4-yl) pyridin-2-yl)-5-methylbenzoyl)-2-fluorobenzenesulfonohydrazide To a stirred solution of 77 (60 mg, 0.11 mmol) in DCM (4 mL) at 0° C. was added Et$_3$N (0.04 mL, 0.30 mmol) followed by acryloyl chloride (8.1 mg, 0.09 mmol). The reaction was stirred at the same temperature for 30 min. After completion of the reaction (monitored by TLC), the reaction mixture was concentrated under reduced pressure. The crude compound was purified using prep HPLC to afford the title compound (3.5 mg, 6.73%) as an off-white solid. TLC: 10% MeOH/DCM (R$_f$ 0.5). (Analytical data in Table1).

Synthetic Example 42

Synthesis of 2-fluoro-N'-(3-methyl-5-(4-(1-(vinylsulfonyl)piperidin-4-yl)pyridin-2-yl)benzoyl) benzenesulfonohydrazide To a stirred solution of compound 77 (200 mg, 0.35 mmol) in THF (5 mL) at 0° C. was added NaH [60% dispersion in mineral oil] (42 mg, 1.05 mmol) and the contents were stirred for 15 min at the same temperature. After, ethenesulfonyl chloride (80 mg, 0.64 mmol) was added, and the reaction was allowed to stir at room temperature for 2 h. After completion of the reaction (monitored by TLC), the reaction mixture was quenched with ice water and extracted with ethyl acetate. The combined organic layer was dried over anhydrous Na$_2$SO$_4$, filtered and concentrated under reduced pressure. The crude compound was purified by Prep-HPLC to afford the title compound (5 mg, 2.53%) as a white solid. TLC: 5% MeOH/DCM (R$_f$ 0.2); (Analytical data in Table1).

Synthetic Example 43

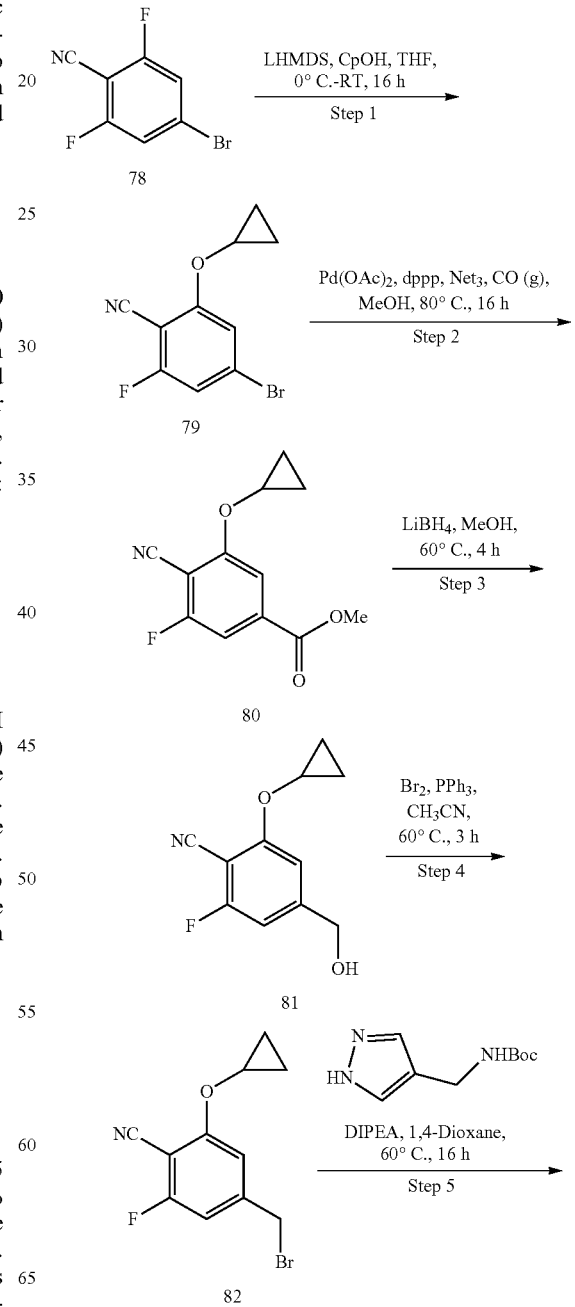

-continued

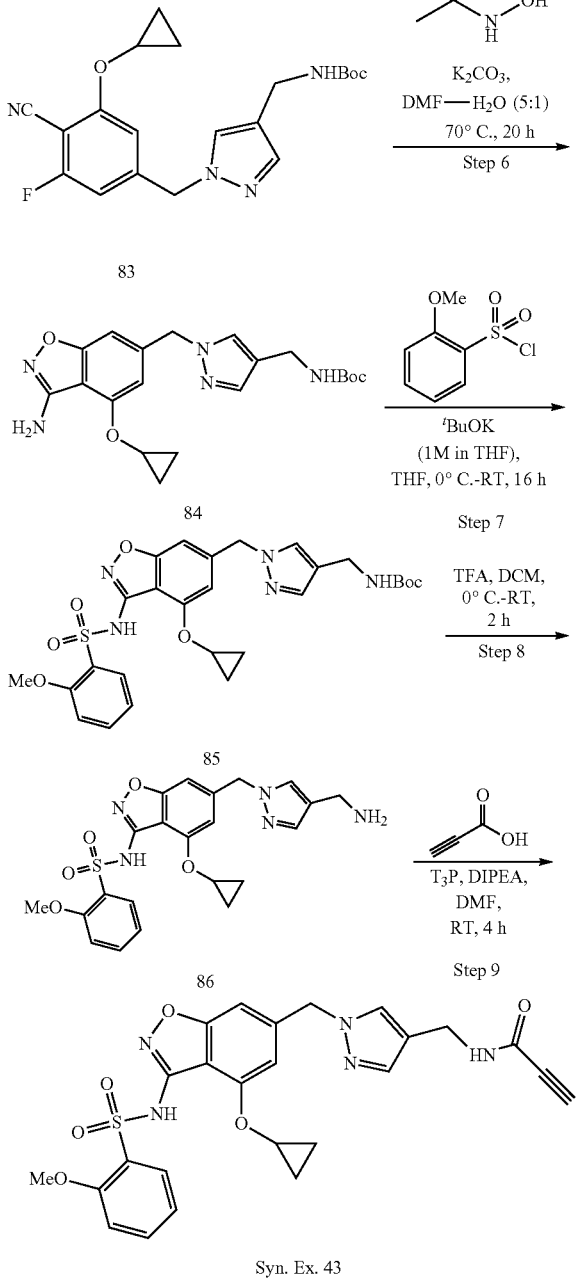

Syn. Ex. 43

Synthesis of 4-bromo-2-cyclopropoxy-6-fluorobenzonitrile (79)

To a stirred solution of cyclopropanol (1.6 g, 27.64 mmol) in THF (50 mL) at 0° C. was added a 1.0 M solution of LHMDS in THF (27.64 mL, 27.64 mmol) and the contents were stirred at the same temperature for 1 h. After, a pre-dissolved solution of compound 78 (5 g, 23.04 mmol) in THF (5 mL) was added and the resulting reaction mixture was slowly allowed to stir at room temperature for 16 h. After completion of the reaction (monitored by TLC), reaction mixture was quenched with saturated $NH_4Cl$ solution and extracted with ethyl acetate. The organic layer was collected, washed with brine, dried over anhydrous $Na_2SO_4$, filtered and concentrated under reduced pressure. The crude compound was purified by combi-flash chromatography using a gradient method of 40-70% EtOAc/Heptane to afford the title compound 79 (2.5 g, 42.37%) as a pale-yellow liquid. TLC: 30% EtOAc/Heptane ($R_f$ 0.4). $^1$H NMR (400 MHz, DMSO-$d_6$): δ 7.57 (s, 1H), 7.54 (d, J=8.8 Hz, 1H), 4.19-4.16 (m, 1H), 0.91-086 (m, 2H), 0.85-0.79 (m, 2H); LCMS Calculated for $C_{10}H_7BrFNO$: 256.07; Found: 256.1 (M+1).

Synthesis of methyl 4-cyano-3-cyclopropoxy-5-fluorobenzoate (80)

To an argon purged solution of Compound 79 (2.8 g, 10.93 mmol) in MeOH (70 mL) was added TEA (4.73 mL, 32.80 mmol), followed by $Pd(OAC)_2$ (0.122 g, 0.54 mmol) and 1,3-bis(diphenylphosphino)propane (0.45 g, 1.09 mmol). The reaction was purged again with argon for 15 min. After, the resulting reaction mixture was filled with CO (g) and the reaction was allowed to stir in a steel bomb at 80° C. for 16 h. The progress of the reaction was monitored by TLC. After completion, the reaction mixture was filtered through a pad of Celite and which was washed with ethyl acetate. The filtrate was concentrated under reduced pressure. The crude compound was purified by combi-flash chromatography using a gradient method of 10-40% EtOAc/Heptane to afford the title compound 80 (1.76 g, 68.71%) as a pale-yellow liquid. TLC: 50% EtOAc/Heptane ($R_f$ 0.4); $^1$H NMR (400 MHz, DMSO-$d_6$): δ 7.78 (s, 1H), 7.57 (d, J=9.2 Hz, 1H), 4.72-4.60 (m, 1H), 3.92 (s, 3H), 0.91 (d, J=5.2 Hz, 2H), 0.81 (s, 2H); LCMS Calculated for $C_{12}H_{10}FNO_3$: 235.21; Found: 236.40 (M+1).

Synthesis of 2-cyclopropoxy-6-fluoro-4-(hydroxymethyl)benzonitrile (81)

To a stirred solution of compound 80 (2 g, 8.50 mmol) in THF (20 mL) at room temperature was added LiBH4 (0.56 g, 25.50 mmol) and the resulting reaction mixture was stirred at 60° C. for 4 h. After completion (reaction monitored by TLC), the reaction mixture was quenched with ice water and extracted with ethyl acetate. The organic layer was collected, washed with brine, dried over anhydrous $Na_2SO_4$ and concentrated under reduced pressure to afford the title compound 81 (1.5 g, crude) as an off white solid. TLC: 30% EtOAc/Heptane ($R_f$ 0.35). $^1$H NMR (400 MHz, DMSO-$d_6$): δ 7.31 (s, 1H), 7.01 (d, J=10.0 Hz, 1H), 5.61-5.52 (m, 1H), 4.59 (d, J=5.2 Hz, 2H), 4.06 (s, 1H), 0.87 (d, J=6.0 Hz, 2H), 0.77 (s, 2H); LCMS Calculated for $C_{11}H_{10}FNO_2$: 207.20; Found: 208.2 (M+1).

Synthesis of 4-(bromomethyl)-2-cyclopropoxy-6-fluorobenzonitrile (82)

To a stirred solution of compound 81 (1.5 g, 7.23 mmol) in ACN (15 mL) at 0° C. was added $PPh_3$ (3.03 g, 11.58 mmol), followed by $Br_2$ (0.61 mL, 12.00 mmol) and the resulting reaction mixture was stirred at 60° C. for 3 h. After completion (reaction monitored by TLC), the mixture was quenched with ice water and extracted with ethyl acetate.

The organic layer was collected, washed with brine, dried over anhydrous $Na_2SO_4$ and concentrated under reduced pressure. The crude compound was purified by combi-flash chromatography using a gradient method of 20-30% EtOAc/Heptane to afford the title compound 82 (1.5 g, 76.9%) as an off white solid. TLC: 50% EtOAc/Heptane ($R_f$ 0.45). $^1H$ NMR (400 MHz, DMSO-$d_6$): δ 7.46 (s, 1H), 7.23 (d, J=10.0 Hz, 1H), 4.74 (s, 2H), 3.61-3.52 (m, 1H), 0.89 (d, J=6.0 Hz, 2H), 0.78 (s, 2H); LCMS Calculated for $C_{11}H_9BrFNO$: 270.10; Found: 269.7 (M−1).

Synthesis of tert-butyl ((1-(4-cyano-3-cyclopropoxy-5-fluorobenzyl)-1H-pyrazol-4-yl) methyl) carbamate (83)

To a stirred solution of compound 82 (1.5 g, 5.55 mmol) in 1,4-Dioxane (15 mL) at room temperature was added DIPEA (1.93 mL, 11.10 mmol), followed by tert-butyl ((1H-pyrazol-4-yl)methyl)carbamate (1.2 g, 6.10 mmol) and the resulting reaction mixture was heated at 60° C. for 16 h. After completion (reaction monitored by TLC), the reaction mixture was cooled to room temperature, water added and extracted with ethyl acetate. The organic layer was collected, washed with brine, dried over anhydrous $Na_2SO_4$ and concentrated under reduced pressure. The crude compound was purified by Combi-flash chromatography using a gradient method of 30-40% EtOAc/Heptane to afford the title compound 83 (1.25 g, 58.41%) as a yellow gummy-solid. TLC: 50% EtOAc/Heptane ($R_f$ 0.5). $^1H$ NMR (400 MHz, DMSO-$d_6$): δ 7.72 (s, 1H), 7.40 (s, 1H), 7.16-7.13 (m, 2H), 6.75 (d, J=10.0 Hz, 1H), 5.41 (s, 2H), 4.05 (s, 2H), 4.00-3.96 (m, 1H), 1.37 (s, 9H), 0.84 (d, J=5.6 Hz, 2H), 0.74 (s, 2H); LCMS Calculated for $C_{20}H_{23}FN_4O_3$: 386.43; Found: 387.43 (M+1).

Synthesis of tert-butyl ((1-((3-amino-4-cyclopropoxybenzo[d]isoxazol-6-yl)methyl)-1H-pyrazol-4-yl)methyl)carbamate (84)

To a stirred solution of compound 83 (1.1 g, 2.84 mmol) in a 6:1 mixture of DMF:$H_2O$ (7 mL) at room temperature was added N-hydroxy acetamide (0.64 g, 8.54 mmol) and followed by $K_2CO_3$ (1.97 g, 14.23 mmol). The reaction mixture was allowed to stir at 70° C. for 16 h. After completion of the reaction (monitored by TLC), the reaction mixture was cooled to room temperature, ice water added and extracted with ethyl acetate. The organic layer was collected, washed with brine, dried over anhydrous $Na_2SO_4$ and concentrated under reduced pressure. The crude compound was purified by Combi flash chromatography using a gradient method of 50-60% EtOAc/Heptane to afford the title compound 84 (0.90 g, 79.64%) as a brown semi-solid. TLC: 80% EtOAc/Heptane ($R_f$ 0.30). $^1H$ NMR (400 MHz, DMSO-$d_6$): δ 7.68 (s, 1H), 7.36 (s, 1H), 7.14 (br s, 1H), 6.85 (s, 1H), 6.71 (s, 1H), 5.82 (s, 2H), 5.37 (s, 2H), 4.05-4.00 (m, 1H), 3.96-3.92 (m, 2H), 1.36 (s, 9H), 0.81 (d, J=4.0 Hz, 4H); LCMS Calculated for $C_{20}H_{25}N_5O_4$: 399.45; Found: 400.02 (M+1).

Synthesis of tertbutyl((1((4cyclopropoxy3 ((2methoxyphenyl) sulfonamido) benzo[d]isoxazol-6-yl) methyl)-1H-pyrazol-4-yl)methyl)carbamate (85)

To a stirred solution of compound 84 (0.3 g, 0.75 mmol) in THF (5 mL) at 0° C. was added 1.0 M solution of KO$^t$Bu in THF (2.25 mL, 2.25 mmol) followed by 2-methoxybenzenesulfonyl chloride (0.31 g, 1.50 mmol) and the reaction was allowed to stir at room temperature for 16 h. After completion of the reaction (monitored by TLC), the mixture was diluted with ethyl acetate, water added and extracted. The organic layer was collected, washed with brine, dried over anhydrous $Na_2SO_4$ and concentrated under reduced pressure. The crude compound was purified by Combi flash column chromatography using a gradient method of 40-60% EtOAc/Heptane to afford the title compound 85 (0.180 g, 42.55%) as an off white solid. TLC: 70% EtOAc ($R_f$ 0.5). $^1H$ NMR (400 MHz, DMSO-$d_6$): δ 10.11 (s, 1H), 7.81-7.79 (d, J=6.8, Hz, 1H), 7.67 (s, 1H), 7.62 (br s, 2H), 7.36 (s, 1H), 7.18 (d, J=8.4 Hz, 2H), 7.10 (t, J=7.2 Hz, 1H), 6.94 (s, 1H), 6.88 (s, 1H), 5.41 (s, 2H), 3.96 (d, J=5.6 Hz, 2H), 3.67 (s, 3H), 1.36 (s, 9H), 0.78 (d, J=5.6 Hz, 2H), 0.63 (s, 2H); LCMS Calculated for $C_{27}H_{31}N_5O_7S$: 569.63; Found: 570.8 (M+1).

Synthesis of N-(4-cyclopropoxy-6-((4-(((2,2,2-trifluoroacetyl)-14-azaneyl)methyl)-1H-pyrazol-1-yl) methyl)benzo[d]isoxazol-3-yl)-2-methoxybenzenesulfonamide (86)

To a stirred solution of compound 85 (0.15 g, 0.26 mmol) in DCM (3 mL) at 0° C., TFA (0.2 mL, 2.63 mmol) was added and the reaction was allowed to stir at room temperature for 2 h. After completion of the reaction (monitored by TLC), the mixture was concentrated under reduced pressure to get the residue, which was washed with diethyl ether/heptane to afford the title compound 86 (0.1 g, 80.8%) as a brown gummy solid. TLC: 10% MeOH/DCM ($R_f$ 0.5). LCMS Calculated for $C_{22}H_{23}N_5O_5S$: 469.52; Found: 470.4 (M+1).

Synthesis of N-((1-((4-cyclopropoxy-3-((2-methoxyphenyl)sulfonamido)benzo[d]isoxazol-6-yl) methyl)-1H-pyrazol-4-yl)methyl)propiolamide To a stirred solution of compound 86 (100 mg, 0.21 mmol) in DMF (2 mL) at 0° C. was added DIPEA (0.1 mL, 0.63 mmol), followed by $T_3P$ (87 mg, 0.27 mmol) and the contents were allowed to stir at room temperature for 20 min. After that, a pre-dissolved solution of propiolic acid (17.6 mg, 0.25 mmol) in DMF (0.3 mL) was added in a drop-wise manner and the reaction was allowed to stir at room temperature for 4 h. After completion (reaction monitored by TLC), the reaction mixture was quenched with water and extracted with ethyl acetate. The organic layer was collected, washed with brine, dried over anhydrous $Na_2SO_4$ and concentrated under reduced pressure. The crude compound was purified by using prep. HPLC to afford the title compound (5 mg, 4.5%) as an off white solid. TLC: 10% MeOH/DCM ($R_f$ 0.5). (Analytical data in Table1).

Synthetic Example 44
Scheme 25: Synthesis of 2-methoxy-N-(4-methoxy-6-(((3aR,6aS)-5-propioloylhexahydropyrrolo[3,4-c]pyrrol-2-(1H)-yl)methyl)benzo[d]isoxazol-3-yl)benzenesulfonamide
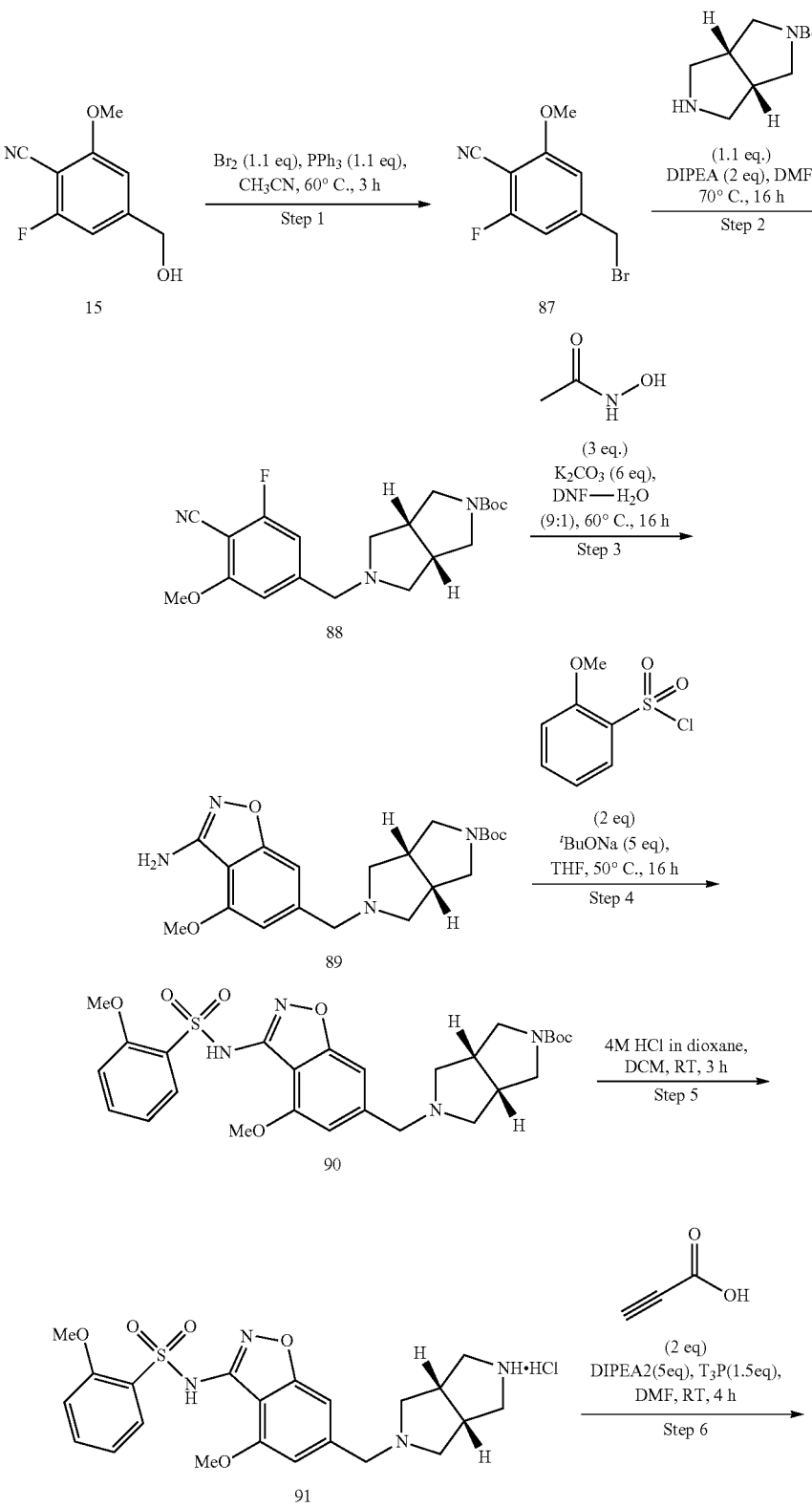

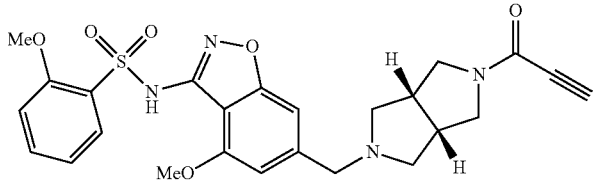

Syn. Ex. 44

Synthesis of 4-(bromomethyl)-2-fluoro-6-methoxybenzonitrile (87)

To a stirred solution of 2-fluoro-4-(hydroxymethyl)-6-methoxybenzonitrile 15 (3 g, 16.54 mmol) in ACN (15 mL) at 0° C. was added PPh$_3$ (6.94 g, 26.46 mmol) followed by Br$_2$ (1.34 mL, 26.46 mmol). The reaction was stirred at 60° C. for 3 h. After completion (monitored by TLC), the reaction mixture was quenched with ice water and extracted with ethyl acetate. The organic layer was washed with brine, dried over anhydrous Na$_2$SO$_4$ and concentrated under reduced pressure. The crude compound was purified by combi-flash chromatography using a gradient method of 20-30% EtOAc/Heptane to afford the title compound 87 (3 g, 74.62%) as a brown solid. TLC: 50% EtOAc/Heptane (Rf: 0.45). LCMS Calculated for C$_9$H$_7$BrFNO: 242.97; Found: 244.7 (M+2).

Synthesis of tert-butyl (3aR,6aS)-5-(4-cyano-3-fluoro-5-methoxybenzyl) hexahydropyrrolo[3,4-c] pyrrole-2(1H)-carboxylate (88)

To a stirred solution of 4-(bromomethyl)-2-fluoro-6-methoxybenzonitrile 87 (0.5 g, 2.048 mmol) in DMF (5 mL) at room temperature was added tert-butyl (3aR,6aS)-hexahydropyrrolo[3,4-c] pyrrole-2(1H)-carboxylate 87 (0.478 g, 2.25 mmol) followed by DIPEA (1.14 mL, 4.09 mmol). The reaction mixture was allowed to stir at 70° C. for 16 h. After completion f the reaction (monitored by TLC), the reaction mixture was cooled to room temperature, quenched with ice water and extracted with ethyl acetate. The organic layer was dried over anhydrous Na$_2$SO$_4$ and concentrated under reduced pressure to afford the title compound 88 (0.550 g, 71.52%) as an off-white solid. TLC: 90% EtOAc/Heptane (Rf: 0.40). 1H NMR is complicated and indicates a regioisomeric mixture. LCMS Calculated for C$_{20}$H$_{26}$FN$_3$O$_3$: 375.20; Found: 376.42 (M+1).

Synthesis of tert-butyl (3aR,6aS)-5-((3-amino-4-methoxybenzo[d]isoxazol-6-yl) methyl) hexahydropyrrolo[3,4-c] pyrrole-2(1H)-carboxylate (89)

To a stirred solution of compound of tert-butyl (3aR,6aS)-5-(4-cyano-3-fluoro-5-methoxybenzyl) hexahydropyrrolo[3,4-c] pyrrole-2(1H)-carboxylate 88 (0.85 g, 2.26 mmol) in a mixture of DMF:H$_2$O (20 mL, 18:2) at room temperature was added N-hydroxy acetamide (0.4 g, 6.79 mmol) and followed by K$_2$CO$_3$ (1.87 g, 13.56 mmol). The reaction mixture was allowed to stir at 60° C. for 16 h. After completion of the reaction (monitored by TLC), the reaction mixture was cooled to room temperature, quenched with water and extracted with ethyl acetate. The organic layer was washed with brine, dried over anhydrous Na$_2$SO$_4$ and concentrated under reduced pressure. The crude compound was purified by combi flash chromatography (230-400 mesh silica) using a gradient method of 1-5% MeOH in DCM to afford the title compound 89 (800 mg, 92%) as a brown semi-solid. TLC: 5% MeOH/DCM (Rf: 0.40). LCMS Calculated for C$_{20}$H$_{28}$N$_4$O$_4$: 388.21; Found: 389.4 (M+1).

Synthesis of tert-butyl (3aR,6aS)-5-((4-methoxy-3-((2-methoxyphenyl) sulfonamido) benzo[d]isoxazol-6-yl) methyl) hexahydropyrrolo[3,4-c] pyrrole-2 (1H)-carboxylate (90)

To a stirred solution of tert-butyl (3aR,6aS)-5-((3-amino-4-methoxybenzo[d]isoxazol-6-yl) methyl) hexahydropyrrolo[3,4-c] pyrrole-2(1H)-carboxylate 89 (0.15 g, 0.386 mmol) in THF (1.5 mL) at the room temperature was added tBuONa (0.186 g, 1.93 mmol) and stirred for 15 min. followed by addition of 3-methoxybenzenesulfonyl chloride (0.159 g, 0.772 mmol). The reaction was allowed to stir at 50° C. for 16 h. After completion of the reaction (monitored by TLC), the reaction mixture was concentrated under reduced pressure. The crude compound was purified by over combi flash chromatography using a gradient of 5% Methanol/DCM/Heptane to afford the title compound 90 (0.2 g, 93.02%) as a pale-yellow solid. TLC: EtOAc/Heptane (Rf: 0.50). LCMS Calculated for C$_{27}$H$_{34}$N$_4$O$_7$S: 558.21; Found: 559.02 (M+1).

Synthesis of N-(6-(((3aR,6aS)-hexahydropyrrolo[3,4-c] pyrrol-2(1H)-yl) methyl)-4-methoxybenzo[d]isoxazol-3-yl)-2-methoxybenzenesulfonamide hydrochloride (91)

To a stirred solution of tert-butyl (3aR,6aS)-5-((4-methoxy-3-((2-methoxyphenyl) sulfonamido) benzo[d] isoxazol-6-yl) methyl) hexahydropyrrolo[3,4-c] pyrrole-2 (1H)-carboxylate 90 (0.8 g, 1.43 mmol) in DCM (5 mL) at 0° C. was added 4M HCl in 1,4-dioxane (5 mL). The reaction was allowed to stir at the room temperature for 3 h. After completion of the reaction (monitored by TLC), the reaction mixture was concentrated under reduced pressure to afford the title compound 91 (0.690 g, 97.45%, HCl salt) as an off-white solid. TLC: 10% MeOH/DCM (Rf: 0.5). LCMS Calculated for C$_{22}$H$_{27}$ClN$_4$O$_5$S: 494.14; Found: NA (M+1). Salt was taken forward for the next step without any further purification.

Synthesis of 2-methoxy-N-(4-methoxy-6-(((3aR,6aS)-5-propioloylhexahydropyrrolo[3,4-c]pyrrol-2 (1H)-yl)methyl)benzo[d]isoxazol-3-yl)benzenesulfonamide To a stirred solution of N-(6-(((3aR,6aS)-hexahydropyrrolo[3,4-c] pyrrol-2(1H)-yl) methyl)-4-methoxybenzo[d] isoxazol-3-yl)-2-methoxybenzenesulfonamide hydrochloride 91 (0.2 g, 0.404 mmol) in DMF (1 mL) at 0° C. was added DIPEA (0.176 mL, 1.01 mmol), T₃P (0.192 g, 0.606 mmol) followed by propiolic acid (56 mg, 0.808 mmol). The reaction was allowed to stir at the room temperature for 4 h. After completion (reaction monitored by TLC), the reaction mixture was concentrated under reduced pressure to get brown gummy solid. The crude was purified through combi-flash chromatography using gradient 5%-10% to get compound which is further purified by prep HPLC to afford the title compound (55 mg, 26.6%) as an off-white solid. TLC: 10% MeOH/DCM (Rf: 0.40). (See Table 1 for analytical data).

Synthetic Example 45

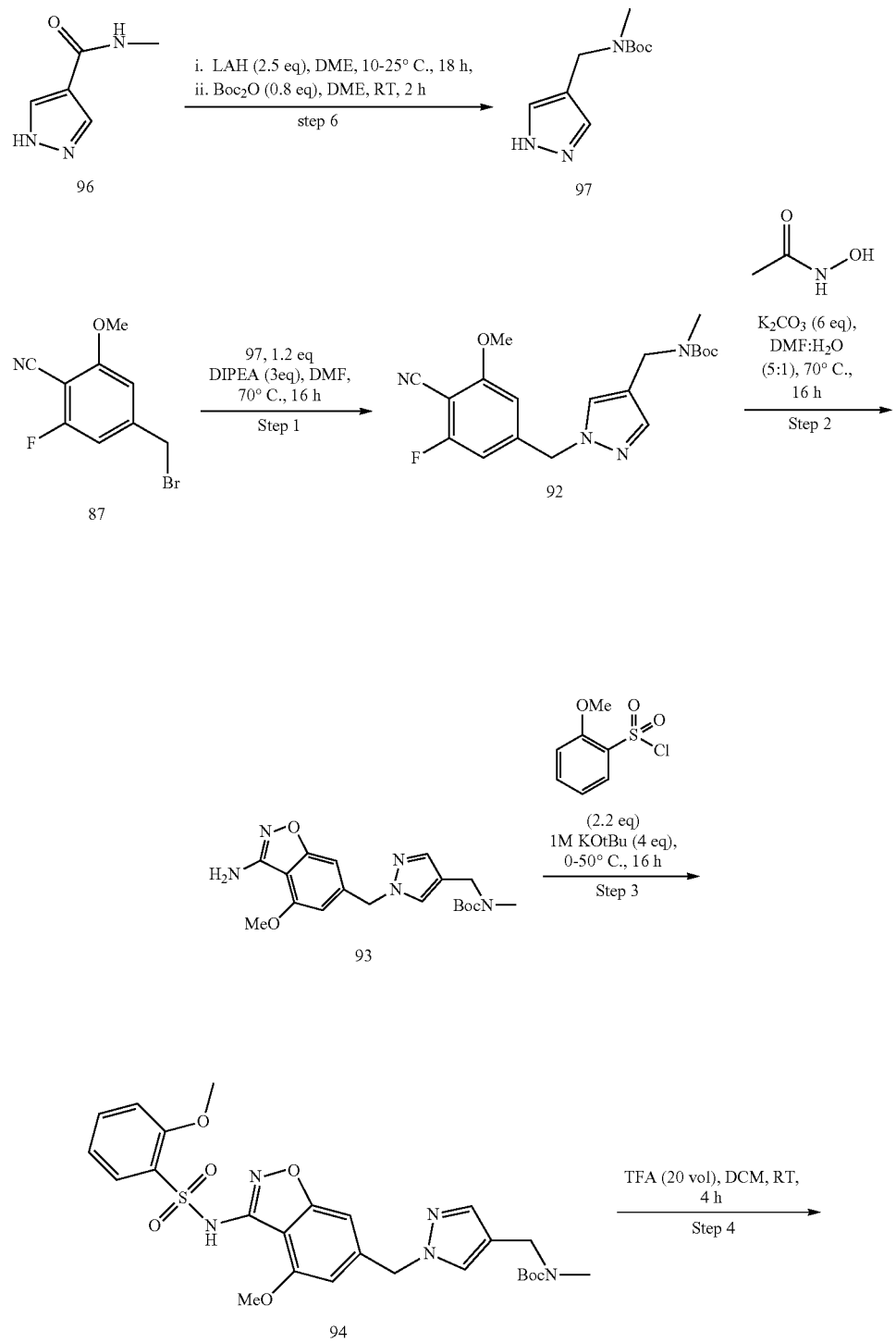

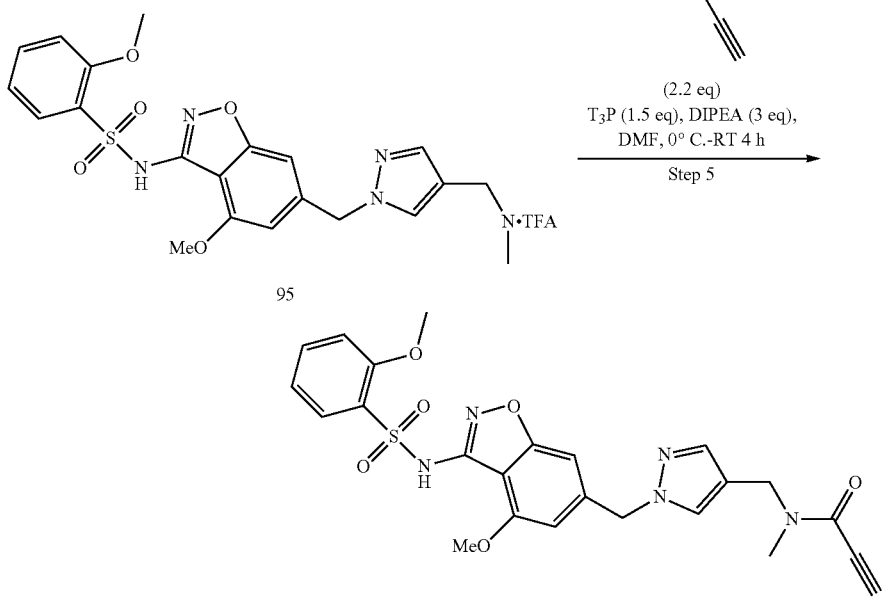

Syn. Ex. 45

Synthesis of tert-butyl ((1-(4-cyano-3-fluoro-5-methoxybenzyl)-1H-pyrazol-4-yl)methyl)(methyl)carbamate (92)

To a stirred solution of 4-(bromomethyl)-2-fluoro-6-methoxybenzonitrile 87 (1.2 g, 4.916 mmol) in DMF (12 mL) at room temperature was added DIPEA (2.57 mL, 14.75 mmol) and allowed to stir for 10 min. followed by addition tert-butyl ((1H-pyrazol-4-yl) methyl) (methyl) carbamate 97 (1.2 g, 5.89 mmol). The reaction mixture was stirred at 70° C. for 16 h. After completion of the reaction (monitored by TLC), the reaction mixture was diluted with water and extracted with ethyl acetate. The organic layer was washed with brine, dried over anhydrous $Na_2SO_4$ and concentrated under reduced pressure. The crude compound was purified by combi-flash chromatography (100-200 mesh) using gradient method of 0-50% EtOAc/Heptane to offer the title compound 92 (0.6 g, 33.33%) as a gummy Solid. TLC: 50% EtOAc/Heptane ($R_f$: 0.30) LCMS Calculated for $C_{19}H_{23}FN_4O_3$: 374.18; Found: 375.3.

Synthesis of tert-butyl ((1-((3-amino-4-methoxybenzo[d]isoxazol-6-yl) methyl)-1H-pyrazol-4-yl) methyl) (methyl)carbamate (93)

To a stirred solution of tert-butyl ((1-(4-cyano-3-fluoro-5-methoxybenzyl)-1H-pyrazol-4-yl) methyl) (methyl) carbamate 92 (0.5 g, 1.33 mmol) in solution of $DMF:H_2O$ (5 mL, 5:1) at room temperature was added N-hydroxyl acetamide (0.35 g, 3.99 mmol) and $K_2CO_3$ (1.1 g, 7.98 mmol). The reaction mixture was allowed to stir at 70° C. for 16 h. After completion of the reaction (monitored by TLC), the reaction mixture was cooled to room temperature, diluted with water and ethyl acetate, and extracted with ethyl acetate. The organic layer was dried over anhydrous $Na_2SO_4$ and concentrated under reduced pressure to afford the tert-butyl ((1-((3-amino-4-methoxybenzo[d]isoxazol-6-yl) methyl)-1H-pyrazol-4-yl) methyl) (methyl)carbamate 93 (0.4 g, 77.36%) as a brown semi-solid. TLC: 50% EtOAc/Heptane (Rf: 0.20). LCMS Calculated for $C_{19}H_{25}N_5O_4$: 387.19; Found: 388.4 (M+1).

Synthesis of tert-butyl ((1-((4-methoxy-3-((2-methoxyphenyl) sulfonamido) benzo[d]isoxazol-6-yl) methyl)-1H-pyrazol-4-yl) methyl) (methyl)carbamate (94)

To a stirred solution of tert-butyl ((1-((3-amino-4-methoxybenzo[d]isoxazol-6-yl) methyl)-1H-pyrazol-4-yl) methyl) (methyl)carbamate 93 (0.33 g, 0.851 mmol) in THF (3 mL) at 0° C. was added 1.0 M solution of KOtBu (3.4 mL, 3.406 mmol) in THF followed by 2-methoxybenzenesulfonyl chloride (386 mg, 1.87 mmol). The reaction was allowed to stir at room temperature for 16 h. After completion of the reaction (monitored by TLC), the reaction mixture was quenched with water and extracted with ethyl acetate. The organic layer was dried over anhydrous $Na_2SO_4$ and concentrated under reduced pressure. The crude compound was purified by Combi flash (100-200 mesh) column chromatography using a gradient method of 100% EtOAc/Heptane to afford the title compound 94 (0.130 g, 27.42%) as an off-white solid. TLC: 70% EtOAc (Rf: 0.5). LCMS Calculated for C26H31N5O7S: 557.19; Found: 558.5 (M+1).

2,2,2-trifluoro-N-((1-((4-methoxy-3-((2-methoxyphenyl) sulfonamido) benzo[d]isoxazol-6-yl) methyl)-1H-pyrazol-4-yl) methyl)-N-methylacetamide (95)

To a stirred solution of tert-butyl ((1-((4-methoxy-3-((2-methoxyphenyl) sulfonamido) benzo[d]isoxazol-6-yl) methyl)-1H-pyrazol-4-yl) methyl) (methyl)carbamate 94 (13 mg, 0.233 mmol) in DCM (5 mL) at 0° C., was added TFA (0.52 mL). The reaction was allowed to stirred at the room temperature for 4 h. After completion of the reaction (monitored by TLC), the reaction mixture was concentrated under reduced pressure to afford the title compound 95 (100 mg, 94%) as a brown gummy solid. TLC: 10% MeOH/DCM (Rf: 0.5). LCMS Calculated for C23H22F3N5O6S: 553.12; Found: 458.0 (M+1). This was taken forward for the next step without any further purification.

Synthesis of N-((1-((4-methoxy-3-((2-methoxyphenyl) sulfonamido) benzo[d]isoxazol-6-yl) methyl)-1H-pyrazol-4-yl) methyl)-N-methylpropiolamide To a stirred solution of 2,2,2-trifluoro-N-((1-((4-methoxy-3-((2-methoxyphenyl) sulfonamido) benzo[d]isoxazol-6-yl) methyl)-1H-pyrazol-4-yl) methyl)-N-methylacetamide 95 (90 mg, 0.162 mmol) in DMF (1 mL) at 0° C. was added DIPEA (0.08 mL, 0.487 mmol), T$_3$P 50% solution in EtOAc (77 mg, 0.243 mmol). The reaction was allowed to stir at the room temperature for 15 min. After that, a pre-dissolved solution of propiolic acid (13.6 mg, 0.194 mmol) in DMF (0.5 mL) was added dropwise. The reaction was allowed to stir at the room temperature for 4 h. After completion (monitored by TLC), the reaction mixture was quenched with water and extracted with ethyl acetate. The organic layer was dried over anhydrous Na$_2$SO$_4$ and concentrated under reduced pressure. The crude compound was purified by using prep HPLC to afford the title compound (39 mg, 85%) as an off-white solid. TLC: 10% MeOH/DCM (Rf: 0.5). (See analytical data for Table 1). TLC: 10% MeOH/DCM (Rf: 0.4). LCMS Calculated for C$_{24}$H$_{23}$N$_5$O$_6$S: 509.14; Found: 510.1 (M+1) (See Table 1 for analytical data).

Synthesis of tert-butyl ((1H-pyrazol-4-yl)methyl) (methyl)carbamate (97)

To a stirred solution of N-methyl-1H-pyrazole-4-carboxamide 96 (2 g, 15.98 mmol) in DMF (10 mL) at −10° C. was added LAH (1.5 g, 39.95 mmol). The reaction was allowed to stir at the 80° C. for 16 h. After completion of reaction (monitored by TLC), the reaction mixture was quenched with 20% NaOH (100 mL) and diluted with DCM (20 mL). The organic layer was collected and (Boc)$_2$O (2.78 mL, 12.78 mmol) was added dropwise and the mixture was stirred at room temperature for 2 h. After completion of reaction (monitored by TLC) the mixture was concentrated under reduced pressure. The crude compound was purified by Combi flash chromatography (230-400 mesh) to afford the title compound 97 (1.2 g, 35.6%) TLC: 20% EA/Heptane (Rf: 0.3). LCMS Calculated for C$_{10}$H$_{17}$N$_3$O$_2$: 211.13; Found: 212.60 (M+1).

Synthetic Example 46

Scheme 27: Synthesis of -(N-(4-methoxy-6-((4-(propiolamidomethyl)-1H-pyrazol-1-yl) methyl) benzo[d]isoxazol-3-yl) sulfamoyl)-N-methylbenzamide

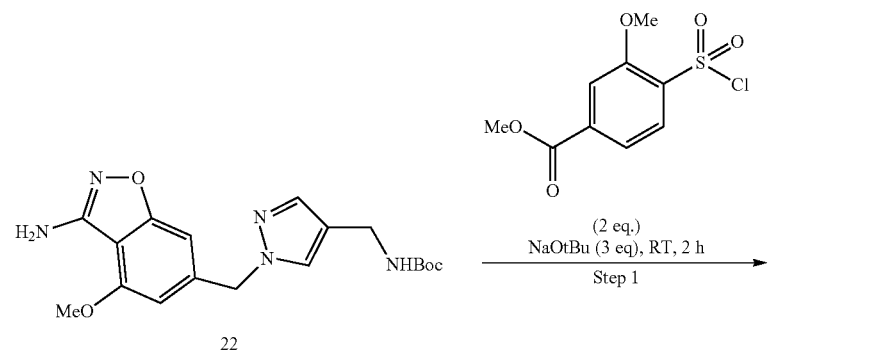

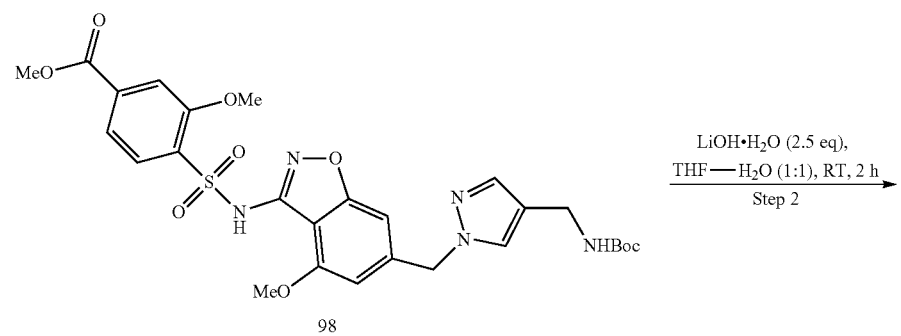

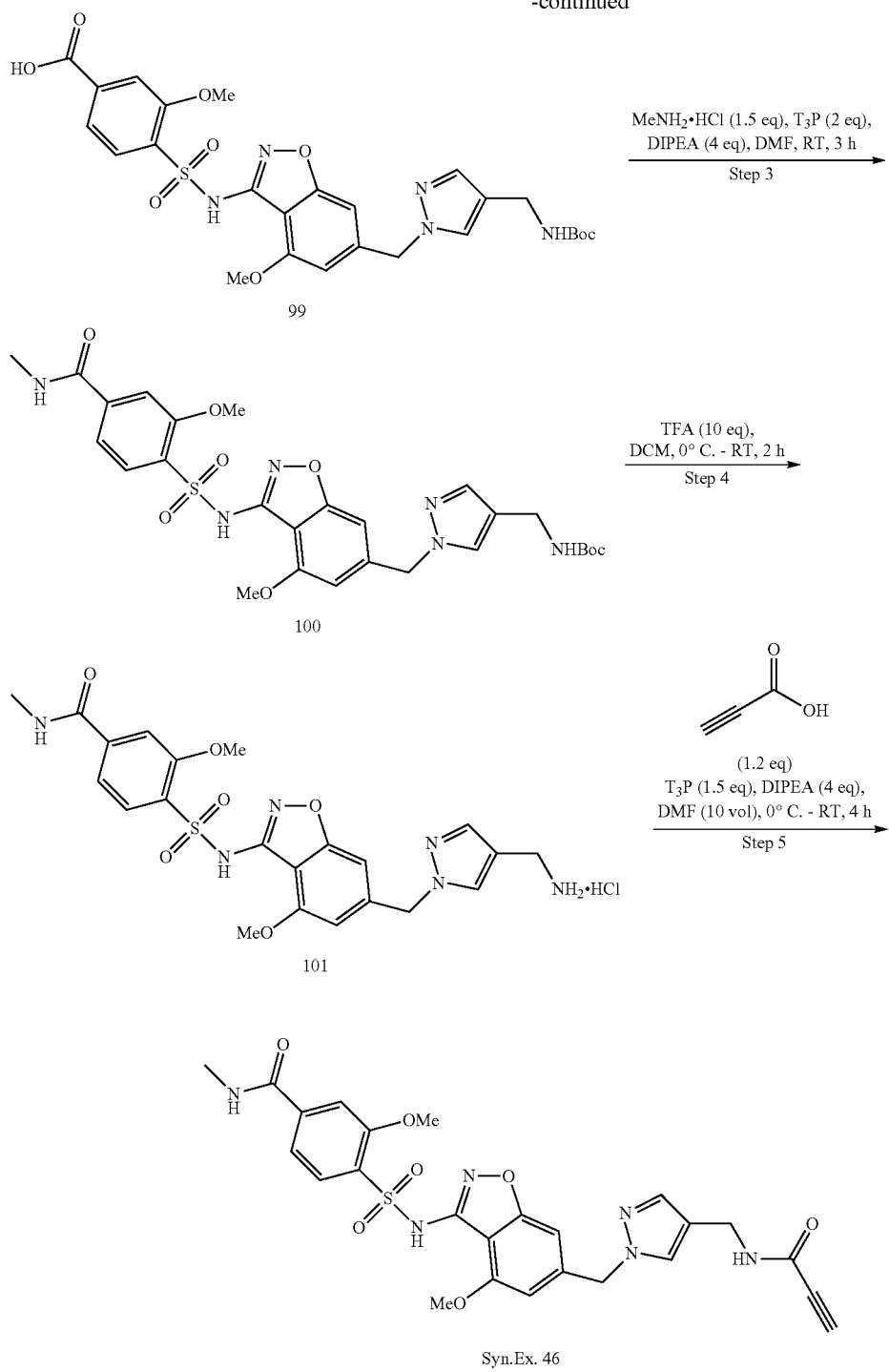

Methyl 4-(N-(6-((4-(((tert-butoxycarbonyl) amino) methyl)-1H-pyrazol-1-yl) methyl)-4-methoxybenzo[d]isoxazol-3-yl) sulfamoyl)-3-methoxybenzoate (98)

To a stirred solution of tert-butyl (((1-((3-amino-4-methoxybenzo[d]isoxazol-6-yl)methyl)-1H-pyrazol-4-yl)methyl)carbamate 22 (200 mg, 0.535 mmol) in THF (3 mL) was added NaOtBu (154 mg, 1.605 mmol) followed by methyl 4-(chlorosulfonyl)-3-methoxybenzoate (283 mg, 1.07 mmol). The reaction mixture was allowed to stir at the room temperature for 2 h. After completion (monitored by TLC), the reaction mixture was quenched with ice water then extracted with ethyl acetate. The organic layer was dried over anhydrous $Na_2SO_4$ and concentrated under reduced pressure. The crude compound was purified by combi flash chromatography (neutral alumina) to afford the title compound 98 (92 mg, 28.57%), yellow solid. TLC: 100 EtOAc (Rf: 0.6). LCMS Calculated for C27H31N5O9S: 601.18; Found: 602.5 (M+1).

Synthesis of 4-(N-(6-((4-(((tert-butoxycarbonyl) amino)methyl)-1H-pyrazol-1-yl)methyl)-4-methoxy-benzo[d]isoxazol-3-yl)sulfamoyl)-3-methoxybenzoic acid (99)

To a stirred solution of methyl 4-(N-(6-((4-(((tert-butoxycarbonyl)amino)methyl)-1H-pyrazol-1-yl)methyl)-4-methoxybenzo[d]isoxazol-3-yl)sulfamoyl)-3-methoxybenzoate 98 (80 mg, 0.132 mmol) in solution of THF-H₂O (1.6 mL, 1:1) was added LiOH·H₂O (13.96 mg, 0.332 mmol). The reaction mixture was stirred at the room temperature for 2 h. After completion (reaction monitored by TLC), the reaction mixture was diluted with water and washed with ethyl acetate. The aqueous layer was neutralized with 1N HCl (pH=5) and extracted with 10% MeOH/DCM. The organic layer was washed with brine, dried over anhydrous Na₂SO₄ and concentrated under reduced pressure to afford the crude title compound 99 (70 mg, 89.74%) as a gummy solid. TLC: 10% MeOH/DCM (Rf: 0.2) LCMS Calculated for C26H29N5O9S: 587.17; Found: 589.08 (M+1).

Synthesis of tert-butyl ((1-((4-methoxy-3-((2-methoxy-4-(methylcarbamoyl) phenyl) sulfonamido)benzo[d]isoxazol-6-yl)methyl)-1H-pyrazol-4-yl)methyl)carbamate (100)

To a stirred solution of 4-(N-(6-((4-(((tert-butoxycarbonyl) amino) methyl)-1H-pyrazol-1-yl) methyl)-4-methoxybenzo[d]isoxazol-3-yl) sulfamoyl)-3-methoxybenzoic acid 99 (60 mg, 0.1021 mmol) in DMF (2 mL) at 0° C. was added methylamine hydrochloride (10.34 mg, 0.153 mmol), DIPEA (0.071 mL, 0.408 mmol), followed by T₃P 50% solution in EtOAc (0.129 mL, 0.204 mmol). The reaction was allowed to stir at the room temperature for 3 h. After completion (reaction monitored by TLC), the reaction mixture was quenched with ice-water and extracted with ethyl acetate. The organic layer was dried over anhydrous Na₂SO₄, concentrated under reduced pressure to afford the crude compound 100 (70 mg, crude) as a white solid. TLC: 10% MeOH/DCM (Rf: 0.5). LCMS Calculated for C27H32N6O8S: 600.20; Found: 601.8 (M+1) The crude compound used for next reaction without any purification.

Synthesis of 4-(N-(6-((4-(aminomethyl)-1H-pyrazol-1-yl) methyl)-4-methoxybenzo[d]isoxazol-3-yl) sulfamoyl)-3-methoxy-N-methylbenzamide hydrochloride (101)

To a stirred solution of tert-butyl ((1-((4-methoxy-3-((2-methoxy-4-(methylcarbamoyl) phenyl) sulfonamido) benzo[d]isoxazol-6-yl) methyl)-1H-pyrazol-4-yl) methyl) carbamate 100 (70 mg, 0.1165 mmol) in DCM (1 mL) at 0° C. was added TFA (0.094 mL, 1.165 mmol). The reaction was allowed to stir at the room temperature for 2 h. After completion (reaction monitored by TLC), the reaction mixture was concentrated under reduced pressure and co distilled with toluene to afford the title compound 101 (72 mg, crude) as a brown oil. TLC: 10% MeOH/DCM (Rf: 0.3). LCMS Calculated for C22H25ClN6O6S: 536.12: Found: 501.50 (M+1).

Synthesis of 3-methoxy-4-(N-(4-methoxy-6-((4-(propiolamidomethyl)-1H-pyrazol-1-yl) methyl) benzo[d]isoxazol-3-yl) sulfamoyl)-N-methylbenzamide To a stirred solution of 4-(N-(6-((4-(aminomethyl)-1H-pyrazol-1-yl)methyl)-4-methoxybenzo[d]isoxazol-3-yl)sulfamoyl)-3-methoxy-N-methylbenzamide hydrochloride 101 (50 mg, 0.093 mmol) in DMF (1 mL) at 0° C. was added propiolic acid (7.8 mg, 0.111 mmol) followed by DIPEA (0.064 mL, 0.372 mmol). The reaction was allowed to stir at the room temperature for 10 min and T₃P (44 mg, 0.139 mmol) was added. The reaction was allowed to stir at the room temperature for 3 h. After completion (monitored by TLC), the reaction mixture was quenched with ice water and extracted with ethyl acetate. The organic layer was dried over anhydrous Na₂SO₄ and concentrated under reduced pressure. The crude compound was purified by using prep HPLC to afford the title compound (7 mg, 13.7%) as an off-white solid, TLC: 10% MeOH/DCM (Rf: 05). (See Table 1 for analytical data)

Synthetic Example 47

Scheme 28: Synthesis of N-((1-((4-methoxy-3-((2-methoxyphenyl) sulfonamido) benzo[d]isoxazol-6-yl)methyl)-1H-pyrazol-4-yl)methyl)-N-methylacrylamide

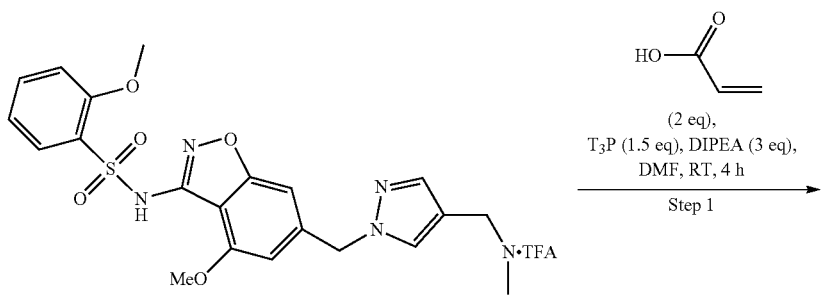

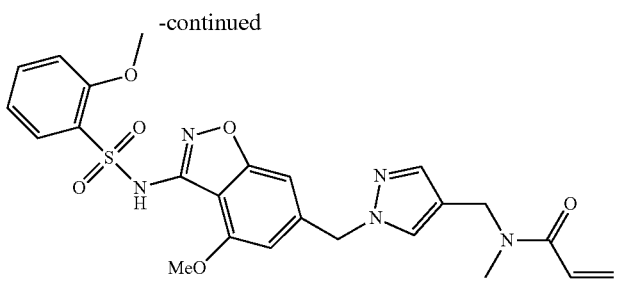

Syn. Ex. 47

Synthesis of N-((1-((4-methoxy-3-((2-methoxyphenyl) sulfonamido) benzo[d]isoxazol-6-yl)methyl)-1H-pyrazol-4-yl)methyl)-N-methylacrylamide To a stirred solution of 2-methoxy-N-(4-methoxy-6-((4-((methyl(2,2,2-trifluoroacetyl)-14-azaneyl)methyl)-1H-pyrazol-1-yl)methyl)benzo[d]isoxazol-3-yl)benzenesulfonamide 95 (0.100 g, 0.180 mmol) in DMF (1 mL) at 0° C. was added DIPEA (0.094 mL, 0.54 mmol) and T₃P 50% solution in EtOAc (0.114 mL, 0.270 mmol). The reaction was allowed to stir at the room temperature for 10 min. followed by addition of a pre-dissolved solution of acrylic acid (25 mg, 0.360 mmol) in DMF (0.3 mL) dropwise. The reaction was allowed to stir at the room temperature for 4 h. After completion (reaction monitored by TLC), the reaction mixture was concentrated under reduced pressure. The crude compound was purified by using prep HPLC to afford the title compound (32 mg, 34.78%) as an off-white solid. TLC: 10% MeOH/DCM (Rf: 0.5). (See analytical data for Table 1)

Synthetic Example 48

Scheme 29: Synthesis of N-(1-((4-methoxy-3-((2-methoxyphenyl)sulfonamido)benzo[d]isoxazol-6-yl)methyl)pyrrolidin-3-yl)propiolamide

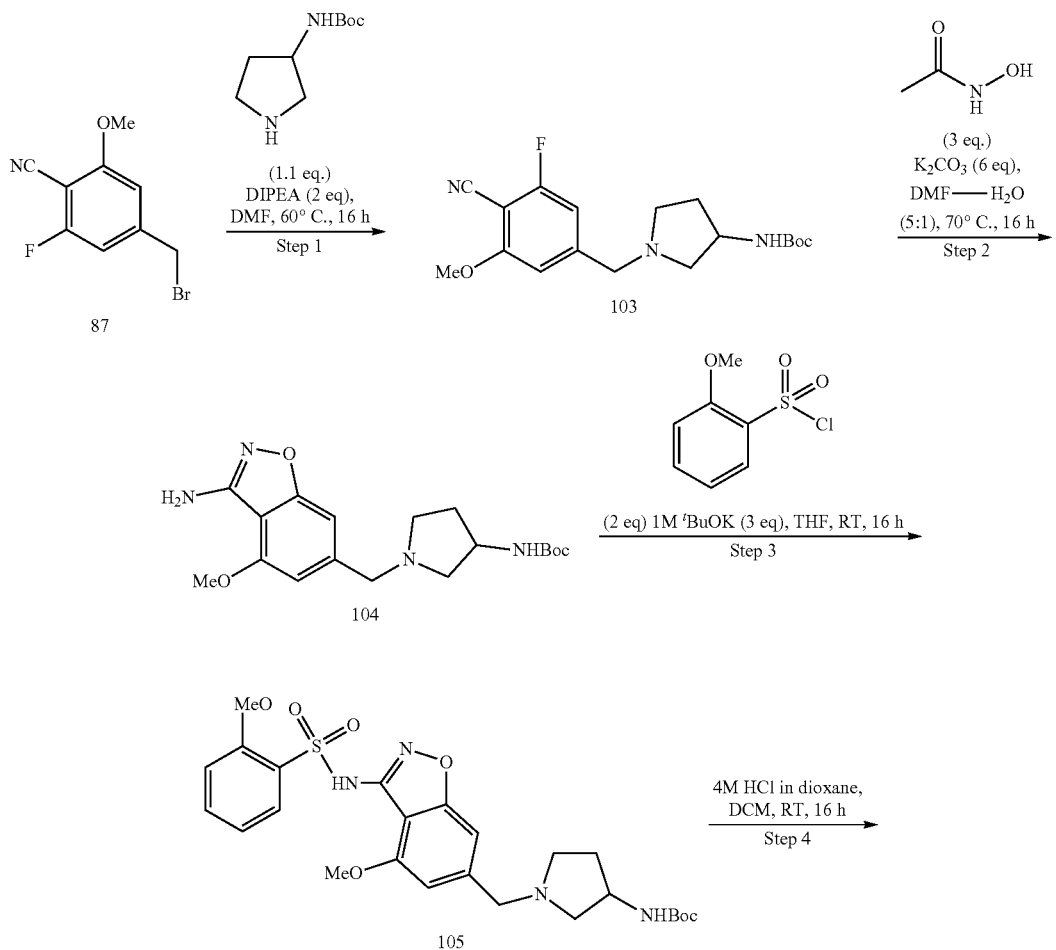

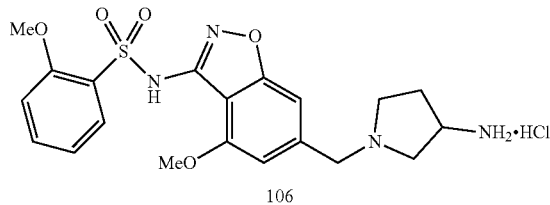
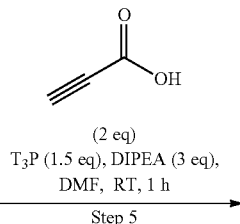
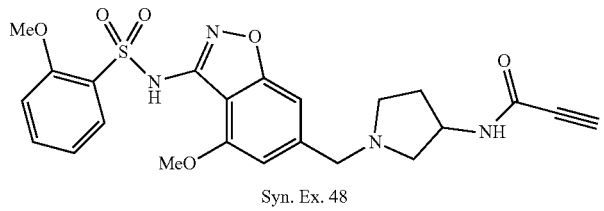

Syn. Ex. 48

Synthesis of tert-butyl (1-(4-cyano-3-fluoro-5-methoxybenzyl)pyrrolidin-3-yl)carbamate (103)

To a stirred solution of 4-(bromomethyl)-2-fluoro-6-methoxybenzonitrile 87 (1.5 g, 6.14 mmol) in DMF (10 mL) at room temperature was added DIPEA (2.14 mL, 12.28 mmol), followed by tert-butyl pyrrolidin-3-ylcarbamate (1.25 g, 6.76 mmol). The reaction was heated at 60° C. for 16 h. After completion (monitored by TLC), the reaction mixture was cooled to room temperature, ice cold water added and extracted with ethyl acetate. The organic layer was washed with brine, dried over anhydrous $Na_2SO_4$ and concentrated under reduced pressure to afford the title compound 103 (1g, 46.72%) as a yellow solid. TLC: 100% EtOAc (Rf: 0.5). LCMS Calculated for $C18H24FN3O3$: 349.18; Found: 350.4 (M+1).

Synthesis of tert-butyl (1-((3-amino-4-methoxybenzo[d]isoxazol-6-yl)methyl)pyrrolidin-3-yl)carbamate (104)

To a stirred solution of tert-butyl (1-(4-cyano-3-fluoro-5-methoxybenzyl) pyrrolidin-3-yl) carbamate 103 (1 g, 2.86 mmol) in $DMF:H_2O$ (7 mL, 6:1) at room temperature was added N-hydroxy acetamide (0.644 g, 8.59 mmol) and followed by $K_2CO_3$ (2.37 g, 17.16 mmol). The reaction mixture was allowed to stir at 70° C. for 16 h. After completion (monitored by TLC), the reaction mixture was poured on ice water and extracted with ethyl acetate. The organic layer was washed with brine, dried over anhydrous $Na_2SO_4$ and concentrated under reduced pressure. The crude compound was purified by Combi flash chromatography using a gradient method of 70% EtOAc/heptane to afford the title compound 104 (600 mg, 58.25%) as a brown semi-solid. TLC: 100% EtOAc (Rf: 0.50); LCMS Calculated for $C18H26N4O4$: 362.20; Found: 363.02 (M+1).

Synthesis of tert-butyl (1-((4-methoxy-3-((2-methoxyphenyl) sulfonamido) benzo[d]isoxazol-6-yl) methyl) pyrrolidin-3-yl) carbamate (105)

To a stirred solution of tert-butyl (1-((3-amino-4-methoxybenzo[d]isoxazol-6-yl) methyl) pyrrolidin-3-yl)carbamate 104 (0.6 g, 1.65 mmol) in THF (6 mL) at 0° C. was added KOtBu 1M solution in THF (5.0 mL, 4.96 mmol) followed by 3-methoxybenzenesulfonyl chloride (0.681 g, 3.31 mmol). The reaction was allowed to stir at room temperature for 16 h. After completion (monitored by TLC), the reaction mixture was quenched with saturated ammonium chloride solution and extracted with ethyl acetate. The combined organic layer was dried over anhydrous $Na_2SO_4$, filtered and concentrated under reduced pressure. The crude compound was purified by using combi flash chromatography (230-400 mesh) using a gradient of 70-80% ethyl acetate/heptane to afford the title compound 105 (300 mg, 34.09%) as a white solid. TLC: 10% MeOH/DCM (Rf: 0.5); LCMS Calculated for $C25H32N4O7S$: 532.20: Found: 533.02 (M+1).

Synthesis of N-(6-((3-aminopyrrolidin-1-yl)methyl)-4-methoxybenzo[d]isoxazol-3-yl)-2-methoxybenzenesulfonamide hydrochloride (106)

To a stirred solution of tert-butyl (1-((4-methoxy-3-((2-methoxyphenyl) sulfonamido) benzo[d]isoxazol-6-yl) methyl) pyrrolidin-3-yl) carbamate 105 (0.3 g, 0.563 mmol) in DCM (3 mL) at 0° C. was added 4M HCl in 1,4-Dioxane (3 mL). The reaction was allowed to stir at the room temperature for 2 h. After completion (monitored by TLC), the reaction mixture was concentrated under reduced pressure. The crude product was washed with diethyl ether and heptane to afford the title compound 106 (250 mg, salt) as a pale brown semi solid. TLC: 10% MeOH/DCM (Rf: 0.5). LCMS Calculated for $C_{22}H_{24}F_3N_4O_6S$: 529.14; Found: 432.08 (Freebase+1).

Synthesis of N-(1-((4-methoxy-3-((2-methoxyphenyl)sulfonamido)benzo[d]isoxazol-6-yl)methyl)pyrrolidin-3-yl)propiolamide To a stirred solution of N-(6-((3-aminopyrrolidin-1-yl) methyl)-4-methoxybenzo[d]isoxazol-3-yl)-2-methoxybenzenesulfonamide hydrochloride 106 (35 mg, 0.066 mmol) in DMF (1 mL) at 0° C. was added DIPEA (0.034 mL, 0.198 mmol), $T_3P$ 50% solution in EtOAc (0.062 mL, 0.099 mmol) followed by propiolic acid (9.2 mg, 0.132 mmol). The reaction was allowed to stir at the room temperature for 1 h. After completion (reaction monitored by TLC), the reaction mixture was concentrated under reduced pressure, quenched with ice water, and extracted with ethyl acetate. The organic layer was washed with brine, dried over anhydrous Na$_2$SO$_4$, and concentrated under reduced pressure. The crude was purified by prep HPLC to afford the title compound (5 mg, 15.62%) as an off-white solid. TLC: 5% MeOH/DCM (R$_f$ 0.6). (See Table 1 for analytical data).

Synthetic Example 49

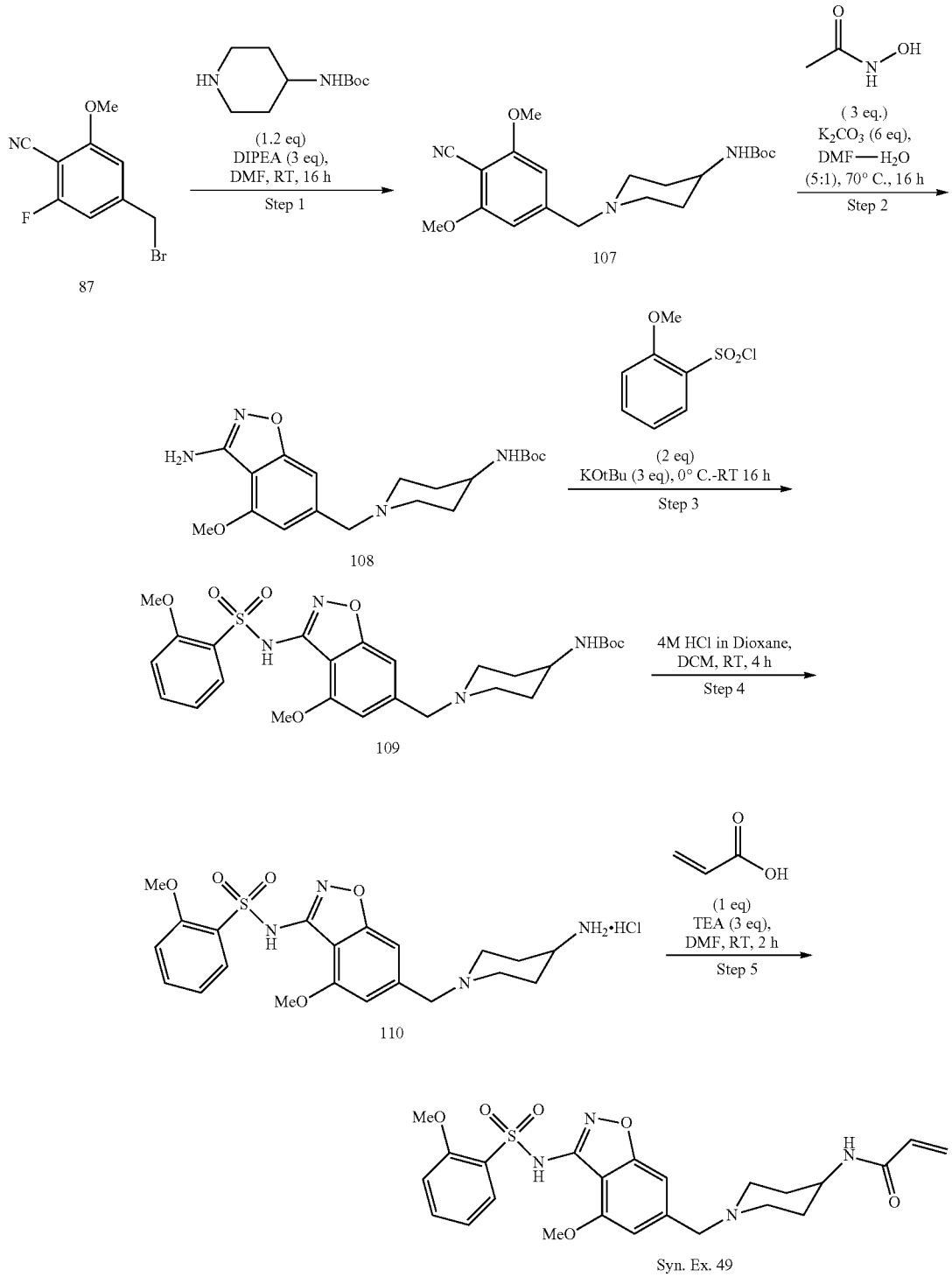

Synthesis of tert-butyl (1-(4-cyano-3-fluoro-5-methoxybenzyl)piperidin-4-yl)carbamate (107)

To a stirred solution of 4-(bromomethyl)-2-fluoro-6-methoxybenzonitrile 87 (1 g, 4.09 mmol) in DMF (10 mL) at 0° C. was added tert-butyl piperidin-4-ylcarbamate (0.984 g, 4.915) and DIPEA (2.14 mL, 12.27 mmol). The reaction mixture was allowed to stir at the room temperature for 16 h. After completion (monitored by TLC), the reaction mixture was quenched with ice cold water and extracted with ethyl acetate. The organic layer was washed with brine, dried over anhydrous $Na_2SO_4$, and concentrated under reduced pressure. The crude compound was purified by using combi flash chromatography using a gradient method of 20-40% EtOAc/Heptane to afford the title compound 107 (850 mg, 57.43%) as a pale-yellow solid. TLC: 70% EtOAc/Pentane (Rf: 0.4): LCMS Calculated for $C19H26FN3O3$: 363.20; Found: 364.0 (M+1).

Synthesis of tert-butyl (1-((3-amino-4-methoxybenzo[d]isoxazol-6-yl) methyl)piperidin-4-yl)carbamate (108)

To a stirred solution of compound tert-butyl (1-(4-cyano-3-fluoro-5-methoxybenzyl) piperidin-4-yl) carbamate 107 (0.3 g, 0.825 mmol) in solution of $DMF:H_2O$ (10.5 mL, 6:1) at room temperature was added $K_2CO_3$ (0.684 g, 4.95 mmol). The mixture was allowed to stir for 10 min followed by addition of N-hydroxyl acetamide (0.185 g, 2.475 mmol). The mixture was allowed to stir at 70° C. for 16 h. After completion (monitored by TLC), the reaction mixture was cooled to room temperature, diluted with water, and extracted with ethyl acetate. The organic layer was dried over anhydrous $Na_2SO_4$ and concentrated under reduced pressure. The crude compound was purified by using combi flash chromatography using a gradient method of 10-70% EtOAc/Heptane to afford the title compound 108 (290 mg, 93.54%) as a brown semi-solid. TLC: 80% EtOAc/Heptane ($R_f$ 0.50); LCMS Calculated for $C_{19}H_{28}N_4O_4$: 376.21; Found: 377.4 (M+1).

Synthesis of tert-butyl (1-((4-methoxy-3-((2-methoxyphenyl) sulfonamido) benzo[d]isoxazol-6-yl) methyl) piperidin-4-yl) carbamate (109)

To a stirred solution of compound tert-butyl (1-((3-amino-4-methoxybenzo[d]isoxazol-6-yl) methyl) piperidin-4-yl) carbamate 108 (0.5 g, 1.328 mmol) in THF (5 mL) at 0° C. was added KOtBu 1.0 M in THF (3.98 mL, 3.98 mmol) followed by 2-methoxybenzenesulfonyl chloride (0.548 g, 2.656 mmol). The reaction was allowed to stir at room temperature for 16 h. After completion (monitored by TLC), the reaction mixture was quenched with water and extracted with ethyl acetate. The organic layer was dried over $Na_2SO_4$ and concentrated under reduced pressure. The crude compound was purified by Combi flash column chromatography using a gradient method of 0-5% MeOH/DCM to afford the title compound 109 (0.250 g, 34.4%) as a white solid. TLC: 70% EtOAc/Pentane (Rf: 0.45); LCMS Calculated for $C26H34N4O7S$: 546.21; Found: 547.5 (M+1).

Synthesis of N (6((4aminopiperidinlyl) methyl) 4methoxybenzo[d]isoxazol3yl)2methoxybenzenesulfonamide hydrochloride (110)

To a stirred solution of compound tert-butyl (1-((4-methoxy-3-((2-methoxyphenyl) sulfonamido) benzo[d] isoxazol-6-yl) methyl) piperidin-4-yl) carbamate 109 (0.250 g, 0.4573 mmol) in DCM (5 mL) at 0° C. was added 4M HCl in 1,4-Dioxane (2.5 mL). The reaction was allowed to stir at the room temperature for 4 h. After completion (reaction monitored by TLC), the reaction mixture was concentrated under reduced pressure to afford the title compound 110 (240 mg, 100%) as. TLC: 10% MeOH/DCM (Rf: 0.5). LCMS Calculated for $C_{21}H_{27}ClN_4O_5S$; 482.14; Found: 447.0 (Freebase+1).

Synthesis of N-(1-((4-methoxy-3-((2-methoxyphenyl)sulfonamido)benzo[d]isoxazol-6-yl)methyl)piperidin-4-yl)acrylamide To a stirred solution of N-(6-((4-aminopiperidin-1-yl) methyl)-4-methoxybenzo[d]isoxazol-3-yl)-2-methoxybenzenesulfonamide hydrochloride 110 (0.100 mg, 0.207 mmol) in DCM (4 mL) at 0° C. was added TEA (0.087 mL, 0.621 mmol) and acryloyl chloride (15 mg, 0.207 mmol). The resulting reaction mixture was allowed to stir at 0° C. for 2 h. After completion (monitored by TLC), the reaction mixture was quenched with water and extracted with DCM. The organic layer was dried over anhydrous $Na_2SO_4$ and concentrated under reduced pressure. The crude compound was purified by prep HPLC to afford the title compound (15 mg, 13.3%) as an off-white solid. TLC: 10% MeOH/DCM (Rf: 0.5). LCMS Calculated for $C_{24}H_{28}N_4O_6S$: 500.17; Found: 501.5 (M+1). (See Table 1 for analytical data)

Synthetic Example 50

Scheme 31: Synthesis of N-(6-(((3aR,6aS)-5-acryloylhexahy dropyrrolo[3.4-c]pyrrol-2(1H-yl) methyl-4-methoxybenzo[d]isoxazol-3-yl)-2-methoxybenzenesulfonamide

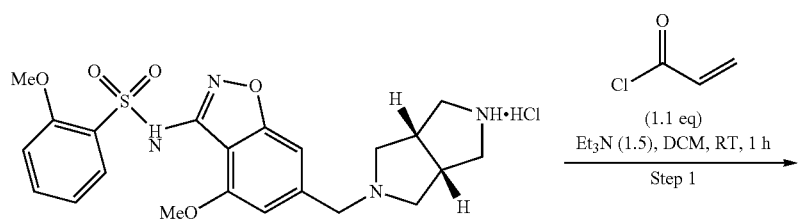

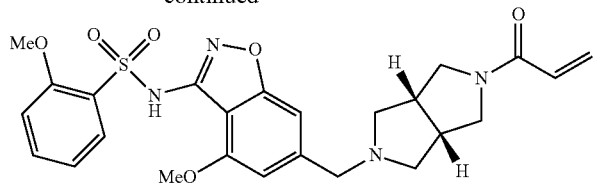

Syn. Ex. 50

Synthesis of N-(6-(((3aR,6aS)-5-acryloylhexahydro-pyrrolo[3,4-c]pyrrol-2(1H)-yl)methyl)-4-methoxy-benzo[d]isoxazol-3-yl)-2-methoxybenzenesulfonamide To a stirred solution of N-(6-(((3aR,6aS)-hexahydropyr-rolo[3,4-c]pyrrol-2(1H)-yl) methyl)-4-methoxybenzo[d] isoxazol-3-yl)-2-methoxybenzenesulfonamide hydrochloride 91 (0.1 g, 0.202 mmol) in DMF (1 mL) at 0° C. was added TEA (0.0425 mL, 0.303 mmol) and acryloyl chloride (20 mg, 0.222 mmol). The reaction was allowed to stir at the room temperature for 4 h. After completion (monitored by TLC), the reaction mixture was concentrated under reduced pressure to get a brown gummy product. The crude was purified over combi-flash chromatography using gradient 5-10% MeOH in DCM and further purified by prep HPLC to afford the title compound (8.5 mg, 8.09%) as an off white solid. TLC: 10% MeOH/DCM (Rf: 0.40). (See analytical data for Table 1).

Synthetic Example 51

Scheme 32: Synthesis of N-((1-((4-methoxy-3-((2-methoxyphenyl)sulfonamido)benzo[d]isoxazol-6-yl)methyl)-1H-pyrazol-4-yl)methyl)acrylamide Scheme 32: Synthesis of N-((1-((4-methoxy-3-((2-methoxyphenyl)sulfonamido)benzo[d]isoxazol-6-yl)methyl)-1H-pyrazol-4-yl)methyl)acrylamide

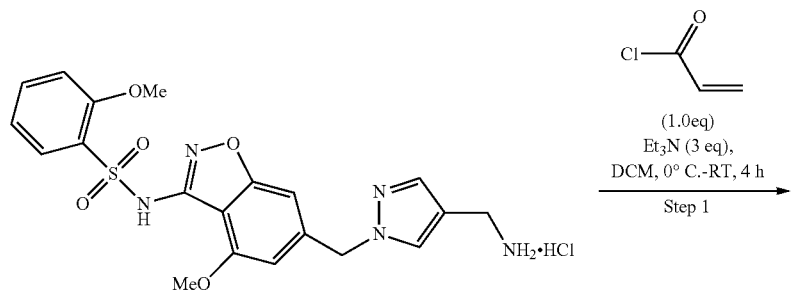

56

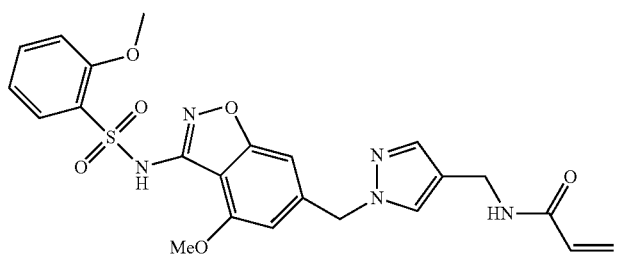

Syn. Ex. 51

Synthesis of N-((1-((4-methoxy-3-((2-methoxyphenyl)sulfonamido)benzo[d]isoxazol-6-yl)methyl)-1H-pyrazol-4-yl)methyl)acrylamide To a stirred solution of N-(6-((4-(aminomethyl)-1H-pyrazol-1-yl)methyl)-4-methoxybenzo[d]isoxazol-3-yl)-2-methoxybenzenesulfonamide hydrochloride 56 (60 mg, 0.125 mmol) in DCM (2 mL) at 0° C. was added TEA (0.05 mL, 0.375 mmol) and a solution of acryloyl chloride (11 mg, 0.125 mmol) in DCM (0.6 mL). The reaction mixture was allowed to stir at the 0° C. for 4 h. After completion (monitored by TLC), the reaction mixture was quenched with water and extracted with DCM. The organic layer was dried over anhydrous $Na_2SO_4$ and concentrated under reduced pressure. The crude was purified by prep HPLC to afford the title compound (8 mg, 12.90%) as an off-white solid. TLC: 10% MeOH/DCM (Rf: 0.5). (See Table 1 for analytical data).

Synthetic Example 52

Scheme 33: Synthesis 3-(N-(4-methoxy-6-((4-(propiolamidomethyl-1H-pyrazol-1-yl) methyl) benzo[d]isoxazol-3-yl) sulfonyl)-N-methylbenzamide

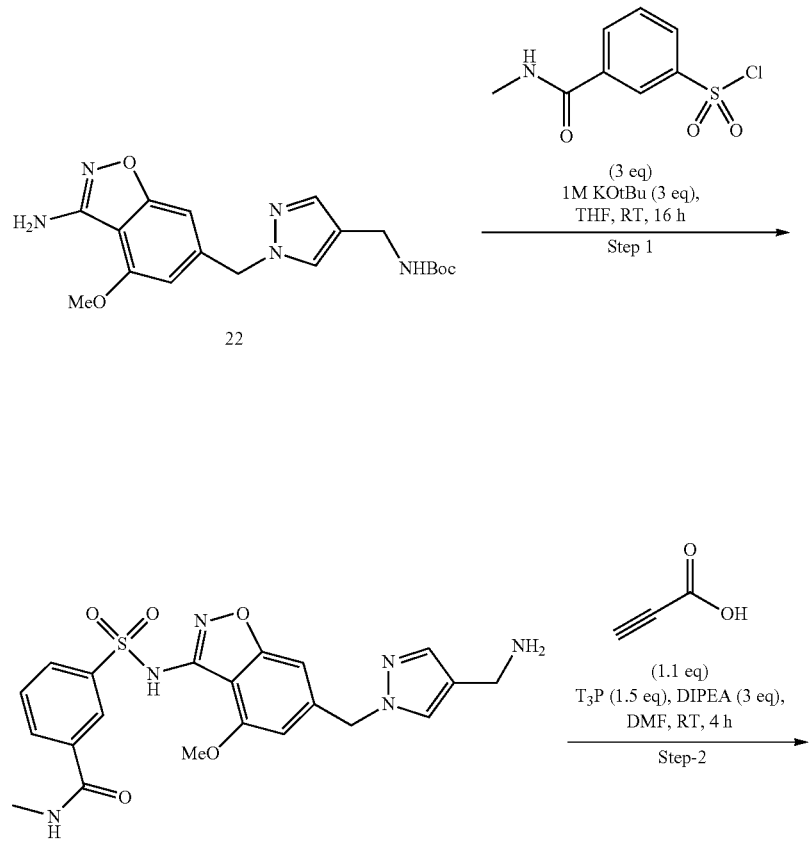

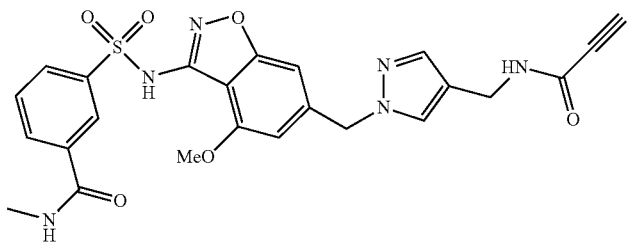

Syn. Ex. 52

Synthesis of 3-(N-(6-((4-(aminomethyl)-1Hpyrazol-lyl) methyl)4methoxybenzo[d]isoxazol-3-yl) sulfamoyl)-N-methyl benzamide (111)

To a stirred solution of tert-butyl ((1-((3-amino-4-methoxybenzo[d]isoxazol-6-yl)methyl)-1H-pyrazol-4-yl) methyl)carbamate 22 (100 mg, 0.267 mmol) in THF (5 mL) at 0° C. was added 1.0 M solution of KOtBu in THF (0.8 mL 0.8034 mmol). The reaction was allowed to stir at room temperature for 15 min followed by addition of 3-(methyl carbamoyl) benzene sulfonyl chloride (187 mg, 0.801 mmol). The reaction was allowed to stir at room temperature for 16 h. After completion (monitored by TLC), the reaction mixture was quenched with water and extracted ethyl acetate. The organic layer was dried over anhydrous $Na_2SO_4$ and concentrated under reduced pressure. The crude compound was purified by Combi flash column chromatography using a gradient method of 40-60% EtOAc/Heptane to afford the title compound 111 (110 mg, 88%) as an off-white solid. TLC: 70% EtOAc (Rf: 0.5). LCMS Calculated for $C_{21}H_{22}N_6O_5S$: 470.14; Found: 471.8 (M+1).

Synthesis 3-(N-(4-methoxy-6-((4-(propiolamidomethyl)-1H-pyrazol-1-yl) methyl) benzo[d]isoxazol-3-yl) sulfonyl)-N-methylbenzamide To a stirred solution of 3-(N-(6-((4-(aminomethyl)-1H-pyrazol-1-yl) methyl)-4-methoxybenzo[d]isoxazol-3-yl) sulfamoyl)-N-methyl benzamide 111 (110 mg, 0.233 mmol) in DMF (1.5 mL) at 0° C. was added DIPEA (122 mg, 0.699 mmol), $T_3P$ (111 mg, 0.349 mmol). The reaction mixture was allowed to stir at the room temperature for 10 min. After that, a pre-dissolved solution of propiolic acid (44.6 mg, 0.63 mmol) in $T_3P$ (0.304 g, 0.95 mmol) was added dropwise. The reaction was stirred at the room temperature for 4 h. After completion (monitored by TLC), the reaction mixture was concentrated under reduced pressure. The crude compound was purified by prep. HPLC to afford the title compound (5.5 mg, 3.3%) as an off-white solid. TLC: 10% MeOH/DCM (Rf: 0.2). LCMS Calculated for $C_{24}H_{22}N_6O_6S$: 522.13; Found: 523.47 (M−1). (See Table 1 for analytical data)

Synthetic Example 53 and 54

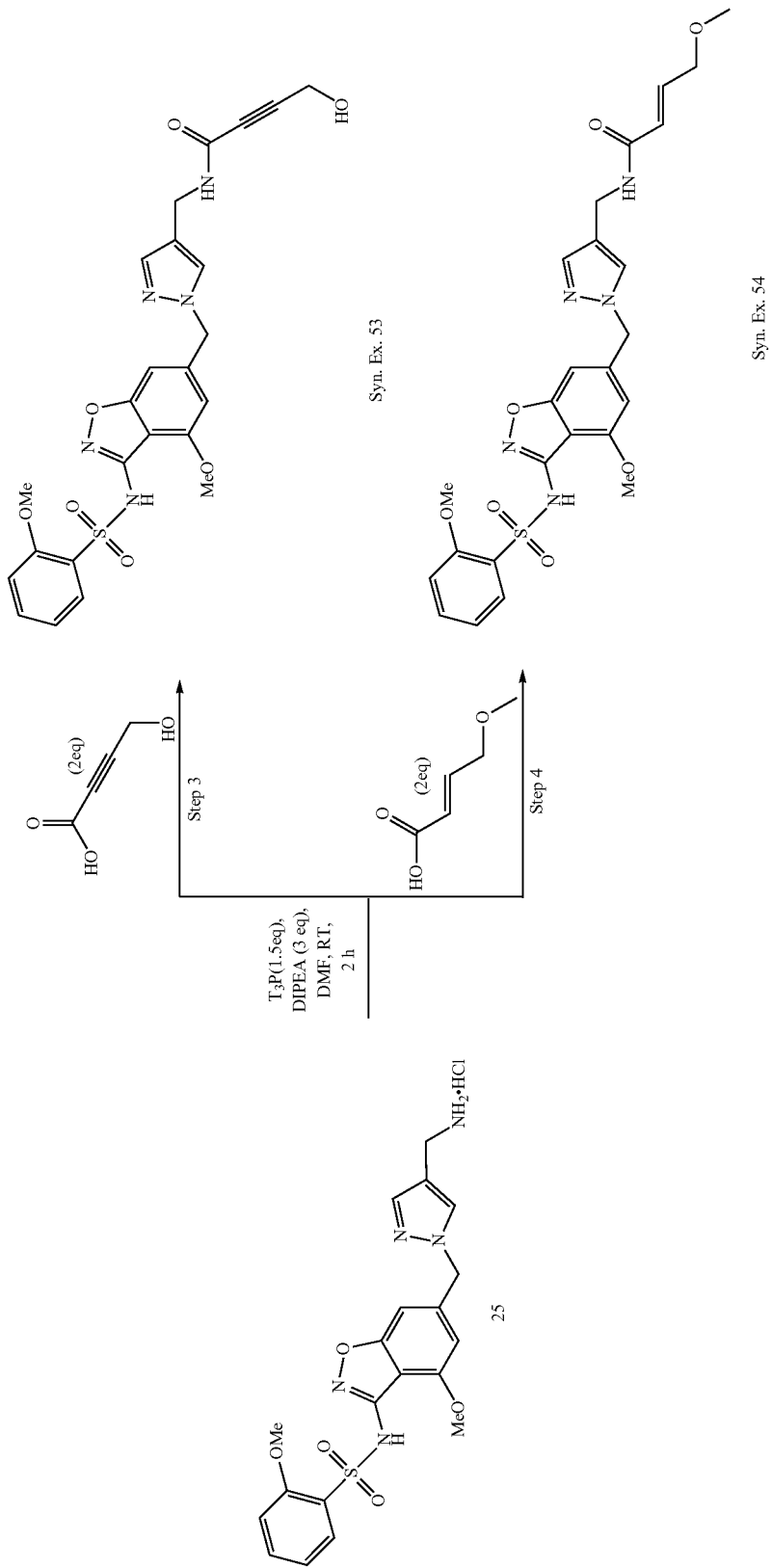
Scheme 34: Synthesis of 4-hydroxy-N-((1-((4-methoxy-3-((2-methoxyphenyl)sulfonamido(benzo[d]isoxazol-6-yl) methyl-1H-pyrazol-4-yl) methyl but-2-ynamide and Synthesis of (E)-4-methoxy-N-((1-((4-methoxy-3-((2-methoxyphenyl) sulfonamido)benzo[d]isoxazol-6-yl) methyl)-1H-pyrazol-4-yl)methyl)but-2-enamide

Synthesis of 4-hydroxy-N-((1-((4-methoxy-3-((2-methoxyphenyl) sulfonamido) benzo[d]isoxazol-6-yl) methyl)-1H-pyrazol-4-yl) methyl) but-2-ynamide To a stirred solution of N-(6-((4-(aminomethyl)-1H-pyrazol-1-yl) methyl)-4-methoxybenzo[d]isoxazol-3-yl)-2-methoxybenzenesulfonamide hydrochloride 25 (0.1 g, 0.208 mmol) in DMF (1 mL) at 0° C. was added DIPEA (0.11 mL, 0.626 mmol), T₃P 50% solution in EtOAc (0.198 mL, 0.312 mmol) followed by 4-hydroxybut-2-ynoic acid (41 mg, 0.416 mmol). The reaction was allowed to stir at the room temperature for 4 h. After completion (reaction monitored by TLC), the reaction mixture was concentrated. The crude compound was purified by using prep-HPLC to afford the title compound (20 mg, 18.34%) as an off-white solid; TLC: 10% MeOH/DCM (Rf: 0.6). (See Table 1 for analytical data).

Synthesis of (E)-4-methoxy-N-((1-((4-methoxy-3-((2-methoxyphenyl) sulfonamido) benzo[d]isoxazol-6-yl) methyl)-1H-pyrazol-4-yl)methyl)but-2-enamide To a stirred solution of N-(6-((4-(aminomethyl)-1H-pyrazol-1-yl) methyl)-4-methoxybenzo[d]isoxazol-3-yl)-2-methoxybenzenesulfonamide hydrochloride 25 (0.1 g, 0.208 mmol) in DMF (1 mL) at 0° C. was added DIPEA (0.11 mL, 0.626 mmol), T₃P 50% solution in EtOAc (0.198 mL, 0.312 mmol) followed by (E)-4-methoxybut-2-enoic acid (48 mg, 0.416 mmol). The reaction was allowed to stir at the room temperature for 4 h. After completion (reaction monitored by TLC), the reaction mixture was concentrated. The crude compound was purified by using prep-HPLC to afford the title compound (22.5 mg, 18.86%) as an off-white solid; TLC: 10% MeOH/DCM (Rf: 0.6). (See Table 1 for analytical data).

Synthetic Example 55

Scheme 35: Synthesis of N-methyl-3-[[[3-methyl-5-[4-[(prop-2-ynoylamino) methyl]-2-pyridyl] benzoyl] amino] sulfamoyl] benzamide

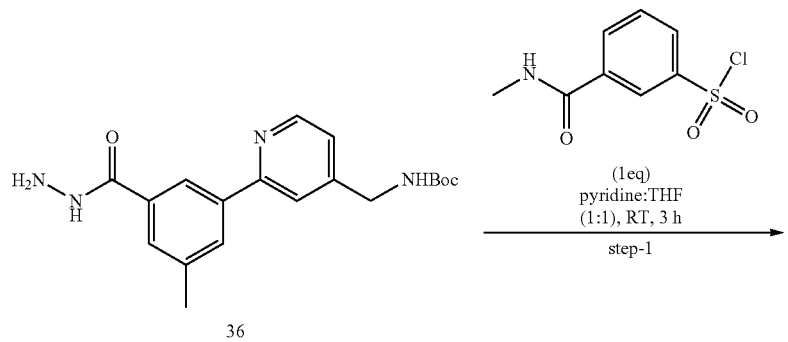

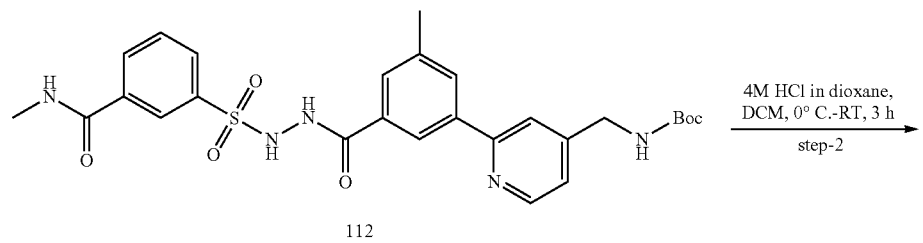

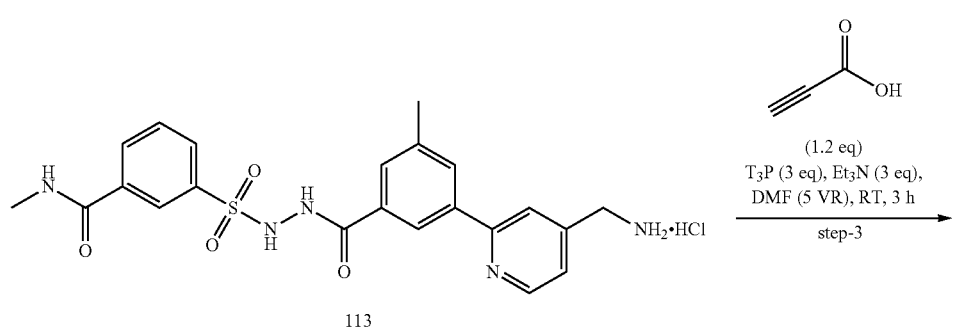

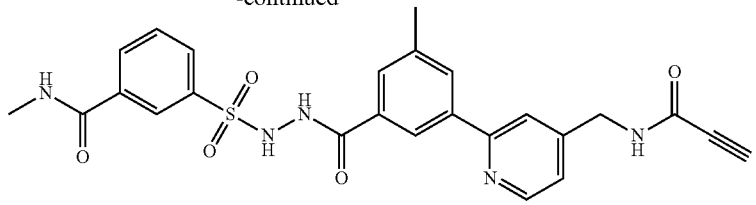

Syn. Ex. 55

Synthesis of tert-butyl N-[[2-[3-methyl-5-[[[3-(methylcarbamoyl) phenyl]sulfonylamino]carbamoyl]phenyl]-4-pyridyl]methyl]carbamate (112)

To a stirred solution of tert-butyl ((2-(3-(hydrazinecarbonyl)-5-methylphenyl) pyridin-4-yl)methyl)carbamate 36 (0.25 g, 0.701 mmol) in THF:Pyridine (10 mL, 1:1) at the room temperature was added 3-(methylcarbamoyl)benzenesulfonyl chloride (163 mg, 0.701 mmol). The reaction was allowed to stir at room temperature for 3 h. After completion (monitored by TLC), the reaction mixture was neutralized with 1N HCl and extracted with ethyl acetate. The organic layer was washed with brine, dried over anhydrous $Na_2SO_4$ and concentrated under reduced pressure. The crude compound was purified by Combi flash column chromatography using a gradient method of 40-48% EtOAc/Heptane to afford the title compound 112 (220 mg, 56.70%) as a white solid. TLC: 60% EtOAc/Heptane (Rf: 0.4); LCMS Calculated for $C_{27}H_{31}N_5O_6S$: 553.20; Found: 554.01 (M+1).

Synthesis of 3-((2-(3-(4-(aminomethyl) pyridin-2-yl)-5-methylbenzoyl) hydrazineyl) sulfonyl)-N-methylbenzamide hydrochloride (113)

To a stirred solution of tert-butyl ((2-(3-methyl-5-(2-((3-(methylcarbamoyl) phenyl) sulfonyl) hydrazine-1-carbonyl) phenyl)pyridin-4-yl)methyl)carbamate 112 (170 mg, 0.307 mmol) in DCM (3.4 mL) at 0° C. was added 4M HCl in 1,4-Dioxane (1.7 mL). The reaction was allowed to stir at room temperature for 2 h. After completion (monitored by TLC), the reaction mixture was concentrated under reduced pressure. Crude compound was washed with diethyl ether and heptane to afford the title compound 113 (0.130 g, HCl salt) as a brown solid. TLC: 10% MeOH/DCM (Rf: 0.5). LCMS Calculated for C20H22ClN5O5S: 489.12; Found: 454.08 (Freebase+1).

Synthesis of N-methyl-3-[[[3-methyl-5-[4-[(prop-2-ynoylamino) methyl]-2-pyridyl]benzoyl]amino]sulfamoyl]benzamide To a stirred solution of 3-((2-(3-(4-(aminomethyl) pyridin-2-yl)-5-methylbenzoyl) hydrazineyl) sulfonyl)-N-methylbenzamide hydrochloride 113 (80 mg, 0.163 mmol) in DMF (1 mL) at 0° C. was added $Et_3N$ (0.068 mL, 0.489 mmol). The reaction mixture was stirred 15 min followed by addition of propiolic acid (13 mg, 0.195 mmol) and $T_3P$ 50% solution in EtOAc (0.311 mL, 0.489 mmol). The reaction mixture was allowed to stir at the room temperature for 3 h. After completion (reaction monitored by TLC), the reaction mixture was quenched with water and extracted with ethyl acetate. The organic layer was washed with brine, dried over anhydrous $Na_2SO_4$, and concentrated under reduced pressure. The crude compound was purified by using preparative HPLC to afford the title compound (23 mg, 28.04%) as an off-white solid. TLC: 10% MeOH/DCM (Rf: 0.5). (See Table 1 for analytical data)

Synthetic Example 56

Scheme 36: Synthesis of N-(6-(3-(4-acryloylpiperazin-1-yl)phenyl)-4-methoxybenzo[d]isoxazol-3-yl)-2,6-dimethoxybenzenesulfonamide

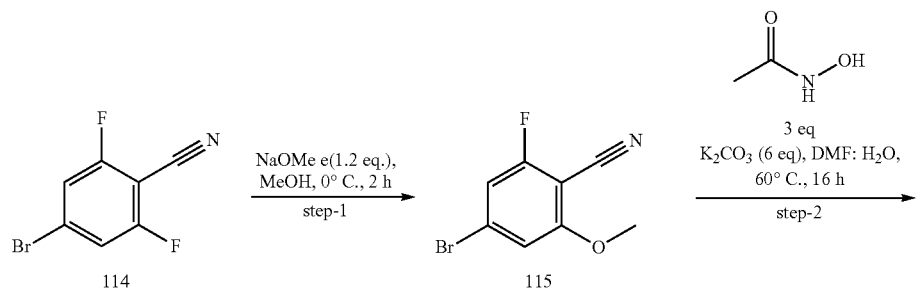

-continued
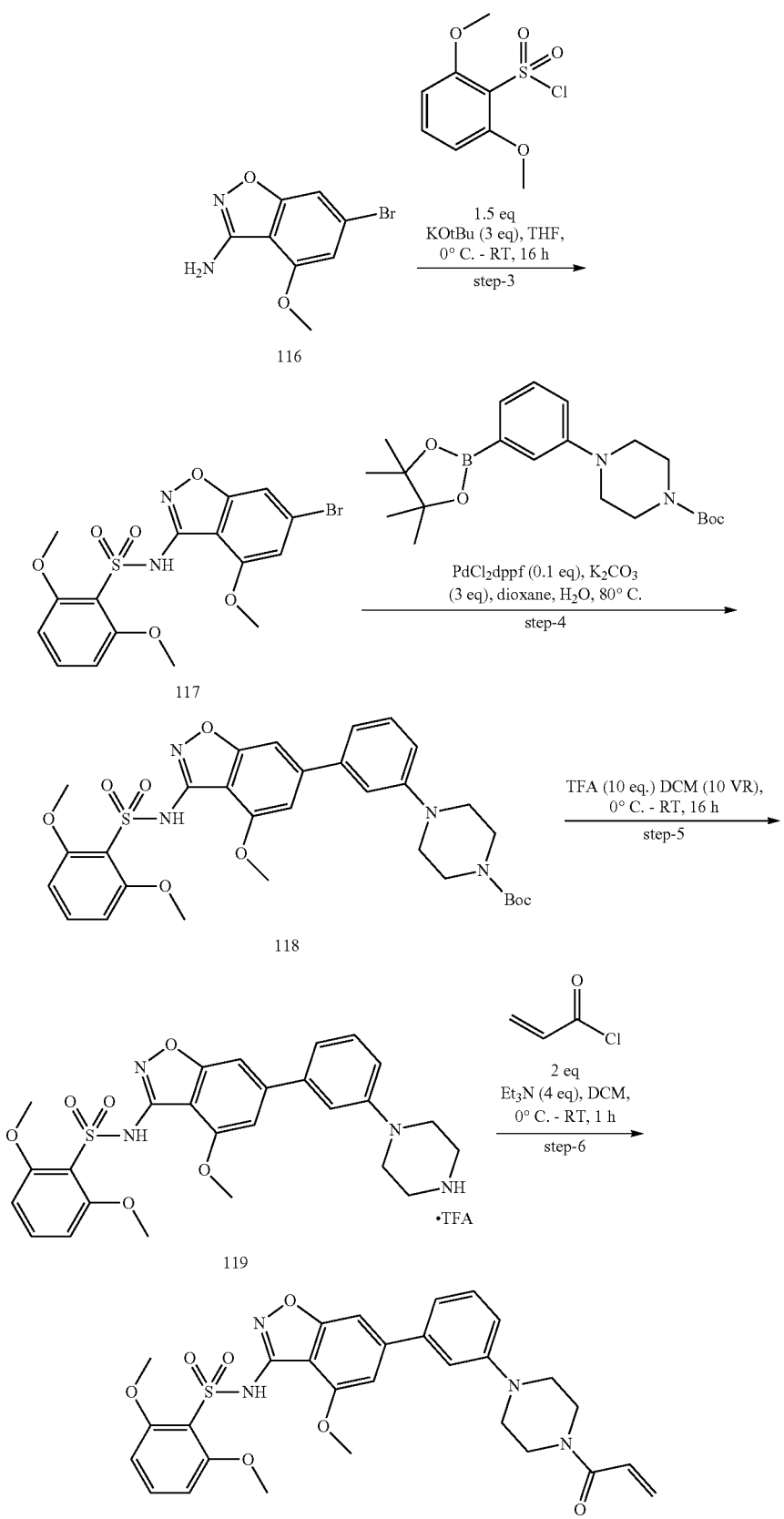
Syn. Ex. 56

Synthesis of 4-bromo-2-fluoro-6-methoxybenzonitrile (115)

To a stirred solution of 4-bromo-2,6-difluorobenzonitrile 114 (50 mg, 229.35 mmol) in MeOH (500 mL) was added NaOMe (14.86 g, 275.22 mmol) and the reaction mixture was allowed to stir at 0° C. for 2 h. After completion (monitored by TLC), the reaction mixture was quenched with ice water and extracted with ethyl acetate. The organic layer was dried over anhydrous $Na_2SO_4$ and concentrated under reduced pressure at 30° C. to afford the title compound 115 (55 g, crude) as a yellow solid. TLC: 100 EtOAc (Rf: 0.6). LCMS Calculated for C8H5BrFNO: 228.95; Found: 229.5 (M+1). The crude compound was used in the next step without purification.

Synthesis of 6-bromo-4-methoxybenzo[d]isoxazol-3-amine (116)

To a stirred solution of 4-bromo-2-fluoro-6-methoxybenzonitrile 115 (15 g, 65.20 mmol) in 6:1 mixture of DMF:$H_2O$ (7 mL) at room temperature was added N-hydroxy acetamide (14.68 g, 195.61 mmol) and followed by $K_2CO_3$ (27 g, 195.6 mmol). The reaction mixture was allowed to stir at 70° C. for 16 h. After completion (monitored by TLC), the reaction mixture was poured in ice water and extracted with ethyl acetate. The organic layer was washed with brine, dried over anhydrous $Na_2SO_4$ and concentrated under reduced pressure. The crude compound was purified by Combi flash chromatography using a gradient method of 70% EtOAc/Heptane to afford the title compound 116 (7g, 44.19%) as a white solid. TLC: 100% EtOAc (Rf: 0.50); LCMS Calculated for C8H7BrN2O2: 241.97; Found: 242.02 (M+1).

Synthesis of N-(6-bromo-4-methoxybenzo[d]isoxazol-3-yl)-2,6-dimethoxybenzenesulfonamide (117)

To a stirred solution of 6-bromo-4-methoxybenzo[d]isoxazol-3-amine 116 (1 g, 4.11 mmol) in THF (10 mL) was added NaOtPn (1.18 g, 12.34 mmol) followed by 2,6-dimethoxybenzenesulfonyl chloride (3.40 g, 14.4 mmol) and the reaction mixture was allowed to stir at the room temperature for 2 h. After completion (monitored by TLC), the reaction mixture was quenched with ice water and extracted with ethyl acetate. The organic layer was dried over anhydrous $Na_2SO_4$ and concentrated under reduced pressure. The crude compound was purified by combi flash chromatography (neutral alumina) to afford the title compound 117 (1 g, 54.94%) as a yellow solid. TLC: 100 EtOAc (Rf: 0.6). LCMS Calculated for C16H15BrN2O6S: 441.98; Found: 442.5 (M+1).

Synthesis of tert-butyl 4-(3-(3-((2,6-dimethoxyphenyl) sulfonamido)-4-methoxybenzo[d]isoxazol-6-yl) phenyl) piperazine-1-carboxylate (118)

To a stirred solution of N-(6-bromo-4-methoxybenzo[d]isoxazol-3-yl)-2,6-dimethoxybenzenesulfonamide 117 (200 mg, 0.451 mmol) and tert-butyl 4-(3-(4,4,5,5-tetramethyl-1,3,2-dioxaborolan-2-yl)phenyl)piperazine-1-carboxylate (210 mg, 0.541 mmol) in a 2:1 mixture of 1,4-Dioxane:$H_2O$ (9 mL) was added $K_2CO_3$ (0.187 g, 1.353 mmol). The reaction mixture was degassed with Argon followed by addition of Pd(dppf)Cl$_2$ (33 mg, 0.0451 mmol) and degassed again for 5 min. The reaction mixture was stirred at 80° C. for 12 h. After completion (monitored by TLC), the reaction mixture was diluted with ethyl-acetate filtered on a Celite pad and concentrated under reduced pressure. The crude compound was purified by combi flash-chromatography using a gradient method of 0-30% EtOAc/Heptane to afford the title compound 118 (180 mg, 64.05%) as a pale-yellow solid. TLC: 40% EtOAc/Heptane (Rf: 0.4). LCMS Calculated for C31H36N4O8S: 624.23; Found: 625.02 (M+1).

Synthesis of 2,6-dimethoxy-N-(4-methoxy-6-(3-(4-(2,2,2-trifluoroacetyl)-414-piperazin-1-yl) phenyl) benzo[d]isoxazol-3-yl) benzenesulfonamide (119)

To a stirred solution of tert-butyl 4-(3-(3-((2,6-dimethoxyphenyl) sulfonamido)-4-methoxybenzo[d]isoxazol-6-yl) phenyl) piperazine-1-carboxylate 118 (150 mg, 0.240 mmol) in DCM (2 mL) at 0° C. was added TFA (0.185 mL, 2.401 mmol). The reaction was allowed to stir at room temperature for 2 h. After completion (monitored by TLC), the reaction mixture was concentrated under reduced pressure and co distilled with Toluene to afford the title compound 119 (120 mg, crude TFA salt) as a brown oil. TLC: 5% MeOH/DCM (Rf: 0.3). LCMS Calculated for C28H28F3N4O7S: 621.16: Found: 525.50 (Freebase+1).

Synthesis of N-(6-(3-(4-acryloylpiperazin-1-yl)phenyl)-4-methoxybenzo[d]isoxazol-3-yl)-2,6-dimethoxybenzenesulfonamide To a stirred solution of 2,6-dimethoxy-N-(4-methoxy-6-(3-(4-(2,2,2-trifluoroacetyl)-414-piperazin-1-yl) phenyl) benzo[d]isoxazol-3-yl) benzenesulfonamide 119 (120 mg, 0.193 mmol) in DMF (2 mL) at 0° C. was added DIPEA (0.101 mL, 0.579 mmol), acryloyl chloride (20 mg, 0.231 mmol) followed by T$_3$P 50% solution in EtOAc (0.184 mL, 0.289 mmol). The reaction mixture was allowed to stir at room temperature for 12 h. After completion (monitored by TLC), the reaction mixture was concentrated under reduced pressure and the crude was purified by using prep HPLC to afford the title compound (8.9 mg, 8%) as an off-white solid. TLC: 5% MeOH/DCM (Rf: 0.5). (See analytical data in Table 1).

Synthetic Example 57

Scheme 37: Synthesis of N-[[1-[[4-methoxy-3-[(2-methoxyphenyl) sulfonylamino]-1,2-benzoxazol-6-yl] methyl] pyrazol-4-yl] methyl] but-2-ynamide

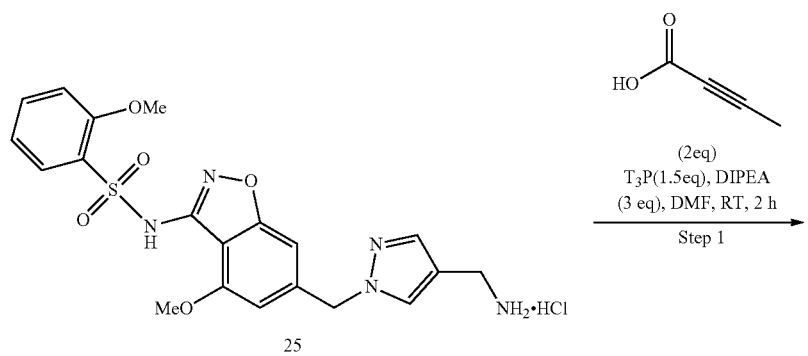

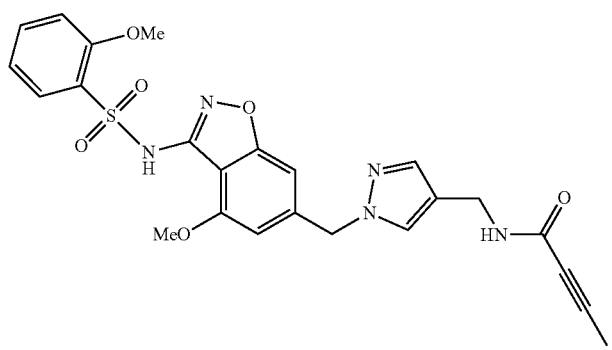

Syn. Ex. 57

Synthesis of N-[[1-[[4-methoxy-3-[(2-methoxyphenyl) sulfonylamino]-1,2-benzoxazol-6-yl]methyl] pyrazol-4-yl]methyl]but-2-ynamide To a stirred solution of N-(6-((4-(aminomethyl)-1H-pyrazol-1-yl) methyl)-4-methoxybenzo[d]isoxazol-3-yl)-2-methoxybenzenesulfonamide hydrochloride 25 (0.1 g, 0.208 mmol) in DMF (1 mL) at 0° C. was added DIPEA (0.11 mL, 0.626 mmol), T$_3$P 50% solution in EtOAc (0.198 mL, 0.312 mmol) followed by but-2-ynoic acid (35 mg, 0.416 mmol). The reaction was allowed to stir at the room temperature for 4 h. After completion (monitored by TLC), the reaction mixture was evaporated under reduced pressure. The crude compound was purified by using prep HPLC to afford the title compound (20 mg, 18.86%) as an off-white solid; TLC: 10% MeOH/DCM (Rf: 0.6). (See Table 1 for analytical data).

Synthetic Example 58

Scheme 38: Synthesis of N-(6-(2-(4-acryloylpiperazin-1-yl)phenyl)-4-methoxybenzo[d]isoxazol-3-yl)-2,6-dimethoxybenzenesulfonamide

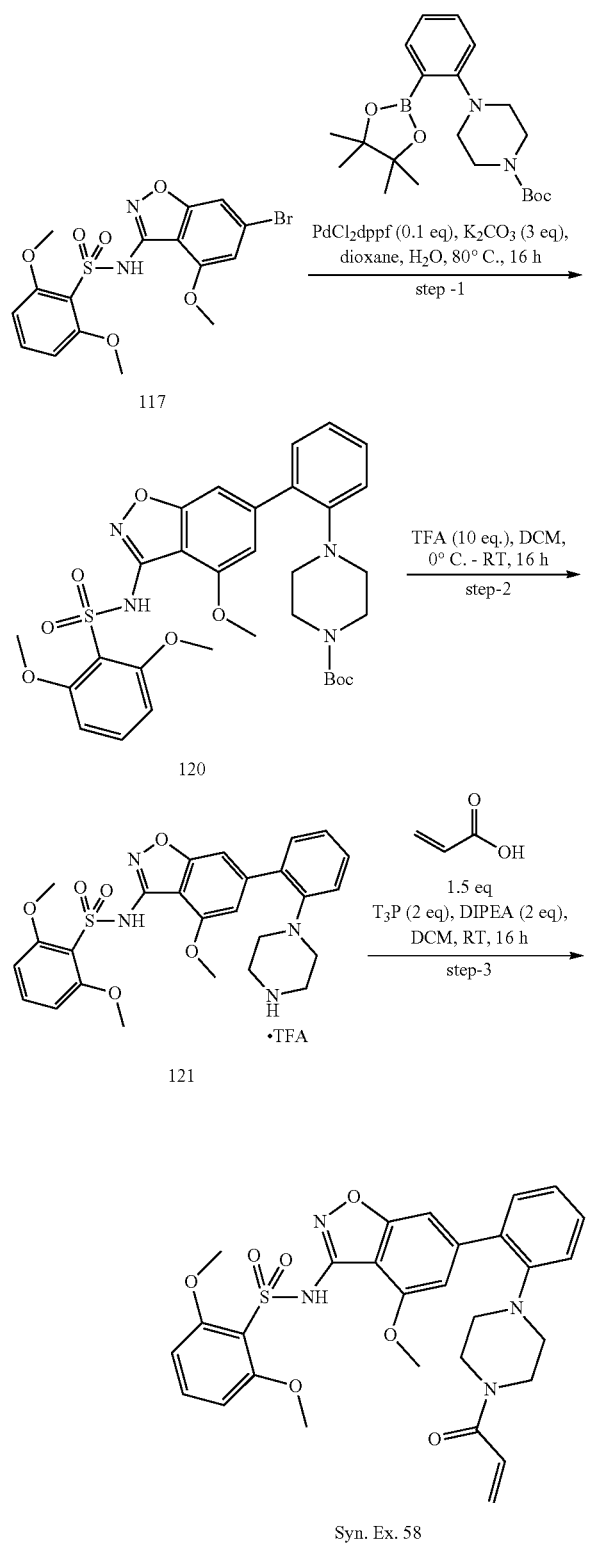

Syn. Ex. 58

Synthesis of tert-butyl 4-(2-(3-((2,6-dimethoxyphenyl) sulfonamido)-4-methoxybenzo[d]isoxazol-6-yl) phenyl) piperazine-1-carboxylate (120)

To a stirred solution of N-(6-bromo-4-methoxybenzo[d] isoxazol-3-yl)-2,6-dimethoxybenzenesulfonamide 117 (200 mg, 0.451 mmol) and tert-butyl 4-(2-(4,4,5,5-tetramethyl-1,3,2-dioxaborolan-2-yl)phenyl)piperazine-1-carboxylate (210 mg, 0.541 mmol) in a 2:1 mixture of 1,4-Dioxane:H$_2$O (9 mL) was added K$_2$CO$_3$ (0.187 g, 1.353 mmol). The reaction mixture was degassed with Argon followed by addition of Pd(dppf)Cl$_2$ (33 mg, 0.0451 mmol) and degassed again for 5 min. The reaction mixture was stirred at 80° C. for 12 h. After completion (monitored by TLC), the reaction mixture was diluted with ethyl-acetate filtered on Celite pad and the filtrate was concentrated under reduced pressure. The crude compound was purified by combi flash-chromatography using a gradient method of 10-50% EtOAc/Heptane to afford the title compound 120 (220 mg, 72.36%) as a pale-yellow solid.

Synthesis of 2,6-dimethoxy-N-(4-methoxy-6-(2-(4-(2,2,2-trifluoroacetyl)-414-piperazin-1-yl)phenyl) benzo[d]isoxazol-3-yl)benzenesulfonamide (121)

To a stirred solution of tert-butyl 4-(2-(3-((2,6-dimethoxyphenyl) sulfonamido)-4-methoxybenzo[d]isoxazol-6-yl) phenyl) piperazine-1-carboxylate 120 (150 mg, 0.240 mmol) in DCM (2 mL) at 0° C. was added TFA (0.185 mL, 2.401 mmol). The reaction was allowed to stir at room temperature for 2 h. After completion (monitored by TLC), the reaction mixture was concentrated under reduced pressure and co distilled with Toluene to afford the title compound 121 (200 mg, crude TFA salt) as a brown gummy solid. TLC: 5% MeOH/DCM (Rf: 0.3). LCMS Calculated for C28H28F3N4O7S: 621.16: Found: 525.50 (Freebase+1).

Synthesis of N-(6-(2-(4-acryloylpiperazin-1-yl)phenyl)-4-methoxybenzo[d]isoxazol-3-yl)-2,6-dimethoxybenzenesulfonamide To a stirred solution of 2,6-dimethoxy-N-(4-methoxy-6-(2-(4-(2,2,2-trifluoroacetyl)-414-piperazin-1-yl)phenyl) benzo[d]isoxazol-3-yl)benzenesulfonamide 121 (100 mg, 0.160 mmol) in DMF (2 mL) at 0° C. was added DIPEA (0.083 mL, 0.48 mmol), acryloyl chloride (14 mg, 0.193 mmol) followed by T$_3$P 50% solution in EtOAc (0.152 mL, 0.24 mmol) and reaction mixture was allowed to stir at room temperature for 12 h. After completion (monitored by TLC), the reaction mixture was concentrated under reduced pressure and the crude was purified by using prep HPLC to afford the title compound (3.6 mg, 3.87%) as an off-white solid. TLC: 5% MeOH/DCM (Rf: 0.5). (See analytical data in Table 1).

Synthetic Example 59

Scheme 39: Synthesis of 2-methoxy-N-(4-methoxy-6-(((3aR,6aS)-5-(vinylsulfonyl)hexahydropyrrolo[3,4-c]pyrrol-2-(1H)yl)methyl)benzo[d]isoxazol-3-yl)benzenesulfonamide

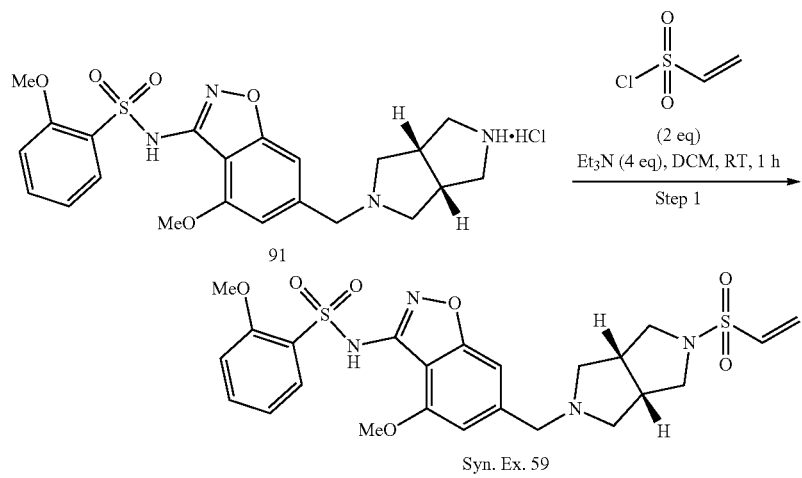

To a stirred solution of N-(6-(((3aR,6aS)-hexahydropyrrolo[3,4-c]pyrrol-2(1H)-yl) methyl)-4-methoxybenzo[d]isoxazol-3-yl)-2-methoxybenzenesulfonamide hydrochloride 91 (0.1 g, 0.202 mmol) in DMF (1 mL) at 0° C. was added TEA (0.0425 mL, 0.303 mmol) followed by ethenesulfonyl chloride (51 mg, 0.404 mmol). The reaction was allowed to stir at room temperature for 4 h. After completion (monitored by TLC), the reaction mixture was quenched with ice water and extracted with ethyl acetate. The organic layer was washed with brine, dried over anhydrous $Na_2SO_4$, and concentrated under reduced pressure. The crude compound was purified by prep HPLC to afford the title compound (1.85 mg, 1.68%) as an off-white solid. TLC: 10% MeOH/DCM (Rf: 0.40). (See Table 1 for analytical data).

Synthetic Example 60 and 61

Scheme 40: Synthesis of N-(2-(((1-((4-methoxy-3-((2-methoxyphenyl)sulfonamido)benzo[d]isoxanzol-6-yl)methyl)-1H-pyrazole-4-yl)methyl)amino)-2-oxoethyl)propiolamide and Synthesis of N-[2-[[1-[[4-methoxy-3-[(2-methoxyphenyl)sulfonylamino]1,2-benzoxazol-6-yl]methyl]pyrazol-4-yl]methylamino]-2-oxo-ethyl]prop-2-enamide

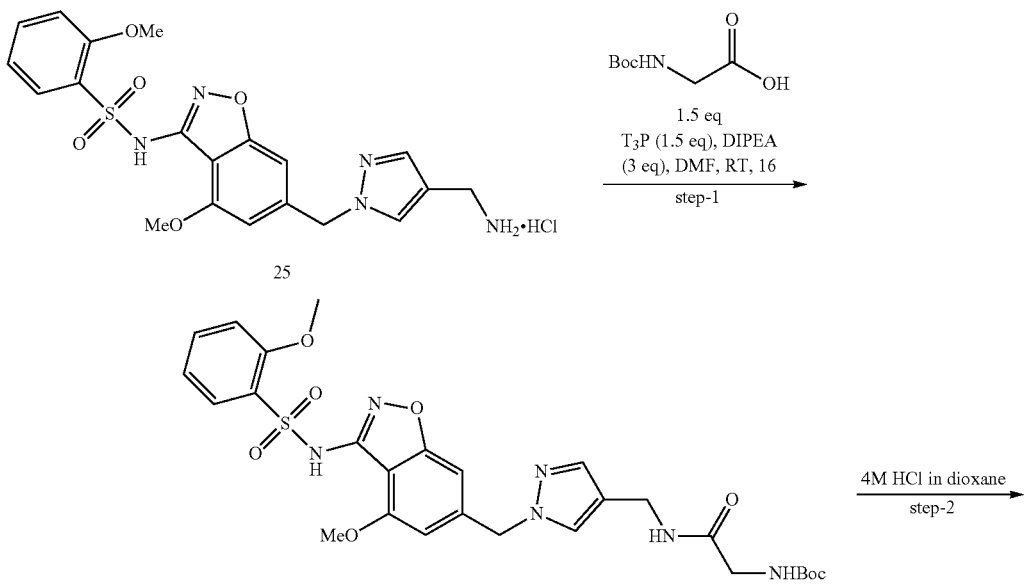

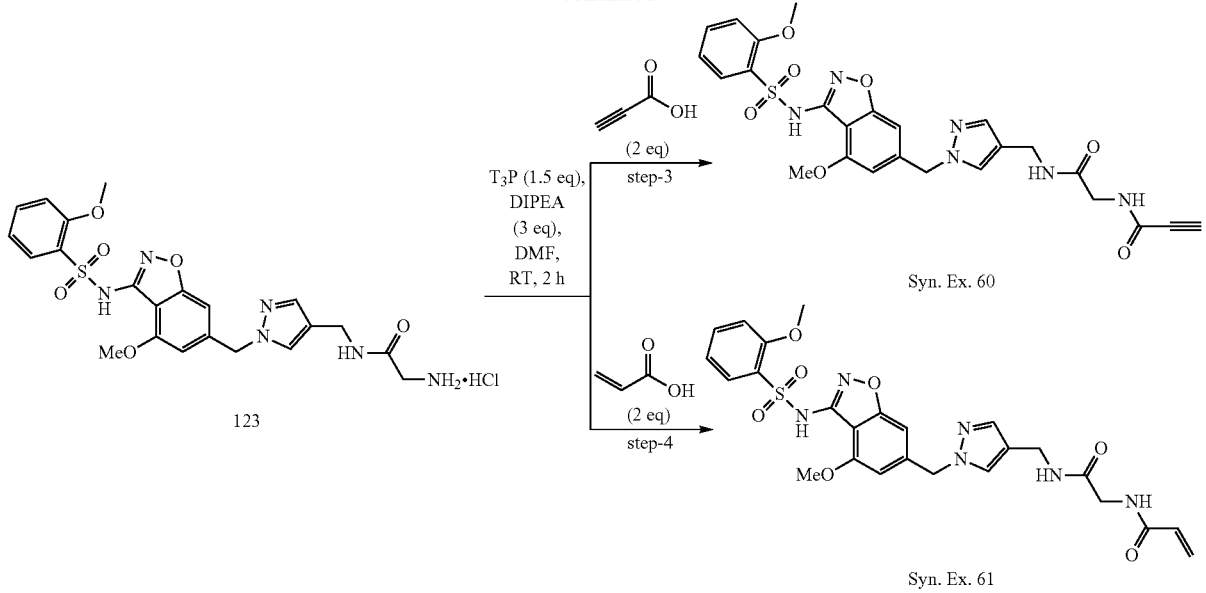

Synthesis of tert-butyl (2-(((1-((4-methoxy-3-((2-methoxyphenyl) sulfonamido) benzo[d]isoxazol-6-yl) methyl)-1H-pyrazol-4-yl) methyl) amino)-2-oxoethyl) carbamate (122)

To a stirred solution of compound 25 (0.12 g, 0.25 mmol) in DMF (1 mL) at 0° C. was added DIPEA (0.13 mL, 0.75 mmol) and (tert-butoxycarbonyl) glycine (29 mg, 0.16 mmol) followed by T₃P 50% solution in EtOAc (0.1 mL, 0.16 mmol). The reaction mixture was stirred at the room temperature for 16 h. After completion (monitored by TLC), the reaction mixture was quenched with aqueous ammonium chloride and extracted with ethyl acetate. The organic layer was dried over anhydrous Na₂SO₄ and concentrated to afford the title compound 122 (0.110 g, 74.07%) as a white solid. TLC: 10% MeOH/DCM (Rf: 0.5). LCMS Calculated for C27H32N6O8S: 600.20; Found: 601.5 (M+1).

Synthesis of 2-amino-N-[[1-[[4-methoxy-3-[(2-methoxyphenyl) sulfonylamino]-1,2-benzoxazol-6-yl]methyl]pyrazol-4-yl]methyl]acetamide; hydrochloride (123)

To a stirred solution of compound 122 (0.110 g, 0.183 mmol) in DCM (3 mL) at 0° C. was added 4M HCl in 1,4-dioxane (3 mL). The reaction was allowed to stir at room temperature for 2 h. After completion (monitored by TLC), the reaction mixture was concentrated under reduced pressure. The crude was triturated with diethyl ether and dried under reduced pressure to afford the title compound 123 (150 mg, HCl Salt) as a yellow solid. TLC: 15% MeOH/DCM (Rf: 0.3); LCMS Calculated for C22H25ClN6O6S: 536.12; Found: 501.8 (Freebase M+1).

Synthesis of N-(2-(((1-((4-methoxy-3-((2-methoxyphenyl)sulfonamido)benzo[d]isoxazol-6-yl)methyl)-1H-pyrazol-4-yl)methyl)amino)-2-oxoethyl)propiolamide To a stirred solution of 2-amino-N-((1-((4-methoxy-3-((2-methoxyphenyl) sulfonamido) benzo[d]isoxazol-6-yl) methyl)-1H-pyrazol-4-yl) methyl) acetamide hydrochloride 123 (60 mg, 0.11 mmol) in DMF (1 mL) at 0° C. was added DIPEA (0.058 mL, 0.33 mmol) followed by T₃P 50% solution in EtOAc (0.1 mL, 0.165 mmol), propiolic acid (15 mg, 0.22 mmol). The reaction mixture was stirred at the room temperature for 2 h. After completion (monitored by TLC), the reaction mixture was concentrated under reduced pressure. The crude was purified by using prep-HPLC to afford the title compound (4 mg, 6.55%) as a white solid. TLC: 10% MeOH/DCM (Rf: 0.5). (See Table 1 for analytical data).

Synthesis of N-[2-[[1-[[4-methoxy-3-[(2-methoxyphenyl)sulfonylamino]-1,2-benzoxazol-6-yl]methyl]pyrazol-4-yl]methylamino]-2-oxo-ethyl]prop-2-enamide To a stirred solution of 2-amino-N-((1-((4-methoxy-3-((2-methoxyphenyl) sulfonamido) benzo[d]isoxazol-6-yl) methyl)-1H-pyrazol-4-yl) methyl) acetamide hydrochloride 123 (60 mg, 0.11 mmol) in DMF (1 mL) at 0° C. was added DIPEA (0.058 mL, 0.33 mmol) and followed by T₃P 50% solution in EtOAc (0.1 mL, 0.165 mmol) and acrylic acid (15 mg, 0.22 mmol). The reaction mixture was stirred at the room temperature for 2 h. After completion monitored by TLC), the reaction mixture was concentrated under reduced pressure which was purified by using prep-HPLC to afford the title compound (13.2 mg, 21.63%) as a white solid. TLC: 10% MeOH/DCM (Rf: 0.5). (See Table 1 for analytical data).

Synthetic Example 62

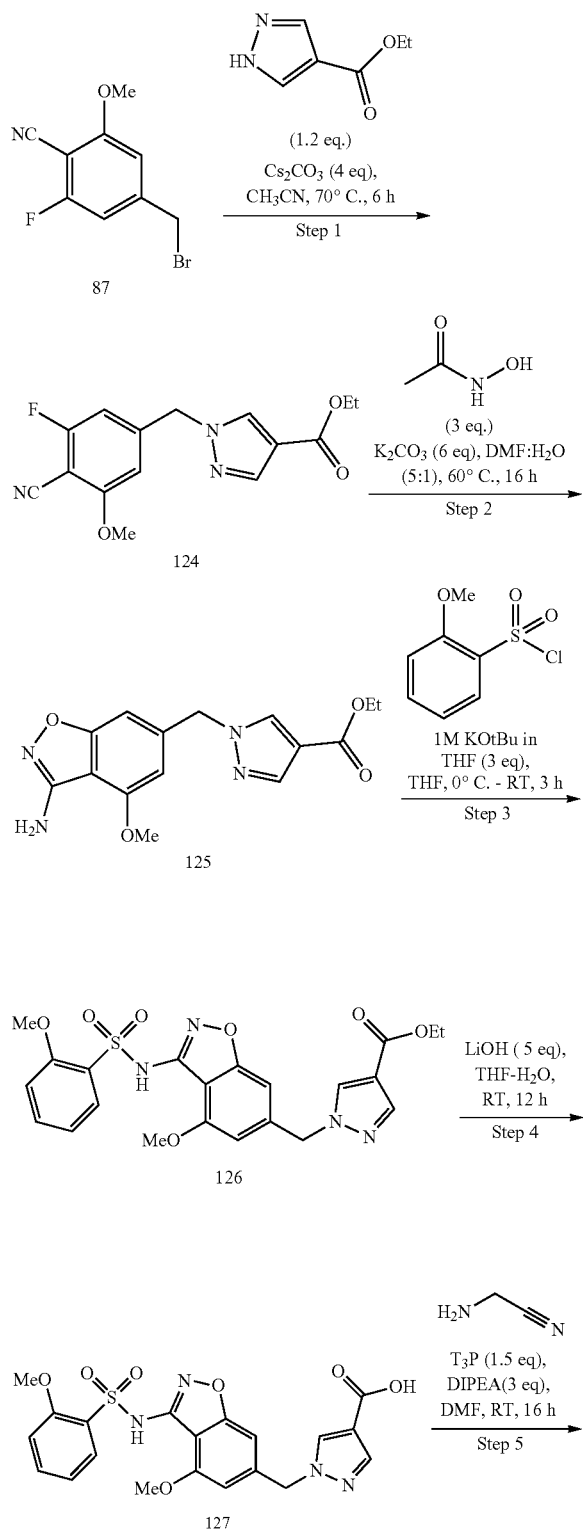

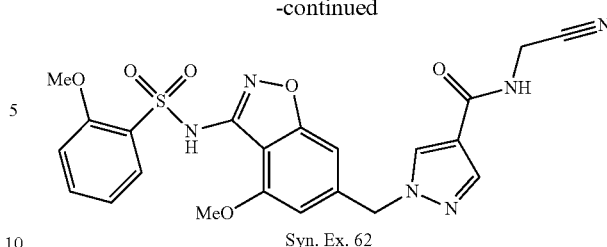

Syn. Ex. 62

Synthesis of ethyl 1-(4-cyano-3-fluoro-5-methoxybenzyl)-1H-pyrazole-4-carboxylate (124)

To a stirred solution of 4-(bromomethyl)-2-fluoro-6-methoxybenzonitrile 87 (1 g, 4.01 mmol) in acetonitrile (5 mL) at the room temperature was added $Cs_2CO_3$ (5.2 g, 16.04 mmol) followed by ethyl 1H-pyrazole-4-carboxylate (0.674 g, 4.81 mmol) and the reaction mixture was heated at 70° C. for 6 h. After completion (monitored by TLC), the reaction mixture was quenched with ice water and extracted with ethyl acetate. The organic layer was washed with brine, dried over anhydrous $Na_2SO_4$ and concentrated under reduced pressure. The crude compound was purified by Combi-flash chromatography using a gradient method of 40-70% EtOAc/Heptane to afford the title compound 124 (800 mg, 45.4%) as a brown semi solid. TLC: 80% EtOAc/Heptane (Rf: 0.45). LCMS Calculated for C15H14FN3O3: 303.10; Found: 304.08 (M+1).

Synthesis of ethyl 1-((3-amino-4-methoxybenzo[d]isoxazol-6-yl)methyl)-1H-pyrazole-4-carboxylate (125)

To a stirred solution of ethyl 1-(4-cyano-3-fluoro-5-methoxybenzyl)-1H-pyrazole-4-carboxylate 124 (800 mg, 2.63 mmol) in a 5:1 mixture of DMF:$H_2O$ (6 mL) at room temperature was added acetohydroxamic acid (59 mg, 7.91 mmol) followed by $K_2CO_3$ (2.18 g, 15.78 mmol). The reaction mixture was allowed to stir at 60° C. for 16 h. After completion (monitored by TLC), the reaction mixture was quenched with ice water and extracted with ethyl acetate. The organic layer was washed with brine, dried over anhydrous $Na_2SO_4$ and concentrated under reduced pressure. The crude compound was purified by Combi flash chromatography using a gradient method of 30-50% EtOAc/Heptane to afford the title compound 125 (800 g, 95.9%) as a brown semi solid. TLC: 80% EtOAc/Heptane (Rf: 0.40). LCMS Calculated for C15H16N4O4: 316.12; Found: 317.02 (M+1).

Synthesis of ethyl 1-((4-methoxy-3-((2-methoxyphenyl)sulfonamido)benzo[d]isoxazol-6-yl)methyl)-1H-pyrazole-4-carboxylate (126)

To a stirred solution of ethyl 1-((3-amino-4-methoxybenzo[d]isoxazol-6-yl) methyl)-1H-pyrazole-4-carboxylate 125 (0.800 g, 2.52 mmol) in THF (5 mL) at 0° C. was added 1M tBuOK in THF (7.5 mL, 7.58 mmol) followed by 2-methoxybenzenesulfonyl chloride (0.52 g, 3.02 mmol) and the reaction was allowed to stir at the room temperature for 3 h. After completion (monitored by TLC), the reaction mixture was quenched with water and extracted with Ethyl acetate. The organic layer was washed with brine, dried over anhydrous $Na_2SO_4$ and concentrated under reduced pressure. The crude compound was purified by Combi flash chromatography using a gradient method of 40-60% EtOAc/Heptane to afford the title compound 126 (300 mg, 24.39%) as a brown solid. TLC: 80% EtOAc/Heptane (Rf: 0.35). LCMS Calculated for C22H22N4O7S: 486.12; Found: 487.03 (M+1).

Synthesis of 1-((4-methoxy-3-((2-methoxyphenyl) sulfonamido)benzo[d]isoxazol-6-yl)methyl)-1H-pyrazole-4-carboxylic acid (127)

To a stirred solution of compound ethyl 1-((4-methoxy-3-((2-methoxyphenyl) sulfonamido)benzo[d]isoxazol-6-yl) methyl)-1H-pyrazole-4-carboxylate 126 (150 mg, 0.308 mmol) a mixture of (5:1) in THF-H$_2$O (6 mL) at 0° C., LiOH·H$_2$O (64 mg, 1.54 mmol) was added, and the reaction was allowed to stir at the room temperature for 12 h. After completion (monitored by TLC), the reaction mixture neutralized with 1N HCl ~pH 7.0 and extracted with Ethyl acetate. The organic layer was dried over anhydrous Na$_2$SO$_4$ and concentrated under reduced pressure. The crude compound was purified by Combi flash column chromatography using a gradient method of 3-5% MeOH/DCM to afford the title compound 127 (6 mg, 11.36%) as an off-white solid. TLC: 5% MeOH/DCM (Rf: 0.5). LCMS Calculated for C20H18N4O7S: 458.09; Found: 459.5 (M+1).

Synthesis of N-(cyanomethyl)-1-((4-methoxy-3-((2-methoxyphenyl) sulfonamido) benzo[d]isoxazol-6-yl) methyl)-1H-pyrazole-4-carboxamide To a stirred solution of 1-((4-methoxy-3-((2-methoxyphenyl) sulfonamido) benzo[d]isoxazol-6-yl) methyl)-1H-pyrazole-4-carboxylic acid 127 (60 mg, 0.130 mmol) in DMF (2 mL) at 0° C. was added DIPEA (0.068 mL, 0.39 mmol), pre-dissolved solution of 2-aminoacetonitrile (17 mg, 0.156 mmol) in DMF (0.5 mL), followed by HATU (74 mg, 0.195 mmol). The reaction was allowed to stir at the room temperature for 16 h. After completion (monitored by TLC), the reaction mixture was concentrated under reduced pressure. The crude compound was purified by using prep. HPLC to afford the title compound (15 mg, 23.43%) as an off-white solid. TLC: 10% MeOH/DCM (Rf: 0.5) (See analytical data for Table 1)

Synthetic Example 63

Scheme 42: Synthesis of N-(cyanomethyl)-1-((4-methoxy-3-((2-methoxyphenyl)sulfonamido)benzo[d]isoxazol-6-yl)methyl)piperidine-4-carboxamide

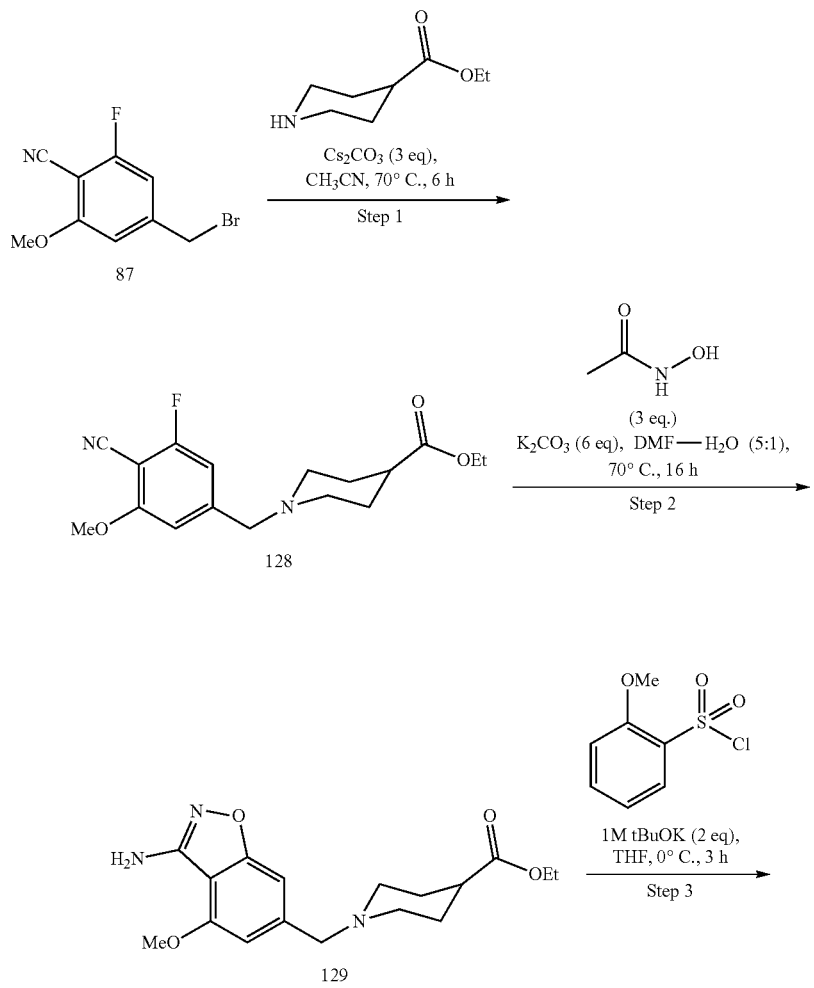

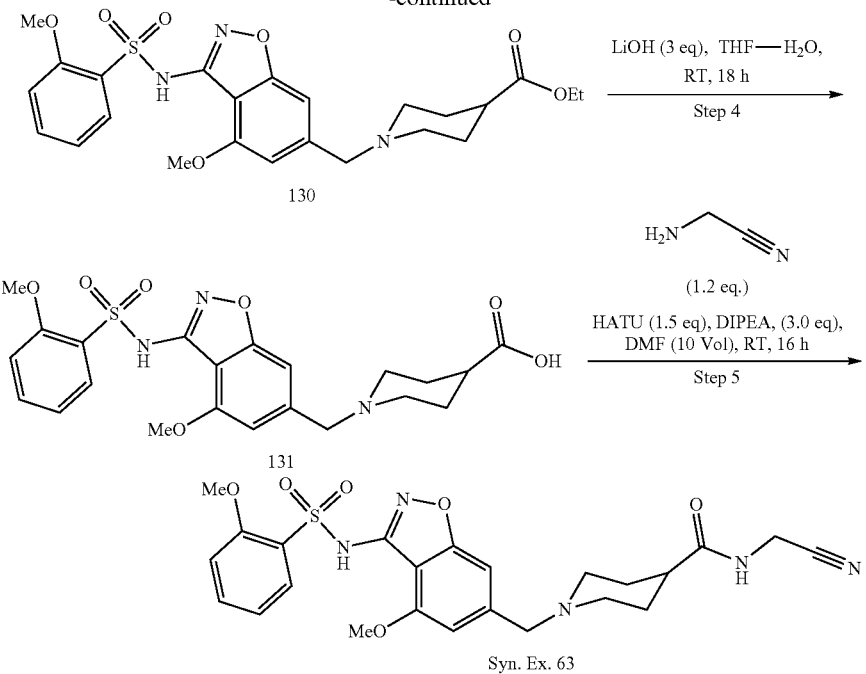

Syn. Ex. 63

Synthesis of ethyl 1-(4-cyano-3-fluoro-5-methoxybenzyl)piperidine-4-carboxylate (128)

To a stirred solution of 4-(bromomethyl)-2-fluoro-6-methoxybenzonitrile 87 (0.2 g, 0.819 mmol) in acetonitrile (5 mL) at the room temperature was added Cs$_2$CO$_3$ (0.8 g, 2.45 mmol) followed by ethyl 1-(methylsulfonyl) piperidine-4-carboxylate (0.231 g, 0.982 mmol) and reaction mixture was heated at 70° C. for 6 h. After completion (monitored by TLC), reaction mixture was quenched with ice water and extracted with ethyl acetate. The organic layer was washed with brine, dried over anhydrous Na$_2$SO$_4$ and concentrated under reduced pressure. The crude compound was purified by Combi-flash chromatography using a gradient method of 40-70% EtOAc/Heptane to afford the title compound 128 (0.180 g, 68.70%) as a brown semi solid. TLC: 80% EtOAc/Heptane (Rf: 0.45). LCMS Calculated for C17H21FN2O3: 320.15; Found: 321.02 (M+1).

Synthesis ethyl 1-((3-amino-4-methoxybenzo[d]isoxazol-6-yl)methyl)piperidine-4-carboxylate (129)

To a stirred solution of compound ethyl 1-(4-cyano-3-fluoro-5-methoxybenzyl)piperidine-4-carboxylate 128 (0.18 g, 0.56 mmol) in a 6:1 mixture of DMF:H$_2$O (7 mL) at the room temperature was added acetohydroxamic acid (0.126 g, 1.68 mmol) followed by K$_2$CO$_3$ (0.465 g, 3.37 mmol). The reaction mixture was allowed to stir at 60° C. for 16 h. After completion (monitored by TLC), the reaction mixture was quenched with ice water and extracted with ethyl acetate. The organic layer was washed with brine, dried over anhydrous Na$_2$SO$_4$ and concentrated under reduced pressure. The crude compound was purified by Combi flash chromatography using a gradient method of 30-60% EtOAc/Heptane to afford the title compound 129 (0.150 g, 80.21%) as an off-white solid. TLC: 80% EtOAc/Heptane (Rf: 0.40). LCMS Calculated for C17H23N3O4: 333.17; Found: 334.05 (M+1).

Synthesis ethyl 1-((4-methoxy-3-((2-methoxyphenyl)sulfonamido)benzo[d]isoxazol-6-yl)methyl)piperidine-4-carboxylate (130)

To a stirred solution of ethyl 1-((3-amino-4-methoxybenzo[d]isoxazol-6-yl)methyl)piperidine-4-carboxylate 129 (0.150 g, 0.449 mmol) in THF (3 mL) at 0° C. was added tBuOK 1 M in THF (0.9 mL, 0.899 mmol) followed by 2-methoxybenzenesulfonyl chloride (185 mg, 0.898 mmol) and the reaction was allowed to stir at 0° C. for 3 h. After completion (monitored by TLC), the reaction mixture was diluted with DCM, water was added and extracted. The organic layer was washed with brine, dried over anhydrous Na$_2$SO$_4$ and concentrated under reduced pressure. The crude compound was purified by Combi flash column chromatography using a gradient method of 40-60% EtOAc/Heptane to afford the title compound 130 (120 mg, 54.09%) as an off-white solid. TLC: 80% EtOAc/Heptane (Rf: 0.35). LCMS Calculated for C$_{24}$H$_{29}$N3O7S: 503.17; Found: 504.03 (M+1).

Synthesis 1-((4-methoxy-3-((2-methoxyphenyl)sulfonamido)benzo[d]isoxazol-6-yl)methyl)piperidine-4-carboxylic acid (131)

To a stirred solution of ethyl 1-((4-methoxy-3-((2-methoxyphenyl)sulfonamido)benzo[d]isoxazol-6-yl)methyl)piperidine-4-carboxylate 130 (120 mg, 0.238 mmol) in a mixture of (5:1) in THF-H$_2$O (6 mL) at 0° C., LiOH·H$_2$O (30 mg, 0.714 mmol) was added. The reaction was allowed to stir at the room temperature for 12 h. After completion (monitored by TLC), the reaction mixture was neutralized with 1N HCl~pH 7.0 and extracted with Ethyl acetate. The organic layer was dried over anhydrous Na2SO4 and concentrated under reduced pressure. The crude compound was purified by Combi flash column chromatography using a gradient method of 3-5% MeOH/DCM to afford the title compound 131 (100 mg, 88.49%) as an off-white solid. TLC: 5% MeOH/DCM (Rf: 0.5). LCMS Calculated for C22H25N3O7S: 475.14; Found: 476.05 (M+1).

Synthesis of N-(cyanomethyl)-1-((4-methoxy-3-((2-methoxyphenyl)sulfonamido)benzo[d]isoxazol-6-yl)methyl)piperidine-4-carboxamide To a stirred solution of 1-((4-methoxy-3-((2-methoxyphenyl)sulfonamido)benzo[d]isoxazol-6-yl)methyl)piperidine-4-carboxylic acid 131 (100 mg, 0.210 mmol) in DMF (2 mL) at 0° C. was added DIPEA (0.11 mL, 0.630 mmol), pre-dissolved solution of 2-aminoacetonitrile (14 mg, 0.252 mmol) in DMF (0.5 mL), followed by HATU (119 mg, 0.315 mmol). The reaction was allowed to stir at the room temperature for 16 h. After completion (monitored by TLC), the reaction mixture was concentrated under reduced pressure. The crude compound was purified using prep HPLC to afford the title compound (8.5 mg, 23.43%) as an off-white solid. TLC: 10% MeOH/DCM (Rf: 0.5) (See Table 1 for analytical data).

Synthetic Example 64

Scheme 43: Synthesis of N-(1-((4-methoxy-3-((2-methoxyphenyl) sulfonamido) benzo[d]isoxazol-6-yl) methyl) piperidin-4-yl) propiolamide

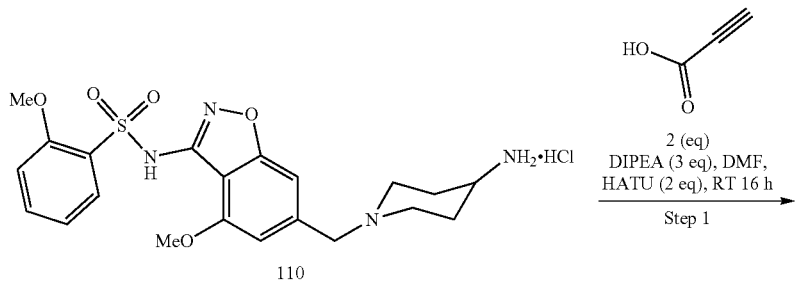

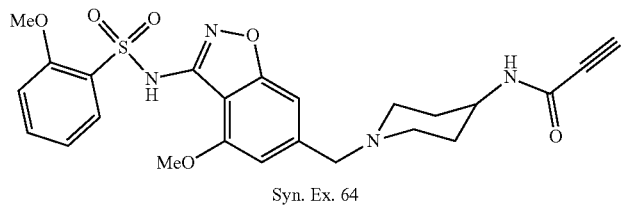

Syn. Ex. 64

To a stirred solution of compound N-[6-[(4-amino-1-piperidyl)methyl]-4-methoxy-1,2-benzoxazol-3-yl]-2-methoxy-benzenesulfonamide 110 (50 mg, 0.103 mmol) in DMF (1 mL) at 0° C. was added DIPEA (0.054 mL, 0.310 mmol) and pre-dissolved solution of propiolic acid (14 mg, 0.206 mmol) in DMF (0.5 mL), followed by HATU (78 mg, 0.206 mmol). The reaction was allowed to stir at the room temperature for 16 h. After completion (reaction monitored by TLC), reaction mixture was concentrated under reduced pressure. The crude compound was purified by using prep HPLC to afford the title compound (15 mg, 29.41%) as an off-white solid. TLC: 10% MeOH/DCM (Rf: 0.5) LCMS Calculated for C24H26N4O6S: 498.16; Found: 499.2 (M+1). (See Table 1 for analytical data)

Synthetic Example 65
Scheme 44: Synthesis of 3-methoxy-4-(N-(4-methoxy-6-((4-(propiolamidomethyl)-1H-pyrazol-1-yl)methyl)benzo[d]isoxazol-3-yl)sulfamoyl)benzoic acid
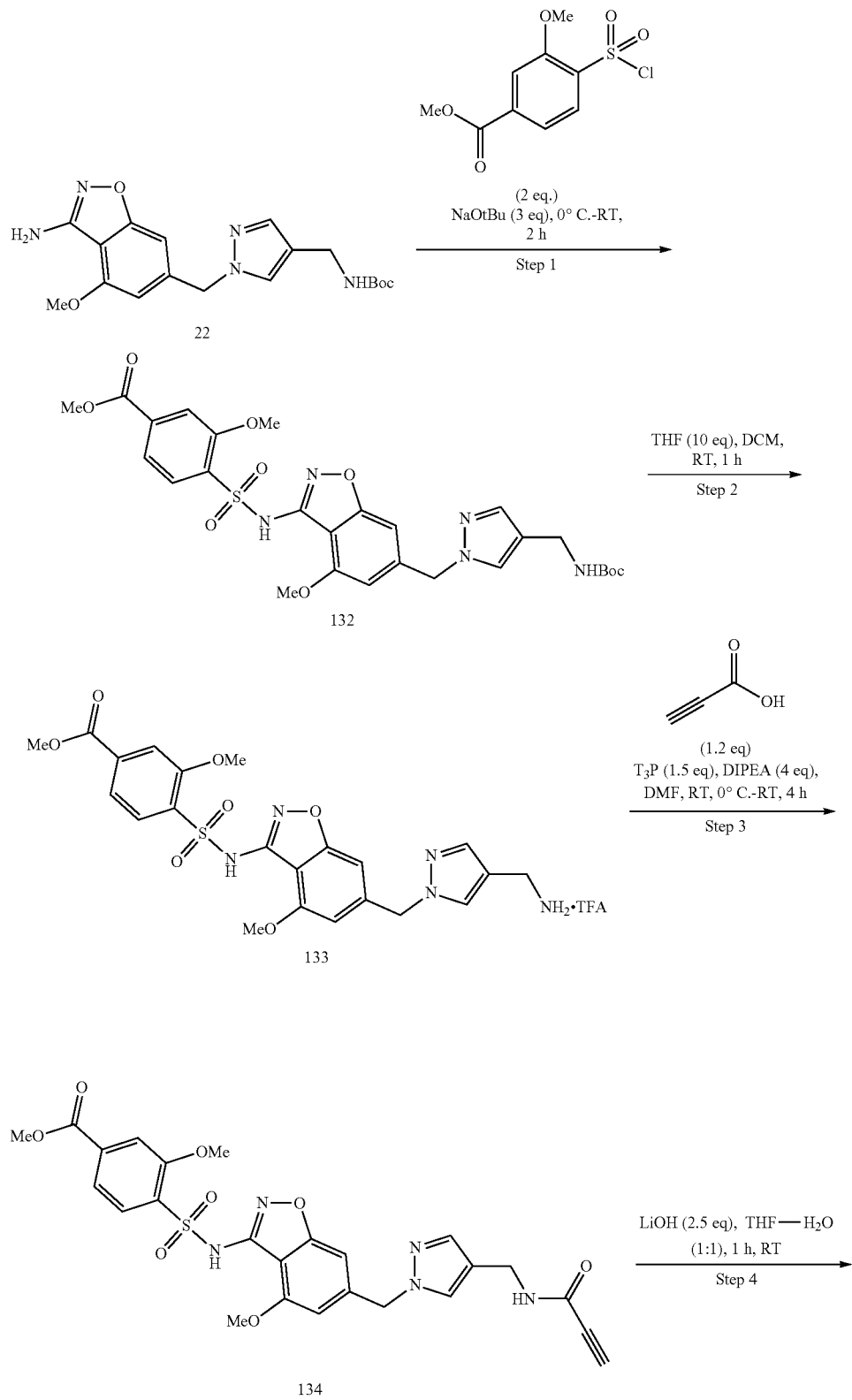

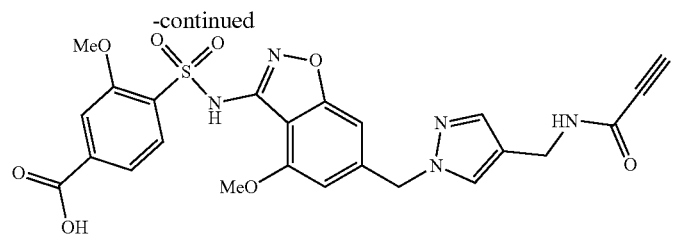

Syn. Ex. 65

Synthesis of methyl 4-(N-(6-((4-(((tert-butoxycarbonyl)amino)methyl)-1H-pyrazol-1-yl)methyl)-4-methoxybenzo[d]isoxazol-3-yl)sulfamoyl)-3-methoxybenzoate (132)

To a stirred solution of tert-butyl ((1-((3-amino-4-methoxybenzo[d]isoxazol-6-yl) methyl)-1H-pyrazol-4-yl) methyl) carbamate 22 (200 mg, 0.5356 mmol) in THF (3 mL) at 0° C. was added NaOtBu (154 mg, 1.6068 mmol) followed by methyl 4-(Chloro sulfonyl)-3-methoxybenzoate (283 mg, 1.0712 mmol). The reaction was allowed to stir at room temperature for 2 h. After completion (monitored by TLC), the reaction mixture was quenched with ice-water and extracted with ethyl acetate. The organic layer was dried over anhydrous $Na_2SO_4$ and concentrated under reduced pressure. The crude was purified by Combi flash chromatography to afford the title compound 132 (180 g, 55.90%) as an off-white solid. TLC: 100% EtOAc (Rf: 0.5) LCMS Calculated for C27H31N5O9S: 601.18; Found: 602.5 (M+1).

Synthesis of methyl 3-methoxy-4-(N-(4-methoxy-6-((4-(((2,2,2-trifluoroacetyl)-14-azaneyl)methyl)-1H-pyrazol-1-yl)methyl)benzo[d]isoxazol-3-yl)sulfamoyl)benzoate (133)

To a stirred solution of compound methyl 4-(N-(6-((4-(((tert-butoxycarbonyl) amino)methyl)-1H-pyrazol-1-yl) methyl)-4-methoxybenzo[d]isoxazol-3-yl)sulfamoyl)-3-methoxybenzoate 132 (90 mg, 0.1495 mmol) in DCM (1 mL) at 0° C. was added TFA (0.12 mL, 1.49 mmol). The reaction was stirred at room temperature for 1 h. After completion (monitored by TLC), the reaction mixture was concentrated under reduced pressure to afford title compound 133 (92 mg, 100%, LCMS Calculated for C24H23F3N5O8S: 598.12; Found: 502.5 (M+1).

Synthesis of methyl-3-methoxy-4-(N-(4-methoxy-6-((4-(propiolamidomethyl)-1H-pyrazol-1-yl) methyl) benzo[d]isoxazol-3-yl) sulfamoyl)benzoate (134)

To a stirred solution of methyl 3-methoxy-4-(N-(4-methoxy-6-((4-(((2,2,2-trifluoroacetyl)-14-azaneyl) methyl)-1H-pyrazol-1-yl)methyl)benzo[d]isoxazol-3-yl) sulfamoyl)benzoate 133 (80 mg, 0.133 mmol) in DMF (1 mL) at 0° C. was added propiolic acid (11 mg, 0.160 mmol), DIPEA (0.09 mL, 0.532 mmol) followed by $T_3P$ 50% solution in EtOAc (0.126 g, 0.199 mmol). The reaction was allowed to stir at the room temperature for 4 h. After completion (monitored by TLC), the reaction mixture was quenched with ice-water and extracted with ethyl acetate. The organic layer was dried over anhydrous $Na_2SO_4$ and concentrated under reduced pressure to afford the title compound 134 (45 mg, crude) as a white solid. TLC: 80% EtOAc/Heptane (Rf: 0.4 LCMS Calculated for C25H23N5O8S: 553.13; Found: 554.8 (M+1). Crude material used in the next step further any purification Synthesis of 3-methoxy-4-(N-(4-methoxy-6-((4-(propiolamidomethyl)-1H-pyrazol-1-yl)methyl) benzo[d]isoxazol-3-yl)sulfamoyl)benzoic acid To a stirred solution of methyl-3-methoxy-4-(N-(4-methoxy-6-((4-(propiolamidomethyl)-1H-pyrazol-1-yl) methyl) benzo[d]isoxazol-3-yl) sulfamoyl) benzoate 134 (45 mg, 0.0182 mmol) in a 1:1 mixture of THF-$H_2O$ (2 mL) was added LiOH·$H_2O$ (8.5 mg, 0.203 mmol). The reaction mixture was stirred at the room temperature for 1 h. The progress of the reaction was monitored by TLC. The reaction mixture was neutralized with 2 N HCl and extracted with ethyl acetate. The organic layer was dried over anhydrous $Na_2SO_4$ and concentrated under reduced pressure. The crude was purified by prep-HPLC purification to afford the title compound (6.2 mg, 14.41%) as an off-white solid. TLC: 100% EtOAc/Heptane (Rf: 0.2) (See Table 1 for analytical data).

Synthetic Example 66

Scheme 45: Synthesis of N-((1-((5-methoxy-3-((2-methoxyphenyl) sulfonamido)-[1,2,4]triazolo[4,3-a]pyridin-7-yl)methyl)-1H-pyrazol-4-yl)methyl)propiolamide

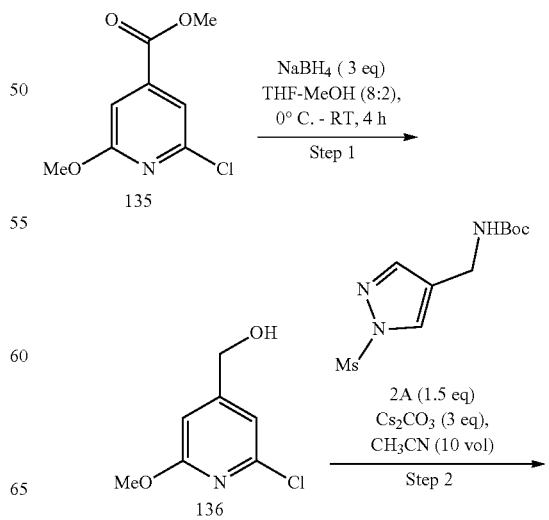

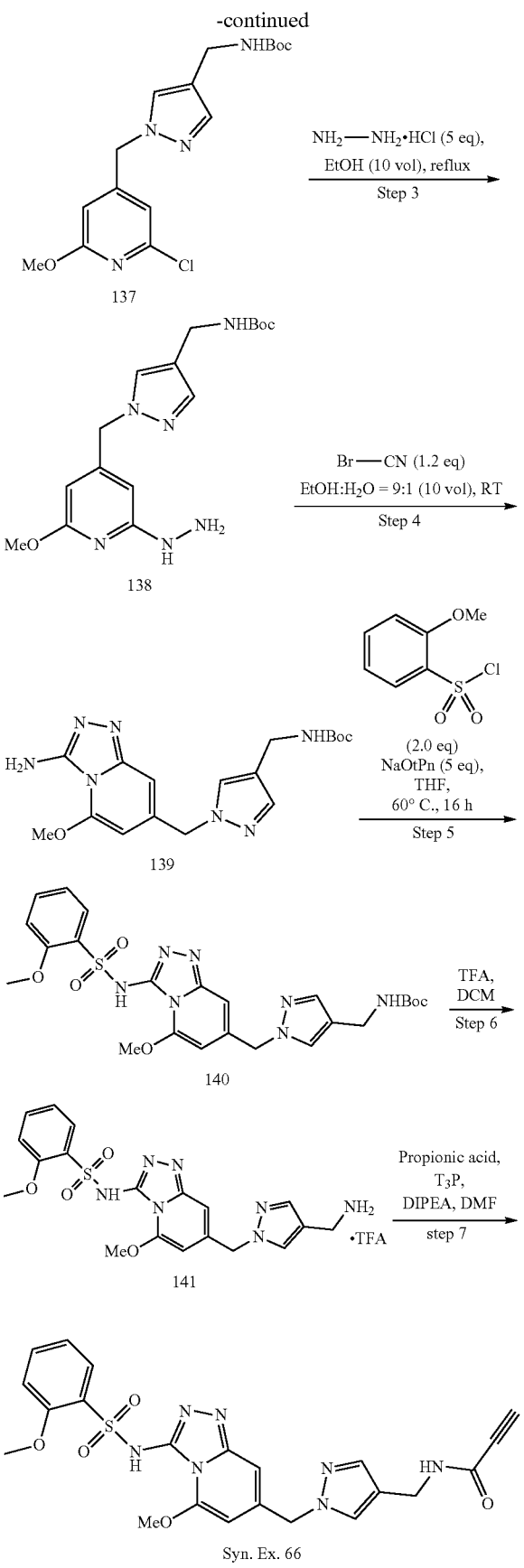

Synthesis (2-chloro-6-methoxypyridin-4-yl)methanol (136)

To a stirred solution of compound 135 (5 g, 29.00 mmol) in THF (50 mL) at 0° C. was added NaBH₄ (1.6 g, 44.00 mmol) and the resulting reaction mixture was stirred at 0° C. for 2 h. After completion of the reaction (monitored by TLC), the reaction mixture was neutralized with 1N HCl and extracted with ethyl acetate. The organic layer was washed with brine, dried over anhydrous Na₂SO₄ and concentrated under reduced pressure to afford the title compound 136 (4.5 g, 88.93%) as a yellow solid. TLC: 30% EtOAc/Heptane (Rf: 0.35). LCMS Calculated for C7H8ClNO2: 173.02; Found: 172.8 (M+1).

Synthesis of tert-butyl ((1-((2-chloro-6-methoxy-pyridin-4-yl) methyl)-1H-pyrazol-4-yl) methyl) carbamate (137)

To a stirred solution of compound 136 (4.5 g, 25.91 mmol) in ACN (50 mL) at 0° C. was added Cs₂CO₃ (25.32 g, 77.73 mmol), tert-butyl ((1-(methylsulfonyl)-1H-pyrazol-4-yl) methyl) carbamate (8.5 g, 31.09 mmol) and the resulting reaction mixture was stirred at 0° C. for 2 h. After completion (monitored by TLC), the reaction mixture was quenched with ice water and extracted with ethyl acetate. The organic layer was washed with brine, dried over anhydrous Na₂SO₄ and concentrated under reduced pressure to afford the title compound 137 (2 g, 21.88%) as a yellow solid. TLC: 40% EtOAc/Heptane (Rf: 0.35). LCMS Calculated for C16H21ClN4O3: 352.13; Found: 353.9 (M+1).

Synthesis of tert-butyl ((1-((2-hydrazineyl-6-methoxypyridin-4-yl) methyl)-1H-pyrazol-4-yl) methyl)carbamate (138)

To a stirred solution of compound 137 (0.5 g, 1.41 mmol) in EtOH (5 mL) at 0° C. was added hydrazine hydrate (0.1 mL, 2.12 mmol) and the resulting reaction mixture was stirred at 70° C. for 16 h. After completion (monitored by TLC), the reaction mixture was concentrated under reduced pressure and extracted with ethyl acetate. The organic layer was dried over anhydrous Na₂SO₄ and concentrated under reduced pressure to afford the title compound 138 (0.3 g, 60.85%) as a yellow solid. TLC: 30% EtOAc/Heptane (Rf: 0.35). LCMS Calculated for C16H24N6O3: 348.19; Found: 349.2 (M+1).

Synthesis of tert-butyl ((1-((3-amino-5-methoxy-[1,2,4]triazolo[4,3-a]pyridin-7-yl) methyl)-1H-pyrazol-4-yl) methyl) carbamate (139)

To a stirred solution of compound 138 (500 mg, 1.435 mmol) in mixture of (4:1) EtOH:H₂O (5 mL) at room temperature was added Cyanogen Bromide (182 mg, 1.72 mmol) and the resulting reaction mixture was stirred at room temperature for 16 h. After completion (monitored by TLC), the reaction mixture was concentrated under reduced pressure and extracted with ethyl acetate. The organic layer was dried over anhydrous Na₂SO₄ and concentrated under reduced pressure to afford the title compound 139 (260 mg, 48.59%) as an off-white solid. TLC: 40% EtOAc/Heptane (Rf: 0.3). LCMS Calculated for C17H23N7O3: 373.19; Found: 374.1 (M+1).

Synthesis of tert-butyl ((1-((5-methoxy-3-((2-methoxyphenyl)sulfonamido)-[1,2,4]triazolo[4,3-a]pyridin-7-yl)methyl)-1H-pyrazol-4-yl)methyl)carbamate (140)

To a stirred solution of compound 139 (260 mg, 0.696 mmol) in THF (5 mL) was added sodium tert-Pentoxide (383 mg, 3.48 mmol) followed by 2-methoxybenzenesulfonyl chloride (287 mg, 1.39 mmol) and the reaction mixture was allowed to stir at 60° C. for 16 h. After completion (reaction monitored by TLC), the reaction mixture was quenched with ice water and extracted with ethyl acetate. The organic layer was dried over anhydrous Na$_2$SO$_4$ and concentrated under reduced pressure. The crude compound was purified by combi flash chromatography (neutral alumina) to afford the title compound 140 (160 mg, 42.32%) as a yellow solid. TLC: 80% EtOAc/Heptane (Rf: 0.6). LCMS Calculated for C24H29N7O6S: 543.19; Found: 544.5 (M+1).

Synthesis of 2-methoxy-N-(5-methoxy-7-((4-(((2,2,2-trifluoroacetyl)-14-azaneyl)methyl)-1H-pyrazol-1-yl)methyl)-[1,2,4]triazolo[4,3-a]pyridin-3-yl)benzenesulfonamide (141)

To a stirred solution of compound 140 (70 mg, 0.129 mmol) in DCM (3 mL) at room temperature, TFA (0.2 mL, 1.29 mmol) was added and the reaction mixture was allowed to stir at room temperature for 2 h. After completion (monitored by TLC), the reaction mixture was concentrated under reduced pressure to afford the title compound 141 (70 mg, TFA salt) as a brown liquid. TLC: 10% MeOH/DCM (Rf: 0.5). LCMS Calculated for C21H20F3N7O5S: 539.12; Found: NA.

Synthesis of N-((1-((5-methoxy-3-((2-methoxyphenyl)sulfonamido)-[1,2,4]triazolo[4,3-a]pyridin-7-yl)methyl)-1H-pyrazol-4-yl)methyl)propiolamide To a stirred solution of compound 141 (70 mg, 0.129 mmol) in DMF (3 mL) at room temperature was added DIPEA (0.067 mL, 0.389 mmol), T$_3$P 50% solution in EtOAc (0.123 mL, 0.193 mmol) followed by propiolic acid (10 mg, 0.154 mmol) and the reaction was allowed to stir at the room temperature for 4 h. After completion (monitored by TLC), the reaction mixture was quenched with ice-water and extracted with ethyl acetate. The organic layer was washed with brine, dried over anhydrous Na$_2$SO$_4$, and concentrated to afford the title compound (14 mg, 21.87%) as a white solid. TLC: 10% MeOH/DCM (Rf: 0.5). (See Table 1 for analytical data).

Synthetic Example 67

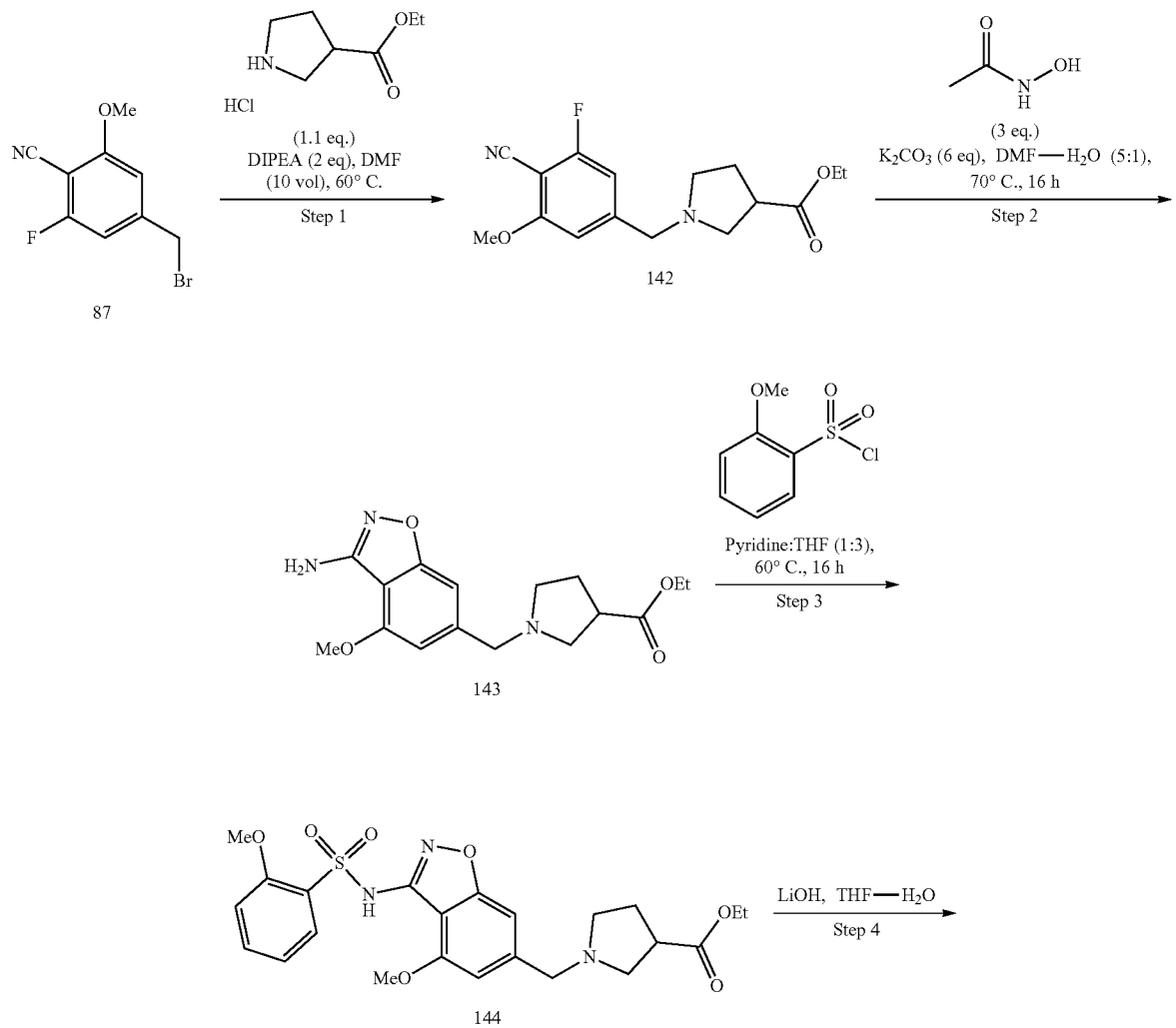

Scheme 46: Synthesis of N-(cyanomethyl)-1-((4-methoxy-3-((2-methoxyphenyl)sulfonamido) benzo[d]isoxazol-6-yl) methyl) pyrrolidine-3-carboxamide

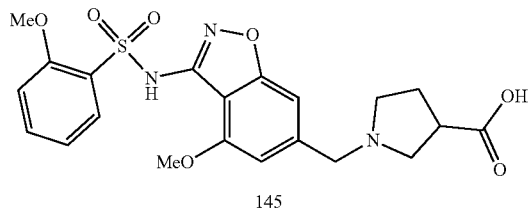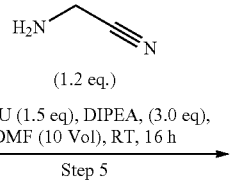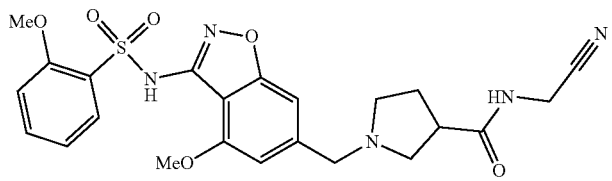

Syn. Ex. 67

Synthesis of ethyl 1-(4-cyano-3-fluoro-5-methoxybenzyl)pyrrolidine-3-carboxylate (142)

To a stirred solution of 4-(bromomethyl)-2-fluoro-6-methoxybenzonitrile 87 (1.5 g, 6.14 mmol) in DMF (10 mL) at the room temperature was added DIPEA (2.14 mL, 12.29 mmol), followed by ethyl 1-(12-chloraneyl) pyrrolidine-3-carboxylate (1.2 g, 6.75 mmol) and the resulting reaction mixture was heated at 60° C. for 16 h. After completion (monitored by TLC), the reaction mixture was quenched with ice cold water and extracted with ethyl acetate. The organic layer was washed with brine, dried over anhydrous $Na_2SO_4$ and concentrated under reduced pressure to afford the title compound 142 (1.3 g, 69.14%) as a yellow solid. TLC: 100% EtOAc (Rf: 0.5). LCMS Calculated for C16H19FN2O3: 306.14; Found: 307.4 (M+1).

Synthesis of ethyl 1-((3-amino-4-methoxybenzo[d]isoxazol-6-yl) methyl)pyrrolidine-3-carboxylate (143)

To a stirred solution of ethyl 1-(4-cyano-3-fluoro-5-methoxybenzyl)pyrrolidine-3-carboxylate 142 (1.3 g, 4.24 mmol) in 6:1 mixture of DMF:H₂O (7 mL) at room temperature was added N-hydroxy acetamide (0.955 g, 12.73 mmol) and followed by $K_2CO_3$ (3.5 g, 25.44 mmol). The reaction mixture was allowed to stir at 70° C. for 16 h. After completion (monitored by TLC), the reaction mixture was poured in ice water and extracted with ethyl acetate. The organic layer was washed with brine, dried over anhydrous $Na_2SO_4$ and concentrated under reduced pressure. The crude compound was purified by Combi flash chromatography using a gradient method of 70% EtOAc/Heptane to afford the title compound 143 (600 mg, 46.15%) as a brown solid. TLC: 100% EtOAc (Rf: 0.50); LCMS Calculated for $C_{16}H_{21}N_3O_4$: 319.15; Found: 320.02 (M+1).

Synthesis of ethyl 1-((4-methoxy-3-((2-methoxyphenyl)sulfonamido)benzo[d]isoxazol-6-yl)methyl)pyrrolidine-3-carboxylate (144)

To a stirred solution of ethyl 1-((3-amino-4-methoxybenzo[d]isoxazol-6-yl)methyl)pyrrolidine-3-carboxylate 143 (600 mg, 1.87 mmol) in mixture of THF:pyridine (20 mL, 3:1) at room temperature was added 2-methoxybenzenesulfonyl chloride (465 mg, 2.25 mmol). The reaction was allowed to stir at 60° C. for 16 h. After completion (monitored by TLC), the reaction mixture was neutralized with 1N HCl and extracted with ethyl acetate. The organic layer was washed with brine, dried over anhydrous $Na_2SO_4$, and concentrated under reduced pressure. The crude compound was purified by Combi flash column chromatography using a gradient method of 40-48% EtOAc/Heptane to afford the title compound 144 (300 mg, 61.11%) as a white solid. TLC: 80% EtOAc/Heptane (Rf: 0.4); LCMS Calculated for C23H27N3O7S: 489.16; Found: 490.01 (M+1).

1-((4-methoxy-3-((2-methoxyphenyl)sulfonamido)benzo[d]isoxazol-6-yl)methyl)pyrrolidine-3-carboxylic acid (145)

To a stirred solution of ethyl 1-((4-methoxy-3-((2-methoxyphenyl)sulfonamido)benzo[d]isoxazol-6-yl)methyl)pyrrolidine-3-carboxylate 144 (0.3 g, 0.612 mmol) in a 1:1 mixture of THF-H₂O (5 mL) was added LiOH·H₂O (77 mg, 1.83 mmol). The reaction mixture was stirred at the room temperature for 16 h. The progress of the reaction was monitored by TLC. After completion, the reaction mixture was quenched with citric acid and concentrated under reduced pressure. The crude was purified by combi-flash chromatography 10-15% of MeOH/DCM to afford the title compound 145 (0.250 g, 88.65%) as an off-white solid. TLC: 5% MeOH/DCM (Rf: 0.2) LCMS Calculated for $C_{21}H_{23}N3O7S$: 461.13; Found: 462.4 (M+1).

Synthesis of N-(cyanomethyl)-1-((4-methoxy-3-((2-methoxyphenyl) sulfonamido) benzo[d]isoxazol-6-yl) methyl) pyrrolidine-3-carboxamide To a stirred solution of 1-((4-methoxy-3-((2-methoxyphenyl)sulfonamido)benzo[d]isoxazol-6-yl)methyl)pyrrolidine-3-carboxylic acid 145 (50 mg, 0.108 mmol) in DMF (2 mL) at 0° C. was added 2-aminoacetonitrile (7 mg, 0.130 mmol), DIPEA (0.055 mL, 0.324 mmol) followed by HATU (123 mg, 0.324 mmol). The reaction was allowed to stir at the room temperature for 16 h. After completion of the reaction (monitored by TLC), the mixture was concentrated under reduced pressure. The crude was purified by using combi-flash chromatography 10-15% EtOAc/Heptane to afford the title compound (3 mg, 5.55%) as an off-white gummy solid. TLC: 10% MeOH/DCM (Rf: 0.6). (See Table 1 for analytical data).

Synthetic Example 68
Scheme 47: Synthesis of 2-(N-(4-methoxy-6-((4-(propiolamidomethyl)-1H-pyrazol-1-yl)methylbenzo[d]isoxazol-3-yl)sulfamoyl)-N-methylbenzamide
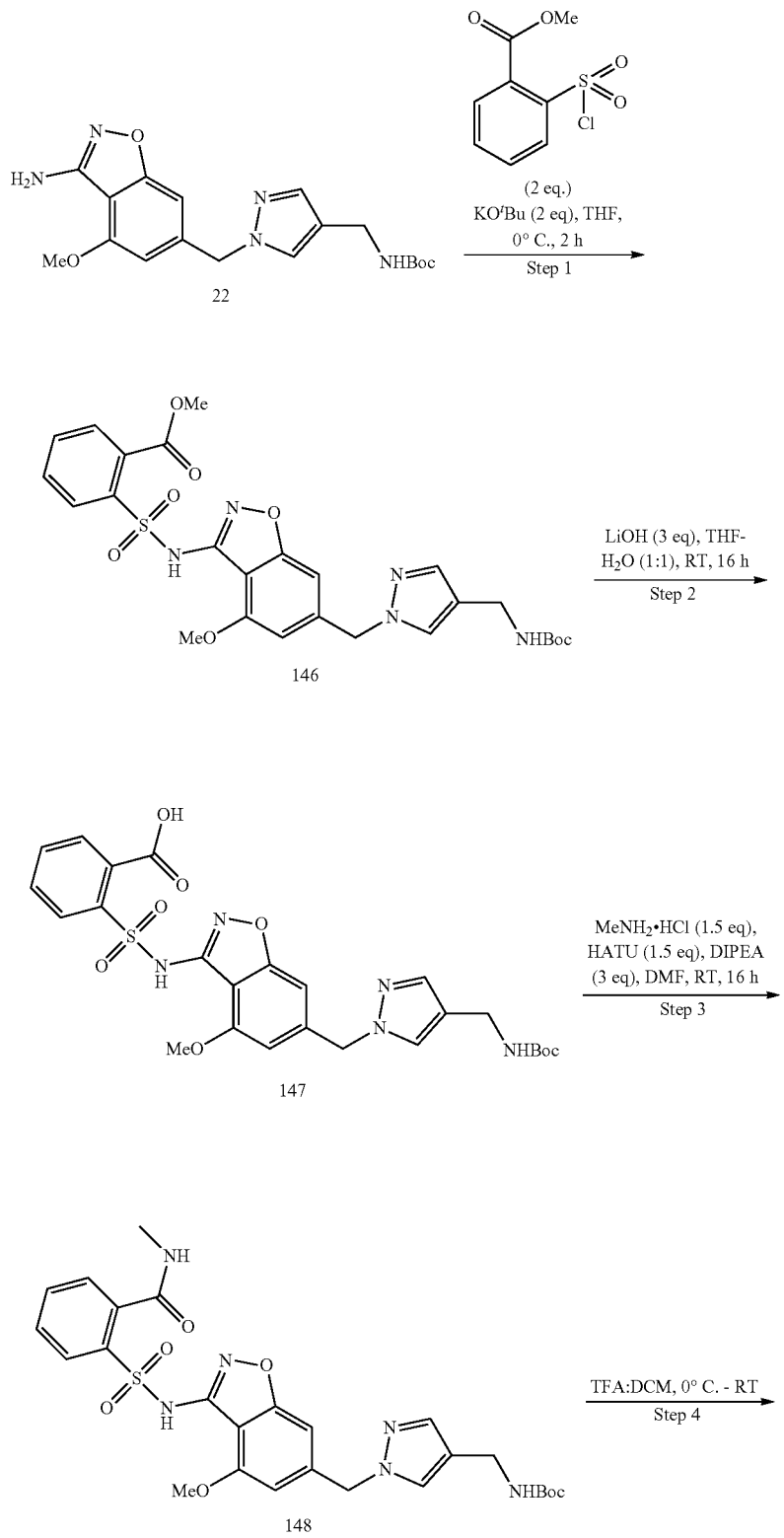

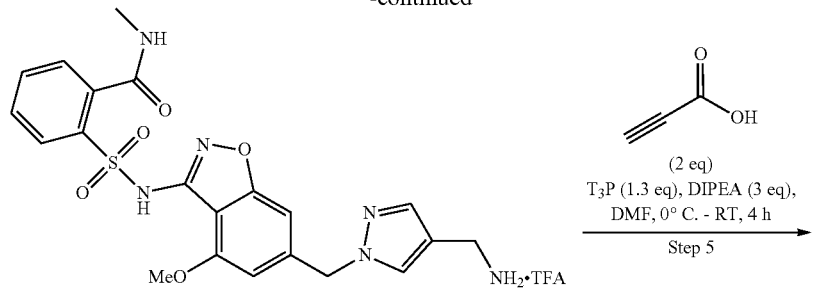

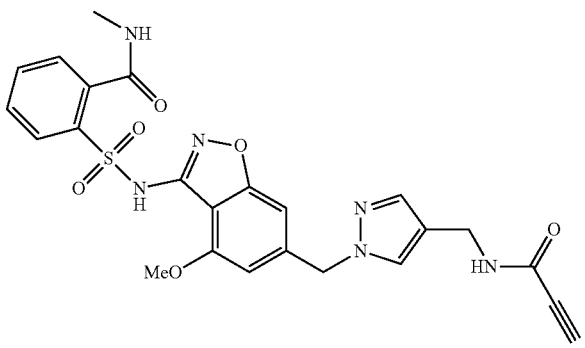

Syn. Ex. 68

Synthesis of methyl 2-(N-(6-((4-(((tert-butoxycarbonyl) amino) methyl)-1H-pyrazol-1-yl) methyl)-4-methoxybenzo[d]isoxazol-3-yl) sulfamoyl) benzoate (146)

To a stirred solution of tert-butyl ((1-((3-amino-4-methoxybenzo[d]isoxazol-6-yl)methyl)-1H-pyrazol-4-yl) methyl)carbamate 22 (0.5 g, 1.33 mmol) in THF (3 mL) at 0° C. was added 1.0 M solution of KOtBu (2.67 mL, 2.67 mmol) in THF followed by methyl 2-(chlorosulfonyl)benzoate (0.624 mg, 2.66 mmol). The reaction was allowed to stir at room temperature for 2 h. After completion (monitored by TLC), the reaction mixture was quenched with water and extracted with ethyl acetate. The organic layer was dried over anhydrous $Na_2SO_4$ and concentrated under reduced pressure. The crude was purified by Combi flash (100-200 mesh) column chromatography using a gradient method of 20-80% EtOAc/Heptane to afford the title compound 146 (0.3 g, 27.42%) as an off-white solid. TLC: 80% EtOAc/Heptane (Rf: 0.5). LCMS Calculated for C26H29N5O8S: 571.17; Found: 572.8 (M+1).

Synthesis 2-(N-(6-((4-(((tert-butoxycarbonyl)amino) methyl)-1H-pyrazol-1-yl)methyl)-4-methoxybenzo [d]isoxazol-3-yl)sulfamoyl)benzoic acid (147)

To a stirred solution of methyl 2-(N-(6-((4-(((tert-butoxycarbonyl) amino) methyl)-1H-pyrazol-1-yl) methyl)-4-methoxybenzo[d]isoxazol-3-yl) sulfamoyl) benzoate 146 (0.3 g, 0.52 mmol) in a 1:1 mixture of $THF-H_2O$ (2 mL) was added $LiOH \cdot H_2O$ (66 mg, 1.57 mmol). The reaction mixture was stirred at the room temperature for 16 h. The progress of the reaction was monitored by TLC. After completion (monitored by TLC), the reaction mixture was quenched with citric acid concentrated under reduced pressure. The crude was purified by combi-flash chromatography 10-15% of MeOH/DCM to afford the title compound 147 (0.250 g, 85.61%) as a brown semi solid. TLC: 5% MeOH/DCM (Rf: 0.2) LCMS Calculated for C25H27N5O8S: 557.16; Found: 558.4 (M+1).

Synthesis of tert-butyl ((1-((4-methoxy-3-((2-(methylcarbamoyl) phenyl) sulfonamido) benzo[d]isoxazol-6-yl) methyl)-1H-pyrazol-4-yl) methyl) carbamate (148)

To a stirred solution of 2-(N-(6-((4-(((tert-butoxycarbonyl) amino) methyl)-1H-pyrazol-1-yl) methyl)-4-methoxybenzo[d]isoxazol-3-yl) sulfamoyl) benzoic acid 147 (0.15 g, 0.269 mmol) in DMF (5 mL) at 0° C. was added Methyl amine hydrochloride (27 mg, 0.40 mmol), DIPEA (0.14 mL, 0.807 mmol) followed by HATU (153 mg, 0.403 mmol). The reaction was allowed to stir at the room temperature for 16 h. After completion (monitored by TLC), the mixture was concentrated under reduced pressure. The crude was purified by using combi-flash chromatography 10-15% EtOAc/Heptane to afford the title compound 148 (0.12 g, 78.43%) as a white solid. TLC: 10% MeOH/DCM (Rf: 0.6). LCMS Calculated for C26H30N6O7S: 570.19; Found: 571.4 (M+1).

Synthesis of 2-(N-(4-methoxy-6-((4-(((2,2,2-trifluoroacetyl)-14-azaneyl)methyl)-1H-pyrazol-1-yl) methyl)benzo[d]isoxazol-3-yl)sulfamoyl)-N-methylbenzamide (149)

To a stirred solution of compound 148 (0.2 g, 0.35 mmol) in DCM (2 mL) at 0° C., was added TFA (1 mL) the reaction mixture was allowed to stir at the room temperature for 2 h. After completion (monitored by TLC), the reaction mixture was concentrated under reduced pressure to afford the title compound 149 (70 mg, TFA salt) as an off-white solid. TLC:

10% MeOH/DCM (Rf: 0.5). LCMS Calculated for C23H22F3N6O6S: 567.13; Found: N.A. This was taken forward for the next step without any further purification.

Synthesis of 2-(N-(4-methoxy-6-((4-(propiolamidomethyl)-1H-pyrazol-1-yl) methyl) benzo[d]isoxazol-3-yl) sulfamoyl)-N-methylbenzamide To a stirred solution of 2-(N-(4-methoxy-6-((4-(((2,2,2-trifluoroacetyl)-14-azaneyl) methyl)-1H-pyrazol-1-yl) methyl) benzo[d]isoxazol-3-yl)sulfamoyl)-N-methylbenzamide 149 (60 mg, 0.105 mmol) in DMF (5 mL) at 0° C. was added DIPEA (0.055 mL, 0.317 mmol), followed by T₃P (43 mg, 0.136 mmol). The reaction mixture was stirred at the room temperature for 5 min. After that, a pre-dissolved solution of propiolic acid (14 mg, 0.21 mmol) in DMF (0.5 mL) was added dropwise. The reaction was allowed to stir at the room temperature for 4 h. After completion (monitored by TLC), the reaction mixture concentrated under reduced pressure. The crude was purified by using prep HPLC to afford the title compound (20 mg, 36.36%) as a white solid. TLC: 10% MeOH/DCM (Rf: 0.5); (See analytical data for Table 1).

Synthetic Example 69

Scheme 48: Synthesis of N-((1-((3-((5-ethyl-2-methoxyphenyl) sulfonamido)-4-methoxybenzo[d]isoxazol-6-yl) methyl)-1H-pyrazol-4-yl) methyl) propiolamide

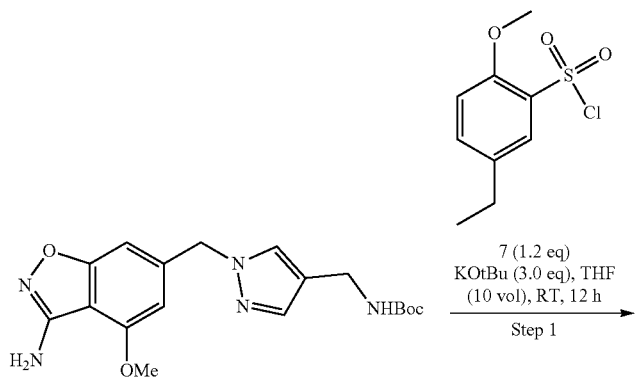

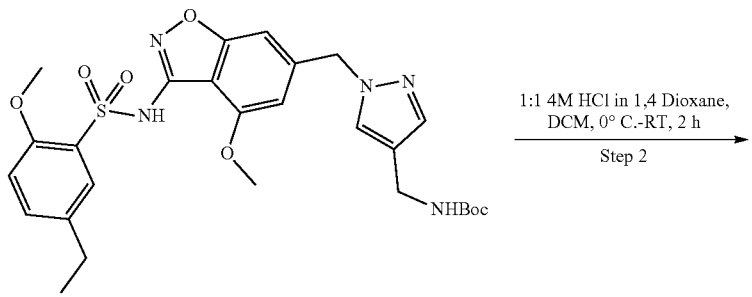

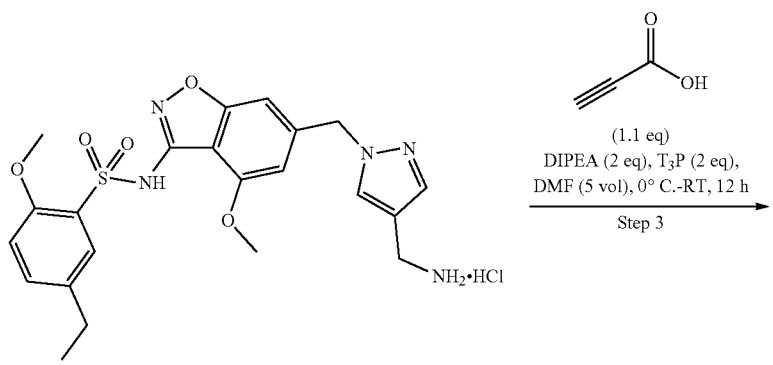

-continued

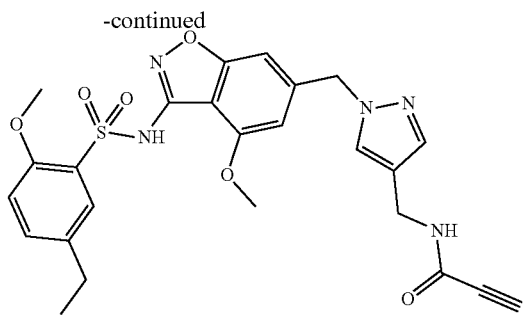

Syn. Ex. 69

Synthesis of tert-butyl ((1-((3-((5-ethyl-2-methoxyphenyl) sulfonamido)-4-methoxybenzo[d]isoxazol-6-yl) methyl)-1H-pyrazol-4-yl) methyl) carbamate (150)

To a stirred solution of compound 22 (0.150 g, 0.401 mmol) in THF (3 mL) at 0° C. was added tBuOK 1 M in THF (1.2 mL, 1.20 mmol) followed by 5-ethyl-2-methoxybenzenesulfonyl chloride (185 mg, 0.898 mmol). The reaction was allowed to stir at 0° C. for 3 h. After completion (monitored by TLC), reaction mixture was diluted with DCM, water was added and extracted with Ethyl acetate. The organic layer was washed with brine, dried over anhydrous $Na_2SO_4$ and concentrated under reduced pressure. The crude compound was purified by Combi flash column chromatography using a gradient method of 40-60% EtOAc/Heptane to afford the title compound 150 (130 mg, 56.76%) as an off-white solid. TLC: 80% EtOAc/Heptane (Rf: 0.35). LCMS Calculated for C27H33N5O7S: 571.21; Found: 578.03 (M+1).

Synthesis of N-(6-((4-(aminomethyl)-1H-pyrazol-1-yl) methyl)-4-methoxybenzo[d]isoxazol-3-yl)-5-ethyl-2-methoxybenzenesulfonamide hydrochloride (151)

To a stirred solution of tert-butyl ((1-((3-((5-ethyl-2-methoxyphenyl) sulfonamido)-4-methoxybenzo[d]isoxazol-6-yl) methyl)-1H-pyrazol-4-yl)methyl)carbamate 150 (130 mg, 0.227 mmol) in DCM (2 mL) at 0° C. was added 4M HCl in 1,4-dioxane (2 mL). The reaction mixture was allowed to stir at room temperature for 2 h. After completion (monitored by TLC), the organic solvent was evaporated under reduced pressure and the residue obtained was triturated with DCM/Heptane to afford 151 (100 mg, salt) as an off-white solid. TLC: 5% MeOH/DCM (Rf: 0.3). LCMS Calculated for C22H26ClN5O5S: 507.13; Found: NA.

Synthesis of N-((1-((3-((5-ethyl-2-methoxyphenyl) sulfonamido)-4-methoxybenzo[d]isoxazol-6-yl) methyl)-1H-pyrazol-4-yl) methyl) propiolamide To a stirred solution of compound 151 (100 mg, 0.196 mmol) in DMF (2 mL) at 0° C. was added DIPEA (0.068 mL, 0.393 mmol), propiolic acid (15 mg, 0.215 mmol) followed by T3P 50% solution in EtOAc (0.249 mL, 0.392 mmol). The reaction mixture was allowed to stir at room temperature for 12 h. After completion (monitored by TLC), the reaction mixture was concentrated under reduced pressure and the crude compound obtained was purified by using prep HPLC to afford the title compound (14 mg, 13.46%) as a white solid. TLC: 10% MeOH/DCM (Rf: 0.5). (See Table 1 for analytical data).

Synthetic Example 70

Scheme 49: Synthesis of 2,3,4,5,6-pentafluoro-N-((1-((4-methoxy-3-((2-methoxyphenyl) sulfonamido) benzo[d]isoxazol-6-yl)methyl)-1H-pyrazol-4-yl)methyl)benzenesulfonamide

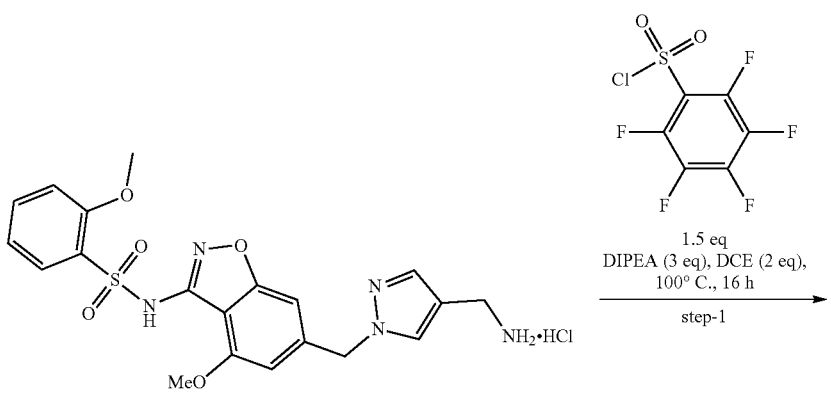

1.5 eq
DIPEA (3 eq), DCE (2 eq),
100° C., 16 h
→
step-1

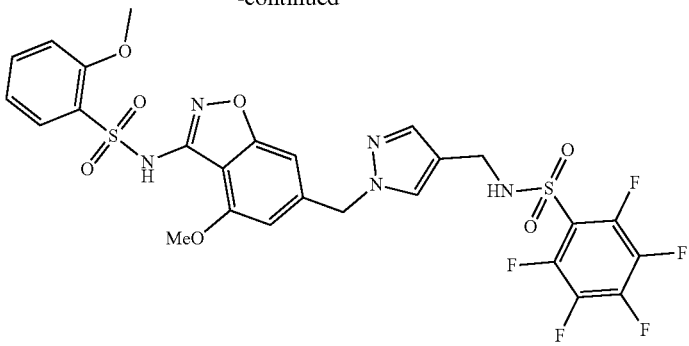

Syn. Ex. 70

Synthesis of 2,3,4,5,6-pentafluoro-N-((1-((4-methoxy-3-((2-methoxyphenyl) sulfonamido) benzo[d]isoxazol-6-yl)methyl)-1H-pyrazol-4-yl)methyl) benzenesulfonamide To a stirred solution of 25 (50 mg, 0.104 mmol) in DCE (2 mL) at 0° C. was added DIPEA (0.054 mL, 0.312 mmol) followed by 2,3,4,5,6-pentafluorobenzenesulfonyl chloride (41 mg, 0.156 mmol). The reaction was allowed to stir at 100° C. for 12 h. After completion (monitored by TLC), the reaction mixture was concentrated under reduced pressure and crude compound was purified by using prep HPLC to afford the title compound (11.2 mg, 16%) as an off-white solid. TLC: 80% EtOAc/Heptane (Rf: 0.5). (See Table 1 for analytical data).

Synthetic Example 71

Scheme 50: Synthesis of 2,6-dimethyoxy-N-(4-methoxy-6-(3-(4-propioloylpiperazin-1-yl) phenyl) benzo[d]isoxazol-3-yl) benzenesulfonamide

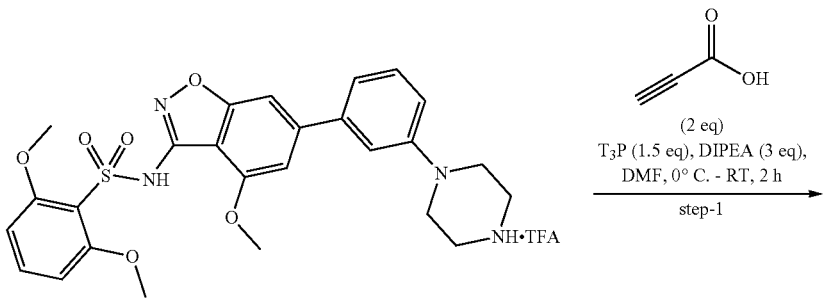

119

(2 eq)
T₃P (1.5 eq), DIPEA (3 eq),
DMF, 0° C. - RT, 2 h
→
step-1

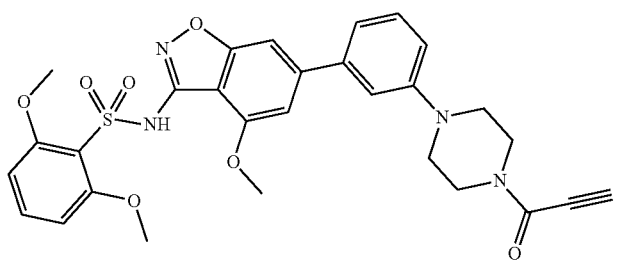

Syn. Ex. 71

Synthesis of 2,6-dimethoxy-N-(4-methoxy-6-(3-(4-propioloylpiperazin-1-yl) phenyl) benzo[d]isoxazol-3-yl) benzenesulfonamide To a stirred solution of 2,6-dimethoxy-N-(4-methoxy-6-(3-(4-(2,2,2-trifluoroacetyl)-414-piperazin-1-yl)phenyl) benzo[d]isoxazol-3-yl)benzenesulfonamide 119 (120 mg, 0.193 mmol) in DMF (2 mL) at 0° C. was added DIPEA (0.101 mL, 0.579 mmol), propiolic acid (16 mg, 0.231 mmol) followed by $T_3P$ 50% solution in EtOAc (0.184 mL, 0.289 mmol). The reaction mixture was allowed to stir at room temperature for 12 h. After completion (monitored by TLC), the reaction mixture was concentrated under reduced pressure and the crude compound was purified by using prep HPLC to afford the title compound (26 mg, 23.42%) as a white solid. TLC: 5% MeOH/DCM (Rf: 0.5). (See Table 1 for analytical data)

Synthetic Example 72 and 73

Scheme 51: Synthesis of 2,6-dimethoxy-N-(4-methoxy-6-(3-(4-(vinylsulfonyl) piperazin-1-yl) phenyl) benzo[d]isoxazol-3-yl) benzenesulfonamide and N-(6-(3-(4-(2-chloroacetyl) piperazin-1-yl) phenyl)-4-methoxybenzo[d]isoxazol-3-yl)-2,6-dimethoxybenzenesulfonamide

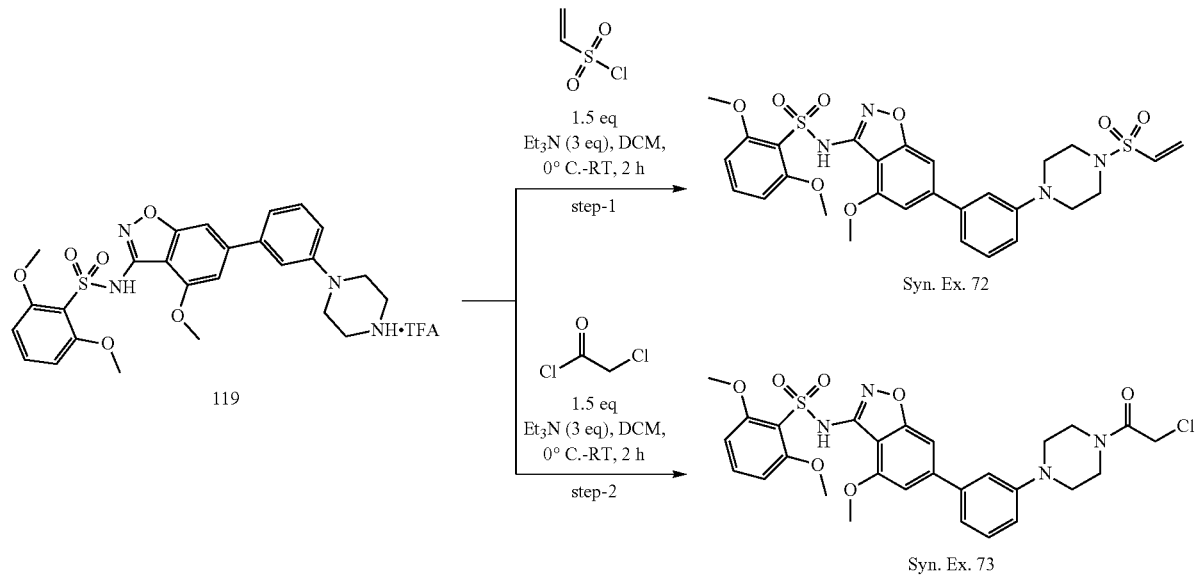

Synthesis of 2,6-dimethoxy-N-(4-methoxy-6-(3-(4-(vinylsulfonyl) piperazin-1-yl) phenyl) benzo[d] isoxazol-3-yl) benzenesulfonamide To a stirred solution of compound 119 (0.12 g, 0.193 mmol) in DMF (1 mL) at 0° C. was added TEA (0.081 mL, 0.579 mmol) followed by ethene sulfonyl chloride (36 mg, 0.289 mmol). The reaction was allowed to stir at room temperature for 2 h. After completion (monitored by TLC), the reaction mixture was concentrated under reduced pressure to get brown gummy crude. The crude was purified by combi-flash chromatography using gradient of 5%-10% MeOH in DCM to get the desired compound which was further purified by prep HPLC to afford the title compound (10 mg, 8.47%) as an off-white solid. TLC: 10% MeOH/DCM (Rf: 0.40). (See Table 1 for analytical data).

Synthesis of N-(6-(3-(4-(2-chloroacetyl) piperazin-1-yl) phenyl)-4-methoxybenzo[d]isoxazol-3-yl)-2,6-dimethoxybenzenesulfonamide To a stirred solution of compound 119 (0.12 g, 0.193 mmol) in DMF (1 mL) at 0° C. was added TEA (0.081 mL, 0.579 mmol) followed by 2-chloroacetyl chloride (32 mg, 0.289 mmol). The reaction was allowed to stir at room temperature for 2 h. After completion (monitored by TLC), the reaction mixture was concentrated under reduced pressure to get brown gummy crude. The crude was purified by combi-flash chromatography using gradient of 5%-10% MeOH in DCM to get desired compound which was further purified by prep HPLC to afford the title compound (9 mg, 7.75%) as an off-white solid. TLC: 10% MeOH/DCM (Rf: 0.40). (See Table 1 for analytical data).

Synthetic Example 74
Scheme 52: Synthesis of 2-methoxy-N-(4-methoxy-6-(3-(4-propioloylpiperazin-1-yl)phenyl)benzo[d]isoxazol-3-yl)benzenesulfonamide
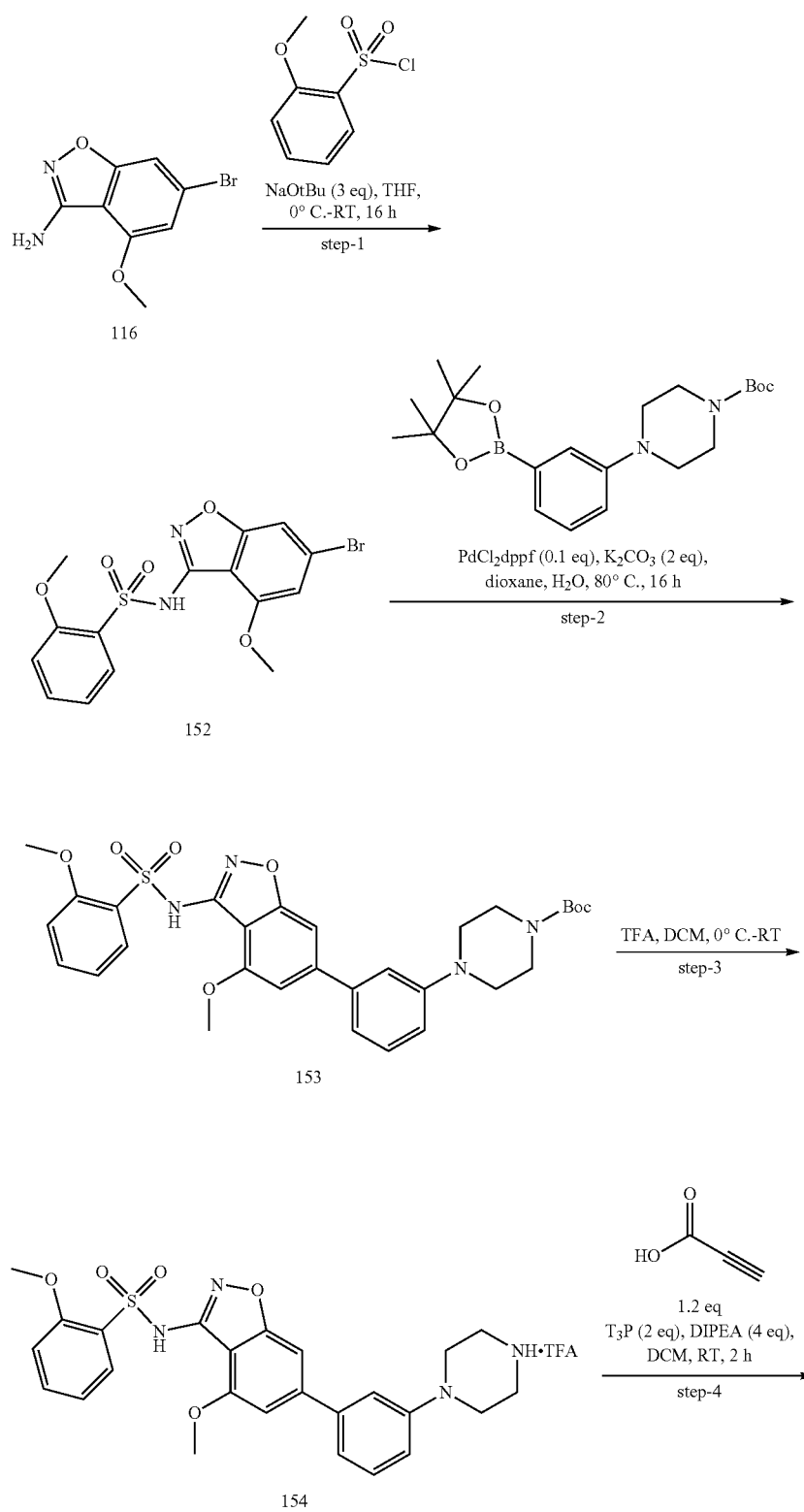

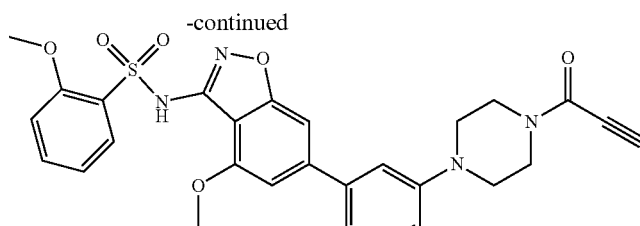

Syn. Ex. 74

Synthesis of N-(6-bromo-4-methoxybenzo[d]isoxazol-3-yl)-2-methoxybenzenesulfonamide (152)

To a stirred solution of compound 116 (1 g, 4.11 mmol) in THF (10 mL) was added NaOtBu (1.18 g, 12.33 mmol) followed by 2-methoxybenzenesulfonyl chloride (1.02 g, 4.93 mmol) and the reaction mixture was allowed to stir at room temperature for 16 h. After completion (monitored by TLC), the reaction mixture was quenched with ice water and extracted with ethyl acetate. The organic layer was dried over anhydrous $Na_2SO_4$ and concentrated under reduced pressure. The crude compound was purified by combi flash chromatography (neutral alumina) to afford the title compound 152 (300 mg, 17.64%) as a brown solid. TLC: 80% EtOAc in Heptane (Rf: 0.5). LCMS Calculated for $C_{15}H_{13}BrN_2O_5S$: 411.97; Found: 412.5 (M+1).

Synthesis of tert-butyl 4-(3-(4-methoxy-3-((2-methoxyphenyl) sulfonamido) benzo[d]isoxazol-6-yl) phenyl) piperazine-1-carboxylate (153)

To a stirred solution of compound 152 (300 mg, 0.725 mmol) and tert-butyl 4-(3-(4,4,5,5-tetramethyl-1,3,2-dioxaborolan-2-yl)phenyl)piperazine-1-carboxylate (310 mg, 0.798 mmol) in a 2:1 mixture of 1,4 Dioxane:water (9 mL) was added $K_2CO_3$ (200 mg, 1.45 mmol). The reaction mixture was degassed with Argon atmosphere followed by addition of Pd(dppf)$Cl_2$ (58 mg, 0.0725 mmol) and further degassed for 5 min. The reaction mixture was stirred at 80° C. for 16 h. After completion (monitored by TLC), the reaction mixture was diluted with ethyl-acetate, filtered on Celite pad and concentrated under reduced pressure. The crude was purified by combi flash-chromatography using a gradient method of 0-30% EtOAc/Heptane to afford the title compound 153 (380 mg, 86.75%) as a pale brown solid. TLC: 80% EtOAc/Heptane (Rf: 0.4). LCMS Calculated for C30H34N4O7S: 594.21; Found: 595.02 (M+1).

Synthesis of 2-methoxy-N-(4-methoxy-6-(3-(4-(2,2,2-trifluoroacetyl)-414-piperazin-1-yl) phenyl) benzo [d]isoxazol-3-yl)benzenesulfonamide (154)

To a stirred solution of compound 153 (350 mg, 0.588 mmol) in DCM (2 mL) at 0° C. was added TFA (0.47 mL, 5.88 mmol) and the reaction was allowed to stir at the room temperature for 2 h. After completion (monitored by TLC), the reaction mixture was concentrated under reduced pressure and co distilled with ether to afford the title compound 154 (320 mg, crude TFA salt) as a brown oil. TLC: 5% MeOH/DCM (Rf: 0.3). This was taken to the next step without further analysis.

Synthesis of 2-methoxy-N-(4-methoxy-6-(3-(4-propioloylpiperazin-1-yl)phenyl)benzo[d]isoxazol-3-yl) benzenesulfonamide To a stirred solution of compound 154 (150 mg, 0.253 mmol) in DMF (2 mL) at 0° C. was added DIPEA (0.177 mL, 1.01 mmol), propiolic acid (21 mg, 0.303 mmol) followed by $T_3P$ as a 50% solution in EtOAc (0.321 mL, 0.506 mmol). The reaction mixture was allowed to stir at room temperature for 2 h. After completion (monitored by TLC), the reaction mixture was concentrated under reduced pressure and the crude was purified by using prep HPLC to afford the title compound (10 mg, 7.24%) as an off-white solid. TLC: 5% MeOH/DCM (Rf: 0.5). (See Table 1 for analytical data).

Synthetic Example 75

Scheme 53: Synthesis of N-(6-(2-(1-acryloylpyrrolidin-3-yl)phenyl)-4-methoxybenzo[d]isoxazol-3-yl)-2,6-dimethoxybenzenesulfonamide

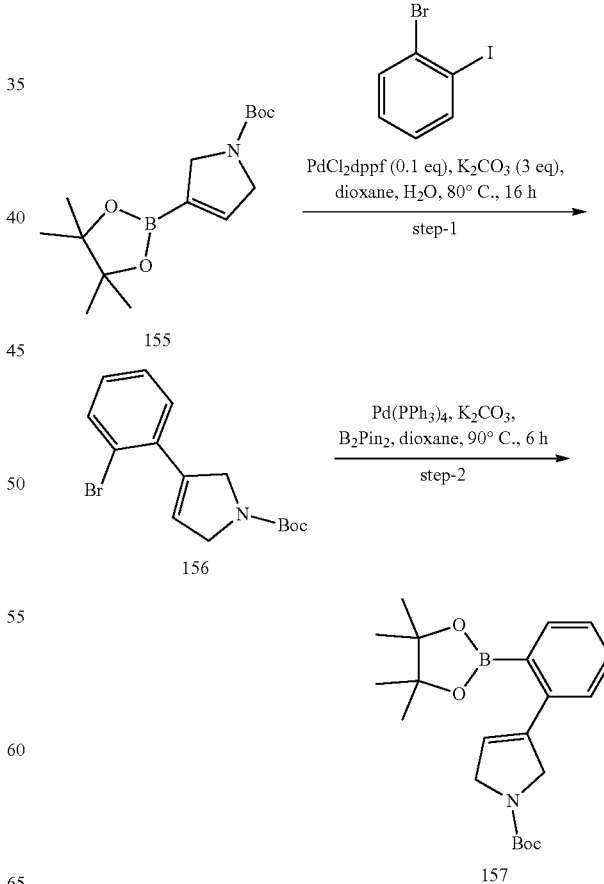

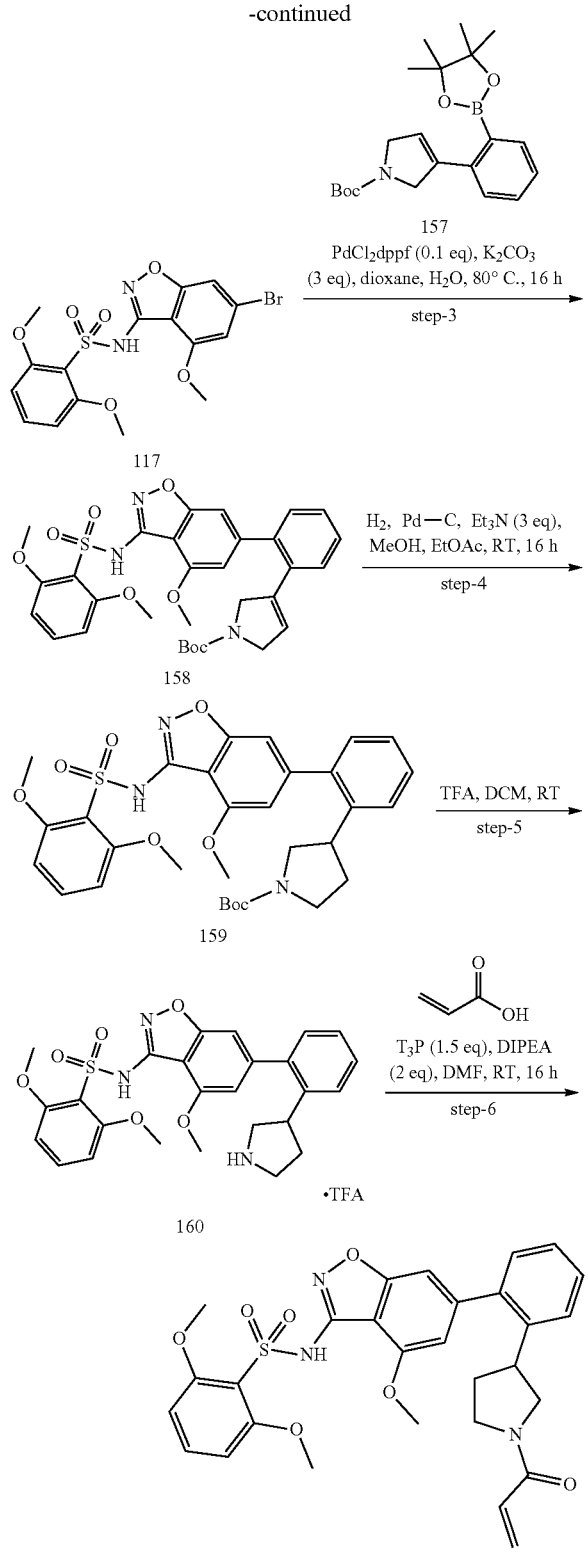

mixture of 1,4 Dioxane:water (9 mL) was added $K_2CO_3$ (0.701 g, 5.079 mmol). The reaction mixture was degassed with Argon atmosphere followed by addition of Pd(dppf)Cl$_2$ (136 mg, 0.169 mmol) and stirred at 80° C. for 12 h. After completion (monitored by TLC), the reaction mixture was diluted with ethyl-acetate, filtered on Celite pad and the reaction mixture was concentrated under reduced pressure. The crude was purified by combi flash-chromatography using a gradient method of 0-30% EtOAc/Heptane to afford the title compound 156 (400 mg, 72.85%) as a pale brown solid. TLC: 50% EtOAc/Heptane (Rf: 0.4). LCMS Calculated for C15H18BrNO2: 323.05; Found: 324.05 (M+1).

tert-butyl 3-(2-(4,4,5,5-tetramethyl-1,3,2-dioxaborolan-2-yl)phenyl)-2,5-dihydro-1H-pyrrole-1-carboxylate (157)

To a stirred solution of 156 (400 mg, 1.233 mmol) in 3:1 mixture of 1,4 Dioxane:water (40 mL), was added $K_2CO_3$ (511 mg, 3.701 mmol) followed by Pd(PPh$_3$)$_4$ (142 mg, 0.1233 mmol) and Bpin$_2$ (469 mg, 1.849 mmol). The resulting reaction mixture was stirred at 90° C. for 16 h. After completion (monitored by TLC), the reaction mixture was cooled to room temperature, diluted, and extracted with ethyl acetate. The organic layer was washed with brine, dried over anhydrous Na$_2$SO$_4$ and concentrated under reduced pressure. The crude compound was purified by combi flash chromatography (using a gradient method of 0-50% EtOAc/Heptane) to afford the title compound 157 (200 mg, 43.66%) as a yellow solid. TLC: 50% EtOAc/Heptane (Rf: 0.5). LCMS Calculated for C21H30BNO4: 371.23; Found: 372.02 (M+1).

Synthesis of tert-butyl 3-(2-(3-((2,6-dimethoxyphenyl)sulfonamido)-4-methoxybenzo[d]isoxazol-6-yl)phenyl)-2,5-dihydro-1H-pyrrole-1-carboxylate (158)

To a stirred solution of compound 117 (1 g, 2.25 mmol) in mixture of dioxane:H$_2$O (5:1, 10 mL) was added K$_2$CO$_3$ (915 mg, 6.767 mmol) followed by tert-butyl 3-(2-(4,4,5,5-tetramethyl-1,3,2-dioxaborolan-2-yl)phenyl)-2,5-dihydro-1H-pyrrole-1-carboxylate 157 (1.25 g, 3.382 mmol) and the reaction mixture was degassed with argon gas for 10 min. PdCl$_2$dppf (167 mg, 0.22 mmol) was added and the mixture heated at 80° C. for 16 h. After completion (monitored by TLC), the reaction mixture was cooled to room temperature, filtered through a celite pad, diluted with water, and extracted with ethyl acetate. The organic layer was dried over anhydrous Na$_2$SO$_4$ and concentrated under reduced pressure. The crude compound was purified by combi flash chromatography (neutral alumina) to afford the title compound 158 (1 g, 72.99%) as an off-white solid. TLC: 80% EtOAc/Heptane (Rf: 0.6). LCMS Calculated for C31H33N3O8S: 607.20; Found: 608.5 (M+1).

Synthesis of tert-butyl 3-(2-(3-((2,6-dimethoxyphenyl) sulfonamido)-4-methoxybenzo[d]isoxazol-6-yl) phenyl) pyrrolidine-1-carboxylate 159

An autoclave was charged with a solution of compound 158 (700 mg 1.151 mmol) in MeOH:EtOAc (15 mL, 2:1) and the mixture was degassed with nitrogen. 10% Pd/C (350 mg) was added under nitrogen atmosphere. The reaction mixture was allowed to stir under hydrogen atmosphere (100 psi) at room temperature for 16 h. After completion (monitored by TLC), the reaction mixture was filtered through a pad of Celite. The filtrate was concentrated under reduced Syn. Ex. 75 tert-butyl 3-(2-bromophenyl)-2,5-dihydro-1H-pyrrole-1-carboxylate (156)

To a stirred solution of 155 (500 mg, 1.693 mmol) and 1-bromo-2-iodobenzene (575 mg, 2.032 mmol) in a 2:1 pressure. The crude product was purified by Combi flash chromatography (using a gradient method of 0-5% MeOH/DCM) to afford the title compound 159 (150 mg, 21.36%) as a white solid. TLC: 50% EtOAc/Heptane ($R_f$ 0.6). LCMS Calculated for C31H35N3O8S: 609.21; Found: 610.08 (M+1).

Synthesis of 2,6-dimethoxy-N-(4-methoxy-6-(2-(1-(2,2,2-trifluoroacetyl)-114-pyrrolidin-3-yl)phenyl)benzo[d]isoxazol-3-yl)benzenesulfonamide (160)

To a stirred solution of compound 159 (150 mg, 0.246 mmol) in DCM (2 mL) at 0° C. was added TFA (0.2 mL, 2.460 mmol). The reaction was allowed to stir at the room temperature for 2 h. After completion (monitored by TLC), the reaction mixture was concentrated under reduced pressure and co distilled with toluene to afford the title compound 160 (120 mg, crude salt) as a brown oil. TLC: 5% MeOH/DCM ($R_f$ 0.3). The crude material was used in the next step without any characterization or purification.

Synthesis of N-(6-(2-(1-acryloylpyrrolidin-3-yl)phenyl)-4-methoxybenzo[d]isoxazol-3-yl)-2,6-dimethoxybenzenesulfonamide To a stirred solution of compound 160 (100 mg, 0.165 mmol) in DMF (1 mL) at 0° C. was added DIPEA (0.057 mL, 0.330 mmol), acrylic acid (14 mg, 0.198 mmol) followed by T$_3$P as a 50% solution in EtOAc (0.157 mL, 0.247 mmol). The reaction mixture was allowed to stir at room temperature for 16 h. After completion (monitored by TLC), the reaction mixture was concentrated under reduced pressure and the crude was purified by using prep HPLC to afford the title compound (4 mg, 4.34%) as an off-white solid. TLC: 5% MeOH/DCM ($R_f$ 0.5). (See Table 1 for analytical data).

Synthetic Example 76

Scheme 54: Synthesis of N-((1-((4-methoxy-3-((2-methoxyphenyl)sulfonamido)-1H-indazol-6-yl)methyl)-1H-pyrazol-4-yl)methyl)propiolamide

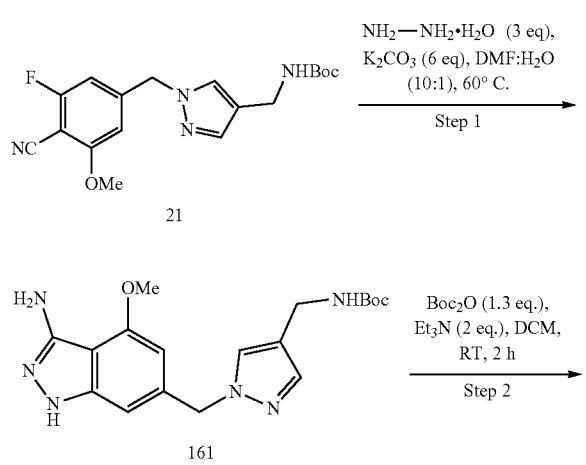

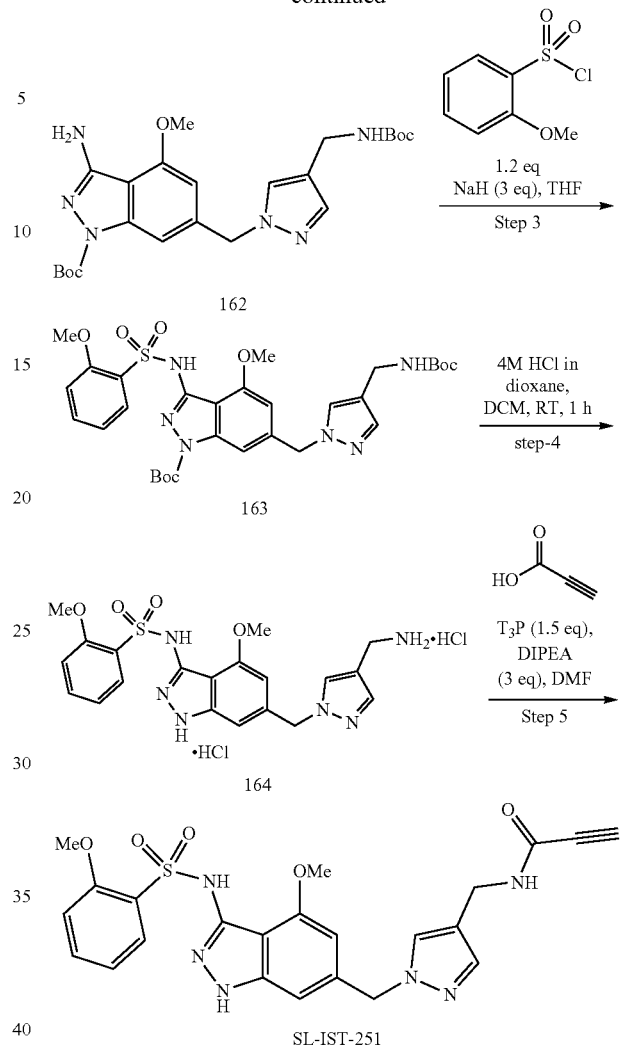

Synthesis of tert-butyl((1-((3-amino-4-methoxy-1H-indazol-6-yl) methyl)-1H-pyrazol-4-yl) methyl) carbamate (161)

To a stirred solution of compound 21 (750 mg, 2.081 mmol) in 6:1 mixture of DMF:H$_2$O (7 mL) at room temperature was added hydrazine hydrate (0.31 mL, 6.243 mmol) followed by K$_2$CO$_3$ (1.72 g, 12.48 mmol). The reaction mixture was allowed to stir at 80° C. for 16 h. After completion (monitored by TLC), the reaction mixture was poured in ice water and extracted with ethyl acetate. The organic layer was washed with brine, dried over anhydrous Na$_2$SO$_4$ and concentrated under reduced pressure. The crude compound was purified by Combi flash chromatography using a gradient method of 70% EtOAc/Heptane to afford the title 161 (700 mg, 90.32%) as a brown semi solid. TLC: 60% EtOAc ($R_f$ 0.50); LCMS Calculated for C18H24N6O3: 372.19; Found: 373.02 (M+1).

Synthesis of tert-butyl 3-amino-6-((4-(((tert-butoxycarbonyl)amino)methyl)-1H-pyrazol-1-yl)methyl)-4-methoxy-1H-indazole-1-carboxylate (162)

To a stirred solution of compound 161 (0.6 g, 1.61 mmol) in MeOH (75 mL) at 0° C. was added TEA (0.45 mL, 3.22 mmol) followed by drop-wise addition of (Boc)₂O (0.46 mL, 2.094 mmol) and the reaction was allowed to stir for 2 h at room temperature. After completion (monitored by TLC), the reaction mixture was poured to ice-cold water and extracted with ethyl acetate. The organic layer was washed with brine, dried over anhydrous Na₂SO₄ and concentrated under reduced pressure. The crude compound was purified by Combi flash chromatography using a gradient method of 50% EtOAc/Heptane to afford the title 162 (220 mg, 28.9%) as an off-white solid. TLC: 50% EtOAc/Heptane (R$_f$ 0.55); LCMS Calculated for C23H32N6O5: 472.24; Found: 473.05 (M+1).

Synthesis of tert-butyl 6-((4-(((tert-butoxycarbonyl) amino) methyl)-1H-pyrazol-1-yl) methyl)-4-methoxy-3-((2-methoxyphenyl) sulfonamido)-1H-indazole-1-carboxylate (163)

To a stirred solution of 162 (100 mg, 0.211 mmol) in THF (6 mL) at 0° C. was added 60% NaH (25 mg, 0.634 mmol) followed by 2-methoxybenzenesulfonyl chloride (0.681 g, 3.31 mmol) at room temperature and the reaction was allowed to stir at room temperature for 16 h. After completion (monitored by TLC), the reaction mixture was quenched with saturated ammonium chloride solution and extracted with 10% MeOH/DCM. The combined organic layer was dried over anhydrous Na₂SO₄, filtered and concentrated under reduced pressure to afford the title compound 163 (150 mg, crude) as a gummy brown solid. TLC: 10% MeOH/DCM (R$_f$ 0.5); LCMS Calculated for C25H32N4O7S: 532.20: Found: 533.02 (M+1). The crude compound was used in the next step without any purification.

Synthesis of N-(6-((4-(aminomethyl)-1H-pyrazol-1-yl) methyl)-4-methoxy-1H-indazol-3-yl)-2-methoxybenzenesulfonamide dihydrochloride (164)

To a stirred solution of compound 163 (100 mg, 0.155 mmol) in DCM (3 mL) at 0° C. was added 4M HCl in 1,4-Dioxane (3 mL) and the reaction was allowed to stir at the room temperature for 2 h. After completion (monitored by TLC), the reaction mixture was concentrated under reduced pressure. The crude was washed with diethyl ether and heptane and dried under reduced pressure to afford the title compound 164 (110 mg, salt) as a pale brown semi-solid. TLC: 10% MeOH/DCM (R$_f$ 0.5). It was used as obtained in the next step.

Synthesis of N-((1-((4-methoxy-3-((2-methoxyphenyl) sulfonamido)-1H-indazol-6-yl)methyl)-1H-pyrazol-4-yl)methyl)propiolamide To a stirred solution of compound 164 (100 mg, 0.194 mmol) in DMF (1 mL) at 0° C. was added DIPEA (0.1 mL, 0.582 mmol), T₃P (50% solution in EtOAc, 0.185 mL, 0.291 mmol) followed by propiolic acid (9.2 mg, 0.132 mmol). The reaction was allowed to stir at the room temperature for 1 h. After completion (monitored by TLC), the reaction mixture was concentrated under reduced pressure, quenched with ice water, and extracted with ethyl acetate. The organic layer was washed with brine, dried over anhydrous Na₂SO₄, and concentrated under reduced pressure. The crude was purified by prep HPLC to afford the title compound (7.6 mg, 6.7%) as an off-white solid. TLC: 5% MeOH/DCM (R$_f$ 0.6). (See Table 1 for analytical data).

Synthetic Example 77

Scheme 55: Synthesis of 2-methoxy-N-(4-methoxy-6-((4-(vinylsulfonamido)piperidin-1-yl)methyl)benzo[d]isoxaozl-3-yl)benzenesulfonamide

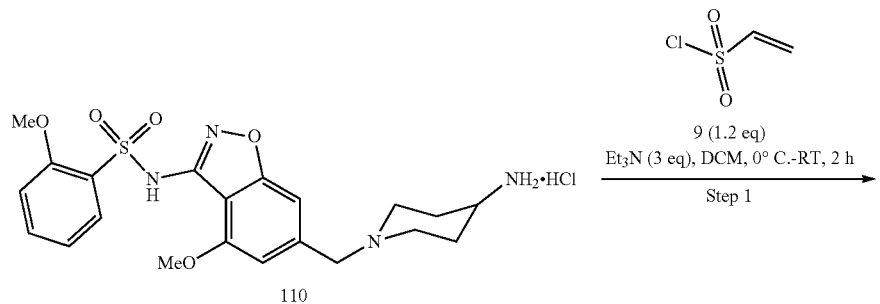

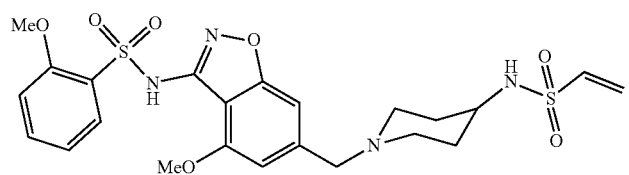

Syn. Ex. 77

Synthesis of 2-methoxy-N-(4-methoxy-6-((4-(vinylsulfonamido) piperidin-1-yl)methyl)benzo[d]isoxazol-3-yl)benzenesulfonamide To a stirred solution of compound 110 (0.1 g, 0.207 mmol) in DMF (1 mL) at 0° C. was added TEA (0.087 mL, 0.621 mmol) followed by Ethene sulfonyl chloride (31 mg, 0.248 mmol). The reaction was allowed to stir at room temperature for 2 h. After completion (monitored by TLC), the reaction mixture was concentrated under reduced pressure, to afford a brown gummy crude. The crude was purified by combi-flash chromatography using gradient of 5-10% to get desired compound which was further purified by prep HPLC to afford the title compound (20 mg, 18%) as an off-white solid. TLC: 10% MeOH/DCM (Rf: 0.40). (See Table 1 for analytical data).

Synthetic Example 78, 79 and 80

Scheme 56: Synthesis of N-(6-((4-(((4-fluorophenyl)sulfinamido)methyl-1H-pyrazol-1-yl)methyl)-4-methoxybenzo[d]isoxazol-3-yl-2-methoxybenzenesulfonamide; Synthesis of 2-methoxy-N-(4-methoxy-6-((4-(phenylsulfonamidomethyl)-1H-pyrazol-1-yl)methyl)benzo[d]isoxazol-3-yl)benzenesulfonamide and Synthesis of 3,4,5-trifluoro-N-((1-((4-methoxy-3-((2-methoxyphenyl) sulfonamido) benzo[d]isoxazol-6-yl) methyl)-1H-pyrazol-4-yl) methyl) benzenesulfonamide

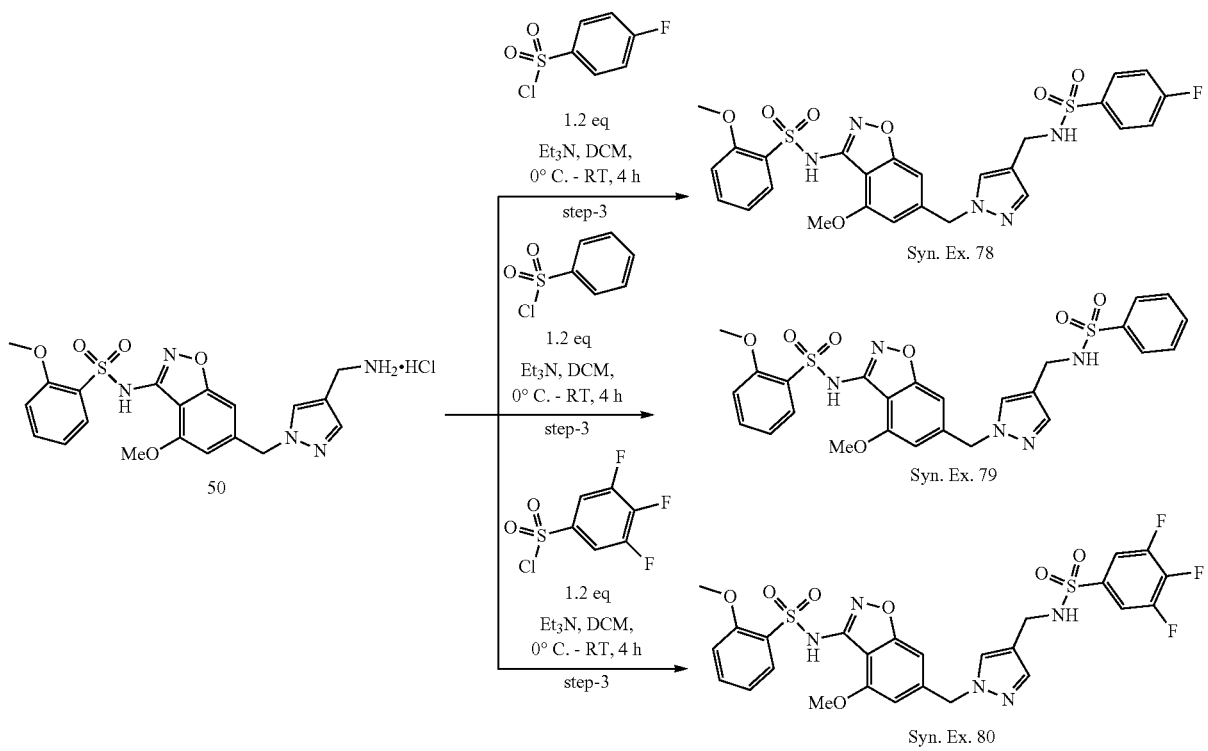

Synthesis of N-(6-((4-(((4-fluorophenyl)sulfonamido)methyl)-1H-pyrazol-1-yl)methyl)-4-methoxybenzo[d]isoxazol-3-yl)-2-methoxybenzenesulfonamide To a stirred solution of compound 50 (100 mg, 0.208 mmol) in DCM (3 mL) at 0° C. was added TEA (0.087 mL, 0.625 mmol) followed by 4-fluorobenzenesulfonyl chloride (48 mg, 0.249 mmol). The reaction was allowed to stir at the room temperature for 4 h. After completion (monitored by TLC), the reaction mixture was concentrated under reduced pressure to get a brown gummy crude which was purified by combi-flash chromatography using gradient of 3% MeOH/DCM and further purified by prep HPLC to afford the title compound (5 mg, 4) as an off-white solid. TLC: 10% MeOH/DCM (Rf: 0.40). (See Table 1 for analytical data).

Synthesis of 2-methoxy-N-(4-methoxy-6-((4-(phenylsulfonamidomethyl)-1H-pyrazol-1-yl)methyl)benzo[d]isoxazol-3-yl)benzenesulfonamide To a stirred solution of compound 50 (100 mg, 0.208 mmol) in DCM (3 m) at 0° C. was added TEA (0.087 mL, 0.625 mmol) followed by benzenesulfonyl chloride (44 mg, 0.249 mmol). The reaction was stirred at room temperature for 4 h. After completion (monitored by TLC), the reaction mixture was concentrated under reduced pressure to get a brown gummy crude. The crude was purified through combi-flash chromatography using gradient of 3% MeOH/DCM and further purified by prep HPLC to afford the title compound (5 mg, 4%) as an off-white solid. TLC: 10% MeOH/DCM (Rf: 0.40). (See Table 1 for analytical data).

Synthesis of 3,4,5-trifluoro-N-((1-((4-methoxy-3-((2-methoxyphenyl) sulfonamido) benzol[d]isoxazol-6-yl) methyl)-1H-pyrazol-4-yl) methyl) benzenesulfonamide To a stirred solution of compound 50 (100 mg, 0.104 mmol) in DCM (3 mL) at 0° C. was added TEA (0.044 mL, 0.312 mmol) followed by 3,4,5-trifluorobenzenesulfonyl chloride (28 mg, 0.124 mmol). The reaction was allowed to stir at the room temperature for 4 h. After completion (monitored by TLC), the reaction mixture was concentrated under reduced pressure, to get brown gummy crude. The crude was purified through combi-flash chromatography using gradient of 3% MeOH/DCM and further purified by prep HPLC to afford the title compound (16 mg, 20.27%) as an off-white solid. TLC: 10% MeOH/DCM (Rf: 0.40). (See Table 1 for analytical data).

Synthetic Example 81

Scheme 57: Synthesis of 5-ethyl-2-methoxy-N-(4-methoxy-6-((4-(vinylsulfonamidomethyl)-1H-pyrazol-1-yl)methyl)benzo[d]isoxazol-3-yl)benzenesulfonamide

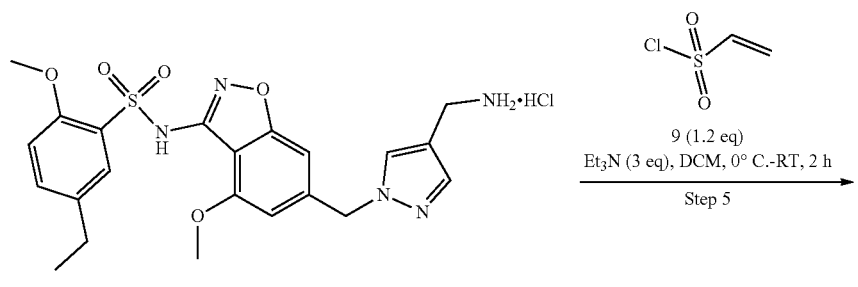

151

9 (1.2 eq)
Et₃N (3 eq), DCM, 0° C.-RT, 2 h
Step 5

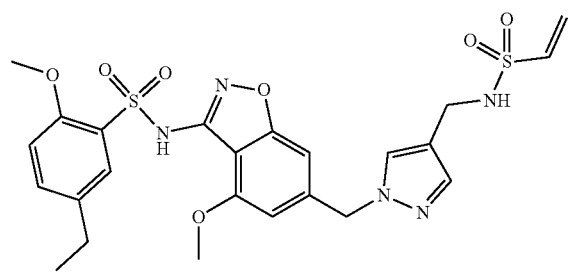

Syn. Ex. 81

Synthesis of 5-ethyl-2-methoxy-N-(4-methoxy-6-((4-(vinylsulfonamidomethyl)-1H-pyrazol-1-yl)methyl)benzo[d]isoxazol-3-yl)benzenesulfonamide To a stirred solution of compound 151 (0.1 g, 0.196 mmol) in DMF (1 mL) at 0° C. was added TEA (0.082 mL, 0.590 mmol) followed by ethene sulfonyl chloride (29 mg, 0.235 mmol). The reaction was allowed to stir at room temperature for 2 h. After completion (monitored by TLC), the reaction mixture was concentrated under reduced pressure to get a brown gummy crude. The crude was purified by combi-flash chromatography using gradient of 5%-10% and further purified by prep HPLC to afford the title compound (10 mg, 9.09%) as an off-white solid. TLC: 10% MeOH/DCM (Rf: 0.40). (See Table 1 for analytical data)

Synthetic Example 82

Scheme 58: Synthesis of 2-methoxy-N-(4-methoxy-6-((5-((perfluorophenyl)sulfonyl)-5,6-dihydropyrrolo[3,4-c]pyrazol-1(4H)-yl)methyl)benzo[d]isoxazol-3-yl)benzenesulfonamide Scheme 58: Synthesis of 2-methoxy-N-(4-methoxy-6-((5-((perfluorophenyl)sulfonyl)-5,6-dihydropyrrolo[3,4-c]pyrazol-1(4H)-yl)methyl)benzo[d]isoxazol-3-yl)benzenesulfonamide

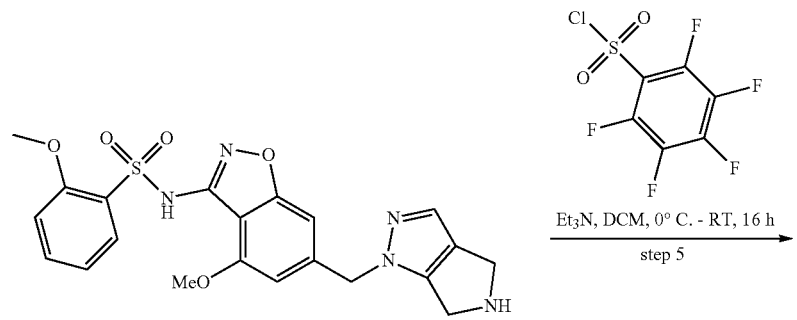

54

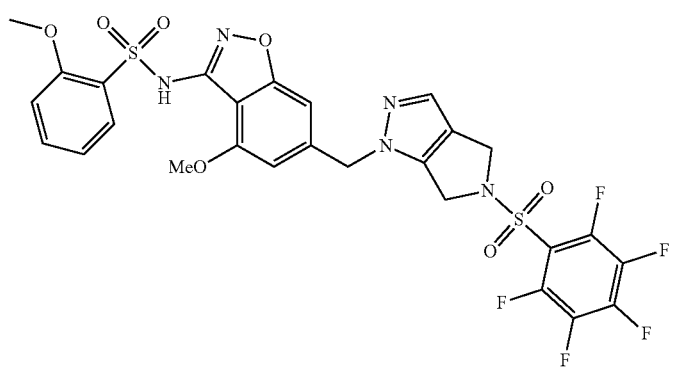

Syn. Ex. 82

To a stirred solution of compound 54 (110 mg, 0.241 mmol) in DMF (1 mL) at 0° C. was added TEA (0.101 mL, 0.724 mmol), followed by 2,3,4,5,6-pentafluorobenzene-sulfonyl chloride (77 mg, 0.289 mmol). The reaction was allowed to stir at the room temperature for 2 h. After completion (monitored by TLC), the reaction mixture was concentrated under reduced pressure to get a brown gummy crude. The crude was passed through combi-flash chromatography using gradient of 5% MeOH/DCM and further purified by prep HPLC to afford the title compound (7 mg, 4.24%) as an off-white solid. TLC: 10% MeOH/DCM (Rf: 0.40). (See Table 1 for analytical data).

Synthetic Example 83 and 84

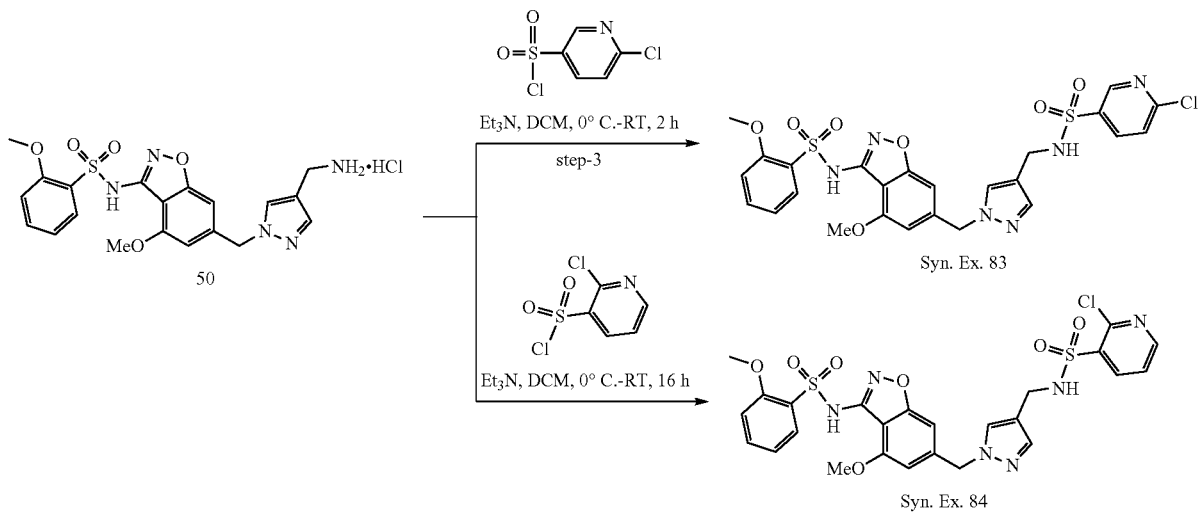

6-chloro-N-((1-((4-methoxy-3-((2-methoxyphenyl) sulfonamido) benzo[d]isoxazol-6-yl)methyl)-1H-pyrazol-4-yl)methyl)pyridine-3-sulfonamide To a stirred solution of compound 50 (180 mg, 1.00 mmol) in DCM (2 mL) at 0° C. was added TEA (0.42 mL, 3.00 mmol) and followed by 6-chloropyridine-3-sulfonyl chloride (424 mg, 2.00 mmol). The reaction was allowed to stir at the room temperature for 2 h. After completion (monitored by TLC), the mixture was concentrated under reduced pressure, to get a brown gummy solid which was passed through combi-flash chromatography gradient using 3% MeOH/DCM, then further purified by prep HPLC to afford the title compound (26 mg, 11.11%) as an off-white solid. TLC: 10% MeOH/DCM (Rf: 0.40). (See Table 1 for analytical data).

Synthesis of 2-chloro-N-((1((4methoxy3((2methoxyphenyl)sulfonamido)benzo[d]isoxazol-6-yl) methyl)-1H-pyrazol-4-yl) methyl) pyridine-3-sulfonamide Using the protocol described above for Syn. Ex. 83, Compound 50 (100 mg, 0.208 mmol) was converted to the title compound (12 mg, 9.37%) which was isolated as an off-white solid. TLC: 10% MeOH/DCM (Rf: 0.40). (See Table 1 for analytical data).

Synthetic Example 85
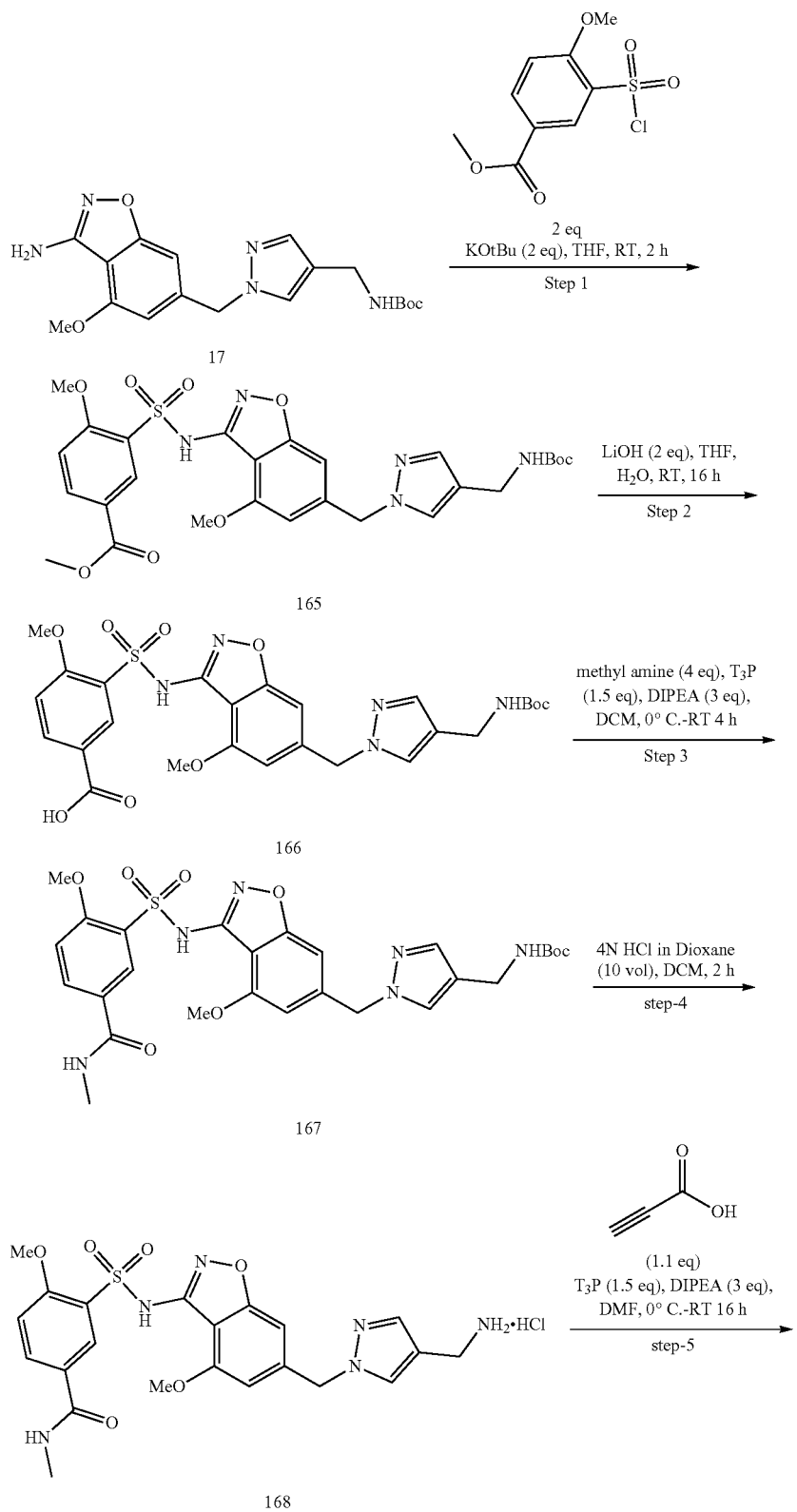
Scheme 60: Synthesis of 4-methoxy-3-(N-(4-methoxy-6-((4-(propiolamidomethyl)-1H-pyrazol-1-yl) methyl) benzo[d]isoxazol-3-yl)sulfamoyl)-N-methylbenzamide -continued

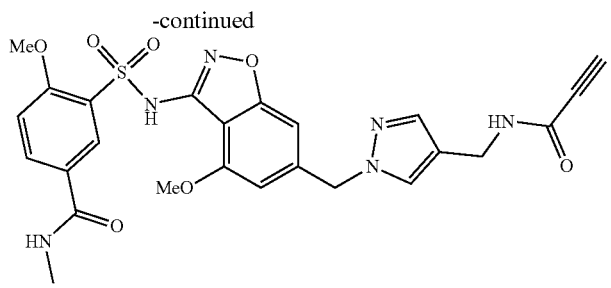

Syn. Ex. 85

Synthesis of methyl 3-(N-(6-((4-(((tert-butoxycarbonyl) amino)methyl)-1H-pyrazol-1-yl)methyl)-4-methoxybenzo[d]isoxazol-3-yl)sulfamoyl)-4-methoxybenzoate (165)

To a stirred solution of compound 17 (1.0 g, 2.678 mmol) in THF (10 mL) at 0° C. was added 1M solution in THF of KO$^t$Bu (0.60 g, 5.356 mmol) followed by methyl 3-(chlorosulfonyl)-4-methoxybenzoate (1.41 g, 5.356 mmol) and the reaction was allowed to stir at 0° C. for 2 h. After completion (monitored by TLC), the reaction mixture was quenched with water and extracted with ethyl acetate. The organic layer was washed with brine, dried over anhydrous Na$_2$SO$_4$, and concentrated under reduced pressure. The crude compound was purified by combi flash column chromatography using a gradient method of 40-100% EtOAc/Heptane to afford the title compound 165 (0.650 g, 40.37%) as a brown solid. TLC: 70% EtOAc/Heptane (R$_f$ 0.38). LCMS Calculated for: C27H31N5O9S: 601.18; Found: 602.2 (M+1).

Synthesis of 3-(N-(6-((4-(((tert-butoxycarbonyl) amino) methyl)-1H-pyrazol-1-yl)methyl)-4-methoxybenzo[d]isoxazol-3-yl)sulfamoyl)-4-methoxybenzoic acid (166)

To a stirred solution of compound 165 (0.2 g, 0.332 mmol) in a mixture of (2:1) THF:H$_2$O (3 mL) was added LiOH·H$_2$O (27 mg, 0.66 mmol). The reaction mixture was stirred at the room temperature for 16 h. After completion (monitored by TLC), the reaction mixture was concentrated under reduced pressure. The residue was neutralized with 1N HCl and extracted with ethyl acetate. The organic layer was washed with brine, dried over anhydrous Na$_2$SO$_4$ and concentrated under reduced pressure to afford the title compound 166 (170 mg, 87.17%) as an off-white solid. TLC: 100% EtOAc/Heptane (R$_f$ 0.3); LCMS Calculated for: C26H29N5O9S: 587.17; Found: 588.50[M+1].

Synthesis of tert-butyl ((1-((4-methoxy-3-((2-methoxy-5-(methylcarbamoyl)phenyl)sulfonamido) benzo[d]isoxazol-6-yl)methyl)-1H-pyrazol-4-yl) methyl)carbamate (167)

To a stirred solution of compound 166 (170 mg, 0.289 mmol) in DMF (1 mL) at 0° C. was added DIPEA (0.155 mL, 0.867 mmol), methyl amine solution, 1M in THF (1.1 mL, 1.156 mmol) followed by T$_3$P as a 50% solution in EtOAc (0.275 mL, 0.433 mmol). The reaction mixture was allowed to stir at room temperature for 4 h. After completion (monitored by TLC), the reaction mixture was concentrated under reduced pressure and the crude was purified by combi flash chromatography using gradient 0-30% EtOAc/Heptane to afford the title 167 (140 mg, 80.9%) as an off-white solid. TLC: 5% MeOH/DCM (R$_f$ 0.5). LCMS Calculated for: C27H32N6O8S: 600.20; Found: 601.50 [M+1].

Synthesis of 3-(N-(6-((4-(aminomethyl)-1H-pyrazol-1-yl) methyl)-4-methoxybenzo[d]isoxazol-3-yl) sulfamoyl)-4-methoxy-N-methylbenzamide hydrochloride (168)

To a stirred solution of compound 167 (140 mg, 0.233 mmol) in DCM (2 mL) at 0° C. was added 4M HCl in 1,4 Dioxane (0.29 mL, 1.165 mmol) and the reaction was allowed to stir at room temperature for 2 h. After completion (monitored by TLC), the reaction mixture was concentrated under reduced pressure and co-evaporated with ether two times to afford the title compound 168 (100 mg, salt) as a white solid. TLC: 5% MeOH/DCM (Rf: 0.2). This was used in the next step without further characterization.

Synthesis of 4-methoxy-3-(N-(4-methoxy-6-((4-(propiolamidomethyl)-1H-pyrazol-1-yl) methyl) benzo[d]isoxazol-3-yl)sulfamoyl)-N-methylbenzamide To a stirred solution of compound 168 (100 mg, 0.280 mmol) in DMF (1 mL) at 0° C. was added DIPEA (0.146 mL, 0.840 mmol), propiolic acid (21 mg, 0.308 mmol) followed by T$_3$P as a 50% solution in EtOAc (0.267 mL, 0.42 mmol). The reaction mixture was allowed to stir at room temperature for 16 h. After completion (monitored by TLC), the reaction mixture was concentrated under reduced pressure and the crude was purified by prep HPLC to afford the title compound (8 mg, 7.9%) as an off-white solid. TLC: 5% MeOH/DCM (Rf: 0.6). (See Table 1 for analytical data).

Synthetic Example 86

Scheme 61: Synthesis of 4-methoxy-3-(N-(4-methoxy-6-((4-(propiolamidomethyl)-1H-pyrazol-1-yl)methyl)benzo[d]isoxazol-3-yl)sulfamoyl)benzoic acid

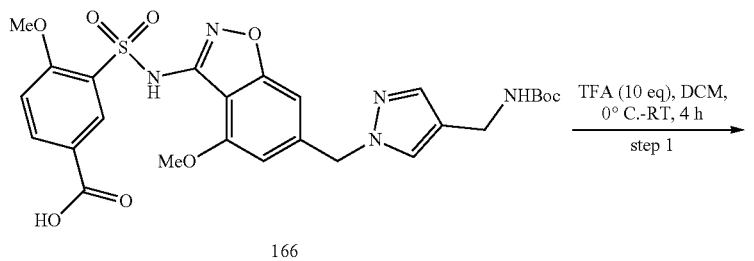

166

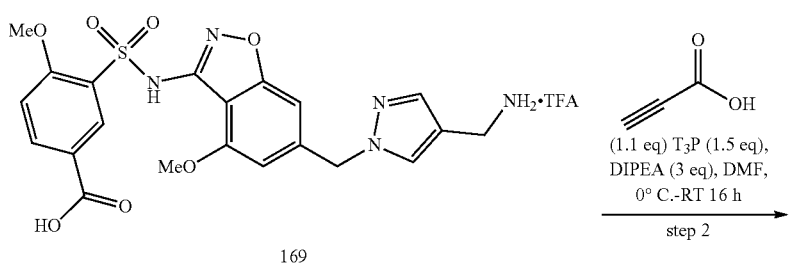

169

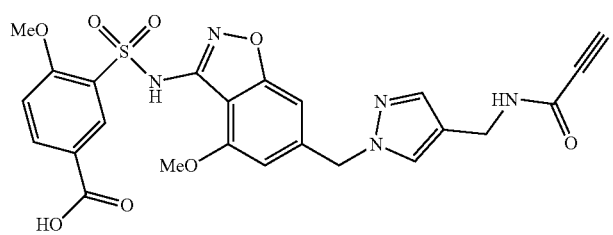

Syn. Ex. 86

Synthesis of 4-methoxy-3-(N-(4-methoxy-6-((4-(((2,2,2-trifluoroacetyl)-14-azaneyl)methyl)-1H-pyrazol-1-yl)methyl)benzo[d]isoxazol-3-yl)sulfamoyl)benzoic acid (169)

To a stirred solution of compound 166 (100 mg, 0.170 mmol) in DCM (2 mL) at 0° C., TFA (0.138 mL, 1.701 mmol) was added at 0° C. and the reaction was allowed to stir at room temperature for 2 h. After completion (monitored by TLC), the reaction mixture was concentrated under reduced pressure, triturated with diethyl ether to afford the title compound 169 (70 mg, salt) as a gummy white solid. TLC: 5% MeOH/DCM (Rf: 0.2). This was used in the next step without further characterization. Synthesis of 4-methoxy-3-(N-(4-methoxy-6-((4-(propiolamidomethyl)-1H-pyrazol-1-yl)methyl)benzo[d]isoxazol-3-yl)sulfamoyl) benzoic acid To a stirred solution of compound 169 (70 mg, 0.119 mmol) in DMF (1 mL) at 0° C. was added DIPEA (0.062 mL, 0.359 mmol), propiolic acid (9 mg, 0.130 mmol) followed by $T_3P$ as a 50% solution in EtOAc (0.113 mL, 0.178 mmol) and the reaction mixture was allowed to stir at room temperature for 16 h. After completion (monitored by TLC), the reaction mixture was concentrated under reduced pressure and the crude was purified by prep HPLC to afford the title compound (10 mg, 10.8%) as an off-white solid. TLC: 5% MeOH/DCM (Rf: 0.5). (See Table 1 for analytical data).

Synthetic Example 87
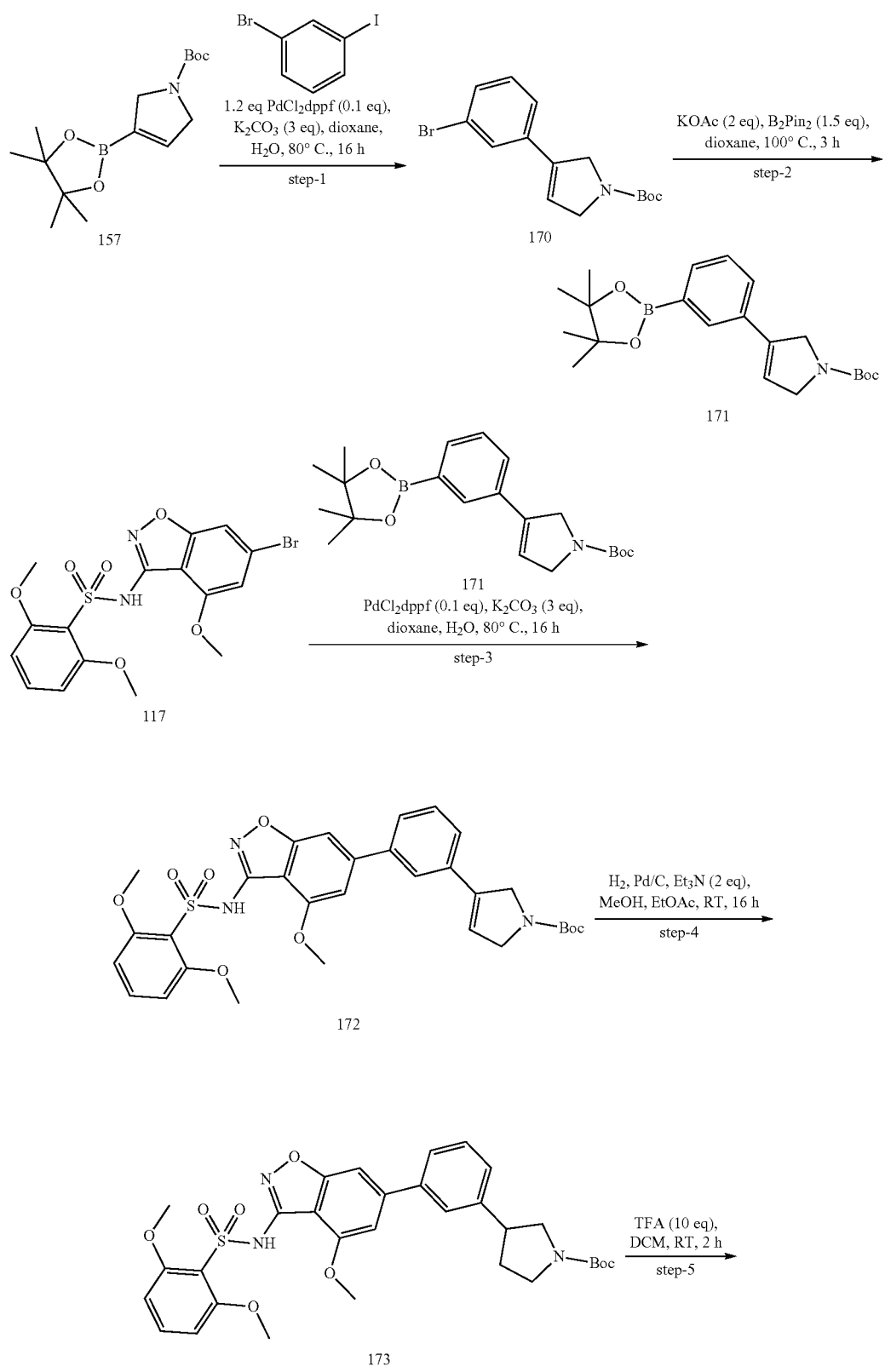
Scheme 62: Synthesis of 2,6-dimethoxy-N-(4-methoxy-6-(3-(1-propiolylpyrrolidin-3-yl)phenyl)benzo[d]isoxazol-3-yl)benzenesulfonamide

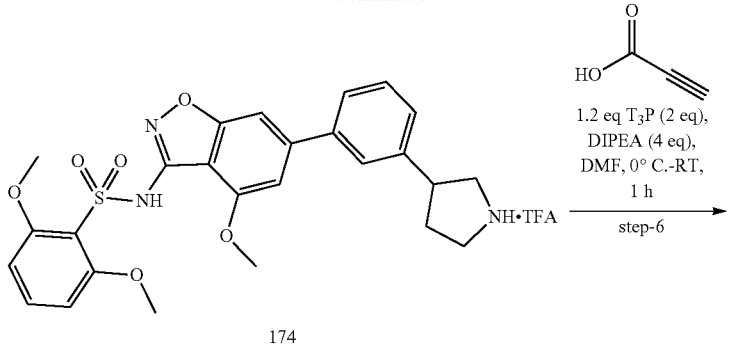

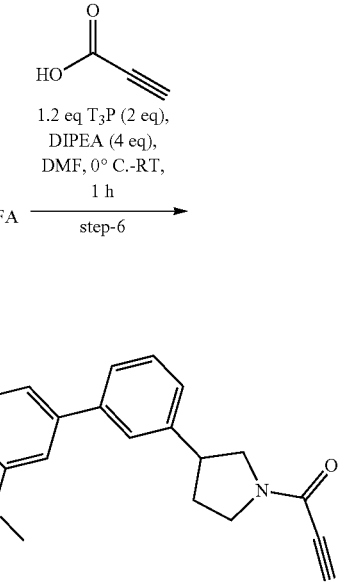

Syn. Ex. 87

Synthesis of tert-butyl 3-(3-bromophenyl)-2,5-dihydro-1H-pyrrole-1-carboxylate (170)

To a stirred solution of 157 (500 mg, 1.693 mmol) and 1-bromo-3-iodobenzene (575 mg, 2.032 mmol) in a 2:1 mixture of 1,4 Dioxane:water (9 mL), was added $K_2CO_3$ (0.701 g, 5.079 mmol) the reaction mixture was degassed with Argon followed by addition of $Pd(dppf)Cl_2$ (136 mg, 0.169 mmol). The reaction mixture was stirred at 80° C. for 16 h. After completion (monitored by TLC), the reaction mixture was filtered on a Celite pad and washed with ethyl acetate and concentrated under reduced pressure. The crude was purified by combi flash-chromatography using a gradient method of 0-30% EtOAc/Heptane to afford the title compound 170 (700 mg; crude) as a pale brown solid. TLC: 50% EtOAc/Heptane (Rf: 0.4). LCMS Calculated for C15H18BrNO2: 323.05; Found: 324.05 (M+1).

Synthesis of tert-butyl 3-(3-(4,4,5,5-tetramethyl-1,3,2-dioxaborolan-2-yl)phenyl)-2,5-dihydro-1H-pyrrole-1-carboxylate (171)

To a stirred solution of 170 (400 mg, 1.233 mmol) in 3:1 mixture of 1,4 Dioxane:water (40 mL) was added KOAc (242 mg, 2.46 mmol) followed by $Bpin_2$ (344 mg, 1.356 mmol). The reaction mixture was degassed with argon gas for 10 min. followed by addition of $Pd(PPh_3)_4$ (142 mg, 0.12 mmol). The reaction mixture was stirred at 90° C. for 16 h. After completion (monitored by TLC), the reaction mixture was filtered through a pad of Celite and washed with EtOAC. The filtrate was concentrated under reduced pressure to afford the title compound 171 (480 mg, crude) as a yellow solid. TLC: 50% EtOAc/Heptane ($R_f$: 0.5). LCMS Calculated for C21H30BNO4: 371.23; Found: 372.02 (M+1).

Synthesis of tert-butyl 3-(3-(3-((2,6-dimethoxyphenyl)sulfonamido)-4-methoxybenzo[d]isoxazol-6-yl)phenyl)-2,5-dihydro-1H-pyrrole-1-carboxylate (172)

To a stirred solution of compound 117 (200 mg, 0.451 mmol) in 3:1 mixture of 1,4 Dioxane:water (4 mL) was added $K_2CO_3$ (124 mg, 0.902 mmol) followed by compound 171 (184 mg, 0,496 mmol). The reaction mixture was allowed to stir at 80° C. for 16 h. After completion (monitored by TLC), the reaction mixture was cooled to room temperature, quenched with ice water and extracted with ethyl acetate. The organic layer was dried over anhydrous $Na_2SO_4$, and concentrated under reduced pressure. The crude compound was purified by combi flash chromatography (neutral alumina) to afford the title compound 172 (180 mg, crude), as an off-white solid. TLC: 50% EtOAc/Heptane ($R_f$, 0.6). LCMS Calculated for C31H33N3O8S: 607.20; Found: 608.5 (M+1).

Synthesis of tert-butyl 3-(3-(3-((2,6-dimethoxyphenyl)sulfonamido)-4-methoxybenzo[d]isoxazol-6-yl)phenyl)pyrrolidine-1-carboxylate (173)

An autoclave was charged with a solution of Compound 172 (150 mg 0.246 mmol) in MeOH:EtOAc (15 mL, 2:1), TEA (0.069, 0.493 mmol) and the mixture was purged with nitrogen for 5 min. followed by addition of 10% Pd/C (52 mg). The reaction mixture was allowed to stir under hydrogen atmosphere (60 psi) at room temperature for 16 h. After completion (monitored by TLC), the reaction mixture was filtered through a pad of Celite and washed with MeOH. The filtrate was concentrated under reduced pressure. The crude product was purified by Combi flash chromatography (using a gradient method of 0-5% MeOH/DCM) to afford the title compound 173 (200 mg, crude) as a white solid. TLC: 50% EtOAc/Heptane ($R_f$, 0.6). LCMS Calculated for C31H35N3O8S: 609.21; Found: 610.08 (M+1).

Synthesis of 2,6-dimethoxy-N-(4-methoxy-6-(3-(1-(2,2,2-trifluoroacetyl)-114-pyrrolidin-3-yl)phenyl)benzo[d]isoxazol-3-yl)benzenesulfonamide (174)

To a stirred solution of compound 173 (200 mg, 0.328 mmol) in DCM (2 mL) was added TFA (0.26 mL, 3.28 mmol) at 0° C. The reaction was allowed to stir at the room temperature for 2 h. After completion (monitored by TLC), the reaction mixture was concentrated under reduced pressure and co-evaporated with toluene to afford the title compound 174 (190 mg, salt) as a thick brown oil. TLC: 5% MeOH/DCM ($R_f$ 0.3). The crude material was used for the next step without any purification.

Synthesis of 2,6-dimethoxy-N-(4-methoxy-6-(3-(1-propioloylpyrrolidin-3-yl)phenyl)benzo[d]isoxazol-3-yl)benzenesulfonamide To a stirred solution of compound 174 (90 mg, 0.148 mmol) in DMF (1 mL) at 0° C. was added DIPEA (0.103 mL, 0.593 mmol) and propiolic acid (12 mg, 0.177 mmol) followed by $T_3P$ as a 50% solution in EtOAc (0.141 mL, 0.222 mmol). The reaction mixture was allowed to stir at room temperature for 16 h. After completion (monitored by TLC), the reaction mixture was concentrated under reduced pressure and the crude was purified by prep HPLC to afford the title compound (4 mg, 4.81%) as an off-white solid. TLC: 5% MeOH/DCM ($R_f$ 0.5). (See Table 1 for analytical data).

Synthetic Example 88

Scheme 63: Synthesis of N-(2-((3-((5-ethyl-2-methoxyphenyl)sulfonamido)-4-methoxybenzo[d]isoxazol-6-yl)methoxy)ethyl)propiolamide

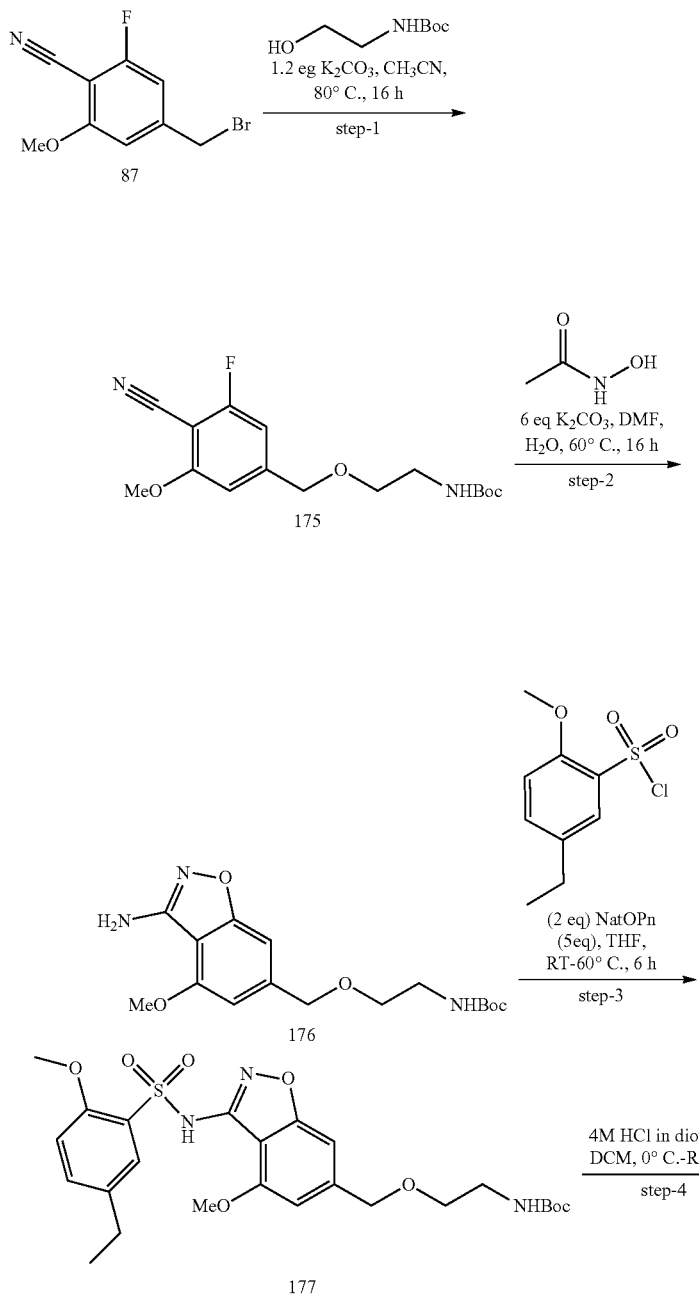

-continued

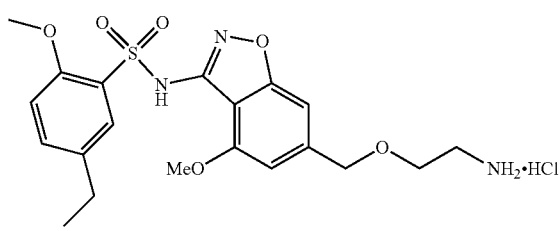
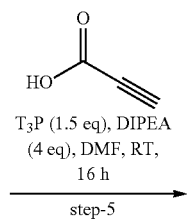

178

T₃P (1.5 eq), DIPEA (4 eq), DMF, RT, 16 h
→
step-5

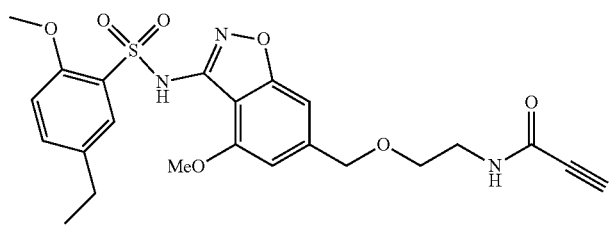

Syn. Ex. 88

Synthesis of tert-butyl (2-((4-cyano-3-fluoro-5-methoxybenzyl)oxy)ethyl)carbamate (175)

To a stirred solution of compound 87 (250 mg, 1.024 mmol) in ACN (5 mL) was added K₂CO₃ (283 mg, 2.048 mmol) followed by tert-butyl (2-hydroxyethyl)carbamate (54 mg, 0.339 mmol). The reaction mixture was stirred at 80° C. for 16 h. After completion (monitored by TLC), the reaction mixture was cooled to room temperature, quenched with ice cold water and extracted with ethyl acetate. The organic layer was washed with brine, dried over anhydrous Na₂SO₄ and concentrated under reduced pressure. The crude compound was purified by combi flash chromatography (using a gradient method of 0-30% EtOAc/Heptane) to afford the title compound 175 (300 mg, 90.36%) as a yellow solid. TLC: 50% EtOAc/Heptane (Rf: 0.5). LCMS Calculated for C16H21FN2O4: 324.15; Found: 325.5 (M+H).

Synthesis of tert-butyl (2-((3-amino-4-methoxybenzo[d]isoxazol-6-yl)methoxy)ethyl)carbamate (176)

To a stirred solution of compound 175 (300 mg, 0.924 mmol) in a 6:1 mixture of DMF:H₂O (7 mL) at room temperature was added N-hydroxyacetamide (208 mg, 2.774 mmol) followed by K₂CO₃ (0.766 g, 5.544 mmol). The reaction mixture was allowed to stir at 60° C. for 16 h. After completion (monitored by TLC), the reaction mixture was cooled to room temperature, quenched with ice cold water and extracted with ethyl acetate. The organic layer was washed with brine, dried over anhydrous Na₂SO₄ and concentrated under reduced pressure. The crude compound was purified by combi flash chromatography using a gradient method of 50-90% EtOAc/Heptane to afford the title compound 176 (250 mg, 80.12%) as a colorless gummy oil. TLC: 80% EtOAc/Heptane (Rf: 0.40). LCMS Calculated for C16H23N3O5: 337.16; Found: 338.02 (M+1).

Synthesis of tert-butyl (2-((3-((5-ethyl-2-methoxyphenyl)sulfonamido)-4-methoxybenzo[d]isoxazol-6-yl)methoxy)ethyl)carbamate (177)

To a stirred solution of compound 176 (120 mg, 0.355 mmol) in THF (5 mL) at 0° C. was added Na^tOPn (195 mg, 1.775 mmol) followed by 5-ethyl-2-methoxybenzenesulfonyl chloride (166 mg, 0.711 mmol). The reaction was allowed to stir at 60° C. for 6 h. After completion (monitored by TLC), the reaction mixture was quenched with water and extracted with ethyl acetate. The organic layer was washed with brine, dried over anhydrous Na₂SO₄, and concentrated under reduced pressure. The crude compound was purified by combi flash column chromatography using a gradient method of 20-60% EtOAc/Heptane to afford the title compound 177 (180 mg, 94.73%) as an off-white solid. TLC: 80% EtOAc (Rf: 0.5). LCMS Calculated for: C25H33N3O8S: 535.20; Found: 536.5 (M+1).

Synthesis of N-(6-((2-aminoethoxy)methyl)-4-methoxybenzo[d]isoxazol-3-yl)-5-ethyl-2-methoxybenzenesulfonamide hydrochloride (178)

To a stirred solution of compound 177 (0.15 g, 0.26 mmol) in DCM (1 mL) was added 4M HCl in Dioxane (1 mL) at 0° C. The reaction was allowed to stir at the room temperature for 2 h. After completion (monitored by TLC), the reaction mixture was concentrated under reduced pressure and washed with diethyl ether and heptane to afford the title compound 178 (115 mg, HCl salt) as a yellow solid. TLC: 10% MeOH/DCM (Rf: 0.5).

The crude material was used for the next step without any purification.

Synthesis of N-(2-((3-((5-ethyl-2-methoxyphenyl)sulfonamido)-4-methoxybenzo[d]isoxazol-6-yl)methoxy)ethyl)propiolamide To a stirred solution of compound 178 (115 mg, 0.243 mmol) in DMF (2 mL) at 0° C. was added DIPEA (0.127 mL, 0.729 mmol) followed by T₃P as a 50% solution in ethyl acetate (0.231 mL, 0.364 mmol). The reaction was allowed to stir at the room temperature for 50 min. After that, a pre-dissolved solution of propiolic acid (34 mg, 0.486 mmol) in DMF (0.3 mL) was added dropwise and the reaction was allowed to stir at the room temperature for 4 h. After completion (monitored by TLC), the reaction mixture was quenched with water and extracted with Ethyl acetate. The organic layer was washed with brine, dried over anhydrous Na₂SO₄, and concentrated under reduced pressure. The crude compound was purified by using prep HPLC to afford the title compound (11.4 mg, 9.66%) as an off-white solid. TLC: 10% MeOH/DCM (Rf: 0.5). (See Table1 for analytical data)

Synthetic Example 89 and 90

Scheme 64: Synthesis of N-(3-((3-((5-ethyl-2-methoxyphenyl) sulfonamido)-4-methoxybenzo[d]isoxazol-6-yl) methoxy) propyl) propiolamide and Synthesis of 5-ethyl-2-methoxy-N-(4-methoxy-6-((3-(vinylsulfonamido) propoxy) methyl) benzo[d]isoxazol-3-yl)benzenesulfonamide

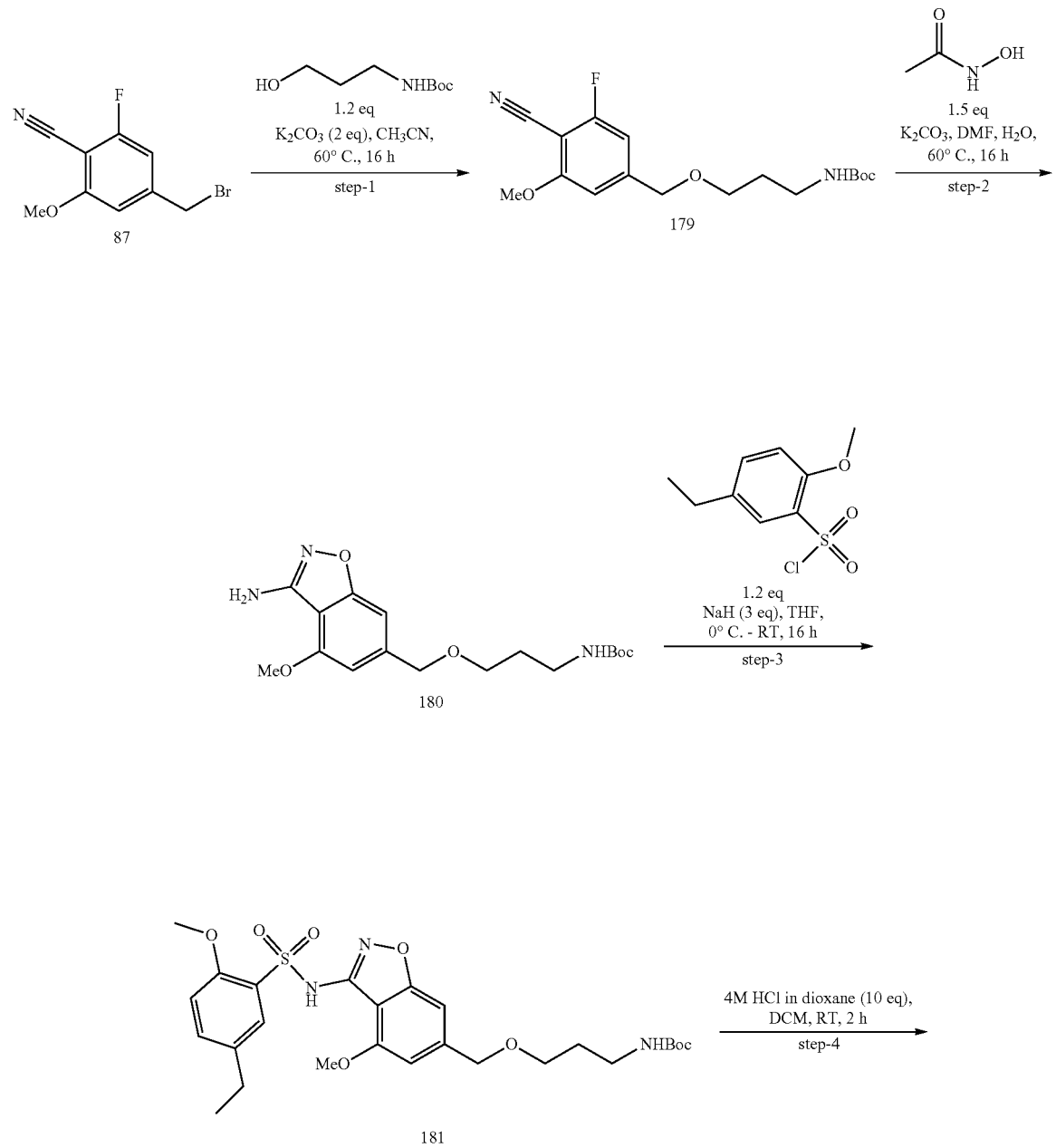

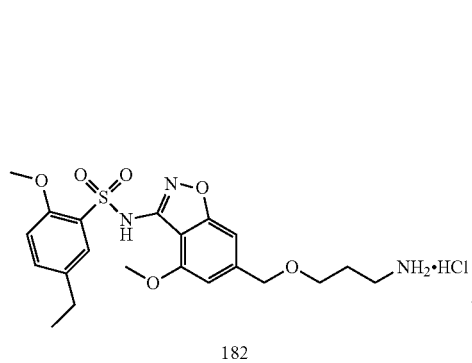
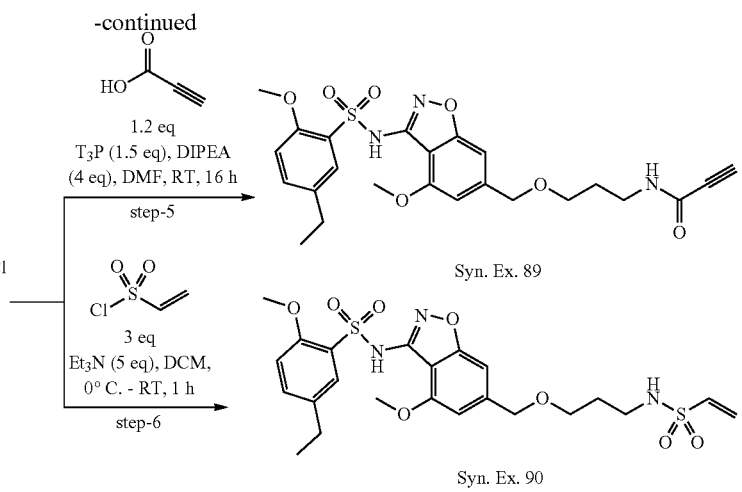

Syn. Ex. 89

Syn. Ex. 90

Synthesis of tert-butyl (3-((4-cyano-3-fluoro-5-methoxybenzyl)oxy)propyl)carbamate (179)

To a stirred solution of compound 87 (1.5 g, 6.146 mmol) in ACN (20 mL) was added $K_2CO_3$ (1.7 g, 12.292 mmol) at 0° C. and stirred for 15 min. After, tert-butyl (3-hydroxypropyl) carbamate (1.34 g, 6.93 mmol) was added, and the reaction was allowed to stir at the room temperature for 16 h. After completion (monitored by TLC), the reaction mixture was quenched with ice cold water and extracted with ethyl acetate. The organic layer was dried over anhydrous $Na_2SO_4$, filtered and concentrated under reduced pressure. The crude compound was purified by silica gel [100-200 mesh] column chromatography to afford the title compound 179 (1.2 g, 57.97%) as a white solid. TLC: 5% MeOH/DCM (Rf. 0.2); LCMS Calculated for $C_{17}H_{23}FN_2O_4$: 338.16; Found: 339.15 (M+1).

Synthesis of tert-butyl (3-((3-amino-4-methoxybenzo[d]isoxazol-6-yl) methoxy) propyl) carbamate (180)

To a stirred solution of compound 179 (1.2 g, 3.546 mmol) in a 6:1 mixture of $DMF:H_2O$ (7 mL) at room temperature was added N-hydroxyacetamide (0.399 g, 5.319 mmol) followed by $K_2CO_3$ (1.47 g, 10.638 mmol). The reaction mixture was allowed to stir at 60° C. for 16 h. After completion (monitored by TLC), the reaction mixture was quenched with ice cold water and extracted with ethyl acetate. The organic layer was washed with brine, dried over anhydrous $Na_2SO_4$ and concentrated under reduced pressure to offer the title 180 (800 mg, 64.20%) as a brown semisolid. TLC: 70% EtOAc/Heptane (Rf: 0.40). LCMS Calculated for C17H25N3O5: 351.18; Found: 352.02 (M+1).

Synthesis of tert-butyl (3-((3-((5-ethyl-2-methoxyphenyl) sulfonamido)-4-methoxybenzo[d]isoxazol-6-yl) methoxy) propyl) carbamate (181)

To a stirred solution of compound 180 (0.8 g, 2.276 mmol) in THF (5 mL) at 0° C. was added NaH (60% dispersion in mineral oil, 0.273 mg, 6.829 mmol) followed by 5-ethyl-2-methoxybenzenesulfonyl chloride (640 mg, 2.731 mmol). The reaction was allowed to stir at 60° C. for 16 h. After completion (monitored by TLC), the reaction mixture was quenched with water and extracted with ethyl acetate. The organic layer was washed with brine, dried over anhydrous $Na_2SO_4$ and concentrated under reduced pressure. The crude was purified by combi flash using gradient 0-50% EA/Heptane to afford the title compound 181 (900 mg, 72%) as a colourless gummy solid. TLC: 50% EtOAc (Rf. 0.5). LCMS Calculated for C26H35N3O8S: 549.21; Found: 550.02 (M+1).

Synthesis of N-(6-((3-aminopropoxy) methyl)-4-methoxybenzo[d]isoxazol-3-yl)-5-ethyl-2-methoxybenzenesulfonamide hydrochloride (182)

To a stirred solution of compound 181 (900 mg, 1.637 mmol) in DCM (4 mL) was added 4M HCl in dioxane (4 mL, 16.374 mmol) at 0° C. The reaction was allowed to stir at the room temperature for 2 h. After completion (monitored by TLC), the reaction mixture was concentrated under reduced pressure. The crude compound was triturated with diethyl ether (20 mL) to afford the title compound 182 (500 mg, HCl salt) as a yellow solid. TLC: 10% MeOH/DCM (Rf. 0.3). The crude material was used in the next step without any purification.

Synthesis of N-(3-((3-((5-ethyl-2-methoxyphenyl) sulfonamido)-4-methoxybenzo[d]isoxazol-6-yl) methoxy) propyl) propiolamide To a stirred solution of compound 182 (500 mg, 1.028 mmol) in DMF (5 mL) at 0° C. was added DIPEA (0.54 mL, 3.086 mmol), propiolic acid (86 mg, 1.233 mmol) followed by $T_3P$ as a 50% solution in EtOAc (0.98 mL, 1.542 mmol). The reaction mixture was allowed to stir at room temperature for 16 h. After completion (monitored by TLC), the reaction mixture was concentrated under reduced pressure. The crude was purified by using prep HPLC to afford the title compound (47 mg, 9.1%) as an off-white solid. TLC: 5% MeOH/DCM (Rf. 0.5). (See Table 1 for analytical data).

Synthesis of 5-ethyl-2-methoxy-N-(4-methoxy-6-((3-(vinylsulfonamido) propoxy) methyl) benzo[d]isoxazol-3-yl)benzenesulfonamide To a stirred solution of compound 182 (300 mg, 0.617 mmol) in DMF (1 mL) at 0° C. was added TEA (0.173 mL, 1.234 mmol) followed by ethenesulfonyl chloride (0.23 mg, 1.851 mmol). The reaction mixture was allowed to stir at 0°

C. for 1 h. After completion (monitored by TLC), the reaction mixture was quenched with ice cold water and extracted with EtOAc. The organic layer was washed with brine, dried over anhydrous Na₂SO₄, and concentrated under reduced pressure. The crude was purified by using prep HPLC to afford the title compound (24 mg, 7.20%) as an off-white solid. TLC: 5% MeOH/DCM ($R_f$ 0.5). (See Table 1 for analytical data).

Synthetic Example 91

Scheme 65: Synthesis of N-((1-(2-(2-((2-fluorophenyl) sulfonyl) hydrazine-1-carbonyl)-6-methylpyridin-4-yl)-1H-pyrazol-4-yl) methyl) propiolamide

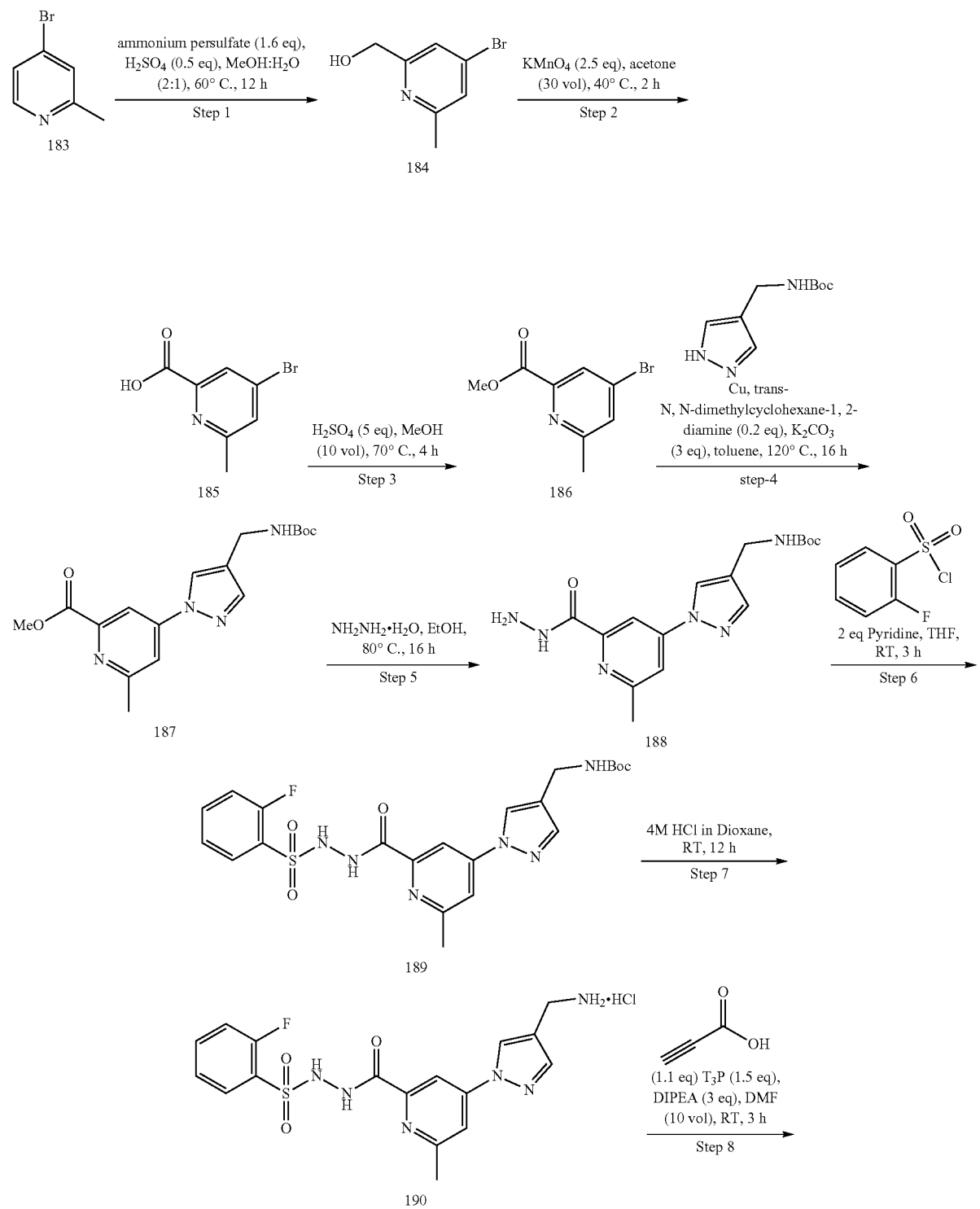

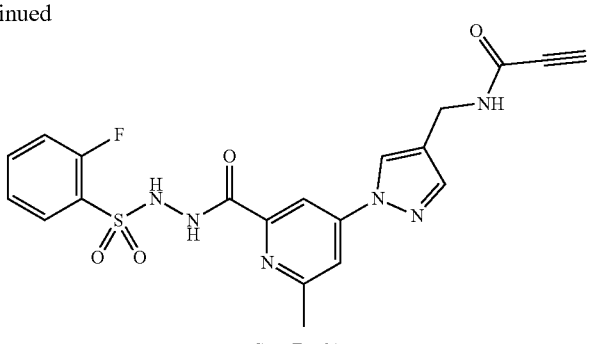

Syn. Ex. 91

Synthesis of (4-bromo-6-methylpyridin-2-yl)methanol (184)

To a stirred solution of compound 183 (5 g, 29.064 mmol) in MeOH (90 mL) at 0° C. was added $H_2SO_4$ (25 mL) and reaction was allowed to stir at 80° C. for 1 h. A premixed solution of ammonium persulfate (166 mg, 87.192 mmol) in $H_2O$ was added in the reaction mixture. The reaction was allowed to stir at 80° C. for 16 h. After completion (monitored by TLC), the reaction mixture was concentrated under reduced pressure and extracted with Ethyl Acetate. The organic layer was washed with brine, dried over anhydrous $Na_2SO_4$, and concentrated under reduced pressure. The crude compound was purified by combi flash column chromatography using a gradient method of 20-60% EtOAc/Heptane to afford the title compound 184 (800 mg, 13.62%) as an off-white solid. TLC: 80% EtOAc ($R_f$ 0.5). LCMS Calculated for: C7H8BrNO: 200.95; Found: 201.5 (M+1).

Synthesis of 4-bromo-6-methylpicolinic acid (185)

To a stirred solution of 184 (3.4 g, 19.76 mmol) in ACN (27 mL) and water (37 mL) was added $KMnO_4$ (7.93 g, 50.200 mmol). The reaction mixture was stirred at 40° C. for 2 h. After completion (monitored by TLC), the reaction mixture was concentrated under reduced pressure. The crude was purified by using prep HPLC to afford the title compound 185 (3.6 g, 85%) as an off-white solid. TLC: 10% MeOH/DCM ($R_f$ 0.5). LCMS Calculated for C7H6BrNO2: 214.96; Found: 216.1 (M+2). The crude compound was used to the next step without purification.

Synthesis of methyl 4-bromo-6-methylpicolinate (186)

To a stirred solution of 4-bromo-6-methyl-pyridine-2-carboxylic acid 185 (3.6 g, 16.66 mmol) in methanol (75 mL, 1850 mmol) was added $H_2SO_4$ (8.16 mL, 83.3 mmol) and water (1.8 mL). The reaction mixture was stirred at 75° C. for 16 h. After completion (monitored by TLC), the reaction mixture was concentrated under reduced pressure to get crude. The crude was quenched with saturated sodium bicarbonate solution and was extracted with ethyl acetate. The combined organic layer was dried over sodium sulphate and filtered and concentrated under reduced pressure to get crude. The crude was purified by combi flash chromatography using gradient 11% EA/Heptane to offer title compound 186 (1.4 g, 36.84%) as a white solid. TLC: 10% MeOH/DCM ($R_f$ 0.5). LCMS Calculated for C8H8BrNO2: 228.97; Found: 229.5 (M+1).

Synthesis of methyl 4-(4-(((tert-butoxycarbonyl)amino)methyl)-1H-pyrazol-1-yl)-6-methylpicolinate (187)

To a stirred solution of methyl 4-bromo-6-methyl-pyridine-2-carboxylate 186 (500 mg, 2.173 mmol) in Toluene (8 mL) was added tert-butyl ((1H-pyrazol-4-yl)methyl)carbamate (557 mg, 2.825 mmol) and $K_2CO_3$ (900 mg, 6.519 mmol). The reaction mixture was purged with nitrogen for 10 min followed by addition of Copper(I) iodide (82 mg, 0.434 mmol) and trans-N,N-dimethylcyclohexane-1,2-diamine (61 mg, 0.43467 mmol). The reaction mixture was stirred at 150° C. for 2 h under microwave irradiation. After completion (monitored by TLC), the reaction was quenched with ice cold water and extracted with ethyl acetate. The combined organic layer was washed with brine solution, dried over sodium sulphate filtered and concentrated under reduced pressure to get crude compound. The crude was purified by combiflash chromatography using gradient 55% EA/Heptane to offer the title compound 187 (307 mg, 40.82%) as a brown semi solid. LCMS Calculated for C17H22N4O4: 346.16; Found: 347.3 (M+1).

Synthesis of tert-butyl ((1-(2-(hydrazinecarbonyl)-6-methylpyridin-4-yl)-1H-pyrazol-4-yl)methyl)carbamate (188)

To a stirred of compound 187 (135 mg, 0.3897 mmol) in EtOH (5 mL), was added $NH_2NH_2·H_2O$ (0.2 mL). The reaction mixture was stirred at 85° C. for 16 h. After completion (monitored by TLC), the reaction mixture was concentrated under reduced pressure to get crude. The crude was triturated with DCM/Pentane (20 mL, 1:9 ratio) to offer title compound 188 (120 mg, 88.88% yield) as a brown solid. This was used in the next step without further characterization.

Synthesis of tert-butyl ((1-(2-(2-((2-fluorophenyl)sulfonyl)hydrazine-1-carbonyl)-6-methylpyridin-4-yl)-1H-pyrazol-4-yl)methyl)carbamate (189)

To a stirred of compound 188 (110 mg, 0.3176 mmol) in THF (1.0 mL) and pyridine (1.0 mL) was added 2-fluorobenzenesulfonyl chloride (123 mg, 0.6351 mmol). The reaction mixture was stirred at room temperature for 3 h. After completion (monitored by TLC), the reaction mixture was quenched with 1N HCl and was extracted with ethyl acetate. The organic layer was washed with brine solution, dried over sodium sulphate filtered and concentrated under reduced pressure. The crude was purified by combi flash column chromatography using gradient 75-90% EA/Heptane to offer title compound 189 (100 mg, 62.5%) as a brown solid. TLC: 10% MeOH/DCM ($R_f$, 0.3). LCMS Calculated for: $C_{22}H_{25}FN_6O_5S$: 504.16; Found: 505.7 (M+1).

Synthesis of N'-(4-(4-(aminomethyl)-1H-pyrazol-1-yl)-6-methylpicolinoyl)-2-fluorobenzenesulfonohydrazide hydrochloride (190)

To a stirred solution of compound 189 (90 mg, 0.1784 mmol) in DCM (3 mL) was added 4M HCl in Dioxane (0.44 mL, 1.784 mmol). The reaction mixture was stirred at RT for 2 h. After completion (monitored by TLC), the reaction mixture was concentrated under reduced pressure. The crude was triturated with 1:9 ratio of DCM/n-pentane to offer the title compound 190 (70 mg, 0.167 mmol, 93.8% Yield) as a brown solid. This was used in the next step without further characterization. Synthesis of N-((1-(2-(2-((2-fluorophenyl) sulfonyl) hydrazine-1-carbonyl)-6-methylpyridin-4-yl)-1H-pyrazol-4-yl) methyl) propiolamide To a stirred solution of compound 190 (70 mg, 0.158 mmol) in DMF (4 mL) was added DIPEA (0.083 mL, 0.476 mmol), propiolic acid (13 mg, 0.189 mmol) followed by $T_3P$ as a 50% solution in EtOAc (0.603 mL, 0.948 mmol) at 0° C. The reaction mixture was stirred at RT for 2 h. After completion (monitored by TLC), reaction mixture was quenched with ice cold water and extracted with ethyl acetate. The organic layer was dried over anhydrous $Na_2SO_4$ and concentrated under reduced pressure. The crude compound was purified by using prep HPLC to afford the title compound (4.3 mg, 4.1%) as a brown gummy solid. TLC: 10% MeOH/DCM ($R_f$, 0.4). (See Table 1 for analytical data).

Synthetic Example 92

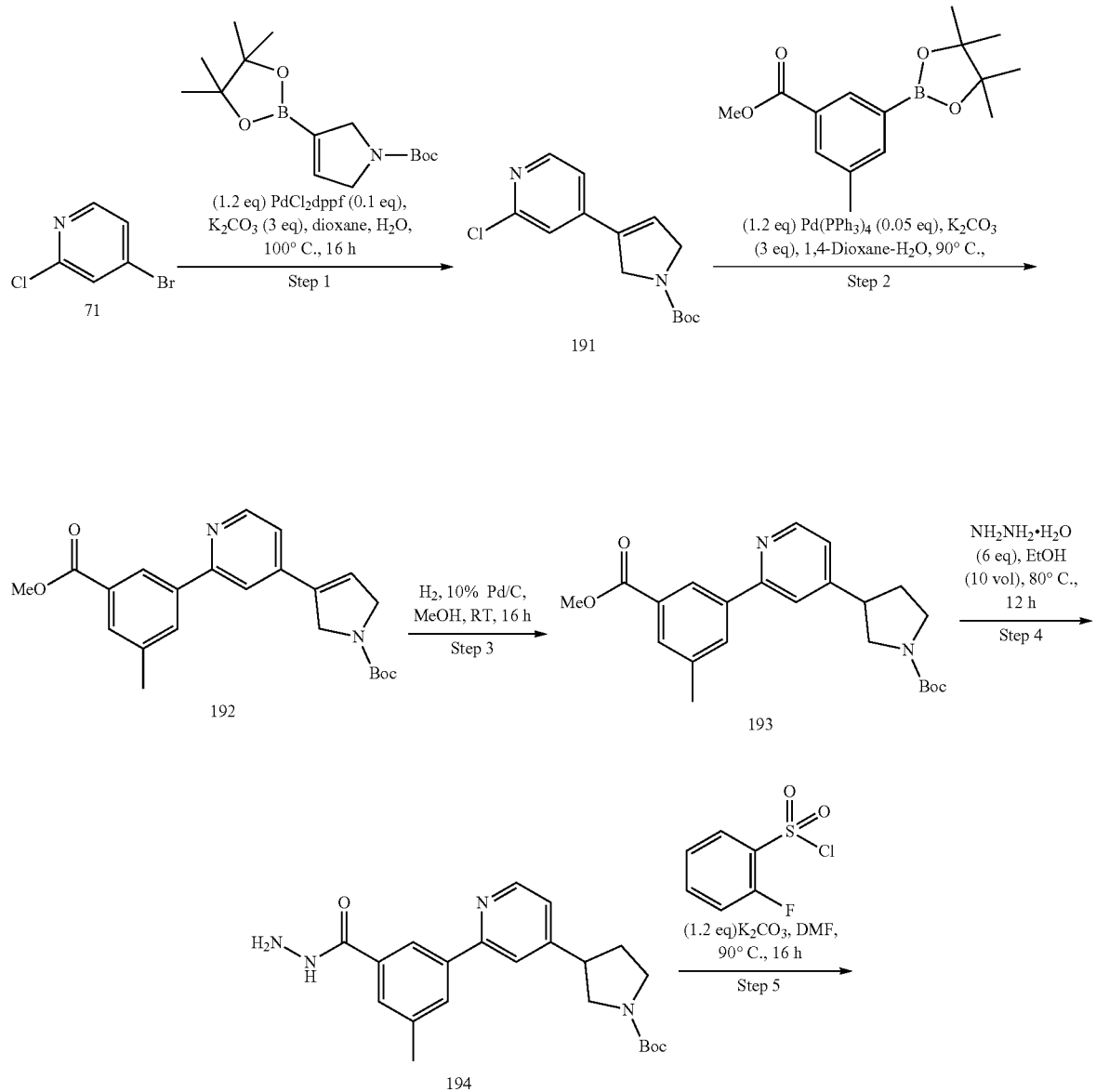

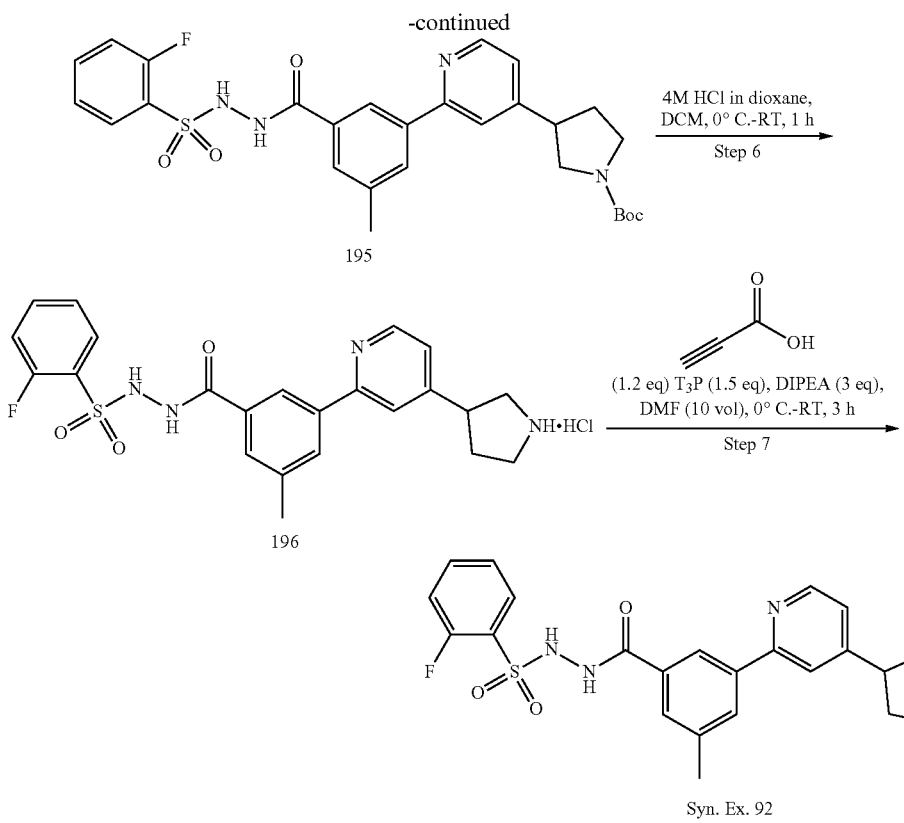

Syn. Ex. 92

Synthesis of tert-butyl 3-(2-chloropyridin-4-yl)-2,5-dihydro-1H-pyrrole-1-carboxylate (191)

To a stirred solution of compound 71 (400 mg, 2.078 mmol) in 3:1 mixture of 1,4 Dioxane:water (10 mL) was added $K_2CO_3$ (862 mg, 6.235 mmol) and tert-butyl 3-(4,4,5,5-tetramethyl-1,3,2-dioxaborolan-2-yl)-2,5-dihydro-1H-pyrrole-1-carboxylate (736 mg, 2.49 mmol). The reaction mixture was purged under nitrogen atmosphere followed by addition of $Pd(PPh_3)_4$ (0.120 g, 0.1039 mmol). The reaction mixture was stirred at 100° C. for 16 h. After completion (monitored by TLC), the reaction mixture was filtered through a pad of celite, diluted with water and extracted with ethyl acetate. The organic layer was washed with brine, dried over anhydrous $Na_2SO_4$ and concentrated under reduced pressure. The crude compound was purified by combi flash chromatography (using a gradient method of 0-30% EtOAc/Heptane) to afford the title compound 191 (350 mg, 60%) as a yellow solid. TLC: 50% EtOAc/Heptane ($R_f$ 0.5). LCMS Calculated for $C_{14}H_{17}ClN_2O_2$: 280.10; Found: 281.5 (M+H).

Synthesis of tert-butyl 3-(2-(3-(methoxycarbonyl)-5-methylphenyl)pyridin-4-yl)-2,5-dihydro-1H-pyrrole-1-carboxylate (192)

To a stirred solution of compound 191 (350 mg, 1.246 mmol) in 3:1 mixture of 1,4 Dioxane:water (40 mL) was added $K_2CO_3$ (517 mg, 3.73 mmol) and methyl 3-methyl-5-(4,4,5,5-tetramethyl-1,3,2-dioxaborolan-2-yl)benzoate (412 mg, 1.495 mmol). The reaction mixture was purged under nitrogen atmosphere followed by addition of $Pd(PPh_3)_4$ (71 mg, 0.0623 mmol). The resulting reaction mixture was stirred at 90° C. for 12 h. After completion (monitored by TLC), the reaction mixture was filtered through a pad of celite, diluted with water and extracted with ethyl acetate. The organic layer was washed with brine, dried over anhydrous $Na_2SO_4$ and concentrated under reduced pressure. The crude compound was purified by combi flash chromatography (using a gradient method of 0-50% EtOAc/Heptane) to afford the title compound 192 (394 mg, 80.24%) as a pale-yellow solid. TLC: 50% EtOAc/Heptane ($R_f$ 0.5). LCMS Calculated for $C_{23}H_{26}N_2O_4$: 394.19; Found: 395.5 (M+1).

Synthesis of tert-butyl 3-(2-(3-(methoxycarbonyl)-5-methylphenyl)pyridin-4-yl)pyrrolidine-1-carboxylate (193)

An autoclave was charged with a solution of Compound 192 (280 mg 0.709 mmol) in MeOH (15 mL) and the mixture was degassed with nitrogen atmosphere three times followed by addition of 10% Pd/C (50 mg). The reaction mixture was purged with hydrogen gas and was allowed to stir under hydrogen atmosphere (100 psi) at room temperature for 16 h. After completion (monitored by TLC), the reaction mixture was filtered through a pad of Celite and washed with MeOH. The filtrate was concentrated under reduced pressure to the dryness. The crude product was purified by combi flash chromatography (using a gradient method of 0-5% MeOH/DCM) to afford the desired title compound 193 (250 mg, crude) as a white solid. TLC: 50% EtOAc/Heptane ($R_f$ 0.6). LCMS Calculated for $C_{23}H_{28}N_2O_4$: 396.20; Found: 397.08 (M+1).

Synthesis of tert-butyl 3-(2-(3-(hydrazinecarbonyl)-5-methylphenyl)pyridin-4-yl)pyrrolidine-1-carboxylate (194)

To a stirred solution of compound 193 (0.3 g, 0.756 mmol) in EtOH (20 mL) was added hydrazine hydrate (0.22 mL, 4.539 mmol) and the reaction was allowed to stir at 80° C. for 16 h. After completion (monitored by TLC), the reaction mixture was concentrated under reduced pressure. The crude was triturated with DCM/n-Heptane and concentrated under reduced pressure to afford the title compound 194 (200 mg, 66.66%) as a pale-yellow solid. TLC: 5% MeOH/DCM ($R_f$ 0.3). LCMS Calculated for $C_{22}H_{28}N_4O_3$: 396.22; Found: 397.01 (M+1).

Synthesis of tert-butyl 3-(2-(3-(2-((2-fluorophenyl)sulfonyl)hydrazine-1-carbonyl)-5-methylphenyl)pyridin-4-yl)pyrrolidine-1-carboxylate (195)

To a solution of compound 194 (0.200 g, 0.504 mmol) in DMF (5 mL) at 0° C. was added $K_2CO_3$ (0.209 g, 1.513 mmol) followed by 2-fluorobenzenesulfonyl chloride (0.117 g, 0.604 mmol). The reaction mixture was stirred at 90° C. for 16 h. After completion (monitored by TLC), the reaction mixture was diluted with $H_2O$ and extracted with EtOAc. The organic layer was washed with brine, dried over anhydrous $Na_2SO_4$ and concentrated under reduced pressure. The crude compound was purified by combi flash chromatography (using a gradient method of 0-50% EtOAc/Heptane) to afford the title compound 195 (180 mg, 80.24%) as pale-yellow solid. TLC: 50% EtOAc/Heptane ($R_f$ 0.5). LCMS Calculated for C28H31FN4O5S: 554.20; Found: 555.5 (M+1).

Synthesis of 2-fluoro-N'-(3-methyl-5-(4-(pyrrolidin-3-yl)pyridin-2-yl)benzoyl)benzenesulfonohydrazide hydrochloride (196)

To a stirred solution of compound 195 (180 mg, 0.324 mmol) in DCM (3 mL) at 0° C. was added 4M HCl in dioxane (0.48 mL, 1.94 mmol). The reaction was allowed to stir at the room temperature for 1 h. After completion of the reaction (monitored by TLC), the reaction mixture was concentrated under reduced pressure. The crude compound was triturated with diethyl ether to afford the title compound 196 (90 mg, HCl salt) as a brown solid. TLC: 5% MeOH/DCM ($R_f$ 0.5). This was used in the next step without further characterization.

Synthesis of 2-fluoro-N'-(3-methyl-5-(4-(1-propioloylpyrrolidin-3-yl)pyridin-2-yl)benzoyl)benzenesulfonohydrazide To a stirred solution of compound 196 (90 mg, 0.183 mmol) in DMF (1 mL) at 0° C. was added DIPEA (0.096 mL, 0.549 mmol), Propiolic acid (15 mg, 0.219 mmol) followed by $T_3P$ as a 50% solution in EtOAc (0.174 mL, 0.274 mmol). The reaction mixture was allowed to stir at room temperature for 16 h. After completion (monitored by TLC), the reaction mixture was concentrated under reduced pressure and the crude was purified by using prep HPLC to afford the title compound (22 mg, 4.81%) as an off-white solid. TLC: 5% MeOH/DCM ($R_f$ 0.5). (See Table 1 for analytical data).

Synthetic Example 93

Scheme 67: Synthesis of N-((1-((3-((5-ethyl-2-methoxyphenyl) sulfonamido)-4-methoxybenzo[d]isoxazol-6-yl) methyl)-1H-pyrazol-4-yl) methyl)-2-(vinylsulfonamido)acetamide

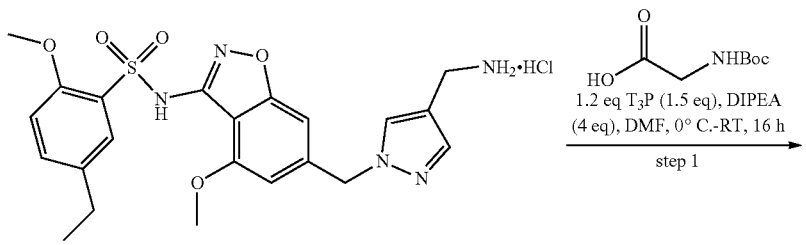

151

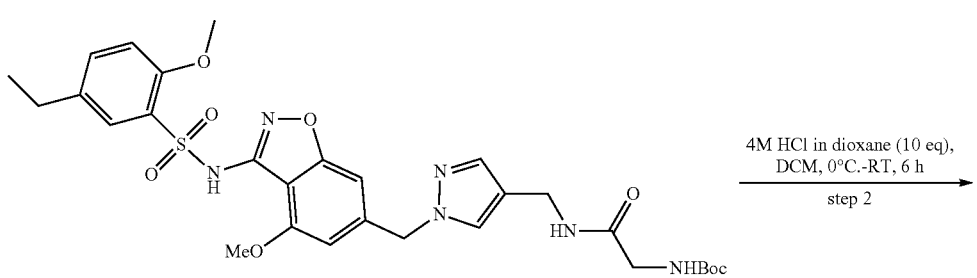

197

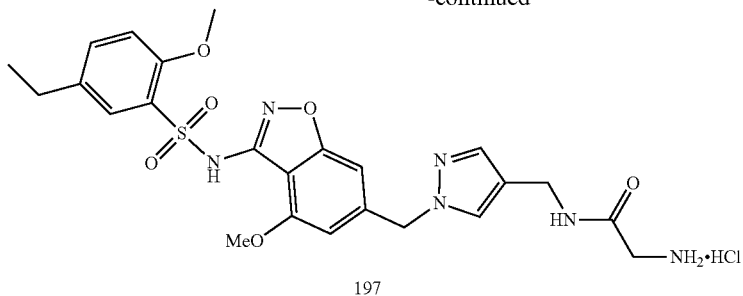
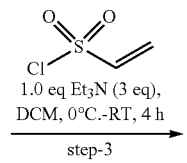

-continued

197

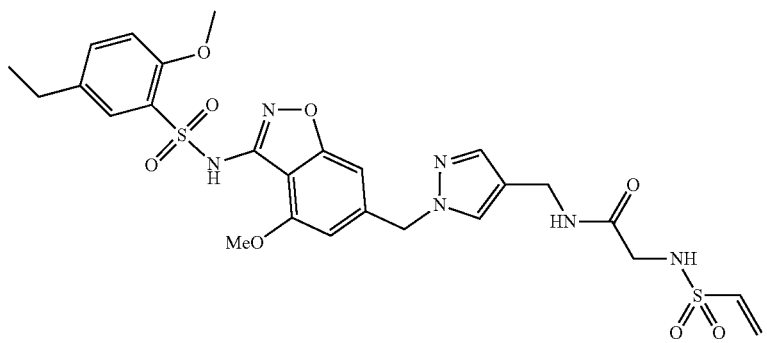

Syn. Ex. 93

Synthesis of tert-butyl (2-(((1-((3-((5-ethyl-2-methoxyphenyl) sulfonamido)-4-methoxybenzo[d]isoxazol-6-yl) methyl)-1H-pyrazol-4-yl) methyl) amino)-2-oxoethyl) carbamate (197)

To a stirred solution of compound 151 (180 mg, 0.354 mmol) in DMF (1 mL) at 0° C. was added DIPEA (0.185 mL, 1.063 mmol), (tert-butoxycarbonyl) glycine (124 mg, 0.708 mmol) followed by $T_3P$ as a 50% solution in EtOAc (0.337 mL, 0.531 mmol). The reaction mixture was stirred at the room temperature for 16 h. After completion (monitored by TLC), the reaction mixture was quenched with aqueous ammonium chloride and extracted with ethyl acetate. The organic layer was dried over anhydrous $Na_2SO_4$, to afford the title compound 197 (150 mg, 67.56%) as a pale brown gummy solid. TLC: 10% MeOH/DCM ($R_f$: 0.5). LCMS Calculated for C29H36N6O8S: 628.28; Found: 629.5 (M+1).

Synthesis of 2-amino-N-((1-((3-((5-ethyl-2-methoxyphenyl)sulfonamido)-4-methoxybenzo[d]isoxazol-6-yl)methyl)-1H-pyrazol-4-yl)methyl)acetamide hydrochloride (198)

To a stirred solution of compound 197 (150 g, 0.238 mmol) in DCM (3 mL) at 0° C. was added 4M HCl in 1,4-dioxane (0.596 mL, 2.385 mmol). The reaction was allowed to stir at the room temperature for 4 h. After completion (monitored by TLC), the reaction mixture was concentrated under reduced pressure and Co distilled with diethyl ether to afford the title 198 (150 mg, HCl Salt) as a yellow solid. TLC: 15% MeOH/DCM ($R_f$: 0.2); This was used in the next step without further characterization.

Synthesis of N-((1-((3-((5-ethyl-2-methoxyphenyl) sulfonamido)-4-methoxybenzo[d]isoxazol-6-yl) methyl)-1H-pyrazol-4-yl) methyl)-2-(vinylsulfonamido) acetamide To a stirred solution of compound 198 (100 mg, 0.176 mmol) in DCM (4 mL) at 0° C. was added TEA (0.074 mL, 0.530 mmol) and ethene sulfonyl chloride (22 mg, 0.22 mmol). The reaction mixture was stirred at 0° C. for 4 h. After completion (monitored by TLC), the reaction mixture was concentrated under reduced pressure. The crude was purified by using prep HPLC to afford the title compound (9.4 mg, 9.03%) as an off-white solid. TLC: 10% MeOH/DCM ($R_f$: 0.6). (See Table 1 for analytical data).

Synthetic Example 94
Scheme 68: Synthesis of 1-((3-((5-ethyl-2-methoxyphenyl) sulfonamido)-4-methoxybenzo[d]isoxazol-6-yl)methyl)-N-(2-propiolamidoethyl)-1H-pyrazole-4-carboxamide
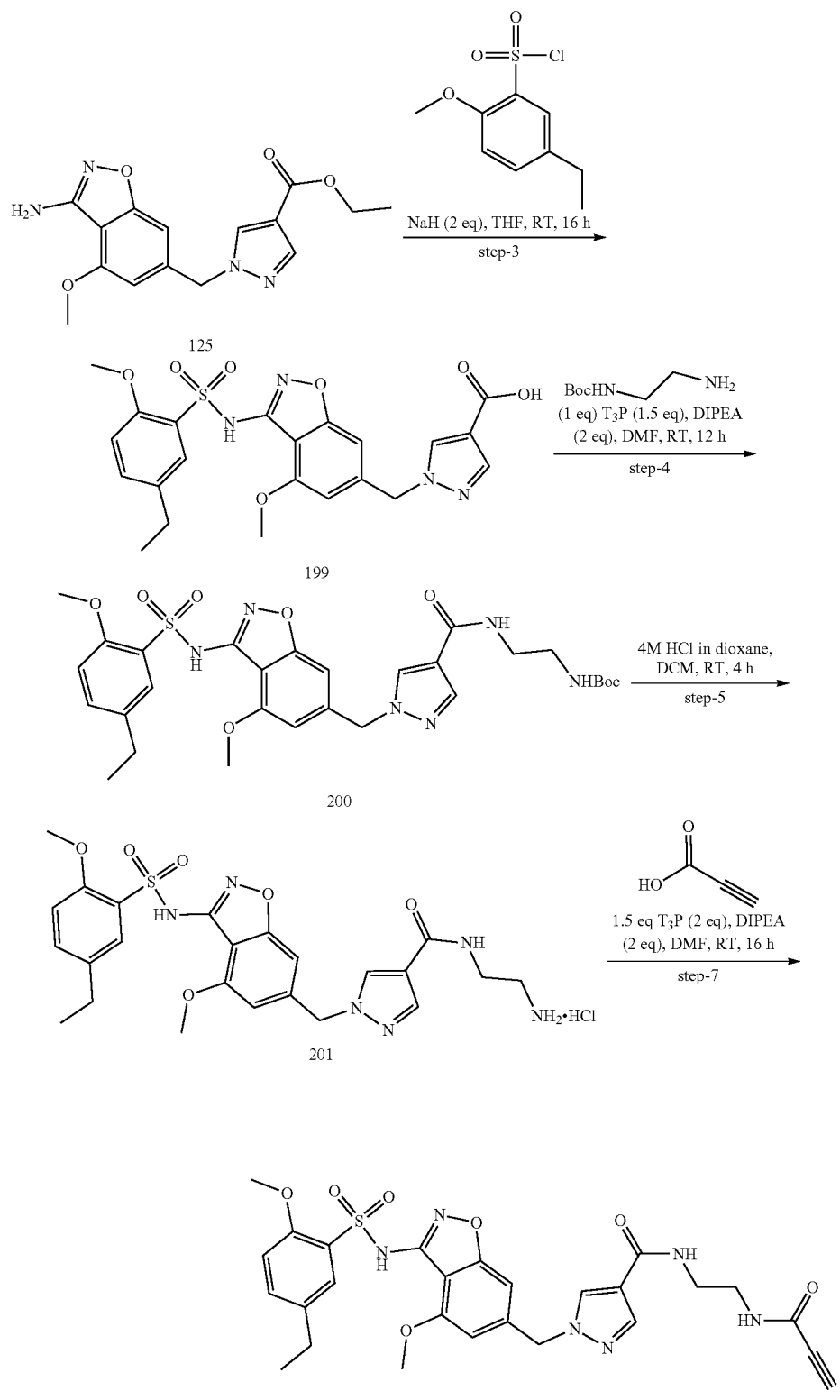
Syn. Ex. 94

Synthesis of 1-((3-((5-ethyl-2-methoxyphenyl)sulfonamido)-4-methoxybenzo[d]isoxazol-6-yl)methyl)-1H-pyrazole-4-carboxylic acid (199)

To a stirred solution of compound 125 (400 mg, 1.264 mmol) in THF (5 mL) at 0° C. was added NaH as a 60% dispersion in mineral oil (0.101 mg, 2.529 mmol) followed by 5-ethyl-2-methoxybenzenesulfonyl chloride (444 mg, 1.896 mmol). The reaction was allowed to stir at 60° C. for 16 h. After completion (monitored by TLC), the reaction mixture was quenched with ice cold water and acidified the aqueous layer by citric acid aqueous solution to pH~6. The aqueous layer was extracted with ethyl acetate. The organic layer was collected, washed with brine, dried over anhydrous $Na_2SO_4$, and concentrated under reduced pressure to afford the title compound 199 (150 mg, 23.07%) as a colourless gummy solid. TLC: 50% EtOAc ($R_f$, 0.5). LCMS Calculated for C22H22N4O7S: 486.12; Found: 487.02 (M+1).

Synthesis of tert-butyl (2-(1-((3-((5-ethyl-2-methoxyphenyl) sulfonamido)-4-methoxybenzo[d]isoxazol-6-yl) methyl)-1H-pyrazole-4-carboxamido) ethyl) carbamate (200)

To a stirred solution of compound 199 (120 mg, 0.246 mmol) in DMF (2 mL) at 0° C. was added DIPEA (0.086 mL, 0.493 mmol), tert-butyl (2-aminoethyl)carbamate (39 mg, 0.246 mmol) followed by $T_3P$ as a 50% solution in EtOAc (0.234 mL, 0.369 mmol). The reaction mixture was allowed to stir at room temperature for 12 h. After completion (monitored by TLC), the reaction mixture was quenched with water and extracted with Ethyl Acetate. The organic layer was washed with brine, dried over anhydrous $Na_2SO_4$, and concentrated under reduced pressure. The crude was purified by combi flash chromatography using gradient 20-50% EA/Heptane to afford the title compound 200 (90 mg, 58.06%) as an off-white solid. TLC: 5% MeOH/DCM ($R_f$, 0.5). LCMS Calculated for C29H36N6O8S: 628.23; Found: 629.02 (M+1).

Synthesis of N-(2-aminoethyl)-1-((3-((5-ethyl-2-methoxyphenyl) sulfonamido)-4-methoxybenzo[d] isoxazol-6-yl) methyl)-1H-pyrazole-4-carboxamide hydrochloride (201)

To a stirred solution of compound 200 (90 mg, 0.143 mmol) in DCM (3 mL) at 0° C. was added 4M HCl in Dioxane (0.35 mL, 1.431 mmol). The reaction mixture was allowed to stir at room temperature for 4 h. After completion (monitored by TLC), the reaction mixture was concentrated under reduced pressure. The crude was triturated with Diethyl ether/Heptane to afford the title compound 201 (62 mg, 77.5%) as an off-white gummy solid. TLC: 5% MeOH/DCM ($R_f$, 0.2). This was used in the next step without further characterization.

Synthesis of 1-((3-((5-ethyl-2-methoxyphenyl) sulfonamido)-4-methoxybenzo[d]isoxazol-6-yl) methyl)-N-(2-propiolamidoethyl)-1H-pyrazole-4-carboxamide To a stirred solution of compound 201 (62 mg, 0.109 mmol) in DMF (1 mL) at 0° C. was added DIPEA (0.038 mL, 0.218 mmol), Propiolic acid (15 mg, 0.218 mmol) followed by $T_3P$ as a 50% solution in EtOAc (0.138 mL, 0.218 mmol). The reaction mixture was allowed to stir at room temperature for 16 h. After completion (monitored by TLC), the reaction mixture was concentrated under reduced pressure. The crude was purified by using prep HPLC to afford the title compound (14.8 mg, 4.81%) as an off-white solid. TLC: 5% MeOH/DCM ($R_f$, 0.5). (See Table 1 for analytical data).

Synthetic Example 95

Scheme 69: Synthesis of 5-ethyl-2-methoxy-N-(4-methoxy-6-((4-(4-propioloylpiperazine-1-carbonyl)-1H-pyrazol-1-yl)methyl)benzo[d]isoxazol-3-yl)benzensulfonamide

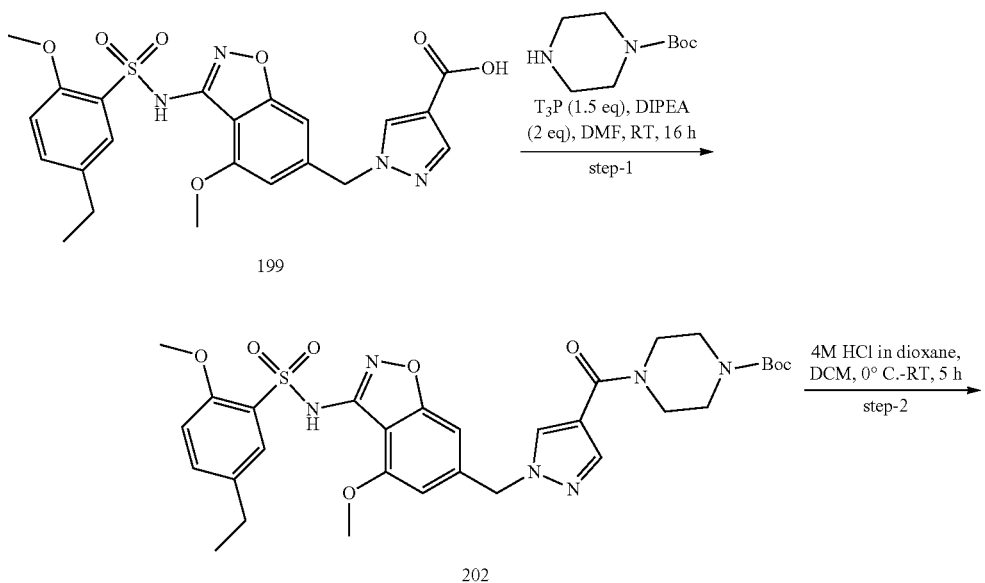

-continued

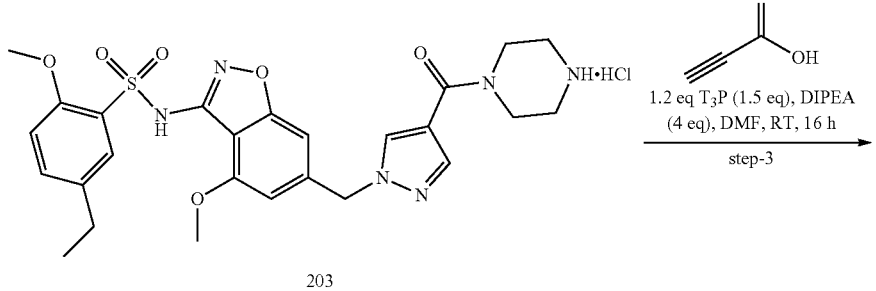

203

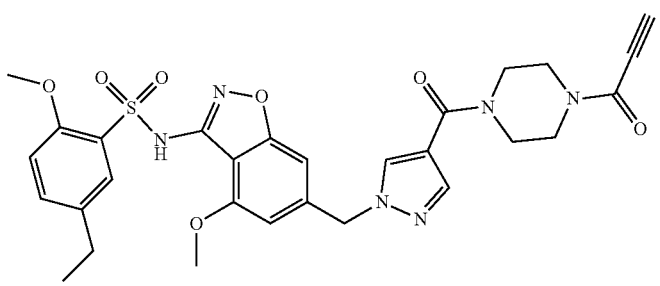

Syn. Ex. 95

Synthesis of tert-butyl 4-(1-((3-((5-ethyl-2-methoxyphenyl)sulfonamido)-4-methoxybenzo[d]isoxazol-6-yl)methyl)-1H-pyrazole-4-carbonyl)piperazine-1-carboxylate (202)

To a stirred solution of Boc-piperazine (128 mg, 0.690 mmol) in DMF (1 mL) at 0° C. was added DIPEA (0.3 mL, 1.725 mmol), compound 199 (280 mg, 0.575 mmol) followed by $T_3P$ as a 50% solution in EtOAc (0.548 mL, 0.862 mmol). The reaction mixture was allowed to stir at room temperature for 16 h. After completion (monitored by TLC), the reaction mixture was concentrated under reduced pressure and the crude was purified by using prep HPLC to afford the title compound 202 (120 mg, 31.91%) as a brown liquid. TLC: 5% MeOH/DCM ($R_f$ 0.5). LCMS Calculated for C31H38N6O8S: 654.28; Found: 655.21.

Synthesis of 5-ethyl-2-methoxy-N-(4-methoxy-6-((4-(piperazine-1-carbonyl)-1H-pyrazol-1-yl)methyl)benzo[d]isoxazol-3-yl)benzenesulfonamide hydrochloride (203)

To a stirred solution of compound 202 (100 mg, 0.152 mmol) in DCM (3 mL) at 0° C. was added 4M HCl in dioxane (0.38 mL, 1.527 mmol). The reaction was allowed to stir at the room temperature for 5 h. After completion (monitored by TLC), concentrated under reduced pressure and the crude compound was triturated with diethyl ether to afford the title compound 203 (70 mg, HCl salt) as pale-yellow solid. TLC: 50% EA/Heptane ($R_f$ 0.2). This was used in the next step without further characterization.

Synthesis of 5-ethyl-2-methoxy-N-(4-methoxy-6-((4-(4-propioloylpiperazine-1-carbonyl)-1H-pyrazol-1-yl)methyl)benzo[d]isoxazol-3-yl)benzenesulfonamide To a stirred solution of compound 203 (70 mg, 0.188 mmol) in DMF (1 mL) at 0° C. was added DIPEA (0.062 mL, 0.355 mmol), Propiolic acid (15 mg, 0.225 mmol) followed by $T_3P$ as a 50% solution in EtOAc (0.179 mL, 0.282 mmol). The reaction mixture was allowed to stir at room temperature for 6 h. After completion (monitored by TLC), the reaction mixture was concentrated under reduced pressure and the crude was purified by using prep HPLC to afford the title compound (41 mg, 41.84%) as an off-white solid. TLC: 5% MeOH/DCM ($R_f$ 0.5). (See Table 1 for analytical data).

Synthetic Example 96

Scheme 70: Synthesis of 2,6-dimethoxy-N-(4-methoxy-6-(6-(4-propioloylpiperazin-1-yl)pyridin-2-yl)benzo[d]isoxazol-3-yl)benzenesulfonamide

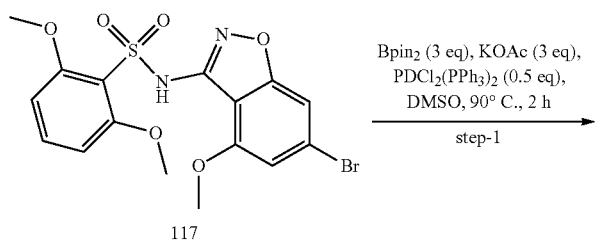

117

343

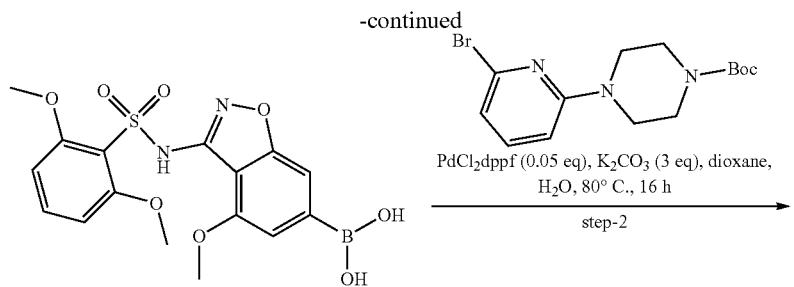

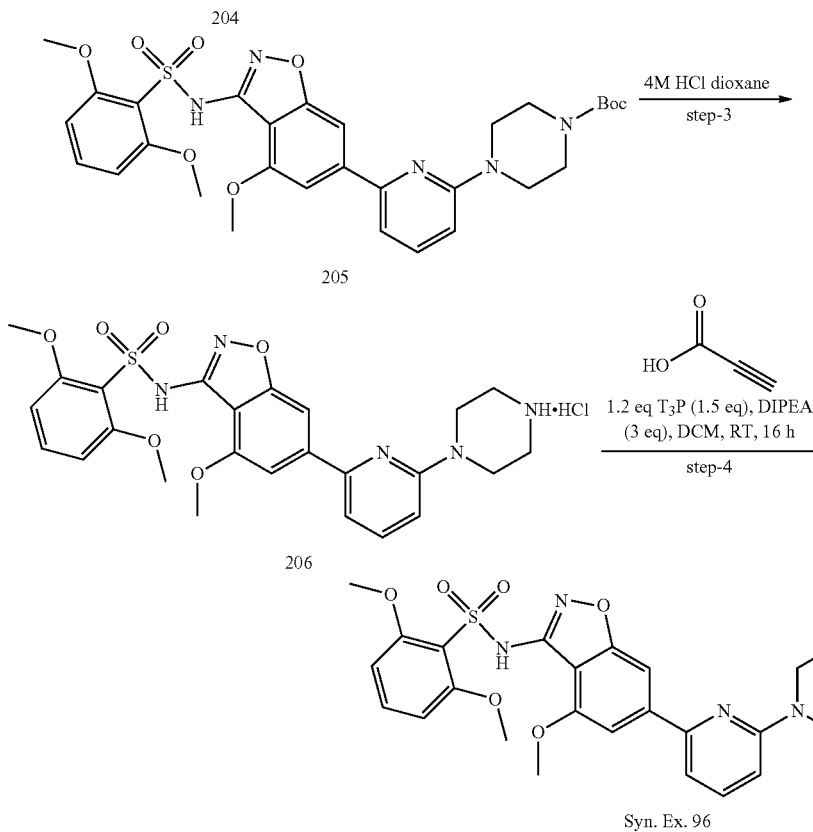

344

Synthesis of (3-((2,6-dimethoxyphenyl) sulfonamido)-4-methoxybenzo[d]isoxazol-6-yl) boronic acid (204)

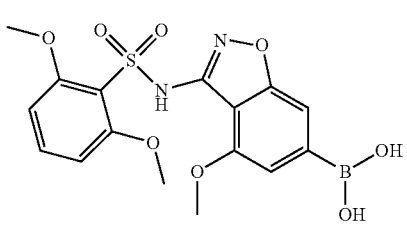

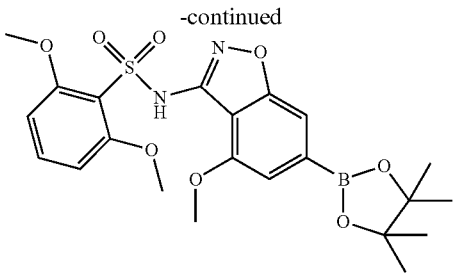

204

To a stirred solution of compound 117 (1 g, 2.255 mmol) in DMSO (3 mL) at room temperature was added B₂pin₂ (1.71 g, 6.765 mmol) and KOAc (0.663 mg, 6.765 mmol). The reaction mixture was degassed with nitrogen atmosphere for 10 min, followed by addition of bis(triphenylphosphine)palladium chloride (79 mg, 0.112 mmol). The reaction mixture was stirred at 90° C. for 12 h. After completion (monitored by TLC), the reaction mixture was quenched with ice cold water, filtered through a pad of celite and filtrate was extracted with ethyl acetate. The organic layer was washed with brine, dried over anhydrous $Na_2SO_4$ and concentrated under reduced pressure. The crude compound was purified by using combi flash chromatography using a gradient method of 0-30% EtOAc/Heptane to afford the title compound 204 (800 mg, 86.95%) as a pale-yellow solid. TLC: 50% EtOAc/Heptane ($R_f$ 0.5). LCMS Calculated for C16H17BN2O8S: 408.08; Found: 409.5 and 491.6 (M+1). (mixture of boronic acid and ester).

Synthesis of tert-butyl 4-(6-(3-((2,6-dimethoxyphenyl) sulfonamido)-4-methoxybenzo[d]isoxazol-6-yl) pyridin-2-yl)piperazine-1-carboxylate (205)

To a stirred solution of tert-butyl 4-(6-bromopyridin-2-yl)piperazine-1-carboxylate (1.0 g, 2.939 mmol) in 1,4-dioxane:$H_2O$ (5:1, 12 mL) was added compound 204 (0.8 g, 1.959 mmol) followed by the addition of $K_2CO_3$ (0.812 g, 5.877 mmol) and purged with argon gas for 15 min. $PdCl_2$ (dppf) (71 mg, 0.0959 mmol) and XPhos (45 mg, 0.0959 mmol) were added to the reaction mixture and purged with argon for 5 min. The reaction mixture was heated at 80° C. for 16 h. After completion (monitored by TLC), the reaction mixture was diluted with $H_2O$ and extracted with EtOAc. The combined organic layer was washed with brine solution, dried over anhydrous $Na_2SO_4$ and concentrated under reduced pressure. The crude was purified by combi-flash chromatography using gradient 0-35% EtOAc/hexanes to afford title compound 205 (500 mg, 40.98%) as an off-white solid, TLC: 50% EA/Heptane ($R_f$ 0.2). LCMS Calculated for C30H35N5O8S: 625.22; Found: 626.5.

Synthesis of 2,6-dimethoxy-N-(4-methoxy-6-(6-(piperazin-1-yl)pyridin-2-yl)benzo[d]isoxazol-3-yl) benzenesulfonamide hydrochloride (206)

To a stirred solution of compound 205 (500 mg, 0.799 mmol) in DCM (3 mL) at 0° C. was added 4M HCl in dioxane (2 mL, 7.991 mmol). The reaction was allowed to stir at room temperature for 5 h. After completion (monitored by TLC), the reaction mixture was concentrated under reduced pressure and the crude compound was triturated with diethyl ether to afford the title compound 206 (350 mg, HCl salt) as a colourless semi solid. TLC: 50% MeOH/DCM ($R_f$ 0.2). This was used in the next step without further characterization. Synthesis of 2,6-dimethoxy-N-(4-methoxy-6-(6-(4-propioloylpiperazin-1-yl)pyridin-2-yl) benzo[d]isoxazol-3-yl)benzenesulfonamide To a stirred solution of compound 206 (200 mg, 0.355 mmol) in DMF (1 mL) at 0° C. was added DIPEA (0.186 mL, 1.067 mmol), Propiolic acid (29 mg, 0.426 mmol) followed by $T_3P$ as a 50% solution in EtOAc (0.338 mL, 0.532 mmol). The reaction mixture was allowed to stir at room temperature for 4 h. After completion (monitored by TLC), the reaction mixture was concentrated under reduced pressure and the crude was purified by using prep HPLC to afford the title compound (8 mg, 3.9%) as a brown solid. TLC: 5% MeOH/DCM ($R_f$ 0.5). (See Table 1 for analytical data).

Synthetic Example 97

Scheme 71: Synthesis of 2,6-dimethoxy-N-(4-methoxy-6-(2-(4-propioloylpiperazin-1-yl) thiazol-4-yl)benzo[d]isoxazol-3-yl)benzenesulfonamide

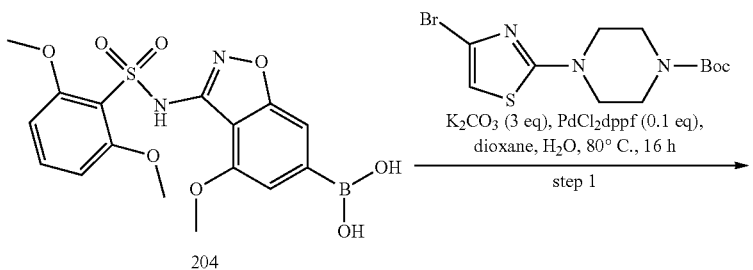

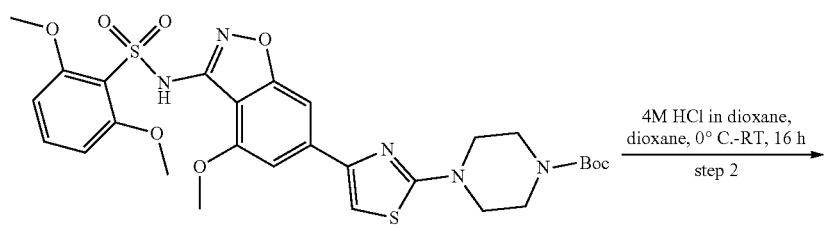

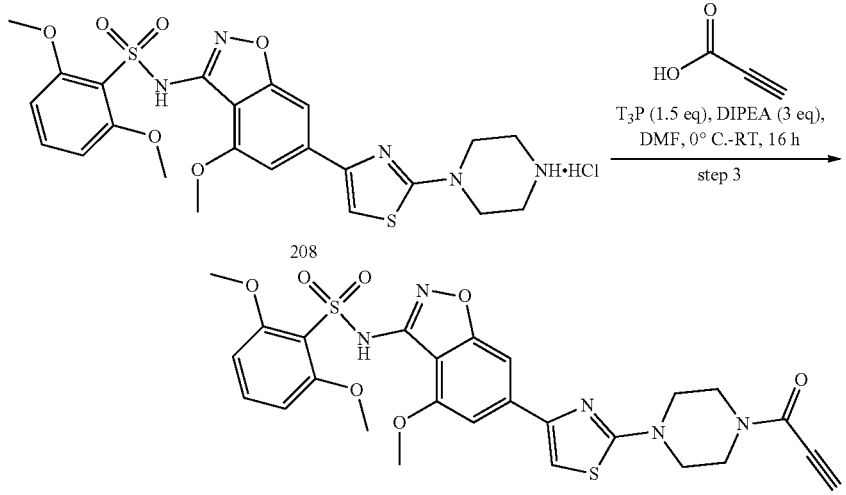

Syn. Ex. 97

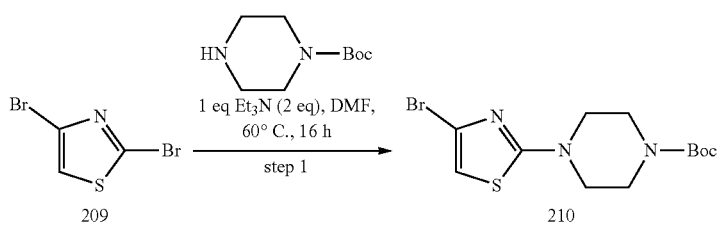

Synthesis of tert-butyl 4-(4-bromothiazol-2-yl) piperazine-1-carboxylate (210)

To a stirred solution of compound 209 (1 g, 4.116 mmol) in DMF (10 mL) at 0° C. was added TEA (1.15 mL, 8.233 mmol) followed by tert-butyl piperazine-1-carboxylate (0.766 mg, 4.116 mmol). The reaction mixture was allowed to stir at 60° C. for 16 h. After completion (monitored by TLC), the reaction mixture was quenched with ice cold water and extracted with EtOAc. The organic layer was washed with brine, dried over anhydrous $Na_2SO_4$, and concentrated under reduced pressure. The crude was purified by using trituration with diethyl ether/pentane to afford the title compound 210 (900 mg, 74%) as an off-white solid. TLC: 5% MeOH/DCM ($R_f$ 0.5)

Synthesis of tert-butyl 4-(4-(3-((2,6-dimethoxyphenyl) sulfonamido)-4-methoxybenzo[d]isoxazol-6-yl) thiazol-2-yl) piperazine-1-carboxylate (207)

To a stirred solution of compound 210 (500 mg, 1.435 mmol) in 3:1 mixture of 1,4 Dioxane:water (4:1, 10 mL) was added $K_2CO_3$ (595 mg, 4.305 mmol) and comp 204 (702 mg, 1.722 mmol). The reaction mixture was purged with nitrogen gas for 10 min followed by addition of [Pd(PPh$_3$)$_4$] (0.117 g, 0.143 mmol). The resulting reaction mixture was stirred at 80° C. for 16 h. After completion (monitored by TLC), the reaction mixture was filtered through a pad of celite. The filtrate was quenched with water and extracted with ethyl acetate. The organic layer was washed with brine, dried over anhydrous $Na_2SO_4$ and concentrated under reduced pressure. The crude compound was purified by combi flash chromatography (using a gradient method of 0-30% EtOAc/Heptane) to afford the title compound 207 (0.1 g, 12.93%) as a yellow solid. TLC: 50% EtOAc/Heptane ($R_f$ 0.5). LCMS Calculated for C28H33N5O8S2: 631.18; Found: 632.5 (M+H).

Synthesis of 2,6-dimethoxy-N-(4-methoxy-6-(2-(piperazin-1-yl) thiazol-4-yl) benzo[d]isoxazol-3-yl) benzenesulfonamide hydrochloride (208)

To a stirred solution of compound 207 (100 mg, 0.158 mmol) in DCM (2 mL) at 0° C. was added 4M HCl in dioxane (0.4 mL, 1.582 mmol). The reaction was allowed to stir at room temperature for 1 h. After completion (monitored by TLC), the reaction mixture was concentrated under reduced pressure and the crude compound was triturated with diethyl ether to afford the title compound 208 (80 mg, HCl salt) as a colourless gummy solid. TLC: 5% MeOH/DCM ($R_f$ 0.5). This was used in the next step without further characterization. Synthesis of 2,6-dimethoxy-N-(4-methoxy-6-(2-(4-propioloylpiperazin-1-yl) thiazol-4-yl) benzo[d]isoxazol-3-yl)benzenesulfonamide To a stirred solution of compound 208 (80 mg, 0.140 mmol) in DMF (1 mL) at 0° C. was added DIPEA (0.073 mL, 0.422 mmol), Propiolic acid (11 mg, 0.168 mmol) followed by T$_3$P as a 50% solution in EtOAc (0.133 mL, 0.21 mmol). The reaction mixture was allowed to stir at room temperature for 16 h. After completion (monitored by TLC), the reaction mixture was concentrated under reduced pressure and the crude was purified by prep HPLC to afford the title compound (20 mg, 24.39%) as an off-white solid. TLC: 5% MeOH/DCM ($R_f$ 0.5). (See Table 1 for analytical data).

Synthetic Example 98
Scheme 72: Synthesis of 5-ethyl-2-methoxy-N-(4-methoxy-6-(3-(4-propioloylpiperazin-1-yl) phenyl) benzo[d]isoxazol-3-yl) benzenesulfonamide
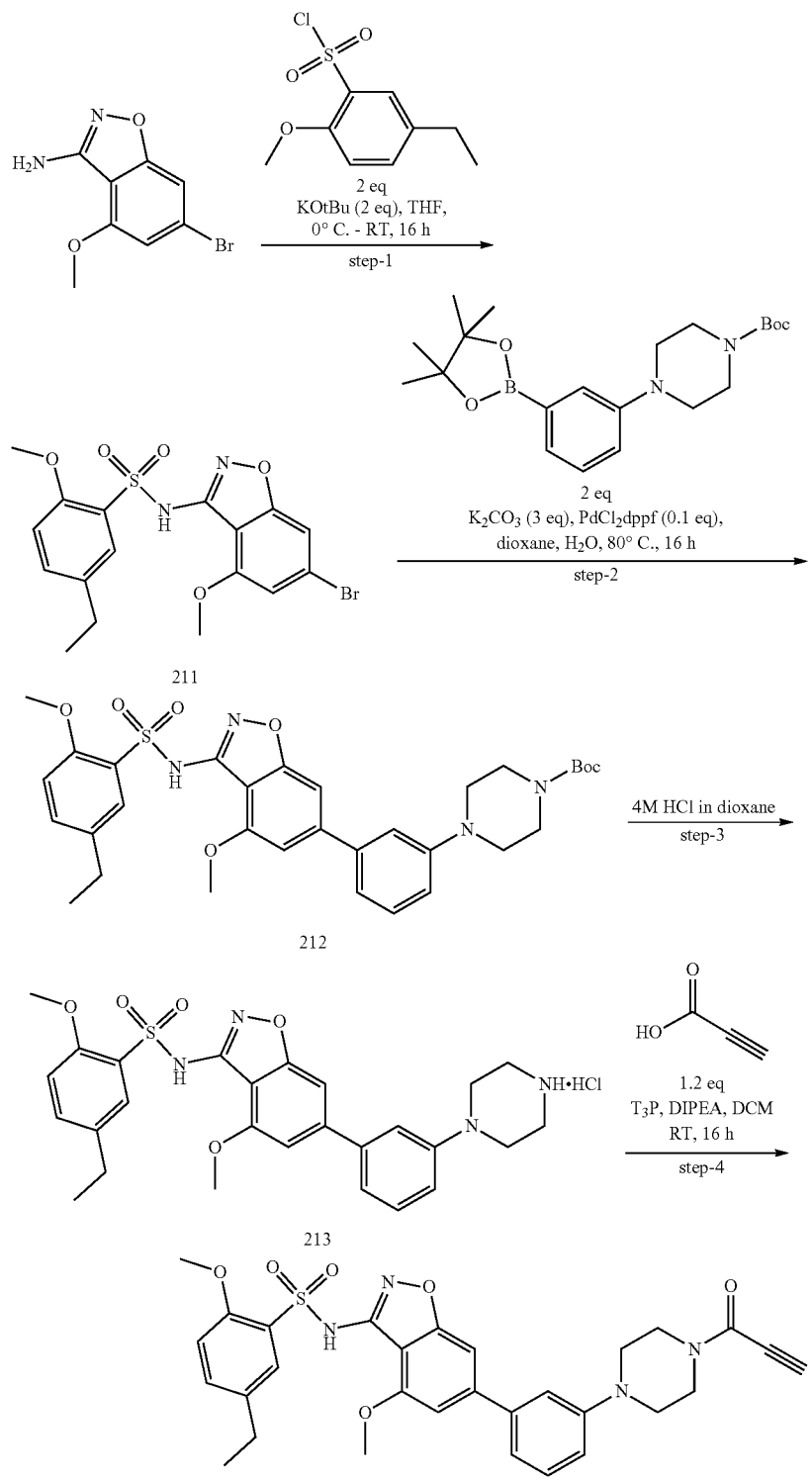
Syn. Ex. 98

Synthesis of N-(6-bromo-4-methoxybenzo[d]isoxa-zol-3-yl)-5-ethyl-2-methoxybenzenesulfonamide (211)

To a stirred solution of compound 116 (800 mg, 3.291 mmol) in THF (10 mL) was added KO$^t$Bu as a 1.0 M solution in THF (9.8 mL, 9.874 mmol) followed by 5-ethyl-2-methoxybenzenesulfonyl chloride (1.5 g, 6.582 mmol) at 0° C. The reaction mixture was allowed to stir at the room temperature for 16 h. After completion (monitored by TLC), the reaction mixture was quenched with ice cold water and extracted with ethyl acetate. The organic layer was dried over anhydrous $Na_2SO_4$ and concentrated under reduced pressure. The crude compound was triturated with diethyl ether/Heptane to afford the title compound 211 (400 mg, 27.58%), as a yellow solid. TLC: 60% EtOAc/Heptane ($R_f$ 0.6). LCMS Calculated for C17H17BrN2O5S: 440.00; Found: 442.5 (M+2).

Synthesis of tert-butyl 4-(3-(3-((5-ethyl-2-methoxy-phenyl)sulfonamido)-4-methoxybenzo[d]isoxazol-6-yl)phenyl)piperazine-1-carboxylate (212)

To a stirred solution of 211 (400 mg, 0.906 mmol) and tert-butyl 4-(3-(4,4,5,5-tetramethyl-1,3,2-dioxaborolan-2-yl)phenyl)piperazine-1-carboxylate (386 mg, 0.996 mmol) in a 2:1 mixture of 1,4 Dioxane:water (9 mL) was added $K_2CO_3$ (0.375 g, 2.718 mmol). The reaction mixture was degassed with Argon atmosphere followed by addition of Pd(dppf)Cl$_2$ (73 mg, 0.0906 mmol). The reaction mixture was stirred at 80° C. for 12 h. After completion (monitored by TLC), the reaction mixture was diluted with ethyl acetate filtered through a Celite pad and the reaction mixture was concentrated under reduced pressure. The crude was purified by combi flash-chromatography using a gradient method of 0-30% EtOAc/Heptane to afford the tert-butyl 4-(3-(3-((5-ethyl-2-methoxyphenyl) sulfonamido)-4-methoxybenzo[d] isoxazol-6-yl) phenyl) piperazine-1-carboxylate 212 (300 mg, 53.15%) as a pale-yellow solid. TLC: 40% EtOAc/Heptane ($R_f$ 0.4). LCMS Calculated for C32H38N4O7S: 622.25; Found: 623.02 (M+1).

Synthesis of 5-ethyl-2-methoxy-N-(4-methoxy-6-(3-(piperazin-1-yl) phenyl) benzo[d]isoxazol-3-yl) ben-zenesulfonamide hydrochloride (213)

To a stirred solution of compound 212 (300 mg, 0.481 mmol) in DCM (2 mL) at 0° C. was added 4M HCl in 1,4 Dioxane (0.24 mL, 0.963 mmol). The reaction was allowed to stir at the room temperature for 2 h. After completion (monitored by TLC), the reaction mixture was concentrated under reduced pressure and Co-Distilled with diethyl ether and dried in vacuo to afford title compound 213 (200 mg, HCl salt) as a yellow solid. TLC: 5% MeOH/DCM ($R_f$ 0.3). This was used in the next step without further characterization. Synthesis of 5-ethyl-2-methoxy-N-(4-methoxy-6-(3-(4-propioloylpiperazin-1-yl) phenyl) benzo[d]isoxazol-3-yl) benzenesulfonamide To a stirred solution of compound 213 (200 mg, 0.357 mmol) in DMF (2 mL) at 0° C. was added DIPEA (0.187 mL, 1.073 mmol), propiolic acid (50 mg, 0.714 mmol) followed by T$_3$P as a 50% solution in EtOAc (0.340 mL, 0.535 mmol). The reaction mixture was allowed to stir at room temperature for 2 h. After completion (monitored by TLC), the reaction mixture was concentrated under reduced pressure and crude was purified by prep HPLC to afford the title compound (65 mg, 31.70%) as an off-white solid. TLC: 5% MeOH/DCM ($R_f$ 0.5). (See Table 1 for analytical data).

Synthetic Example 99

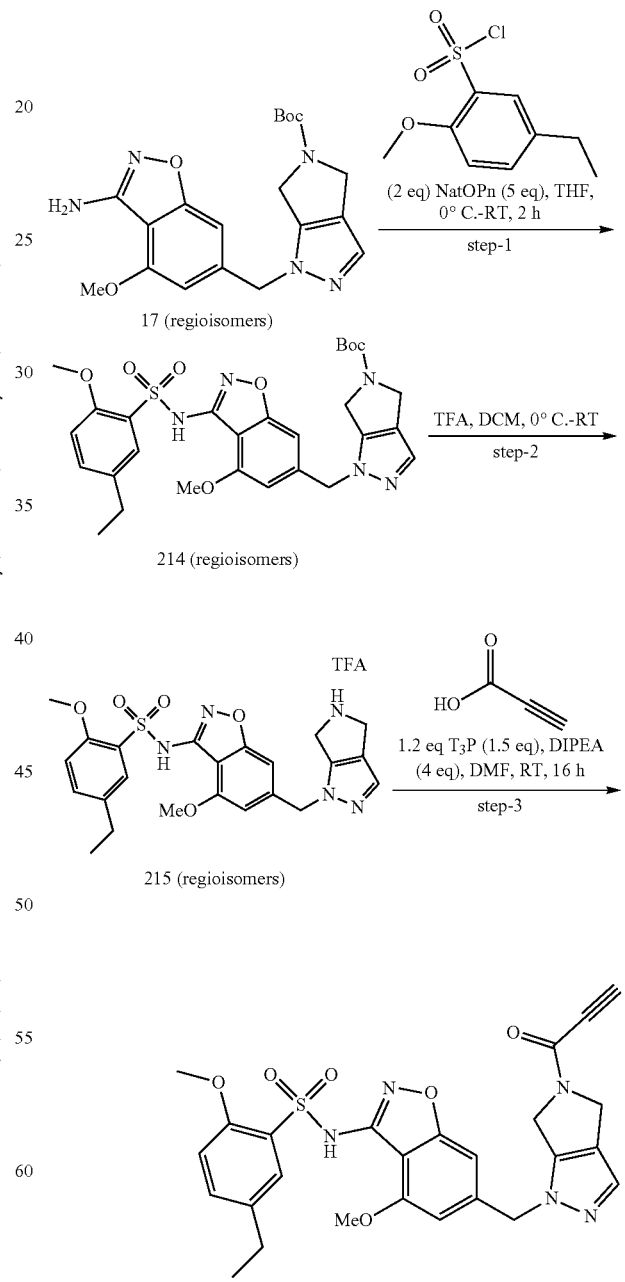

Scheme 73: Synthesis of 5-ethyl-2-methoxy-N-(4-methoxy-6-((5-propioloyl-5,6-dihydropyrrolo[3,4-c]pyrazol-1(4H)-yl)methyl)benzo[d]isoxazol-3-yl)benzenesulfonamide

Synthesis of tert-butyl 1-((3-((5-ethyl-2-methoxyphenyl)sulfonamido)-4-methoxybenzo[d]isoxazol-6-yl)methyl)-4,6-dihydropyrrolo[3,4-c]pyrazole-5(1H)-carboxylate (214)

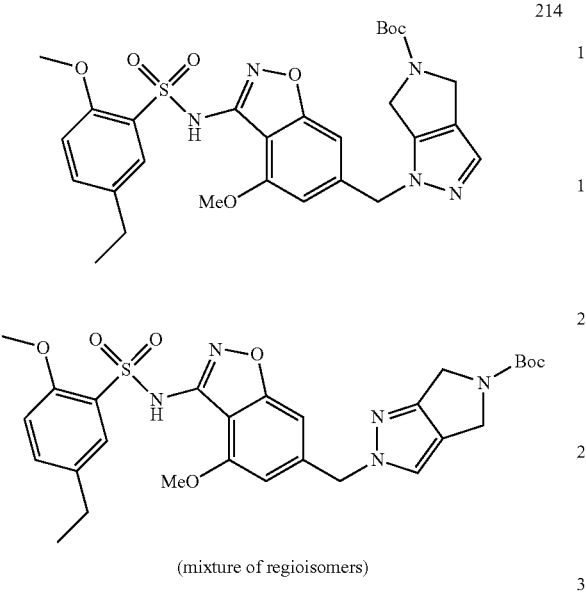

(mixture of regioisomers)

To a stirred solution of compound 17 (300 mg, 0.778 mmol) in THF (5 mL) at 0° C. was added Na'OPn (428 mg, 3.89 mmol) followed by 5-ethyl-2-methoxybenzenesulfonyl chloride (365 mg, 1.556 mmol) and the reaction was allowed to stir at 60° C. for 2 h. After completion (monitored by TLC), the reaction mixture was quenched with water and extracted with ethyl acetate. The organic layer was washed with brine, dried over anhydrous $Na_2SO_4$, and concentrated under reduced pressure. The crude was purified by Combi flash column chromatography using a gradient method of 20-60% EtOAc/Heptane to afford the title compound 214 (200 mg, 44.15%, obtained as a mixture of regioisomers) as a pale-yellow solid. TLC: 100% EtOAc ($R_f$ 0.5). LCMS Calculated for: C28H33N5O7S: 583.21; Found: 584.5 (M+1).

Synthesis of 5-ethyl-2-methoxy-N-(4-methoxy-6-((5-(2,2,2-trifluoroacetyl)-5,6-dihydro-514-pyrrolo[3,4-c]pyrazol-1(4H)-yl)methyl)benzo[d]isoxazol-3-yl)benzenesulfonamide (215)

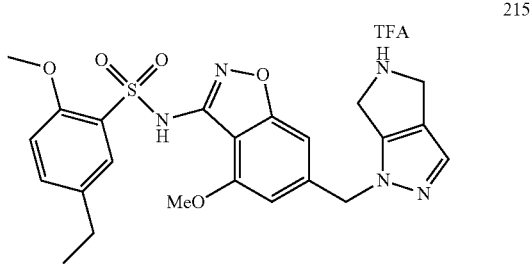

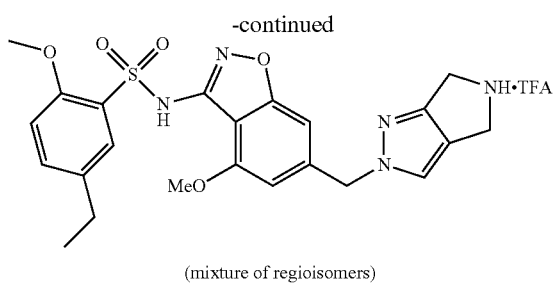

(mixture of regioisomers)

To a stirred solution of compound 214 (150 mg, 0.256 mmol) in DCM (2 mL) at 0° C. was added TFA (0.2 mL, 2.569 mmol). The reaction mixture was allowed to stir at room temperature for 2 h. After completion (monitored by TLC), reaction mixture was concentrated under reduced pressure, triturated with diethyl ether to afford the title crude compound 215 (160 mg, TFA salt) as a gummy brown solid. TLC: 5% MeOH/DCM ($R_f$ 0.2). This mixture of regioisomers was used in the next step without further characterization.

Synthesis of 5-ethyl-2-methoxy-N-(4-methoxy-6-((5-propioloyl-5,6-dihydropyrrolo[3,4-c]pyrazol-1(4H)-yl)methyl)benzo[d]isoxazol-3-yl)benzenesulfonamide To a stirred solution of compound 215 (150 mg, 0.258 mmol) in DMF (1 mL) at 0° C. was added DIPEA (0.135 mL, 0.775 mmol), propiolic acid (27 mg, 0.387 mmol) followed by $T_3P$ as a 50% solution in EtOAc (0.328 mL, 0.516 mmol). The reaction mixture was allowed to stir at room temperature for 16 h. After completion (monitored by TLC), the reaction mixture was concentrated under reduced pressure. The crude was purified by using chiral HPLC purification to afford the title compound 5-ethyl-2-methoxy-N-(4-methoxy-6-((5-propioloyl-5,6-dihydropyrrolo[3,4-c]pyrazol-1(4H)-yl)methyl)benzo[d]isoxazol-3-yl)benzenesulfonamide (8.5 mg, 6.1%) as an off white solid. TLC: 5% MeOH/DCM ($R_f$ 0.5) (See Table 1 for analytical data). The other regioisomer could not be isolated in sufficient quantity for analysis or testing.

Synthetic Example 100
Scheme 74: Synthesis of 2,6-dimethoxy-N-(4-methoxy-6-(3-(4-propioloyl-1,4-diazepan-1-yl (phenyl)benzo[d]isoxazol-3-yl)benzenesulfonamide
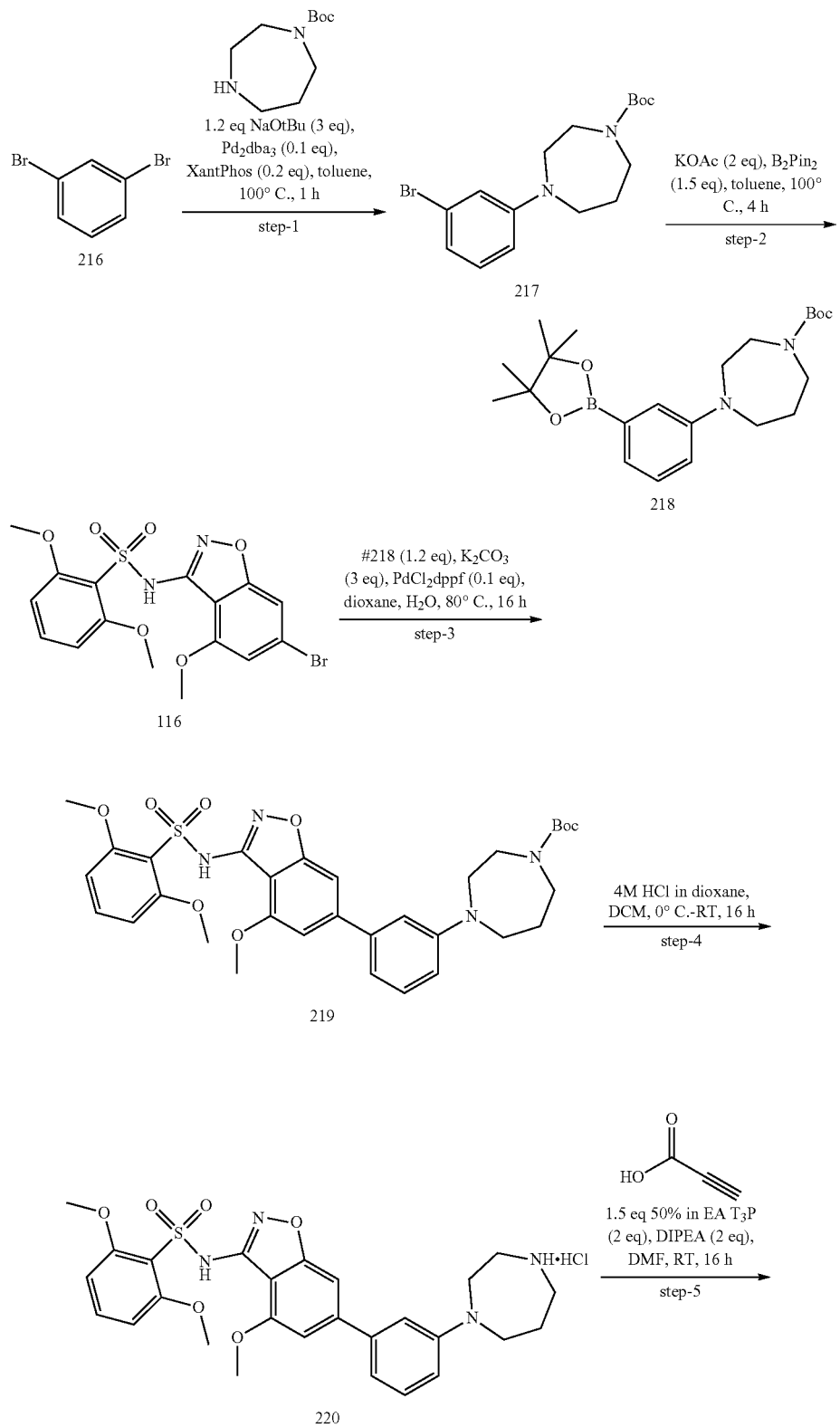

-continued

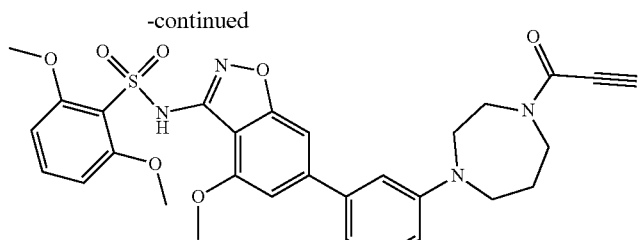

Syn. Ex. 100

Synthesis of tert-butyl 4-(3-bromophenyl)-1,4-diazepane-1-carboxylate (217)

To a stirred solution of compound 216 (1 g, 4.328 mmol) in toluene (15 mL) was added Na$^t$OBu (1.22 g, 12.716 mmol) followed by tert-butyl 1,4-diazepane-1-carboxylate (1.04 g, 5.193 mmol) and purged with argon gas for 10 min followed by addition of XantPhos (500 mg, 0.865 mmol) and Pd$_2$dba$_3$ (396 mg, 0.432 mmol). The reaction mixture was stirred at 120° C. for 16 h. After completion (monitored by TLC), the reaction mixture was filtered through a pad of celite, and the filtrate was quenched with ice cold water and extracted with ethyl acetate. The organic layer was washed with brine solution dried over sodium sulphate and concentrated under reduced pressure to get crude compound. The crude was purified by combi flash chromatography using gradient 15% EA\Heptane to offer the title compound 217 (400 mg, 26.66%) as a colourless liquid. LCMS Calculated for C16H23BrN2O2: 354.09; Found: 355.3 (M+1).

Synthesis of tert-butyl 4-(3-(4,4,5,5-tetramethyl-1,3,2-dioxaborolan-2-yl)phenyl)-1,4-diazepane-1-carboxylate (218)

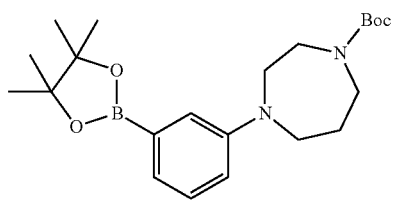

218

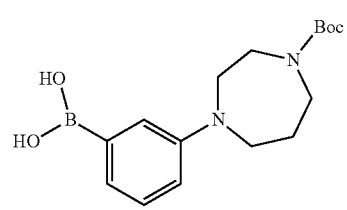

To a stirred solution of compound 217 (400 mg, 1.125 mmol) in 1,4 Dioxane (3 mL) at room temperature was added B$_2$pin$_2$ (428 mg, 1.688 mmol), KOAc (0.331 mg, 3.375 mmol). The reaction mixture was degassed for 10 min followed by addition of Pd(dppf)Cl$_2$·DCM (92 mg, 0.1125 mmol). The reaction mixture was stirred at 100° C. for 16 h. After completion (monitored by TLC), the reaction mixture was quenched with ice cold water, filtered through a Celite pad and extracted with ethyl acetate. The organic layer was washed with brine, dried over anhydrous Na$_2$SO$_4$ and concentrated under reduced pressure to afford the title compound 218 (1.2 g, crude) as a brown semi-solid. TLC: 50% EtOAc/Heptane (R$_f$, 0.5). LCMS Calculated for C22H35BN2O4: 402.27; Found: 403.5 and 321.6 (M+1). (Crude obtained as a mixture of corresponding boronic acid and boronate ester).

Synthesis of tert-butyl 4-(3-(3-((2,6-dimethoxyphenyl) sulfonamido)-4-methoxybenzo[d]isoxazol-6-yl) phenyl)-1,4-diazepane-1-carboxylate (219)

To a stirred solution of 116 (500 mg, 1.127 mmol) in 3:1 mixture of 1,4 Dioxane:water (10 mL) was added K$_2$CO$_3$ (467 mg, 3.383 mmol), compound 218 and purged with argon gas for 10 min followed by addition of Pd(dppf)Cl$_2$ (92 mg, 0.112 mmol). The resulting reaction mixture was stirred at 80° C. for 16 h. After completion (monitored by TLC), the reaction mixture was quenched with water and extracted with ethyl acetate. The organic layer was washed with brine, dried over anhydrous Na$_2$SO$_4$ and concentrated under reduced pressure. The crude compound was purified by combi flash chromatography (using a gradient method of 0-30% EtOAc/Heptane) to afford the title compound 219 (330 mg, 45.83%) as an off-white solid. TLC: 40% EtOAc/Heptane (R$_f$, 0.5). LCMS Calculated for C32H38N4O8S: 638.24; Found: 639.5 (M+1).

Synthesis of N-(6-(3-(1,4-diazepan-1-yl) phenyl)-4-methoxybenzo[d]isoxazol-3-yl)-2,6-dimethoxybenzenesulfonamide hydrochloride (220)

To a stirred solution of compound 219 (300 mg, 0.521 mmol) in DCM (2 mL) at 0° C. was added 4M HCl in 1,4 Dioxane (1.3 mL, 5.216 mmol). The reaction was allowed to stir at the room temperature for 2 h. After completion (monitored by TLC), the reaction mixture was concentrated under reduced pressure and Co-Distilled with diethyl ether to afford title compound 220 (200 mg, HCl salt) as a yellow solid. TLC: 5% MeOH/DCM (R$_f$, 0.3). This was used in the next step without further characterization.

Synthesis of 2,6-dimethoxy-N-(4-methoxy-6-(3-(4-propioloyl-1,4-diazepan-1-yl)phenyl)benzo[d]isoxazol-3-yl)benzenesulfonamide To a stirred solution of compound 220 (150 mg, 0.260 mmol) in DMF (1 mL) at 0° C. was added DIPEA (0.136 mL, 0.782 mmol), Propiolic acid (27 mg, 0.39 mmol) followed by T₃P as a 50% solution in EtOAc (0.330 mL, 0.52 mmol). The reaction mixture was allowed to stir at room temperature for 1 h. After completion (monitored by TLC), the reaction mixture was concentrated under reduced pressure and crude was purified by using prep HPLC to afford the title compound (60 mg, 38.96%) as an off white solid. TLC: 5% MeOH/DCM ($R_f$ 0.5). (See Table 1 for analytical data).

Synthetic Example 101

Scheme 75: Synthesis of 2,6-dimethoxy-N-(4-methoxy-6-(3-(1-propioloylpiperidin-4-yl) phenyl) benzo[d]isoxazol-3-yl) benzenesulfonamide

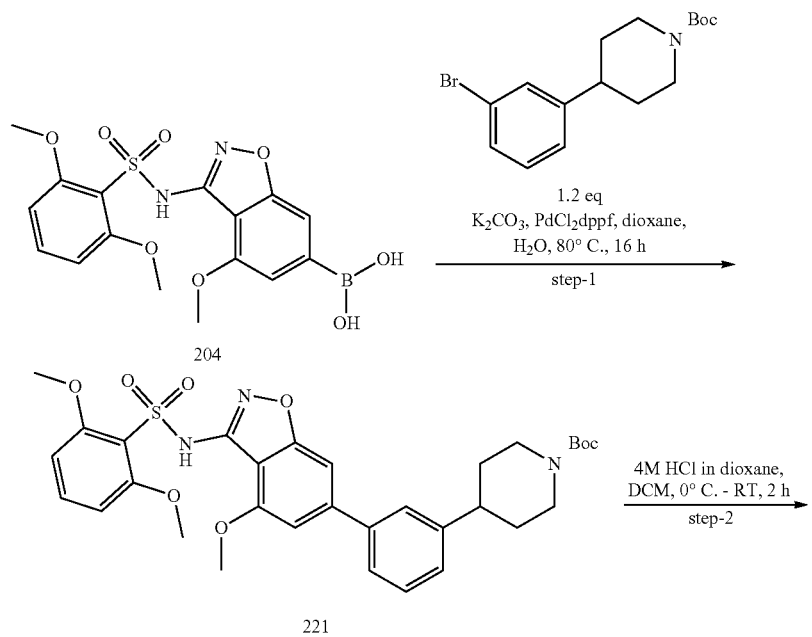

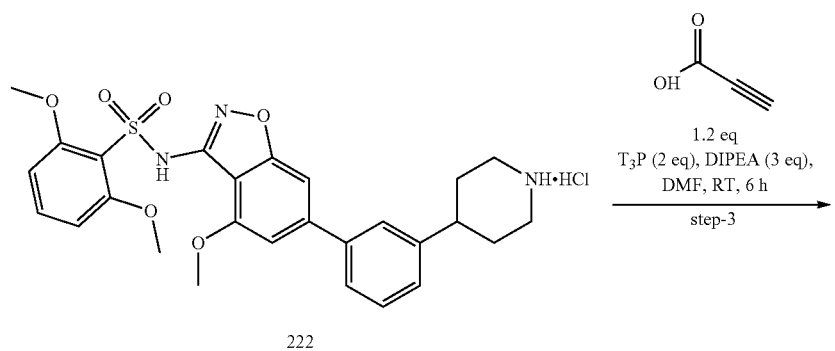

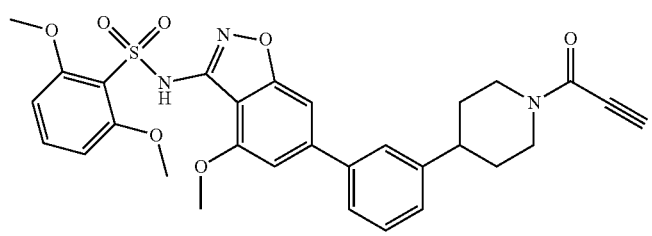

Syn. Ex. 101

Synthesis of tert-butyl 4-(3-(3-((2,6-dimethoxyphenyl) sulfonamido)-4-methoxybenzo[d]isoxazol-6-yl) phenyl) piperidine-1-carboxylate (221)

To a stirred solution of compound 204 (500 mg, 1.224 mmol) and tert-butyl 4-(3-bromophenyl) piperidine-1-carboxylate (386 mg, 1.469 mmol) in a 2:1 mixture of 1,4 Dioxane:water (9 mL), was added K$_2$CO$_3$ (507 mg, 3.672 mmol). The reaction mixture was degassed with Argon atmosphere followed by addition of Pd(dppf)Cl$_2$ (99 mg, 0.1224 mmol). The reaction mixture was stirred at 80° C. for 16 h. After completion (monitored by TLC), the reaction mixture was diluted with ethyl-acetate, filtered on a Celite pad and the reaction mixture was concentrated under reduced pressure. The crude was purified by combi flash-chromatography using a gradient method of 0-30% EtOAc/Heptane to afford the compound 221 (270 mg, 38.24%) as a pale-yellow solid. TLC: 40% EtOAc/Heptane (R$_f$, 0.4). LCMS Calculated for C32H37N3O8S: 623.23; Found: 624.02 (M+1).

Synthesis of 2,6-dimethoxy-N-(4-methoxy-6-(3-(piperidin-4-yl) phenyl)benzo[d]isoxazol-3-yl)benzenesulfonamide hydrochloride (222)

To a stirred solution of compound 221 (120 mg, 0.192 mmol) in DCM (4 mL) at 0° C. was added 4M HCl in dioxane (0.48 mL, 1.923 mmol). The reaction was allowed to stir at the room temperature for 2 h. After completion (monitored by TLC), the reaction mixture was concentrated under reduced pressure. The crude was triturated with diethyl ether and dried under reduced pressure to afford the title compound 222 (180 mg, HCl salt) as a colorless gummy solid. TLC: 5% MeOH/DCM (R$_f$, 0.5). This was used in the next step without further characterization.

Synthesis of 2,6-dimethoxy-N-(4-methoxy-6-(3-(1-propioloylpiperidin-4-yl) phenyl) benzo[d]isoxazol-3-yl) benzenesulfonamide To a stirred solution of compound 222 (180 mg, 0.321 mmol) in DMF (1 mL) at 0° C. was added DIPEA (0.168 mL, 0.963 mmol), Propiolic acid (26 mg, 0.385 mmol) followed by T$_3$P as a 50% solution in EtOAc (0.612 mL, 0.963 mmol). The reaction mixture was allowed to stir at room temperature for 1 h. After completion (monitored by TLC), the reaction mixture was concentrated under reduced pressure and the crude was purified by using prep HPLC to afford the title compound (45 mg, 24.32%) as an off-white solid. TLC: 5% MeOH/DCM (R$_f$, 0.5). (See Table 1 for analytical data).

Synthetic Example 102

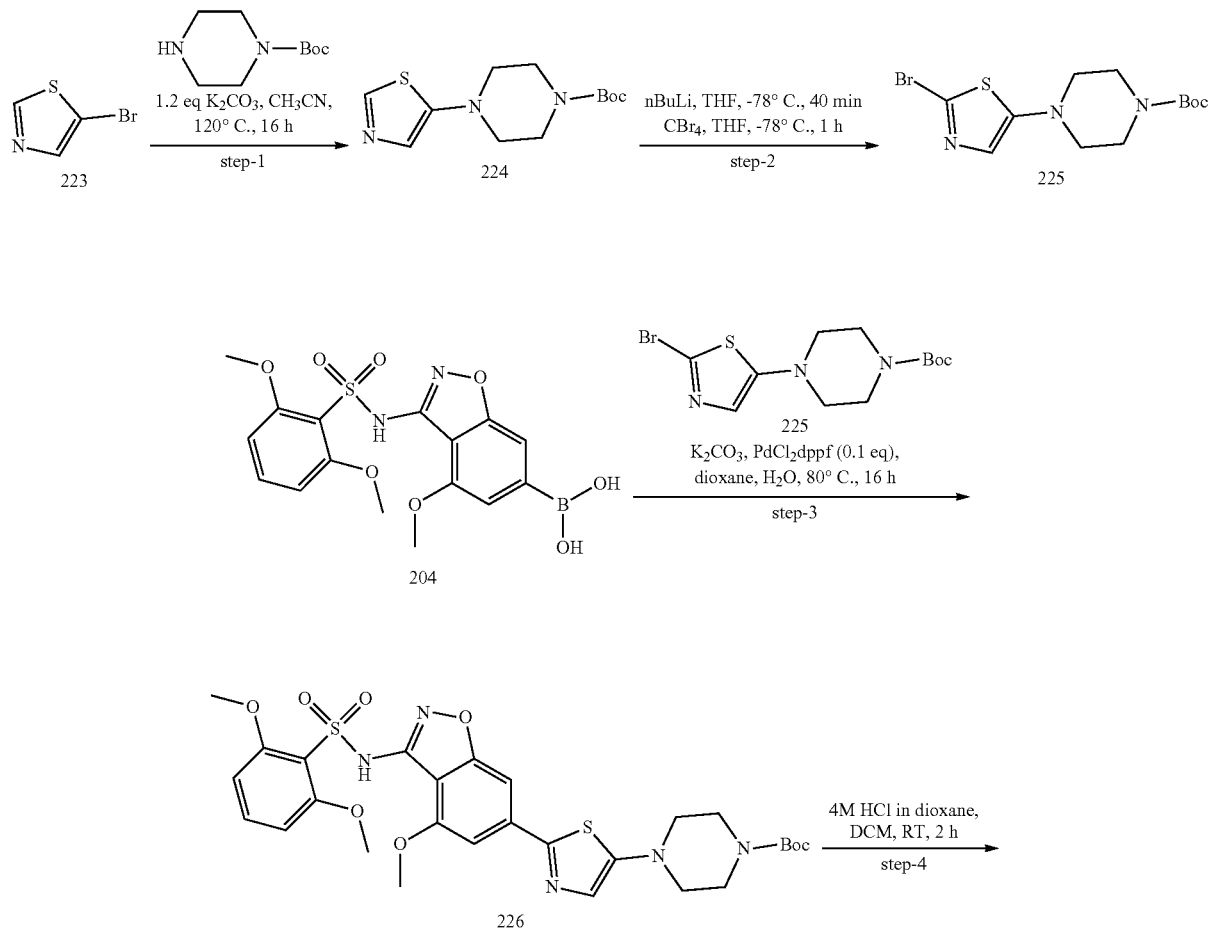

Scheme 76: Synthesis of 2,6-dimethoxy-N-(4-methyl-6-(5-(4-propioloylpiprtazin-1-yl) thiazol-2-yl)benzo[d]isoxazol-3-yl)benzenesulfonamide

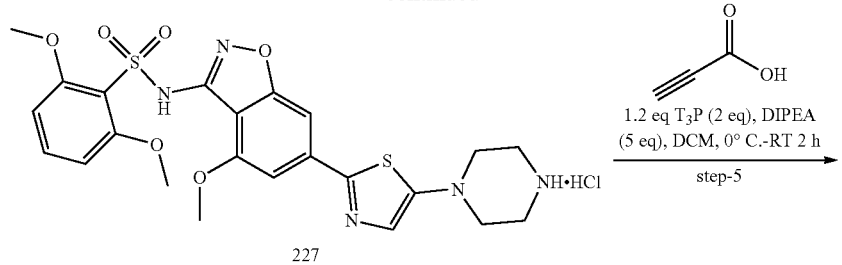

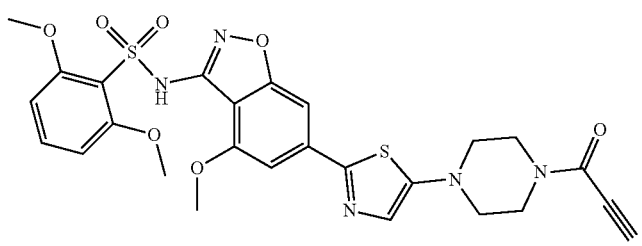

Syn. Ex. 102

Synthesis of tert-butyl 4-(4-bromothiazol-2-yl) piperazine-1-carboxylate (224)

To a stirred solution of compound 223 (1.5 g, 9.145 mmol) in DMF (10 mL) at 0° C. was added $K_2CO_3$ (3.79 g, 27.435 mmol) followed by tert-butyl piperazine-1-carboxylate (2.0 g, 10.974 mmol). The reaction mixture was allowed to stir at 100° C. for 16 h. After completion (monitored by TLC), the reaction mixture was quenched with ice cold water and extracted with EtOAc. The organic layer was washed with brine, dried over anhydrous $Na_2SO_4$, and concentrated under reduced pressure. The crude was purified by combi flash chromatography using gradient 2-8% EA/Heptane to afford the title compound 224 (1.6 g, 74%) as an off-white solid. TLC: 5% MeOH/DCM ($R_f$ 0.5). LCMS Calculated for C12H19N3O2S: 269.12; Found: 270.05 (M+H).

Synthesis of tert-butyl 4-(2-bromothiazol-5-yl) piperazine-1-carboxylate (225)

To a stirred solution of tert-butyl 4-(thiazol-5-yl) piperazine-1-carboxylate 224 (1.6 g, 5.940 mmol) in THF (60 mL) was added n-BuLi [1.6 mol/L in hexanes (5.56 mL, 8.910 mmol)] at −78° C. The reaction mixture was stirred at −78° C. for 40 min, and a solution of $CBr_4$ (2.95 g, 8.910 mmol) 1.5 mL in THF was added. The reaction mixture was stirred at −78° C. for another 1 h. After completion (monitored by TLC), the reaction mixture was quenched with ice cold water and extracted with EtOAc. The organic layer was washed with brine, dried over anhydrous $Na_2SO_4$, and concentrated under reduced pressure. The crude was purified by combi flash chromatography using gradient 4-8% EA/Heptane to afford the title compound 225 (1.6 g, 77.66%) as a brown semi solid. TLC: 5% MeOH/DCM ($R_f$ 0.7). LCMS Calculated for C12H18BrN3O2S: 347.03; Found: 348.05 (M+H).

Synthesis of tert-butyl 4-(2-(3-((2,6-dimethoxyphenyl) sulfonamido)-4-methoxybenzo[d]isoxazol-6-yl) thiazol-5-yl) piperazine-1-carboxylate (226)

To a stirred solution of compound 225 (200 mg, 0.574 mmol) in 3:1 mixture of 1,4 Dioxane:water (10 mL) was added $K_2CO_3$ (238 mg, 1.722 mmol) and compound 204 (281 mg, 0.688 mmol). The reaction mixture was purged with argon gas for 10 min and Pd $(PPh_3)_4$ (33 mg, 0.0287 mmol) was added. The resulting reaction mixture was stirred at 100° C. for 16 h. After completion (monitored by TLC), the reaction mixture was quenched with ice cold water and extracted with ethyl acetate. The organic layer was washed with brine, dried over anhydrous $Na_2SO_4$ and concentrated under reduced pressure. The crude compound was purified by combi flash chromatography (using a gradient method of 80-90% EtOAc/Heptane) to afford the title compound 226 (55 mg, 15.19%) as a brown semi solid. TLC: 80% EtOAc/Heptane ($R_f$ 0.4). LCMS Calculated for C28H33N5O8S2: 631.18; Found: 632.2 (M+H).

Synthesis of 2,6-dimethoxy-N-(4-methoxy-6-(5-(piperazin-1-yl) thiazol-2-yl) benzo[d]isoxazol-3-yl) benzenesulfonamide hydrochloride (227)

To a stirred solution of compound 226 (55 mg, 0.087 mmol) in DCM (2 mL) at 0° C. was added 4M HCl in dioxane (0.21 mL, 0.870 mmol). The reaction was allowed to stir at the room temperature for 3 h. After completion (monitored by TLC), the reaction mixture was concentrated under reduced pressure. The crude was triturated with EtOAc (20 mL), DCM (20 mL) and dried in vacuo to afford the title compound 227 (53 mg, HCl salt) as a colorless gummy solid. TLC: 5% MeOH/DCM ($R_f$ 0.2). This was used in the next step without further characterization.

Synthesis of 2,6-dimethoxy-N-(4-methoxy-6-(5-(4-propioloylpiperazin-1-yl) thiazol-2-yl)benzo[d]isoxazol-3-yl)benzenesulfonamide To a stirred solution of compound 227 (50 mg, 0.088 mmol) in DMF (1 mL) at 0° C. was added DIPEA (0.076 mL, 0.44 mmol), Propiolic acid (7.4 mg, 0.105 mmol) followed by T₃P as a 50% solution in EtOAc (0.111 mL, 0.176 mmol). The reaction mixture was allowed to stir at room temperature for 16 h. After completion (monitored by TLC), the reaction mixture was concentrated under reduced pressure and the crude was purified by prep HPLC to afford the title compound (5.8 mg, 11.37%) as an off-white solid. TLC: 5% MeOH/DCM ($R_f$ 0.5). (See Table 1 for analytical data).

Synthetic Example 103

Scheme 77: Synthesis of 2-fluoro-N'-(3-methyl-5-(4-(4-propioloylpiperazin-1-yl)pyridin-2-yl) benzoyl) benzenesulfonohydrazide

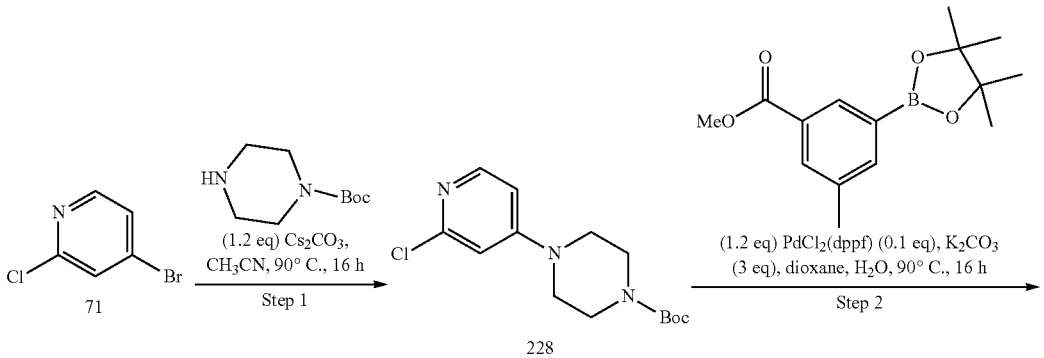

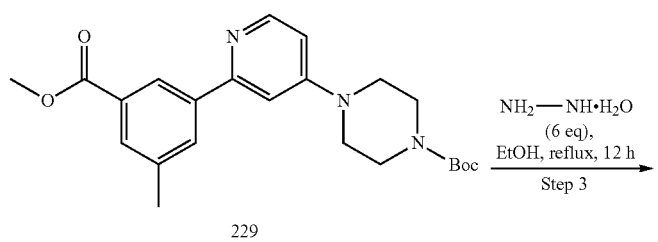

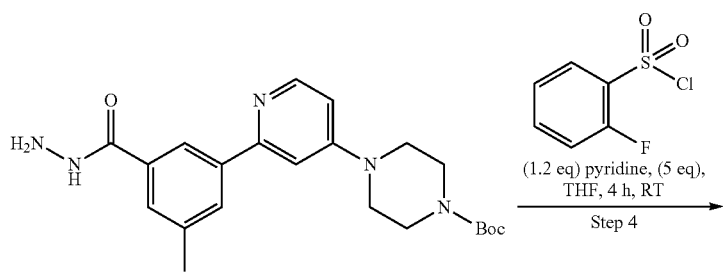

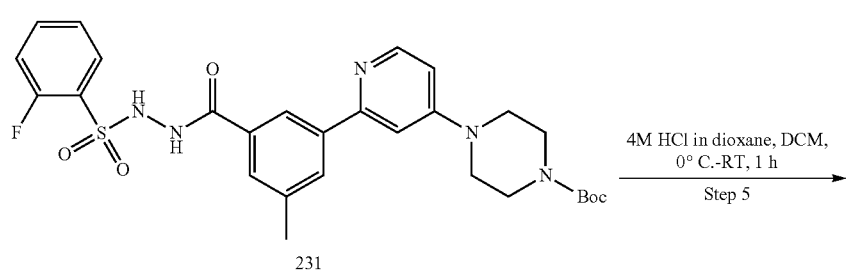

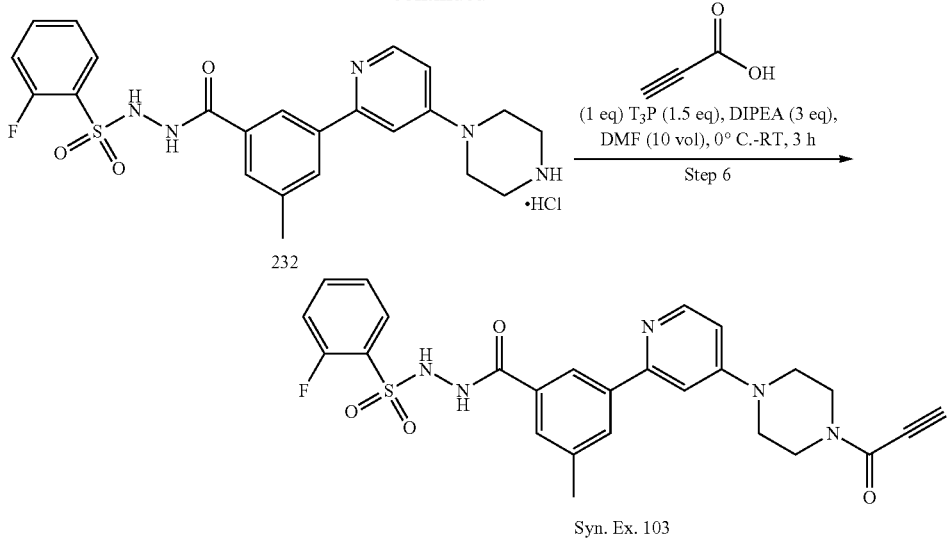

Syn. Ex. 103

Synthesis of tert-butyl 4-(2-chloropyridin-4-yl) piperazine-1-carboxylate (228)

To a stirred solution of compound 71 (1 g, 5.196 mmol) in ACN (10 mL), was added $Cs_2CO_3$ (2.5 g, 7.794 mmol) followed by tert-butyl piperazine-1-carboxylate (1.16 g, 6.235 mmol). The reaction mixture was stirred at 90° C. for 16 h. After completion (monitored by TLC), the reaction mixture was quenched with ice cold water and extracted with ethyl acetate. The organic layer was washed with brine, dried over anhydrous $Na_2SO_4$ and concentrated under reduced pressure. The crude compound was purified by combi flash chromatography (using a gradient method of 0-30% EtOAc/Heptane) to afford the title compound 228 (600 mg, 38.96%) as an off-white solid. TLC: 60% EtOAc/Heptane ($R_f$ 0.4). LCMS Calculated for C14H20ClN3O2: 297.12; Found: 298.05 (M+H).

Synthesis of tert-butyl 4-(2-(3-(methoxycarbonyl)-5-methylphenyl) pyridin-4-yl) piperazine-1-carboxylate (229)

To a stirred solution of compound 228 (600 mg, 2.014 mmol) in 3:1 mixture of 1,4 Dioxane:water (40 mL), was added $K_2CO_3$ (517 mg, 3.73 mmol) and methyl 3-methyl-5-(4,4,5,5-tetramethyl-1,3,2-dioxaborolan-2-yl) benzoate (667 mg, 2.417 mmol). The reaction mixture was purged with argon gas for 10 min followed by addition of and $PdCl_2(dppf)$ (73 mg, 0.10 mmol). The reaction mixture was stirred at 90° C. for 12 h. After completion (monitored by TLC), the reaction mixture was quenched with water and extracted with ethyl acetate. The organic layer washed with brine, dried over anhydrous $Na_2SO_4$ and concentrated under reduced pressure. The crude compound was purified by combi flash chromatography (using a gradient method of 30-40% EtOAc/Heptane) to afford the title compound 229 (400 mg, 48.25%) as a pale brown solid. TLC: 40% EtOAc/Heptane ($R_f$ 0.5). LCMS Calculated for C23H29N3O4: 411.22; Found: 412.2 (M+1).

Synthesis of tert-butyl 4-(2-(3-(hydrazinecarbonyl)-5-methylphenyl) pyridin-4-yl)piperazine-1-carboxylate (230)

To a stirred solution of compound 229 (400 mg 0.972 mmol) in EtOH (20 mL) was added hydrazine mono hydrate (0.291 mL, 5.832 mmol). The reaction was allowed to stir at 90° C. for 8 h. After completion (monitored by TLC), the reaction mixture was concentrated under reduced pressure to obtain crude which was triturated with DCM/n-Heptane and concentrated under reduced pressure to afford the title compound 230 (310 mg, 77.50%) as a pale-yellow gummy solid. TLC: 5% MeOH/DCM ($R_f$ 0.3). LCMS Calculated for $C_{22}H_{29}N_5O_3$: 411.23; Found: 412.01 (M+1).

Synthesis of tert-butyl 4-(2-(3-(2-((2-fluorophenyl) sulfonyl) hydrazine-1-carbonyl)-5-methylphenyl) pyridin-4-yl)piperazine-1-carboxylate (231)

To a stirred solution of compound 230 (200 mg, 0.486 mmol) in THF (2 mL) and Pyridine (2 mL, 24.7 mmol) at 0° C. was added 2-fluorobenzenesulfonyl chloride (114 mg, 0.5832 mmol) at 0° C. The resulted reaction mixture was stirred for 4 h at RT. After completion (monitored by TLC and LCMS), the reaction mixture was quenched with ice water and extracted with EtOAc. The organic layer was washed with brine, dried over anhydrous $Na_2SO_4$ and concentrated under reduced pressure. The crude compound was purified by combi flash chromatography (using a gradient method of 30-40% EtOAc/Heptane) to afford the title compound 231 (220 mg, 79.71%) as pale brown solid. TLC: 50% EtOAc/Heptane ($R_f$ 0.6). LCMS Calculated for C28H32FN5O5S: 569.21; Found: 570.2 (M+1).

Synthesis of 2-fluoro-N'-(3-methyl-5-(4-(piperazin-1-yl) pyridin-2-yl) benzoyl) benzenesulfonohydrazide hydrochloride (232)

To a stirred solution of compound 231 (200 mg, 0.351 mmol) in DCM (3 mL) at 0° C. was added 4M HCl in dioxane (0.877 mL, 3.510 mmol). The reaction was allowed to stir at the room temperature for 1 h. After completion (monitored by TLC), the reaction mixture was concentrated under reduced pressure, triturated with $Et_2O$ (10 mL) and dried in vacuo to afford the title compound 232 (80 mg, HCl salt) as a brown semi solid. TLC: 5% MeOH/DCM ($R_f$ 0.2). This was used in the next step without further characterization.

Synthesis of 2-fluoro-N'-(3-methyl-5-(4-(4-propi-oloylpiperazin-1-yl) pyridin-2-yl) benzoyl) benzene-sulfonohydrazide To a stirred solution of compound 232 (80 mg, 0.158 mmol) in DMF (1 mL) at 0° C. was added DIPEA (0.082 mL, 0.474 mmol), Propiolic acid (13 mg, 0.189 mmol) followed by T₃P as a 50% solution in EtOAc (0.150 mL, 0.237 mmol). The reaction mixture was allowed to stir at room temperature for 16 h. After completion (monitored by TLC), the reaction mixture was concentrated under reduced pressure and the crude was purified by prep HPLC to afford the title compound (6 mg, 7.3%) as an off-white solid. TLC: 5% MeOH/DCM ($R_f$, 0.5). (See Table 1 for analytical data)

Synthetic Example 104

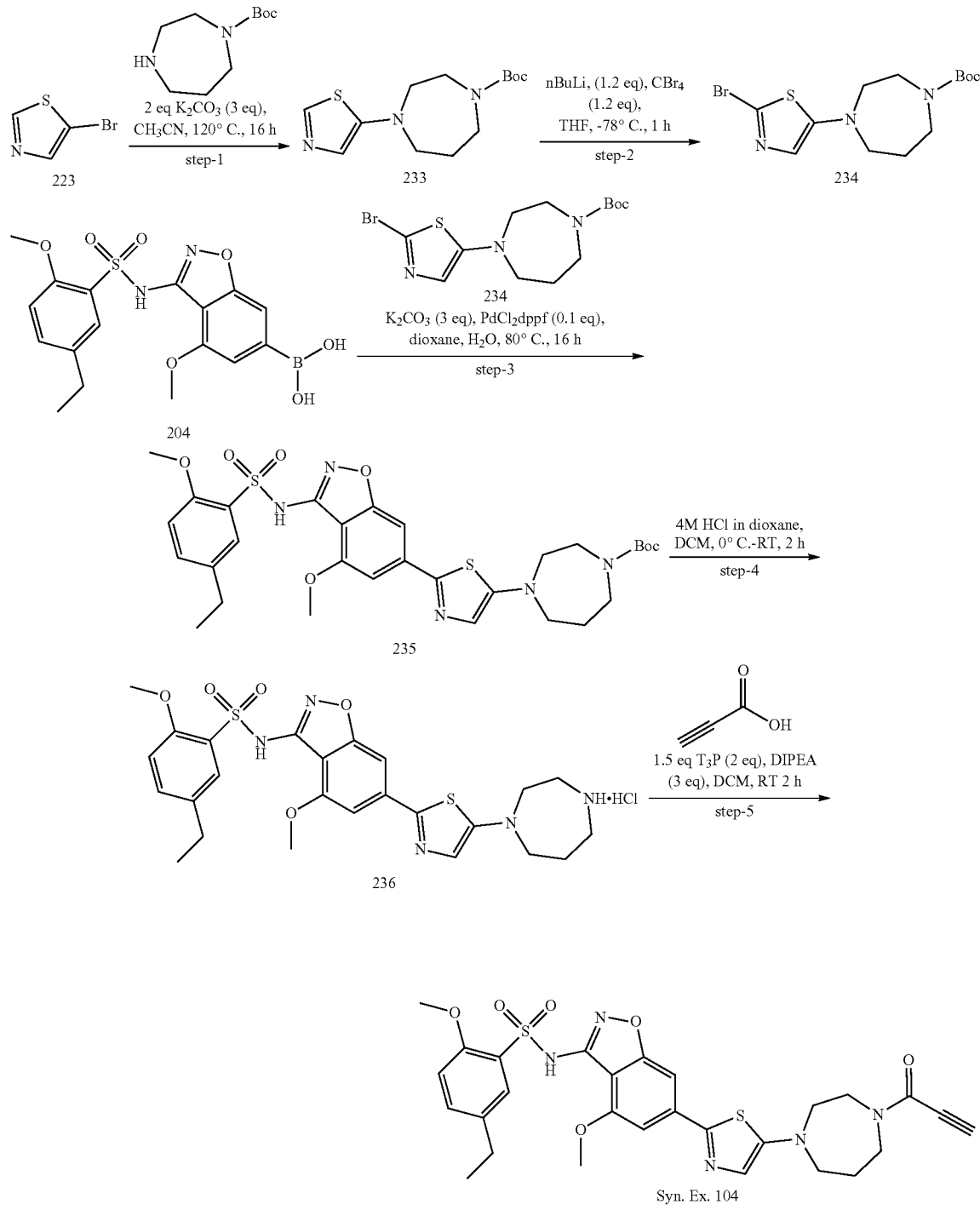

Synthesis of tert-butyl 4-(thiazol-5-yl)-1,4-diazepane-1-carboxylate (233)

To a stirred solution of compound 223 (1 g, 18.290 mmol) in DMF (5 mL) at 0° C. was added $K_2CO_3$ (7.58 g, 54.871 mmol) and tert-butyl 1,4-diazepane-1-carboxylate (7.3 g, 36.58 mmol). The reaction mixture was allowed to stir at 100° C. for 16 h. After completion (monitored by TLC), the reaction mixture was quenched with ice cold water and extracted with EtOAc. The organic layer was washed with brine, dried over anhydrous $Na_2SO_4$, and concentrated under reduced pressure. The crude was purified by combi flash chromatography using gradient 10% EA/Heptane to afford the title compound 233 (700 mg, 41%) as an off-white solid. TLC: 5% MeOH/DCM ($R_f$, 0.5). LCMS Calculated for C13H21N3O2S: 283.14; Found: 284.05 (M+H).

Synthesis of tert-butyl 4-(2-bromothiazol-5-yl)-1,4-diazepane-1-carboxylate (234)

To a stirred solution of 233 (700 mg, 2.470 mmol) in THF (20 mL) was added n-BuLi (1.6 mol/L) in hexanes (2.31 mL, 3.705 mmol) at –78° C. The reaction mixture was stirred at –78° C. for 40 min, and a solution of $CBr_4$ (1.2 g, 3.705 mmol) in THF (1.5 mL) was added. The reaction mixture was stirred at –78° C. for another 1 h. After completion (monitored by TLC), the reaction mixture was quenched with ice cold water and extracted with EtOAc. The organic layer was washed with brine, dried over anhydrous $Na_2SO_4$, and concentrated under reduced pressure. The crude was purified by combi flash chromatography using gradient 5% EA/Heptane to afford the title compound 234 (600 mg, 67.11%) as a brown oil. TLC: 5% EA/Heptane ($R_f$, 0.7). LCMS Calculated for C13H20BrN3O2S: 361.05; Found: 362.05 (M+H).

Synthesis of tert-butyl 4-(2-(3-((5-ethyl-2-methoxyphenyl)sulfonamido)-4-methoxybenzo[d]isoxazol-6-yl)thiazol-5-yl)-1,4-diazepane-1-carboxylate (235)

To a stirred solution of compound 234 (250 mg, 0.690 mmol) in 3:1 mixture of 1,4 Dioxane:water (10 mL) was added $K_2CO_3$ (286 mg, 2.070 mmol) and 204 (308 mg, 0.759 mmol). The reaction mixture was purged with argon gas for 10 min followed by addition of $PdCl_2(dppf)$ (56 mg, 0.0690 mmol). The resulting mixture was stirred at 80° C. for 6 h. After completion (monitored by TLC), the reaction mixture was quenched with ice cold water and extracted with ethyl acetate. The organic layer washed with brine, dried over anhydrous $Na_2SO_4$ and concentrated under reduced pressure. The crude compound triturated $Et_2O$/Heptane and dried under reduced pressure to afford the title compound 235 (300 mg, 67.56%) as a brown semi solid. TLC: 50% EtOAc/Heptane ($R_f$, 0.4). LCMS Calculated for C30H37N5O7S2: 643.21; Found: 644.2 (M+H).

Synthesis of N-(6-(5-(1,4-diazepan-1-yl)thiazol-2-yl)-4-methoxybenzo[d]isoxazol-3-yl)-5-ethyl-2-methoxybenzenesulfonamide hydrochloride (236)

To a stirred solution of compound 235 (250 mg, 0.388 mmol) in DCM (2 mL) at 0° C. was added 4M HCl in dioxane (0.97 mL, 3.883 mmol). The reaction was allowed to stir at the room temperature for 2 h. After completion (monitored by TLC), the reaction mixture was concentrated under reduced pressure. The crude compound triturated with $Et_2O$/Heptane and dried under reduced pressure to afford the title compound 236 (160 mg, HCl salt) as a colourless gummy solid. TLC: 5% MeOH/DCM ($R_f$, 0.2). This was used in the next step without further characterization.

5-ethyl-2-methoxy-N-(4-methoxy-6-(5-(4-propioloyl-1,4-diazepan-1-yl) thiazol-2-yl) benzo[d]isoxazol-3-yl) benzenesulfonamide To a stirred solution of compound 236 (150 mg, 0.258 mmol) in DMF (1 mL) at 0° C. was added DIPEA (0.135 mL, 0.775 mmol), Propiolic acid (27 mg, 0.387 mmol) followed by $T_3P$ 50% solution in EtOAc (0.328 mL, 0.516 mmol). The reaction mixture was allowed to stir at room temperature for 2 h. After completion (monitored by TLC), the reaction mixture was concentrated under reduced pressure and the crude was purified by using prep HPLC to afford the title compound (5 mg, 3.24%) as an off-white solid. TLC: 5% MeOH/DCM ($R_f$, 0.5). (See Table 1 for analytical data).

Synthetic Example 105A and 105B

Scheme 79: Synthesis of 5-ethyl-2-methoxy-N-(4-methoxy-6-((5-propioloyl-4,5,6,7-tetrahydro-1H-pyrazolo[4,3-c]pyridin-1-yl)methyl)benzo[d]isoxazol-3-yl)benzenesulfonamide and 5-ethyl-2-methoxy-N-(4-methoxy-6-((5-propioloyl-4,5,6,7-tetrahydro-2H-pyrazolo[4,3-c]pyridin-2-yl)methyl)benzo[d]isoxazol-3-yl)benzenesulfonamide

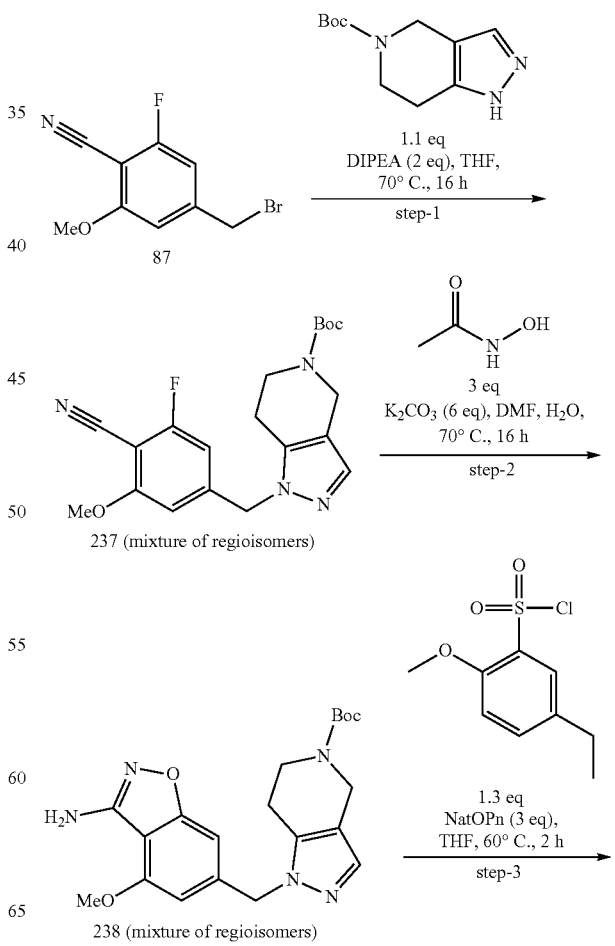

-continued

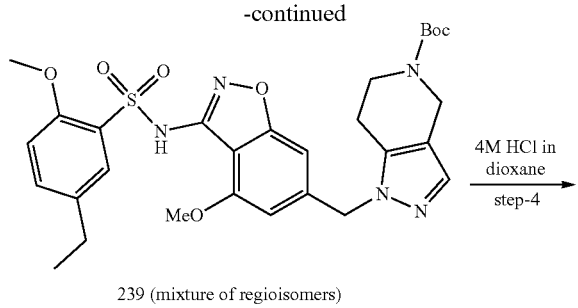

239 (mixture of regioisomers)

4M HCl in dioxane
step-4

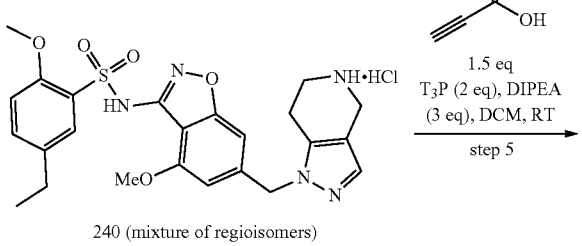

240 (mixture of regioisomers)

1.5 eq
T₃P (2 eq), DIPEA
(3 eq), DCM, RT
step 5

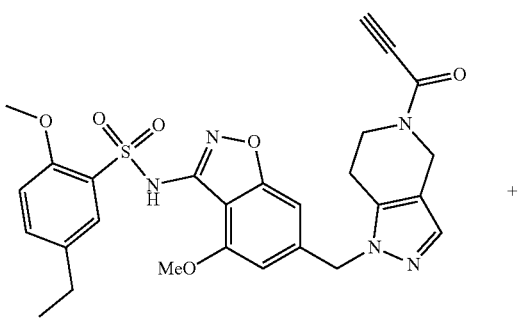

Syn. Ex. 105a

+

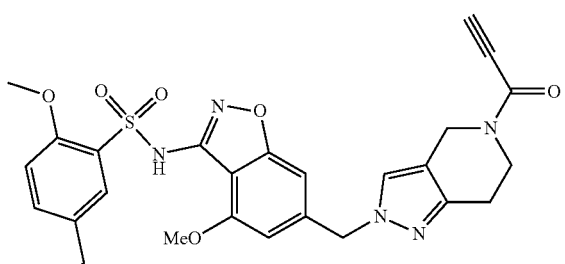

Syn. Ex. 105b

Synthesis of tert-butyl 1-(4-cyano-3-fluoro-5-methoxybenzyl)-1,4,6,7-tetrahydro-5H-pyrazolo[4,3-c]pyridine-5-carboxylate and tert-butyl 2-(4-cyano-3-fluoro-5-methoxybenzyl)-2,4,6,7-tetrahydro-5H-pyrazolo[4,3-c]pyridine-5-carboxylate (237)

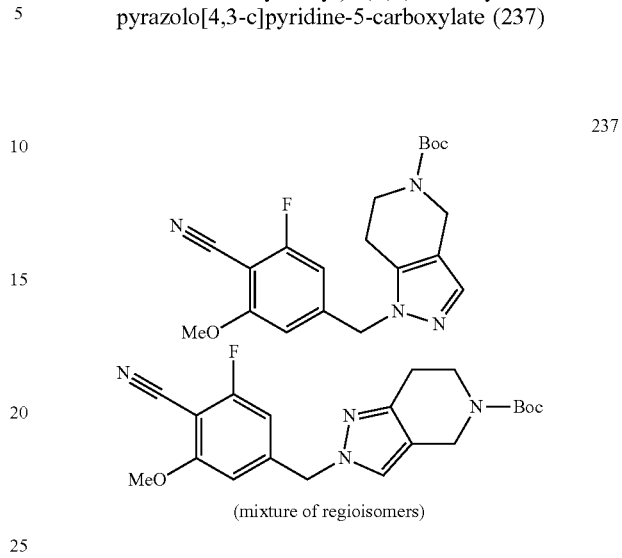

237

(mixture of regioisomers)

To a stirred solution of compound 87 (2 g, 8.194 mmol) in THF (5 mL) at 0° C. was added DIPEA (2.86 mL, 16.388 mmol) followed by tert-butyl 1,4,6,7-tetrahydro-5H-pyrazolo[4,3-c]pyridine-5-carboxylate (2.01 g, 9.014 mmol). The reaction was allowed to stir at 70° C. for 16 h. After completion (monitored by TLC), the reaction mixture was quenched with ice cold water and extracted with ethyl acetate. The organic layer was washed with brine, dried over anhydrous $Na_2SO_4$ and concentrated under reduced pressure. The crude was purified by using combi flash chromatography using gradient 5% EA/Heptane to afford the title compound 237 (2.1 g, 67.74%) as a yellow oil compound. TLC: 5% EA/Heptane ($R_f$ 0.7). LCMS Calculated for C20H23FN4O3: 386.18; Found: 387.05 (M+H).

Synthesis of tert-butyl 1-((3-amino-4-methoxybenzo[d]isoxazol-6-yl) methyl)-1,4,6,7-tetrahydro-5H-pyrazolo[4,3-c]pyridine-5-carboxylate and tert-butyl 2-((3-amino-4-methoxybenzo[d]isoxazol-6-yl) methyl)-2,4,6,7-tetrahydro-5H-pyrazolo[4,3-c]pyridine-5-carboxylate (238)

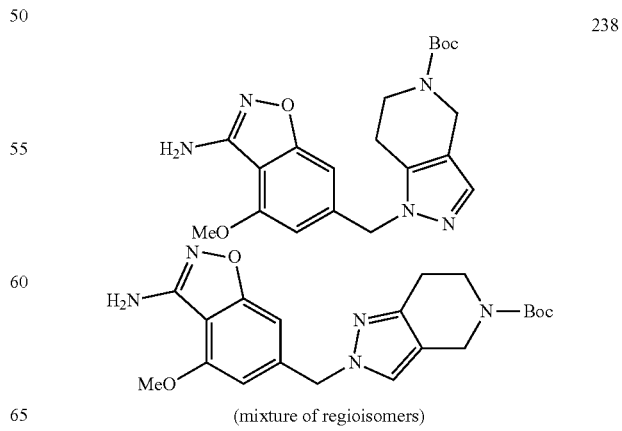

238

(mixture of regioisomers)

To a stirred solution of compound 237 (2 g, 5.175 mmol) in a 6:1 mixture of DMF:H$_2$O (7 mL) at room temperature was added N-hydroxyacetamide (1.165 g, 15.525 mmol) followed by K$_2$CO$_3$ (4.29 g, 31.053 mmol). The reaction mixture was allowed to stir at 60° C. for 12 h. After completion (monitored by TLC), the reaction mixture was quenched with ice water and extracted with ethyl acetate. The organic layer was washed with brine, dried over anhydrous Na$_2$SO$_4$ and concentrated under reduced pressure to offer the title compound 238 (1.9 g, 76.92%, mixture of regioisomers) as a brown semi-solid. TLC: 50% EtOAc/Heptane (R$_f$, 0.45). LCMS Calculated for C20H25N5O4: 399.19; Found: 400.02 (M+1).

Synthesis of tert-butyl 1-((3-((5-ethyl-2-methoxy-phenyl) sulfonamido)-4-methoxybenzo[d]isoxazol-6-yl) methyl)-1,4,6,7-tetrahydro-5H-pyrazolo[4,3-c]pyridine-5-carboxylate and tert-butyl 2-((3-((5-ethyl-2-methoxyphenyl)sulfonamido)-4-methoxybenzo[d]isoxazol-6-yl)methyl)-2,4,6,7-tetrahydro-5H-pyrazolo[4,3-c]pyridine-5-carboxylate (239)

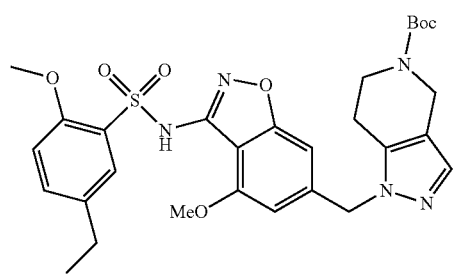

239

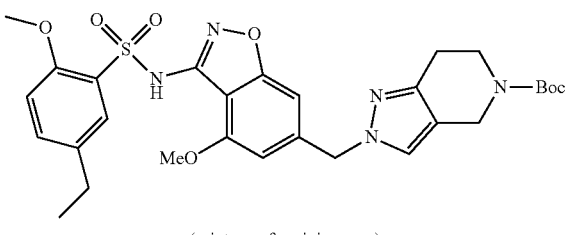

(mixture of regioisomers)

To a stirred solution of compound 238 (300 mg, 0.751 mmol) in THF (10 mL) was added NaO$^t$Pn (0.248 g, 2.253 mmol) followed by 5-ethyl-2-methoxybenzenesulfonyl chloride (0.229 g, 0.976 mmol). The reaction mixture was allowed to stir at the room temperature for 16 h. After completion (monitored by TLC), the reaction mixture was quenched with ice cold water and extracted with ethyl acetate. The organic layer was dried over anhydrous Na$_2$SO$_4$, and concentrated under reduced pressure. The crude compound was purified by combi flash chromatography (neutral alumina) to afford the title compound 239 (200 mg, 44.64%, mixture of regioisomers) as a pale-yellow solid. TLC: 80 EtOAc (R$_f$, 0.5). LCMS Calculated for C29H35N5O7S: 597.23; Found: 598.5 (M+1).

Synthesis of 5-ethyl-2-methoxy-N-(4-methoxy-6-((4,5,6,7-tetrahydro-1H-pyrazolo[4,3-c]pyridin-1-yl) methyl)benzo[d]isoxazol-3-yl)benzenesulfonamide hydrochloride and 5-ethyl-2-methoxy-N-(4-methoxy-6-((4,5,6,7-tetrahydro-2H-pyrazolo[4,3-c]pyridin-2-yl)methyl)benzo[d]isoxazol-3-yl)benzenesulfonamide hydrochloride (240)

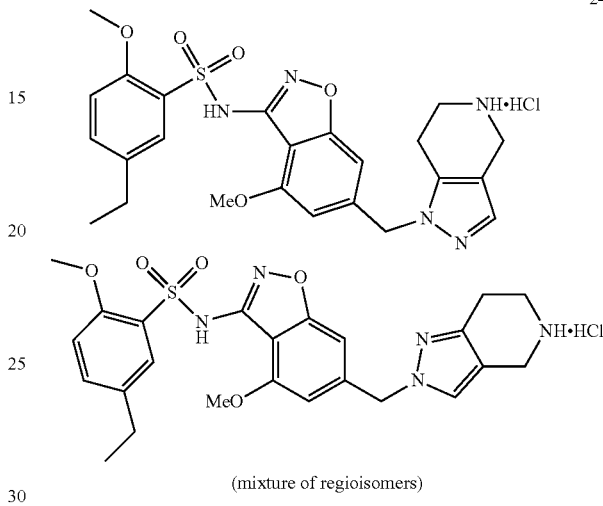

(mixture of regioisomers)

To a stirred solution of compound 239 (150 mg, 0.250 mmol) in DCM (2 mL) at 0° C. was added 4M HCl in dioxane (0.627 mL, 2.509 mmol). The reaction was allowed to stir at the room temperature for 2 h. After completion (monitored by TLC), the reaction mixture was concentrated, triturated with Et$_2$O and dried under reduced pressure to afford the title compound 240 (160 mg, HCl salt, mixture of regioisomers) as a colourless gummy solid. TLC: 5% MeOH/DCM (R$_f$, 0.2). This was used in the next step without further characterization.

Synthesis of 5-ethyl-2-methoxy-N-(4-methoxy-6-((5-propioloyl-4,5,6,7-tetrahydro-1H-pyrazolo[4,3-c]pyridin-1-yl)methyl)benzo[d]isoxazol-3-yl)benzenesulfonamide and 5-ethyl-2-methoxy-N-(4-methoxy-6-((5-propioloyl-4,5,6,7-tetrahydro-2H-pyrazolo[4,3-c]pyridin-2-yl)methyl)benzo[d]isoxazol-3-yl) benzenesulfonamide To a stirred solution of compound 240 (150 mg, 0.280 mmol) in DMF (1 mL) at 0° C. was added DIPEA (0.073 mL, 0.421 mmol), Propiolic acid (58 mg, 0.84 mmol) followed by T$_3$P 50% solution in EtOAc (0.356 mL, 0.56 mmol) and the mixture was allowed to stir at room temperature for 2 h. After completion (monitored by TLC), the reaction mixture was concentrated and the crude was purified by chiral HPLC to afford the 5-ethyl-2-methoxy-N-(4-methoxy-6-(5-(4-propioloyl-1,4-diazepan-1-yl) thiazol-2-yl) benzo[d]isoxazol-3-yl) benzenesulfonamide (8.5 mg, 5.5%) as an off-white solid and 5-ethyl-2-methoxy-N-(4-methoxy-6-((5-propioloyl-4,5,6,7-tetrahydro-2H-pyrazolo[4,3-c]pyridin-2-yl) methyl) benzo[d]isoxazol-3-yl) benzenesulfonamide (2 mg, 1.29%) as an off-white solid. TLC: 5% MeOH/DCM (R$_f$, 0.5). (See Table 1 for analytical data).

Synthetic Example 106

Scheme 80: Synthesis of 2,6-dimethoxy-N-(4-methoxy-6-(2-(4-propioloylpiperazin-1-yl) thiazol-5-yl) benzo[d]isoxazol-3-yl) benzenesulfonamide

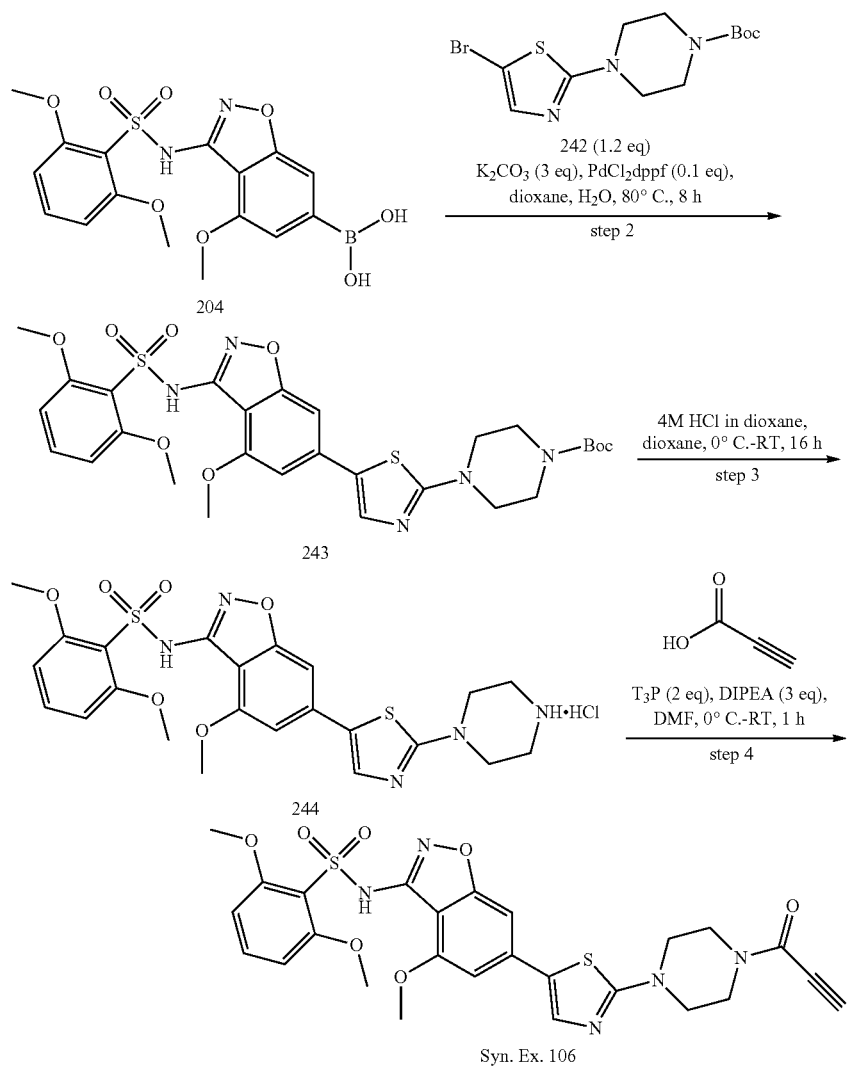

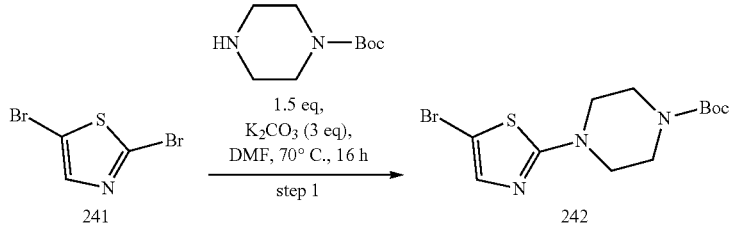

Synthesis of tert-butyl 4-(thiazol-5-yl)piperazine-1-carboxylate (242)

To a stirred solution of compound 241 (2 g, 8.233 mmol) in DMF (10 mL) at 0° C. was added $K_2CO_3$ (3.41 g, 24.699 mmol), followed by tert-butyl piperazine-1-carboxylate (2.3 g, 12.349 mmol). The reaction mixture was allowed to stir at 70° C. for 16 h. After completion (monitored by TLC), the reaction mixture was quenched with ice cold water and extracted with EtOAc. The organic layer was washed with brine, dried over anhydrous $Na_2SO_4$, and concentrated under reduced pressure. The crude was purified by combi flash chromatography using gradient 2-5% EA/Heptane to afford the title compound 242 (1.4 g, 56.45%) as an off-white solid. TLC: 5% MeOH/DCM ($R_f$ 0.6). LCMS Calculated for C12H18BrN3O2S: 347.03; Found: 348.05 (M+H).

Synthesis of tert-butyl 4-(5-(3-((2,6-dimethoxyphenyl)sulfonamido)-4-methoxybenzo[d]isoxazol-6-yl)thiazol-2-yl)piperazine-1-carboxylate (243)

To a stirred solution of compound 242 (600 mg, 1.722 mmol) in 3:1 mixture of 1,4 Dioxane:water (10 mL) was added K₂CO₃ (714 mg, 5.168 mmol) followed by compound 204 (843 mg, 2.066 mmol). The reaction mixture was purged with argon gas for 10 min followed by addition of PdCl₂dppf·DCM (140 mg, 0.1722 mmol). The reaction mixture was stirred at 80° C. for 8 h. After completion (monitored by TLC), the reaction mixture was quenched with ice cold water and extracted with ethyl acetate. The organic layer was washed with brine, dried over anhydrous Na₂SO₄ and concentrated under reduced pressure. The crude compound was purified by combi flash chromatography (using a gradient method of 80-90% EtOAc/Heptane) to afford the title compound 243 (200 mg, 18.51%) as a pale-yellow solid. TLC: 80% EtOAc/Heptane (R_f 0.4). LCMS Calculated for C28H33N5O8S2: 631.18; Found: 632.2 (M+H).

Synthesis of 2,6-dimethoxy-N-(4-methoxy-6-(2-(piperazin-1-yl) thiazol-5-yl) benzo[d]isoxazol-3-yl) benzenesulfonamide hydrochloride (244)

To a stirred solution of compound 243 (200 mg, 0.316 mmol) in DCM (2 mL) at 0° C. was added 4M HCl in dioxane (0.79 mL, 3.165 mmol). The reaction was allowed to stir at the room temperature for 16 h. After completion (monitored by TLC), the reaction mixture was concentrated under reduced pressure and triturated with EtOAc/Heptane to afford the title compound 244 (150 mg, HCl salt) as a colourless gummy solid. TLC: 5% MeOH/DCM (R_f 0.2). LCMS Calculated for C23H26ClN5O6S2: 567.10; Found: 568.2.

Synthesis of 2,6-dimethoxy-N-(4-methoxy-6-(2-(4-propioloylpiperazin-1-yl) thiazol-5-yl) benzo[d]isoxazol-3-yl) benzenesulfonamide To a stirred solution of compound 244 (150 mg, 0.264 mmol) in DMF (1 mL) at 0° C. was added DIPEA (0.138 mL, 0.792 mmol), Propiolic acid (36 mg, 0.528 mmol) followed by T₃P as a 50% solution in EtOAc (0.335 mL, 0.528 mmol). The reaction mixture was allowed to stir at room temperature for 1 h. After completion (monitored by TLC), the reaction mixture was quenched with water and extracted with ethyl acetate. The organic layer was washed with brine, dried over anhydrous Na₂SO₄, and concentrated under reduced pressure. The crude was purified by using combi flash chromatography using gradient 20-50% EA/Heptane to afford the title compound (98 mg, 63.63%) as an off-white solid. TLC: 5% MeOH/DCM (R_f 0.4). (See Table 1 for analytical data).

Synthetic Example 107

Scheme 81: Synthesis of 5-ethyl-2-methoxy-N-(4-methoxy-6-((2-(vinylsulfonamido)ethoxy) methyl) benzo[d]isoxazol-3-yl) benzenesulfonamide

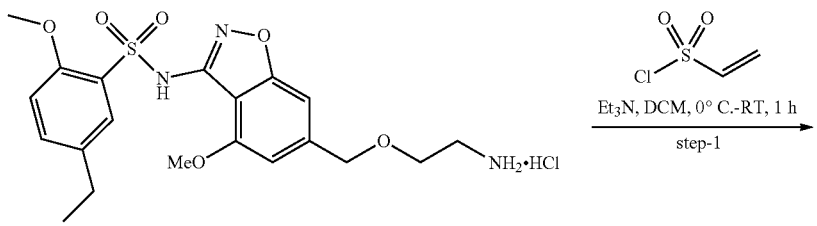

178

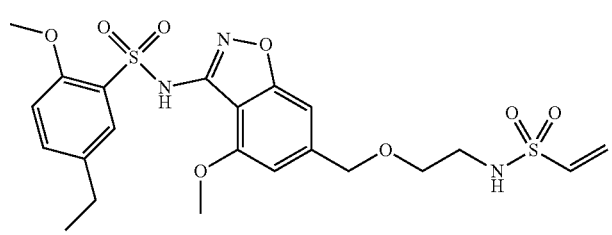

Syn. Ex. 107

To a stirred solution of compound 178 (150 mg, 0.317 mmol) in DCM (2 mL) at 0° C. was added TEA (0.133 mL, 0.953 mmol) and followed by ethene sulfonyl chloride (48 mg, 0.381 mmol) in DCM (1 mL). The reaction was allowed to stir at 0° C. for 1 h. After completion (monitored by TLC), the reaction mixture was quenched with water and extracted with ethyl acetate. The organic layer was washed with brine, dried over anhydrous $Na_2SO_4$, concentrated and purified by prep HPLC to afford the title compound (6 mg, 3.4%) as a yellow solid. TLC: 5% MeOH/DCM ($R_f$ 0.40). (See Table 1 for analytical data).

Synthetic Example 108

Scheme 82: Synthesis of N-(6-((4-(ethylsulfonamidomethyl)-1H-pyrazol-1-yl)methyl)-4-methoxybenzo[d]isoxazol-3-yl)-2,6-dimethoxybenzenesulfonamide

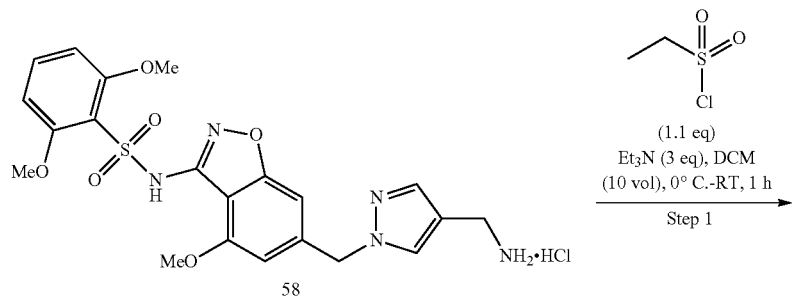

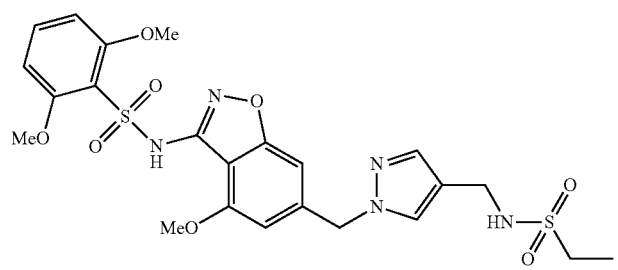

Syn. Ex. 108

To a stirred solution of compound 58 (120 mg, 0.235 mmol) in DCM (2 mL) at 0° C. was added TEA (0.1 mL, 0.705 mmol) and followed by ethanesulfonyl chloride (33 mg, 0.258 mmol) in DCM (0.5 mL). The reaction was allowed to stir at 0° C. for 1 h. After completion (monitored by TLC), the reaction mixture was quenched with ice cold water and extracted with DCM. The organic layer was washed with brine, dried over anhydrous $Na_2SO_4$, concentrated and purified by prep HPLC to afford the title compound (40 mg, 27.63%) as an off-white solid. TLC: 5% MeOH/DCM (Rf: 0.40). (See Table 1 for analytical data).

Synthetic Example 109

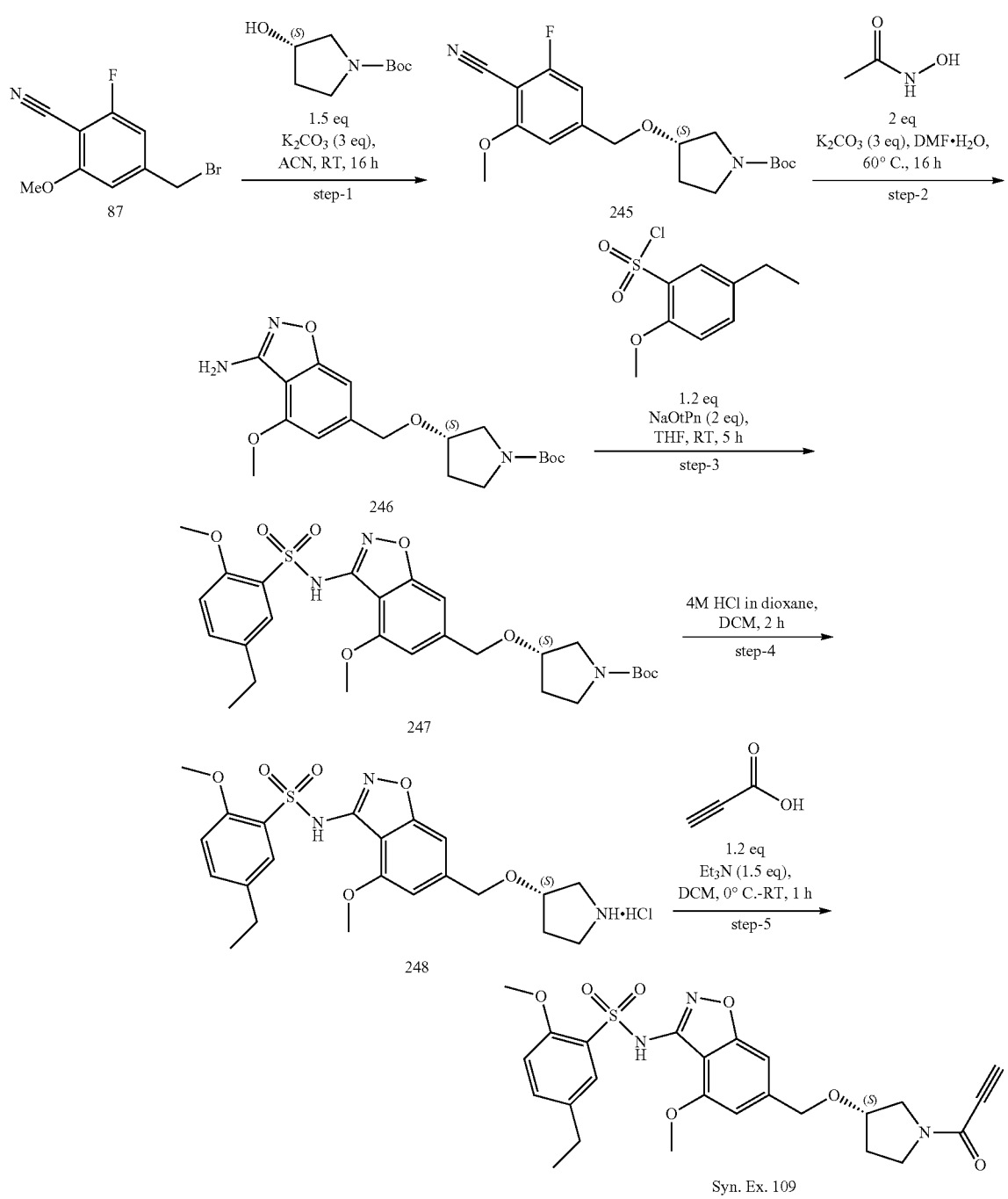

Syn. Ex. 109

To a stirred solution of compound 87 (500 mg, 2.048 mmol) in acetonitrile (5 mL) at 0° C. was added K$_2$CO$_3$ (0.849 mg, 6.146 mmol) followed by tert-butyl (S)-3-hydroxypyrrolidine-1-carboxylate (557 mg, 3.072 mmol). The reaction was allowed to stir at 60° C. for 16 h. After completion (monitored by TLC), the reaction mixture was quenched with ice cold water and extracted with Ethyl Acetate. The organic layer was washed with brine, dried over anhydrous Na$_2$SO$_4$, and concentrated under reduced pressure to get the title compound 245 (500 mg, 48.81%) as colour less gummy solid. TLC: 50% EtOAc (R$_f$, 0.5). LCMS Calculated for C18H23FN2O4: 350.16; Found: 351.02 (M+1). The crude compound was used in next reaction without purification.

Synthesis of tert-butyl (S)-3-((3-amino-4-methoxy-benzo[d]isoxazol-6-yl) methoxy) pyrrolidine-1-carboxylate (246)

To a stirred solution of compound 245 (500 mg, 1.426 mmol) in a 7:1 mixture of DMF:H$_2$O (8 mL) at room temperature was added N-hydroxyacetamide (0.214 g, 2.853 mmol) followed by K$_2$CO$_3$ (591 mg, 4.278 mmol). The reaction mixture was allowed to stir at 60° C. for 16 h. After completion (monitored by TLC), the reaction mixture was quenched with ice water and extracted with ethyl acetate. The organic layer was washed with brine, dried over anhydrous Na$_2$SO$_4$, concentrated and purified by combi flash chromatography using gradient 40-70% EA/Heptane to afford the title compound 246 (210 mg, 76.92%) as a yellow solid. TLC: 70% EtOAc/Heptane (R$_f$ 0.40). LCMS Calculated for C18H25N3O5: 363.18; Found: 364.02 (M+1).

Synthesis of tert-butyl (S)-3-((3-((5-ethyl-2-methoxyphenyl) sulfonamido)-4-methoxybenzo[d] isoxazol-6-yl) methoxy) pyrrolidine-1-carboxylate (247)

To a stirred solution of compound 246 (210 mg, 0.577 mmol) in THF (10 mL) was added NatOPn (0.190 g, 1.733 mmol) followed by 5-ethyl-2-methoxybenzenesulfonyl chloride (0.162 g, 0.692 mmol). The reaction mixture was allowed to stir at the room temperature for 5 h. After completion (monitored by TLC), the reaction mixture was quenched with ice water and extracted with ethyl acetate. The organic layer was dried over anhydrous Na$_2$SO$_4$, and concentrated under reduced pressure. The crude compound was purified by combi flash chromatography (neutral alumina) to afford the title compound 247 (150 mg, 46.29%) as a pale-yellow solid. TLC: 50 EtOAc (R$_f$ 0.5). LCMS Calculated for C27H35N3O8S: 561.21; Found: 562.5 (M+1).

Synthesis of (S)-5-ethyl-2-methoxy-N-(4-methoxy-6-((pyrrolidin-3-yloxy) methyl) benzo[d]isoxazol-3-yl) benzenesulfonamide hydrochloride (248)

To a stirred solution of compound 247 (150 mg, 0.267 mmol) in DCM (2 mL) at 0° C. was added 4M HCl in dioxane (0.66 mL, 2.670 mmol). The reaction was allowed to stir at the room temperature for 2 h. After completion (monitored by TLC), the reaction mixture quenched with ice cold water and extracted with ethyl acetate. The organic layer was dried over Na$_2$SO$_4$, concentrated triturated with EtOAc/Heptane to afford the title compound 248 (120 mg, HCl salt) as a colour less sticky solid. TLC: 5% MeOH/DCM (R$_f$ 0.2). LCMS Calculated for C22H27N3O6S: 461.16; Found: 462.10.

Synthesis of (S)-5-ethyl-2-methoxy-N-(4-methoxy-6-(((1-propioloylpyrrolidin-3-yl) oxy) methyl) benzo[d]isoxazol-3-yl) benzenesulfonamide To a stirred solution of compound 248 (120 mg, 0.240 mmol) in DMF (1 mL) at 0° C. was added DIPEA (0.125 mL, 0.72 mmol), Propiolic acid (20 mg, 0.289 mmol) followed by T$_3$P as a 50% solution in EtOAc (0.229 mL, 0.36 mmol). The reaction mixture was allowed to stir at room temperature for 1 h. After completion (monitored by TLC), the reaction mixture was concentrated under reduced pressure and the crude was purified by using prep HPLC to afford the title compound (50 mg, 40.65%) as an off-white solid. TLC: 5% MeOH/DCM (R$_f$ 0.5). (See Table 1 for analytical data).

Synthetic Example 110

Scheme 84: Synthesis of (R)-5-ethyl-2-methoxy-N-(4-methoxy-6-(((1-propioloylpyrrolidin-3-yl) oxy) methyl) benzo[d]isoxazol-3-yl) benzenesulfonamide

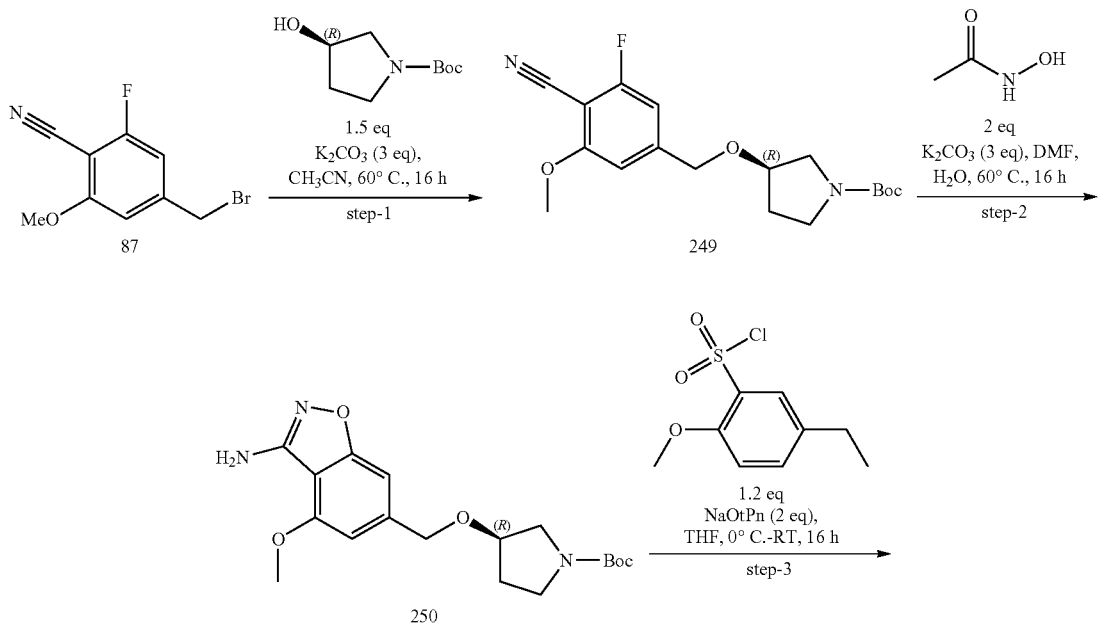

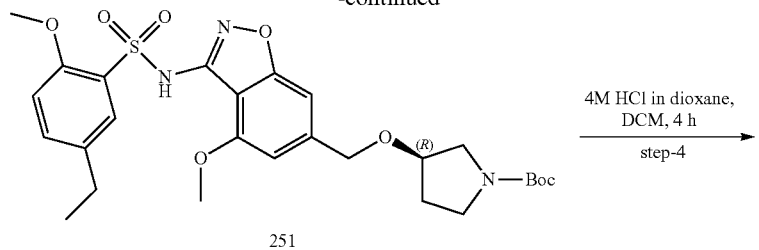

251

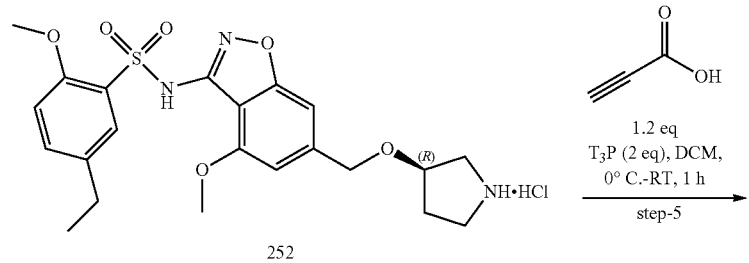

252

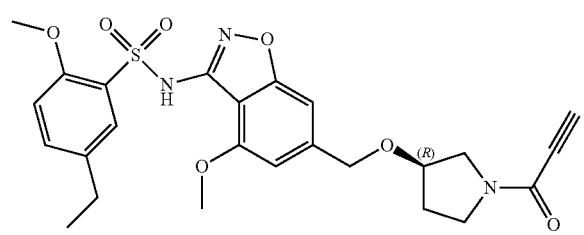

Syn. Ex. 110

Synthesis of tert-butyl (R)-3-((4-cyano-3-fluoro-5-methoxybenzyl)oxy)pyrrolidine-1-carboxylate (249)

To a stirred solution of compound 87 (250 mg, 1.024 mmol) in ACN (5 mL) at 0° C. was added $K_2CO_3$ (0.424 mg, 3.073 mmol) followed by tert-butyl (R)-3-hydroxypyrrolidine-1-carboxylate (557 mg, 1.536 mmol). The reaction was allowed to stir at 60° C. for 16 h. After completion (monitored by TLC), the reaction mixture was quenched with water and extracted with ethyl acetate. The organic layer was washed with brine, dried over anhydrous $Na_2SO_4$, concentrated to afford the title compound 249 (300 mg, 83.79%) as off-white solid. TLC: 50% EtOAc ($R_f$ 0.5). LCMS Calculated for $C_{18}H_{23}FN_2O_4$: 350.16; Found: 351.02 (M+1). The crude compound used in next reaction without purification.

Synthesis of tert-butyl (R)-3-((3-amino-4-methoxybenzo[d]isoxazol-6-yl) methoxy) pyrrolidine-1-carboxylate (250)

To a stirred solution of compound 249 (300 mg, 0.856 mmol) in a 6:1 mixture of $DMF:H_2O$ (7 mL) at room temperature was added N-hydroxy acetamide (0.128 g, 1.712 mmol) followed by $K_2CO_3$ (355 mg, 2.568 mmol). The reaction mixture was allowed to stir at 60° C. for 16 h. After completion (monitored by TLC), the reaction mixture was quenched with ice water added and extracted with ethyl acetate. The organic layer was washed with brine, dried over anhydrous $Na_2SO_4$, concentrated under reduced pressure and purified by combi flash chromatography using gradient 40-70% EA/Heptane to afford the compound 250 (150 mg, 48.23%) as a pale-yellow solid. TLC: 80% EtOAc/Heptane ($R_f$ 0.40). LCMS Calculated for $C_{18}H_{25}N_3O_5$: 363.18; Found: 364.5 (M+1).

Synthesis of tert-butyl (R)-3-((3-((5-ethyl-2-methoxyphenyl) sulfonamido)-4-methoxybenzo[d]isoxazol-6-yl)methoxy)pyrrolidine-1-carboxylate (251)

To a stirred solution of compound 250 (150 mg, 0.412 mmol) in THF (10 mL) was added NaO$^t$Bu (0.135 g, 1.236 mmol) followed by 5-ethyl-2-methoxybenzenesulfonyl chloride (0.116 g, 0.495 mmol). The reaction mixture was allowed to stir at 70° C. for 12 h. After completion (reaction monitored by TLC), the reaction mixture was quenched with ice water and extracted with ethyl acetate. The organic layer was dried over anhydrous $Na_2SO_4$, and concentrated under reduced pressure. The crude compound was purified by combi flash chromatography (neutral alumina) to afford the title compound 251 (100 mg, 43.29%), as a yellow solid. TLC: 60% EtOAc/Heptane ($R_f$ 0.4). LCMS Calculated for $C_{27}H_{35}N_3O_8S$: 561.21; Found: 562.5 (M+1).

Synthesis of (R)-5-ethyl-2-methoxy-N-(4-methoxy-6-((pyrrolidin-3-yloxy) methyl) benzo[d]isoxazol-3-yl) benzenesulfonamide hydrochloride (252)

To a stirred solution of compound 251 (100 mg, 0.276 mmol) in DCM (2 mL) at 0° C. was added 4M HCl in dioxane (0.69 mL, 2.76 mmol). The reaction was allowed to stir at the room temperature for 4 h. After completion (monitored by TLC), the reaction mixture was concentrated triturated with EtOAc/Heptane to afford the title compound 252 (90 mg, HCl salt) as an off-white semi solid. TLC: 5% MeOH/DCM ($R_f$ 0.2). LCMS Calculated for $C_{22}H_{27}N_3O_6S$: 461.16; Found: 462.1.

Synthesis of (R)-5-ethyl-2-methoxy-N-(4-methoxy-6-(((1-propioloylpyrrolidin-3-yl) oxy) methyl) benzo[d]isoxazol-3-yl) benzenesulfonamide To a stirred solution of compound 252 (90 mg, 0.180 mmol) in DMF (1 mL) at 0° C. was added DIPEA (0.094 mL, 0.542 mmol), Propiolic acid (15 mg, 0.216 mmol) followed by T₃P as a 50% solution in EtOAc (0.229 mL, 0.36 mmol). The reaction mixture was allowed to stir at room temperature for 1 h. After completion (monitored by TLC), the reaction mixture was concentrated under reduced pressure and the crude was purified by using prep HPLC to afford the title compound (17 mg, 18.37%) as an off-white solid. TLC: 5% MeOH/DCM ($R_f$, 0.5). (See Table 1 for analytical data).

Synthetic Example 111

Scheme 85: Synthesis of N-[(1S)-1-[[4-(6-methoxy-4-methyl-3-pyridyl) phenyl] methyl]-2-(methylamino)-2-oxo-ethyl] thiazolo [4,5-c] pyridine-6-carboxamide

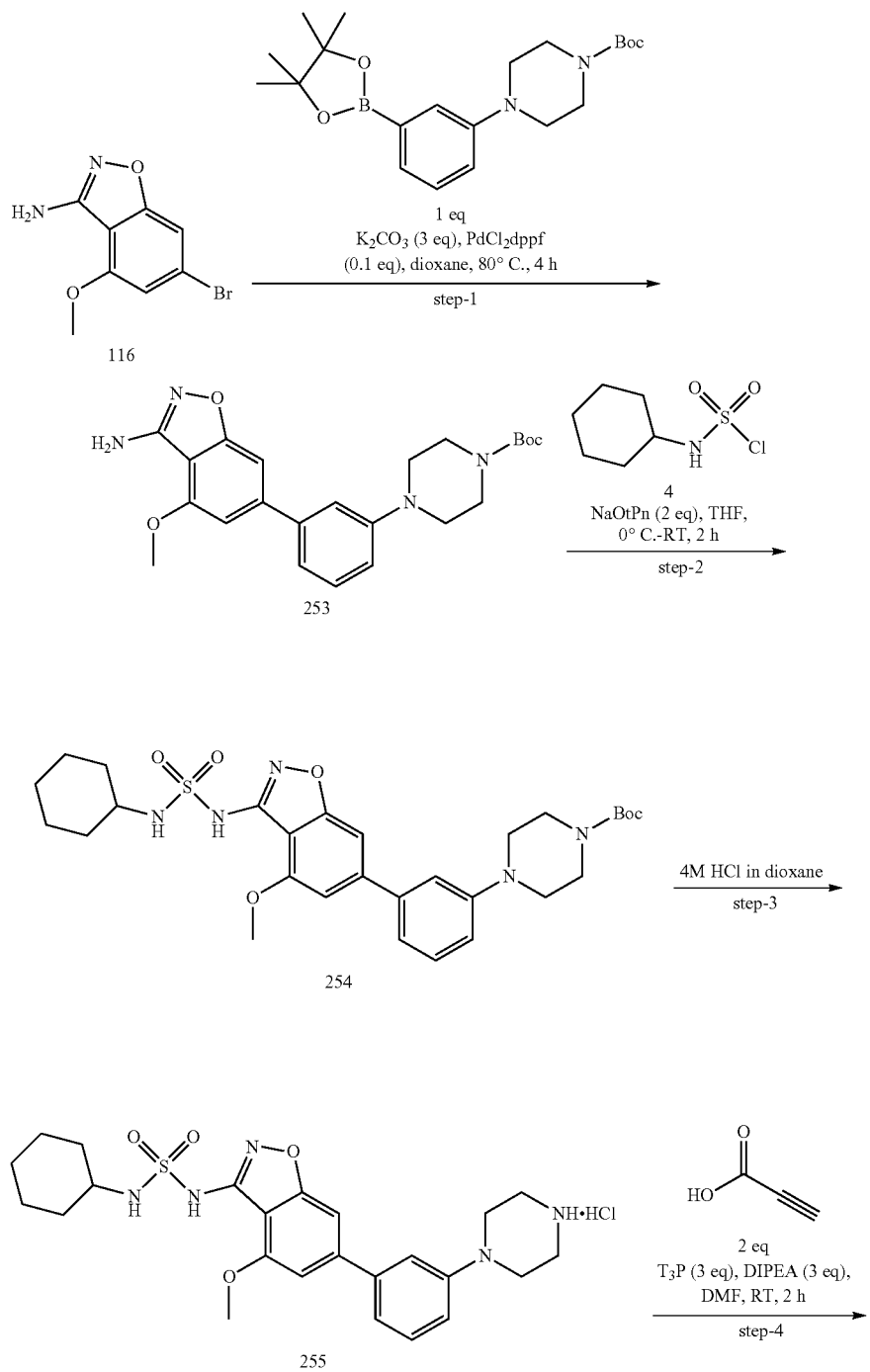

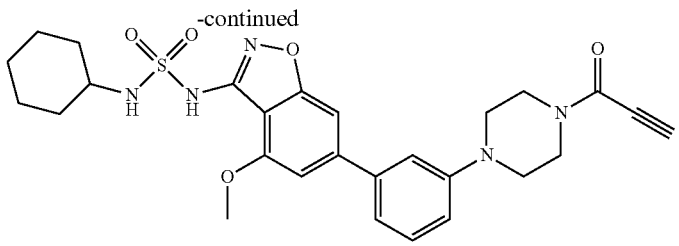

Syn. Ex. 111

Synthesis of tert-butyl 4-(3-(3-amino-4-methoxy-benzo[d]isoxazol-6-yl) phenyl) piperazine-1-carboxylate (253)

To a stirred solution tert-butyl 4-(3-(4,4,5,5-tetramethyl-1,3,2-dioxaborolan-2-yl)phenyl)piperazine-1-carboxylate (798 mg, 2.057 mmol) in dry 1,4-Dioxane (10 mL) was added compound 116 (500 mg, 2.057 mmol) and $K_2CO_3$ (710 mg, 5.142 mmol). The reaction was purged with argon gas for 5 min followed by addition of Pd(dppf)Cl$_2$ (134 mg, 0.164 mmol). The reaction mixture was stirred at 80° C. for 4 h. After completion (monitored by TLC), the reaction mixture was filtered through a pad of celite, the filtrate was concentrated to get crude. The crude was purified by combi flash using gradient 36-50% EA/PE to afford the title compound 253 (400 mg, 45.81%) as a white solid. TLC: 50% EtOAc/Heptane ($R_f$ 0.4). LCMS Calculated for C23H28N4O4: 424.21; Found: 425.02 (M+1).

Synthesis of tert-butyl 4-(3-(3-((N-cyclohexylsulfamoyl) amino)-4-methoxybenzo[d]isoxazol-6-yl) phenyl) piperazine-1-carboxylate (254)

To a stirred solution of compound 253 (200 mg, 0.471 mmol) in THF (10 mL) was added Na$^t$OPn (130 mg, 0.943 mmol) followed by cyclohexylsulfamoyl chloride (186 mg, 0.942 mmol). The reaction mixture was allowed to stir at the room temperature for 16 h. After completion (monitored by TLC), the reaction mixture was quenched with ice water and extracted with ethyl acetate. The organic layer was dried over anhydrous Na$_2$SO$_4$ and concentrated under reduced pressure. The crude compound was purified by combi flash chromatography (neutral alumina) to afford the title compound 254 (150 mg, 54.54%), as a light-yellow solid. TLC: 80 EtOAc ($R_f$ 0.5). LCMS Calculated for C29H39N5O6S: 585.26; Found: 586.5 (M+1).

Synthesis of 4-(3-(3-((N-cyclohexylsulfamoyl) amino)-4-methoxybenzo[d]isoxazol-6-yl) phenyl) piperazine Hydrochloride (255)

To a stirred solution of compound 254 (150 mg, 0.256 mmol) in DCM (2 mL) at 0° C. was added 4M HCl in dioxane (0.64 mL, 2.560 mmol). The reaction was allowed to stir at the room temperature for 2 h. After completion (reaction monitored by TLC), the reaction mixture was concentrated under reduced pressure and triturated with ether to afford the title compound 255 (120 mg, crude HCl salt) as pale-yellow solid. TLC: 5% MeOH/DCM ($R_f$ 0.3). LCMS Calculated for C24H31N5O4S: 485.21: Found: 486.4.

Synthesis of N-[(1S)-1-[[4-(6-methoxy-4-methyl-3-pyridyl) phenyl]methyl]-2-(methylamino)-2-oxo-ethyl]thiazolo [4,5-c]pyridine-6-carboxamide To a stirred solution of compound 255 (120 mg, 0.229 mmol) in DMF (2 mL) at 0° C. was added DIPEA (0.12 mL, 0.687 mmol), propiolic acid (32 mg, 0.458 mmol) followed by T$_3$P as a 50% solution in EtOAc (0.437 mL, 0.687 mmol). The reaction mixture was allowed to stir at room temperature for 1 h. After completion (monitored by TLC), the reaction mixture was concentrated under reduced pressure and the crude was purified by using prep HPLC to afford the title compound (20 mg, 16.26%) as an off-white solid. TLC: 5% MeOH/DCM ($R_f$ 0.5). (See Table 1 for analytical data).

Synthetic Example 112

Scheme 86: Synthesis of 3-[[cyclohwxyl(methyl)sulfamoyl] amino]-4-methoxy-6-[3-(4-prop-2-ynoylpiperazin-1-yl) phenyl]-1,2-benzoxazole

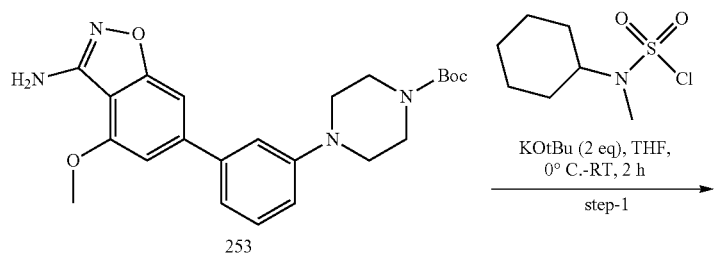

253

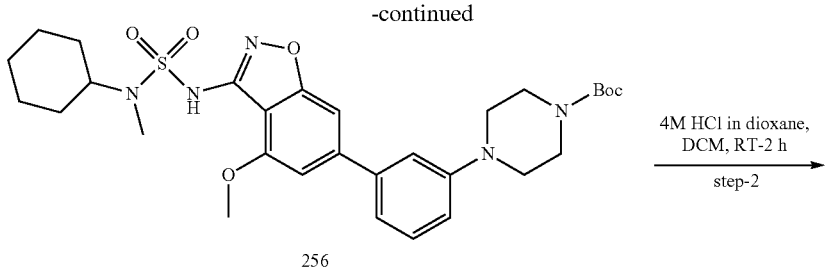

256

4M HCl in dioxane,
DCM, RT-2 h
→
step-2

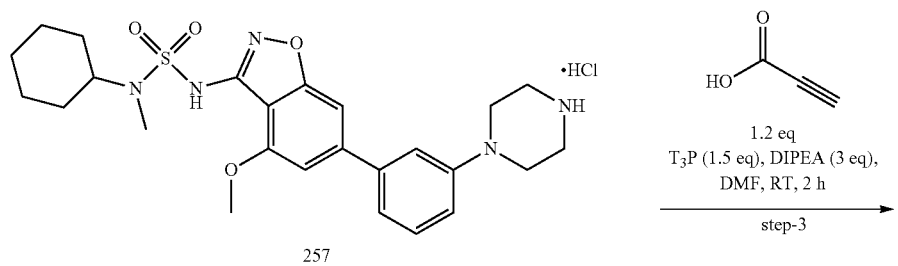

257

1.2 eq
T₃P (1.5 eq), DIPEA (3 eq),
DMF, RT, 2 h
→
step-3

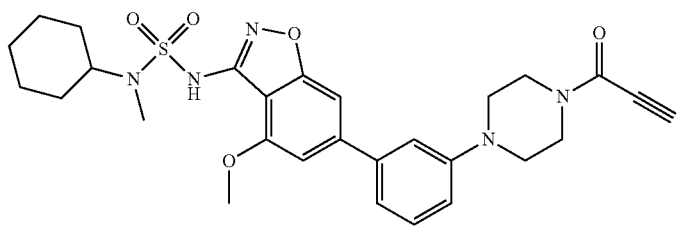

Syn. Ex. 112

Synthesis of tert-butyl 4-(3-(3-((N-cyclohexyl-N-methylsulfamoyl) amino)-4-methoxybenzo[d]isoxazol-6-yl) phenyl) piperazine-1-carboxylate (256)

To a stirred solution of 253 (200 mg, 4.711 mmol) in THF (5 mL) was added KO$^t$Bu (105 mg, 0.942 mmol) followed by cyclohexyl(methyl)sulfamoyl chloride (199 mg, 9.422 mmol). The reaction mixture was allowed to stir at the room temperature for 16 h. After completion (monitored by TLC), the reaction mixture was quenched with ice water and extracted with ethyl acetate. The organic layer was dried over anhydrous Na$_2$SO$_4$, and concentrated under reduced pressure. The crude compound was purified by combi flash chromatography using (neutral alumina) gradient 30-50% EA/Heptane to afford the title compound 256 (150 mg, 54.54%) as a light-yellow solid. TLC: 80 EtOAc (R$_f$ 0.6). LCMS Calculated for C30H41N5O6S: 599.28; Found: 600.5 (M+1).

Synthesis of 3-[[cyclohexyl(methyl)sulfamoyl] amino]-4-methoxy-6-(3-piperazin-1-ylphenyl)-1,2-benzoxazole; hydrochloride (257)

To a stirred solution of compound 256 (120 mg, 0.223 mmol) in DCM (2 mL) at 0° C. was added 4M HCl in dioxane (0.559 mL, 2.238 mmol). The reaction was allowed to stir at the room temperature for 2 h. After completion (monitored by TLC), the reaction mixture was concentrated triturated with ether to afford the title compound 257 (140 mg, crude HCl salt) as pale-yellow solid. TLC: 5% MeOH/DCM (R$_f$ 0.3). LCMS Calculated for C25H33N5O4S: 499.23: Found: 500.3.

Synthesis of 3-[[cyclohexyl(methyl)sulfamoyl] amino]-4-methoxy-6-[3-(4-prop-2-ynoylpiperazin-1-yl) phenyl]-1,2-benzoxazole To a stirred solution of compound 257 (120 mg, 0.223 mmol) in DMF (2 mL) at 0° C. was added DIPEA (0.117 mL, 0.671 mmol), propiolic acid (31 mg, 0.44 mmol) followed by T$_3$P as a 50% solution in EtOAc (0.425 mL, 0.669 mmol). The reaction mixture was allowed to stir at room temperature for 1 h. After completion (monitored by TLC), the reaction mixture was concentrated under reduced pressure and the crude was purified by using prep HPLC to afford the title compound (28 mg, 22.76%) as an off-white solid. TLC: 5% MeOH/DCM (R$_f$ 0.5). (See Table 1 for analytical data).

Synthetic Example 113

Scheme 87: Synthesis of 2,6-dimethoxy-N-(4-methoxy-6-(3-(4-propioloylpiperazin-1-yl)phenyl)isoxazolo[5,4-b]pyridin-3-yl)benzenesulfonamide

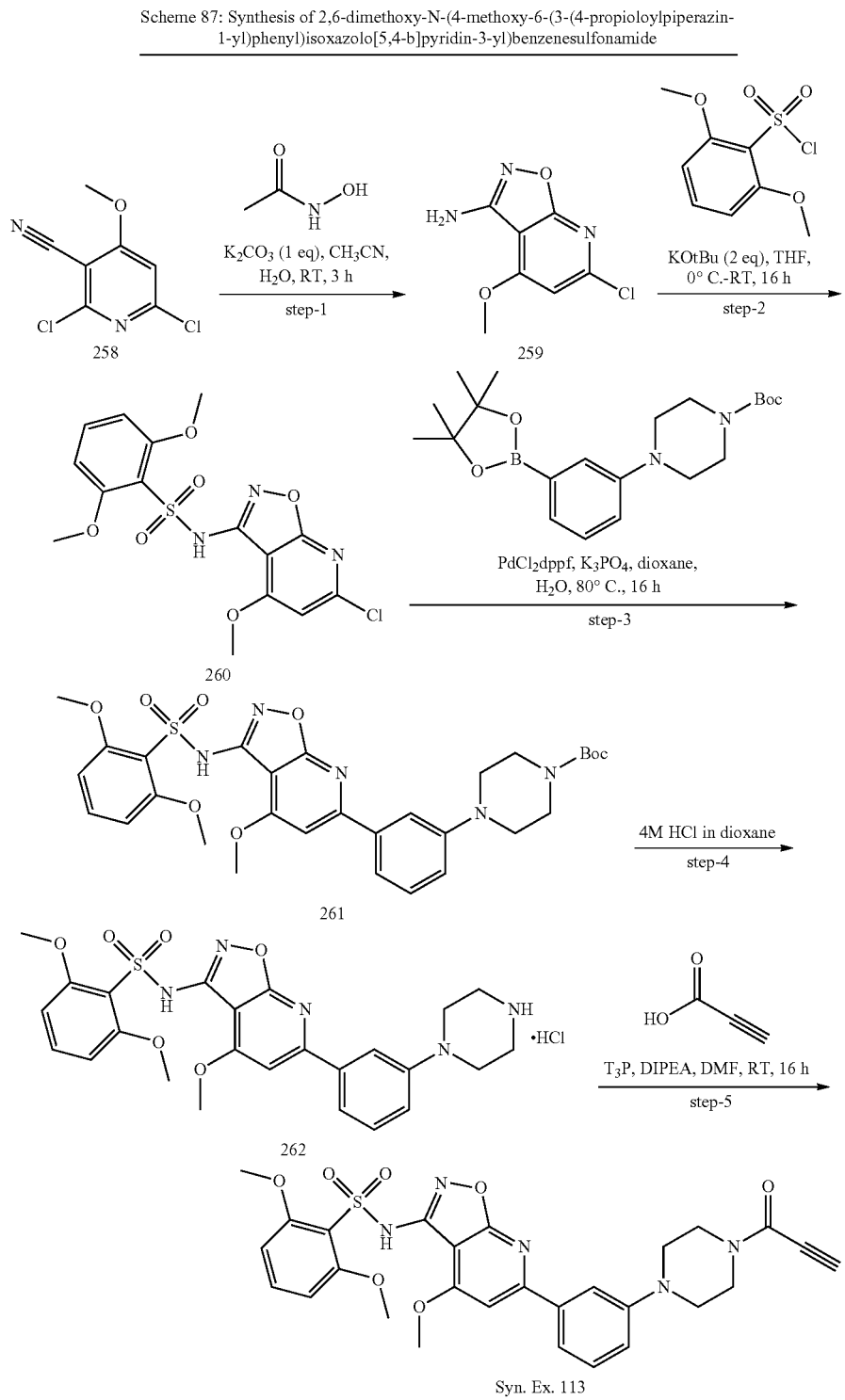

Synthesis of 6-chloro-4-methoxyisoxazolo[5,4-b]pyridin-3-amine (259)

To a stirred solution of compound 258 (8 g, 39.41 mmol; synthesized as reported in WO 2018/106459 A1) in a 7:1 mixture of $CH_3CN$ (100 mL) at room temperature was added N-hydroxyacetamide (2.96 g, 39.41 mmol) followed by $K_2CO_3$ (5.44 g, 39.41 mmol). The reaction mixture was allowed to stir at RT for 3 h. After completion (monitored by TLC), the mixture was quenched with ice water and extracted with ethyl acetate. The organic layer was washed with brine, dried over anhydrous Na$_2$SO$_4$, concentrated and purified by combi flash chromatography using gradient 20-60% EA/Heptane to afford the title compound 259 (1.4 g, 17.80%) as an off-white solid. TLC: 70% EtOAc/Heptane (Rf: 0.40). LCMS Calculated for C7H6ClN3O2: 199.01; Found: 200.10 (M+1).

Synthesis of N-(6-chloro-4-methoxyisoxazolo[5,4-b]pyridin-3-yl)-2,6-dimethoxybenzenesulfonamide (260)

To a stirred solution of compound 259 (1.4 g, 7.01 mmol) in THF (30 mL) was added KO$^t$Bu 1M solution in THF (14 mL, 14.02 mmol) followed by 2,6-dimethoxybenzenesulfonyl chloride (2.98 g, 12.62 mmol). The reaction mixture was allowed to stir at the room temperature for 5 h. After completion (monitored by TLC), the mixture was quenched with ice water and extracted with ethyl acetate. The organic layer was dried over anhydrous Na$_2$SO$_4$ and concentrated under reduced pressure. The crude compound was purified by combi flash chromatography (neutral alumina) to afford the title compound 260 (600 mg, 20.76%) as a pale-yellow solid. TLC: 50 EtOAc (R$_f$, 0.5). LCMS Calculated for C15H14ClN3O6S: 399.03; Found: 399.80 (M+1).

Synthesis of tert-butyl 4-(3-(3-((2,6-dimethoxyphenyl)sulfonamido)-4-methoxyisoxazolo[5,4-b]pyridin-6-yl)phenyl)piperazine-1-carboxylate (261)

To a stirred solution tert-butyl 4-(3-(4,4,5,5-tetramethyl-1,3,2-dioxaborolan-2-yl)phenyl)piperazine-1-carboxylate (350 mg, 0.90 mmol) in dry 1,4-Dioxane (10 mL) was added compound 260 (300 mg, 0.75 mmol) and K$_2$CO$_3$ (311 mg, 2.25 mmol). The reaction was purged with argon gas for 5 min followed by addition of Pd(dppf)Cl$_2$ (54.9 mg, 0.075 mmol). The reaction mixture was stirred at 80° C. for 2 h. After completion (monitored by TLC), the reaction mixture was filtered through a pad of celite, the filtrate was concentrated to get crude. The crude product was used as such in the next reaction without purification.

Synthesis of 2,6-dimethoxy-N-(4-methoxy-6-(3-(piperazin-1-yl)phenyl)isoxazolo[5,4-b]pyridin-3-yl)benzenesulfonamide hydrochloride (262)

To a stirred solution of compound 261 (500 mg, 0.80 mmol) in DCM (4 mL) at 0° C. was added 4M HCl in dioxane (0.8 mL, 3.20 mmol). The reaction was allowed to stir at the room temperature for 2 h. After completion (monitored by TLC), the reaction mixture quenched with ice cold water and extracted with ethyl acetate. The organic layer was dried over Na$_2$SO$_4$, concentrated triturated with Et$_2$O to afford the title compound 262 (200 mg, HCl salt) as a light brown solid. TLC: 5% MeOH/DCM (R$_f$, 0.2). LCMS Calculated for C25H27N5O6S: 525.17; Found: 526.10.

Synthesis of 2,6-dimethoxy-N-(4-methoxy-6-(3-(4-propioloylpiperazin-1-yl)phenyl)isoxazolo[5,4-b]pyridin-3-yl)benzenesulfonamide To a stirred solution of compound 262 (200 mg, 0.35 mmol) in DMF (3 mL) at 0° C. was added DIPEA (0.25 mL, 1.42 mmol), Propiolic acid (30 mg, 0.43 mmol) followed by T$_3$P as a 50% solution in EtOAc (0.453 mL, 0.71 mmol). The reaction mixture was allowed to stir at room temperature for 1 h. After completion (monitored by TLC), the reaction mixture was concentrated under reduced pressure and the crude was purified by using prep HPLC to afford the title compound (9.0 mg, 5.00%) as a light brown solid. TLC: 5% MeOH/DCM (R$_f$, 0.5). (See Table 1 for analytical data).

Synthetic Example 114

Scheme 88: Synthesis of 25-ethyl-2-methoxy-N-(4-methoxy-6-(3-(4-propioloylpiperazin-1-yl)phenyl)isoxazolo[5,4-b]pyridin-3-yl)benzenesulfonamide

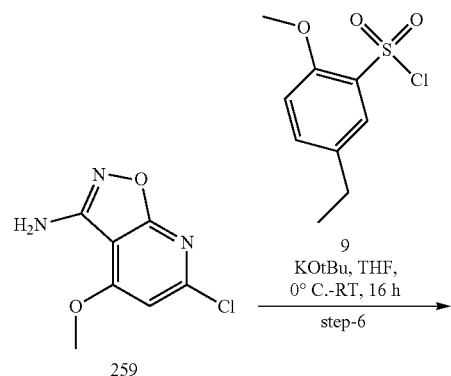

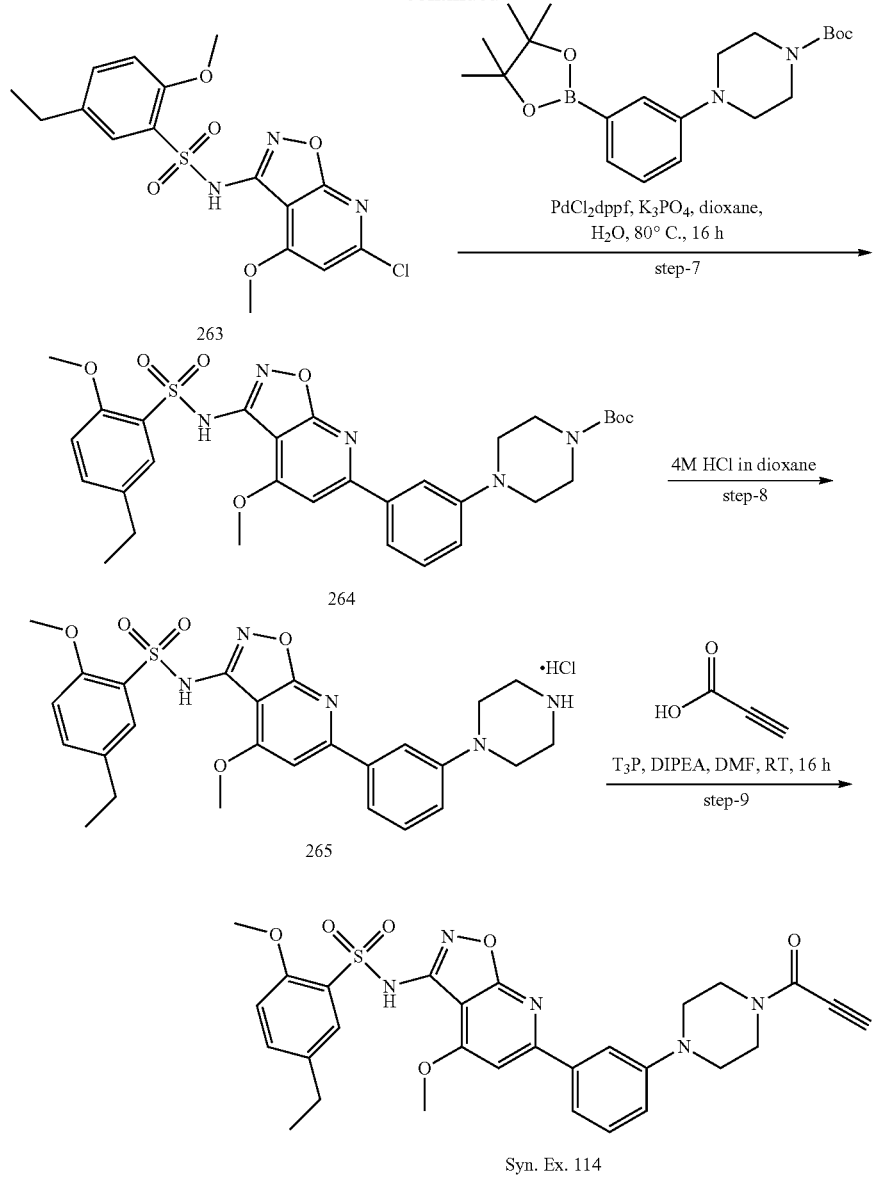

Syn. Ex. 114

Synthesis of N-(6-chloro-4-methoxyisoxazolo[5,4-b]pyridin-3-yl)-5-ethyl-2-methoxybenzenesulfonamide (263)

To a stirred solution of compound 259 (300 mg, 7.01 mmol) in THF (30 mL) was added NaH as a 60% dispersion in oil (14 mL, 14.02 mmol) followed by 5-ethyl-2-methoxybenzenesulfonyl chloride (2.98 g, 12.62 mmol). The reaction mixture was allowed to stir at the room temperature for 5 h. After completion (monitored by TLC), the reaction mixture was quenched with ice cold water and extracted with ethyl acetate. The organic layer was dried over anhydrous $Na_2SO_4$ and concentrated under reduced pressure. The crude compound was purified by combi flash chromatography (neutral alumina) to afford the title compound 263 (350 mg, 20.76%) as a pale-yellow solid. TLC: 50 EtOAc ($R_f$ 0.5). LCMS Calculated for C16H16ClN3O5S: 397.05; Found: 398.10 (M+1).

Synthesis of tert-butyl 4-(3-(3-((5-ethyl-2-methoxyphenyl)sulfonamido)-4-methoxyisoxazolo[5,4-b]pyridin-6-yl)phenyl)piperazine-1-carboxylate (264)

To a stirred solution tert-butyl 4-(3-(4,4,5,5-tetramethyl-1,3,2-dioxaborolan-2-yl)phenyl)piperazine-1-carboxylate (350 mg, 0.90 mmol) in dry 1,4-Dioxane (10 mL) was added compound 263 (300 mg, 0.75 mmol) and $K_2CO_3$ (311 mg, 2.25 mmol). The mixture was purged with argon gas for 5 min followed by addition of Pd(dppf)$Cl_2$ (54.9 mg, 0.075 mmol). The reaction mixture was stirred at 80° C. for 2 h. After completion (monitored by TLC), the reaction mixture was filtered through a pad of celite, the filtrate was concentrated to get crude. The crude product was purified by combi flash using gradient 60% EA/Heptane to afford the title compound 264 (80 mg, 14.62%) as a light brown solid. LCMS Calculated for C30H35N5O8S: 623.24; Found: 624.28 (M+1).

401

Synthesis of 5-ethyl-2-methoxy-N-(4-methoxy-6-(3-(piperazin-1-yl)phenyl)isoxazolo[5,4-b]pyridin-3-yl)benzenesulfonamide hydrochloride (265)

To a stirred solution of compound 264 (80 mg, 0.14 mmol) in DCM (4 mL) at 0° C. was added 4M HCl in dioxane (0.15 mL, 0.57 mmol). The reaction was allowed to stir at the room temperature for 2 h. After completion (monitored by TLC), the reaction mixture quenched with ice cold water and extracted with ethyl acetate. The organic layer was dried over $Na_2SO_4$, concentrated triturated with $Et_2O$ to afford the title compound 265 (60 mg, HCl salt) as a light brown solid. TLC: 5% MeOH/DCM ($R_f$ 0.2). LCMS Calculated for C26H29N5O5S: 523.19; Found: 524.35.

Synthesis of 25-ethyl-2-methoxy-N-(4-methoxy-6-(3-(4-propioloylpiperazin-1-yl)phenyl)isoxazolo[5,4-b]pyridin-3-yl)benzenesulfonamide To a stirred solution of compound 265 (60 mg, 0.107 mmol) in DMF (3 mL) at 0° C. was added DIPEA (0.075 mL, 0.42 mmol), Propiolic acid (9.6 mg, 0.128 mmol) followed by $T_3P$ as a 50% solution in EtOAc (0.14 mL, 0.214 mmol). The reaction mixture was allowed to stir at room temperature for 1 h. After completion (monitored by TLC), the reaction mixture was concentrated under reduced pressure and the crude was purified by using prep HPLC to afford the title compound (6.0 mg, 10.3%) as a light brown solid. TLC: 5% MeOH/DCM ($R_f$ 0.5). (See Table 1 for analytical data).

Synthetic Example 115

Synthetic Scheme 89: Synthesis of N-(6-(3-hydroxy-5-(4-propioloylpiperazin-1-yl)phenyl)-4-methoxybenzo[d]isoxazol-3-yl)-2,6-dimethoxybenzenesulfonamide

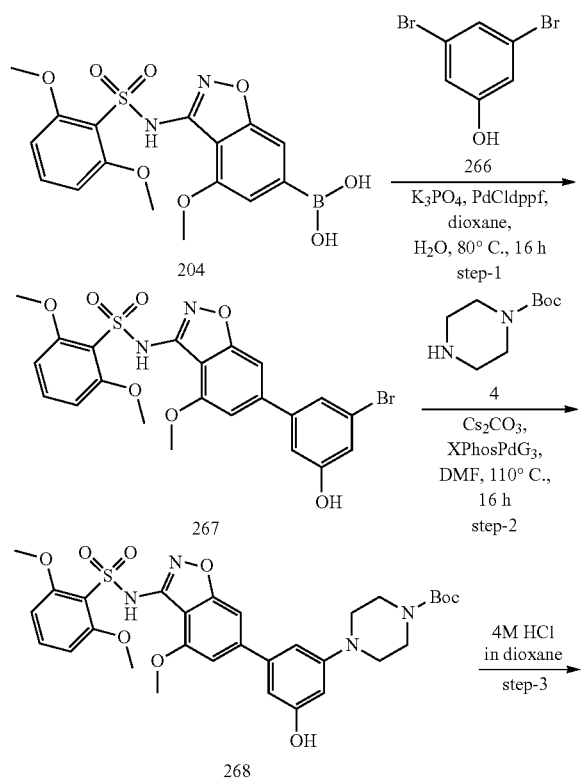

402

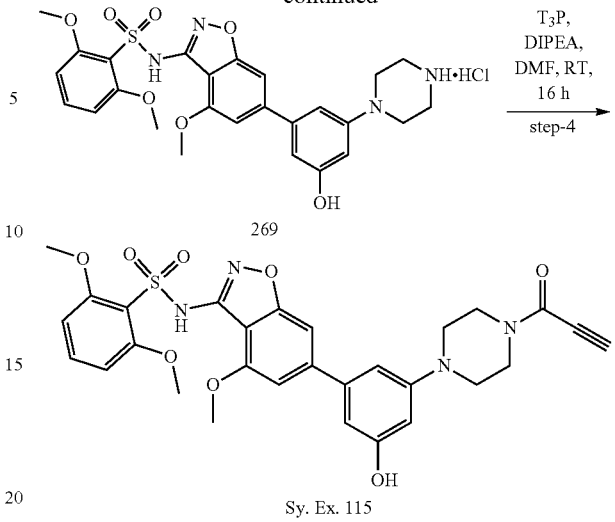

Synthesis of N-(6-(3-bromo-5-hydroxyphenyl)-4-methoxybenzo[d]isoxazol-3-yl)-2,6-dimethoxybenzenesulfonamide (267)

To a stirred solution compound 204 (600 mg, 1.47 mmol) in 3:1 mixture of 1,4-Dioxane:$H_2O$ (10 mL) was added compound 266 (667 mg, 2.64 mmol) and $K_2CO_3$ (610 mg, 4.41 mmol). The reaction was purged with argon gas for 5 min followed by addition of Pd(dppf)$Cl_2$ (81 mg, 0.110 mmol). The reaction mixture was stirred at 80° C. for 2 h. After completion (monitored by TLC), the reaction mixture was filtered through a pad of celite, the filtrate was concentrated to get crude. The crude product was purified by combi flash using gradient 60% EA/Heptane to afford the title compound 267 (200 mg, 14.62%) as a light brown solid. LCMS Calculated for C22H19BrN2O7S: 534.01; Found: 535.20 (M+1).

Synthesis of tert-butyl 4-(3-(3-((2,6-dimethoxyphenyl)sulfonamido)-4-methoxybenzo[d]isoxazol-6-yl)-5-hydroxyphenyl)piperazine-1-carboxylate (268)

To a stirred solution compound 267 (200 mg, 0.37 mmol) in dry DMF (3 mL) was added tert-butyl piperazine-1-carboxylate (83 mg, 0.44 mmol) and $Cs_2CO_3$ (365 mg, 1.12 mmol). The reaction was purged with argon gas for 5 min followed by addition of XPhosPdG3 (32 mg, 0.037 mmol). The reaction mixture was stirred at 80° C. for 16 h. After completion (monitored by TLC), the reaction mixture was filtered through a pad of celite, the filtrate was concentrated to get crude. The crude product was purified by combi flash using gradient 60% EA/Heptane to afford the title compound 268 (150 mg, 62.76%) as a light brown solid. LCMS Calculated for C31H36N4O9S: 640.22; Found: 641.20 (M+1).

N-(6-(3-hydroxy-5-(piperazin-1-yl)phenyl)-4-methoxybenzo[d]isoxazol-3-yl)-2,6-dimethoxybenzenesulfonamide hydrochloride (269)

To a stirred solution of compound 268 (150 mg, 0.234 mmol) in DCM (4 mL) at 0° C. was added 4M HCl in dioxane (0.6 mL, 2.34 mmol). The reaction was allowed to stir at the room temperature for 2 h. After completion (monitored by TLC), the reaction mixture quenched with ice cold water and extracted with ethyl acetate. The organic layer was dried over $Na_2SO_4$, concentrated triturated with $Et_2O$ to afford the title compound 269 (90 mg, HCl salt) as a light brown solid. TLC: 5% MeOH/DCM ($R_f$, 0.2). LCMS Calculated for C26H28N4O7S: 540.17; Found: 541.30.

Synthesis of N-(6-(3-hydroxy-5-(4-propioloylpiper-azin-1-yl)phenyl)-4-methoxybenzo[d]isoxazol-3-yl)-2,6-dimethoxybenzenesulfonamide To a stirred solution of compound 269 (90 mg, 0.16 mmol) in DMF (2 mL) at 0° C. was added DIPEA (0.11 mL, 0.62 mmol), propiolic acid (14 mg, 0.198 mmol) followed by $T_3P$ as a 50% solution in EtOAc (0.198 mL, 0.312 mmol). The reaction mixture was allowed to stir at room temperature for 1 h. After completion (monitored by TLC), the reaction mixture was concentrated under reduced pressure and the crude was purified by using prep HPLC to afford the title compound (3.0 mg, 3.20%) as an off-white solid. TLC: 5% MeOH/DCM ($R_f$, 0.5). (See Table 1 for analytical data).

Synthetic Example 116

Scheme 90: Synthesis of 5-ethyl-2-methoxy-N-(4-methoxy-6-((4-(methylsulfonamidomethyl)-1H-pyrazol-1-yl)methyl)benzo[d]isoxazol-3-yl)benzenesulfonamide

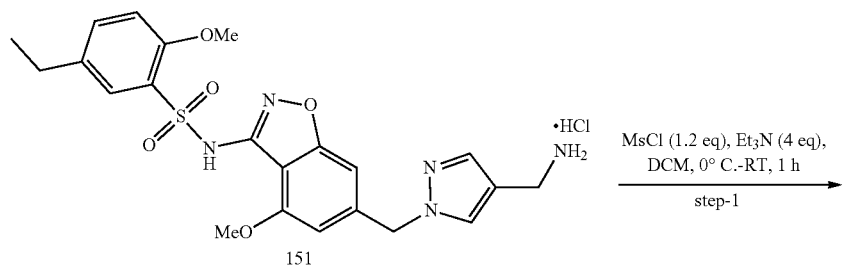

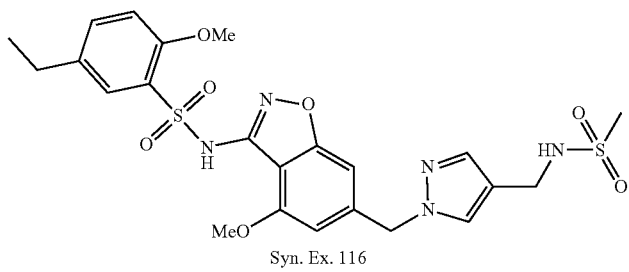

Syn. Ex. 116

To a stirred solution of compound 151 (0.15 g, 0.296 mmol) in DMF (2 mL) at 0° C. was added TEA (0.17 mL, 1.183 mmol) followed by methane sulfonyl chloride (45 mg, 0.355 mmol). The reaction was allowed to stir at room temperature for 2 h. After completion (monitored by TLC), the reaction mixture was concentrated under reduced pressure to get brown gummy crude. The crude was purified by combi-flash chromatography using gradient of 5%-10% MeOH in DCM to get the desired compound which was further purified by prep HPLC to afford the title compound (23 mg, 14.19%) as an off-white solid. TLC: 10% MeOH/DCM (Rf: 0.40). (See Table 1 for analytical data).

Synthetic Example 117

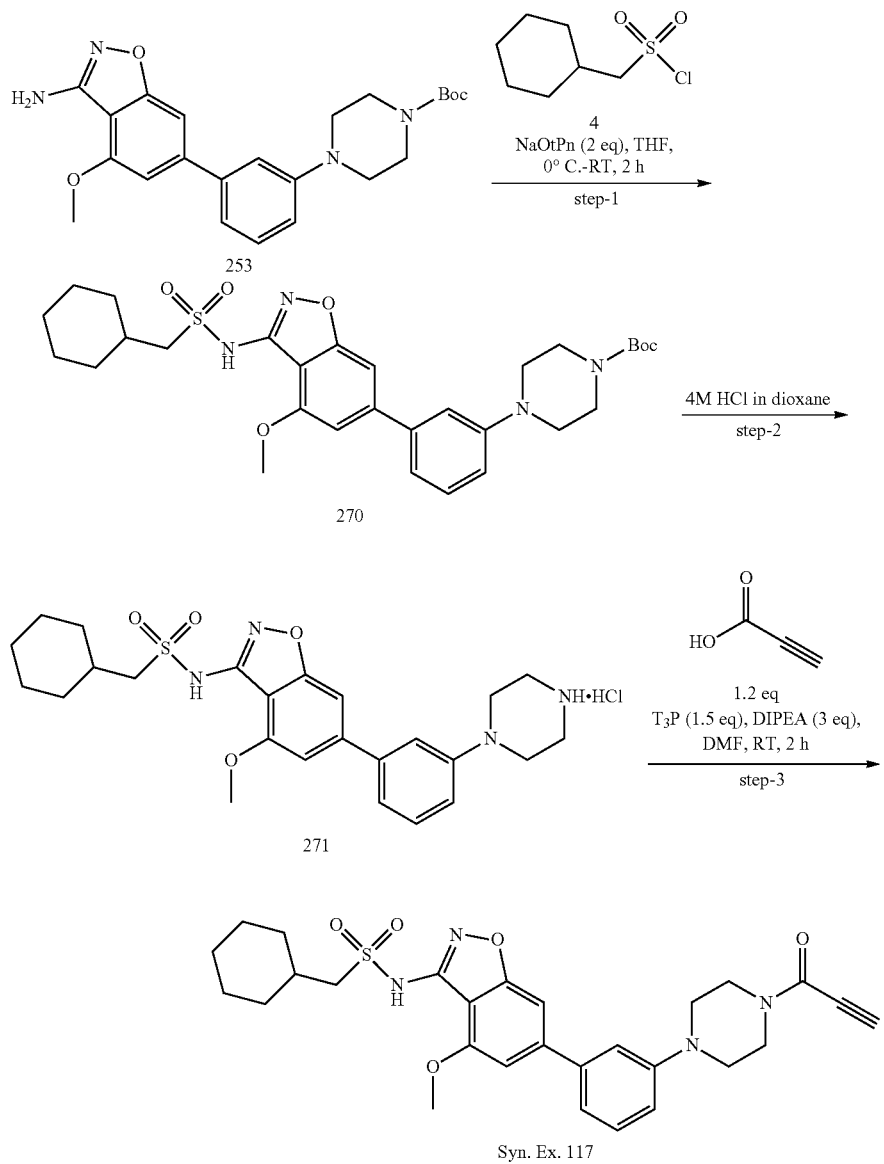

Scheme 91: Synthesis of 1-cyclohexyl-N-(4-methoxy-6-(3-(4-propioloylpiperazin-1-yl) phenyl) benzo[d]isoxazol-3-yl) methanesulfonamide To a stirred solution of compound 253 (200 mg, 0.471 mmol) in THF (10 mL) was added NaO$^t$Pn (0.103 g, 0.942 mmol) followed by cyclohexylmethanesulfonyl chloride (0.138 g, 0.706 mmol). The reaction mixture was allowed to stir at the room temperature for 2 h. After completion (monitored by TLC), the reaction mixture was quenched with ice cold water and extracted with ethyl acetate. The organic layer was dried over anhydrous Na$_2$SO$_4$ and concentrated under reduced pressure. The crude compound was purified by combi flash chromatography (neutral alumina) to afford the title compound 270 (60 mg, 21.810%) as a pale-yellow solid. TLC: 50 EtOAc (R$_f$, 0.5). LCMS Calculated for C30H40N4O6S: 584.27; Found: 585.5 (M+1).

Synthesis of 1-cyclohexyl-N-(4-methoxy-6-(3-(piperazin-1-yl)phenyl)benzo[d]isoxazol-3-yl)methanesulfonamide hydrochloride (271)

To a stirred solution of compound 270 (60 mg, 0.102 mmol) in DCM (2 mL) at 0° C. was added 4M HCl in 1,4 Dioxane (0.25 mL, 1.026 mmol). The reaction was allowed to stir at the room temperature for 2 h. After completion (monitored by TLC), the reaction mixture was concentrated under reduced pressure and triturated with Et$_2$O and dried in vacuo to afford title compound 271 (50 mg, HCl salt) as a colourless sticky solid. TLC: 5% MeOH/DCM (R$_f$, 0.3). LCMS calculated for C25H32N4O4S: 484.21: Found: 485.30.

407

Synthesis of 1-cyclohexyl-N-(4-methoxy-6-(3-(4-propioloylpiperazin-1-yl) phenyl) benzo[d]isoxazol-3-yl) methanesulfonamide To a stirred solution of compound 271 (50 mg, 0.095 mmol) in DMF (2 mL) at 0° C. was added DIPEA (0.05 mL, 0.287 mmol), propiolic acid (8 mg, 0.114 mmol) followed by T$_3$P as a 50% solution in EtOAc (0.45 mg, 0.1425 mmol). The reaction mixture was allowed to stir at room temperature for 2 h. After completion (monitored by TLC), the reaction mixture was concentrated under reduced pressure and crude was purified by using prep HPLC to afford the title compound (4.5 mg, 8.33%) as an off-white solid. TLC: 5% MeOH/DCM (R$_f$ 0.5). (See Table 1 for analytical data)

Synthetic Example 118

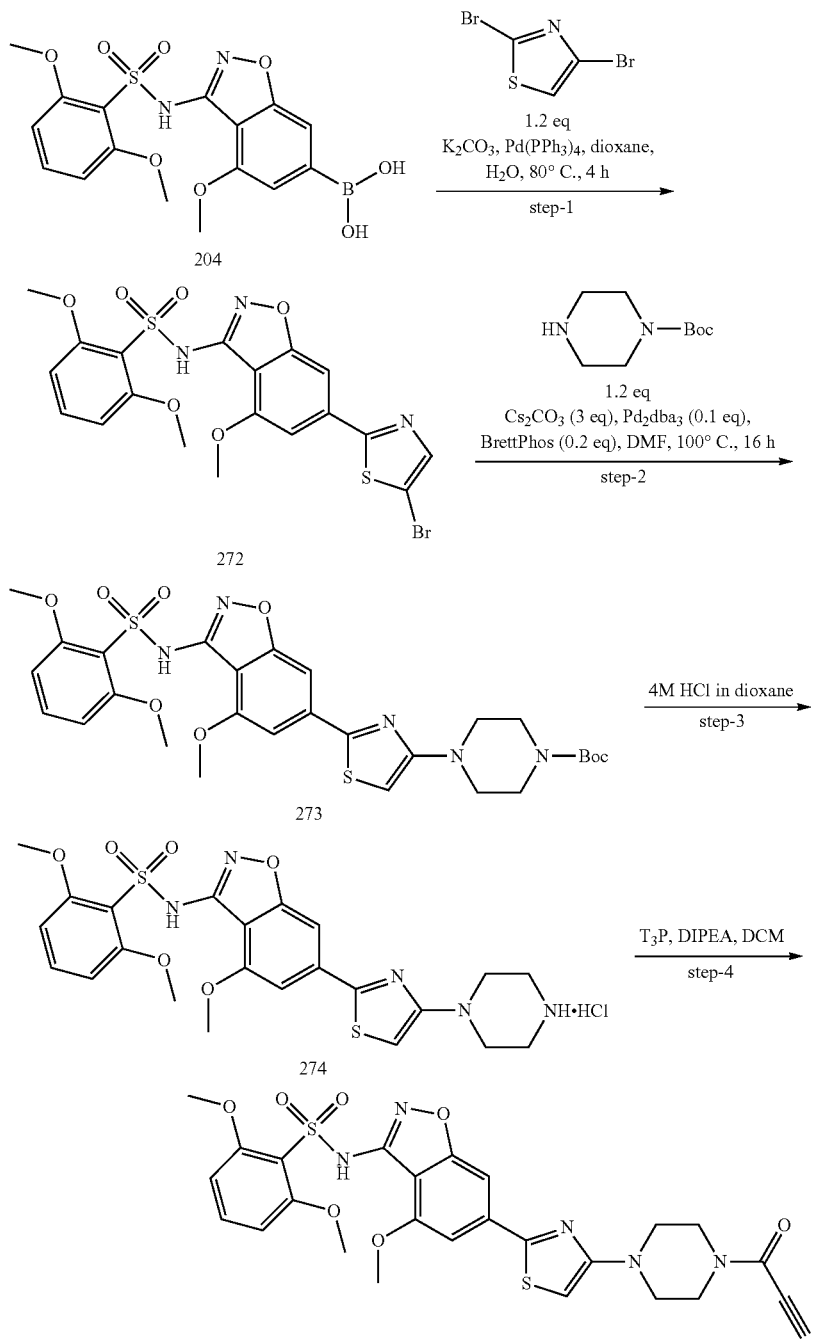

Scheme 92: Synthesis of 2,6-dimethoxy-N-(4-methoxy-6-(4-(4-propiololpiperazin-1-yl)thiazol-2-yl)benzo[d]isoxazol-3-yl)benzenesulfonamide Syn. Ex. 118

Synthesis of N-(6-(4-bromothiazol-2-yl)-4-methoxy-benzo[d]isoxazol-3-yl)-2,6-dimethoxybenzenesulfonamide (272)

To a stirred solution of compound 204 (1 g, 2.449 mmol) in 3:1 mixture of 1,4 Dioxane:water (10 mL) was added $K_2CO_3$ (1.01 g, 7.349 mmol) followed by 2,4-dibromothiazole (713 mg, 2.938 mmol). The reaction mixture was purged with argon gas for 10 min followed by addition of $Pd(PPh_3)_4$ (0.282 g, 0.2449 mmol). The reaction mixture was stirred at 80° C. for 4 h. After completion (monitored by TLC), the reaction mixture was quenched with ice cold water and extracted with ethyl acetate. The organic layer was washed with brine, dried over anhydrous $Na_2SO_4$ and concentrated under reduced pressure. The crude compound was purified by combi flash chromatography (using a gradient method of 5-20% EtOAc/Heptane) to afford the title compound 272 (600 mg, 46.87%) as pale brown solid. TLC: 50% EtOAc/Heptane ($R_f$ 0.6). LCMS Calculated for C19H16BrN3O6S2: 524.97; Found: 525.5 (M+H).

Synthesis of tert-butyl 4-(2-(3-((2,6-dimethoxyphenyl)sulfonamido)-4-methoxybenzo[d]isoxazol-6-yl)thiazol-4-yl)piperazine-1-carboxylate (273)

To a stirred solution of compound 272 (300 mg, 0.569 mmol) in DMF (4 mL) was added $Cs_2CO_3$ (555 mg, 1.709 mmol) followed by tert-butyl piperazine-1-carboxylate (127 mg, 0.682 mmol). The reaction mixture was purged with argon gas for 10 min followed by addition of $Pd_2dba_3$ (52 mg, 0.0569 mmol) and BrettPhos (61 mg, 0.113). The reaction mixture was stirred at 100° C. for 16 h. After completion (monitored by TLC), the reaction mixture was quenched with ice cold water and extracted with ethyl acetate. The organic layer was washed with brine, dried over anhydrous $Na_2SO_4$ and concentrated under reduced pressure. The crude compound was purified by combi flash chromatography (using a gradient method of 0-30% EtOAc/Heptane) to afford the title compound 273 (130 mg, 36.11%) as an off white solid. TLC: 70% EtOAc/Heptane ($R_f$ 0.5). LCMS Calculated for C28H33N5O8S2: 631.18; Found: 632.5 (M+H).

Synthesis of 2,6-dimethoxy-N-(4-methoxy-6-(4-(piperazin-1-yl)thiazol-2-yl)benzo[d]isoxazol-3-yl)benzenesulfonamide hydrochloride (274)

To a stirred solution of compound 273 (130 mg, 0.2057 mmol) in DCM (2 mL) at 0° C. was added 4M HCl in 1,4 Dioxane (0.5 mL, 2.057 mmol) The reaction was allowed to stir at the room temperature for 2 h. After completion (monitored by TLC), the reaction mixture was concentrated under reduced pressure and triturated with $Et_2O$ to afford title compound 274 (110 mg, HCl salt) as a yellow semi solid. TLC: 5% MeOH/DCM ($R_f$ 0.3). LCMS Calculated for $C_{23}H_{25}N_5O_6S_2$: 531.12: Found: 532.20.

Synthesis of 2,6-dimethoxy-N-(4-methoxy-6-(4-(4-propioloylpiperazin-1-yl)thiazol-2-yl)benzo[d]isoxazol-3-yl)benzenesulfonamide To a stirred solution of compound 274 (110 mg, 0.193 mmol) in DMF (2 mL) at 0° C. was added DIPEA (0.1 mL, 0.579 mmol), propiolic acid (16 mg, 0.2316 mmol) followed by $T_3P$ as a 50% solution in EtOAc (0.184 mL, 0.2895 mmol). The reaction mixture was allowed to stir at room temperature for 2 h. After completion (monitored by TLC), the reaction mixture was concentrated under reduced pressure and crude was purified by using prep HPLC to afford the title compound (20 mg, 17.69%) as an off-white solid. TLC: 5% MeOH/DCM ($R_f$ 0.5). (See Table 1 for analytical data).

Synthetic Example 119

Synthetic Scheme 93: Synthesis of 2,6-dimethoxy-N-(4-methoxy-6-(4-(4-propioloylpiperazin-1-yl)pyridin-2-yl)benzo[d]isoxazol-3-yl)benzenesulfonamide

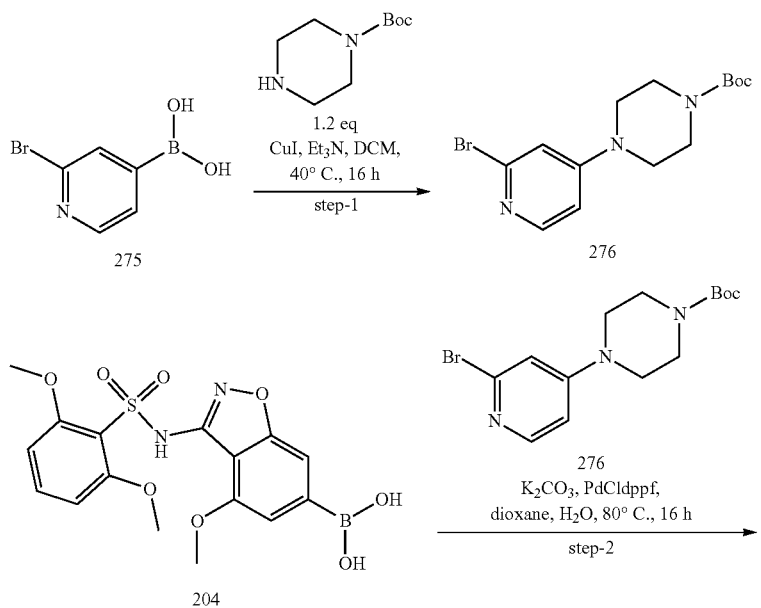

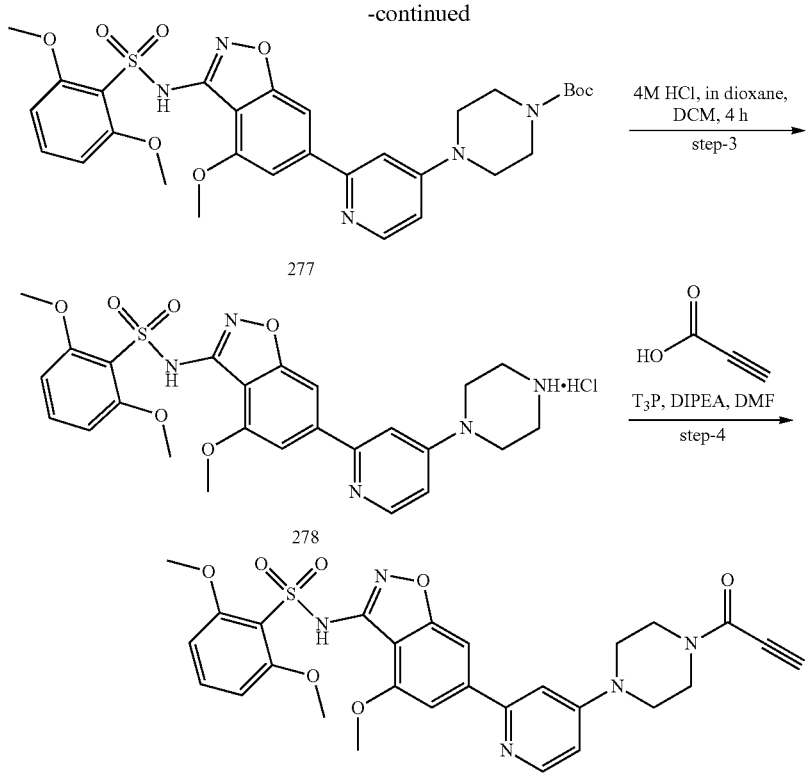

Syn. Ex. 119

Synthesis of tert-butyl 4-(2-bromopyridin-4-yl)piperazine-1-carboxylate (276)

To a stirred solution of compound 275 (1 g, 4.96 mmol) in ACN (5 mL) was added TEA (2 mL, 14.87 mmol) followed by tert-butyl piperazine-1-carboxylate (738 mg, 3.96 mmol) and CuI (94 mg, 0.495 mmol). The resulting reaction mixture was stirred at 80° C. for 16 h. After completion (monitored by TLC), the reaction mixture was quenched with ice cold water and extracted with ethyl acetate. The organic layer was washed with brine, dried over anhydrous $Na_2SO_4$ and concentrated under reduced pressure. The crude compound was purified by combi flash chromatography (using a gradient method 0-30% EtOAc/Heptane) to afford the title compound 276 (250 mg, 14.79%) as an off-white solid. TLC: 50% EtOAc/Heptane ($R_f$ 0.5). LCMS Calculated for C14H20BrN3O2: 341.07; Found: 342.5 (M+H).

Synthesis of tert-butyl 4-(2-(3-((2,6-dimethoxyphenyl)sulfonamido)-4-methoxybenzo[d]isoxazol-6-yl)pyridin-4-yl)piperazine-1-carboxylate (277)

To a stirred solution of compound 204 (300 mg, 0.734 mmol) in 3:1 mixture of 1,4 Dioxane:water (10 mL) was added $K_2CO_3$ (304 mg, 2.204 mmol) followed by compound 276 (301 mg, 0.880 mmol). The reaction mixture was purged with argon gas for 10 min followed by addition of $PdCl_2dppf$ (53 mg, 0.0734 mmol). The reaction mixture was stirred at 80° C. for 16 h. After completion (monitored by TLC), the reaction mixture was quenched with ice cold water and extracted with ethyl acetate. The organic layer was washed with brine, dried over anhydrous $Na_2SO_4$ and concentrated under reduced pressure. The crude compound was purified by combi flash chromatography (using a gradient method 0-20% EtOAc/Heptane) to afford the title compound 277 (100 mg, 21.78%) as an off-white solid. TLC: 50% EtOAc/Heptane ($R_f$ 0.4). LCMS Calculated for C30H35N5O8S: 625.22; Found: 626.2 (M+H).

Synthesis of 2,6-dimethoxy-N-(4-methoxy-6-(4-(piperazin-1-yl)pyridin-2-yl)benzo[d]isoxazol-3-yl)benzenesulfonamide hydrochloride (278)

To a stirred solution compound 277 (100 mg, 0.1598 mmol) in DCM (2 mL) at 0° C. was added 4M HCl in 1,4 Dioxane (0.40 mL, 1.598 mmol). The reaction was allowed to stir at the room temperature for 4 h. After completion (monitored by TLC), the reaction mixture was concentrated under reduced pressure and triturated with $Et_2O$ to afford title compound 278 (85 mg, HCl salt) as an off-white semisolid. TLC: 5% MeOH/DCM ($R_f$ 0.2). LCMS Calculated for C25H27N5O6S: 525.17: Found: 526.30.

Synthesis of 2,6-dimethoxy-N-(4-methoxy-6-(4-(4-propioloylpiperazin-1-yl)pyridin-2-yl)benzo[d]isoxazol-3-yl)benzenesulfonamide To a stirred solution of compound 278 (85 mg, 0.151 mmol) in DMF (2 mL) at 0° C. was added DIPEA (0.08 mL, 0.453 mmol), propiolic acid (12 mg, 0.1812 mmol) followed by $T_3P$ as a 50% solution in EtOAc (0.144 mL, 0.2265 mmol). The reaction mixture was allowed to stir at room temperature for 2 h. After completion (monitored by TLC), the reaction mixture was concentrated under reduced pressure and crude was purified by using prep HPLC to afford the title compound (22 mg, 25.28%) as an off-white solid. TLC: 5% MeOH/DCM ($R_f$ 0.5). (See Table 1 for analytical data).

Synthetic Example 120
Scheme 94: Synthesis of 2,6-dimethoxy-N-(5-methyl-6-(3-(4-propioloylpiperazin-1-yl) phenyl) benzo[d]isoxazol-3-yl) benzenesulfonamide
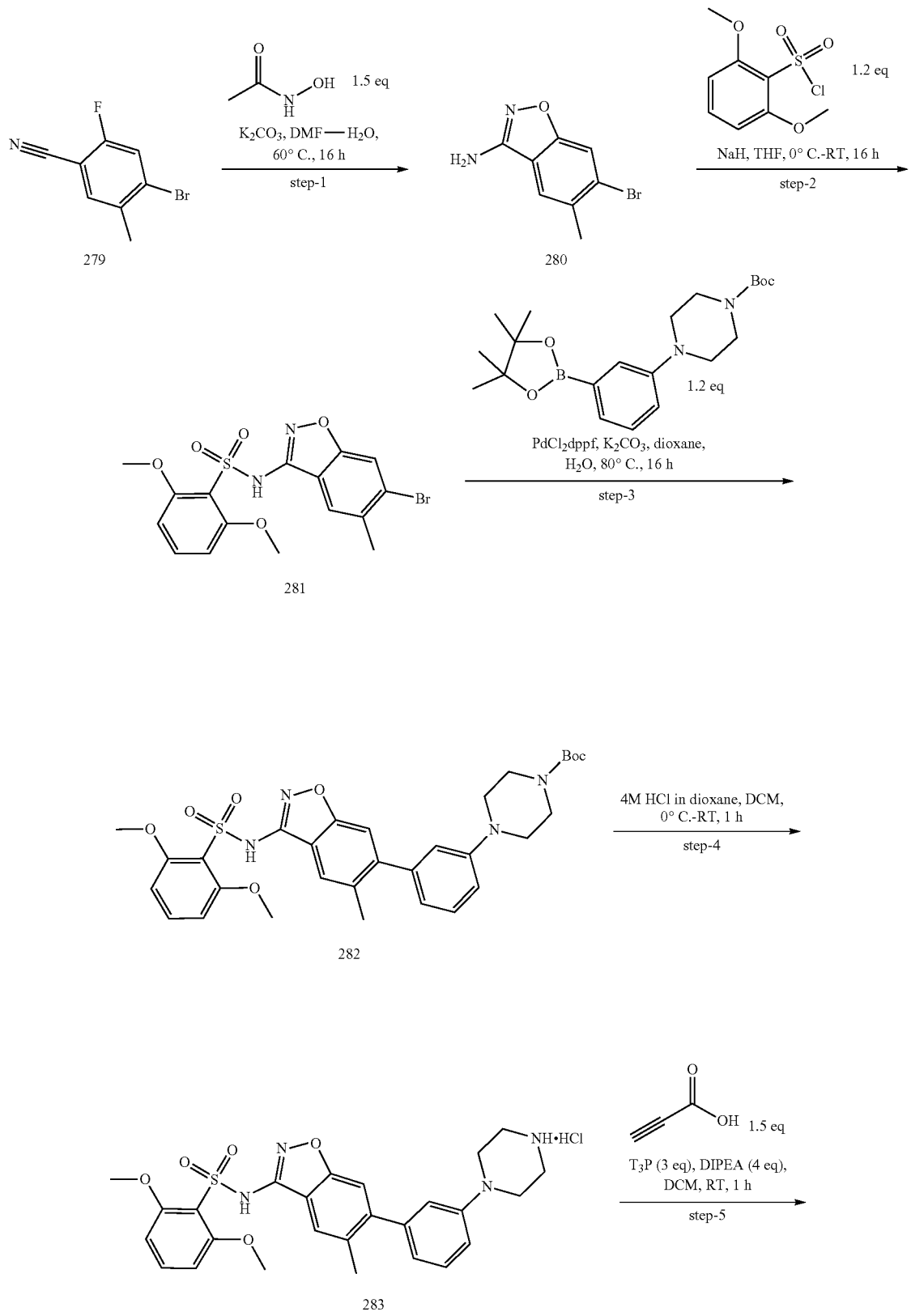

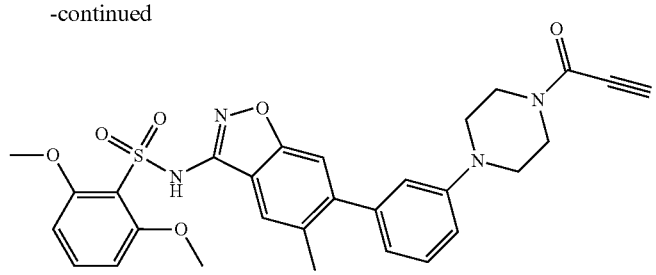

Syn. Ex. 120

Synthesis of 6-bromo-5-methylbenzo[d]isoxazol-3-amine (280)

To a stirred solution of compound 279 (2 g, 9.344 mmol) in a 7:1 mixture of DMF:H$_2$O (8 mL) was added N-hydroxyacetamide (1.05 g, 14.016 mmol) followed by K$_2$CO$_3$ (3.87 g, 28.032 mmol). The reaction mixture was allowed to stir at 60° C. for 16 h. After completion (monitored by TLC), the reaction mixture was quenched with ice cold water and extracted with ethyl acetate. The organic layer was washed with brine, dried over anhydrous Na$_2$SO$_4$ and concentrated under reduced pressure. The crude was purified by using combi flash chromatography using gradient 40-80% EA/Heptane to afford the title compound 280 (2 g, 94.33%) as a brown solid. TLC: 50% EtOAc/Heptane (R$_f$ 0.50). LCMS Calculated for C8H7BrN2O: 225.97; Found: 226.02 (M+1).

Synthesis of N-(6-bromo-5-methylbenzo[d]isoxazol-3-yl)-2,6-dimethoxybenzenesulfonamide (281)

To a stirred solution of compound 280 (1 g, 4.404 mmol) in THF (10 mL) was added 60% NaH (325 mg, 8.808 mmol) followed by 2,6-dimethoxybenzenesulfonyl chloride (1.25 g, 5.284 mmol) at 0° C. The reaction mixture was allowed to stir at the room temperature for 16 h. After completion (monitored by TLC), the reaction mixture was quenched with ice water and extracted with ethyl acetate. The organic layer was dried over anhydrous Na$_2$SO$_4$ and concentrated under reduced pressure. The crude compound was purified by combi flash chromatography (neutral alumina) to afford the title compound 281 (400 mg, 21.27%) as a pale-yellow solid. TLC: 50 EtOAc (R$_f$ 0.5). LCMS Calculated for C16H15BrN2O5S: 425.99; Found: 426.5 (M+1).

Synthesis of tert-butyl 4-(3-(3-((2,6-dimethoxyphenyl) sulfonamido)-5-methylbenzo[d]isoxazol-6-yl) phenyl)piperazine-1-carboxylate (282)

To a stirred solution of compound 281 (400 mg, 0.936 mmol) in 3:1 mixture of 1,4 Dioxane:H$_2$O (10 mL) was added K$_2$CO$_3$ (388 mg, 2.808 mmol) and tert-butyl 4-(3-(4,4,5,5-tetramethyl-1,3,2-dioxaborolan-2-yl)phenyl)piperazine-1-carboxylate (436 mg, 1.123 mmol). The reaction mixture was purged with argon gas for 10 min followed by addition of PdCl$_2$dppf (68 mg, 0.0936 mmol). The resulting reaction mixture was stirred at 80° C. for 16 h. After completion (monitored by TLC), the reaction mixture was quenched with ice cold water and extracted with ethyl acetate. The organic layer was washed with brine, dried over anhydrous Na$_2$SO$_4$ and concentrated under reduced pressure. The crude compound was purified by combi flash chromatography (using a gradient 0-20% EtOAc/Heptane) to afford the title compound 282 (200 mg, 35.14%) as an off-white solid. TLC: 50% EtOAc/Heptane (R$_f$ 0.4). LCMS Calculated for C31H36N4O7S: 608.23; Found: 609.2 (M+H).

Synthesis of 2,6-dimethoxy-N-(5-methyl-6-(3-(piperazin-1-yl) phenyl) benzo[d]isoxazol-3-yl) benzenesulfonamide hydrochloride (283)

To a stirred solution compound 282 (200 mg, 0.328 mmol) in DCM (2 mL) at 0° C. was added 4M HCl in 1,4 Dioxane (0.8 mL, 3.328 mmol). The reaction was allowed to stir at the room temperature for 4 h. After completion (monitored by TLC), the reaction mixture was concentrated under reduced pressure and triturated with Et$_2$O to afford title compound 283 (150 mg, HCl salt) as off-white semi solid. TLC: 5% MeOH/DCM (R$_f$ 0.2). LCMS Calculated for C26H28N4O5S: 508.18: Found: 509.30.

Synthesis of 2,6-dimethoxy-N-(5-methyl-6-(3-(4-propioloylpiperazin-1-yl) phenyl) benzo[d]isoxazol-3-yl) benzenesulfonamide To a stirred solution of compound 283 (150 mg, 0.275 mmol) in DMF (2 mL) at 0° C. was added DIPEA (0.20 mL, 1.109 mmol), propiolic acid (25 mg, 0.330 mmol) followed by T$_3$P as a 50% solution in EtOAc (0.35 mL, 0.550 mmol). The reaction mixture was allowed to stir at room temperature for 2 h. After completion (monitored by TLC), the reaction mixture was concentrated under reduced pressure and crude was purified by using prep HPLC to afford the title compound (27 mg, 17.53%) as an off-white solid. TLC: 5% MeOH/DCM (R$_f$ 0.5). See Table 1 for analytical data.

Synthetic Examples 121, 122, 123, 124 and 125

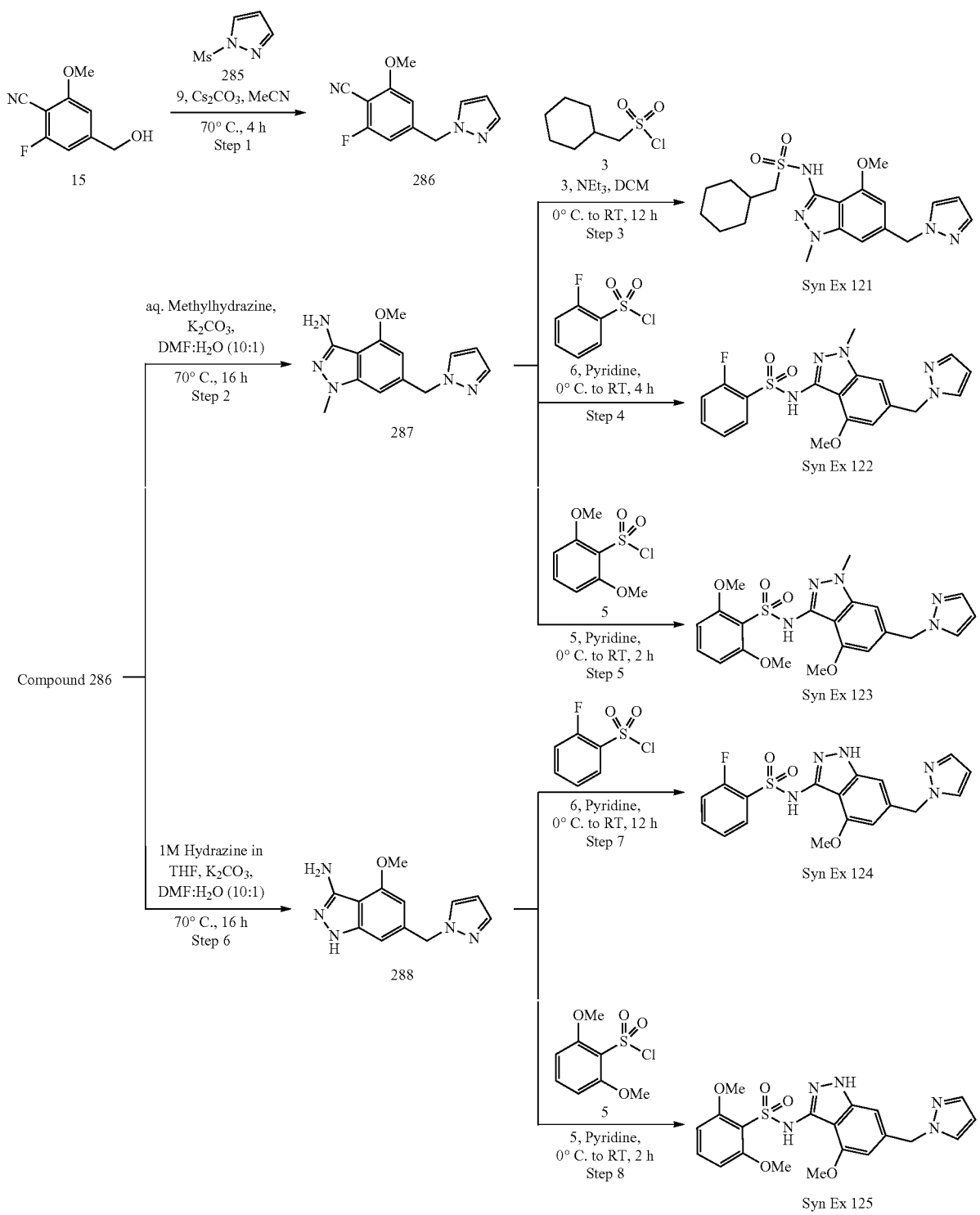

Scheme 95: Synthesis of indazole sulfonamide compounds

Synthesis of 1-(methylsulfonyl)-1H-pyrazole (285)

To a stirred solution of pyrazole (2.0 g, 29.40 mmol) in DCM (20 mL) was added Et₃N (8.2 mL, 58.80 mmol) followed by methane sulfonyl chloride (2.49 mL, 32.2 mmol) and the resulting reaction mixture stirred at 0° C. for 1 h. After completion of the reaction (monitored by TLC), reaction mixture was concentrated under reduced pressure, diluted with ethyl acetate and extracted. The organic layer was collected, washed with saturated NaHCO$_3$ solution, washed with brine, dried over anhydrous Na$_2$SO$_4$ and concentrated under reduced pressure to afford the title compound 285 (1.9 g, 44.25%) as a colorless liquid. TLC: 20% EtOAc/Heptane (R$_f$, 0.4). $^1$H NMR (400 MHz, CDCl$_3$): δ 8.01 (s, 1H), 7.78 (s, 1H), 6.41 (s, 1H), 3.35 (s, 3H).

N-(6-((1H-pyrazol-1-yl)methyl)-4-methoxy-1-methyl-1H-indazol-3-yl)-1-cyclohexylmethanesulfonamide

Step 1: Synthesis of 4-((1H-pyrazol-1-yl) methyl)-2-fluoro-6-methoxybenzonitrile (286)

To a stirred solution of compound 15 (1.5 g, 8.20 mmol) in acetonitrile (50 mL) at room temperature was added Cs$_2$CO$_3$ (4.7 g, 14.70 mmol), followed by compound 285 (1.56 g, 10.70 mmol) and the resulting reaction mixture was heated at 70° C. for 4 h. After completion of the reaction (monitored by TLC), the reaction mixture was cooled to room temperature, diluted with water and extracted with ethyl acetate. The organic layer was collected, washed with brine, dried over anhydrous Na$_2$SO$_4$ and concentrated under reduced pressure. The crude compound was purified by silica gel (100-200 mesh) column chromatography using a gradient method of 0-35% EtOAc/Heptane to afford the title compound 286 (1.7 g, 89%) as a yellow solid. TLC: 60% EtOAc/Heptane (R$_f$, 0.4). $^1$H NMR (400 MHz, DMSO-d$_6$): δ 7.89 (d, J=1.6 Hz, 1H), 7.53 (s, 1H), 6.99 (s, 1H), 6.69 (t, J=9.6 Hz, 1H), 6.33 (s, 1H), 5.43 (s, 2H), 3.90 (s, 3H). LCMS Calculated for C$_{12}$H$_{10}$FN$_3$O: 231.23; Found: 231.85 (M+).

Step 2: Synthesis of 6-((1H-pyrazol-1-yl)methyl)-4-methoxy-1-methyl-1H-indazol-3-amine (287)

To a stirred solution of compound 286 (0.4 g, 1.70 mmol) in DMF:H$_2$O (11 mL) was added K$_2$CO$_3$ (1.4 g, 10.20 mmol) followed by methyl hydrazine (aqueous solution) (0.3 mL, 5.17 mmol) and the resulting reaction mixture was heated at 70° C. for 16 h. After completion of the reaction (monitored by TLC), the reaction mixture was cooled to room temperature, diluted with water and extracted with ethyl acetate. The organic layer was collected, washed with brine, dried over anhydrous Na$_2$SO$_4$ and concentrated under reduced pressure. The crude compound was purified by silica gel (100-200 mesh) column chromatography using a gradient method of 0-50% EtOAc/Heptane to afford the title compound 286 (0.2 g, 44.94%) as an off-white solid. TLC: 80% EtOAc/Heptane (R$_f$, 0.25). $^1$H NMR (400 MHz, DMSO-d$_6$): δ 7.83 (d, J=2.0 Hz, 1H), 7.47 (d, J=0.8 Hz, 1H), 6.69 (s, 1H), 6.27 (d, J=1.6 Hz, 1H), 6.24 (s, 1H), 5.32 (s, 2H), 5.03 (s, 2H), 3.80 (s, 3H), 3.62 (s, 3H). LCMS Calculated for C$_{13}$H$_{15}$N$_5$O: 257.30; Found: 258.35 (M+1).

Step 3: Synthesis of N-(6-((1H-pyrazol-1-yl)methyl)-4-methoxy-1-methyl-1H-indazol-3-yl)-1-cyclohexylmethanesulfonamide (Synthetic Example 121)

To a stirred solution of compound 287 (130 mg, 0.50 mmol) in DCM (2 mL) at 0° C. was added Et$_3$N (0.43 mL, 0.30 mmol) followed by compound 3 (149 mg, 0.76 mmol). The reaction mixture was stirred at the room temperature for 12 h. After completion of the reaction (monitored by TLC), reaction mixture was concentrated under reduced pressure and diluted with water and extracted with ethyl acetate. The organic layer was collected, washed with brine, dried over anhydrous Na$_2$SO$_4$ and concentrated under reduced pressure. The crude compound was purified by using prep HPLC to afford the title compound (21 mg, 9.9%) as an off-white solid. TLC: 80% EtOAc/Heptane (R$_f$, 0.6). See Table 1 for analytical data.

Synthesis of N-(6-((1H-pyrazol-1-yl)methyl)-4-methoxy-1-methyl-1H-indazol-3-yl)-2-fluorobenzenesulfonamide (Synthetic Example 122)

Step 4

To a stirred solution of compound 287 (100 mg, 0.038 mmol) in Pyridine (3 mL) at 0° C. was added 2-fluorobenzenesulfonyl chloride (9 mg, 0.046 mmol) and allowed to stir at the room temperature for 4 h. The reaction mixture was concentrated under reduced pressure and diluted with water and extracted with ethyl acetate. The organic layer was collected, washed with brine, dried over anhydrous Na$_2$SO$_4$ and concentrated under reduced pressure. The crude compound was purified by using prep HPLC to afford the title compound (36 mg, 22.27%) as an off-white solid. TLC: 80% EtOAc/Heptane (R$_f$, 0.4). See Table 1 for analytical data.

Synthesis of N-(6-((1H-pyrazol-1-yl)methyl)-4-methoxy-1-methyl-1H-indazol-3-yl)-2,6-dimethoxybenzenesulfonamide Synthetic Example 123)

Step 5

To a stirred solution of compound 287 (160 mg, 0.62 mmol) in pyridine (5 mL) at 0° C. was added compound 5 (162 mg, 0.68 mmol) and the resulting reaction mixture was allowed to stir at the room temperature for 2 h. After completion (monitored by TLC), the reaction mixture was concentrated under vacuum, the residue was quenched with water and extracted with ethyl acetate. The organic layer was collected, washed with brine, dried over anhydrous Na$_2$SO$_4$ and concentrated under reduced pressure. The crude compound was purified by using prep HPLC to afford the title compound (60 mg, 21.1%) as an off-white solid. TLC: 80% EtOAc/Heptane (R$_f$, 0.3). See Table 1 for analytical data.

Synthesis of N-(6-((1H-pyrazol-1-yl)methyl)-4-methoxy-1H-indazol-3-yl)-2-fluorobenzenesulfonamide (Synthetic Example 124)

Step 6: Synthesis of 6-((1H-pyrazol-1-yl)methyl)-4-methoxy-1H-indazol-3-amine (288)

To a stirred solution of compound 286 (0.6 g, 2.59 mmol) in DMF:H$_2$O (11 mL) was added K$_2$CO$_3$ (2.14 g, 15.5 mmol) followed by hydrazine hydrate [1M in THF] (7.7 mL, 7.7 mmol) and the reaction mixture was heated at 70° C. for 16 h. After completion of the reaction (monitored by TLC), the reaction mixture was cooled to room temperature, diluted with water and extracted with ethyl acetate. The organic layer was collected, washed with brine, dried over anhydrous Na$_2$SO$_4$ and concentrated under reduced pressure. The crude compound was purified by silica gel (100-200 mesh) column chromatography using a gradient method of 0-60% EtOAc/Heptane to afford the title compound 288 (0.3 g, 47.5%) as a yellow solid. TLC: 80% EtOAc/Heptane (R$_f$, 0.25). $^1$H NMR (400 MHz, DMSO-d$_6$): δ 11.34 (s, 1H), 7.82 (s, 1H), 7.47 (s, 1H), 6.48 (s, 1H), 6.27 (t, J=1.6 Hz, 1H), 6.24 (s, 1H), 5.33 (s, 2H), 4.95 (s, 2H), 3.83 (s, 3H). LCMS Calculated for $C_{12}H_{13}N_5O$: 243.27; Found: 243.95 (M+).

Step 7: Synthesis of N-(6-((1H-pyrazol-1-yl)methyl)-4-methoxy-1H-indazol-3-yl)-2-fluorobenzenesulfonamide (Synthetic Example 124)

To a stirred solution of compound 288 (100 mg, 0.41 mmol) in Pyridine (3 mL) at 0° C. was added compound 6 (80 mg, 0.41 mmol) and the reaction was allowed to stir at the room temperature for 12 h. After completion (monitored by TLC), reaction mixture was concentrated under high vacuum. The residue was quenched with water and extracted with ethyl acetate. The organic layer was collected, washed with brine, dried over anhydrous $Na_2SO_4$ and concentrated under reduced pressure. The crude compound was purified by using prep HPLC to afford the title compound (25 mg, 15.14%) as an off-white solid. TLC: 80% EtOAc/Heptane ($R_f$ 0.5). See Table 1 for analytical data.

Synthesis of N-(6-((1H-pyrazol-1-yl)methyl)-4-methoxy-1H-indazol-3-yl)-2,6-dimethoxybenzenesulfonamide (Synthetic Example 125)

Step 8

To a stirred solution of compound 17 (160 mg, 0.65 mmol) in pyridine (5 mL) at 0° C. was added compound 5 (170 mg, 0.72 mmol) and the reaction was allowed to stir at the room temperature for 2 h. After completion (monitored by TLC), reaction mixture was concentrated under high vacuum. The residue was quenched with water and extracted with ethyl acetate. The organic layer was collected, washed with brine, dried over anhydrous $Na_2SO_4$ and concentrated under reduced pressure. The crude compound was purified by using prep HPLC to afford the title compound (38 mg, 13%) as an off-white solid. TLC: 80% EtOAc/Heptane ($R_f$ 0.35). See Table 1 for analytical data.

Synthetic Example 126

Scheme 96: Synthesis of N-(6-((4-cyano-1H-pyrazol-1-yl)methyl-4-methoxybenzo[d]isoxazol-3-yl)-1-cyclohexylmethanesulfonamide

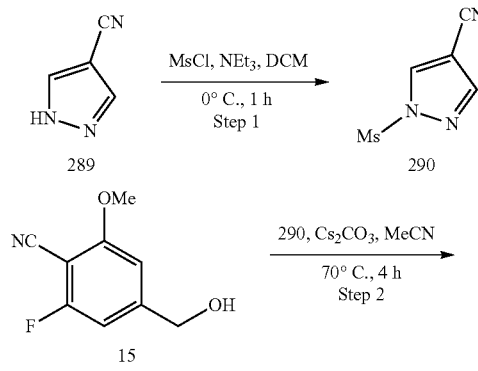

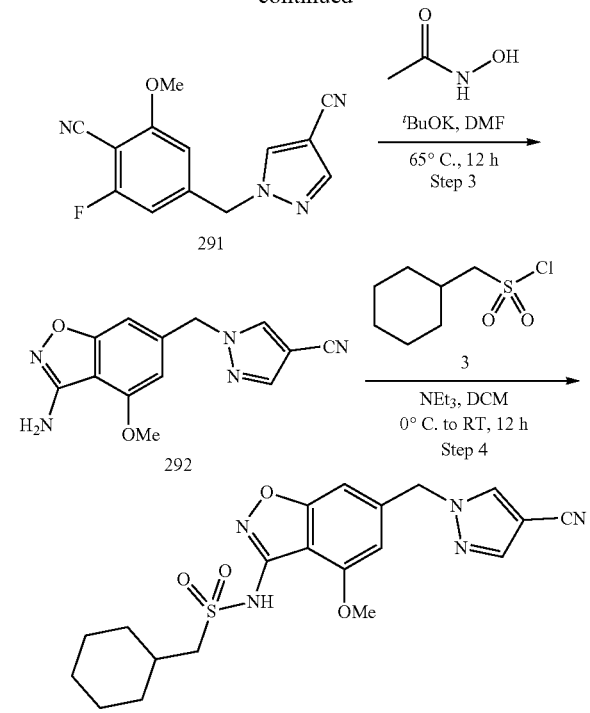

Syn. Ex. 126

Step 1: Synthesis of 1-(methylsulfonyl)-1H-pyrazole-4-carbonitrile (290)

To a stirred solution of compound 289 (2.0 g, 21.50 mmol) in DCM (20 mL) was added $Et_3N$ (4.5 mL, 32.2 mmol) followed by methane sulfonyl chloride (2.49 mL, 32.2 mmol) and the resulting reaction mixture stirred at 0° C. for 1 h. After completion of the reaction (monitored by TLC), the reaction mixture was concentrated under reduced pressure, diluted with ethyl acetate and extracted. The organic layer was collected; washed with saturated $NaHCO_3$ solution; washed with brine; dried over anhydrous $Na_2SO_4$ and concentrated under reduced pressure to afford the title compound 290 (2.1 g, 57.10%) as a white solid. TLC: 30% EtOAc/Heptane ($R_f$ 0.3). $^1H$ NMR (400 MHz, $CDCl_3$): δ 8.48 (s, 1H), 8.05 (s, 1H), 3.44 (s, 3H).

Step 2: Synthesis of 1-(4-cyano-3-fluoro-5-methoxybenzyl)-1H-pyrazole-4-carbonitrile (291)

To a stirred solution of compound 15 (0.4 g, 2.20 mmol) in acetonitrile (5 mL) was added $Cs_2CO_3$ (1.0 g, 3.31 mmol) followed by compound 290 (0.45 g, 2.65 mmol) and the resulting reaction mixture was heated at 70° C. for 4 h. After completion of the reaction (monitored by TLC), the reaction mixture was cooled to room temperature, diluted with ethyl acetate and extracted. The organic layer was collected, washed with brine, dried over anhydrous $Na_2SO_4$ and concentrated under reduced pressure. The crude compound was purified by silica gel (100-200 mesh) column chromatography using a gradient method of 0-50% EtOAc/Heptane to afford the title compound 291 (0.27 g, 47.72%) as a yellow solid. TLC: 80% EtOAc/Heptane ($R_f$ 0.45). $^1H$ NMR (400 MHz, DMSO-$d_6$): δ 8.71 (s, 1H), 8.13 (s, 1H), 7.08 (s, 1H), 6.84 (d, J=11.2 Hz, 1H), 5.50 (s, 2H), 3.94 (s, 3H).

Step 3: Synthesis of 1-((3-amino-4-methoxybenzo[d]isoxazol-6-yl)methyl)-1H-pyrazole-4-carbonitrile (292)

To a stirred solution of compound 291 (0.27 g, 1.05 mmol) in DMF (3 mL) was added acetohydroxamic acid (0.237 g, 3.16 mmol) followed by 'BuOK (0.35 g, 3.16 mmol) and the reaction mixture was allowed to stir at 65° C. for 12 h. After completion of the reaction (monitored by TLC), reaction mixture was cooled to room temperature, diluted with ethyl acetate and extracted. The organic layer was collected, washed with brine, dried over anhydrous Na₂SO₄ and concentrated under reduced pressure. The crude compound was purified by silica gel (100-200 mesh) column chromatography using a gradient method of 0-50% EtOAc/Heptane to afford the title compound to afford the title crude compound 292 (0.18 g, 63.44%) as a brown solid. TLC: 80% EtOAc/Heptane (R$_f$ 0.35). $^1$H NMR (400 MHz, DMSO-d$_6$): δ 8.71 (s, 1H), 8.11 (s, 1H), 6.84 (s, 1H), 6.69 (s, 1H), 5.97 (s, 2H), 5.47 (s, 2H), 3.88 (s, 3H). LCMS Calculated for $C_{13}H_{11}N_5O_2$: 269.26; Found: 269.90.

Step 4: Synthesis of N-(6-((4-cyano-1H-pyrazol-1-yl)methyl)-4-methoxybenzo[d]isoxazol-3-yl)-1-cyclohexylmethanesulfonamide (Synthetic Example 126)

To a stirred solution of compound 292 (100 mg, 0.37 mmol) in DCM (1 mL) at 0° C. was added Et₃N (0.05 mL, 0.40 mmol) followed by compound 3 (80 mg, 0.40 mmol) and the reaction was allowed to stir at room temperature for 12 h. After completion of the reaction (monitored by TLC), reaction mixture was again cooled to room temperature, diluted with DCM and extracted. The organic layer was collected, washed with brine, dried over anhydrous Na₂SO₄ and concentrated under reduced pressure. The crude compound was purified by using prep HPLC to afford the title compound (7 mg, 4.4%) as an off-white solid. TLC: 80% EtOAc/Heptane (Rf: 0.35). See Table 1 for analytical data.

Synthetic Example 127

Scheme 97: Synthesis of N-(7-((1H-pyrazol-1-yl)methyl)-5-methoxy-[1,2,4]triazolo[4,3-a]pyridin-3-yl)-1-cyclohexylmethanesulfonamide

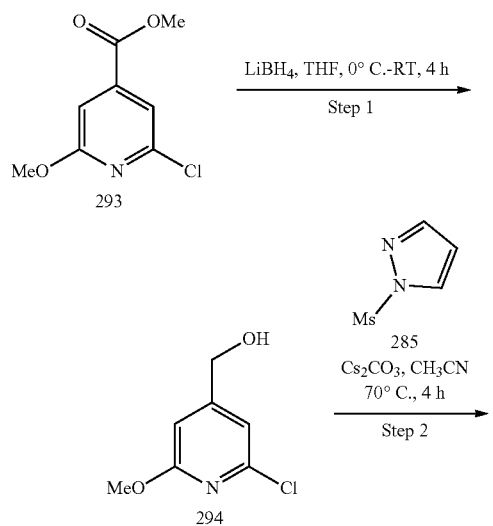

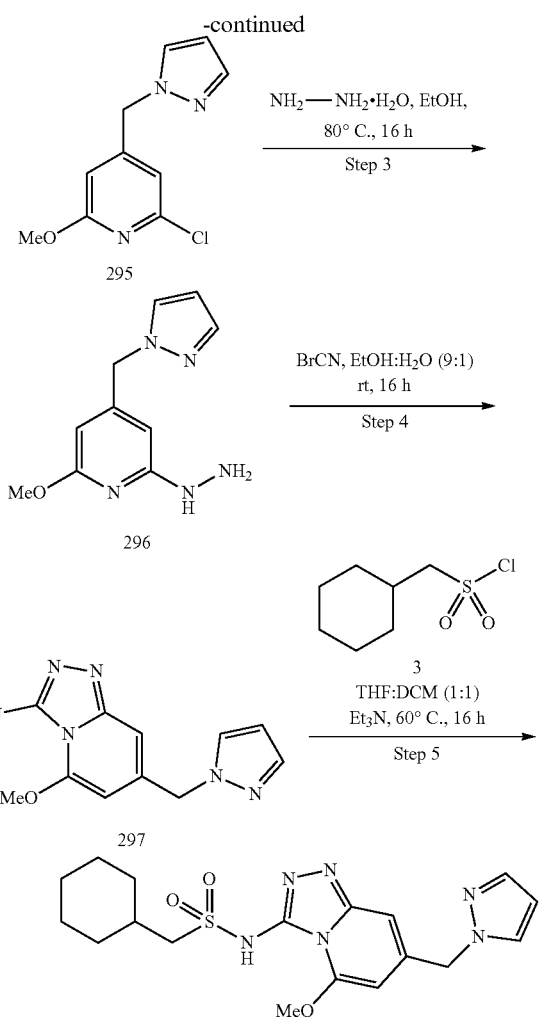

Step 1: Synthesis of (2-chloro-6-methoxypyridin-4-yl)methanol (294)

To a stirred solution of compound 293 (2 g, 9.95 mmol) in THF (20 mL) was added LiBH4 (0.647 g, 29.8 mmol) at 0° C. and the reaction mixture was allowed to stir at the room temperature for 4 h. The progress of the reaction was monitored by TLC. After completion, the mixture was acidified with 1N HCl and extracted with ethyl acetate. The organic layer was collected, washed with brine, dried over anhydrous Na₂SO₄ and concentrated under reduced pressure to afford the title compound 294 (1.1 g, 96.32%) as a yellow solid. TLC: 30% EtOAc/Heptane (R$_f$ 0.3); $^1$H NMR (400 MHz, DMSO-d$_6$): δ 7.00 (s, 1H), 6.74 (s, 1H), 5.50 (broad s, 1H), 4.49 (s, 2H), 3.83 (s, 3H). LCMS Calculated for $C_7H_8ClNO_2$: 173.60; Found: 174.2 (M+1).

Step 2: Synthesis of 4-((1H-pyrazol-1-yl)methyl)-2-chloro-6-methoxypyridine (295)

To a stirred solution of compound 294 (0.5 g, 2.89 mmol) in CH₃CN (5 mL) was added Cs₂CO₃ (2.8 g, 8.67 mmol) followed by compound 285 (0.63 g, 4.33 mmol) and the resulting mixture was heated at 70° C. for 4 h. After completion of the reaction (monitored by TLC), the reaction mixture was filtered through a pad of Celite and washed with ethyl acetate. The filtrate was collected, washed with brine, dried over anhydrous $Na_2SO_4$ and concentrated under reduced pressure. The crude compound was purified by combi flash column chromatography using a gradient method of 0-30% EtOAc/Heptane to afford the title compound 295 (1 g, 71%) as a yellow solid. TLC: 50% EtOAc/Heptane ($R_f$, 0.4). $^1$H NMR (400 MHz, DMSO-$d_6$): δ 7.61 (s, 1H), 7.45 (d, J=2.0 Hz, 1H), 6.66 (s, 1H), 6.36 (s, 2H), 5.29 (s, 2H), 3.91 (s, 3H). LCMS Calculated for $C_{10}H_{10}ClN_3O$: 223.66; Found: 223.80 (M+).

Step 3: Synthesis of 4-((1H-pyrazol-1-yl)methyl)-2-hydrazineyl-6-methoxypyridine (296)

To a stirred solution of compound 295 (1.0 g, 4.48 mmol) in ethanol (10 mL) was added hydrazine hydrate (286 mg, 8.96 mmol) and the reaction mixture was allowed to stir at 80° C. for 16 h. After completion (monitored by TLC), the reaction mixture was concentrated under reduced pressure to afford the title compound 296 (0.4 g, 40%) as a brown gummy solid. TLC: 50% EtOAc/Heptane ($R_f$, 0.2); $^1$H NMR (400 MHz, DMSO-$d_6$): δ 7.79 (s, 1H), 7.47 (s, 1H), 7.34 (s, 1H), 6.23 (s, 1H), 6.07 (s, 1H), 5.64 (s, 1H), 5.18 (s, 2H), 4.06 (s, 2H), 3.72 (s, 3H). LCMS Calculated for $C_{10}H_{13}N_5O$: 219.25; Found: 219.95 (M+).

Step 4: Synthesis of 7-((1H-pyrazol-1-yl)methyl)-5-methoxy-[1,2,4]triazolo[4,3-a]pyridin-3-amine (297)

To a stirred solution of compound 296 (200 mg, 0.82 mmol) in a 9:1 mixture of EtOH:$H_2O$ (9:1) (2 mL) was added a pre-dissolved solution of cyanogen bromide (104 mg, 0.98 mmol) in EtOH:$H_2O$ (1:1, 2 mL) at 0° C. and the reaction mixture was allowed to stir at the room temperature for 16 h. The progress of reaction was monitored by TLC and LCMS. After completion, the reaction mixture was concentrated under reduced pressure to get crude compound which was triturated with n-pentane/EtOAc and dried under vacuum to afford the title compound 297 (110 mg, 55.0%) as a brown solid. TLC: 80% EtOAc/Heptane (Rf 0.15). $^1$H NMR (400 MHz, DMSO-$d_6$): δ 7.93 (s, 1H), 7.74-7.46 (m, 3H), 6.57 (s, 1H), 6.37 (s, 1H), 6.32 (s, 1H), 5.42 (s, 2H), 4.03 (s, 3H). LCMS Calculated for $C_{11}H_{12}N_6O$: 244.26; Found: 245.2 (M+1).

Step 5: Synthesis of N-(7-((1H-pyrazol-1-yl)methyl)-5-methoxy-[1,2,4]triazolo[4,3-a]pyridin-3-yl)-1-cyclohexylmethanesulfonamide (Synthetic Example 127)

To a stirred solution of compound 297 (150 mg, 0.61 mmol) in THF:DCM (1:1, 1 mL) was added $Et_3N$ (0.23 mL, 1.83 mmol) followed by compound 3 (140 mg, 0.737 mmol) and the reaction mixture was allowed to stir at 60° C. for 16 h. The progress of the reaction was monitored by LCMS and TLC. After completion, the reaction mixture was diluted with ethyl acetate and extracted. The combined organic layer was collected, washed with brine, dried over anhydrous $Na_2SO_4$ and concentrated under reduced pressure. The crude compound was purified by prep HPLC to afford the title compound (7 mg, 2.8%) as a white solid. TLC: 5% MeOH/DCM ($R_f$, 0.25). See Table 1 for analytical data.

Synthetic Example 128, 129

Scheme 98:
Scheme for the synthesis of N-(6-((4-(aminomethyl)-1H-pyrazol-1-yl)methyl)-4-methoxybenzo[d]isoxazol-3-yl)-1-cyclohexylmethanesulfonamide and N-((1-((3-((cyclohexylmethyl)sulfonamido)-4-methoxybenzo[d]isoxazol-6-yl)methyl)-1H-pyrazol-3-yl)methyl)propionamide

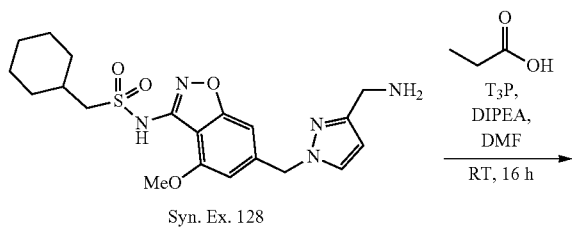

Syn. Ex. 128

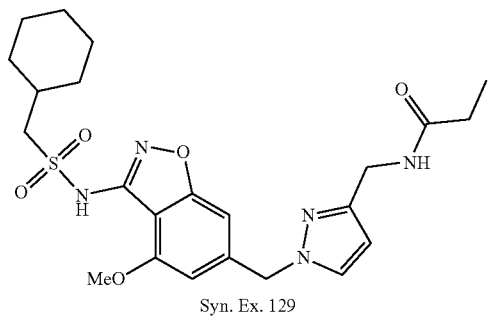

Syn. Ex. 129

The synthesis of Synthetic Example 128 was described in Scheme 14, compound 48. See Table 1 for analytical data.

To a stirred solution of compound of Synthetic Example 128 (80 mg, 0.18 mmol) in DMF (2.5 mL) at 0° C. was added DIPEA (0.12 mL, 0.72 mmol), followed by $T_3P$ (0.17 mL, 0.27 mmol). The reaction was allowed to stir at room temperature for 20 min. After that, a pre-dissolved solution of propionic acid (13 mg, 0.18 mmol) in DMF (0.5 mL) was added in a drop-wise manner and the reaction was allowed to stir at room temperature for 16 h. After completion (monitored by TLC), the solvent was concentrated under vacuum. The residue was quenched with water and extracted with ethyl acetate. The organic layer was collected, washed with brine, dried over anhydrous $Na_2SO_4$ and concentrated under reduced pressure to afford the crude product which was purified by using prep-HPLC to obtain inseparable mixture of isomers. The isomers were further separated by using Chiral HPLC (Method: Chiral-Met-B 30%_1.0 mL/cm; Mobile phase: A; 0.1% DEA in n-Hexane; B; DCM:MEOH (50:50) A:B, 70:30; Injection volume: 5 µL; Flow rate: 1.0 mL/min; Column: CHIRAL PAK IG (250*4.6 mm, 5 µm); Duration up to 25 min.) to afford the title compound of Synthetic Example 129 (18 mg, 20%) as an off-white solid. TLC: 100% EtOAc ($R_f$ 0.5). Minor isomer was not isolated in enough quantity due to merged impurities. See Table 1 for analytical data.

Synthetic Example 130

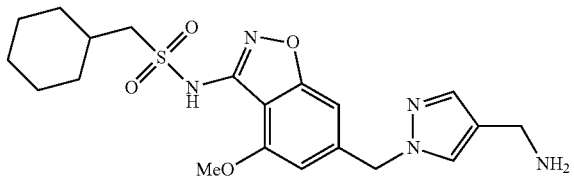 [SMILES: COc1cc(Cn2cc(CN)cn2)cc2onc(NS(=O)(=O)CC3CCCCC3)c12]

The synthesis of Synthetic Example 130 was described in Scheme 7, compound 23a. The crude compound was purified by prep HPLC to afford the title compound as an off-white solid. See Table 1 for analytical data.

TABLE 1

Analytical data for final compounds

| Syn. Ex. No. | Mass Spec. Found (m/z)/ Mass Spec. Calculated | $^1$H-NMR (400 M Hz, DMSO-$d_6$, unless otherwise stated) |
|---|---|---|
| 1 | 500.05 (M + 1)/ 499.59 for $C_{24}H_{29}N_5O_5S$ | δ 10.41 (s, 1H), 7.78 (d, J = 6.4 Hz, 1H), 6.98-6.95 (m, 1H), 6.85-6.78 (m, 1H), 6.69-6.50 (m, 1H), 6.21 (dd, J = 16.8, 6.8 Hz, 1H), 5.74 (d, J = 10.4 Hz, 1H), 5.45-5.38 (m, 2H), 4.79-4.65 (m, 2H), 4.45 (d, J = 12.4 Hz, 2H), 3.91 (s, 3H), 3.37 (d, J = 6.0 Hz, 2H), 2.01-1.92 (m, 1H), 1.86 (d, J = 11.6 Hz, 2H), 1.64 (d, J = 12.4 Hz, 1H), 1.57 (d, J = 12.0 Hz, 2H), 1.28-1.05 (m, 5H). $^1$H NMR hints for mixture of regio-isomers. The chemical shift values for major isomer have been captured. |
| 2 | 498.10 (M + 1)/ 497.57 for $C_{24}H_{27}N_5O_5S$ | δ 10.39 (d, J = 3.6 Hz, 1H), 7.78 (s, 1H), 6.99 (d, J = 3.6 Hz, 1H), 6.83 (m, J = 13.2 Hz, 1H), 5.45-5.40 (m, 2H), 4.78-4.66 (m, 2H), 4.57-4.55 (m, 1H), 4.46-4.39 (m, 2H), 3.91 (s, 3H), 3.37 (d, J = 6.0 Hz, 2H), 2.01-1.94 (m, 1H), 1.85 (d, J = 11.6 Hz, 2H), 1.64 (d, J = 12.4 Hz, 2H), 1.58 (d, J = 12.4 Hz, 1H), 1.28-1.05 (m, 5H). $^1$H NMR indicates mixture of regio-isomers. The chemical shift values for major isomer have been captured. |
| 3 | 555.35 (M + 1)/ 554.67 for $C_{27}H_{34}N_6O_5S$: | δ 10.42 (broad s, 1H), 7.77 (d, J = 1.6 Hz, 1H), 6.89 (s, 1H), 6.76 (s, 1H), 5.42 (s, 2H), 4.72 (d, J = 2.8 Hz, 2H), 4.43 (s, 2H), 3.88 (s, 3H), 3.51 (s, 2H), 3.30-3.22 (m, 2H), 2.24 (s, 6H), 1.95-1.84 (m, 3H), 1.67-1.52 (m, 3H), 1.24-1.03 (s, 5H). $^1$H NMR hints for minor isomer (<5%). |
| 4 | 488.05 (M + 1)/ 487.05 for $C_{23}H_{29}N_5O_5S$ | δ 8.36 (s, 1H), 8.15 (s, 1H), 7.74 (s, 1H), 7.40 (s, 1H), 6.68 (s, 1H), 6.56 (s, 1H), 6.26-6.15 (m, 1H), 6.12-6.04 (m, 1H), 5.57 (d, J = 9.6 Hz, 1H), 5.32 (s, 2H), 4.18 (d, J = 4.8 Hz, 2H), 3.81 (s, 3H), 2.99 (broad s, 2H), 2.04-1.72 (m, 3H), 1.64-1.49 (m, 3H), 1.31-1.04 (m, 3H), 1.02-0.89 (m, 2H). |
| 5 | 486.05 (M + 1)/ 485.56 for $C_{23}H_{27}N_5O_5S$ | δ 10.37 (s, 1H), 9.04 (t, J = 5.6 Hz, 1H), 7.76 (s, 1H), 7.40 (s, 1H), 6.91 (s, 1H), 6.77 (s, 1H), 5.40 (s, 2H), 4.13 (d, J = 5.6 Hz, 2H), 4.11 (s, 1H), 3.89 (s, 3H), 3.30 (merged m, 2H), 1.99-1.92 (m, 1H), 1.86 (d, J = 10.4 Hz, 2H), 1.66-1.62 (m, 2H), 1.58 (d, J = 11.2 Hz, 1H), 1.28-1.14 (m, 2H), 1.11-1.04 (m, 3H). |
| 6 | 524.05 (M + 1)/ 523.62 for $C_{22}H_{29}N_5O_6S_2$ | δ 10.39 (s, 1H), 7.79 (s, 1H), 7.57 (t, J = 5.6 Hz, 1H), 7.43 (s, 1H), 6.90 (s, 1H), 6.80 (s, 1H), 6.63 (dd, J = 16.4, 1.2 Hz, 1H), 6.01 (d, J = 16.8 Hz, 1H), 5.91 (d, J = 10.0 Hz, 1H), 5.42 (s, 2H), 3.92 (d, J = 6.0 Hz, 2H), 3.88 (s, 3H), 3.37 (d, J = 6.0 Hz, 2H), 2.03-1.92 (m, 1H), 1.86 (d, J = 12.4 Hz, 2H), 1.65 (d, J = 12.8 Hz, 2H), 1.57 (d, J = 13.2 Hz, 1H), 1.28-1.04 (m, 5H). |
| 7 | 488.05 (M + 1)/ 487.05 for $C_{23}H_{29}N_5O_5S$ | δ 10.37 (s, 1H), 8.47-8.42 (m, 1H), 7.78 (d, J = 2.0 Hz, 1H), 6.89 (s, 1H), 6.75 (s, 1H), 6.26-6.02 (m, 3H), 5.55 (dd, J = 9.6, 2.0 Hz, 1H), 5.37 (s, 2H), 4.26 (d, J = 5.6 Hz, 2H), 3.86 (s, 3H), 3.35-3.33 (m, 2H), 1.96-1.88 (m, 1H), 1.83 (d, J = 12.0 Hz, 2H), 1.64- |

TABLE 1-continued

Analytical data for final compounds

| Syn. Ex. No. | Mass Spec. Found (m/z)/ Mass Spec. Calculated | $^1$H-NMR (400 M Hz, DMSO-$d_6$, unless otherwise stated) |
|---|---|---|
| | | 1.52 (m, 3H), 1.25-1.04 (m, 5H). $^1$H NMR hints for mixture of regio-isomers. The chemical shift values for major isomer have been captured. |
| 8 | 486.10 (M + 1)/ 485.56 for $C_{23}H_{27}N_5O_5S$ | δ 10.37 (s, 1H), 9.11 (t, J = 6.0 Hz, 1H), 7.80 (d, J = 2.4 Hz, 1H), 6.92 (s, 1H), 6.77 (s, 1H), 6.16 (d, J = 2.4 Hz, 1H), 5.40 (d, J = 6.4 Hz, 2H), 4.23 (d, J = 6.0 Hz, 2H), 4.12 (s, 1H), 3.89 (s, 3H), 3.35 (d, J = 6.4 Hz, 2H), 2.02-1.92 (m, 1H), 1.86 (d, J = 6.4 Hz, 2H), 1.68-1.54 (m, 3H), 1.29-1.04 (m, 5H). $^1$H NMR hints for single isomer and the structure further confirmed from its nOe study. |
| 9 | 490.10 (M + 1)/ 489.59 for $C_{23}H_{31}N_5O_5S$ | δ 10.38 (s, 1H), 8.11 (t, J = 5.6 Hz, 1H), 7.79 (d, J = 2.0 Hz, 1H), 6.92 (s, 1H), 6.78 (s, 1H), 6.15 (d, J = 2.4 Hz, 1H), 5.39 (s, 2H), 4.19 (d, J = 5.6 Hz, 2H), 3.90 (s, 3H), 3.36 (d, J = 6.0 Hz, 2H), 2.09 (q, J = 7.6 Hz, 2H), 2.02-1.93 (m, 1H), 1.86 (d, J = 11.2 Hz, 2H), 1.68-1.54 (m, 3H), 1.29-1.02 (m, 5H), 0.99 (t, J = 7.6 Hz, 3H). $^1$H NMR indicates single isomer and the structure further confirmed from its nOe study. |
| 10 | 401.15 (M − 1)/ 402.40 for $C_{19}H_{15}FN_2O_5S$ | δ 8.68 (t, J = 6.0 Hz, 1H), 7.98 (t, J = 6.4 Hz, 1H), 7.83-7.68 (m, 3H), 7.51 (s, 1H), 7.41 (q, J = 8.0 Hz, 2H), 7.26 (d, J = 7.6 Hz, 1H), 6.28 (dd, J = 16.8, 10.0 Hz, 1H), 6.13 (dd, J = 16.4, 2.0 Hz, 1H), 5.63 (dd, J = 10.0, 2.4 Hz, 1H), 4.48 (d, J = 5.6 Hz, 2H). NH proton not observed. |
| 11 | 401.00 (M + 1)/ 400.38 for $C_{19}H_{13}FN_2O_5S$ | δ 9.32 (t, J = 6.0 Hz, 1H), 7.99 (t, J = 6.4 Hz, 1H), 7.85 (broad s, 1H), 7.79-7.71 (m, 2H), 7.50 (s, 1H), 7.43 (q, J = 8.0 Hz, 2H), 7.25 (d, J = 8.0 Hz, 1H), 4.42 (d, J = 6.0 Hz, 2H), 4.18 (s, 1H). NH proton not observed. |
| 12 | 468.91 (M + 1)/ 468.50 for $C_{23}H_{21}FN_4O_4S$ | δ 10.79 (broad s, 1H), 10.26 (broad s, 1H), 8.74 (t, J = 5.6 Hz, 1H), 8.60 (d, J = 4.8 Hz, 1H), 8.17 (s, 1H), 8.05 (s, 1H), 7.86 (s, 1H), 7.81 (t, J = 6.0, 1H), 7.73-7.64 (m, 1H), 7.57 (s, 1H), 7.40 (t, J = 9.2 Hz, 1H), 7.30 (t, J = 7.6 Hz, 1H), 7.24 (d, J = 4.4 Hz, 1H), 6.32 (dd, J = 16.8, 10.0 Hz, 1H), 6.16 (dd, J = 17.2, 2.0 Hz, 1H), 5.67 (dd, J = 10.4, 2.0 Hz, 1H), 4.46 (d, J = 6.0 Hz, 2H), 2.41 (s, 3H). |
| 13 | 466.97 (M + 1)/ 466.19 for $C_{23}H_{19}FN_4O_4S$ | δ 10.82 (broad s, 1H), 10.32 (broad s, 1H), 9.39 (t, J = 6.0 Hz, 1H), 8.62 (d, J = 5.2 Hz, 1H), 8.17 (s, 1H), 8.05 (s, 1H), 7.85-7.79 (m, 2H), 7.67 (q, J = 6.4 Hz, 1H), 7.58 (s, 1H), 7.40 (t, J = 9.2 Hz, 1H), 7.30 (t, J = 7.2 Hz, 1H), 7.23 (d, J = 5.2 Hz, 1H), 4.40 (d, J = 6.0 Hz, 2H), 4.26 (s, 1H), 2.41 (s, 3H). |
| 14 | 512.15 (M − 1)/ 513.54 for $C_{25}H_{24}FN_3O_6S$ | _ (CD$_3$OD): 8.09 (dt, J = 7.2, 1.2 Hz, 1H), 7.76-7.65 (m, 3H), 7.53 (s, 1H), 7.42 (t, J = 7.2 Hz, 1H), 7.31-7-29 (m, 2H), 6.77-6.74 (m, 1H), 6.18-6.16 (m, 1H), 5.72 (dd, J = 10.4, 2.0 Hz, 1H), 4.56 (d, J = 13.2 Hz, 1H), 4.49 (s, 2H), 4.15 (d, J = 14.0 Hz, 1H), 3.17 (t, J = 13.2 Hz, 1H), 2.79 (t, J = 12.4 Hz, 1H), 2.60-2.51 (m, 1H), 1.88 (d, J = 11.2 Hz, 2H), 1.71-1.62 (m, 2H). |
| 15 | 509.07 (M − 1)/ 510.57 for $C_{25}H_{26}N_4O_6S$ | δ 10.81 (brs, 1H), 9.15 (brs, 1H), 8.74 (s, 1H), 8.60 (d, J = 4.8 Hz, 1H), 8.18 (s, 1H), 8.03 (s, 1H), 7.86 (s, 1H), 7.57 (s, 1H), 7.48 (t, J = 8.4 Hz, 1H), 7.24 (d, J = 4.8 Hz, 1H), 6.74 (d, J = 8.0 Hz, 2H), 6.35-6.28 (m, 1H), 6.15 (d, J = 16.8 Hz, 1H), 5.68 (d, J = 10.8 Hz, 1H), 4.46 (d, J = 6.0 Hz, 2H), 3.87 (s, 6H), 2.40 (s, 3H) |
| 16 | 509.2 (M + 1)/ 508.55 for $C_{25}H_{24}N_4O_6S$ | δ 9.38 (brs, 1H), 8.61 (d, J = 4.8 Hz, 1H), 8.18 (s, 1H), 8.01 (s, 1H), 7.83 (s, 1H), 7.58 (s, 1H), 7.48 (t, J = 8.4 Hz, 1H), 7.23 (d, J = 4.8 Hz, 1H), 6.74 (d, J = 8.4 Hz, 2H), 4.40 (d, J = 5.6 Hz, 2H), 4.25 (s, 1H) 3.86 (s, 6H), 2.40 (s, 3H). |
| 17 | 522.05 (M + 1)/ 521.54 for $C_{21}H_{20}FN_5O_6S_2$ | δ 7.87-7.80 (m, 2H), 7.68 (t, J = 6.0 Hz, 2H), 7.62 (brs, 1H), 7.31 (brs, 1H), 6.77 (brs, 1H), 6.68-6.56 (m, 1H), 6.24 (d, J = 2.0 Hz, 1H), 5.95 (d, J = 3.6 Hz, 1H), 5.82 (d, J = 6.0 Hz, 1H), 5.35 (s, 2H), 3.99 (d, J = 6.4 Hz, 2H), 3.79 (s, 3H). $^1$H-NMR didn't show exchangeable protons and further indicates a mixture of regio-isomers. The chemical shift values for major isomer have been captured and the structure further confirmed from its nOe study. |
| 18 | 485.93 (M + 1)/ 485.49 for $C_{22}H_{20}FN_5O_5S$ | δ 11.28 (br s, 1H), 8.45 (t, J = 5.2 Hz, 1H), 7.88 (t, J = 1.6 Hz, 1H), 7.85 (s, 1H), 7.73 (q, J = 5.6 Hz, 1H), 7.46-7.36 (m, 2H), 6.89 (s, 1H), 6.73 (s, 1H), 6.27-6.07 (m, 3H), 5.59 (dd, J = 10.0, 6.4 Hz, 1H), 5.37 (s, 2H), 4.28 (d, J = 5.6 Hz, 2H), 3.77 (s, 3H). $^1$H-NMR indicates the single regioisomer and the structure was further confirmed from its nOe study. |
| 19 | 564.3 (M + 1)/ 563.60 for $C_{23}H_{25}N_5O_8S_2$ | δ 9.58 (s, 1H), 7.82 (d, J = 2.0 Hz, 1H), 7.69 (t, J = 6.0 Hz, 1H), 7.49 (t, J = 8.4 Hz, 1H), 6.84 (s, 1H), 6.77 (d, J = 8.4 Hz, 3H), 6.63-6.56 (m, 1H), 6.25 (d, J = 2.0 Hz, 1H), 5.97 (d, J = 16.4 Hz, 1H), 5.82 (d, J = 10.0 Hz, 1H), 5.38 (s, 2H), 3.99 (d, J = 6.0 |

TABLE 1-continued

Analytical data for final compounds

| Syn. Ex. No. | Mass Spec. Found (m/z)/ Mass Spec. Calculated | $^1$H-NMR (400 M Hz, DMSO-$d_6$, unless otherwise stated) |
|---|---|---|
| | | Hz, 2H), 3.87 (s, 3H), 3.56 (s, 6H, merged). $^1$H-NMR indicates a single regioisomer. |
| 20 | 482.2 (M + 1)/ 481.53 for $C_{23}H_{23}N_5O_5S$ | δ 10.56 (s, 1H), 8.46 (t, J = 2.0 Hz, 1H), 7.82 (d, J = 2.0 Hz, 1H), 7.39-7.35 (m, 5H, merged), 6.96 (s, 1H), 6.78 (s, 1H), 6.29-6.18 (m, 1H), 6.12 (d, J = 2.4 Hz, 2H), 5.59 (dd, J = 10.0, 2.0 Hz, 1H), 5.41 (s, 2H), 4.77 (s, 2H), 4.30 (d, J = 5.6 Hz, 2H), 3.86 (s, 3H). $^1$H-NMR indicates a single regioisomer and the structure further confirmed from its nOe study. |
| 21 | 518.2 (M + 1)/ 517.58 for $C_{22}H_{23}N_5O_6S_2$ | δ 7.81 (d, J = 2.0 Hz, 1H), 7.71 (t, J = 6.4 Hz, 1H), 7.25-7.18 (m, 5H), 6.64 (d, J = 2.0 Hz, 1H), 6.61-6.57 (m, 1H), 6.51 (s, 1H), 6.24 (d, J = 2.0 Hz, 1H), 5.98 (d, J = 16.4 Hz, 1H), 5.83 (d, J = 10.0 Hz, 1H), 5.29 (s, 2H), 4.30 (brs, 2H), 4.01 (d, J = 6.0 Hz, 2H), 3.84 (s, 3H). $^1$H-NMR didn't show one exchangeable proton and indicates a single regioisomer. |
| 22 | 534.2 (M + 1)/ 533.57 for $C_{22}H_{23}N_5O_7S_2$ | δ 10.11 (s, 1H), 7.80 (dd, J = 9.2, 2.4 Hz, 1H), 7.67 (d, J = 6.0 Hz, 1H), 7.62 (t, J = 8.0 Hz, 1H), 7.20 (d, J = 8.0 Hz, 1H), 7.08 (t, J = 7.6 Hz, 1H), 6.84 (s, 1H), 6.75 (s, 1H), 6.63-6.56 (m, 1H), 6.24 (d, J = 2.0 Hz, 1H), 5.98 (d, J = 16.4 Hz, 1H), 5.83 (d, J = 10.0 Hz, 1H), 5.37 (s, 2H), 3.99 (d, J = 6.0 Hz, 2H), 3.82 (s, 3H), 3.78 (s, 3H). $^1$H-NMR didn't show one exchangeable proton and indicates a single regioisomer. |
| 23 | 506.2 (M + 1)/ 505.57 for $C_{23}H_{28}FN_5O_5S$ | δ 10.37 (s, 1H), 8.92 (t, J = 5.6 Hz, 1H), 7.79 (d, J = 2.0 Hz, 1H), 6.91 (s, 1H), 6.75 (s, 1H), 6.17 (d, J = 2.0 Hz, 1H), 5.59-5.46 (m, 1H), 5.39 (s, 2H), 5.27 (dd, J = 16.0, 3.6 Hz, 1H), 4.31 (d, J = 6.0 Hz, 2H), 3.88 (s, 3H), 3.34 (t, J = 6.4 Hz, 2H), 1.94-1.90 (m, 1H), 1.88 (d, J = 12.8 Hz, 2H), 1.65 (d, J = 3.2 Hz, 2H), 1.62-1.56 (m, 1H), 1.27-1.03 (m, 5H). $^1$H-NMR indicates a single regioisomer and the structure further confirmed from its nOe study. |
| 24 | 524.00 (M + 1)/ 523.62 for $C_{22}H_{29}N_5O_6S_2$ | δ 10.37 (brs, 1H), 7.83 (d, J = 2.0 Hz, 1H), 7.69 (t, J = 6.0 Hz, 1H), 6.87 (s, 1H), 6.76 (s, 1H), 6.66-6.57 (m, 1H), 6.26 (d, J = 2.4 Hz, 1H), 5.98 (d, J = 16.8 Hz, 1H), 5.85 (d, J = 10.0 Hz, 1H), 5.39 (s, 2H), 4.00 (d, J = 6.0 Hz, 2H), 3.89 (s, 3H), 1.97-1.84 (m, 2H), 1.65-1.55 (m, 2H), 1.27-1.03 (m, 9H). $^1$H-NMR showed traces of impurities and a mixture of regio-isomers. The chemical shift values for major isomer have been captured. |
| 25a | 538.05 (M + 1)/ 537.55 for $C_{25}H_{23}N_5O_7S$ | δ 9.59 (brs, 1H), 7.47 (s, 1H), 7.35 (s, 1H), 6.94 (d, J = 12.8 Hz, 1H), 6.78-6.74 (m, 3H), 5.39 (d, J = 9.6 Hz, 2H), 4.75 (s, 1H), 4.64 (s, 1H), 4.56 (d, J = 3.6 Hz, 1H), 4.42 (s, 1H), 4.38 (s, 1H), 3.89 (d, J = 1.6 Hz, 3H), 3.75 (s, 6H, merged). $^1$H-NMR indicates a single regioisomer and the structure further confirmed from its nOe study. |
| 25b | 538.10 (M + 1)/ 537.55 for $C_{25}H_{23}N_5O_7S$ | δ 9.59 (br s, 1H), 7.75 (s, 1H), 7.48 (t, J = 6.8 Hz, 1H), 6.89 (s, 1H), 6.80 (s, 1H), 6.76 (d, J = 8.4 Hz, 2H), 5.41 (s, 2H), 4.71 (d, J = 2.0 Hz, 2H), 4.56 (d, J = 6.4 Hz, 1H), 4.42 (s, 2H), 3.78 (s, 3H), 3.70 (s, 6H, merged). $^1$H-NMR indicates a single regioisomer and the structure further confirmed from its nOe study. |
| 26a | 508.3 (M + 1)/ 507.52 for $C_{24}H_{21}N_5O_6S$ | δ 10.13 (s, 1H), 7.81 (d, J = 6.8 Hz, 1H), 7.62 (t, J = 7.6 Hz, 1H), 7.35 (s, 1H), 7.18 (d, J = 8.4 Hz, 1H), 7.09 (t, J = 7.6 Hz, 1H), 6.95 (d, J = 11.6 Hz, 1H), 6.77 (s, 1H), 5.40 (d, J = 10.0 Hz, 2H), 4.76 (s, 1H), 4.65 (s, 1H), 4.56 (d, J = 4.4 Hz, 1H), 4.43 (s, 1H), 4.38 (s, 1H), 3.84 (d, J = 2.4 Hz, 3H), 3.78 (s, 3H). $^1$H-NMR indicates a single regioisomer. |
| 26b | 506.01 (M − 1)/ 507.52 for $C_{24}H_{21}N_5O_6S$ | δ 10.12 (s, 1H), 7.80 (dd, J = 8.0, 2.0 Hz, 1H), 7.75 (s, 1H), 7.62 (t, J = 7.2 Hz, 1H), 7.20 (d, J = 8.4 Hz, 1H), 7.09 (t, J = 7.2 Hz, 1H), 6.92 (s, 1H), 6.80 (s, 1H), 5.41 (s, 2H), 4.70 (d, J = 1.2 Hz, 2H), 4.56 (d, J = 6.4 Hz, 1H), 4.42 (s, 2H), 3.84 (s, 3H), 3.79 (s, 3H). $^1$H-NMR indicates a single regioisomer. |
| 27a | 446.0 (M + 1)/ 545.59 for $C_{23}H_{23}N_5O_7S_2$ | δ 10.12 (br s, 1H), 7.80 (dd, J = 8.0, 2.0 Hz, 1H), 7.71 (s, 1H), 7.60 (t, J = 8.0 Hz, 1H), 7.18 (d, J = 8.4 Hz, 1H), 7.08 (t, J = 7.6 Hz, 1H), 6.96-6.89 (m, 2H), 6.78 (s, 1H), 6.16 (s, 1H), 6.11 (d, J = 10.0 Hz, 1H), 5.40 (s, 2H), 4.32 (d, J = 2.8 Hz, 4H), 3.83 (s, 3H), 3.78 (s, 3H). $^1$H-NMR indicates a single regioisomer and the structure further confirmed from its nOe study. |
| 27b | 546.0 (M + 1)/ 545.59 for $C_{23}H_{23}N_5O_7S_2$ | δ 10.14 (s, 1H), 7.81 (dd, J = 8.0, 1.6 Hz, 1H), 7.62 (t, J = 8.0 Hz, 1H), 7.31 (s, 1H), 7.19 (d, J = 8.4 Hz, 1H), 7.09 (t, J = 8.0 Hz, 1H), 6.94-6.87 (m, 2H), 6.74 (s, 1H), 6.12 (d, J = 5.2 Hz, 1H), 6.08 (d, J = 1.2 Hz, 1H), 5.32 (s, 2H), 4.35 (s, 2H), 4.29 (s, 2H), 3.83 (s, 3H), 3.78 (s, 3H). $^1$H-NMR indicates a single regioisomer and the structure further confirmed from its nOe study. |

TABLE 1-continued

Analytical data for final compounds

| Syn. Ex. No. | Mass Spec. Found (m/z)/ Mass Spec. Calculated | $^1$H-NMR (400 M Hz, DMSO-$d_6$, unless otherwise stated) |
|---|---|---|
| 28a | 444.3 (M − 1)/ 445.54 for $C_{21}H_{27}N_5O_4S$ | δ 7.27 (s, 1H), 6.67 (s, 1H), 6.52 (s, 1H), 5.29 (s, 2H), 3.99 (s, 2H), 3.93 (s, 2H), 3.80 (s, 3H), 2.94 (d, J = 6.0 Hz, 2H), 1.87-1.78 (m, 3H), 1.65-1.51 (m, 3H), 1.27-1.10 (m, 5H), 0.99-0.93 (m, 2H). $^1$H-NMR indicates a single-isomer and the structure further confirmed from its nOe study. |
| 28b | 444.5 (M − 1)/ 445.54 for $C_{21}H_{27}N_5O_4S$ | δ 7.72 (s, 1H), 6.64 (s, 1H), 6.56 (s, 1H), 5.34 (s, 2H), 4.15 (s, 4H), 3.80 (s, 3H), 2.93 (d, J = 6.0 Hz, 2H), 1.90-1.77 (m, 3H), 1.61-1.50 (m, 3H), 1.23-1.07 (m, 5H), 0.99-0.93 (m, 2H). $^1$H-NMR indicates a single regioisomer and the structure further confirmed from its nOe study. |
| 29a | 500.1 (M + 1)/ 499.59 for $C_{24}H_{29}N_5O_5S$ | δ 10.39 (s, 1H), 7.37 (d, J = 2.4 Hz, 1H), 7.00-6.95 (m, 1H), 6.80 (d, J = 12.0 Hz, 1H), 6.64-6.50 (m, 1H), 6.20 (dt, J = 16.4, 2.4 Hz, 1H), 5.73 (dt, J = 10.0, 2.4 Hz, 1H), 5.41 (d, J = 10.8 Hz, 2H), 4.77 (s, 1H), 4.65 (s, 1H), 4.47 (s, 1H), 4.43 (s, 1H), 3.91 (s, 3H), 3.36 (d, J = 6.0 Hz, 2H), 1.98-1.93 (m, 1H), 1.86 (d, J = 12.8 Hz, 2H), 1.65 (dd, J = 10.0, 2.8 Hz, 2H), 1.58 (d, J = 12.8 Hz, 1H), 1.27-1.04 (m, 5H). $^1$H-NMR indicates a single regioisomer and the structure further confirmed from its nOe study. |
| 29b | 500.2 (M + 1)/ 499.59 for $C_{24}H_{29}N_5O_5S$ | δ 10.32 (brs, 1H), 7.76 (d, J = 5.6 Hz, 1H), 6.86 (s, 1H), 6.74 (s, 1H), 6.69-6.61 (m, 1H), 6.21 (dt, J = 16.8, 1.6 Hz, 1H), 5.73 (dt, J = 10.0, 2.4 Hz, 1H), 5.41 (s, 2H), 4.71 (d, J = 5.6 Hz, 2H), 4.45 (s, 2H), 3.87 (s, 3H), 3.21 (s, 2H), 1.95-1.82 (m, 3H), 1.58-1.52 (m, 3H), 1.29-0.98 (m, 5H). $^1$H-NMR indicates a single regioisomer and the structure further confirmed from its nOe study. |
| 30a | 498.05 (M + 1)/ 497.57 for $C_{24}H_{27}N_5O_5S$ | δ 10.40 (s, 1H), 7.37 (s, 1H), 7.01 (d, J = 12.0 Hz, 1H), 6.80 (s, 1H), 5.43 (d, J = 9.6 Hz, 2H), 4.78 (s, 1H), 4.66 (s, 1H), 4.58 (d, J = 3.6 Hz, 1H), 4.46 (s, 1H), 4.40 (s, 1H), 3.91 (s, 3H), 3.31 (s, 2H), 1.97-1.90 (m, 1H), 1.88 (d, J = 10.0 Hz, 2H), 1.66 (d, J = 17.2 Hz, 2H), 1.59 (d, J = 11.6 Hz, 1H), 1.26-1.08 (m, 5H). $^1$H-NMR indicates a single regioisomer and the structure further confirmed from its nOe study. |
| 30b | 498.05 (M + 1)/ 497.57 for $C_{24}H_{27}N_5O_5S$ | δ 10.41 (s, 1H), 7.77 (s, 1H), 6.96 (s, 1H), 6.82 (s, 1H), 5.44 (s, 2H), 4.72 (s, 2H), 4.57 (d, J = 6.4 Hz, 1H), 4.43 (s, 2H), 3.90 (s, 3H), 3.17 (d, J = 4.8 Hz, 2H), 1.98-1.92 (m, 1H), 1.86 (d, J = 11.6 Hz, 2H), 1.70-1.56 (m, 3H), 1.25-1.07 (m, 5H). $^1$H-NMR indicates a single regioisomer and the structure further confirmed from its nOe study. |
| 31 | 495.96 (M + 1)/ 495.51 for $C_{23}H_{21}N_5O_6S$ | δ 10.21 (brs, 1H), 9.01 (brs, 1H), 7.75 (d, J = 7.2 Hz, 1H), 7.70 (s, 1H), 7.51 (brs, 1H), 7.34 (s, 1H), 7.18-6.92 (m, 3H), 6.82-6.61 (m, 2H), 5.32 (s, 2H), 4.08 (s, 2H), 3.79 (s, 3H), 3.72 (s, 3H). |
| 32 | 534.0 (M + 1)/ 533.57 for $C_{22}H_{23}N_5O_7S_2$ | δ 10.15 (brs, 1H), 7.80-7.77 (m, 2H), 7.58 (t, J = 6.0 Hz, 2H), 7.41 (s, 1H), 7.18 (d, J = 7.6 Hz, 1H), 7.07-7.08 (m, 1H), 6.82 (2, 1H), 6.74 (s, 1H), 6.65 (q, J = 10.0, 10.0 Hz, 1H), 6.02 (d, J = 16.4 Hz, 1H), 5.91 (d, J = 10.0 Hz, 1H), 5.38 (s, 2H), 3.91 (d, J = 6.0 Hz, 2H), 3.82 (s, 3H), 3.77 (2, 3H). |
| 33 | 563.89 (M + 1)/ 563.60 for $C_{23}H_{25}N_5O_8S_2$ | δ 7.74 (s, 1H), 7.40 (s, 1H), 7.18 (t, J = 8.4 Hz, 2H), 6.63-6.50 (m, 5H), 6.04-5.97 (m, 5H), 5.89 (d, J = 10.0 Hz, 1H), 5.30 (s, 2H), 3.91 (s, 2H), 3.83 (s, 3H), 3.55 (s, 3H). |
| 34 | 525.93 (M + 1)/ 525.54 for $C_{24}H_{23}N_5O_7S$ | δ 9.53 (s, 1H), 9.03 (t, J = 5.2 Hz, 1H), 7.75 (s, 1H), 7.46 (t, J = 8.4 Hz, 1H), 7.38 (s, 1H), 6.83 (s, 1H), 6.75 (d, J = 8.4 Hz, 3H), 5.37 (s, 2H), 4.13 (s, 2H), 4.10 (d, J = 4.0 Hz, 1H), 3.87 (s, 3H), 3.74 (s, 6H, merged). |
| 35 | 496.20 (M + 1)/ 495.51 for $C_{23}H_{21}N_5O_6S$ | δ 10.92 (s, 1H), 9.06-9.00 (m, 1H), 7.72 (s, 1H), 7.48-7.41 (m, 2H), 7.37 (s, 1H), 7.22-6.95 (m, 2H), 6.76 (s, 1H), 6.65 (s, 1H), 5.34 (s, 2H), 4.11 (dd, J = 10.0, 5.6 Hz, 3H), 3.84 (s, 3H), 3.77 (s, 3H). |
| 36 | 524.3 (M + 1)/ 523.52 for $C_{24}H_{21}N_5O_7S$ | δ 10.38 (br s, 1H), 9.03 (brs, 1H), 8.03 (br s, 1H), 7.80-7.73 (m, 4H), 7.37 (s, 1H), 6.86 (s, 1H), 6.72 (s, 1H), 5.36 (s, 2H), 4.12 (s, 1H), 4.10 (s, 2H), 3.80 (s, 3H), 3.78 (s, 3H). |
| 37 | 510.0 (M + 1)/ 509.49 for $C_{23}H_{19}N_5O_7S$ | δ 9.02 (t, J = 7.2 Hz, 1H), 8.05 (dd, J = 7.2, 2.0 Hz, 1H), 7.80 (dd, J = 6.4, 2.0 Hz, 1H), 7.74-7.71 (m, 3H), 7.37 (s, 1H), 6.87 (s, 1H), 6.72 (s, 1H), 5.36 (s, 2H), 4.12 (s, 1H), 4.10 (s, 2H), 3.84 (s, 3H); $^1$H-NMR didn't show 2 exchangeable protons. |
| 38 | 524.2 (M + 1)/ 523.52 for $C_{24}H_{21}N_5O_7S$ | δ 9.03 (t, J = 5.6 Hz, 1H), 8.13-7.98 (m, 4H), 7.71 (s, 1H), 7.36 (s, 1H), 7.39 (d, J = 12.0 Hz, 1H), 6.71 (s, 1H), 6.62 (s, 1H), 5.33 (s, 2H), 4.11 (d, J = 5.6 Hz, 2H), 4.09 (s, 2H), 3.86 (s, 3H), 3.82 (s, 3H). |
| 39 | 459.95 (M + 1)/ 459.45 for $C_{21}H_{18}FN_3O_6S$ | δ 8.49 (t, J = 5.6 Hz, 1H), 8.39 (t, J = 5.6 Hz, 1H), 7.85 (t, J = 7.6 Hz, 1H), 7.61 (d, J = 8.0 Hz, 1H), 7.51 (d, J = 5.2 Hz, 1H), 7.45 (s, 1H), 7.27-7.15 (m, 4H), 6.33-6.26 (m, 1H), 6.12 (d, J = |

TABLE 1-continued

Analytical data for final compounds

| Syn. Ex. No. | Mass Spec. Found (m/z)/ Mass Spec. Calculated | $^1$H-NMR (400 M Hz, DMSO-$d_6$, unless otherwise stated) |
|---|---|---|
| | | 15.2 Hz, 1H), 5.61 (dd, J = 10.0, 2.0 Hz, 1H), 4.40 (d, J = 6.0 Hz, 2H), 3.83 (d, J = 6.0 Hz, 2H), 3.16 (s, 1H). |
| 40 | 500.04 (M + 1)/ 499.51 for $C_{24}H_{22}FN_3O_6S$ | δ 8.59 (q, J = 6.0 Hz, 1H), 7.84-7.80 (m, 1H), 7.60 (d, J = 8.0 Hz, 1H), 7.48-7.42 (m, 2H), 7.24-6.96 (m, 5H), 6.61-6.52 (m, 1H), 6.13 (dt, J = 13.2, 2.4 Hz, 1H), 5.65 (dd, J = 10.0, 2.4 Hz, 1H), 4.44-4.32 (m, 2H), 3.80-3.46 (m, 4H), 3.13-2.95 (m, 1H), 2.18-1.89 (m, 2H). |
| 41 | 523.15 (M + 1)/ 522.60 for $C_{27}H_{27}FN_4O_4S$ | δ 10.78 (d, J = 2.0 Hz, 1H), 10.29 (d, J = 2.4 Hz, 1H), 8.57 (d, J = 4.8 Hz, 1H), 8.20 (s, 1H), 8.10 (s, 1H), 7.87 (s, 1H), 7.80 (t, J = 7.2 Hz, 1H), 7.69 (q, J = 5.6 Hz, 1H), 7.55 (s, 1H), 7.39 (t, J = 9.6 Hz, 1H), 7.29 (t, J = 7.6 Hz, 2H), 6.89-6.82 (m, 1H), 6.12 (dd, J = 16.4, 2.4 Hz, 1H), 5.69 (dd, J = 10.4, 2.4 Hz, 1H), 4.64 (d, J = 12.0 Hz, 1H), 4.23 (d, J = 13.2 Hz, 1H), 3.18 (t, J = 11.2 Hz, 1H), 2.93 (t, J = 12.0 Hz, 1H), 2.73 (t, J = 12.0 Hz, 1H), 2.40 (s, 3H), 1.91 (d, J = 13.2 Hz, 2H), 1.64 (t, J = 12.0 Hz, 2H). |
| 42 | 559.0 (M + 1)/ 558.64 for $C_{26}H_{27}FN_4O_5S_2$ | δ 10.78 (d, J = 2.4 Hz, 1H), 10.29 (d, J = 2.4 Hz, 1H), 8.59 (d, J = 5.2 Hz, 1H), 8.20 (s, 1H), 8.11 (s, 1H), 7.90 (s, 1H), 7.80 (t, J = 7.2 Hz, 1H), 7.68 (q, J = 6.8 Hz, 1H), 7.57 (s, 1H), 7.39 (t, J = 10.0 Hz, 1H), 7.34-7.28 (m, 2H), 6.90-6.83 (m, 1H), 6.21-6.12 (m, 2H), 3.71 (d, J = 11.6 Hz, 2H), 2.81-2.65 (m, 3H), 2.41 (s, 3H), 1.95 (d, J = 10.8 Hz, 2H), 1.86-1.75 (m, 2H). |
| 43 | 522.4 (M + 1)/ 521.55 for $C_{25}H_{23}N_5O_6S$ | δ 10.08 (br s, 1H), 9.04 (br s, 1H), 7.78 (d, J = 7.2 Hz, 1H), 7.75 (s, 1H), 7.62 (t, J = 7.6 Hz, 1H), 7.39 (s, 1H), 7.17 (d, J = 8.4 Hz, 1H), 7.08 (t, J = 7.6 Hz, 2H), 6.92 (s, 2H), 5.41 (s, 2H), 4.12 (d, J = 8.4 Hz, 3H), 3.87 (br s, 1H), 3.66 (s, 3H), 0.78 (d, J = 6.0 Hz, 2H), 0.63 (s, 2H). |
| 44 | 511.5(M + 1)/ 510.16 for $C_{25}H_{26}N_4O_6S$ | δ 10.21 (s, 1H), 7.80 (d, J = 8.0 Hz, 1H), 7.62 (t, J = 7.6 Hz, 1H), 7.18 (d, J = 8.4 Hz, 1H), 7.09 (t, J = 7.6 Hz, 2H), 6.78 (s, 1H), 3.76-3.78 (m, 6H), 3.58 (d, J = 10.4 Hz, 2H), 3.40-3.39 (m, 3H), 2.82 (s, 2H), 2.64-2.56 (m, 2H), 1.46-1.50 (m, 2H) 0.92-0.90 (m, 2H). |
| 45 | 510.1(M + 1)/ 509.14 for $C_{24}H_{23}N_5O_6S$ | δ 10.08 (s, 1H), 7.86 (s, 1H), 7.79-7.77 (m, 1H), 7.59-7.60 (m, 1H), 7.17 (d, J = 8.4 Hz, 1H), 7.60-7.04 (m, 1H), 6.85 (s, 1H), 6.68 (s, 1H), 5.38 (d, J = 8.4 Hz, 2H), 4.58 (s, 2H), 4.50 (s, 1H), 4.32 (s, 2H), 3.79 (s, 3H), 3.75 (s, 3H), 3.05 (s, 3H). |
| 46 | 553.1(M + 1)/ 552.14 for $C_{25}H_{24}N_6O_7S$ | δ 10.45 (s, 1H), 9.05 (t, J = 5.2 Hz, 1H), 8.62 (d, J = 3.2 Hz, 1H), 7.86 (d, J = 8.0 Hz, 1H), 7.74 (s, 1H), 7.53 (s, 1H), 7.49 (d, J = 8.0 Hz, 1H), 7.38 (s, 1H), 6.86 (s, 1H), 6.74 (s, 1H), 5.37 (s, 2H), 4.12 (d, J = 5.6 Hz, 3H), 3.83 (s, 3H), 3.79 (s, 3H) 2.79 (d, J = 4.4 Hz, 3H), |
| 47 | 512.1(M + 1)/ 511.15 for $C_{24}H_{25}N_5O_6S$ | δ 10.15 (s, 1H), 7.82-7.78 (m, 2H), 7.64-7.60 (m, 1H), 7.42 (d, J = 4.8 Hz, 1H), 7.20 (d, J = 8.0 Hz, 1H), 7.11-7.07 (m, 1H), 6.91-6.84 (m, 1H), 6.76-6.69 (m, 1H), 6.14 (dd, J = 2.4, 2.4 Hz, 2H), 5.68-5.63 (m, 1H), 5.39 (d, J = 4.0 Hz, 2H), 4.36 (s, 2H), 3.80 (s, 3H), 3.77 (s, 3H), 2.97-2.86 (s, 3H). |
| 48 | 485.1(M + 1)/ 484.14 for $C_{23}H_{24}N_4O_6S$ | δ 8.92 (d, J = 6.8 Hz, 1H), 8.25 (s, 1H), 7.78 (d, J = 7.2 Hz, 1H), 7.31-7.25 (m, 1H), 6.97 (d, J = 8.0 Hz, 1H), 6.90 (t, J = 8.0 Hz, 1H), 6.79 (s, 1H), 6.54 (s, 1H), 4.16 (s, 1H), 4.08 (s, 1H), 3.84 (s, 3H), 3.71 (s, 3H), 3.63-3.60 (m, 2H), 2.66 (s, 1H), 2.32 (s, 2H), 2.06-2.63 (m, 2H), 1.35-1.25 (m, 1H), |
| 49 | 501.4(M + 1)/ 500.17for $C_{24}H_{28}N_4O_6S$ | δ 9.99 (brs, 1H), 8.03 (d, J = 7.2 Hz, 1H), 7.82 (dd, J = 8.0, 8.0 Hz, 1H), 7.63 (t, J = 8.4 Hz, 1H), 7.20 (d, J = 8.4 Hz, 1H), 7.10 (d, J = 7.6 Hz, 2H), 6.79 (s, 1H), 6.23-6.16 (m, 1H), 6.08 (dd, J = 16.8, 17.2 Hz, 1H), 5.58 (dd, J = 10.0, 10.0 Hz, 1H), 3.86 (s, 3H), 3.79 (s, 3H), 3.71-3.66 (m, 3H), 2.95-2.87 (m, 2H), 2.27-2.15 (m, 2H), 1.80-1.77 (m, 2H), 1.49-1.45 (m, 2H). |
| 50 | 513.2 (M + 1)/ 512.17 for $C_{25}H_{28}N_4O_6S$ | δ 10.04 (s, 1H), 7.81 (d, J = 8.0 Hz, 1H), 7.56 (t, J = 6.4 Hz, 1H), 7.16 (d, J = 8.8 Hz, 1H), 7.08 (t, J = 8.0 Hz, 2H), 6.72 (s, 1H), 6.63-6.50 (m, 1H), 6.13 (dd, J = 16.4, 16.8 Hz, 1H), 5.66 (dd, J = 10.8, 10.4 Hz, 1H), 3.82 (s, 3H), 3.81 (s, 3H), 3.74-3.71 (m, 1H), 3.65 (s, 2H), 3.60-3.37 (m, 5H), 2.85-2.76 (m, 2H), 2.25-2.54 (m, 2H). |
| 51 | 498.5 (M + 1)/ 497.14 for $C_{23}H_{23}N_5O_6S$ | δ 10.13 (s, 1H), 8.35-8.30 (m, 1H), 7.77 (d, J = 7.2 Hz, 2H), 7.38 (s, 2H), 7.01-6.94 (m, 2H), 6.61-6.59 (m, 2H), 6.24-6.17 (m, 1H), 6.10 (dd, J = 16.8, 16.8 Hz, 1H), 5.58 (dd, J = 10.0, 10.0 Hz, 1H), 5.32 (s, 2H), 4.17 (d, J = 5.2 Hz, 2H), 3.82 (s, 3H), 3.73 (s, 3H). |
| 52 | 523.47 (M + 1)/ 522.54 for $C_{24}H_{22}N_6O_6S$ | δ 11.09 (broad s, 1H), 9.06 (t, J = 5.6 Hz, 1H), 8.68 (s, 1H), 8.41 (s, 1H), 8.07 (d, J = 7.6 Hz, 2H), 7.73 (s, 2H), 7.37 (s, 1H), 6.82 (s, 1H), 6.71 (s, 1H), 5.36 (s, 2H), 4.12 (t, J = 3.2 Hz, 3H), 3.84 (s, 3H), 2.79 (d, J = 4.4 Hz, 3H). |

TABLE 1-continued

Analytical data for final compounds

| Syn. Ex. No. | Mass Spec. Found (m/z)/ Mass Spec. Calculated | $^1$H-NMR (400 M Hz, DMSO-$d_6$, unless otherwise stated) |
|---|---|---|
| 53 | 526.5(M + 1)/ 525.54 for C24H23N5O7S | δ 10.11 (s, 1H), 8.90 (m, 1H), 7.79 (d, J = 7.6 Hz, 1H), 7.71 (s, 1H), 7.60 (t, J = 8.0 Hz, 1H), 7.35 (s, 1H), 7.18 (d, J = 8.4 Hz, 1H), 7.09 (t, J = 8.0 Hz, 1H), 6.84 (s, 1H), 6.72 (s, 1H), 5.35 (s, 2H), 4.17 (s, 2H), 4.10 (d, J = 5.6 Hz, 2H), 3.80 (s, 3H), 3.76 (s, 3H). —OH proton not observed |
| 54 | 542.38(M + 1)/ 541.58 for C25H27N5O7S | δ 10.15 (s, 1H), 8.32 (t, J = 5.6 Hz, 1H), 7.81 (dd, J = 8.0, 8.0 Hz, 1H), 7.73 (s, 1H), 7.64-7.60 (m, 1H), 7.38 (s, 1H), 7.20 (d, J = 8.4 Hz, 1H), 7.11-7.07 (m, 1H), 6.86 (s, 1H), 6.75 (s, 1H), 6.63-6.58 (m, 1H), 6.10-6.05 (m, 1H), 5.37 (s, 2H), 4.16 (d, J = 5.6 Hz, 2H), 4.01 (dd, J = 4.4, 4.4 Hz, 2H), 3.83 (s, 3H), 3.79 (s, 3H), 3.26 (s, 3H). |
| 55 | 506.1 (M + 1)/ 505.55 for C25H23N5O5S | δ 10.78 (s, 1H), 10.15(s, 1H), 9.38 (t, J = 6.0 Hz, 1H), 8.66 (d, J = 4.0 Hz, 1H), 8.62 (d, J = 5.2 Hz, 1H), 8.34 (s, 1H), 8.13 (s, 1H), 8.07-8.04 (m, 2H), 7.98 (d, J = 8.0 Hz, 1H), 7.84 (s, 1H), 7.65 (t, J = 8.0 Hz, 1H), 7.55 (s, 1H), 7.24 (d, J = 4.8 Hz, 1H), 4.42 (d, J = 6.0 Hz, 2H), 4.24 (s, 1H), 2.76 (d, J = 4.4 Hz, 3H), 2.41 (s, 3H). |
| 56 | 579.4(M + 1)/ 578.64for C29H30N4O7S | δ 9.57 (s, 1H), 7.50-7.53 (m, 1H), 7.43 (s, 1H), 7.31-7.25 (m, 1H), 7.28 (s, 1H), 7.15 (d, J = 4.0 Hz, 1H), 7.05 (s, 2H), 7.01-6.90 (m, 1H), 6.80 (d, J = 8.4 Hz, 2H), 6.15-6.12 (m, 1H), 5.71-5.69 (m, 1H), 4.02 (s, 3H), 3.79 (s, 6H), 3.71-3.70 (m, 4H), 3.25 (s, 4H). |
| 57 | 510.1(M + 1)/ 509.54 for C24H23N5O6S | δ 10.14 (s, 1H), 8.80 (t, J = 5.2 Hz, 1H), 7.80 (d, J = 8.0 Hz, 1H), 7.71 (s, 1H), 7.61 (s, 1H), 7.36 (s, 1H), 7.17 (s, 1H), 7.08 (s, 1H), 6.84 (s, 1H), 6.73 (s, 1H), 5.36 (s, 2H), 4.09 (d, J = 6.0 Hz, 2H), 3.82 (s, 3H), 3.77 (s, 3H), 1.92 (s, 3H). |
| 58 | 579.1(M + 1)/ 578.64 for C29H30N4O7S | δ 9.61 (s, 1H), 7.49-7.47(m, 1H), 7.37-7.32 (m, 3H), 7.17-7.10 (m, 3H), 6.79-6.70 (m, 3H), 6.11 (dd, J = 16.4, 16.4 Hz, 1H), 5.66 (dd, J = 10.0, 10.0 Hz, 1H), 3.95 (s, 3H), 3.77 (s, 6H), 3.44-3.32 (m, 4H), 2.78-2.32 (m, 4H). |
| 59 | 548.97(M + 1)/ 548.63 for $C_{24}H_{28}N_4O_7S_2$ | $^1$H-NMR (400 MHz, CD$_3$OD) δ7.97 (dd, J = 7.2, 7.6 Hz, 1H), 7.58-7.54 (m, 1H), 7.12-7.05 (m, 2H), 6.99 (s, 1H), 6.82 (s, 1H), 6.75-6.66 (m, 1H), 6.21-6.17 (m, 2H), 3.98 (s, 3H), 3.84 (s, 3H), 3.69 (s, 2H), 3.30 (m, 2H merged in solvent peak), 3.09-3.06 (m, 2H), 2.87-2.86 (m, 2H), 2.75-2.70 (m, 2H), 2.44 (dd, J = 9.6, 9.2 Hz, 2H). |
| 60 | 553.1(M + 1)/ 552.56 for C25H24N6O7S | δ 10.20 (s, 1H), 8.90 (t, J = 5.6 Hz, 1H), 8.22 (t, J = 5.6 Hz, 1H), 7.79 (t, J = 6.4 Hz, 1H), 7.70 (s, 1H), 7.54 (brs, 1H), 7.37 (s, 1H), 7.12 (d, J = 10.8 Hz, 2H), 6.79 (t, J = 8.0 Hz, 2H), 5.34 (s, 2H), 4.16 (s, 1H), 4.10 (d, J = 5.6 Hz, 2H), 3.82 (s, 3H), 3.75 (s, 3H), 3.68 (d, J = 6.4 Hz, 2H). |
| 61 | 555.1(M + 1)/ 554.58 for C25H26N6O7S | δ 10.14 (s, 1H), 8.33 (t, J = 5.6 Hz, 1H), 8.22 (t, J = 5.6 Hz, 1H), 7.79 (t, J = 7.2 Hz, 1H), 7.21 (s, 1H), 7.61 (brs, 1H), 7.37 (s, 1H), 7.17 (d, J = 6.4 Hz, 2H), 6.85-6.73 (m, 2H), 6.32-6.25 (m, 1H), 6.10 (dd, J = 16.8, 17.2 Hz, 1H), 6.60 (dd, J = 10.0, 10.4 Hz, 1H), 5.35 (s, 2H), 4.11(d, J = 5.6 Hz, 2H), 3.82 (s, 3H), 3.77 (t, J = 6.8 Hz, 5H). |
| 62 | 496.90(M + 1)/ 496.50 for C22H20N6O6S | δ 8.80 (t, J = 5.2 Hz, 1H), 8.29 (s, 1H), 7.90 (s, 1H), 7.78 (d, J = 7.6 Hz, 1H), 7.37 (t, J = 7.6 Hz, 1H), 7.19 (brs, 1H), 6.99 (d, J = 8.0 Hz, 1H), 6.93 (t, J = 7.2 Hz, 1H), 6.71 (s, 1H), 6.57 (s, 1H), 5.39 (s, 2H), 4.23 (d, J = 5.2 Hz, 2H), 3.83 (s, 3H), 3.71 (s, 3H). |
| 63 | 514.4(M + 1)/ 513.57 for C24H27N5O6S | δ 8.51 (s, 1H), 8.13 (s, 1H), 7.80 (d, J = 7.2 Hz, 1H), 7.52 (brs, 1H), 7.13 (d, J = 8.0 Hz, 1H), 7.02-6.98 (m, 2H), 6.71 (s, 1H), 4.09 (d, J = 4.8 Hz, 2H), 3.84 (s, 3H), 3.76 (s, 3H), 3.57 (s, 2H), 2.85 (d, J = 9.2 Hz, 2H), 2.16 (brs, 1H), 2.01-2.05 (m, 2H), 1.65-1.58 (m, 4H). |
| 64 | 499.2 (M + 1)/ 498.55 for C24H26N4O6S | 10.01(brs, 1H), 8.67 (s, 1H), 7.80 (s, 1H), 7.61 (s, 1H), 7.19 (d, J = 7.2 Hz, 3H), 6.79 (s, 1H), 4.10 (s, 1H), 3.85 (s, 3H), 3.78 (s, 3H), 3.65 (brs, 2H), 2.89 (s, 3H), 2.65-2.49 (m, 2H), 1.78-1.73 (m, 2H), 1.49-1.51 (m, 2H), |
| 65 | 540.2 (M + 1)/ 539.52 for C24H21N5O8S | 10.54 (brs, 1H), 9.02 (s, 1H), 7.91 (d, J = 8.0 Hz, 1H), 7.73 (s, 1H), 7.60 (s, 2H), 7.37 (s, 1H), 6.84 (s, 1H), 6.71 (s, 1H), 5.36 (s, 2H), 4.12 (t, J = 5.6 Hz, 2H), 3.83 (s, 3H), 3.79 (s, 3H), 2.95 (brs, 1H) Acid proton not observed. |
| 66 | 496.4 (M + 1)/ 495.51 for C22H21N7O5S | 9.05 (brs, 1H), 7.83 (d, J = 7.2 Hz, 1H), 7.72 (s, 1H), 7.39 (s, 1H), 7.34 (t, J = 8.0 Hz, 1H), 6.94-6.87 (m, 2H), 6.47 (s, 1H), 6.64 (s, 1H), 5.15 (s, 2H), 4.14 (d, J = 5.6 Hz, 2H), 3.72 (s, 3H), 3.56 (s, 3H) Exchangeable proton —NH—NH not observed. |

TABLE 1-continued

Analytical data for final compounds

| Syn. Ex. No. | Mass Spec. Found (m/z)/ Mass Spec. Calculated | $^1$H-NMR (400 M Hz, DMSO-$d_6$, unless otherwise stated) |
|---|---|---|
| 67 | 500.25 (M + 1)/ 499.54 for C23H25N5O6S | 10.05 (brs, 1H), 8.51 (s, 1H), 7.82 (q, J = 8.0, 7.6 Hz, 1H), 7.55 (brs, 1H), 7.15 (d, J = 8.0 Hz, 1H), 7.05 (d, J = 6.8 Hz, 2H), 6.75 (s, 1H), 4.11 (d, J = 5.6 Hz, 2H), 3.85 (s, 3H), 3.77 (s, 3H), 3.70 (s, 2H), 2.91 (t, J = 8.4 Hz, 1H) 2.82 (t, J = 7.6 Hz, 1H), 2.50-2.49 (s, 3H), 1.96 (q, J = 14.0, 14.0 Hz, 2H). |
| 68 | 523.1 (M + 1)/ 522.54 for C24H22N6O6S | 9.90 (brs, 1H), 8.98 (s, 1H), 7.92 (brs, 1H), 7.67 (s, 2H), 7.55-7.92 (m, 5H), 6.51-6.52 (m, 1H), 5.29 (s, 2H), 4.09 (t, J = 5.2 3H), 3.81(s, 3H) 2.76 (s, 2H). |
| 69 | 524.3 (M + 1)/ 523.56 for C25H25N5O6S | 10.05 (s, 1H), 9.06 (t, J = 5.6 Hz, 1H), 7.74 (s, 1H), 7.62 (d, J = 2.4 Hz, 1H), 7.46 (d, J = 8.4 Hz, 1H), 7.38 (s, 1H), 7.11 (d, J = 8.4 Hz, 1H), 6.86 (s, 1H), 6.74 (s, 1H) 5.37 (s, 2H), 7.12 (t, J = 1.6 Hz, 3H), 3.81 (s, 3H), 3.73 (s, 3H), 2.62 (q, J = 15.2, J = 15.2 Hz, 2H) 1.23 (t, J = 9.2 Hz, 3H) |
| 70 | 673.76 (M + H)/ 673.59 for C26H20F5N5O7S2 | 10.15 (brs, 1H), 9.01 (s, 1H), 7.80 (d, J = 6.4 Hz, 1H), 7.71 (s, 1H), 7.59 (brs, 1H), 7.31 (s, 1H), 7.16-7.12 (m, 2H), 6.74 (brs, 2H), 5.31 (s, 2H), 4.10 (d, J = 2.4 Hz, 2H), 3.84 (s, 3H), 3.77 (s, 3H). |
| 71 | 577.3 (M + 1)/ 576.62 for C29H28N4O7S | 9.60 (s, 1H), 7.53 (t, J = 8.8 Hz, 1H), 7.44 (s, 1H), 7.29 (s, 1H), 7.22 (d, J = 5.6 Hz, 1H), 7.04 (s, 1H), 7.03 (d, J = 2.0 Hz, 2H), 6.80 (s, 1H), 6.78 (s, 1H), 4.61 (s, 1H), 4.02 (s, 3H), 3.85 (t, J = 4.8 Hz, 2H), 3.79 (s, 6H), 3.66 (t, J = 4.8 Hz, 2H), 3.29 (t, J = 9.6 Hz, 2H), 3.26 (t, J = 5.2 Hz, 2H). |
| 72 | 615.2(M + 1)/ 614.69 for C28H30N4O8S2 | δ 9.59 (s, 1H), 7.51 (t, J = 8.5 Hz, 1H), 7.43 (s, 1H), 7.38-7.31 (m, 1H), 7.28 (s, 1H), 7.22 (d, J = 7.8 Hz, 1H), 7.06-6.98 (m, 2H), 6.88 (dd, J = 10.0, 16.5 Hz, 1H), 6.79 (d, J = 8.5 Hz, 2H), 6.24-6.17 (m, 2H), 4.02 (s, 3H), 3.79 (s, 6H), 3.38-3.32 (m, 4H), 3.24-3.15 (m, 4H). |
| 73 | 600.14(M + 1)/ 601.07 for C28H29ClN4O7S | δ 9.60 (br d, J = 2.1 Hz, 1H), 7.51 (t, J = 8.5 Hz, 2H), 7.44 (s, 1H), 7.38-7.31 (m, 1H), 7.29 (s, 1H), 7.21 (d, J = 7.6 Hz, 1H), 7.08-7.00 (m, 1H), 6.79 (d, J = 8.5 Hz, 2H), 4.45 (s, 2H), 4.02 (s, 3H), 3.81-3.77 (m, 6H), 3.67-3.60 (m, 4H), 3.25 (br d, J = 5.0 Hz, 2H), 2.54 (s, 2H). |
| 74 | 546.16(M + 1)/ 546.60 for C28H26N4O6S | δ 10.20-10.07 (m, 1H), 7.83 (dd, J = 1.6, 7.8 Hz, 1H), 7.72-7.59 (m, 1H), 7.46-7.39 (m, 1H), 7.38-7.32 (m, 2H), 7.28 (s, 1H), 7.21 (br d, J = 8.0 Hz, 2H), 7.13-7.01 (m, 1H), 6.52-6.51 (m, 1H), 4.61 (s, 1H), 4.16-4.11 (m, 1H), 3.97 (s, 1H), 3.87-3.82 (m, 3H), 3.81 (s, 3H), 3.68-3.63 (m, 2H), 3.30 (br s, 2H), 3.27-3.22 (m, 2H). |
| 75 | 564.2(M + 1)/ 563.63 for C29H29N3O7S | δ 8.97-8.91 (m, 1H), 8.16 (br s, 1H), 7.54-7.47 (m, 1H), 7.36-7.31 (m, 1H), 6.79 (dd, J = 2.3, 8.6 Hz, 1H), 6.55-6.51 (m, 1H), 6.50-6.42 (m, 2H), 6.18-6.14 (m, 1H), 6.13-6.09 (m, 1H), 5.75 (br d, J = 1.1 Hz, 1H), 5.70 (d, J = 2.2 Hz, 1H), 5.67 (d, J = 2.3 Hz, 1H), 5.66-5.64 (m, 1H), 5.63 (d, J = 2.3 Hz, 1H), 4.45 (br d, J = 1.6 Hz, 1H), 4.40 (br d, J = 2.2 Hz, 2H), 4.16 (br d, J = 2.9 Hz, 2H), 3.82-3.80 (m, 9H). |
| 76 | 495.0(M + 1)/ 494.53 for C23H22N6O5S | δ 12.51 (br d, J = 5.6 Hz, 1H), 9.30-9.13 (m, 1H), 9.11-8.96 (m, 1H), 8.37-8.33 (m, 1H), 7.72-7.65 (m, 2H), 7.60-7.52 (m, 1H), 7.36 (s, 1H), 7.17 (d, J = 8.3 Hz, 1H), 7.05-6.97 (m, 1H), 6.68 (s, 1H), 5.32-5.29 (m, 2H), 4.13-4.09 (m, 3H), 3.80 (s, 3H), 3.72 (s, 3H). |
| 77 | 537.3(M + 1)/ 536.62 for C23H28N4O7S2 | δ 10.18-9.92 (m, 1H), 7.81 (dd, J = 1.6, 7.9 Hz, 1H), 7.57 (br t, J = 7.6 Hz, 1H), 7.34 (d, J = 7.1 Hz, 1H), 7.16 (br d, J = 8.4 Hz, 1H), 7.06 (br t, J = 7.7 Hz, 1H), 7.01 (s, 1H), 6.77-6.66 (m, 1H), 6.01 (d, J = 16.4 Hz, 1H), 5.91 (d, J = 10.0 Hz, 1H), 3.87-3.82 (m, 3H), 3.80-3.75 (m, 4H), 3.60-3.55 (m, 2H), 3.04-2.95 (m, 1H), 2.83-2.71 (m, 2H), 2.05 (br d, J = 7.1 Hz, 2H), 1.79-1.71 (m, 2H), 1.55-1.40 (m, 2H). |
| 78 | 602.2(M + 1)/ 601.62 for C26H24FN5O7S2 | δ 10.15 (s, 1H), 7.93 (t, J = 5.9 Hz, 1H), 7.85-7.77 (m, 3H), 7.67-7.58 (m, 2H), 7.41-7.32 (m, 2H), 7.25 (s, 1H), 7.19 (d, J = 8.4 Hz, 1H), 7.13-7.07 (m, 1H), 6.79-6.71 (m, 2H), 5.33 (s, 2H), 3.85 (br d, J = 5.9 Hz, 3H), 3.83 (s, 2H), 3.79 (s, 3H). |
| 79 | 584.5(M + 1)/ 583.63 for C26H25N5O7S2 | δ 10.13 (br s, 1H), 7.89 (br t, J = 5.9 Hz, 1H), 7.82-7.73 (m, 3H), 7.63-7.47 (m, 5H), 7.23 (s, 1H), 7.21-7.01 (m, 1H), 6.74 (br d, J = 17.6 Hz, 1H), 5.31 (s, 2H), 3.92-3.81 (m, 3H), 3.78 (s, 2H), 3.41-3.33 (m, 3H) —NH protons not observed. |
| 80 | 636.0(M − 1)/ 637.61 for C26H22F3N5O7S2 | δ 10.12 (s, 1H), 8.21-8.12 (m, 1H), 7.80 (dd, J = 1.6, 7.8 Hz, 1H), 7.71-7.55 (m, 4H), 7.29 (s, 1H), 7.19 (br d, J = 7.9 Hz, 1H), 7.13-7.04 (m, 1H), 6.83-6.69 (m, 2H), 5.33 (s, 2H), 3.93 (d, J = 5.8 Hz, 2H), 3.83 (s, 3H), 3.78 (s, 3H). |

TABLE 1-continued

Analytical data for final compounds

| Syn. Ex. No. | Mass Spec. Found (m/z)/ Mass Spec. Calculated | $^1$H-NMR (400 M Hz, DMSO-$d_6$, unless otherwise stated) |
|---|---|---|
| 81 | 562.2(M + 1)/ 561.63 for C24H27N5O7S2 | δ 7.96-7.67 (m, 1H), 7.62 (s, 1H), 7.56 (br t, J = 5.4 Hz, 1H), 7.48-7.38 (m, 1H), 7.07-6.97 (m, 1H), 6.70-6.55 (m, 2H), 6.53-6.45 (m, 1H), 6.04 (br s, 1H), 5.85 (br s, 1H), 5.40-5.32 (m, 2H), 3.94-3.89 (m, 4H), 3.84-3.81 (m, 2H), 3.75-3.68 (m, 3H), 3.22-3.15 (m, 3H), 1.19-1.09 (m, 3H). |
| 82 | 686.5(M + 1)/ 685.60 for C27H20F5N5O7S2 | δ 10.03 (s, 1H), 7.69 (d, J = 6.6 Hz, 1H), 7.62 (d, J = 1.5 Hz, 1H), 7.45 (br d, J = 7.8 Hz, 2H), 7.11 (br d, J = 8.4 Hz, 1H), 6.91 (br d, J = 5.6 Hz, 1H), 6.80 (br s, 1H), 5.34 (s, 2H), 4.75 (s, 1H), 4.62 (s, 1H), 4.57 (s, 1H), 4.52 (s, 1H), 3.84 (s, 3H), 3.77-3.74 (m, 3H). |
| 83 | 619.2(M + 1)/ 618.08 for C25H23ClN6O7S2 | δ 10.13 (s, 1H), 8.71 (d, J = 2.1 Hz, 1H), 8.24 (t, J = 5.8 Hz, 1H), 8.11 (dd, J = 2.5, 8.4 Hz, 1H), 7.80 (dd, J = 1.6, 7.9 Hz, 1H), 7.68-7.58 (m, 3H), 7.26 (s, 1H), 7.20 (d, J = 8.1 Hz, 1H), 7.09 (t, J = 7.3 Hz, 1H), 6.81 (s, 1H), 6.75 (s, 1H), 5.32 (s, 2H), 3.95 (d, J = 5.8 Hz, 2H), 3.83 (s, 3H), 3.79 (s, 3H). |
| 84 | 619.1(M + 1)/ 618.08 for C25H23ClN6O7S21 | δ 10.17-10.07 (m, 1H), 8.71 (d, J = 2.1 Hz, 1H), 8.24 (t, J = 5.8 Hz, 1H), 8.11 (dd, J = 2.6, 8.4 Hz, 1H), 7.80 (dd, J = 1.5, 7.8 Hz, 1H), 7.70-7.55 (m, 3H), 7.26 (s, 1H), 7.20-7.13 (m, 1H), 7.11-7.04 (m, 1H), 6.82-6.71 (m, 2H), 5.31 (s, 2H), 3.95 (d, J = 5.9 Hz, 2H), 3.83 (s, 3H), 3.78 (s, 3H). |
| 85 | 553.5(M + 1)/ 552.56 for C25H24N6O7S | δ 9.19-8.85 (m, 1H), 8.57-8.22 (m, 1H), 8.06-7.80 (m, 1H), 7.77-7.67 (m, 1H), 7.33 (br s, 3H), 7.23-6.99 (m, 2H), 5.28 (br s, 3H), 4.15-4.05 (m, 2H), 3.86-3.71 (m, 3H), 3.19-3.13 (m, 3H), 2.75 (br d, J = 3.4 Hz, 3H). amine proton not observed. |
| 86 | 540.5(M + 1)/ 539.52 for C24H21N5O8S | δ 10.73-10.47 (m, 1H), 9.04 (br t, J = 5.3 Hz, 1H), 8.44-8.31 (m, 1H), 8.22-8.08 (m, 1H), 7.82-7.69 (m, 1H), 7.40-7.25 (m, 2H), 6.98-6.65 (m, 2H), 5.52 (s, 3H), 4.23-3.96 (m, 2H), 3.83-3.67 (m, 6H). carboxylic acid proton not observed. |
| 87 | 562.6(M + 1)/ 561.61 for C29H27N3O7S | δ 13.11-12.97 (m, 1H), 8.96 (br s, 1H), 8.16 (br s, 1H), 7.82-7.74 (m, 1H), 7.71-7.65 (m, 1H), 7.59-7.52 (m, 1H), 7.50 (s, 1H), 7.50-7.46 (m, 1H), 6.80 (d, J = 8.5 Hz, 1H), 6.61-6.58 (m, 1H), 4.87 (br s, 1H), 4.63-4.56 (m, 4H), 4.40-4.28 (m, 1H), 3.98-3.96 (m, 3H), 3.85-3.81 (m, 6H), 3.77 (br d, J = 11.1 Hz, 2H). |
| 88 | 488.3(M + 1)/ 487.53 for C23H25N3O7S | δ 10.15-9.88 (m, 1H), 8.85 (br t, J = 5.6 Hz, 1H), 7.64 (d, J = 2.3 Hz, 1H), 7.47 (br d, J = 7.9 Hz, 1H), 7.14-7.07 (m, 2H), 6.78 (s, 1H), 4.57 (s, 2H), 4.13 (s, 1H), 3.86 (s, 3H), 3.74 (s, 3H), 3.51-3.42 (m, 2H), 3.32 (s, 2H), 2.61 (q, J = 7.5 Hz, 2H), 1.15 (t, J = 7.6 Hz, 3H). |
| 89 | 502.1(M + 1)/ 501.16 for C24H27N3O7S | δ 9.97 (s, 1H), 8.85-8.61 (m, 1H), 7.64 (d, J = 2.2 Hz, 1H), 7.47 (dd, J = 2.0, 8.4 Hz, 1H), 7.15-7.07 (m, 2H), 6.77 (s, 1H), 4.54 (s, 2H), 4.09 (s, 1H), 3.86 (s, 3H), 3.75 (s, 3H), 3.51-3.44 (m, 2H), 3.22-3.10 (m, 2H), 2.61 (q, J = 7.6 Hz, 2H), 1.80-1.63 (m, 2H), 1.15 (t, J = 7.6 Hz, 3H). |
| 90 | 540.1(M + 1)/ 539.14 for C23H29N3O8S2 | δ 10.06 (s, 1H), 7.64 (d, J = 2.3 Hz, 1H), 7.51-7.41 (m, 1H), 7.24 (t, J = 5.7 Hz, 1H), 7.09 (br s, 1H), 6.80-6.57 (m, 2H), 6.05-5.90 (m, 3H), 4.54 (s, 2H), 3.86 (s, 3H), 3.74 (s, 3H), 3.54-3.44 (m, 2H), 2.96-2.87 (m, 2H), 2.60 (q, J = 7.4 Hz, 2H), 1.73 (quin, J = 6.6 Hz, 2H), 1.15 (t, J = 7.6 Hz, 3H). |
| 91 | 457.3 (M + 1)/ 456.45 for C20H17FN6O4S | δ 10.57-10.42 (m, 1H), 9.14 (t, J = 5.6 Hz, 1H), 8.64 (s, 1H), 8.23-8.19 (m, 1H), 8.04 (d, J = 1.9 Hz, 1H), 7.91 (d, J = 1.9 Hz, 1H), 7.82-7.78 (m, 1H), 7.76 (s, 1H), 7.67-7.60 (m, 1H), 7.41-7.32 (m, 1H), 7.29-7.20 (m, 1H), 4.29-4.19 (m, 2H), 4.16 (s, 1H), 2.50 (td, J = 1.8, 3.6 Hz, 3H). |
| 92 | 507.4(M + 1)/ 506.14 for C26H23FN4O4S | δ 10.91-10.69 (m, 1H), 10.42 (brs, 1H), 8.61 (dd, J = 2.3, 4.9 Hz, 1H), 8.29-8.18 (m, 1H), 8.11 (s, 1H), 7.94 (d, J = 13.5 Hz, 1H), 7.81 (br t, J = 7.5 Hz, 1H), 7.70-7.61 (m, 1H), 7.57 (s, 1H), 7.45-7.23 (m, 3H), 4.52 (s, 1H), 3.96 (dd, J = 7.9, 11.8 Hz, 1H), 3.92-3.85 (m, 1H), 3.71-3.61 (m, 1H), 3.59-3.49 (m, 1H), 3.44-3.35 (m, 1H), 2.54 (br d, J = 3.1 Hz, 1H), 2.41 (s, 3H), 2.22-2.07 (m, 1H). |
| 93 | 617.1(M − 1)/ 618.16 for C26H30N6O8S2 | δ 8.19 (br t, J = 5.3 Hz, 1H), 7.71 (s, 1H), 7.62 (d, J = 2.1 Hz, 1H), 7.58-7.53 (m, 1H), 7.43-7.35 (m, 2H), 7.14-7.05 (m, 1H), 6.88-6.71 (m, 2H), 6.70-6.64 (m, 1H), 5.99 (d, J = 16.6 Hz, 1H), 5.89 (d, J = 10.0 Hz, 1H), 5.36 (s, 2H), 4.11 (d, J = 5.6 Hz, 2H), 3.82 (s, 3H), 3.74 (s, 3H), 3.48 (d, J = 6.1 Hz, 2H), 2.59 (br d, J = 7.6 Hz, 2H), 1.14 (t, J = 7.6 Hz, 3H). amine proton not observed. |

TABLE 1-continued

Analytical data for final compounds

| Syn. Ex. No. | Mass Spec. Found (m/z)/ Mass Spec. Calculated | $^1$H-NMR (400 MHz, DMSO-$d_6$, unless otherwise stated) |
|---|---|---|
| 94 | 581.1(M + 1)/ 580.17 for C27H28N6O7S | δ 10.27-10.02 (m, 1H), 8.77 (br t, J = 4.9 Hz, 1H), 8.25 (s, 1H), 8.21-8.12 (m, 1H), 7.88 (s, 1H), 7.63 (d, J = 2.3 Hz, 1H), 7.49-7.34 (m, 1H), 7.08 (td, J = 2.3, 4.8 Hz, 1H), 6.96-6.88 (m, 1H), 6.75 (br d, J = 11.0 Hz, 1H), 5.43 (s, 2H), 4.12 (s, 1H), 3.84 (s, 6H), 3.25-3.13 (m, 4H), 2.64-2.56 (m, 2H), 1.14 (t, J = 7.6 Hz, 3H). |
| 95 | 607.2(M + 1)/ 606.19 for C29H30N6O7S | δ 10.21-9.98 (m, 1H), 8.30 (s, 1H), 7.76 (s, 1H), 7.62 (d, J = 2.1 Hz, 1H), 7.46 (br d, J = 8.1 Hz, 1H), 7.11 (br d, J = 8.6 Hz, 1H), 6.96 (s, 1H), 6.81 (s, 1H), 5.45 (s, 2H), 4.61 (s, 1H), 3.84 (s, 3H), 3.78-3.73 (m, 5H), 3.70-3.58 (m, 4H), 3.57-3.52 (m, 2H), 2.60 (q, J = 7.7 Hz, 2H), 1.14 (t, J = 7.6 Hz, 3H). |
| 96 | 578.3(M + 1)/ 577.16 for C28H27N5O7S | δ 9.61 (s, 1H), 7.83 (s, 1H), 7.71 (t, J = 8.0 Hz, 1H), 7.52-7.48 (m, 2H), 7.45 (d, J = 7.4 Hz, 1H), 6.94 (d, J = 8.5 Hz, 1H), 6.81-6.76 (m, 2H), 4.62 (s, 1H), 4.03 (s, 3H), 3.86-3.81 (m, 2H), 3.79 (s, 6H), 3.74-3.69 (m, 2H), 3.64 (s, 4H). |
| 97 | 584.1(M + 1)/ 583.12 for: C26H25N5O7S2 | δ 9.58 (s, 1H), 7.64 (d, J = 7.7 Hz, 2H), 7.50 (t, J = 8.5 Hz, 1H), 7.32 (s, 1H), 6.78 (d, J = 8.6 Hz, 2H), 4.64 (s, 1H), 3.99 (s, 3H), 3.91-3.83 (m, 2H), 3.78 (s, 6H), 3.70-3.65 (m, 2H), 3.63-3.57 (m, 2H), 3.56-3.48 (m, 2H). |
| 98 | 575.3(M + 1)/ 574.19 for C30H30N4O6S | δ 10.17-9.87 (m, 1H), 7.66 (d, J = 2.3 Hz, 1H), 7.50-7.39 (m, 2H), 7.38-7.30 (m, 1H), 7.28 (s, 1H), 7.21 (d, J = 7.8 Hz, 1H), 7.12 (br d, J = 8.5 Hz, 1H), 7.07-7.00 (m, 2H), 4.61 (s, 1H), 3.96 (s, 3H), 3.85 (t, J = 5.0 Hz, 3H), 3.78 (s, 3H), 3.69-3.62 (m, 3H), 3.26-3.22 (m, 2H), 2.65-2.57 (m, 2H), 1.16 (t, J = 7.6 Hz, 3H). |
| 99 | 536.1(M + 1)/ 535.15 for C26H25N5O6S | δ 10.06 (s, 1H), 7.78-7.59 (m, 1H), 7.51-7.42 (m, 1H), 7.35 (s, 1H), 7.17-7.07 (m, 1H), 6.95 (br d, J = 12.1 Hz, 1H), 6.77 (s, 1H), 5.39 (d, J = 9.9 Hz, 2H), 4.77 (s, 1H), 4.65 (s, 1H), 4.57 (s, 1H), 4.41 (br d, J = 19.5 Hz, 2H), 3.84 (d, J = 2.1 Hz, 3H), 3.74 (s, 3H), 2.60 (q, J = 7.5 Hz, 2H), 1.18-1.09 (m, 3H). |
| 100 | 591.3(M + 1)/ 590.18 for C30H30N4O7S | δ 9.56 (br s, 1H), 7.50 (t, J = 8.4 Hz, 1H), 7.40 (s, 1H), 7.26 (t, J = 7.8 Hz, 1H), 7.06-6.93 (m, 3H), 6.86-6.74 (m, 3H), 4.49-4.45 (m, 1H), 4.38 (s, 1H), 4.02 (s, 3H), 3.94-3.87 (m, 1H), 3.79 (s, 7H), 3.70 (s, 2H), 3.68-3.57 (m, 3H), 3.45-3.37 (m, 1H), 1.82 (quin, J = 5.7 Hz, 1H). |
| 101 | 576.1(M + 1)/ 575.17 for C30H29N3O7S | δ 9.63 (brs, 1H), 7.66 (s, 1H), 7.62 (d, J = 7.9 Hz, 1H), 7.50 (t, J = 8.5 Hz, 1H), 7.46-7.43 (m, 1H), 7.42-7.39 (m, 1H), 7.32 (d, J = 7.7 Hz, 1H), 7.06 (s, 1H), 6.79 (s, 1H), 6.77 (s, 1H), 4.51-4.44 (m, 1H), 4.42-4.35 (m, 2H), 4.02 (s, 3H), 3.79 (s, 6H), 3.28-3.23 (m, 1H), 2.90 (tt, J = 3.2, 12.1 Hz, 1H), 2.79 (dt, J = 2.7, 12.8 Hz, 1H), 1.96-1.82 (m, 2H), 1.77-1.55 (m, 2H). |
| 102 | 584.1(M + 1)/ 583.12 for C26H25N5O7S2 | δ 9.66 (br s, 1H), 7.57-7.43 (m, 2H), 7.23 (d, J = 5.5 Hz, 2H), 6.78 (d, J = 8.6 Hz, 2H), 4.63 (s, 1H), 3.98 (s, 3H), 3.90-3.81 (m, 3H), 3.78 (s, 6H), 3.71-3.62 (m, 3H), 3.25-3.18 (m, 2H). |
| 103 | 522.2(M + 1)/ 521.15 for C26H24FN5O4S | δ 10.94-10.70 (m, 1H), 10.29 (br s, 1H), 8.29 (br d, J = 6.0 Hz, 1H), 8.19-8.11 (m, 1H), 8.05 (br s, 1H), 7.83-7.74 (m, 1H), 7.72-7.62 (m, 1H), 7.56-7.51 (m, 1H), 7.45-7.34 (m, 2H), 7.32-7.26 (m, 1H), 6.91-6.82 (m, 1H), 4.64 (s, 1H), 3.88-3.79 (m, 3H), 3.70-3.59 (m, 4H), 3.57-3.46 (m, 4H). |
| 104 | 596.2(M + 1)/ 595.16 for C28H29N5O6S2 | δ 10.06 (br s, 1H), 7.65 (d, J = 2.0 Hz, 1H), 7.51-7.44 (m, 1H), 7.40-7.34 (m, 1H), 7.12 (br dd, J = 5.2, 8.1 Hz, 2H), 7.01 (br d, J = 10.0 Hz, 1H), 4.52 (s, 1H), 4.49 (s, 1H), 3.91 (s, 3H), 3.77-3.67 (m, 8H), 3.61-3.55 (m, 2H), 3.55-3.46 (m, 2H), 2.64-2.55 (m, 1H), 1.97-1.81 (m, 1H), 1.15 (t, J = 7.5 Hz, 3H). |
| 105a | 550.2(M + 1)/ 549.17 for C27H27N5O6S | δ 10.01 (br s, 1H), 7.63 (s, 1H), 7.50-7.34 (m, 2H), 7.11 (br d, J = 8.3 Hz, 1H), 6.76 (s, 1H), 6.69 (s, 1H), 5.35 (br s, 2H), 4.78-4.45 (m, 3H), 4.00-3.89 (m, 2H), 3.88-3.78 (m, 4H), 3.74 (s, 3H), 2.85-2.55 (m, 6H). |
| 105b | 550.2(M + 1)/ 549.17 for C27H27N5O6S | δ 10.28-9.89 (m, 1H), 7.63 (s, 1H), 7.52-7.36 (m, 2H), 7.11 (br d, J = 8.3 Hz, 1H), 6.76 (s, 1H), 6.69 (s, 1H), 5.35 (br s, 2H), 4.72 (s, 1H), 4.63 (s, 1H), 4.57 (s, 1H), 4.50 (s, 1H), 3.99-3.90 (m, 1H), 3.86-3.79 (m, 3H), 3.74 (s, 2H), 2.80-2.57 (m, 4H), 1.29-1.09 (m, 4H). |
| 106 | 584.4(M + 1)/ 583.12 for C26H25N5O7S2 | δ 9.55 (s, 1H), 7.91 (s, 1H), 7.56-7.45 (m, 1H), 7.22 (s, 1H), 6.95 (s, 1H), 6.78 (d, J = 8.4 Hz, 2H), 4.64 (s, 1H), 3.97 (s, 3H), 3.89-3.82 (m, 2H), 3.78 (s, 6H), 3.68-3.64 (m, 2H), 3.62-3.58 (m, 2H), 3.54-3.50 (m, 1H), 3.46-3.45 (m, 2H). |
| 107 | 526.3(M + 1)/ 525.12 for C22H27N3O8S2 | δ 8.15-8.13 (m, 1H), 7.65 (d, J = 2.3 Hz, 1H), 7.48-7.39 (m, 1H), 7.38-7.23 (m, 1H), 7.04-6.89 (m, 2H), 6.76-6.62 (m, 1H), 6.03 (s, 1H), 5.99 (s, 1H), 5.92 (d, J = 10.0 Hz, 1H) 4.55 (s, 2H), 3.86 (s, 3H), 3.71 (s, 3H), 3.50 (t, J = 5.6 Hz, 2H), 3.05 (q, J = 5.7 Hz, 2H), 2.63-2.53 (m, 2H), 1.19-1.08 (m, 3H). |

TABLE 1-continued

Analytical data for final compounds

| Syn. Ex. No. | Mass Spec. Found (m/z)/ Mass Spec. Calculated | $^1$H-NMR (400 MHz, DMSO-$d_6$, unless otherwise stated) |
|---|---|---|
| 108 | 566.1(M + 1)/ 565.13 for $C_{23}H_{27}N_5O_8S_2$ | δ 7.80 (s, 1H), 7.53-7.42 (m, 2H), 7.34 (t, J = 5.9 Hz, 1H), 6.82 (s, 1H), 6.78-6.74 (m, 3H), 5.40 (s, 2H), 3.99 (d, J = 5.9 Hz, 2H), 3.88 (s, 3H), 3.75 (s, 6H), 2.88 (q, J = 7.3 Hz, 2H), 2.07 (s, 1H), 1.09 (t, J = 7.3 Hz, 3H). |
| 109 | 512.1(M − 1)/ 513.16 for $C_{25}H_{27}N_3O_7S$ | δ 9.98 (s, 1H), 7.64 (d, J = 2.3 Hz, 1H), 7.46 (br d, J = 7.4 Hz, 1H), 7.11 (br d, J = 6.9 Hz, 2H), 6.76 (s, 1H), 4.65-4.56 (m, 2H), 4.48 (s, 1H), 4.43 (s, 1H), 4.21 (tt, J = 2.0, 4.3 Hz, 1H), 3.86 (s, 3H), 3.77-3.68 (m, 3H), 3.65-3.56 (m, 1H), 3.52-3.34 (m, 2H), 2.60 (q, J = 7.5 Hz, 2H), 2.17-1.90 (m, 2H), 1.18-1.11 (m, 3H). |
| 110 | 514.2(M + 1)/ 513.16 for $C_{25}H_{27}N_3O_7S$ | δ 9.97 (s, 1H), 7.64 (d, J = 2.2 Hz, 1H), 7.45 (br s, 1H), 7.18-7.05 (m, 2H), 6.76 (s, 1H), 4.68-4.58 (m, 2H), 4.49-4.46 (m, 1H), 4.42 (s, 1H), 4.24-4.18 (m, 1H), 3.86 (s, 3H), 3.75 (d, J = 1.3 Hz, 4H), 3.32 (s, 14H), 2.61 (q, J = 7.6 Hz, 2H), 1.15 (t, J = 7.6 Hz, 4H). |
| 111 | 538.3 (M + 1)/ 537.20 for $C_{27}H_{31}N_5O_5S$ | δ 9.73 (s, 1H), 7.69-7.61 (m, 1H), 7.46 (s, 1H), 7.39-7.33 (m, 1H), 7.31 (s, 1H), 7.23 (d, J = 8.0 Hz, 1H), 7.06 (d, J = 1.8 Hz, 1H), 7.03 (s, 1H), 4.61 (s, 1H), 4.02 (s, 3H), 3.88-3.82 (m, 2H), 3.69-3.64 (m, 2H), 3.34 (br s, 3H), 3.28-3.24 (m, 3H), 1.76 (br d, J = 8.5 Hz, 2H), 1.66-1.59 (m, 2H), 1.48 (br d, J = 11.8 Hz, 1H), 1.24-1.14 (m, 4H). |
| 112 | 552.2 (M + 1)/ 551.22 for $C_{28}H_{33}N_5O_5S$ | δ 10.09-9.91 (m, 1H), 7.49-7.41 (m, 1H), 7.40-7.27 (m, 2H), 7.23 (br d, J = 7.3 Hz, 1H), 7.10-7.00 (m, 2H), 4.62 (s, 1H), 4.03 (s, 3H), 3.85 (br d, J = 4.8 Hz, 2H), 3.82-3.69 (m, 2H), 3.69-3.63 (m, 2H), 3.27-3.19 (m, 2H), 2.84 (s, 3H), 1.77-1.68 (m, 2H), 1.65-1.50 (m, 4H), 1.44-1.31 (m, 2H), 1.29-1.19 (m, 2H), 1.11-1.09 (m, 1H). |
| 113 | 578.25 (M + H)/ 577.16 for $C_{28}H_{27}N_5O_7S$ | δ 10.36-10.31 (m, 1H), 7.73-7.68 (m, 1H), 7.65-7.61 (m, 1H), 7.53-7.44 (m, 2H), 7.44-7.35 (m, 1H), 7.17-7.10 (m, 1H), 6.83-6.74 (m, 2H), 4.63 − (S, 1H), 4.08 (s, 3H), 3.89-3.85 (m, 2H), 3.78 (br s, 6H), 3.70-3.65 (m, 2H), 3.27-3.21 (m, 2H) (2H merged with solvent peak) |
| 114 | 576.32 (M + H)/ 575.18 for $C_{29}H_{29}N_5O_6S$ | 1H NMR (400 MHz, METHANOL-d4) δ = 7.80 (d, J = 2.2 Hz, 1H), 7.72 (s, 1H), 7.58 (d, J = 8.2 Hz, 1H), 7.46 (dd, J = 2.1, 8.7 Hz, 1H), 7.42-7.38 (m, 1H), 7.35 (br s, 1H), 7.18-7.12 (m, 1H), 7.10-7.04 (m, 1H), 4.15 (s, 3H), 4.07-4.04 (m, 1H), 4.04-3.96 (m, 2H), 3.85 (s, 3H), 3.84-3.78 (m, 2H), 3.38-3.34 (m, 4H), 2.72-2.62 (m, 2H), 1.24 (t, J = 7.6 Hz, 3H) (exchangeable NH proton not observed) |
| 115 | 593.20 (M + H)/ 592.16 for $C_{29}H_{28}N_4O_8S$ | 1H NMR (400 MHz, METHANOL-d4) δ = 7.50 (t, J = 8.5 Hz, 1H), 7.23 (s, 1H), 6.99 (s, 1H), 6.80-6.74 (m, 3H), 6.67-6.61 (m, 1H), 6.50 (t, J = 2.1 Hz, 1H), 4.14 (s, 3H), 4.02-3.96 (m, 2H), 3.89 (s, 6H), 3.82-3.76 (m, 2H), 3.31-3.27 (m, 2H), 3.26-3.22 (m, 2H) (2H exchangeable protons not observed for NH and OH) |
| 116 | 550.40 (M + H)/ 549.14 for $C_{23}H_{27}N_5O_7S_2$ | δ 10.02 (br s, 1H), 7.80 (s, 1H), 7.62 (d, J = 2.3 Hz, 1H), 7.45 (s, 2H), 7.27 (t, J = 5.9 Hz, 1H), 7.10 (br d, J = 6.6 Hz, 1H), 6.85 (br s, 1H), 6.79-6.68 (m, 1H), 5.39 (s, 2H), 4.01 (d, J = 5.9 Hz, 2H), 3.82 (s, 3H), 3.74 (s, 3H), 2.81 (s, 3H), 2.64-2.54 (m, 2H), 1.14 (t, J = 7.6 Hz, 3H) |
| 117 | 537.47 (M + H)/ 536.21 for $C_{28}H_{32}N_4O_5S$ | δ 10.47-10.38 (m, 1H), 7.50 (s, 1H), 7.39-7.29 (m, 2H), 7.24 (br d, J = 8.1 Hz, 1H), 7.08-7.01 (m, 2H), 4.61 (s, 1H), 4.04 (s, 3H), 3.90-3.82 (m, 2H), 3.72-3.64 (m, 2H), 3.51-3.37 (m, 3H), 3.29-3.19 (m, 4H), 2.08-1.97 (m, 1H), 1.91-1.82 (m, 2H), 1.72-1.64 (m, 2H), 1.62-1.58 (m, 1H), 1.33-0.99 (m, 4H). |
| 118 | 584.00 (M + H)/ 583.12 for $C_{26}H_{25}N_5O_7S_2$ | δ 9.73 (s, 1H), 7.67 (d, J = 1.0 Hz, 1H), 7.51 (t, J = 8.4 Hz, 1H), 7.27 (d, J = 0.9 Hz, 1H), 6.80 (s, 1H), 6.78 (s, 1H), 6.56 (s, 1H), 4.61 (s, 1H), 4.01 (s, 3H), 3.88-3.83 (m, 2H), 3.78 (s, 6H), 3.70-3.63 (m, 2H), 3.43-3.37 (m, 2H), 2.09-2.06 (m, 2H). |
| 119 | 578.40 (M + H)/ 577.16 for $C_{28}H_{27}N_5O_7S$ | δ 8.32 (d, J = 5.9 Hz, 1H), 7.87 (s, 1H), 7.70-7.37 (m, 4H), 6.89 (dd, J = 2.3, 6.0 Hz, 1H), 6.79 (d, J = 8.5 Hz, 2H), 4.63 (s, 1H), 4.01 (s, 3H), 3.87-3.81 (m, 2H), 3.78 (s, 6H), 3.65-3.61 (m, 2H), 3.59-3.55 (m, 2H), 3.54-3.50 (m, 2H). |
| 120 | 561.40 (M + H)/ 560.17 for $C_{29}H_{28}N_4O_6S$ | δ 8.17 (s, 1H), 7.86 (br s, 1H), 7.44 (br t, J = 8.4 Hz, 2H), 7.37-7.28 (m, 1H), 6.99 (dd, J = 2.0, 8.4 Hz, 1H), 6.93 (s, 2H), 6.81 (d, J = 7.6 Hz, 1H), 6.73 (d, J = 8.5 Hz, 1H), 5.75 (s, 1H), 4.59 (s, 2H), 3.86-3.78 (m, 2H), 3.66-3.60 (m, 6H), 3.28-3.24 (m, 2H), 3.23-3.17 (m, 2H), 2.28-2.25 (m, 3H). |
| 121 | 418.40 (M + 1)/ 417.53 for $C_{20}H_{27}N_5O_3S$ | δ 9.46 (broad s, 1H), 7.85 (d, J = 2.0 Hz, 1H), 7.47 (d, J = 1.6 Hz, 1H), 6.95 (s, 1H), 6.46 (s, 1H), 6.28 (t, J = 2.0 Hz, 1H), 5.39 (s, 2H), 3.86 (s, 3H), 3.82 (s, 3H), 3.23 (d, J = 6.0 Hz, 2H), 1.98-1.86 (m, 3H), 1.66-1.56 (m, 3H), 1.28-1.08 (m, 5H). |

TABLE 1-continued

Analytical data for final compounds

| Syn. Ex. No. | Mass Spec. Found (m/z)/ Mass Spec. Calculated | $^1$H-NMR (400 M Hz, DMSO-$d_6$, unless otherwise stated) |
|---|---|---|
| 122 | 416.2 (M + 1)/ 415.44 for $C_{19}H_{18}FN_5O_3S$ | δ 10.26 (s, 1H), 7.83 (d, J = 2.4 Hz, 1H), 7.70-7.63 (m, 2H), 7.46 (s, 1H), 7.45-7.39 (m, 1H), 7.28 (t, J = 6.8 Hz, 1H), 6.91 (broad s, 1H), 6.36 (broad s, 1H), 6.27 (t, J = 2.0 Hz, 1H), 5.36 (s, 2H), 3.81 (s, 3H), 3.56 (s, 3H). |
| 123 | 458.2 (M + 1)/ 457.51 for $C_{21}H_{23}N_5O_5S$ | δ 8.89 (s, 1H), 7.83 (d, J = 2.0 Hz, 1H), 7.47-7.41 (m, 2H), 6.88 (s, 1H), 6.74 (d, J = 8.4 Hz, 2H), 6.39 (s, 1H), 6.27 (s, 1H), 5.36 (s, 2H), 3.75 (s, 3H), 3.74 (s, 3H), 3.71 (s, 3H), 3.70 (s, 3H). |
| 124 | 402.2 (M + 1)/ 401.42 for C18H16FN5O3S | δ 12.71 (s, 1H), 10.23 (s, 1H), 7.83 (d, J = 2.0 Hz, 1H), 7.72-7.63 (m, 2H), 7.47 (d, J = 1.6 Hz, 1H), 7.43-7.39 (m, 1H), 7.31-7.26 (s, 1H), 6.63 (s, 1H), 6.37 (s, 1H), 6.28 (t, J = 2.0 Hz, 1H), 5.37 (s, 2H), 3.64 (s, 3H). |
| 125 | 444.2 (M + 1)/ 443.48 for $C_{20}H_{21}N_5O_5S$ | δ 12.38 (s, 1H), 8.81 (s, 1H), 7.79 (s, 1H), 7.43 (s, 1H), 7.38 (t, J = 8.4 Hz, 1H), 6.68 (d, J = 8.4 Hz, 2H), 6.56 (s, 1H), 6.37 (s, 1H), 6.24 (s, 1H), 5.33 (s, 2H), 3.74 (s, 3H), 3.71 (s, 3H), 3.70 (s, 3H). |
| 126 | 430.2 (M + 1)/ 429.50 for $C_{20}H_{23}N_5O_4S$ 429.50 | δ 10.41 (broad s, 1H), 8.72 (s, 1H), 8.11 (s, 1H), 7.03 (s, 1H), 6.82 (s, 1H), 5.52 (s, 2H), 3.91 (s, 3H), 3.36-3.34 (m, 1H), 3.17 (d, J = 3.2 Hz, 1H), 2.01-1.92 (m, 1H), 1.85 (d, J = 12.0 Hz, 2H), 1.66-1.53 (m, 3H), 1.28-1.05 (m, 5H). |
| 127 | 405.07 (M + 1)/ 404.16 for $C_{18}H_{24}N_6O_3S$ | (400 MHz, MeOH-d4) δ 7.79 (d, J = 2.0 Hz, 1H), 7.58 (d, J = 1.6 Hz, 1H), 6.62-6.57 (m, 1H), 6.39 (t, J = 2.0 Hz, 1H), 5.97 (broad s, 1H), 5.36 (s, 2H), 4.00 (s, 3H), 3.14 (d, J = 4.0 Hz, 2H), 2.07-1.97 (m, 2H), 1.73-1.63 (m, 3H), 1.37-1.07 (m, 6H). |
| 128 | 434.55 (M + 1)/ 433.53 for $C_{20}H_{27}N_5O_4S$ | δ 8.36 (broad s, 2H), 7.92 (d, J = 2.0 Hz, 1H), 6.66 (s, 1H), 6.54 (s, 1H), 6.37 (d, J = 2.4 Hz, 1H), 5.37 (s, 2H), 4.01 (s, 2H), 3.79 (s, 3H), 2.94 (d, J = 6.0 Hz, 2H), 1.86 (d, J = 12.4 Hz, 2H), 1.79-1.76 (m, 1H), 1.61-1.53 (m, 3H), 1.24-1.05 (m, 3H), 0.94 (q, J = 11.2 Hz, 2H). NH proton not observed. |
| 129 | 490.10 (M + 1)/ 489.59 for C23H31N5O5S | δ 10.38 (s, 1H), 8.11 (t, J = 5.6 Hz, 1H), 7.79 (d, J = 2.0 Hz, 1H), 6.92 (s, 1H), 6.78 (s, 1H), 6.15 (d, J = 2.4 Hz, 1H), 5.39 (s, 2H), 4.19 (d, J = 5.6 Hz, 2H), 3.90 (s, 3H), 3.36 (d, J = 6.0 Hz, 2H), 2.09 (q, J = 7.6 Hz, 2H), 2.02-1.93 (m, 1H), 1.86 (d, J = 11.2 Hz, 2H), 1.68-1.54 (m, 3H), 1.29-1.02 (m, 5H), 0.99 (t, J = 7.6 Hz, 3H). 1H NMR indicates single isomer and the structure was further confirmed from its nOe study |
| 130 | 434.15 (M + 1)/ 433.53 for C20H27N5O4S | δ 10.41 (broad s, 1H), 7.95 (broad s, 2H), 7.91 (s, 1H), 7.58 (s, 1H), 6.92 (s, 1H), 6.83 (s, 1H), 5.48 (s, 2H), 3.91 (merged s, 5H), 3.37 (merged d, J = 5.6 Hz, 2H), 2.04-1.91 (m, 1H), 1.86 (d, J = 12.4 Hz, 2H), 1.61 (d, J = 12.4 Hz, 2H), 1.59-1.51 (m, 1H), 1.29-1.04 (m, 5H). |

Additional compounds, which can be prepared using methods disclosed herein and known to one of ordinary skill in the art and using readily obtainable or commercially available starting materials, include the following:

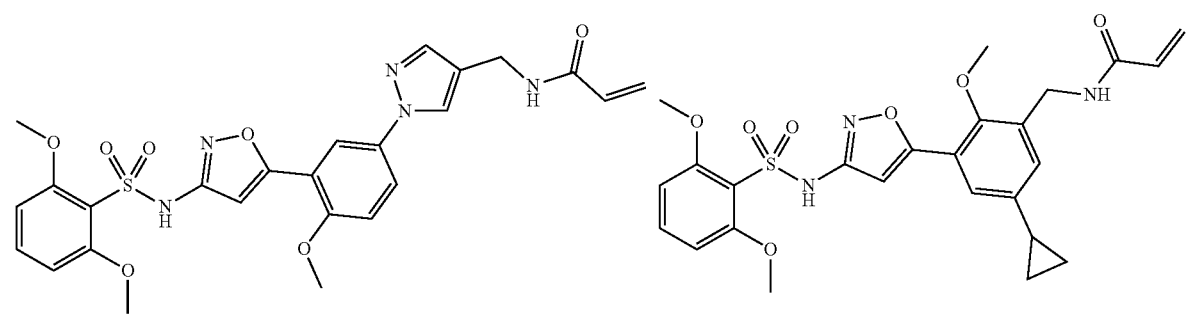

449 450
-continued
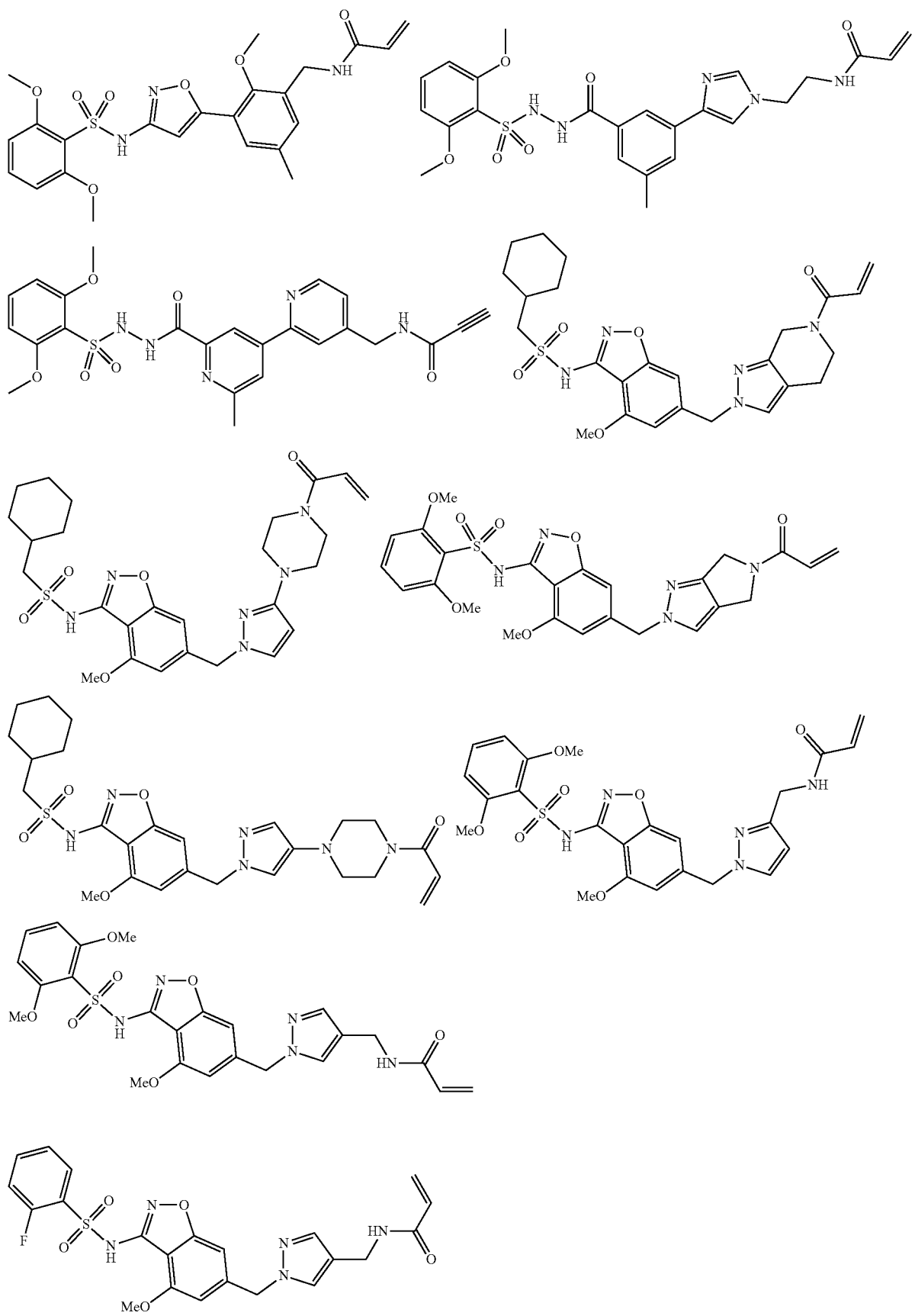

-continued
| 451 | 452 |
|---|---|
| 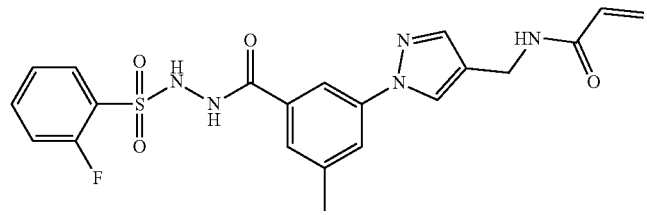 | |
| 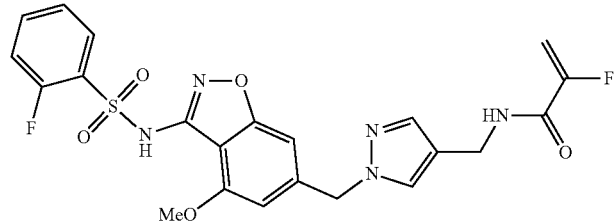 | |
| 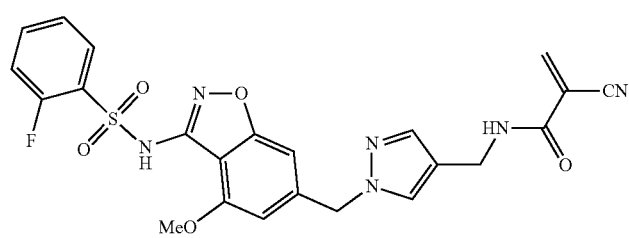 | |
| 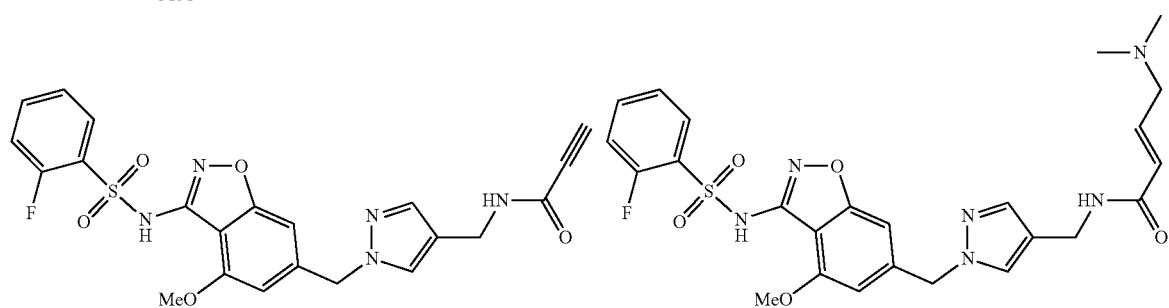 | |
| 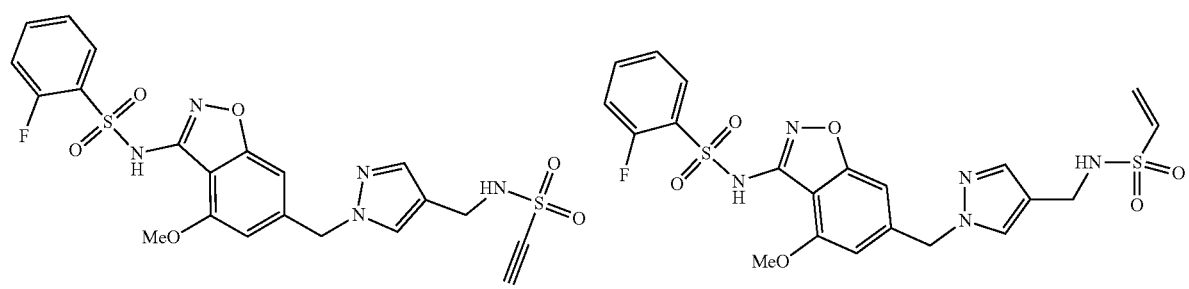 | |
| 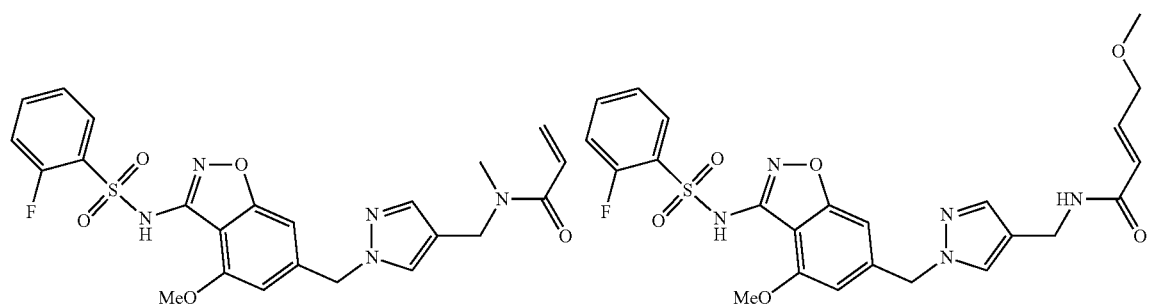 | |

-continued
| 453 | 454 |
|---|---|
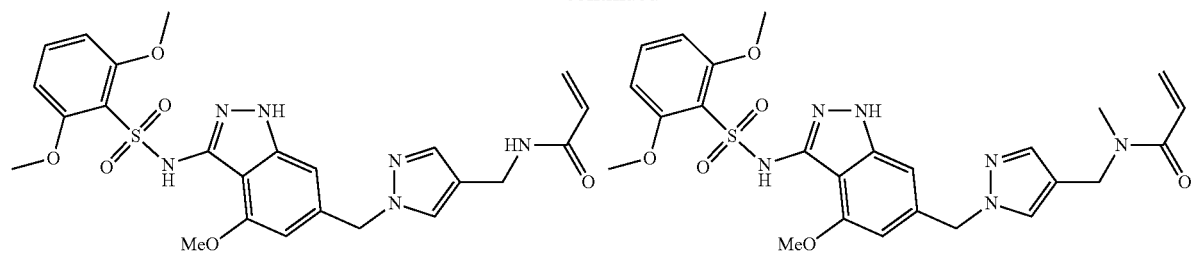
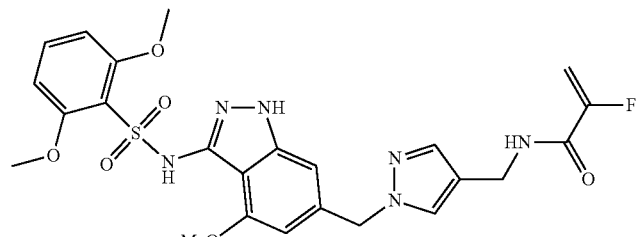
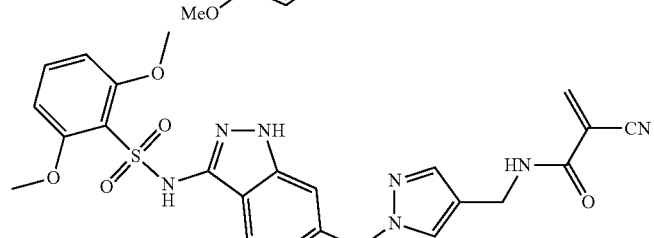
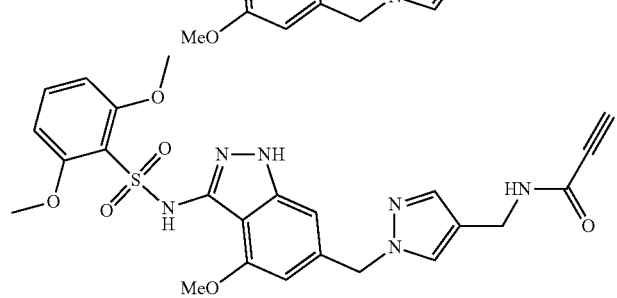
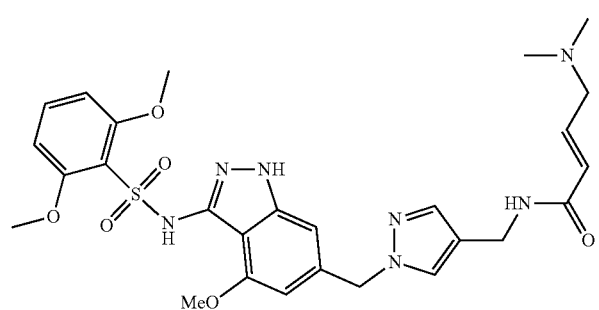
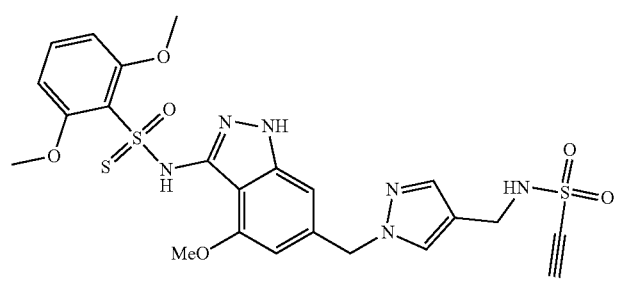

455
456
-continued
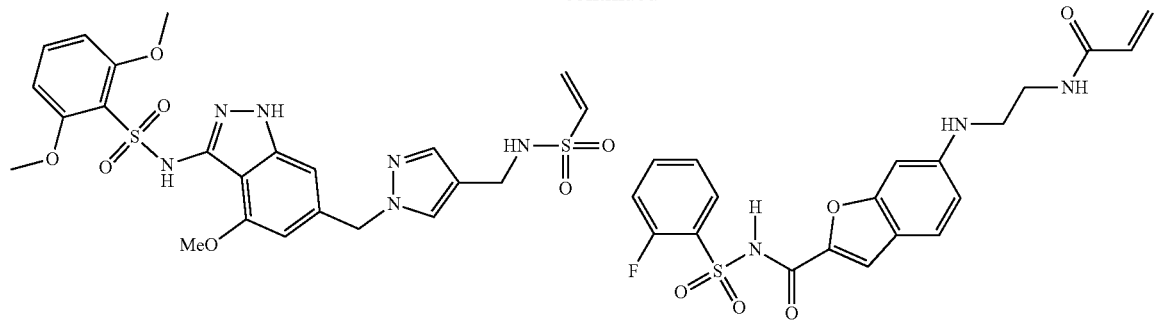
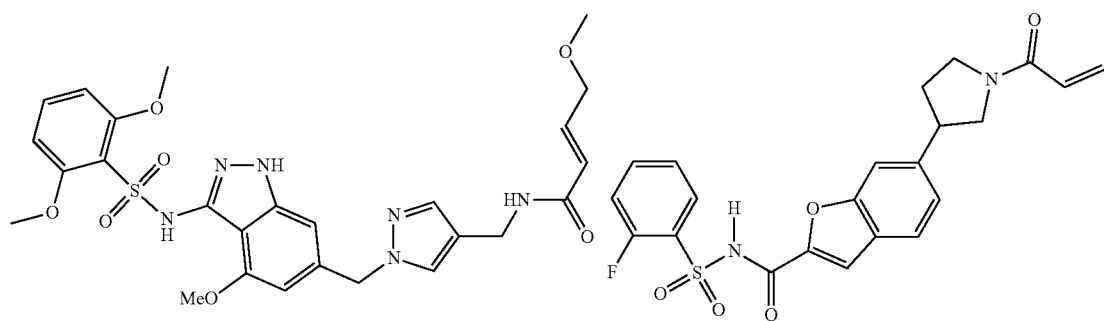
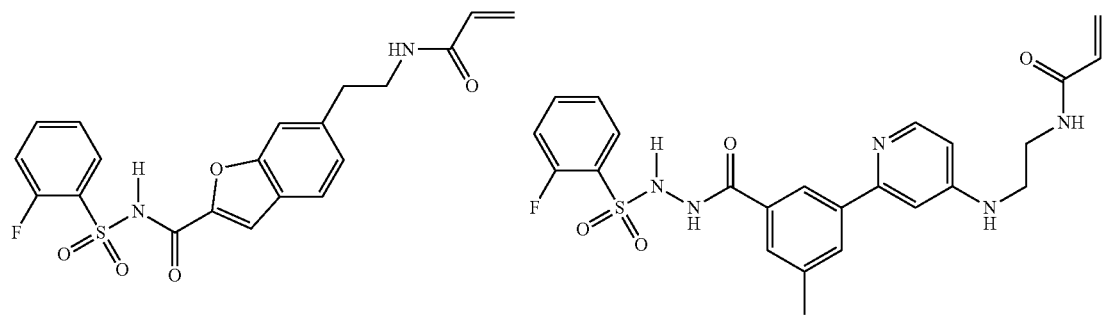
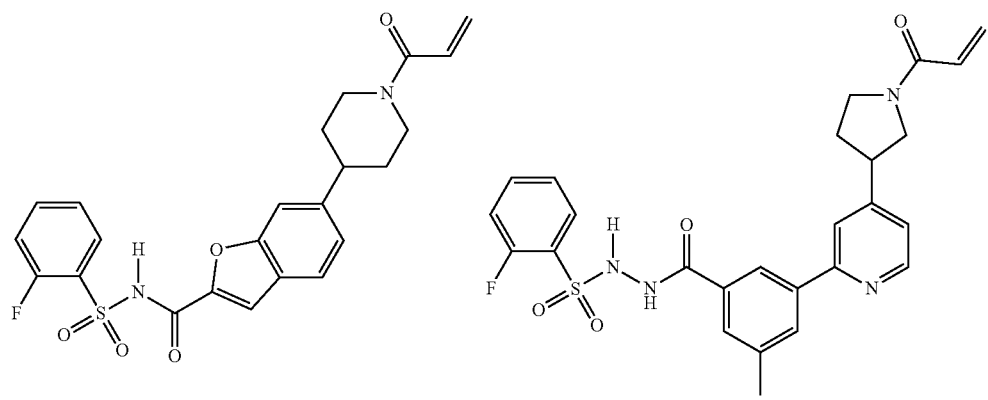

457 458
-continued
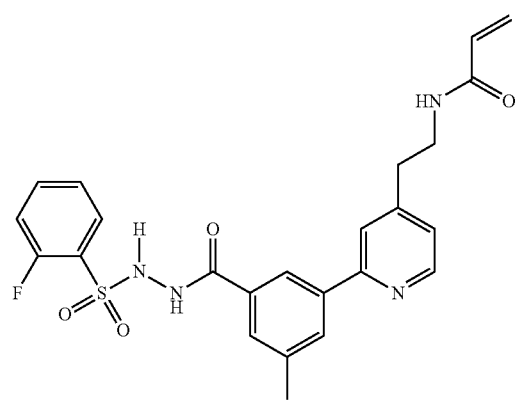
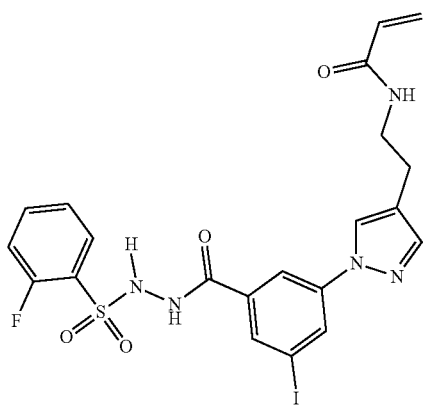
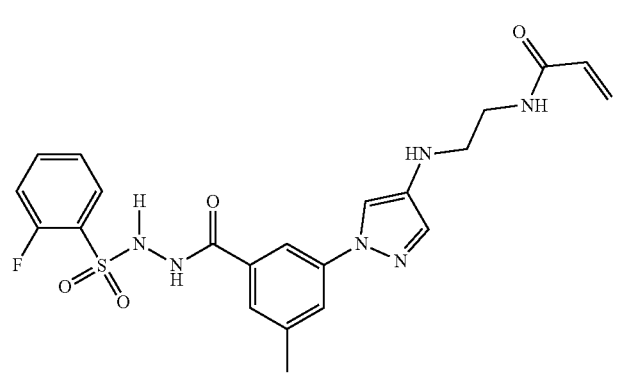
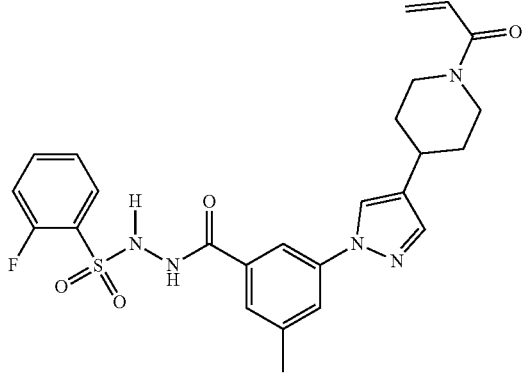
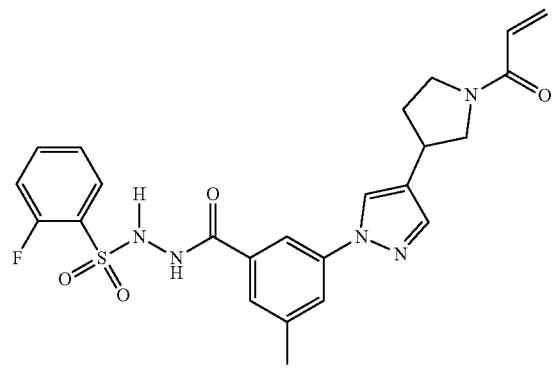
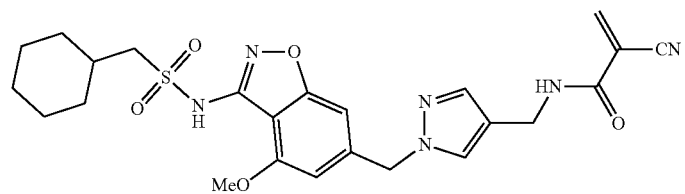
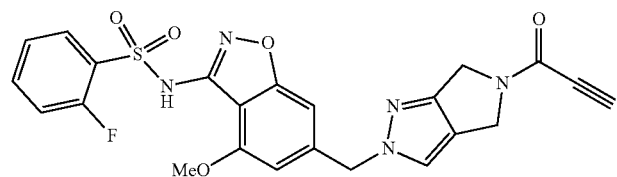

-continued
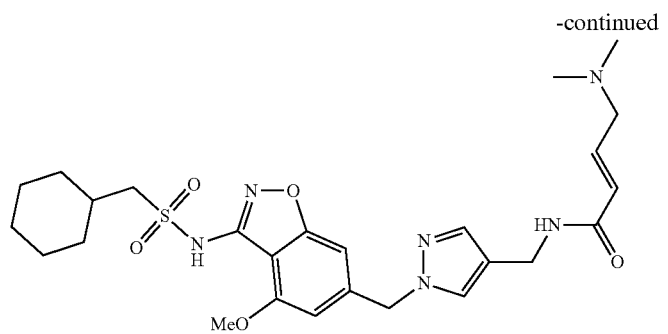
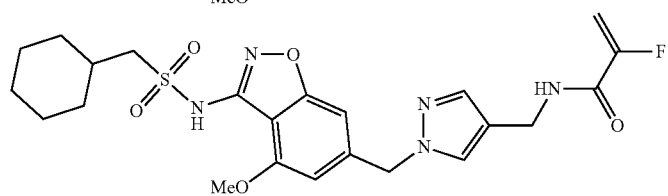
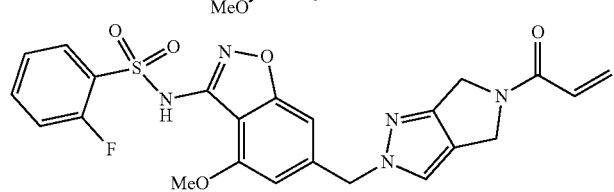
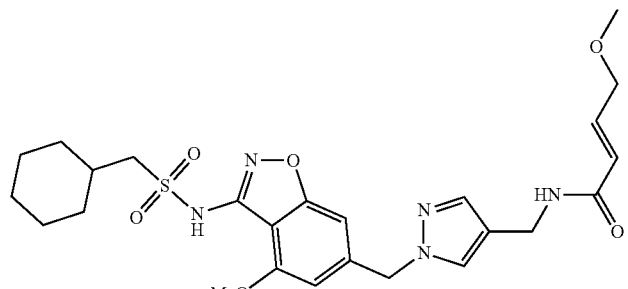
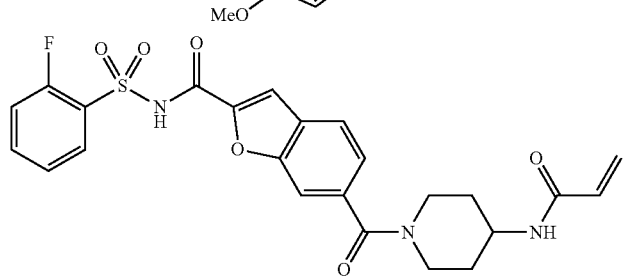
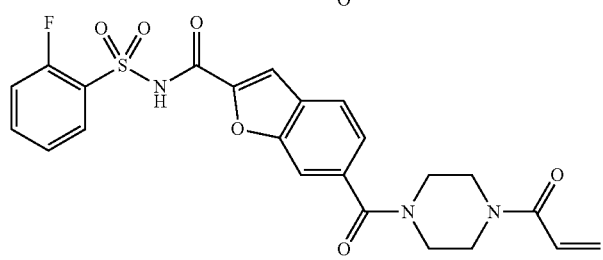
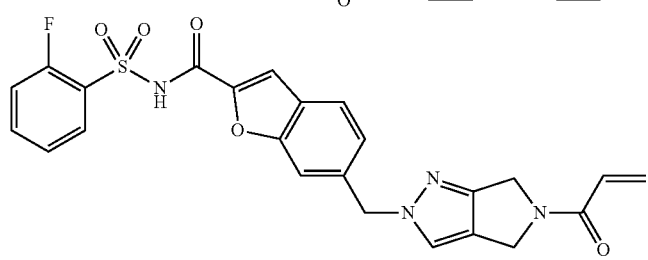

461
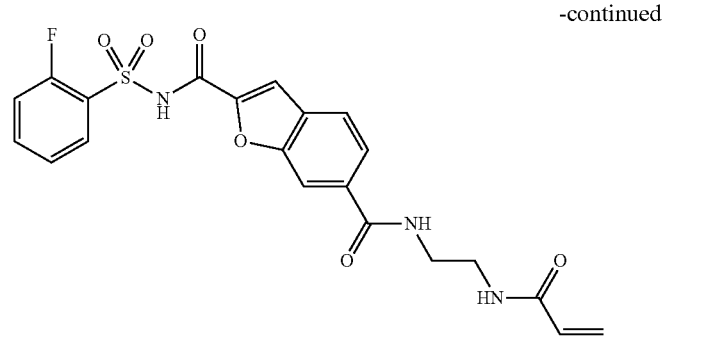
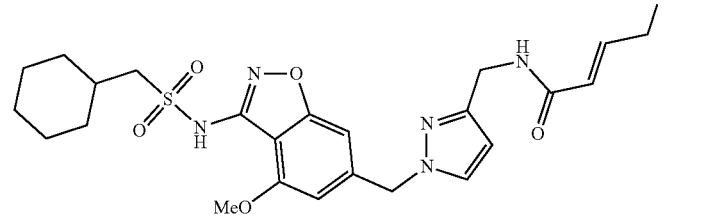
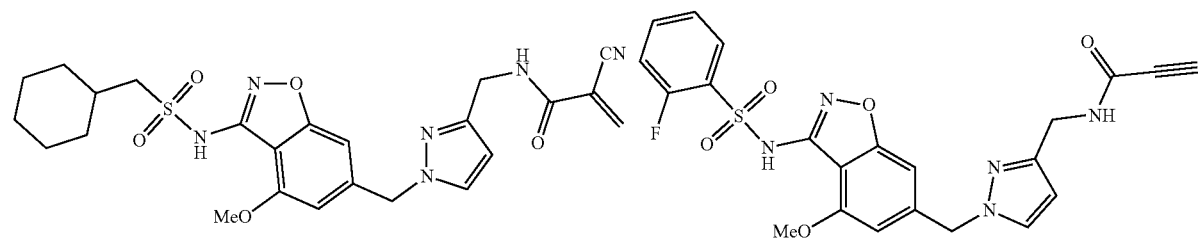
462
-continued
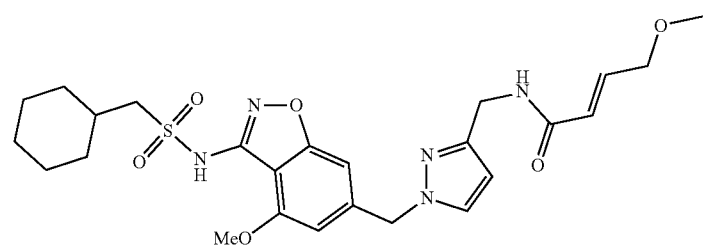
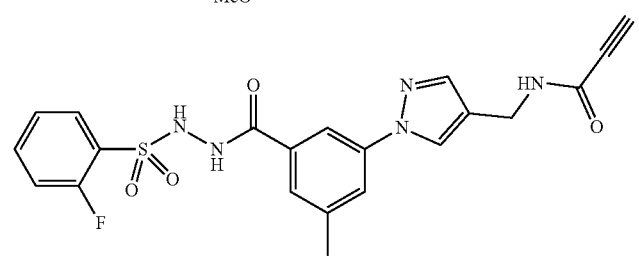
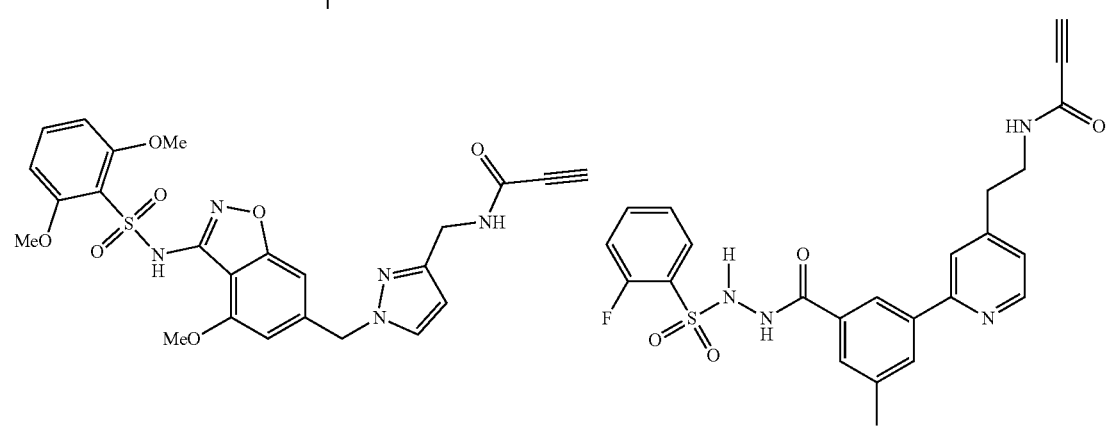

463 464
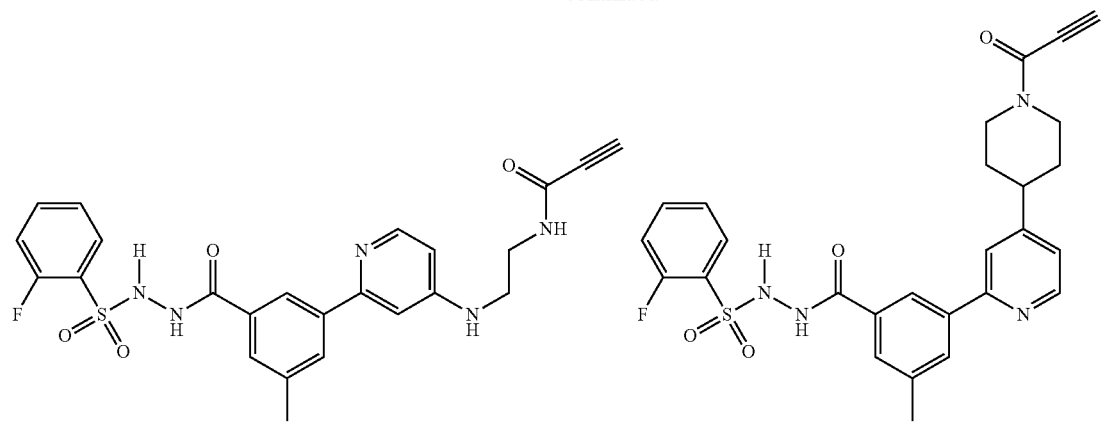
-continued
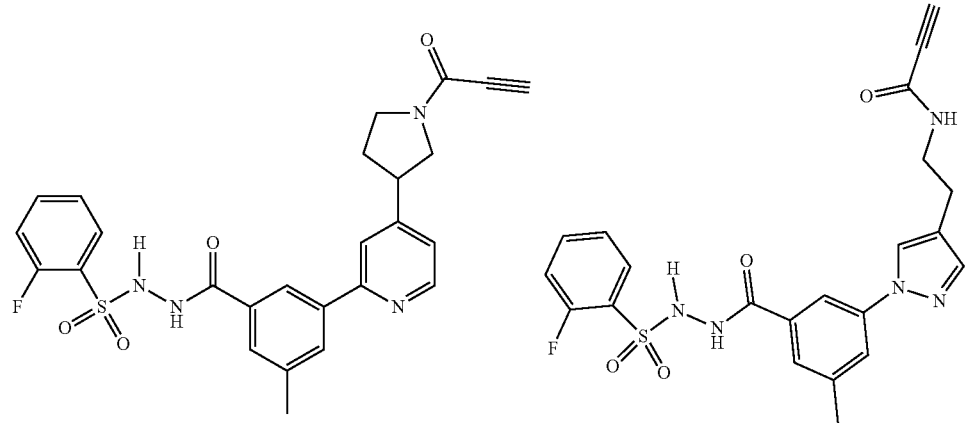
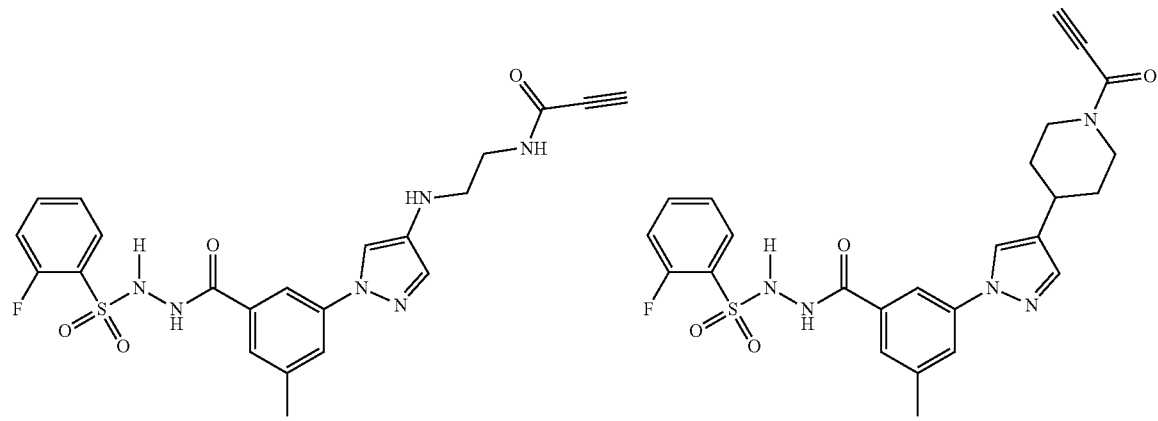
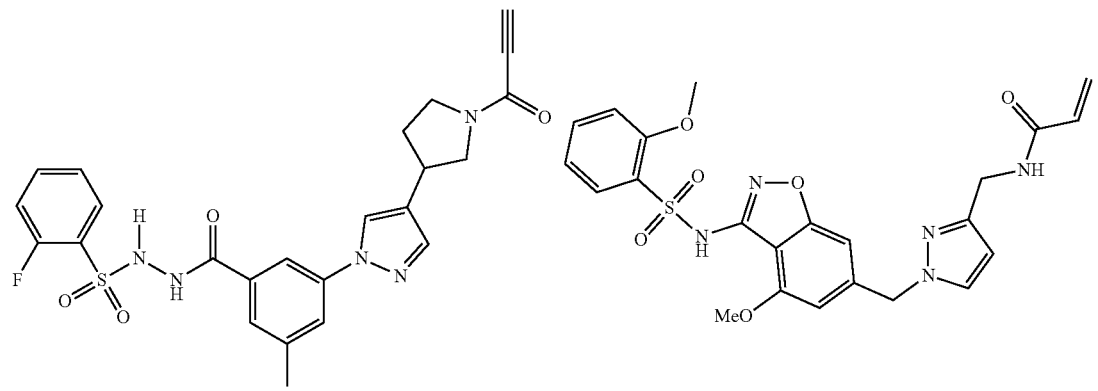

-continued
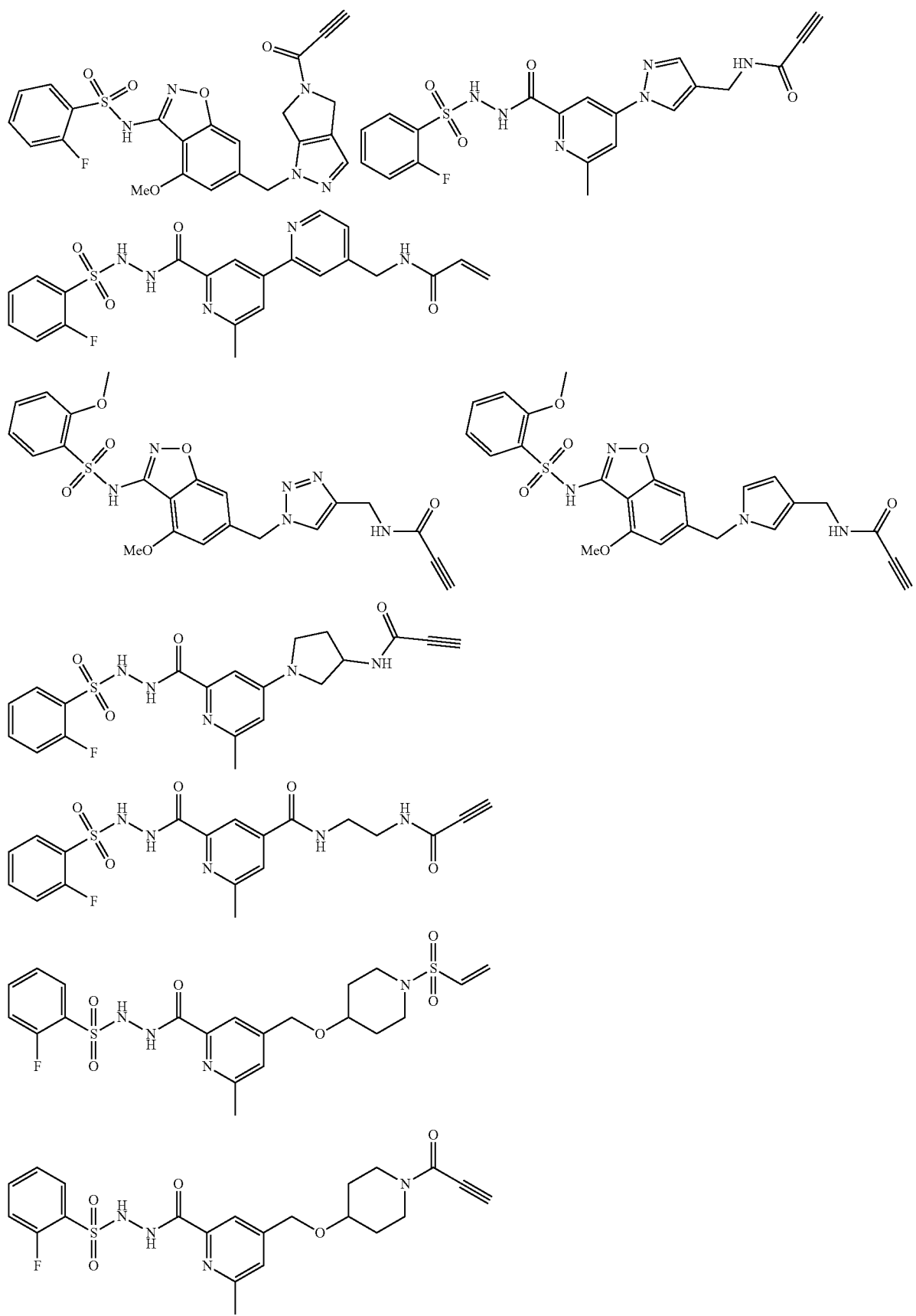

467
-continued
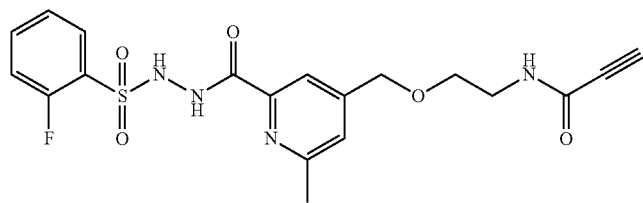
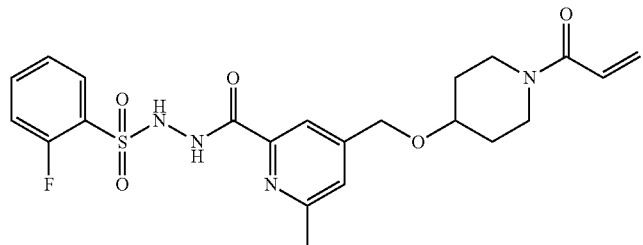
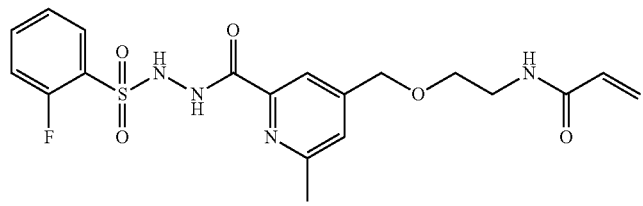
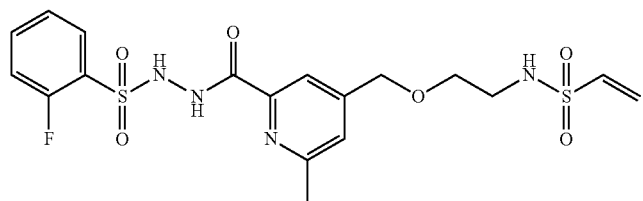
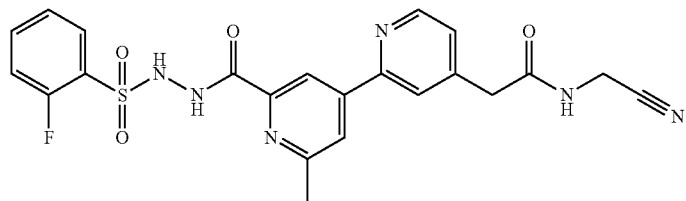
468
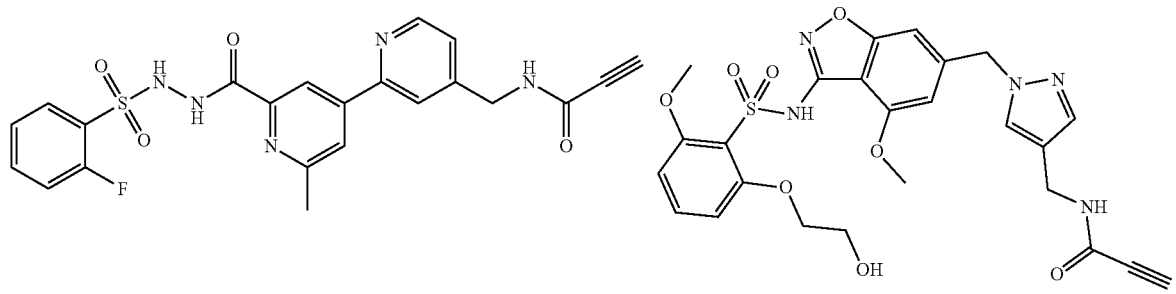
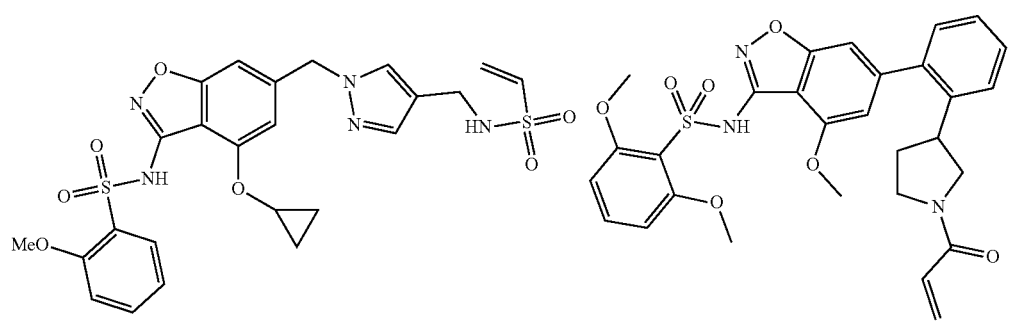

-continued
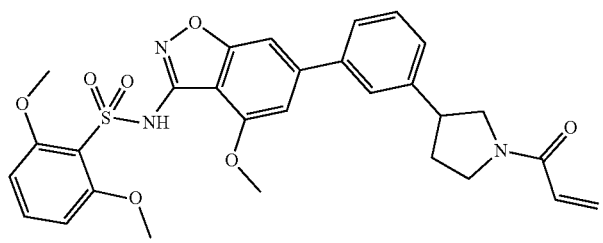
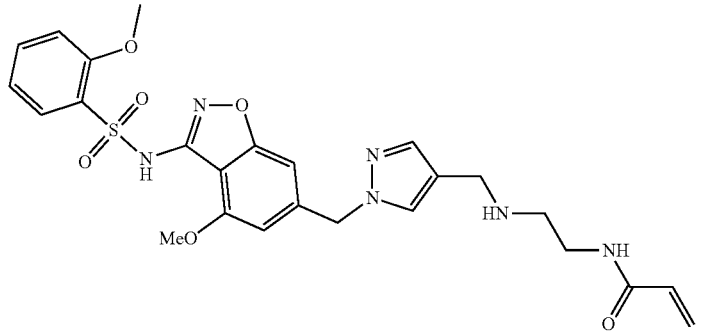
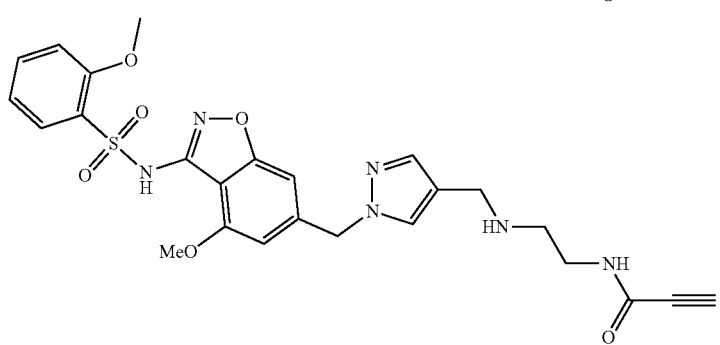
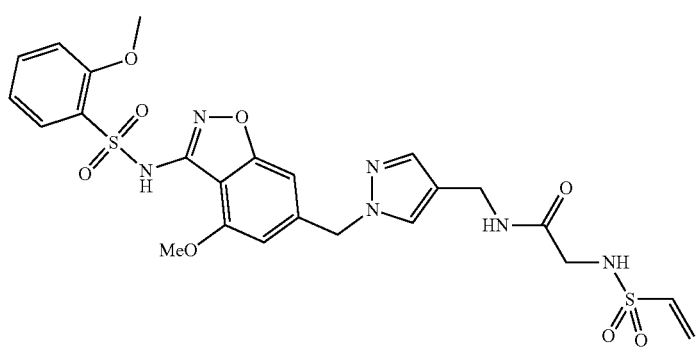
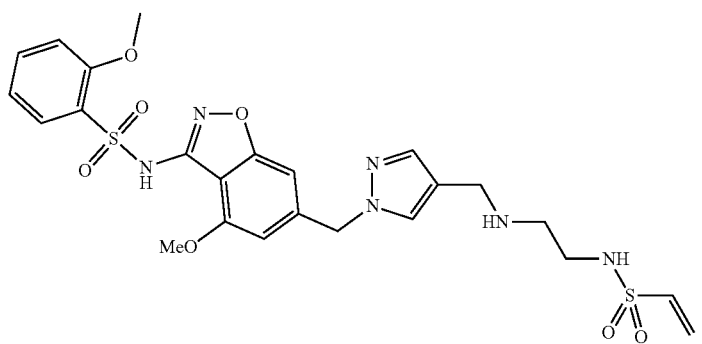

-continued
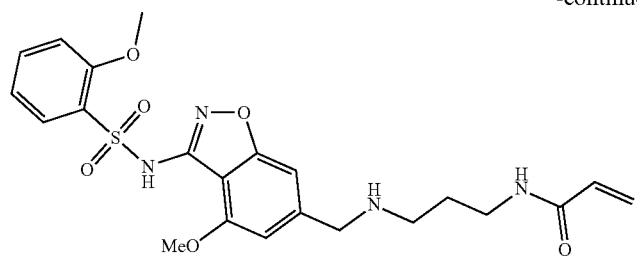
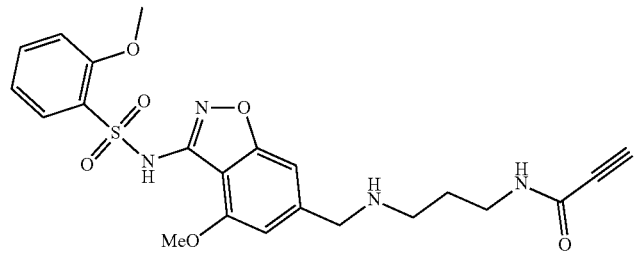
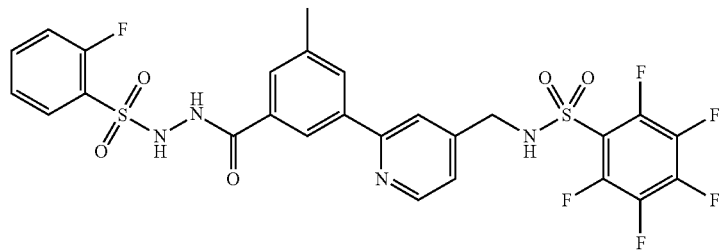
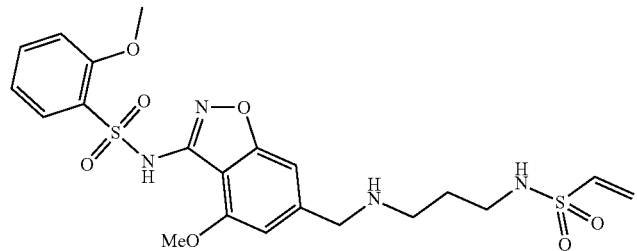
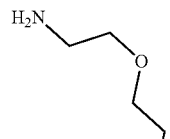
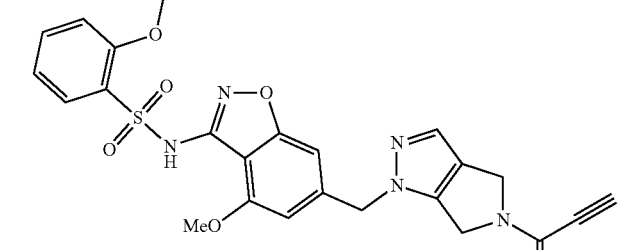
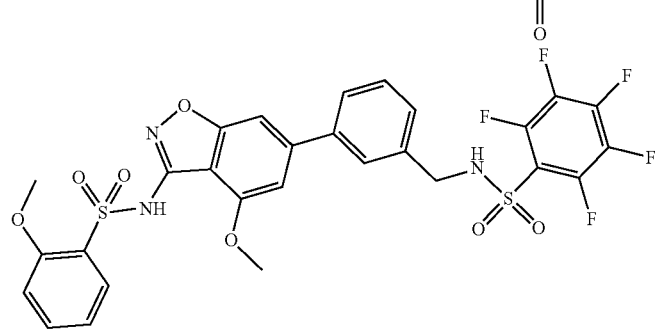

473
474
-continued
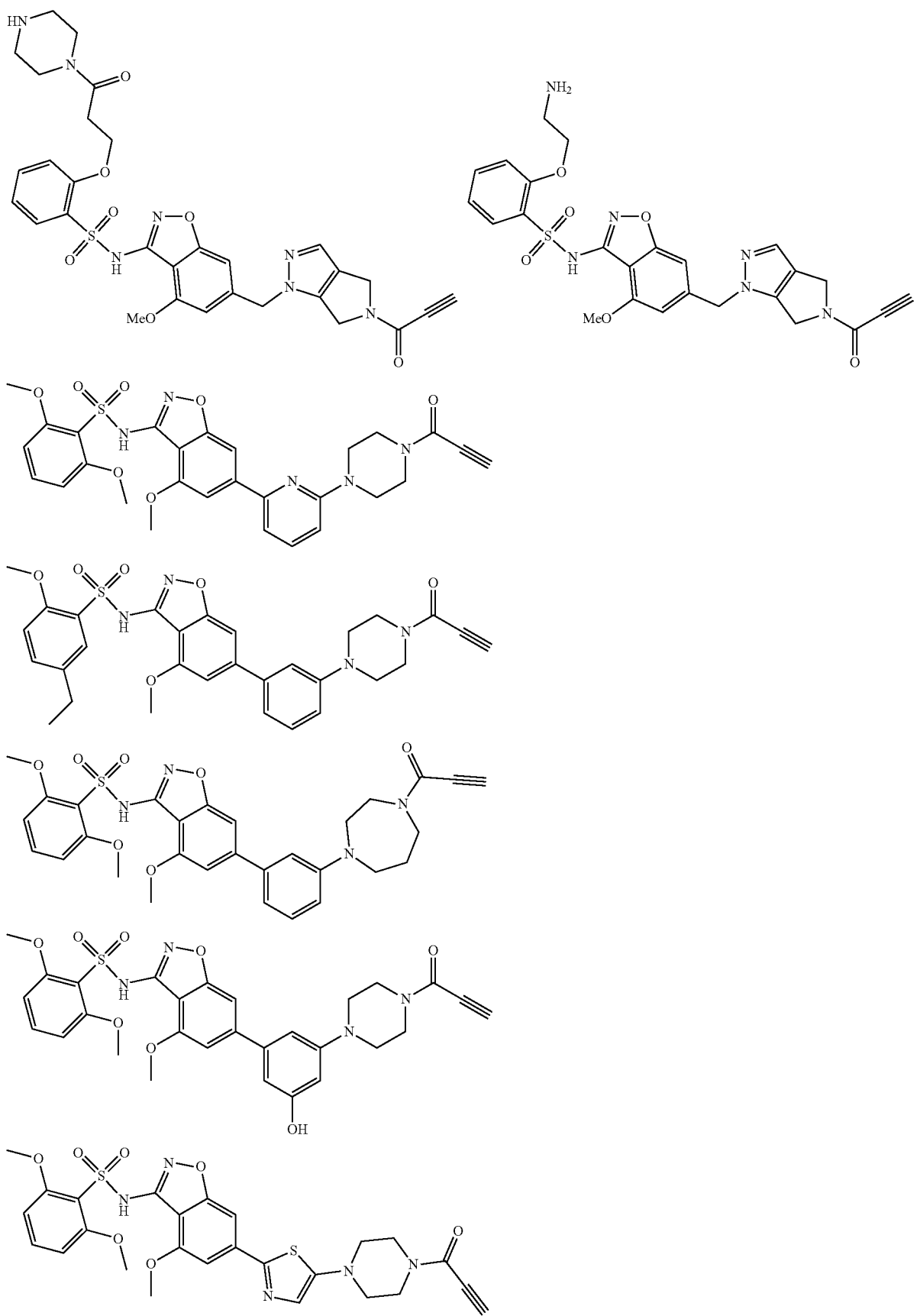

475
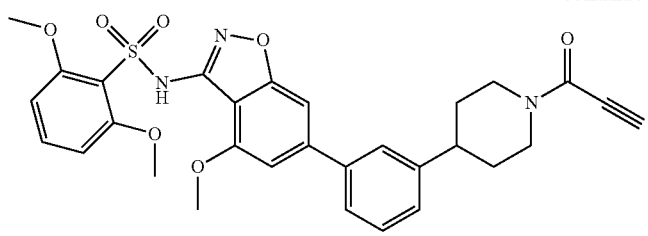
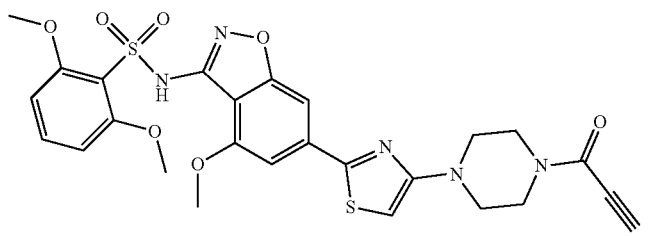
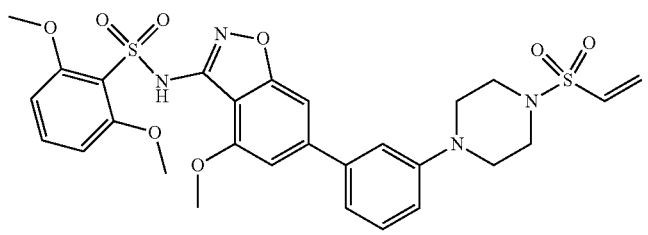
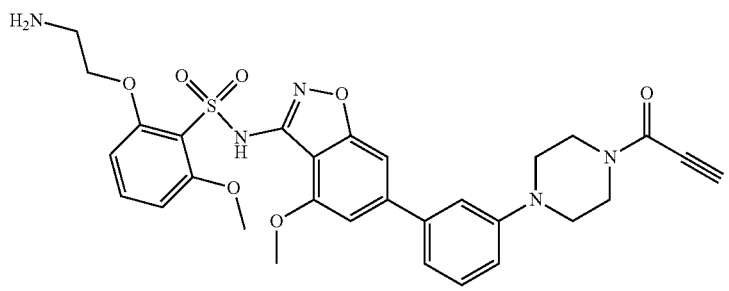
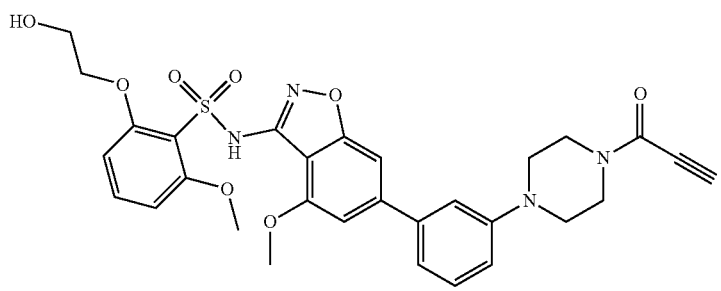
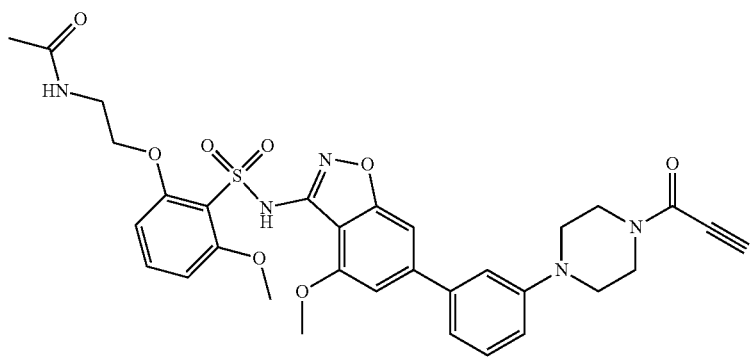
476
-continued

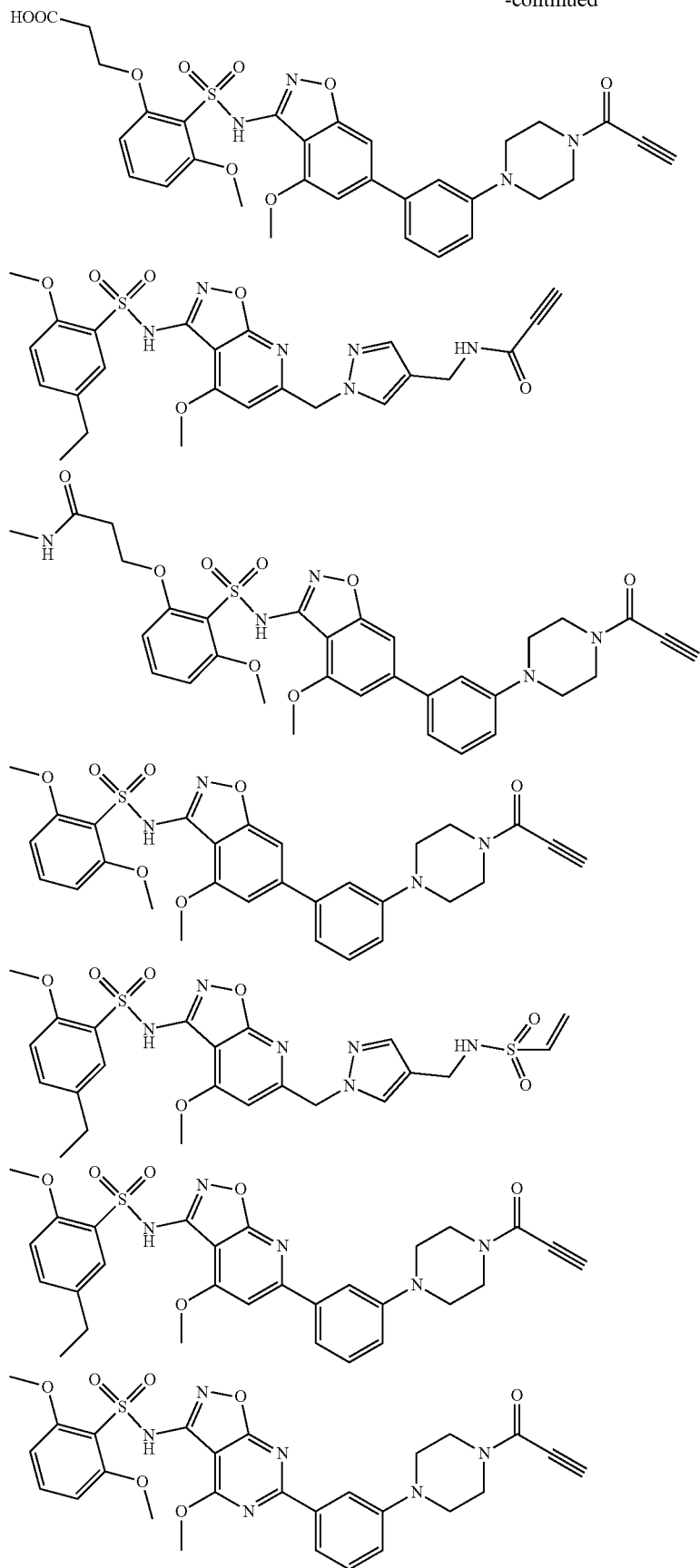

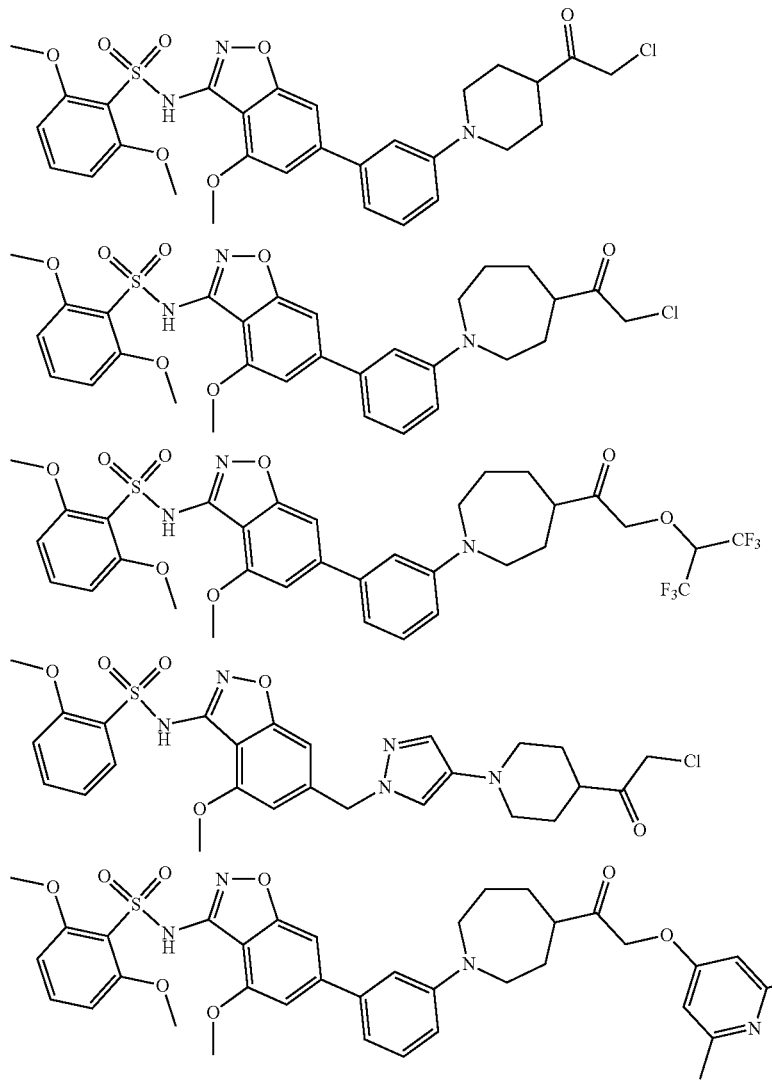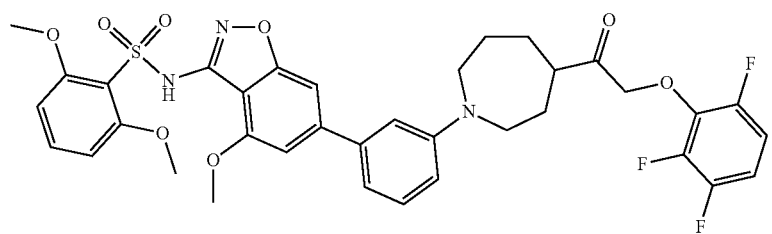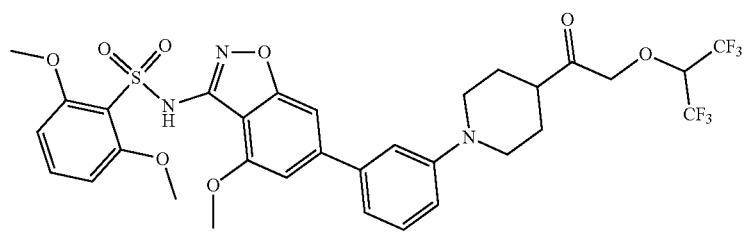

-continued
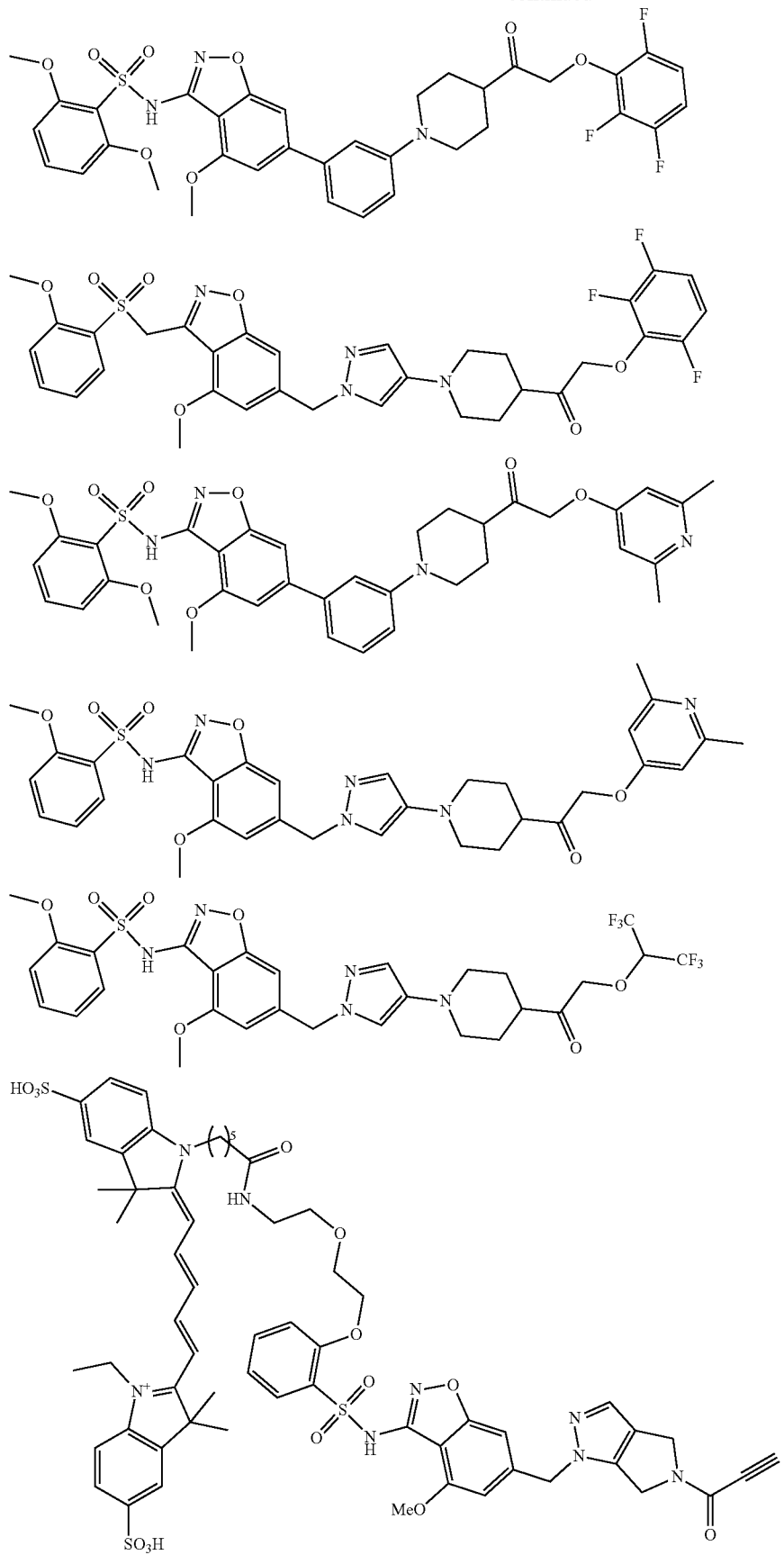

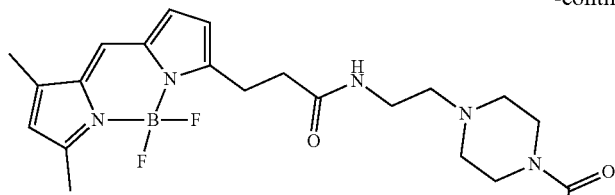
or a stereoisomer, a mixture of stereoisomers, and/or a pharmaceutically acceptable salt thereof.
Additional compounds, which can be prepared using methods disclosed herein and known to one of ordinary skill in the art and using readily obtainable or commercially available starting materials, include the following:
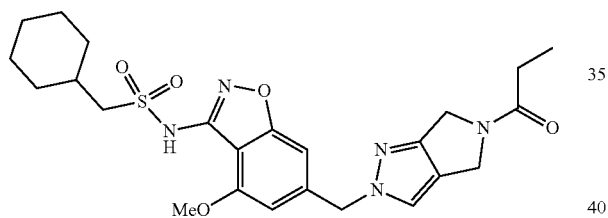
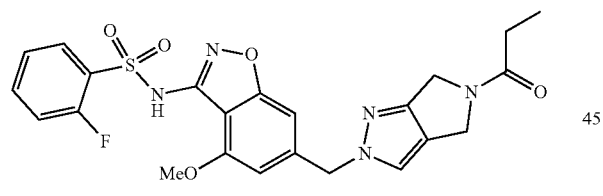
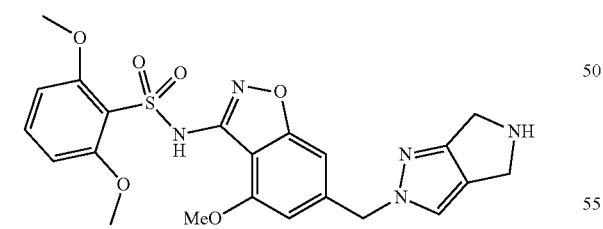
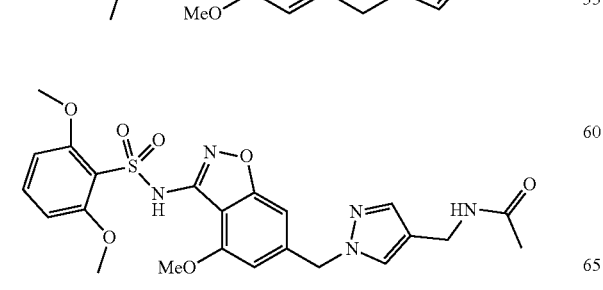
-continued
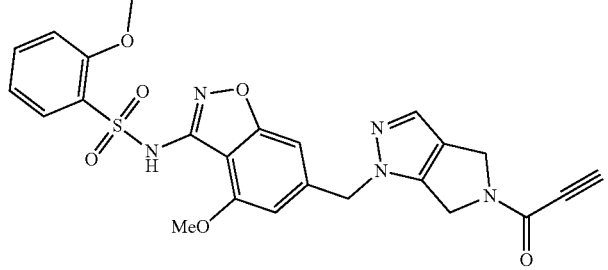
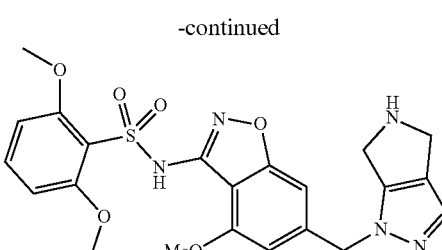
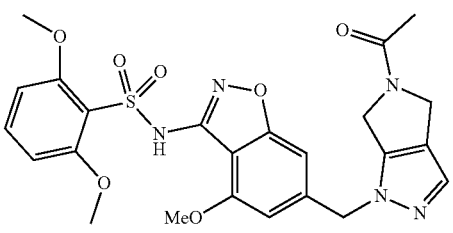
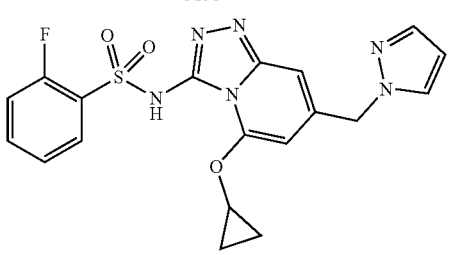
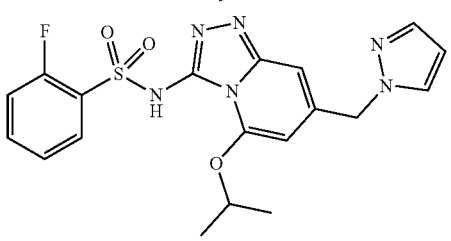

-continued
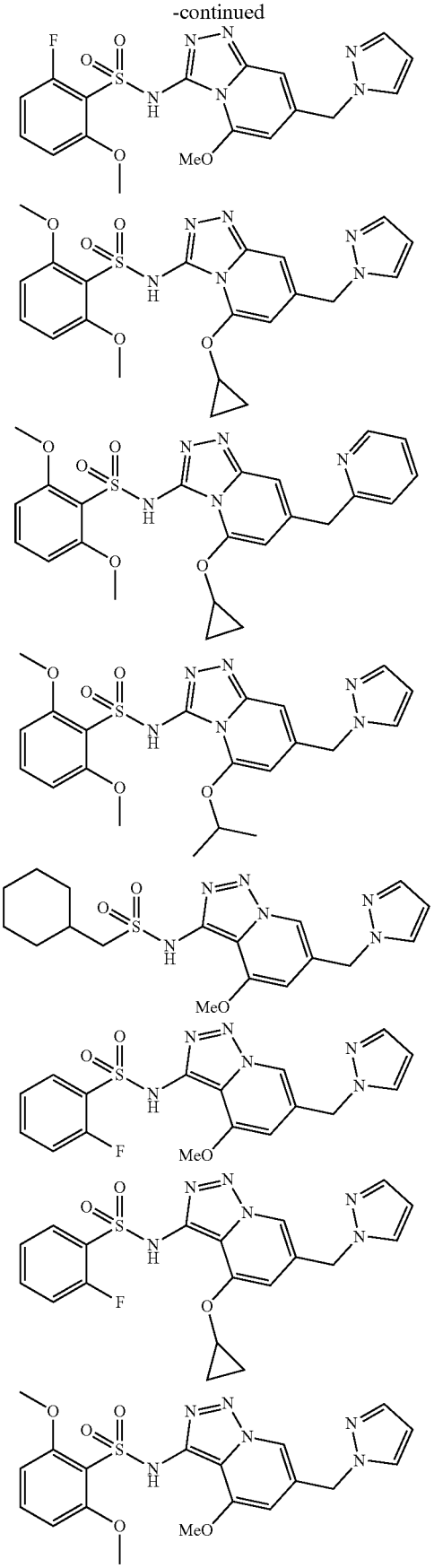
-continued
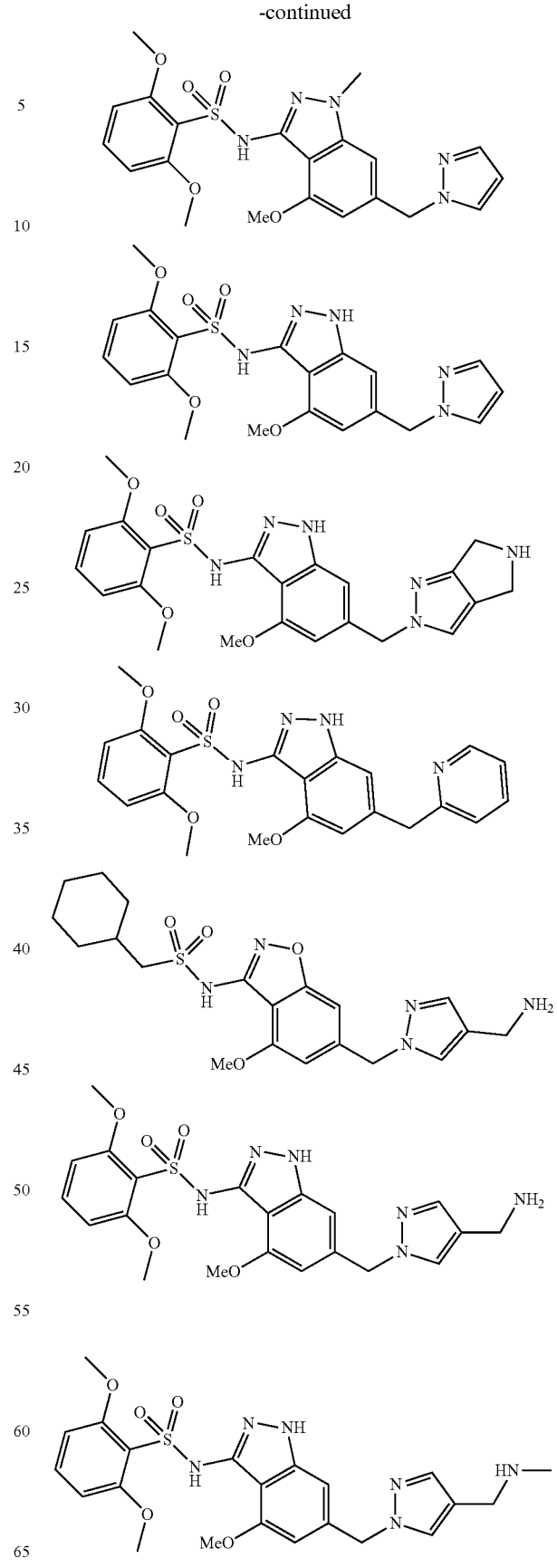

-continued

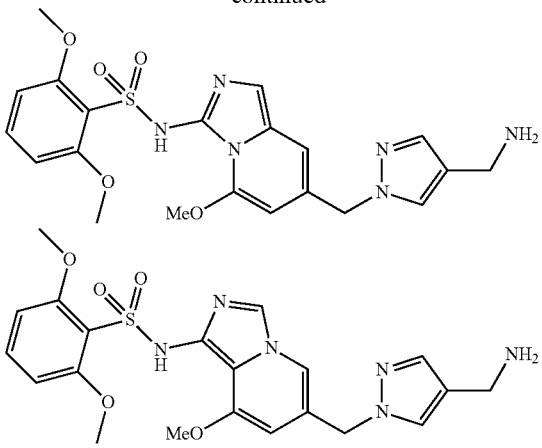

or a stereoisomer, regioisomer or a mixture of stereoisomers, and/or a pharmaceutically acceptable salt thereof.

Biological Example 1

KAT6A Alphalisa Inhibition Screening Assay

The Kat6a inhibitory activity of test compounds was determined using an Alpha Screen-based detection method. The assay reactions were conducted in a volume of 10 μL in Alpha Plate, White 384 well plate (cat #6008280, Perkin Elmer). The enzymatic reactions were performed in assay buffer pH 8.0 (50 mM Tris-HCl, 0.1 mM EDTA, 0.01% Tween-20, 1 mM Dithiothreitol, 0.1% BSA (fatty acid free) and 330 nM TSA (Trichostatin A)). 10 μL reaction volume consisting of 25 nM of Recombinant KAT6A/MOZ (488-778) protein (Active motif, Catalog #81223), 400 nM Acetyl coenzyme A (Catalog #A2056, Sigma), 200 nM of Histone H3 peptide [(amino acids 1-21), biotin-labeled (BPS Biosciences, Catalog #52011)] and a 10-point dose response curve for test/tool compounds were prepared. Enzyme and compounds solution were pre-incubated in assay plate for 60 or 10 min at room temperature then substrate and Acetyl coenzyme A solution were added to the plate. After addition, the plate was sealed with adhesive seals and incubated for 120 minutes at room temperature.

After 120 minutes of incubation, 5 μL (10 μg/mL) of AlphaLISA anti-acetyl-Lysine acceptor beads (Perkin Elmer, Catalog #AL143C) were added to the plate and it was incubated for 60 minutes at room temperature. Then 10 μL (10 μg/mL) of Alpha Streptavidin donor beads (Perkin Elmer, Catalog #6760002S) were added to the plate which was further incubated for 60 minutes at room temperature. After incubation, the alpha signal was recorded by using Perkin Elmer Envision multi-mode reader. Percent inhibition of enzyme activity was determined relative to positive control (1% DMSO) and $IC_{50}$ values were calculated using GraphPad Prism software (four parameter-variable slope equation).

$IC_{50}$ data for compounds as tested according to Biological Example 1 are provided in Table 2. NA means the compound was not active at the concentration tested. A means the compound provided an $IC_{50}$ of ≤10 μM; B means the compound provided an $IC_{50}$ of greater than 10 μM but less than or equal to 20 μM; and C means the compound provided an $IC_{50}$ of greater than 20 μM but less than or equal to 50 μM. NT means not tested.

TABLE 2

Biochemical $IC_{50}$ of selected compounds are provided below.

| Synthetic Example No. | Kat6A biochemical assay: $IC_{50}$ (μM) | ZR-75-1: $EC_{50}$ (μM) |
|---|---|---|
| 1 | NT | NT |
| 2 | $A^b$ | NT |
| 3 | $A^b$ | NT |
| 4 | $A^b$ | NT |
| 5 | $A^b$ | NT |
| 6 | $A^b$ | A |
| 7 | $A^b$ | NT |
| 8 | $A^a$ | NT |
| 9 | $A^a$ | NT |
| 10 | $A^a$ | NT |
| 11 | $C^a$ | NT |
| 12 | $A^a$ | NT |
| 13 | $A^a$ | NT |
| 14 | $C^a$ | NT |
| 15 | $A^b$ | NT |
| 16 | $A^b$ | NT |
| 17 | $A^b$ | NT |
| 18 | $A^b$ | NT |
| 19 | $A^b$ | NT |
| 20 | $A^b$ | NA |
| 21 | $A^b$ | NA |
| 22 | $A^b$ | NT |
| 23 | $A^b$ | NT |
| 24 | $A^b$ | NT |
| 25a | $A^b$ | A |
| 25b | $A^b$ | NA |
| 26a | $A^b$ | A |
| 26b | $A^b$ | NT |
| 27a | $A^b$ | NT |
| 27b | $A^b$ | A |
| 28a | $A^b$ | NT |
| 28b | $B^b$ | NT |
| 29a | $A^b$ | NT |
| 29b | $A^b$ | NT |
| 30a | $A^b$ | A |
| 30b | $A^b$ | A |
| 31 | $A^b$ | A |
| 32 | $A^b$ | A |
| 33 | $A^b$ | A |
| 34 | $A^b$ | |
| 35 | $A^b$ | NT |
| 36 | $A^b$ | A |
| 37 | $A^b$ | A |
| 38 | $A^b$ | NT |
| 39 | $C^a$ | NT |
| 40 | NA | NT |
| 41 | $A^b$ | NT |
| 42 | $A^b$ | NT |
| 43 | $A^b$ | A |
| 27a | $A^b$ | NT |
| 27b | $A^b$ | A |
| 44 | $A^b$ | |
| 45 | $A^b$ | |
| 46 | $A^b$ | |
| 47 | $A^b$ | |
| 48 | $A^b$ | |
| 49 | $A^b$ | |
| 50 | $A^b$ | |
| 51 | $A^b$ | |
| 52 | $A^b$ | |
| 53 | $A^b$ | |
| 54 | $A^b$ | |
| 55 | $A^b$ | |
| 56 | $A^b$ | |
| 57 | $A^b$ | |
| 58 | $A^b$ | |
| 59 | $A^b$ | |
| 60 | $A^b$ | |
| 61 | $A^b$ | |
| 62 | $A^b$ | NT |
| 63 | NA | NT |
| 64 | $A^b$ | |
| 65 | $A^b$ | |
| 66 | $A^b$ | |
| 67 | NA | |

TABLE 2-continued

Biochemical IC$_{50}$ of selected compounds are provided below.

| Synthetic Example No. | Kat6A biochemical assay: IC$_{50}$ (μM) | ZR-75-1: EC$_{50}$ (μM) |
|---|---|---|
| 68 | A$^b$ | |
| 69 | A$^b$ | |
| 70 | A$^b$ | |
| 71 | A$^b$ | |

$^a$10' pre-incubation
$^b$60' pre-incubation

TABLE 3

Biochemical IC$_{50}$ data of selected compounds are provided below.

| Synthetic Example No. | Kat6A Biochemical assay: IC50 (μM) |
|---|---|
| 72 | A$^b$ |
| 73 | A$^b$ |
| 74 | A$^b$ |
| 75 | NA$^b$ |
| 76 | A$^b$ |
| 77 | A$^b$ |
| 78 | A$^b$ |
| 79 | A$^b$ |
| 80 | A$^b$ |
| 81 | A$^b$ |
| 82 | A$^b$ |
| 83 | A$^b$ |
| 84 | A$^b$ |
| 85 | A$^b$ |
| 86 | NA$^b$ |
| 87 | A$^b$ |
| 88 | A$^b$ |
| 89 | A$^b$ |
| 90 | A$^b$ |
| 91 | A$^b$ |
| 92 | A$^b$ |
| 93 | A$^b$ |
| 94 | A$^b$ |
| 95 | A$^b$ |
| 96 | A$^b$ |
| 97 | A$^b$ |
| 98 | A$^b$ |
| 99 | A$^b$ |
| 100 | A$^b$ |
| 101 | A$^b$ |
| 102 | A$^b$ |
| 103 | A$^b$ |
| 104 | A$^b$ |
| 105a | A$^b$ |
| 105b | A$^b$ |
| 106 | A$^b$ |
| 107 | A$^b$ |
| 108 | A$^b$ |
| 109 | A$^b$ |
| 110 | A$^b$ |
| 111 | A$^b$ |
| 112 | A$^b$ |
| 113 | A$^b$ |
| 114 | NA$^b$ |
| 115 | A$^b$ |
| 116 | A$^b$ |
| 117 | A$^b$ |
| 118 | A$^b$ |
| 119 | A$^b$ |
| 120 | A$^b$ |
| 121 | B$^a$ |
| 122 | C$^a$ |
| 123 | B$^a$ |
| 124 | C$^a$ |
| 125 | A$^a$ |
| 126 | A$^a$ |
| 127 | A$^a$ |
| 128 | C$^a$ |

TABLE 3-continued

Biochemical IC$_{50}$ data of selected compounds are provided below.

| Synthetic Example No. | Kat6A Biochemical assay: IC50 (μM) |
|---|---|
| 129 | A$^a$ |
| 130 | A$^a$ |

$^a$10' pre-incubation
$^b$60' pre-incubation

Biological Example 2

KAT6A Alphalisa Assay: Mechanism of Action Study for Reversibility/Irreversibility Compounds may reversibly or irreversibly inhibit an enzyme in the MYST family, including KAT6A and KAT6B. The following describes a two-step mechanism of inhibition for covalent inhibitors.

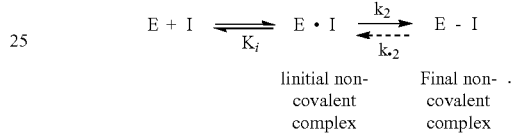

Initial non-covalent complex    Final non-covalent complex

In the above, E is the target enzyme, I is the inhibitor, E•I is the reversibly-bound protein-inhibitor complex, and E-I indicates the covalent bond between the target enzyme and the inhibitor. $K_i$ defines the rate of the first reversible binding event. $K_2$ defines the maximum potential rate of inactivation of the enzyme. $K_{-2}$ defines the potential rate of the reversibility of the binding event. Depending on the test conditions, an inhibitor may be a reversible inhibitor, an irreversible inhibitor, or an inhibitor which progresses toward irreversible inhibition given enough time.

The following protocol was used to determine reversibility/irreversibility of tested compounds.

Zeba™ Spin Desalting Columns, 7K MWCO, 0.5 mL (Catalog number: 89882, Thermo) were used for the assay. Columns were equilibrated by 5 washes with assay buffer (50 mM Tris-HCl, 0.1 mM EDTA, 0.01% Tween-20, 1 mM dithiothreitol, 0.3% BSA (Fatty acid free) and 330 nM TSA (Trichostatin A).

100 nM concentration of Recombinant KAT6A/MOZ (488-778) protein (Active motif, #81223) alone and with test compounds (20× concentration of IC$_{50}$) were incubated for 60 mins. at room temperature and added to spin columns and further incubated for 10 mins. Separate tubes were prepared with the same enzyme/test compound solutions, but were not passed through spin columns, and the tubes were incubated for 10 mins. The spin columns were centrifuged at 1500 g, and flow-through were collected to assess activity. WM-1119 is a KAT6A inhibitor (J. Med. Chem. 2020, 63, 4655-4684) and is used as a positive control.

Enzymatic reactions for samples passed through spin columns and samples which were not passed through spin columns were performed in assay buffer. 10 μL reaction volume consisting of 50 nM of Recombinant KAT6A/MOZ (488-778) protein (Active motif, #81223), 400 nM Acetyl coenzyme A (cat #A2056, Sigma), 200 nM of biotin-labelled histone H$_3$ peptide (1-21)(Cat #52011, BPS Biosciences) and test compounds were added to a plate. After addition, the plate was sealed with adhesive seals and incubated for 120 minutes at room temperature.

After 120 minutes of incubation, 5 μL (10 μg/mL) of AlphaLISA anti-ac-Lysine acceptor beads (cat #AL143C, Perkin Elmer) were added to the plate, and the plate was incubated for 60 minutes at room temperature. 10 μL (10 μg/mL) of Alpha Streptavidin donor beads (cat #6760002S, Perkin Elmer) were added to the plate which was further incubated for 60 minutes at room temperature. After incubation, alpha signal was recorded by using Perkin Elmer Envision multi-mode reader. % Inhibition of enzyme activity was determined relative to positive control (enzyme only) for both sample sets.

Data for selected compounds are shown below:

| Kat6a AlphaLISA Assay: Spin Column | | | | |
|---|---|---|---|---|
| | % Inhibition | | | |
| | Before Column | | After Column | |
| Compounds | N = 1 | N = 2 | N = 1 | N = 2 |
| 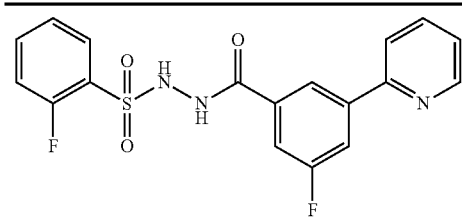 WM-1119 | 98 | 98 | 14 | 40 |
| Syn. Ex. 12 | 99 | 99 | 32 | 53 |
| Syn. Ex. 7 | 95 | 96 | 2 | 17 |
| Syn. Ex. 5 | 100 | 98 | 102 | 95 |
| Syn. Ex. 6 | 94 | 90 | 77 | 69 |
| Syn. Ex. 13 | 99 | 98 | 100 | 91 |

The data above and in FIG. 1 demonstrate that WM-1119 is a reversible inhibitor; Syn. Ex. 5, Syn. Ex. 6, and Syn. Ex. 13 are covalent inhibitors and are irreversibly bound to Kat6A; and Syn. Ex. 7 and Syn. Ex. 12 are reversible inhibitors under the experimental conditions used to test the compounds.

Biological Example 3

In Vitro Cancer Cell Assay

ZR-75-1 and $T_{47}D$ are breast cancer cell lines containing high KAT6A protein expression. Proliferation of these cell lines are inhibited upon treatment with a KAT6A inhibitor. Cell line MCF7 is used as a negative control. MCF7 cells have a low KAT6A protein expression and are not growth inhibited upon treatment with KAT6A inhibitors. WM-1119 is used as a positive control.

1500 cells are seeded per well and incubated overnight at 37° C. and 5% $CO_2$. Cells are treated after 24 hours with a compound (stock solution, 10 mM in DMSO) with 9-10 dilutions and a final DMSO concentration of 0.5%. WM-1119 (10 μM top concentration, 9-10 point DRC, 3 fold dilution in duplicate) is used as a positive control. Test compounds are tested like WM-1119. Plates are incubated at 37° C. and 5% $CO_2$ for 10 days. Media is replenished after every alternate day. At day 10, Cell Titer Glow is added to the wells and luminescence is recorded after 10 min incubation. Data are normalized to 100% with DMSO control and subtracting media blank. Cell viability is of the test compounds is measured.

The above procedure can be followed for determining activity in additional cell lines, for example, ZR-75-1, T47D, CHAGOK1 and other cell lines that have high expression of KAT6A. The number of cells used will be optimized based on growth rate of the individual cell lines.

Biological Example 4

Liver Microsome Stability Assay

A microsomal mixture (microsomes and Kphos buffer) is prepared at a concentration of 1.428 mg/mL in 2 mL tubes. To this microsomal mixture 1.6 μL (1 mM) of test compound and positive control are spiked; from this mixture, 70 μL is transferred to 96 well plate and pre-incubated at 37° C. for 5 min. After pre-incubation, the zero minute time point reaction is stopped using 100 μL of ice-cold acetonitrile containing internal standard and μL of NADPH (3.33 mM in Kphos buffer) is added. The 45-minute time point reaction is initiated by addition of 30 μL of NADPH (3.33 mM in Kphos buffer) and incubated at 37° C. for 15 and 45 min. Reactions without NADPH and buffer controls (minus NADPH) at 0, 15, and 45 minutes were also incubated to rule out non-NADPH metabolism or chemical instability in the incubation buffer. Incubation reactions were stopped with 100 μL of ice-cold acetonitrile containing internal standard. The plates were centrifuged at 4000 RPM for 15 min and 100 μL aliquots were submitted for analysis by LC-MS/MS. (Verapamil in human liver microsomes (HLM) and rat liver microsomes (RLM) was used as positive controls. Imipramine in mouse liver microsomes (MLM) was used as a positive control.) Samples were monitored for parent compound disappearance in MRM mode (multiple reaction monitoring) using LC-MS/MS. The peak area ratios of analyte versus internal standard were used to calculate the % remaining at the end of 45 minutes in the presence of NADPH.

Biological Example 5

In Vivo Model

This model is used to evaluate the anti-cancer potential of test compounds in 5-6-week old female *Mus musculus* (NOD.SCID) mice, NOD/MarkBomTac-Prkd$^{scid}$, with a body weight of 15 to 20 g, bearing on ZR-75-1 human breast adenocarcinoma xenograft. Animals are housed at a temperature of 19 to 25° C., a humidity of 30 to 70%, and watered ad libitum and fed ad libitum, except during fasting period. Female NOD.SCID (nulliparous non pregnant females) are allowed to acclimatize for one to seven days prior to study initiation. During this period, the mice are observed daily for clinical signs, mortality and morbidity, at least once a day. Mice with any abnormalities or ill health or poor physical condition are discarded. Female NOD.SCID mice bearing tumor are randomized based on predetermined tumor size. Each group having mean tumor volume ~100-200 mm³ are selected in the final study and randomized.

Dose formulations are prepared fresh every day prior to dose administration. Test compounds are dissolved in a solvent such as DMSO at a suitable concentration and a dose volume of 10 mL/kg. The test/reference compound suspension formulation is administered orally to the test groups.

ZR-75-1 (Human breast adenocarcinoma cell line) is maintained in RPMI 1640 Medium and supplemented with 10% FBS and in an atmosphere air (with 5% $CO_2$). The cells growing at log phase are washed two times with 1×PBS and harvested by trypsinization and then suspended in a required volume of serum free medium. Cell viability is determined by trypan blue exclusion test. The aliquots of cell suspension containing 50×10⁶ MCF7 cells/ml in serum free cell culture medium is prepared and diluted with equal volume of Matrigel to get 25×10⁶/mL cell suspension and placed on ice to maintain the viability.

All female NOD.SCID mice are injected subcutaneously (SC) 17-β Estradiol pellets (0.72 mg-60 days release) 3-6 days before of ZR-75-1 cells inoculation. The mice are then injected subcutaneously (SC) in the right flank region with 0.2 mL of 5.0×10⁶ cell suspension (Serum free media: Matrigel; 1:1 ratio). After tumor development, tumor growth is measured by digital vernier caliper. Further, tumor volume is calculated by the formula: Tumor volume (mm³)= (Length×Width²)/2. Animals whose tumor volume reaches ~100-200 mm³ are selected for the experiment and randomized based on tumor volume (TV) into different groups G1-G6.

Clinical signs/mortality are observed daily. Body weight and tumor size (with a digital caliper) are measured at the time of randomization and three times a week until the end of the experiment. Percentage change in the body weight for each mouse are calculated as per the given formula:

$$\% \text{ Body Weight Change} = \frac{\text{Body weight at day } x - \text{Initial Body weight}}{\text{Initial Body weight}} \times 100$$

At the end of the study all the animals are humanely sacrificed after last dose and tumors carefully excised and weighed. Part of the tumor is snap frozen for western blot and another part is stored in formalin for IHC (optional) at −80° C. Mean Tumor growth inhibition (TGI) is calculated from tumor volume data, according to the following formula.

$$\frac{\left(\begin{array}{l}\text{Mean } TV \text{ of Vehicle Control on day } x - \\ \text{Mean } TV \text{ of a Test Group on day } x\end{array}\right)}{\text{Mean } TV \text{ of Vehicle Control on day } x} \times 100$$

All the individual animal data are summarized in terms of groups to get mean and standard error of mean (Mean±SEM). Data on each parameter is statistically analyzed by using GraphPad prism and represented in tabular and/or graphical form. All analysis and comparisons are evaluated at 5% level i.e. P≤0.05. The statistical analysis is performed using GraphPad Prism statistical software and two-way ANOVA with Bonferroni's post-hoc test or One-way ANOVA with Tukey's/Dunnett's post-hoc test.

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A compound of Formula (I):

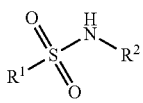

(I)

$R^1$ is $C_3$-$C_8$-cycloalkyl optionally substituted with 1, 2, or 3 $R^{1a}$; $C_3$-$C_8$-cycloalkyl-$C_1$-$C_6$alkyl where the $C_3$-$C_8$-cycloalkyl is optionally substituted with 1, 2, or 3 $R^{1a}$; phenyl optionally substituted with 1, 2, or 3 $R^{1b}$; phenyl-$C_1$-$C_6$alkyl optionally substituted with 1, 2, or 3 $R^{1b}$; naphthyl optionally substituted with 1, 2, or 3 $R^{1b}$; or 5- or 6-membered monocyclic heteroaryl optionally substituted with 1, 2, or 3 $R^{1b}$; 8- to 10-membered bicyclic heteroaryl optionally substituted with 1, 2, or 3 $R^{1b}$;

each $R^{1a}$ is independently selected from hydrogen, halo, $C_1$-$C_6$alkoxy, and $C_3$-$C_8$-cycloalkyloxy;

each $R^{1b}$ is independently selected from hydrogen, halo, $C_1$-$C_6$alkyl, $C_1$-$C_6$alkoxy, hydroxyalkyloxy, —O-alkylene-$NR^{1b1}R^{1b4}$, —O-alkylene-C(O)$OR^{1b1}$, —O-alkylene-O-alkylene-$NR^{1b1}R^{1b4}$,

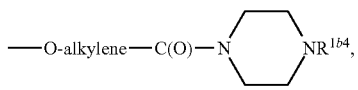

cyano, —(CH$_2$)$_{0-2}$C(O)—$OR^{1b1}$, —(CH$_2$)$_{0-2}$C(O)$NR^{1b1}R^{1b2}$, —(CH$_2$)$_{0-2}$$NR^{1b1}$C(O)$R^{1b3}$, —(CH$_2$)$_{0-2}$OH, and $C_3$-$C_8$-cycloalkyloxy;

$R^{1b1}$ is hydrogen or $C_1$-$C_6$alkyl; $R^{1b2}$ is hydrogen or $C_1$-$C_6$alkyl; $R^{1b3}$ is hydrogen or $C_1$-$C_6$alkyl; and $R^{1b4}$ is hydrogen,

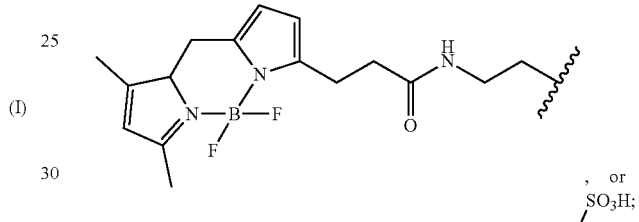

, or SO$_3$H;

$R^2$ is:

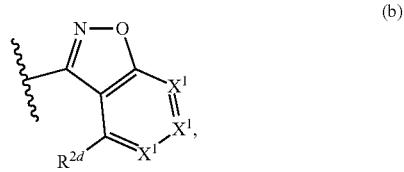

(b)

each $R^{2b}$ is independently hydrogen, halo, —(CH$_2$)$_{0-2}$OH, $C_1$-$C_3$alkyl, cyclopropyl, cyano, —CHF$_2$, —CF$_3$, $C_1$-$C_4$alkoxy, —OCHF$_2$, —OCF$_3$, or $C_3$-$C_8$cycloalkyloxy;

each $R^{2e}$ is independently hydrogen, —OH, halo, $C_1$-$C_6$alkyl, halo-$C_1$-$C_6$alkyl, $C_3$-$C_8$cycloalkyl, $C_1$-$C_6$alkoxy, halo-$C_1$-$C_6$alkoxy, or $C_3$-$C_8$cycloalkyloxy;

wherein, one $X^1$ is $CR^3$ and the other $X^1$ are independently selected from N and $CR^{2b}$;

$R^{2d}$ is hydrogen, halo, $C_1$-$C_6$alkyl, $C_1$-$C_6$cycloalkyl, $C_1$-$C_6$alkoxy, or $C_3$-$C_8$-cycloalkyloxy;

$R^3$ is $-(CH_2)_{0-2}Y$ or $-(CH_2)_{0-2}-L-Y$;

L is $-L^1-L^2-L^3-$, where $L^1$, $L^2$ and $L^3$ are each independently a bond, $-CRR-$, O, $S(O)_{0-2}$, C(O) or NR, where each R is independently H or alkyl;

Y is a 5-membered monocyclic heteroaryl substituted with $R^Y$ and optionally substituted with $R^{2e}$; Y is a 6-membered monocyclic aryl or heteroaryl substituted with $R^Y$ and optionally substituted with 1 or 2 $R^{2e}$; Y is an 8-membered bicyclic heteroaryl substituted with $R^Y$ and optionally substituted with 1 or 2 $R^{2e}$; Y is a 9-membered bicyclic heteroaryl substituted with $R^Y$ and optionally substituted with 1, 2, or 3 $R^{2e}$; Y is a 10-membered bicyclic heteroaryl substituted with $R^Y$ and optionally substituted with 1, 2, or 3 $R^{2e}$; Y is a 8- or 9-membered bicyclic heterocyclic substituted with $R^Y$ and optionally substituted with 1 or 2 $R^{2e}$; Y is a 4-9-membered monocyclic or bicyclic heterocycloalkyl substituted with $R^Y$ and optionally substituted with 1 or 2 $R^{2e}$; Y is

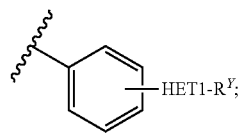

Y is $-(CH_2)_{0-3}NR^{3b}R^Y$; or Y is $-(CH_2)_{0-3}NR^{3b}C(O)R^Y$;

$R^Y$ is $-(CH_2)_{0-3}NR^{3b}C(O)R^{3a}$, $-(CH_2)_{0-2}NR^{3b}S(O)_2R^{3a}$, $-C(O)R^{3a}$, $-S(O)_2R^{3a}$, $-C(O)NR^{3b}R^{3a}C_3-C_8$heterocycloalkyl substituted with $-C(O)R^{3a}$; $-(CH_2)_{0-3}NR^{3b}(C_1-C_6$alkylene$)NR^{3b1}C(O)R^{3a}$, $-(CH_2)_{0-3}NR^{3b}(C_1-C_6$alkylene$)NR^{3b1}S(O)_2R^{3a}$, $-(CH_2)_{0-3}NR^{3b}C(O)(C_1-C_6$alkylene$)NR^{3b1}C(O)R^{3a}$, or $-(CH_2)_{0-3}NR^{3b}C(O)(C_1-C_6$alkylene$)NR^{3b1}S(O)_2R^{3a}$, $R^{3a}$, $R^{3b}$ and $R^{3b1}$ are selected from (i), (ii) or (iii):

(i) one of $R^{3a}$, $R^{3b}$ and $R^{3b1}$ is selected from group a): $C_1-C_6$alkyl substituted with 1 or 2 halo which are independently selected; $C_1-C_6$alkyl substituted with cyano; $C_1-C_6$alkyl substituted with fluoroalkoxy; $C_1-C_6$alkyl substituted with aryloxy or heteroaryloxy, each of which is optionally substituted with 1-3 substituents each independently selected from halo, $C_{1-6}$alkyl, $C_{2-6}$alkenyl, $C_1-C_6$alkoxy, cyano, $C_{3-8}$cycloalkyl or $C_{3-8}$heterocycloalkyl; $C_2-C_6$alkenyl; $C_2-C_6$alkenyl substituted with cyano; $C_2-C_6$alkenyl substituted with halo; $-CH=CH-CH_2-NR^{3c}R^{3d}$; $-CH=CH-CH_2-O-C_1-C_6$alkyl; $C_3-C_8$cycloalkenyl; $-C(O)-C_3-C_8$cycloalkenyl; $C_2-C_6$alkynyl; $-CH=CH-CH_2-NR^{3c}R^{3d}$; $CH=CH-CH_2-OH$; $-CH=CH-CH_2-O-C_1-C_6$alkyl; spirocycloalkyl substituted with cyano; chloropyridyl; fluoropyridyl; chloropyrazinyl; fluoropyrazinyl; chloropyrimidinyl; fluoropyrimidinyl; pentafluorophenyl; tetraflurophenyl; trifluorophenyl, difluorophenyl; and monofluorophenyl; and the others of $R^{3a}$, $R^{3b}$ and $R^{3b1}$ are selected from group b): hydrogen, and $C_1-C_6$alkyl; or (ii) one of $R^{3a}$, $R^{3b}$ and $R^{3b1}$ is selected from group a): hydrogen; $C_1-C_6$alkyl; $C_1-C_6$alkyl substituted with aryloxy or heteroaryloxy, each of which is optionally substituted with 1-3 substituents each independently selected from $C_{1-6}$alkyl, $C_{2-6}$alkenyl, $C_{1-6}$alkoxy, cyano, $C_{3-8}$cycloalkyl or $C_{3-8}$heterocycloalkyl; $C_2-C_6$alkenyl; $C_3-C_8$cycloalkenyl; $-C(O)-C_3-C_8$cycloalkyl; $C_2-C_6$alkynyl; spirocycloalkyl; pyridyl; pyrimidinyl; and phenyl; and the others of $R^{3a}$, $R^{3b}$ and $R^{3b1}$ are selected from group b): hydrogen, and $C_1-C_6$alkyl; or (iii) $R^{3a}$, $R^{3b}$ and $R^{3b1}$ are each independently hydrogen or $C_1-C_6$alkyl;

$R^{3c}$ is hydrogen, or $C_1-C_6$alkyl, and $R^{3d}$ is hydrogen, or $C_1-C_6$alkyl; or $R^{3c}$ and $R^{3d}$ together with the nitrogen to which they are attached form a 3-8 membered, saturated ring where the other 2-7 ring members are carbon; and HET1 is $C_3-C_8$heterocycloalkyl;

or a pharmaceutically acceptable salt or salts thereof, and/or a stereoisomer or mixture of stereoisomers thereof.

2. The compound of claim 1, wherein:

$R^1$ is $C_3-C_8$-cycloalkyl optionally substituted with 1, 2, or 3 $R^{1a}$; $C_3-C_8$-cycloalkyl-$C_1-C_6$alkyl where the $C_3-C_8$-cycloalkyl is optionally substituted with 1, 2, or 3 $R^{1a}$; phenyl optionally substituted with 1, 2, or 3 $R^{1b}$; phenyl-$C_1-C_6$alkyl optionally substituted with 1, 2, or 3 $R^{1b}$; naphthyl optionally substituted with 1, 2, or 3 $R^{1b}$; or 5- or 6-membered monocyclic heteroaryl optionally substituted with 1, 2, or 3 $R^{1b}$; 8- to 10-membered bicyclic heteroaryl optionally substituted with 1, 2, or 3 $R^{1b}$;

each $R^{1a}$ is independently selected from hydrogen, halo, $C_1-C_6$alkoxy, and $C_3-C_8$-cycloalkyloxy;

each $R^{1b}$ is independently selected from hydrogen, halo, $C_1-C_6$alkyl, $C_1-C_6$alkoxy, hydroxyalkyloxy, $-O$-alkylene-$NR^{1b1}R^{1b4}$, $-O$-alkylene-$C(O)OR^{1b1}$, $-O$-alkylene-$O$-alkylene-$NR^{1b1}R^{1b4}$,

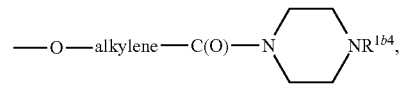

cyano, $-(CH_2)_{0-2}C(O)OR^{1b1}$, $-(CH_2)_{0-2}C(O)NR^{1b2}R^{1b3}$, $-(CH_2)_{0-2}NRC(O)R$, $-(CH_2)_{0-2}OH$, and $C_3-C_8$-cycloalkyloxy;

$R^{1b1}$ is hydrogen or $C_1-C_6$alkyl; $R^{1b2}$ is hydrogen or $C_1-C_6$alkyl; and $R^{1b3}$ is hydrogen or $C_1-C_6$alkyl; and $R^{1b4}$ is hydrogen,

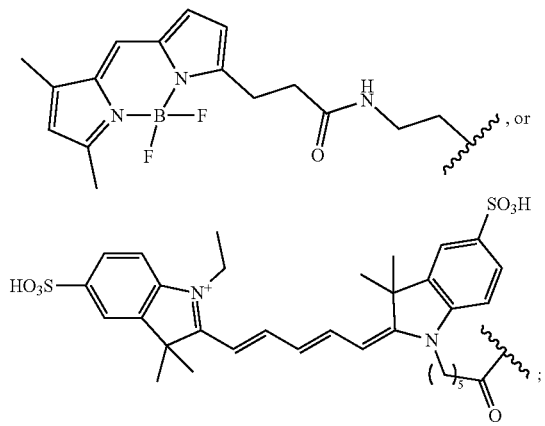

$R^2$ is selected from the group consisting of

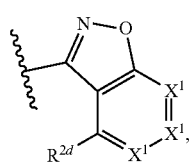

each $R^{2b}$ is independently hydrogen, halo, —$(CH_2)_{0-2}OH$, $C_1$-$C_3$alkyl, cyclopropyl, cyano, —$CHF_2$, —$CF_3$, $C_1$-$C_4$alkoxy, —$OCHF_2$, —$OCF_3$, or $C_3$-$C_8$cycloalkyloxy;

each $R^{2e}$ is independently hydrogen, halo, —OH, $C_1$-$C_6$alkyl, halo-$C_1$-$C_6$alkyl, $C_3$-$C_8$cycloalkyl, $C_1$-$C_6$alkoxy, halo-$C_1$-$C_6$alkoxy, or $C_3$-$C_8$cycloalkyloxy;

wherein, one $X^1$ is $CR^3$ and the other $X^1$ are independently selected from N and $CR^{2b}$;

$R^{2d}$ is hydrogen, halo, $C_1$-$C_6$alkyl, $C_1$-$C_6$cycloalkyl, $C_1$-$C_6$alkoxy, or $C_3$-$C_8$-cycloalkyloxy;

$R^3$ is —$(CH_2)_{0-2}Y$;

Y is a 5-membered monocyclic heteroaryl substituted with $R^Y$ and optionally substituted with $R^{2e}$; Y is a 6-membered monocyclic heteroaryl substituted with $R^Y$ and optionally substituted with 1 or 2 $R^{2e}$; Y is an 8-membered bicyclic heteroaryl substituted with $R^Y$ and optionally substituted with 1 or 2 $R^{2e}$; Y is a 9-membered bicyclic heteroaryl substituted with $R^Y$ and optionally substituted with 1, 2, or 3 $R^{2e}$; Y is a 10-membered bicyclic heteroaryl substituted with $R^Y$ and optionally substituted with 1, 2, or 3 $R^{2e}$; Y is a 8- or 9-membered bicyclic heterocyclic substituted with $R^Y$ and optionally substituted with 1 or 2 $R^{2e}$; Y is a 4-9-membered monocyclic or bicyclic heterocycloalkyl substituted with $R^Y$ and optionally substituted with 1 or 2 $R^{2e}$; Y is

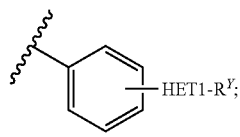

Y is —$(CH_2)_{0-3}NR^{3b}R^Y$; or Y is —$(CH_2)_{0-3}NR^{3b}C(O)R^Y$;

$R^Y$ is —$(CH_2)_{0-3}NR^{3b}C(O)R^{3a}$, —$(CH_2)_{0-2}NR^{3b}S(O)_2R^{3a}$, —$C(O)R^{3a}$, —$S(O)_2R^{3a}$, —$C(O)NR^{3b}R^{3a}$, —$(CH_2)_{0-3}NR^{3b}(C_1$-$C_6$alkylene$)NR^{3b1}C(O)R^{3a}$, —$(CH_2)_{0-3}NR^{3b}(C_1$-$C_6$alkylene$)NR^{3b1}S(O)_2R^{3a}$, —$(CH_2)_{0-3}NR^{3b}C(O)(C_1$-$C_6$alkylene$)NR^{3b1}C(O)R^{3a}$, or —$(CH_2)_{0-3}NR^{3b}C(O)(C_1$-$C_6$alkylene$)NR^{3b1}S(O)_2R^{3a}$, or $C_3$-$C_8$heterocycloalkyl substituted with —$C(O)R^{3a}$;

one of $R^{3a}$, $R^{3b}$ and $R^{3b1}$ is selected from group a): $C_1$-$C_6$alkyl substituted with 1 or 2 halo which are independently selected; $C_1$-$C_6$alkyl substituted with cyano; $C_1$-$C_6$alkyl substituted with fluoroalkoxy; $C_1$-$C_6$alkyl substituted with aryloxy or heteroaryloxy, each of which is optionally substituted with 1-3 substituents each independently selected from halo, $C_{1-6}$alkyl, $C_{2-6}$alkenyl, $C_{1-6}$alkoxy, cyano, $C_{3-8}$cycloalkyl or $C_{3-8}$heterocycloalkyl; $C_2$-$C_6$alkenyl; $C_2$-$C_6$alkenyl substituted with cyano; $C_2$-$C_6$alkenyl substituted with halo; —CH=CH—$CH_2$—$NR^{3c}R^{3d}$; —CH=CH—$CH_2$—O—$C_1$-$C_6$alkyl; $C_3$-$C_8$cycloalkenyl; —C(O)—$C_3$-$C_8$cycloalkyl; $C_2$-$C_6$alkynyl; —CH=CH—$CH_2$—$NR^{3c}R^{3d}$; CH=CH—$CH_2$—OH; —CH=CH—$CH_2$—O—$C_1$-$C_6$alkyl; spirocycloalkyl substituted with cyano; chloropyridyl; fluoropyridyl; chloropyrazinyl; fluoropyrazinyl; chloropyrimidinyl; fluoropyrimidinyl; pentafluorophenyl; tetraflurophenyl; trifluorophenyl; difluorophenyl; and monofluorophenyl; and the others of $R^{3a}$, $R^{3b}$ and $R^{3b1}$ are selected from group b): hydrogen, and $C_1$-$C_6$alkyl;

$R^{3c}$ is hydrogen, or $C_1$-$C_6$alkyl, and $R^{3d}$ is hydrogen, or $C_1$-$C_6$alkyl; or $R^{3c}$ and $R^{3d}$ together with the nitrogen to which they are attached form a 3-8 membered, saturated ring where the other 2-7 ring members are carbon;

HET1 is $C_3$-$C_8$heterocycloalkyl;

or a pharmaceutically acceptable salt or salts thereof; and/or a stereoisomer or mixture of stereoisomers thereof.

3. The compound of claim 2, wherein $R^1$ is $C_3$-$C_8$-cycloalkylalkyl where the $C_3$-$C_8$-cycloalkylalkyl is optionally substituted with 1, 2, or 3 $R^{1a}$, or phenyl optionally substituted with 1, 2, or 3 $R^{1b}$; or a pharmaceutically acceptable salt or salts thereof; and/or a stereoisomer or mixture of stereoisomers thereof.

4. The compound of claim 2, wherein $R^1$ is $C_3$-$C_8$-cycloalkyl optionally substituted with 1, 2, or 3 $R^{1a}$; or a pharmaceutically acceptable salt or salts thereof; and/or a stereoisomer or mixture of stereoisomers thereof.

5. The compound of claim 2, wherein $R^1$ is $C_3$-$C_8$-cycloalkylalkyl where the $C_3$-$C_8$-cycloalkylalkyl is optionally substituted with 1, 2, or 3 $R^{1a}$; or a pharmaceutically acceptable salt or salts thereof; and/or a stereoisomer or mixture of stereoisomers thereof.

6. The compound of claim 2, wherein $R^1$ is phenyl optionally substituted with 1, 2, or 3 $R^{1b}$; or a pharmaceutically acceptable salt or salts thereof; and/or a stereoisomer or mixture of stereoisomers thereof.

7. The compound of claim 2, wherein $R^1$ is phenyl-$C_1$-$C_6$alkyl optionally substituted with 1, 2, or 3 $R^{1b}$; or a pharmaceutically acceptable salt or salts thereof; and/or a stereoisomer or mixture of stereoisomers thereof.

8. The compound of claim 2, wherein $R^1$ is naphthyl optionally substituted with 1, 2, or 3 $R^{1b}$; or a pharmaceutically acceptable salt or salts thereof; and/or a stereoisomer or mixture of stereoisomers thereof.

9. The compound of claim 2, wherein $R^1$ is 5- or 6-membered monocyclic heteroaryl optionally substituted with 1, 2, or 3 $R^{1b}$; or a pharmaceutically acceptable salt or salts thereof; and/or a stereoisomer or mixture of stereoisomers thereof.

10. The compound of claim 1, wherein each Ria is independently hydrogen; or a pharmaceutically acceptable salt or salts thereof; and/or a stereoisomer or mixture of stereoisomers thereof.

11. The compound of claim 2, wherein each $R^{1b}$ is independently selected from hydrogen, halo, —C(O)OH, —C(O)(OCH_3), $C_1$-$C_6$alkyl, and $C_1$-$C_6$alkoxy; or a pharmaceutically acceptable salt or salts thereof; and/or a stereoisomer or mixture of stereoisomers thereof.

12. The compound of claim 2, wherein $R^{2d}$ is $C_1$-$C_3$alkoxy (optionally methoxy); or a pharmaceutically acceptable acceptable salt or salts thereof, and/or a stereoisomer or mixture of stereoisomers thereof.

13. The compound of claim 2, wherein each $R^{2b}$ is hydrogen; or a pharmaceutically acceptable salt or salts thereof, and/or a stereoisomer or mixture of stereoisomers thereof.

14. The compound of claim 2, wherein one $X^1$ is $CR^3$ and is in the meta position with respect to $R^{2d}$, one $X^1$ is N, and the other $X^1$ is $CR^{2b}$; or a pharmaceutically acceptable salt or salts thereof; and/or a stereoisomer or mixture of stereoisomers thereof.

15. The compound of claim 2, wherein one $X^1$ is $CR^3$ and is in the meta position with respect to $R^{2d}$ and the other $X^1$ are CH; or a pharmaceutically acceptable salt or salts thereof, and/or a stereoisomer or mixture of stereoisomers thereof.

16. The compound of claim 2, wherein $R^3$ is —(CH$_2$)—Y; or a pharmaceutically acceptable salt or salts thereof; and/or a stereoisomer or mixture of stereoisomers thereof.

17. The compound of claim 2, wherein $R^3$ is —(CH$_2$)-L-Y; or a pharmaceutically acceptable salt or salts thereof; and/or a stereoisomer or mixture of stereoisomers thereof.

18. The compound of claim 2, wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; or Y is

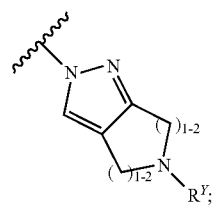

or a pharmaceutically acceptable salt or salts thereof, and/or a stereoisomer or mixture of stereoisomers thereof.

19. The compound of claim 2, wherein Y is a 5-membered monocyclic heteroaryl substituted with $R^Y$; Y is a pyrazolyl substituted with $R^Y$; Y is a 8- or 9-membered bicyclic heterocyclic substituted with $R^Y$; or Y is

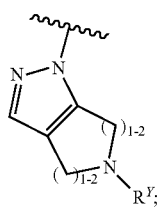

or a pharmaceutically acceptable salt or salts thereof, and/or a stereoisomer or mixture of stereoisomers thereof.

20. The compound of claim 2, wherein each $R^{3b}$ and $R^{3b1}$ is hydrogen; or a pharmaceutically acceptable salt or salts thereof, and/or a stereoisomer or mixture of stereoisomers thereof.

21. The compound of claim 2, wherein $R^Y$ is —(CH$_2$)$_{0-3}$NHC(O)R$^{3a}$, —(CH$_2$)$_{0-2}$NHS(O)$_2$R$^{3a}$, —C(O)R$^{3a}$, —S(O)$_2$R$^{3a}$, —(CH$_2$)$_{0-3}$NH(C$_1$-C$_6$alkylene)NHC(O)R$^{3a}$, —(CH$_2$)$_{0-3}$NH(C$_1$-C$_6$alkylene)NHS(O)$_2$R$^{3a}$, —(CH$_2$)$_{0-3}$NHC(O)(C$_1$-C$_6$alkylene)NHC(O)R$^{3a}$, —(CH$_2$)$_{0-3}$NHC(O)(C$_1$-C$_6$alkylene)NHS(O)$_2$R$^{3a}$, or C$_3$-C$_8$heterocycloalkyl substituted with —C(O)R$^{3a}$;

wherein $R^{3a}$ is selected from group a); or a pharmaceutically acceptable salt or salts thereof, and/or a stereoisomer or mixture of stereoisomers thereof.

22. The compound of claim 2, wherein $R^{3a}$ is —CH$_2$(halo); —(CH$_2$)$_{1-2}$CN; —CH$_2$OCH(CF$_3$)$_2$; —CH$_2$O(trifluorophenyl); —CH$_2$O(tetrafluorophenyl); —CH$_2$O(isoxazolyl, optionally substituted with 1-3 substituents each independently selected from halo, C$_{1-6}$alkyl, C$_{2-6}$alkenyl, C$_{1-6}$alkoxy, cyano, C$_{3-8}$cycloalkyl or C$_{3-8}$heterocycloalkyl); —CH$_2$O(pyrimidinyl, optionally substituted with 1-3 substituents each independently selected from halo, C$_{1-6}$alkyl, C$_{2-6}$alkenyl, C$_{1-6}$alkoxy, cyano, C$_{3-8}$cycloalkyl or C$_{3-8}$heterocycloalkyl); —CH$_2$O(pyridyl, optionally substituted with 1-3 substituents each independently selected from halo, C$_{1-6}$alkyl, C$_{2-6}$alkenyl, C$_{1-6}$alkoxy, cyano, C$_{3-8}$cycloalkyl or C$_{3-8}$heterocycloalkyl); C$_2$-C$_6$alkenyl; C$_2$-C$_4$alkenyl substituted with cyano; C$_2$-C$_4$alkenyl substituted with halo; —CH=CH—CH$_2$—NR$^{3c}$R$^{3d}$; —CH=CH—CH$_2$—O—C$_1$-C$_6$alkyl; tetrafluorophenyl; trifluorophenyl; C$_2$-C$_6$alkynyl; —CH≡CH—CH$_2$—NR$^{3c}$R$^{3d}$; or —CH≡CH—CH$_2$—O—C$_1$-C$_6$alkyl; or a pharmaceutically acceptable salt or salts thereof; and/or a stereoisomer or mixture of stereoisomers thereof.

23. The compound of claim 2, wherein $R^Y$ is

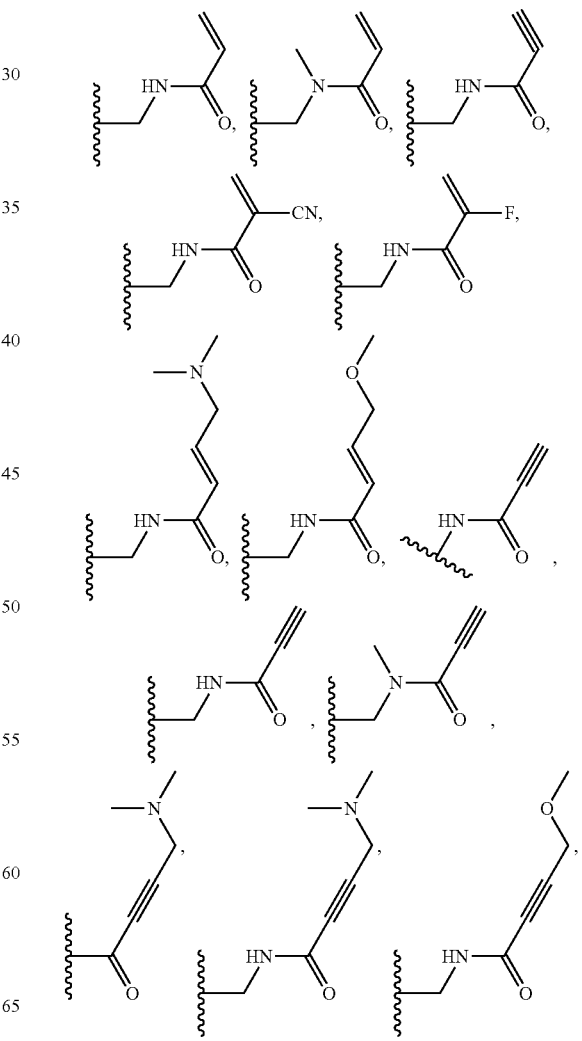

503
-continued

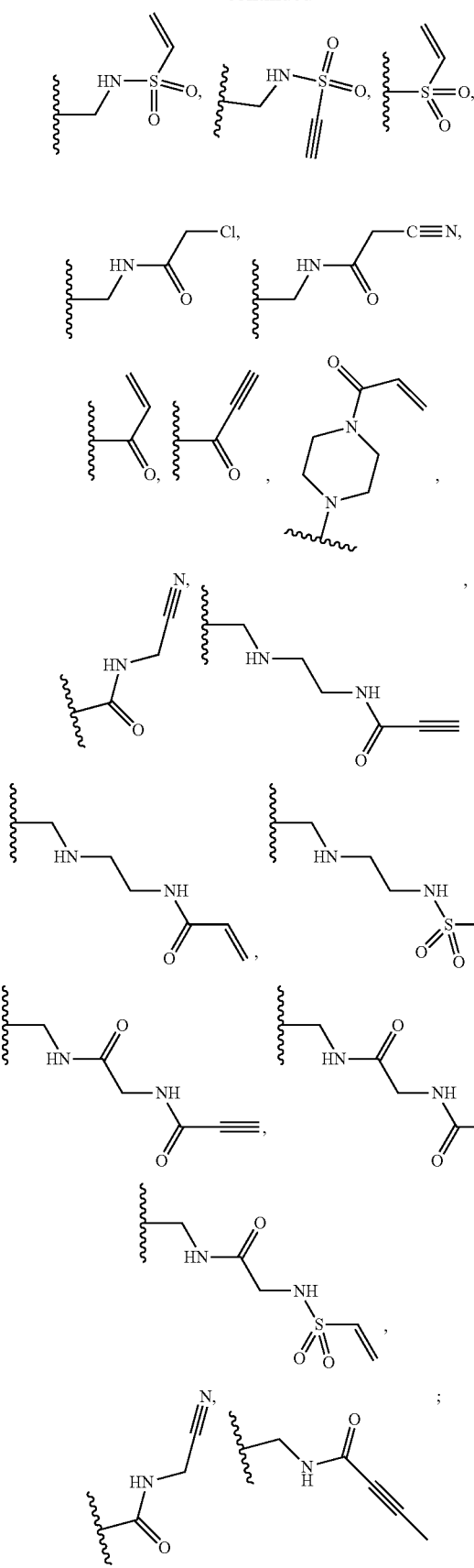

504
-continued

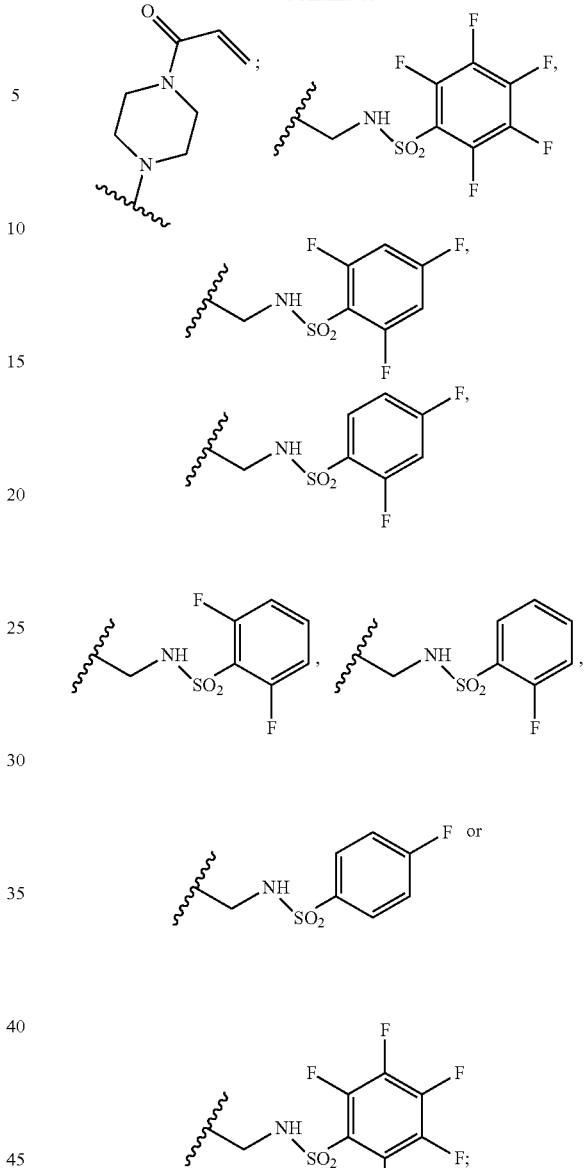

or a pharmaceutically acceptable salt or salts thereof, and/or a stereoisomer or mixture of stereoisomers thereof.

24. The compound of claim 2, wherein each $R^{2e}$ is hydrogen; or a pharmaceutically acceptable salt or salts thereof, and/or a stereoisomer or mixture of stereoisomers thereof.

25. The compound of claim 2, wherein each $R^{2b}$ is independently hydrogen or $C_1$-$C_3$alkyl; or a pharmaceutically acceptable salt or salts thereof, and/or a stereoisomer or mixture of stereoisomers thereof.

26. The compound of claim 2, wherein $R^{3c}$ and $R^{3d}$ are each independently hydrogen or $C_1$-$C_3$alkyl; or where $R^{3c}$ and $R^{3d}$, together with the nitrogen to which they are attached, form a pyrrolidinyl or piperidinyl; or a pharmaceutically acceptable salt or salts thereof; and/or a stereoisomer or mixture of stereoisomers thereof.

27. The compound of claim 1, selected from
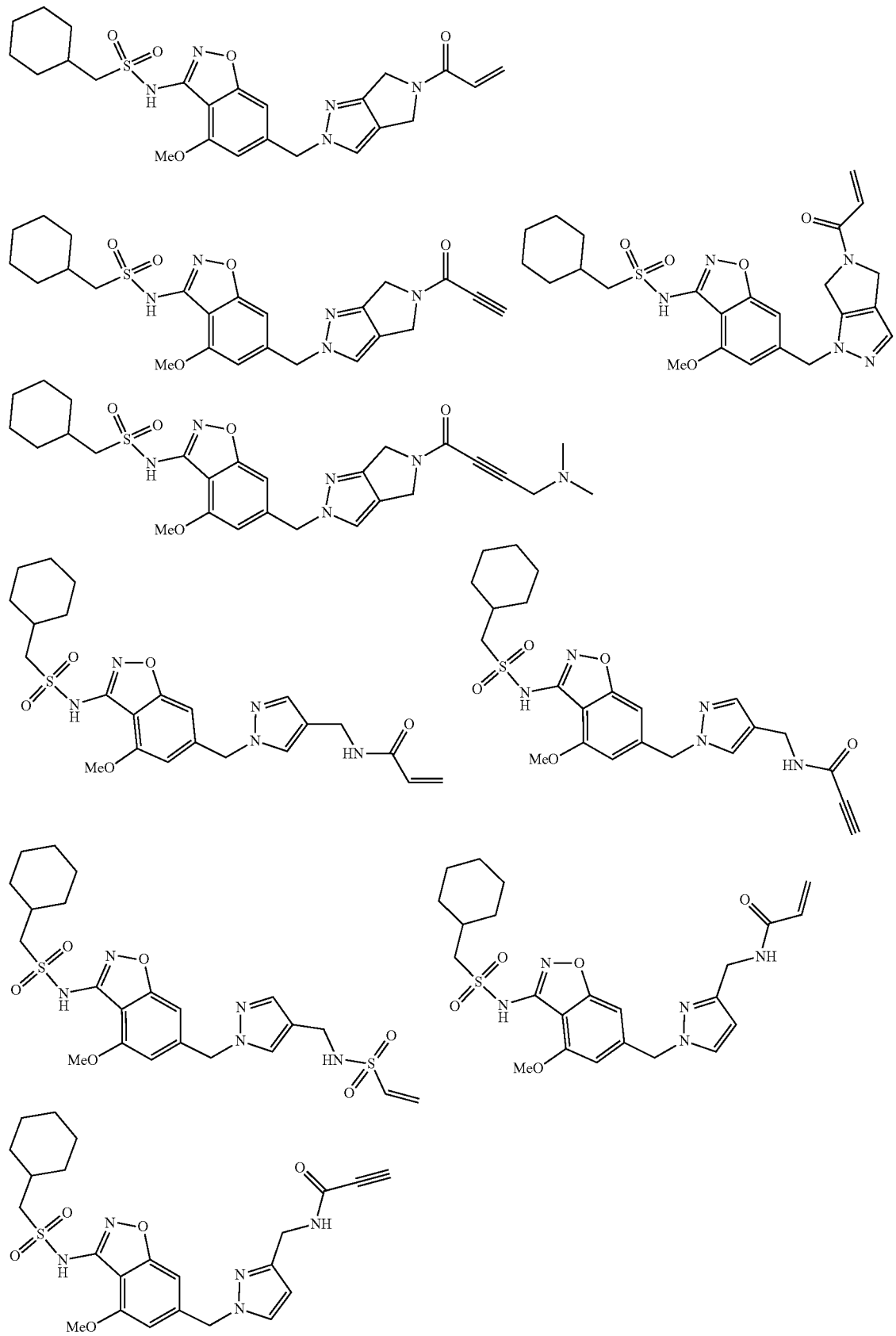

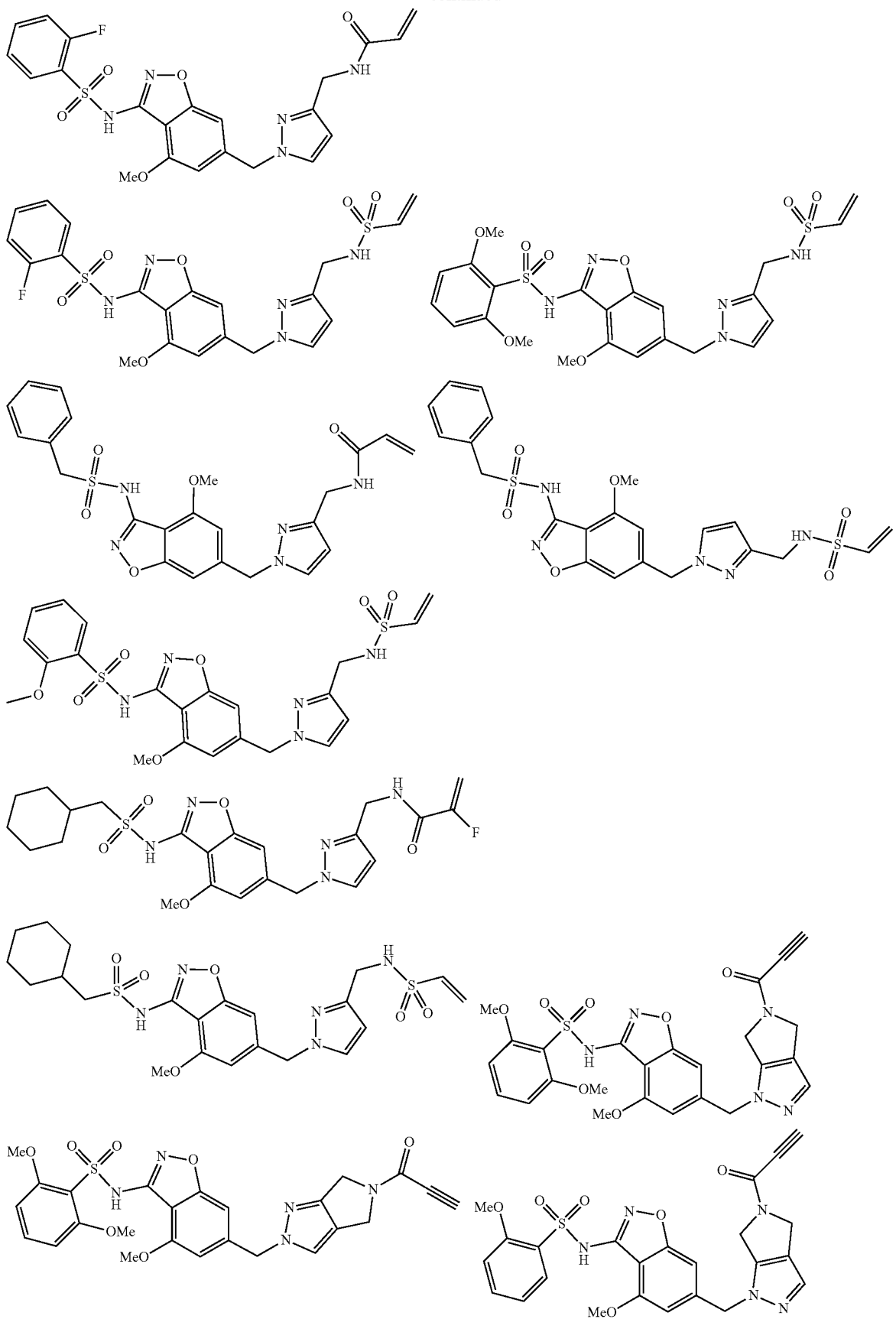

509 510
-continued
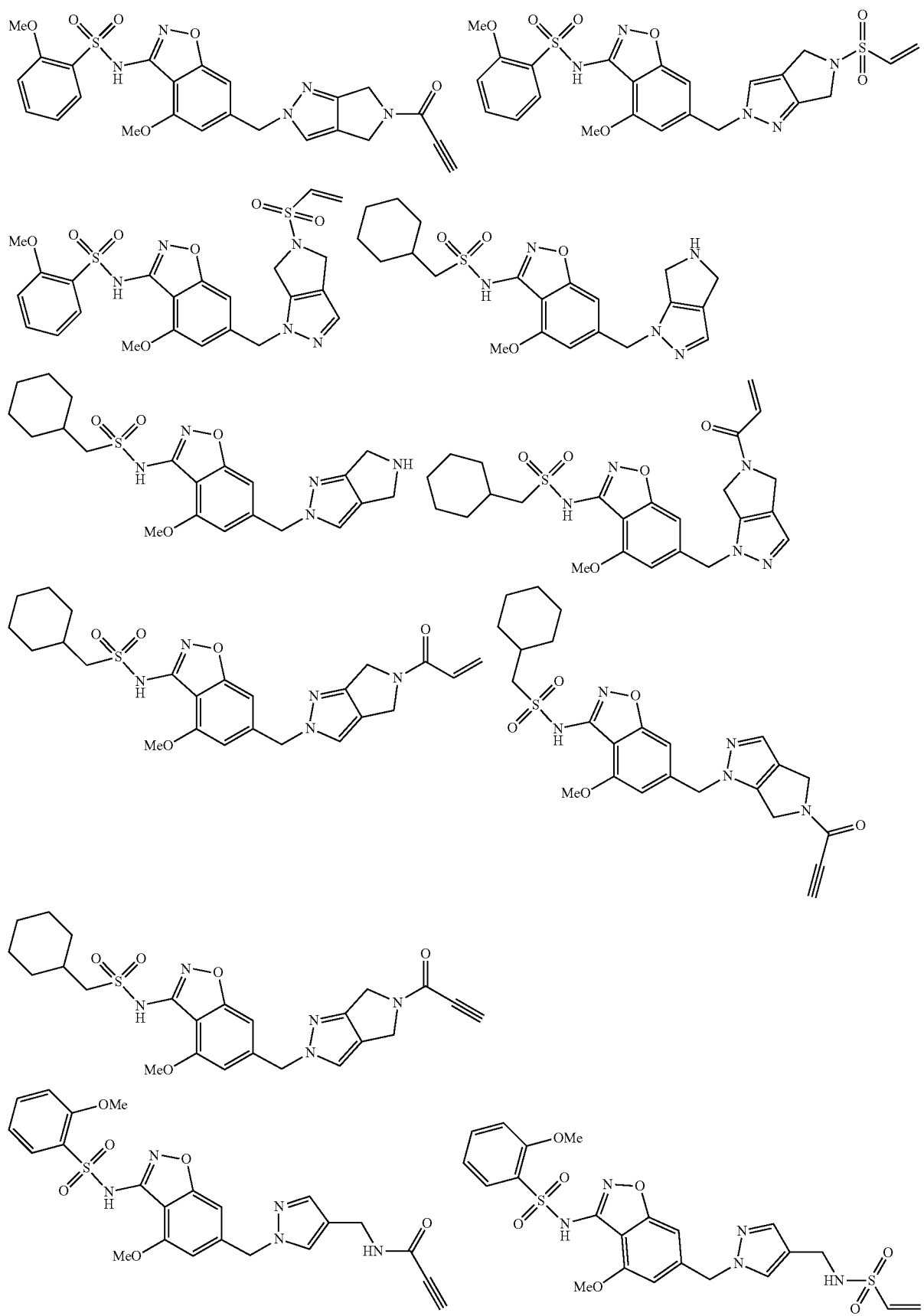

-continued
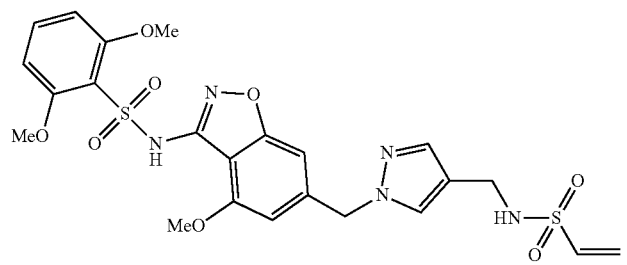
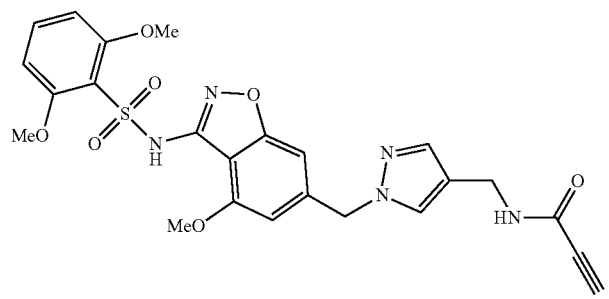
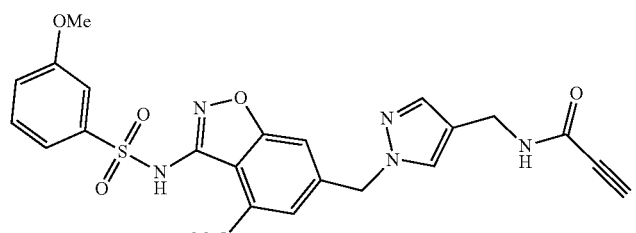
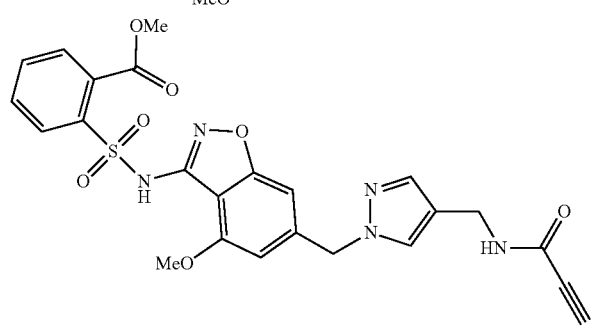
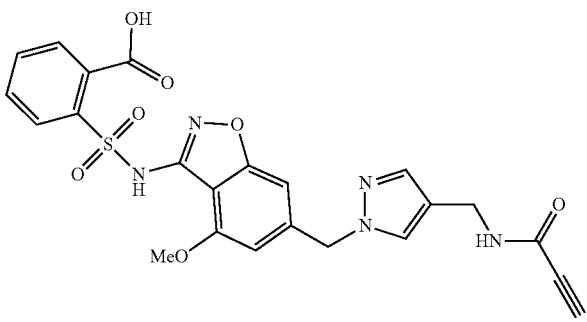
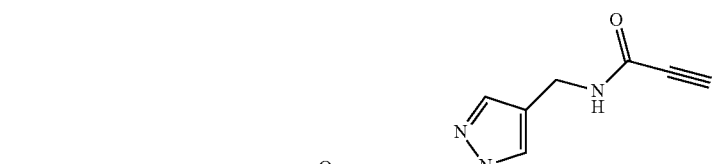
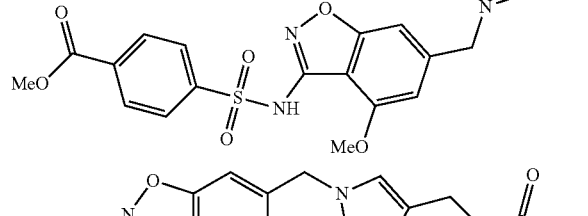
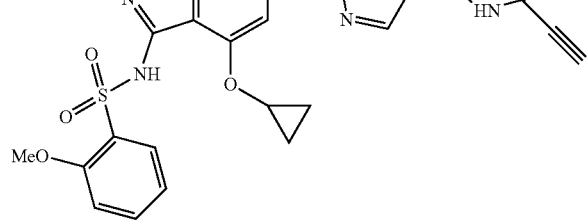

513 514
-continued
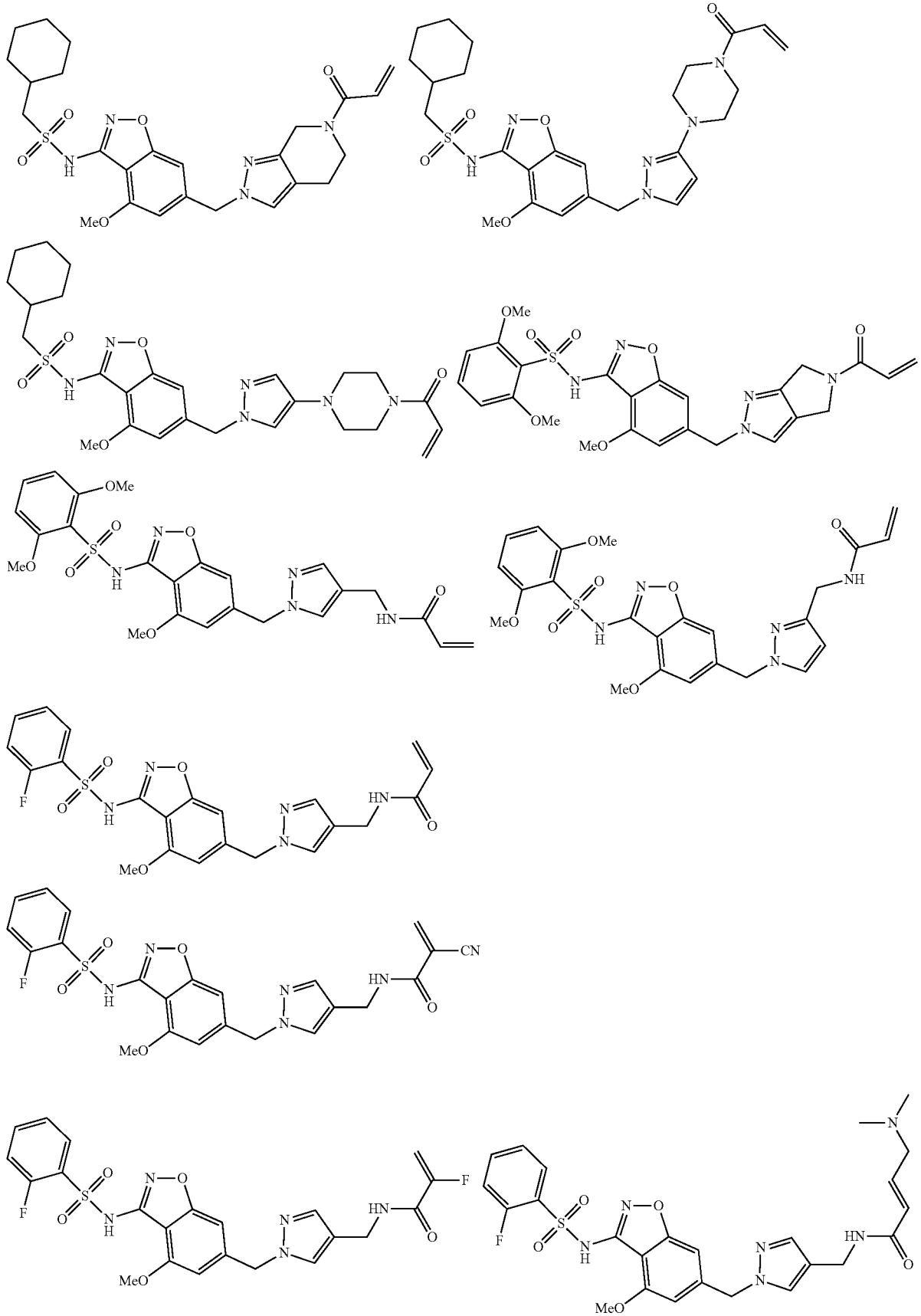

515
-continued
516
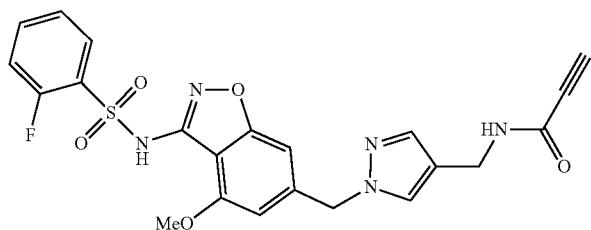
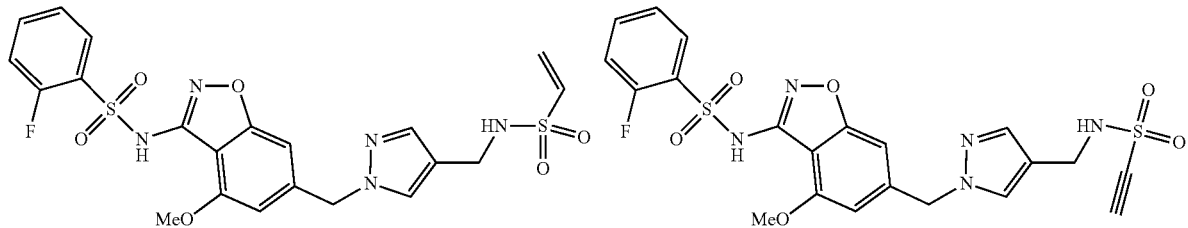
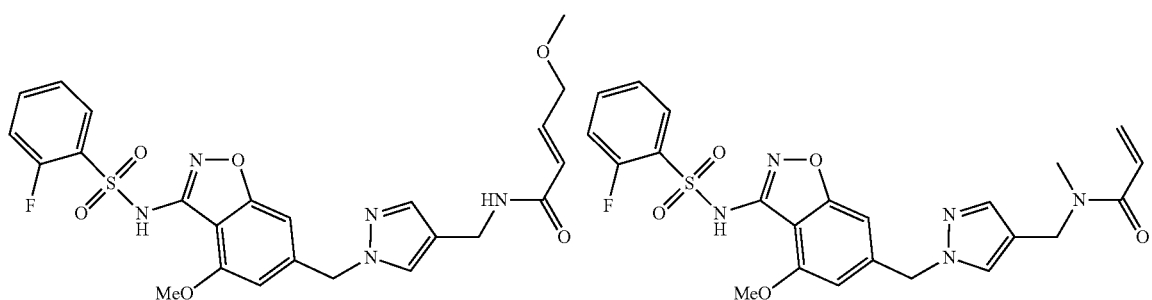
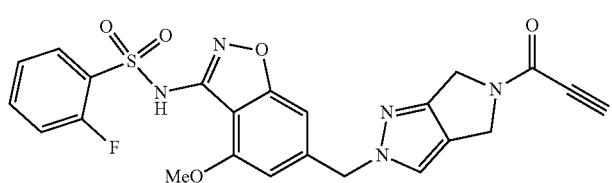
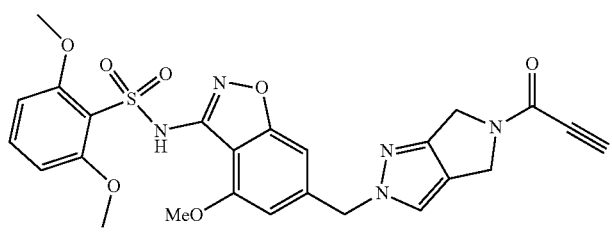
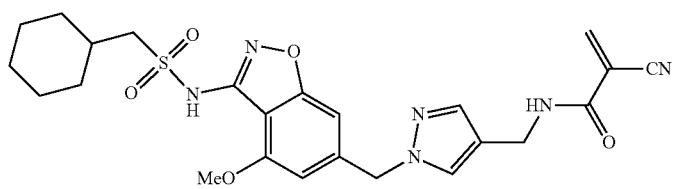
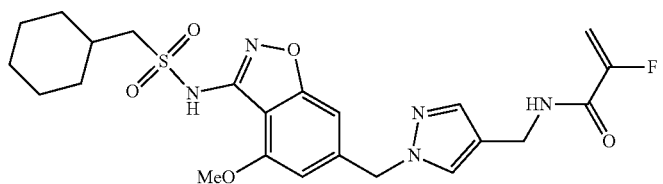

517
-continued
518
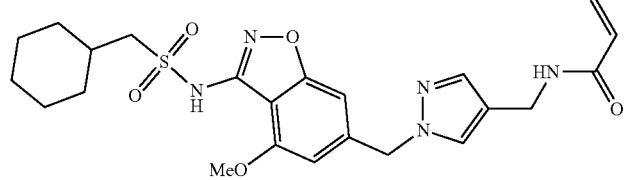
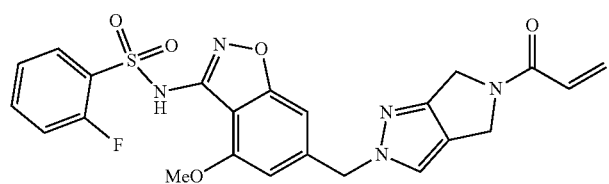
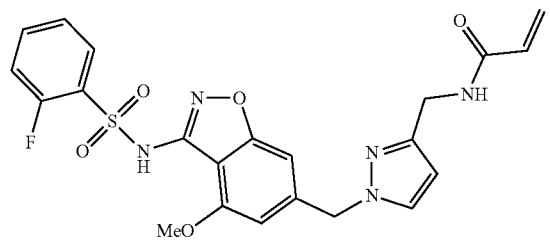
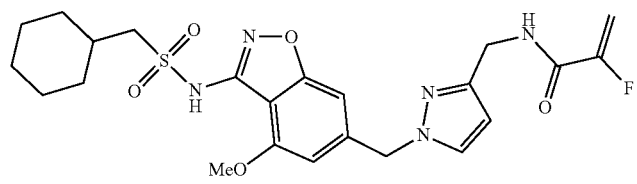
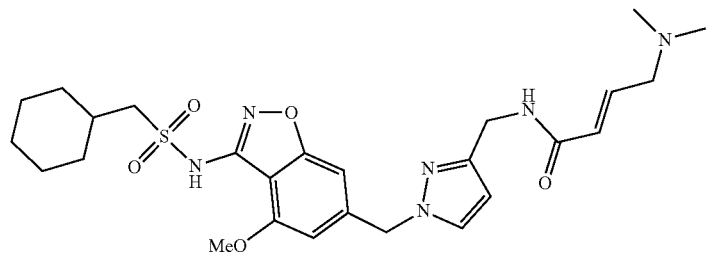
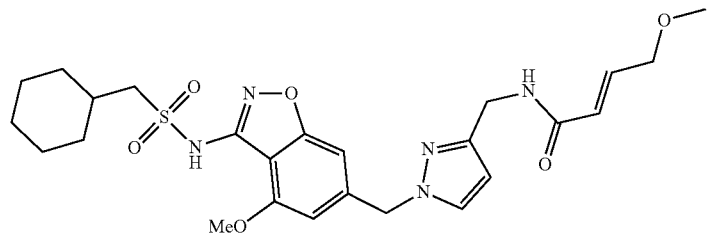

-continued
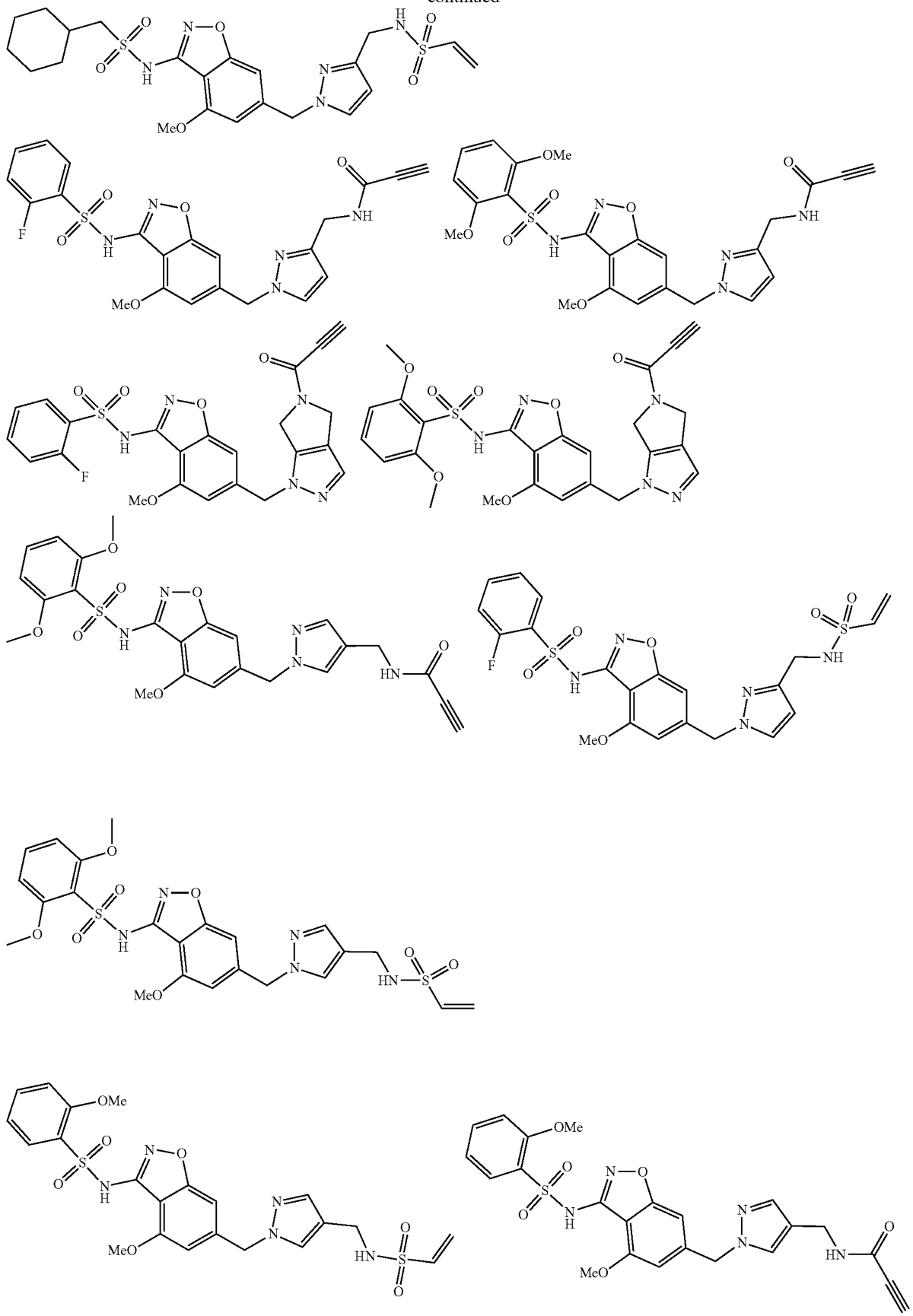

-continued
521
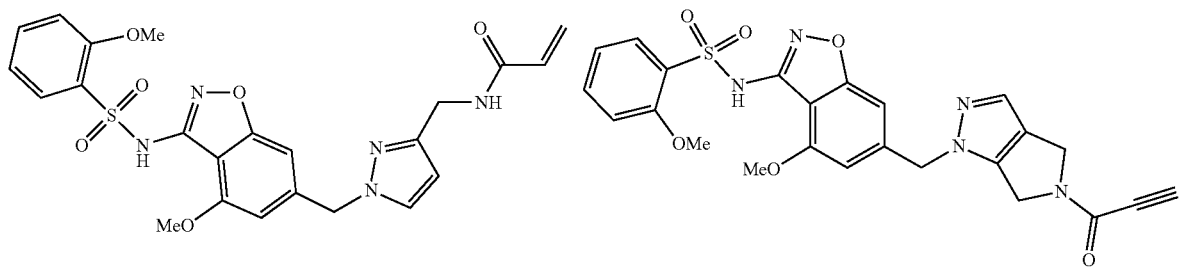
522
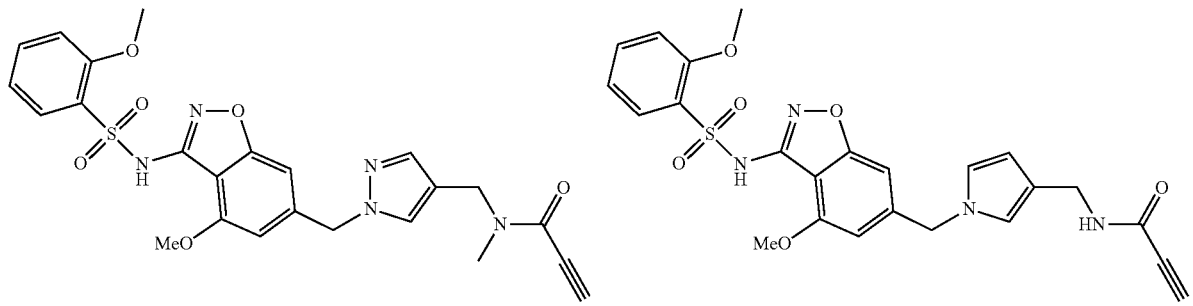
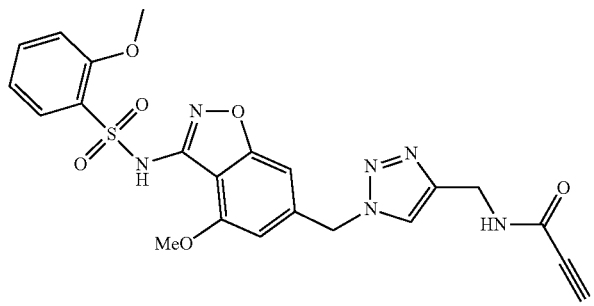
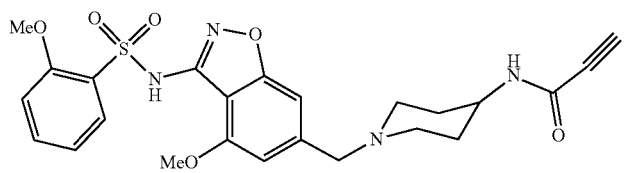
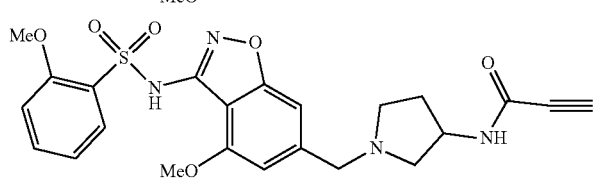
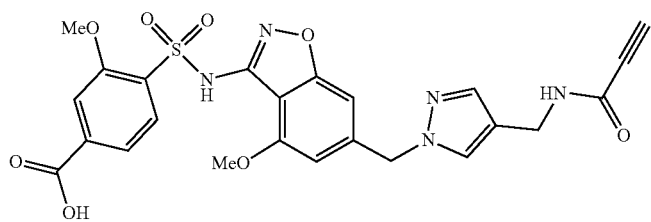
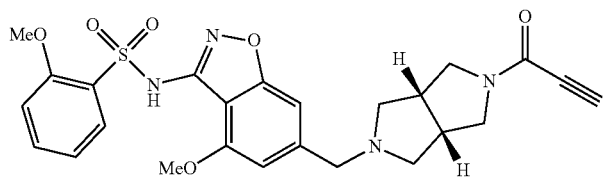

-continued
| 523 | 524 |
|---|---|
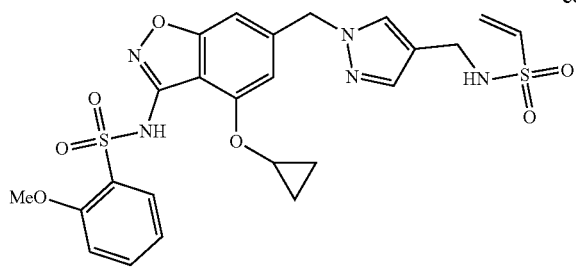
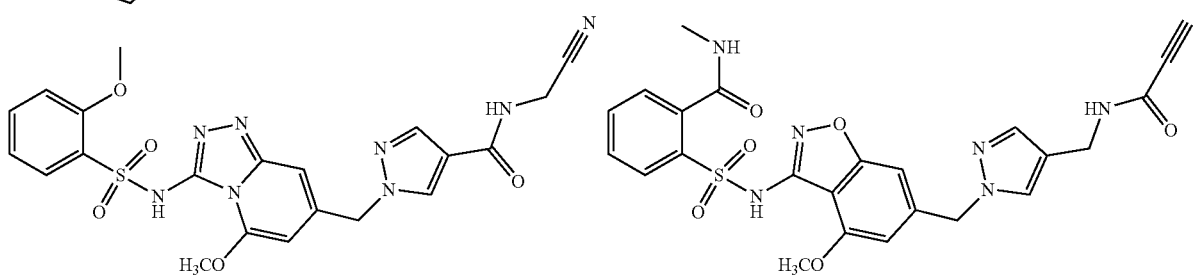
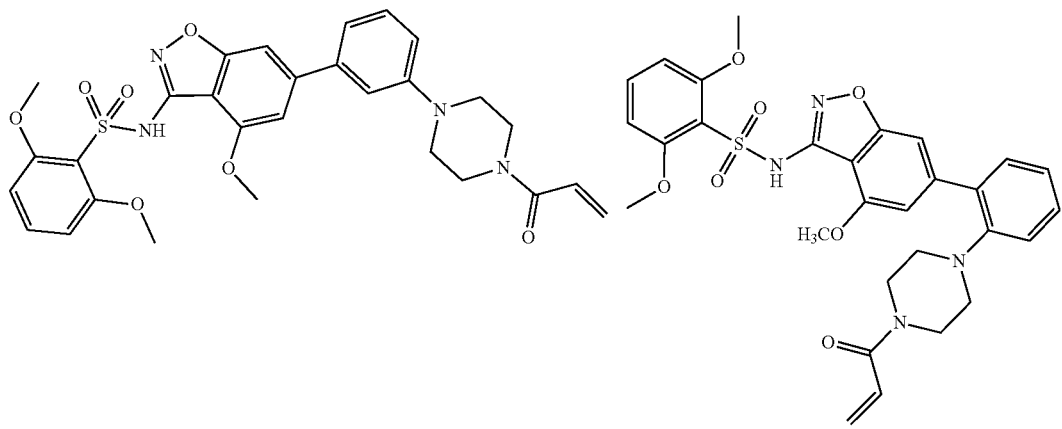
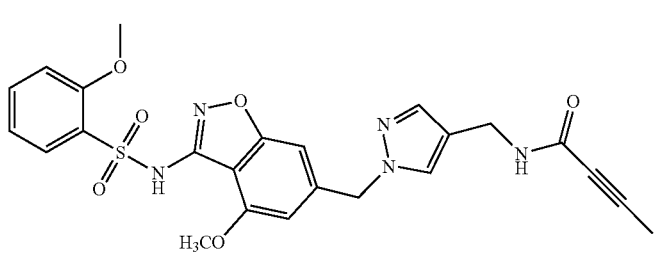
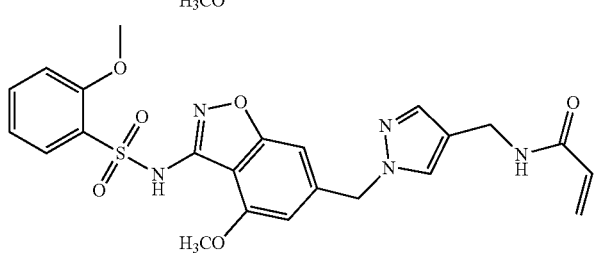
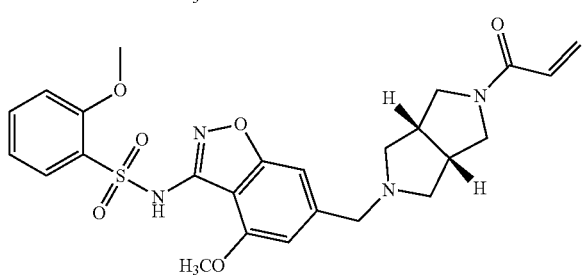

-continued
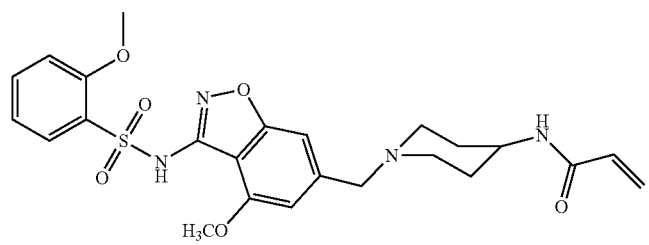
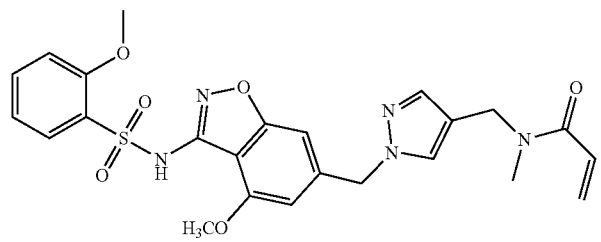
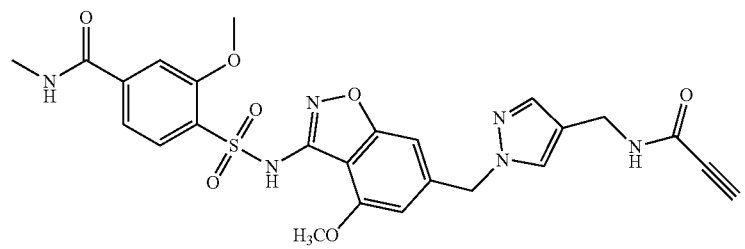
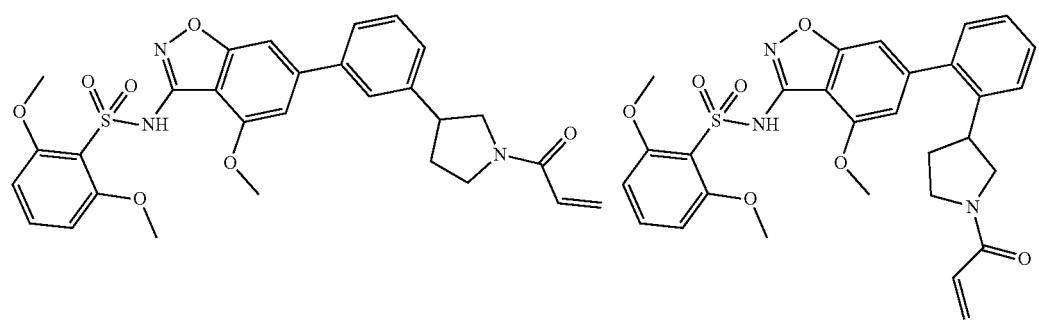
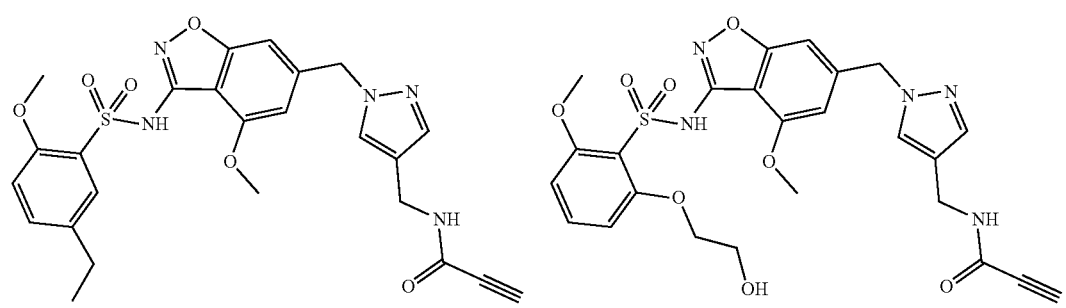
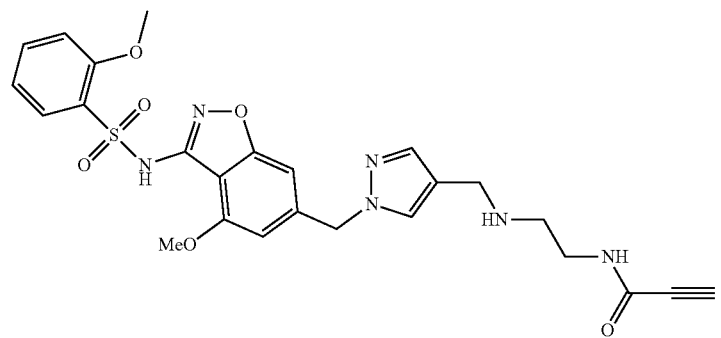

-continued
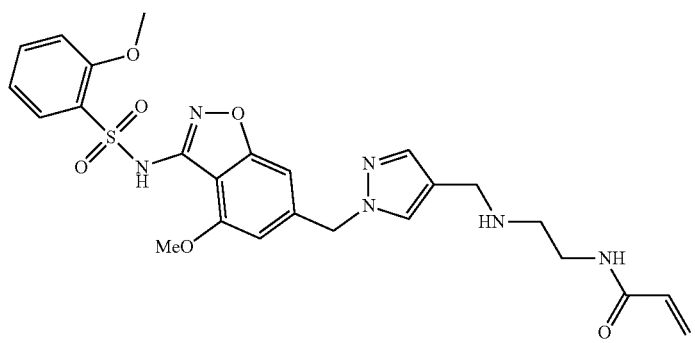
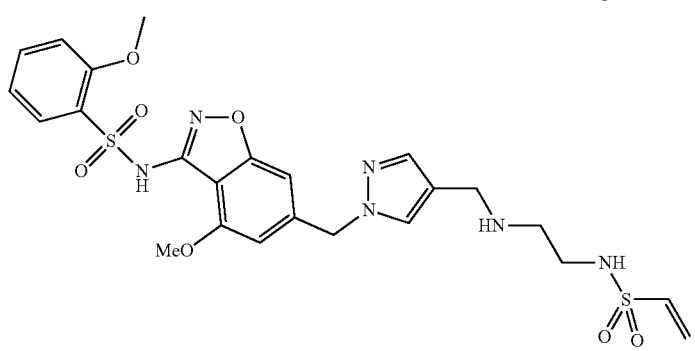
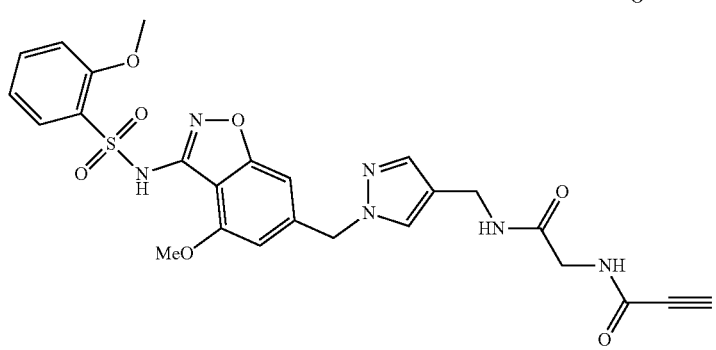
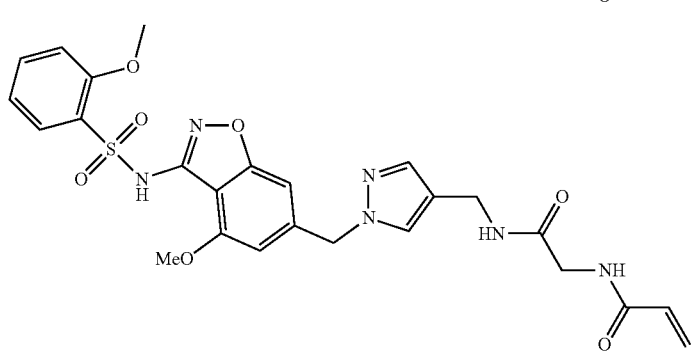
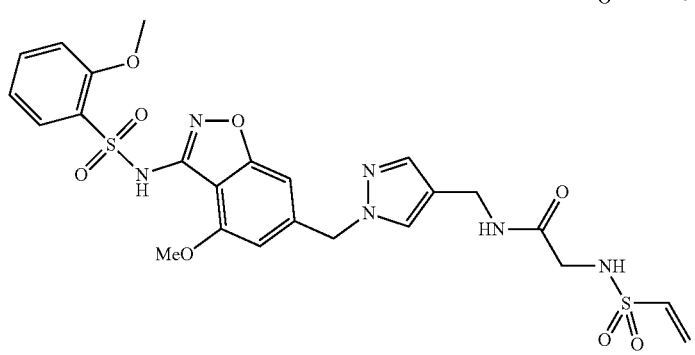

-continued
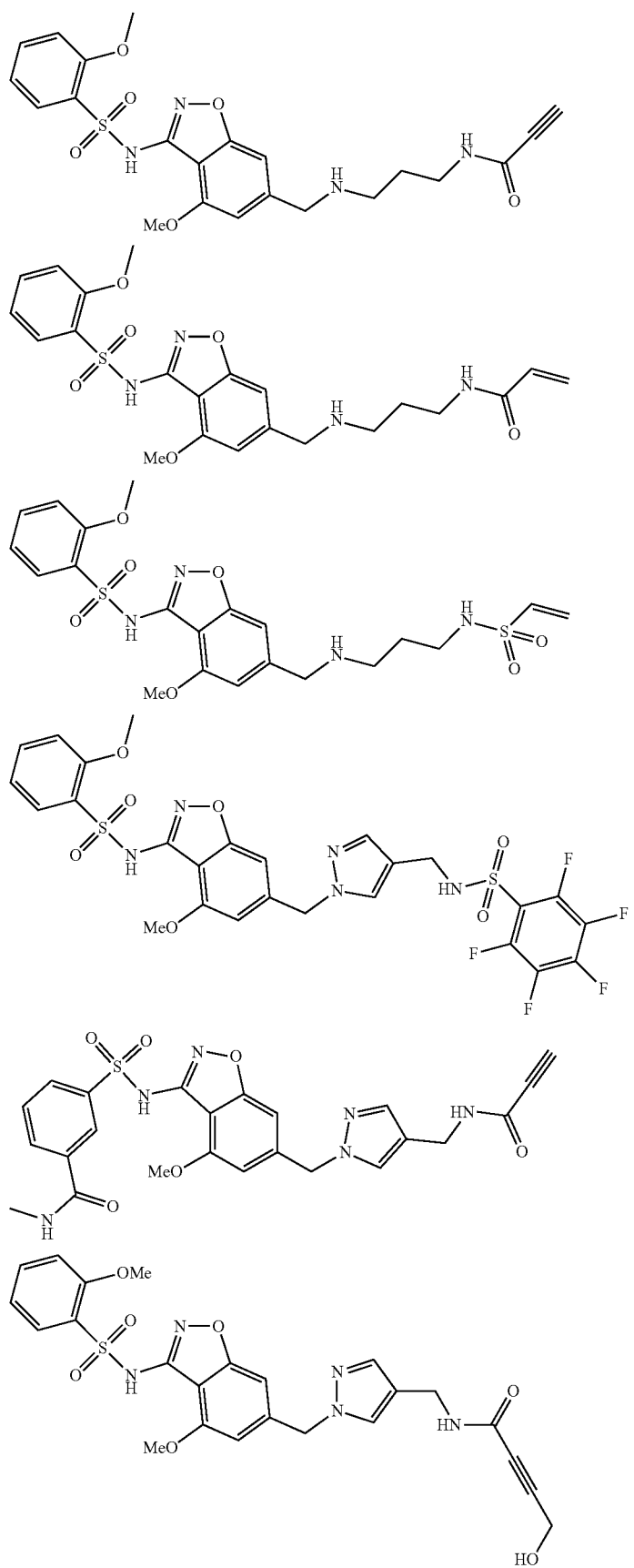

-continued
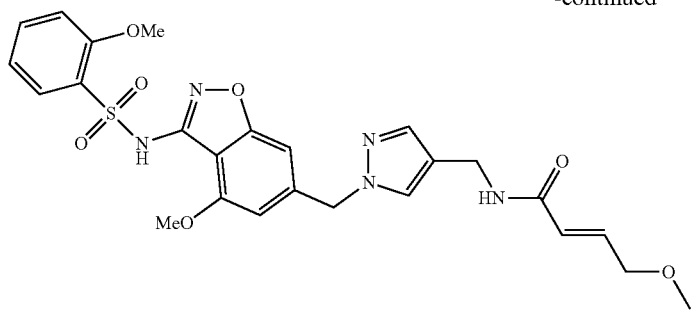
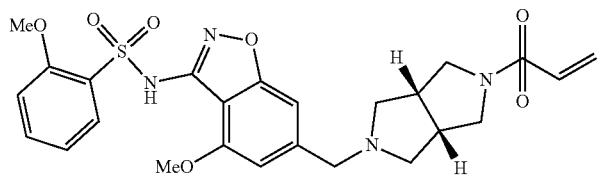
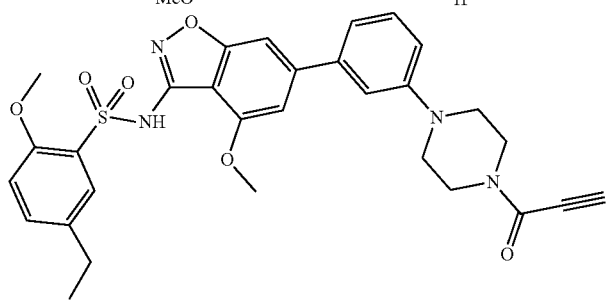
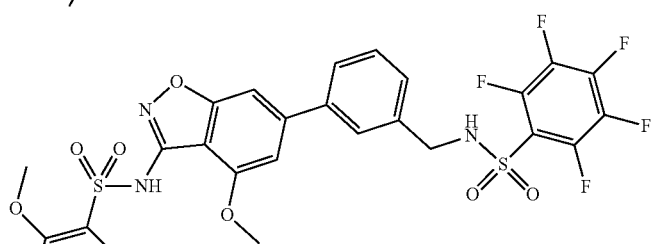
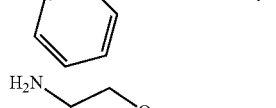
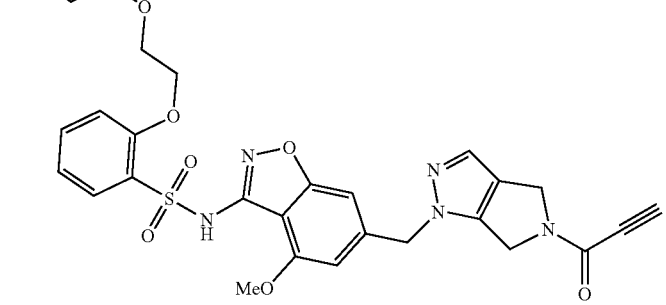
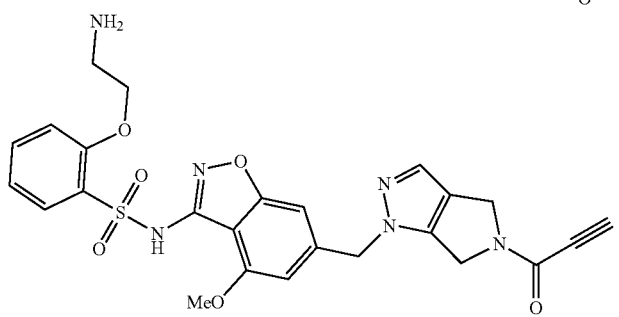

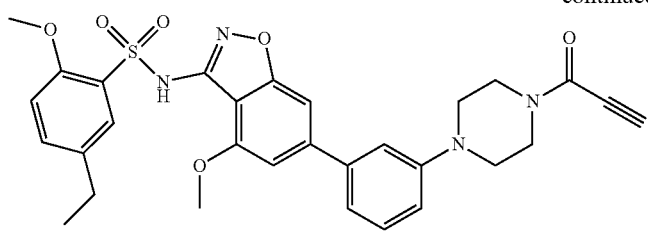
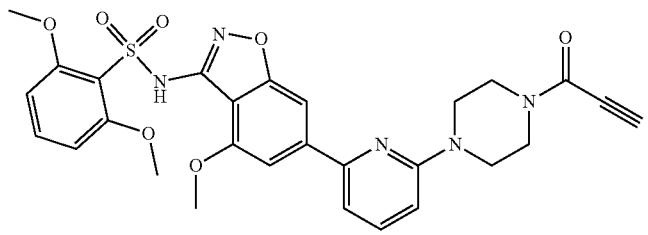
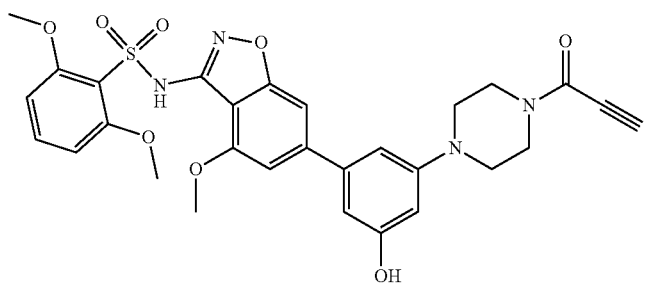
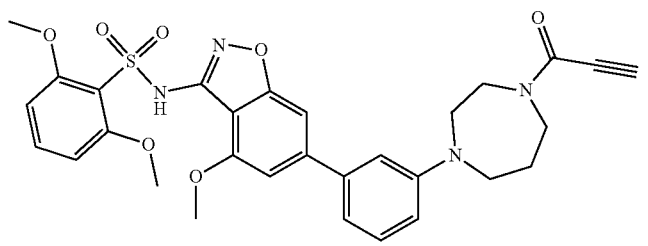
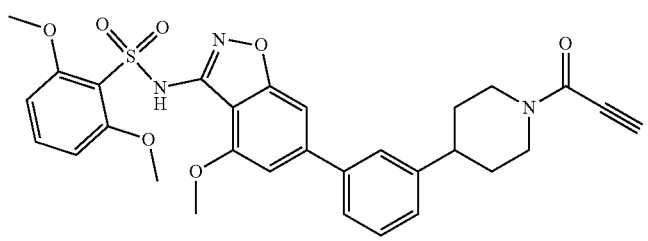
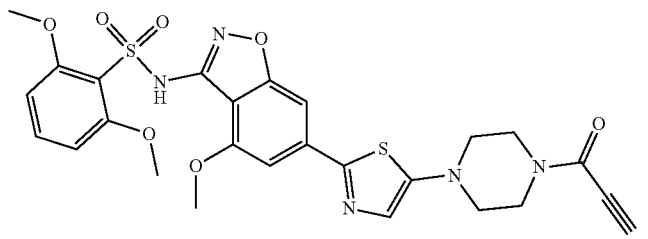
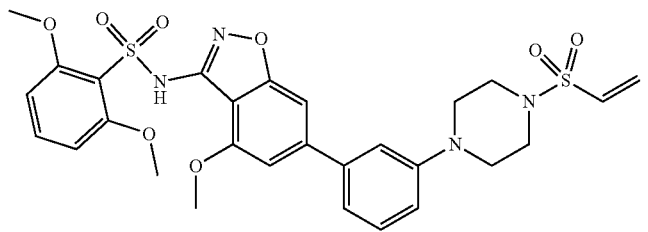

-continued
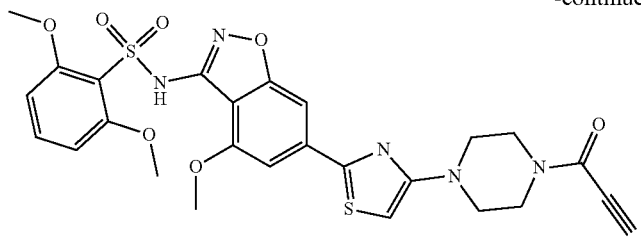
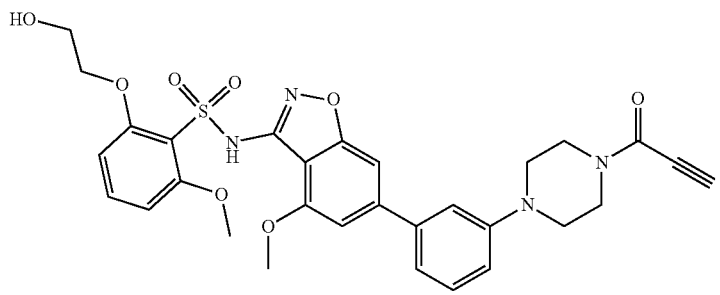
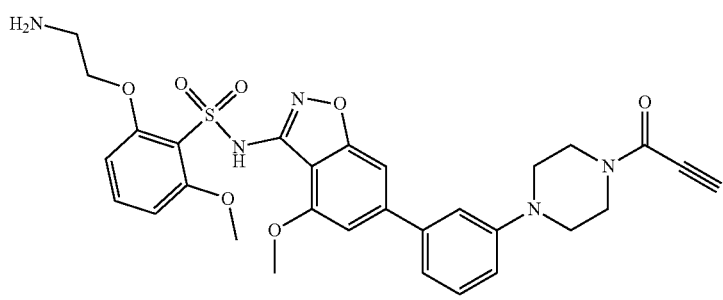
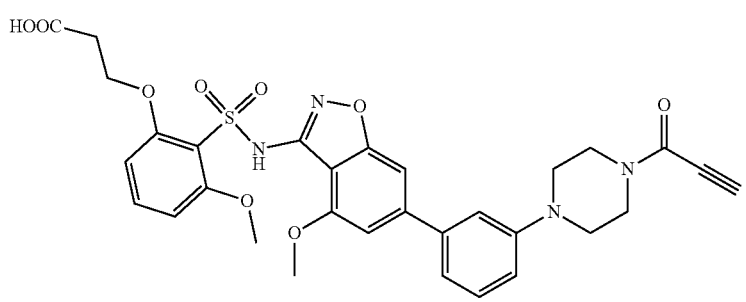
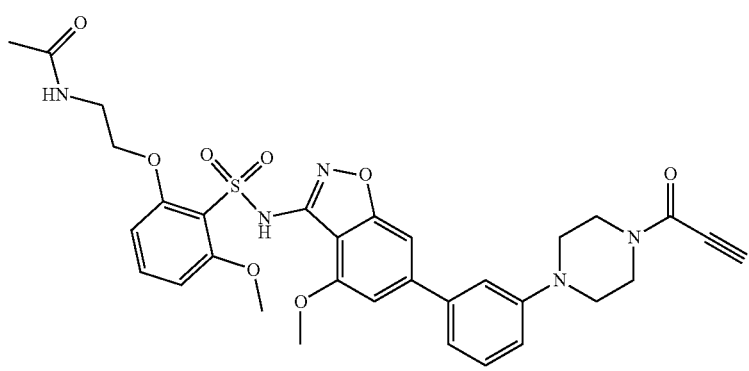

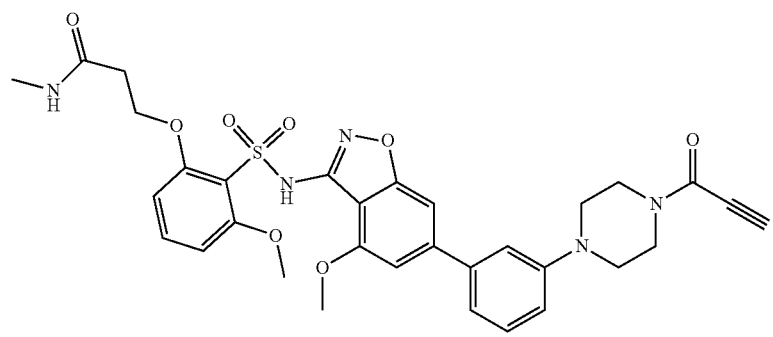
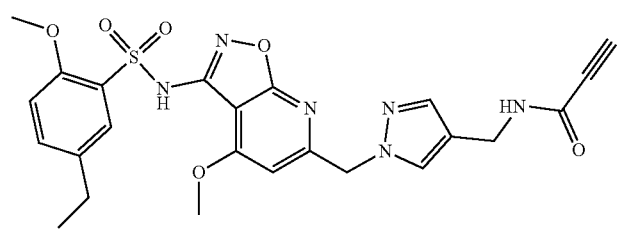
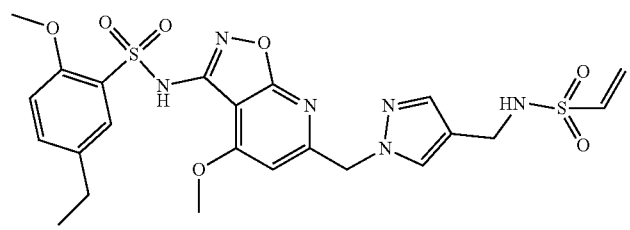
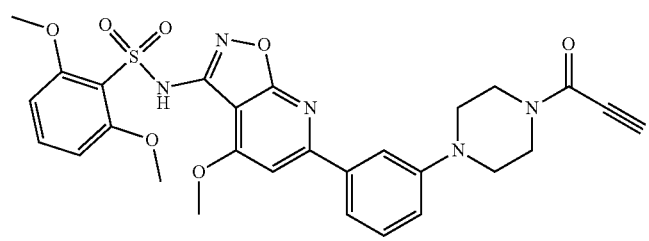
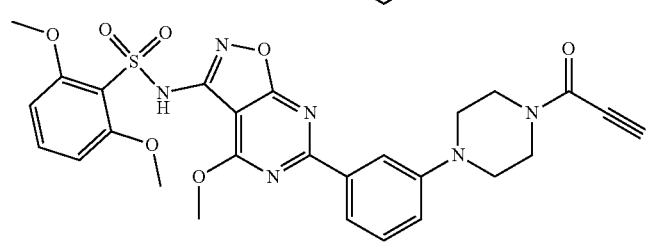
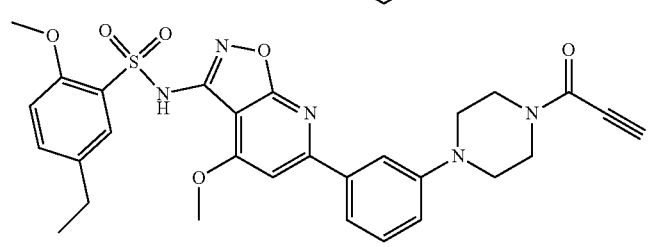
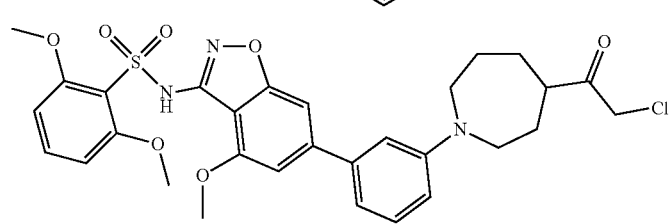

-continued
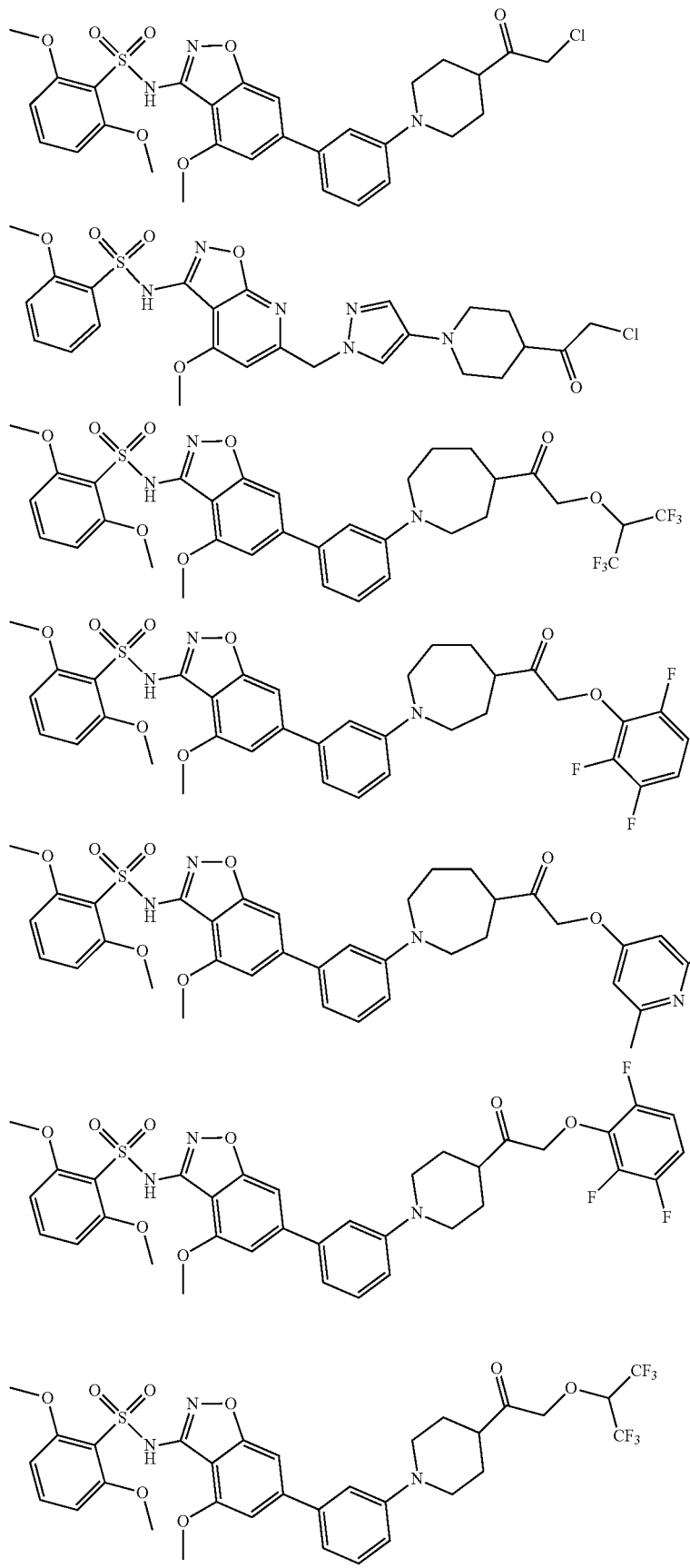

-continued
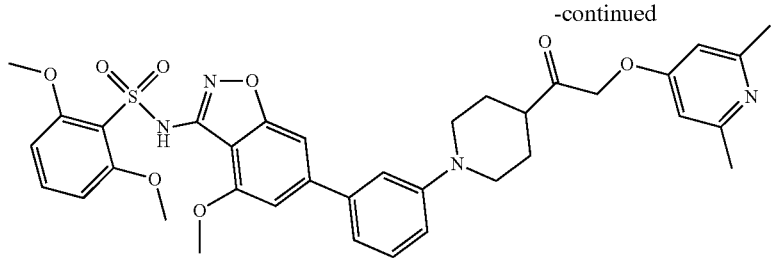
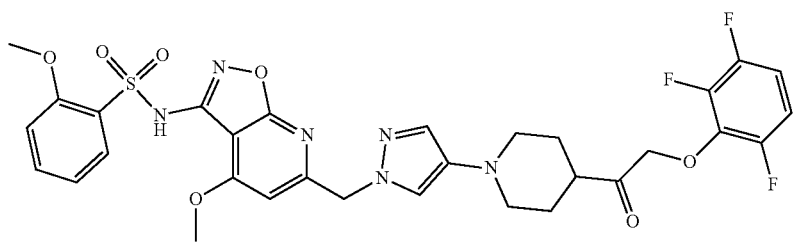
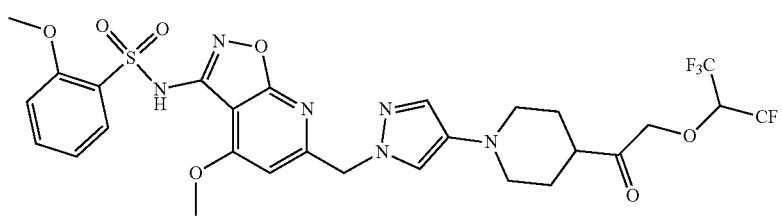
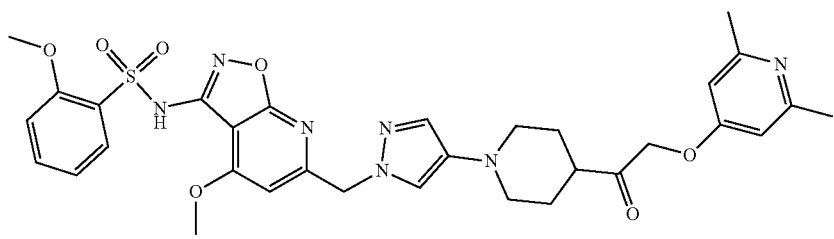
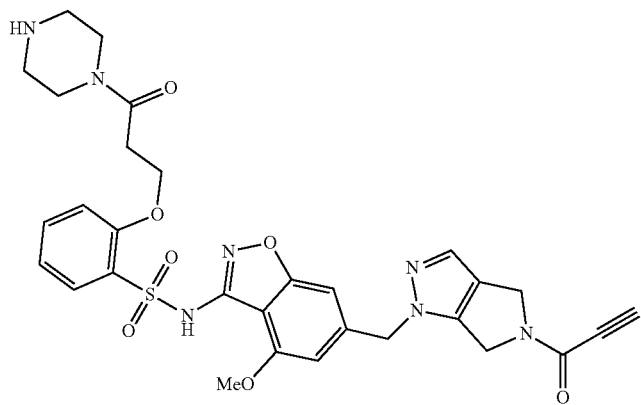

543

-continued

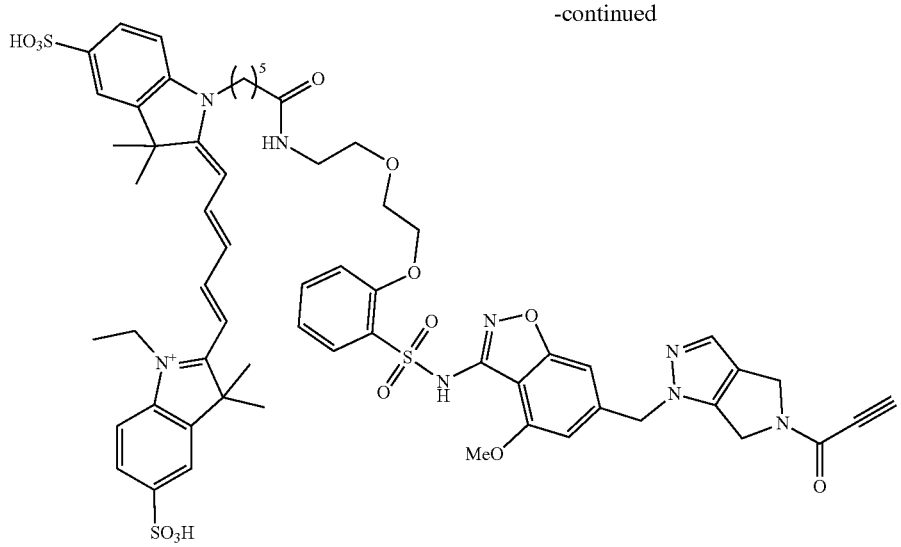

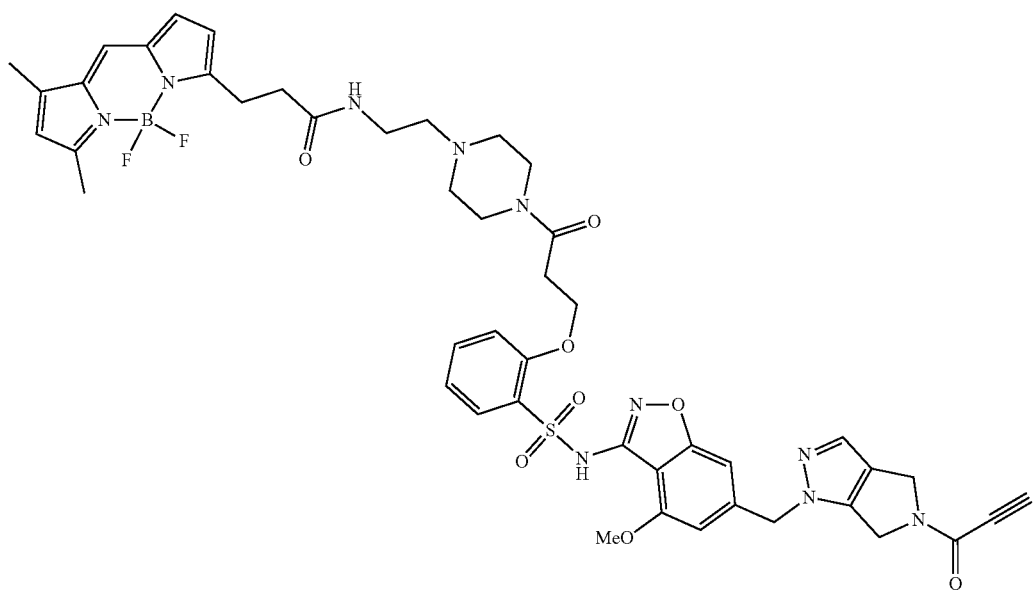

or a stereoisomer, a mixture of stereoisomers, and/or a pharmaceutically acceptable salt thereof.

28. The compound of claim 1, wherein:
R$^1$ is C$_3$-C$_8$-cycloalkyl optionally substituted with 1, 2, or 3 R$^{1a}$; C$_3$-C$_8$-cycloalkylalkyl where the C$_3$-C$_8$-cycloalkyl is optionally substituted with 1, 2, or 3 R$^{1a}$; phenyl optionally substituted with 1, 2, or 3 R$^{1b}$; naphthyl optionally substituted with 1, 2, or 3 R$^{1b}$; 5- or 6-membered monocyclic heteroaryl optionally substituted with 1, 2, or 3 R$^{1b}$; or 8-10-membered bicyclic heteroaryl optionally substituted with 1, 2, or 3 R$^{1b}$;

each R$^{1a}$ is independently selected from H, halo, C$_1$-C$_6$alkoxy, and C$_3$-C$_8$-cycloalkyloxy;

each R$^{1b}$ is independently selected from H, halo, C$_1$-C$_6$alkoxy, cyano and C$_3$-C$_8$-cycloalkyloxy;

R$^2$ is:

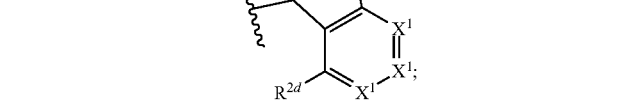

(b)

wherein,
one X$^1$ is C(CH$_2$R$^{2c}$), and the other two X$^1$ are independently selected from N and CR$^{2e}$;
R$^{2c}$ is a 5-membered monocyclic heteroaryl substituted with R$^{2c2}$ and optionally substituted with R$^{2c3}$; R$^{2c}$ is a 8- or 9-membered bicyclic heterocyclic optionally substituted with 1 or 2 $R^{2c}$; $R^{2c}$ is a 8- or 9-membered bicyclic heterocyclic substituted with $R^{2c2}$ and optionally substituted with $R^{2c3}$; $R^{2c}$ is a 6-membered monocyclic heteroaryl substituted with $R^{2c2}$ and optionally substituted with 1 or 2 $R^{2c3}$; $R^2$ is a 9-membered bicyclic heteroaryl substituted with $R^{2c2}$ and optionally substituted with 1 or 2 $R^{2c3}$; or $R^{2c}$ is a 10-membered bicyclic heteroaryl optionally substituted with 1, 2, or 3 $R^{2c1}$;

$R^{2c2}$ is $C_1$-$C_6$alkylcarbonyl, —$CH_2NH_2$, $C_1$-$C_6$alkoxy, —$NC(C_3$-$C_6$alkyl), —$N(C_1$-$C_6$alkyl)$_2$, —$CH_2NHC(O)R^{2f}$, —$(CH_2)_{0-1}NHC(O)OR^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

$R^{2c3}$ is independently H, halo, $C_1$-$C_6$alkyl, $C_1$-$C_6$alkoxy, or $C_3$-$C_8$cycloalkyloxy; and each $R^{2c1}$ is independently H, halo, $C_1$-$C_6$alkyl, $C_1$-$C_6$alkylcarbonyl, $C_1$-$C_6$alkoxy, $C_3$-$C_8$cycloalkyloxy, —CN, —$CH_2NH_2$, —$NH(C_1$-$C_6$alkyl), —$N(C_1$-$C_6$alkyl)$_2$, —$CH_2NHC(O)R^{2f}$, —$(CH_2)_{0-1}NHC(O)OR^{2f}$, 5- or 6-membered monocyclic heteroaryl, or 9- or 10-membered bicyclic heteroaryl; wherein $R^{2f}$ is $C_1$-$C_6$alkyl, $C_3$-$C_6$cycloalkyl, or $C_3$-$C_6$cycloalkyl$C_1$-$C_3$alkyl;

or a pharmaceutically acceptable salt or salts thereof; and/or a stereoisomer or mixture of stereoisomers thereof.

29. The compound of claim 28, wherein $R^1$ is $C_3$-$C_8$-cycloalkylalkyl where the $C_3$-$C_8$-cycloalkylalkyl is optionally substituted with 1, 2, or 3 $R^{1a}$, or phenyl optionally substituted with 1, 2, or 3 $R^{1b}$; or a pharmaceutically acceptable salt or salts thereof; and/or a stereoisomer or mixture of stereoisomers thereof.

30. The compound of claim 28, wherein $R^1$ is $C_3$-$C_8$-cycloalkyl optionally substituted with 1, 2, or 3 $R^{1a}$; or a pharmaceutically acceptable salt or salts thereof; and/or a stereoisomer or mixture of stereoisomers thereof.

31. The compound of claim 28, wherein $R^1$ is $C_3$-$C_8$-cycloalkylalkyl where the $C_3$-$C_8$-cycloalkylalkyl is optionally substituted with 1, 2, or 3 $R^{1a}$; or a pharmaceutically acceptable salt or salts thereof; and/or a stereoisomer or mixture of stereoisomers thereof.

32. The compound of claim 28, wherein $R^1$ is phenyl optionally substituted with 1, 2, or 3 $R^{1b}$; or a pharmaceutically acceptable salt or salts thereof; and/or a stereoisomer or mixture of stereoisomers thereof.

33. The compound of claim 28, wherein $R^1$ is naphthyl optionally substituted with 1, 2, or 3 $R^{1b}$; or a pharmaceutically acceptable salt or salts thereof; and/or a stereoisomer or mixture of stereoisomers thereof.

34. The compound of claim 28, wherein $R^1$ is 5- or 6-membered monocyclic heteroaryl optionally substituted with 1, 2, or 3 $R^{1b}$; or a pharmaceutically acceptable salt or salts thereof; and/or a stereoisomer or mixture of stereoisomers thereof.

35. The compound of claim 28, wherein $R^1$ is 8-10-membered bicyclic heteroaryl optionally substituted with 1, 2, or 3 $R^{1b}$; or a pharmaceutically acceptable salt or salts thereof; and/or a stereoisomer or mixture of stereoisomers thereof.

36. The compound of claim 28, wherein each $R^{1a}$ is independently H; or a pharmaceutically acceptable salt or salts thereof; and/or a stereoisomer or mixture of stereoisomers thereof.

37. The compound of claim 28, wherein each $R^{1b}$ is independently selected from H, halo, and $C_1$-$C_6$alkoxy; or a pharmaceutically acceptable salt or salts thereof, and/or a stereoisomer or mixture of stereoisomers thereof.

38. The compound of claim 28, wherein $R^{2d}$ is halo, $C_1$-$C_3$alkyl, $C_1$-$C_3$alkoxy, or $C_3$-cycloalkyloxy; or a pharmaceutically acceptable salt or salts thereof, and/or a stereoisomer or mixture of stereoisomers thereof.

39. The compound of claim 28, wherein $R^{2d}$ is $C_1$-$C_6$alkoxy; or a pharmaceutically acceptable salt or salts thereof, and/or a stereoisomer or mixture of stereoisomers thereof.

40. The compound of claim 28, wherein $R^{2e}$ is independently hydrogen, fluoro, $C_1$-$C_3$alkyl, cyclopropyl, —$CHF_2$, —$CF_3$, $C_1$-$C_4$alkoxy, —$OCHF_2$, or —$OCF_3$; or a pharmaceutically acceptable salt or salts thereof; and/or a stereoisomer or mixture of stereoisomers thereof.

41. The compound of claim 28, wherein one $X^1$ is $C(CH_2R^{2c})$, and the other two $X^1$ are each $CR^{2e}$; or a pharmaceutically acceptable salt or salts thereof, and/or a stereoisomer or mixture of stereoisomers thereof.

42. The compound of claim 28, wherein one $X^1$ is $C(CH_2R^{2c})$, the second $X^1$ is N, and the third $X^1$ is $CR^{2e}$; or a pharmaceutically acceptable salt or salts thereof, and/or a stereoisomer or mixture of stereoisomers thereof.

43. The compound of claim 28, wherein one $X^1$ is $C(CH_2R^{2c})$, and the other two $X^1$ are each N; or a pharmaceutically acceptable salt or salts thereof; and/or a stereoisomer or mixture of stereoisomers thereof.

44. The compound of claim 28, wherein $C(CH_2R^{2c})$ is in the meta-position with respect to $R^{2d}$; or a pharmaceutically acceptable salt or salts thereof, and/or a stereoisomer or mixture of stereoisomers thereof.

45. The compound of claim 28, wherein the compound of Formula (I) is according to Formula (Ii):

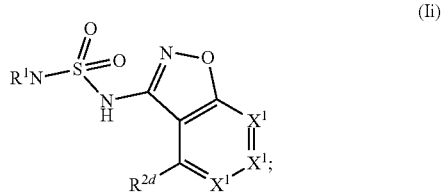

or a pharmaceutically acceptable salt or salts thereof, and/or a stereoisomer or mixture of stereoisomers thereof.

46. The compound of claim 28, wherein $R^{2c}$ is a 5-membered monocyclic heteroaryl substituted with $R^{2c2}$ and optionally substituted with $R^{2c3}$; a 8- or 9-membered bicyclic heterocyclic optionally substituted with 1 or 2 $R^{2c1}$; a 8- or 9-membered bicyclic heterocyclic substituted with $R^{2c2}$ and optionally substituted with $R^{2c3}$; a 6-membered monocyclic heteroaryl substituted with $R^{2c2}$ and optionally substituted with 1 or 2 $R^{2c3}$; or a pharmaceutically acceptable salt or salts thereof; and/or a stereoisomer or mixture of stereoisomers thereof.

47. The compound of claim 46, wherein $R^{2c}$ is a 8- or 9-membered bicyclic heterocyclic group, wherein $R^{2c}$ is optionally substituted with 1 or 2 $R^{2c1}$; or a pharmaceutically acceptable salt or salts thereof, and/or a stereoisomer or mixture of stereoisomers thereof.

48. The compound of claim 46, wherein $R^{2c}$ is a 5-membered monocyclic heteroaryl substituted with $R^{2c2}$ and optionally substituted with $R^{2c3}$; or a pharmaceutically acceptable salt or salts thereof; and/or a stereoisomer or mixture of stereoisomers thereof.

49. The compound of claim 46, wherein $R^{2c}$ is a 5-membered heteroaryl group fused to a nonaromatic cyclic group, wherein $R^{2c}$ is substituted with $R^{2c2}$ and optionally substituted with $R^{2c3}$; or a pharmaceutically acceptable salt or salts thereof; and/or a stereoisomer or mixture of stereoisomers thereof.

50. The compound of claim 46, wherein $R^{2c}$ is a 6-membered monocyclic heteroaryl, substituted with $R^{2c2}$ and optionally substituted with 1 or 2 $R^{2c3}$; or a pharmaceutically acceptable salt or salts thereof, and/or a stereoisomer or mixture of stereoisomers thereof.

51. The compound of claim 48, wherein $R^{2c2}$ is $C_1$-$C_6$alkylcarbonyl, —$CH_2NH_2$, or —$CH_2NHC(O)R^{2f}$, —$(CH_2)_{0-1}NHC(O)OR^{2f}$; wherein $R^{2f}$ is $C_1$-$C_6$alkyl, $C_3$-$C_6$cycloalkyl, or $C_3$-$C_6$cycloalkyl$C_1$-$C_3$alkyl; or a pharmaceutically acceptable salt or salts thereof; and/or a stereoisomer or mixture of stereoisomers thereof.

52. The compound of claim 48, wherein each $R^{2c3}$ is hydrogen; or a pharmaceutically acceptable salt or salts thereof, and/or a stereoisomer or mixture of stereoisomers thereof.

53. The compound of claim 28, wherein each $R^{2c1}$ is hydrogen; or one $R^{2c1}$ is selected from $C_1$-$C_6$alkylcarbonyl, —CN, —$CH_2NH_2$, and —$CH_2NHC(O)R^{2f}$, —$(CH_2)_{0-1}NHC(O)OR^{2f}$, wherein $R^{2f}$ is $C_1$-$C_6$alkyl, $C_3$-$C_6$cycloalkyl, or $C_3$-$C_6$cycloalkyl$C_1$-$C_3$alkyl; and the other one or two $R^{2c1}$ are each hydrogen; or one $R^{2c1}$ is —CN and the other one or two $R^{2c1}$ are each hydrogen; or a pharmaceutically acceptable salt or salts thereof, and/or a stereoisomer or mixture of stereoisomers thereof.

54. The compound of claim 28, selected from

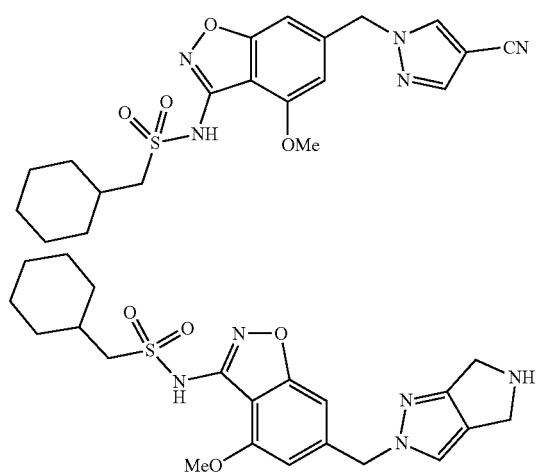

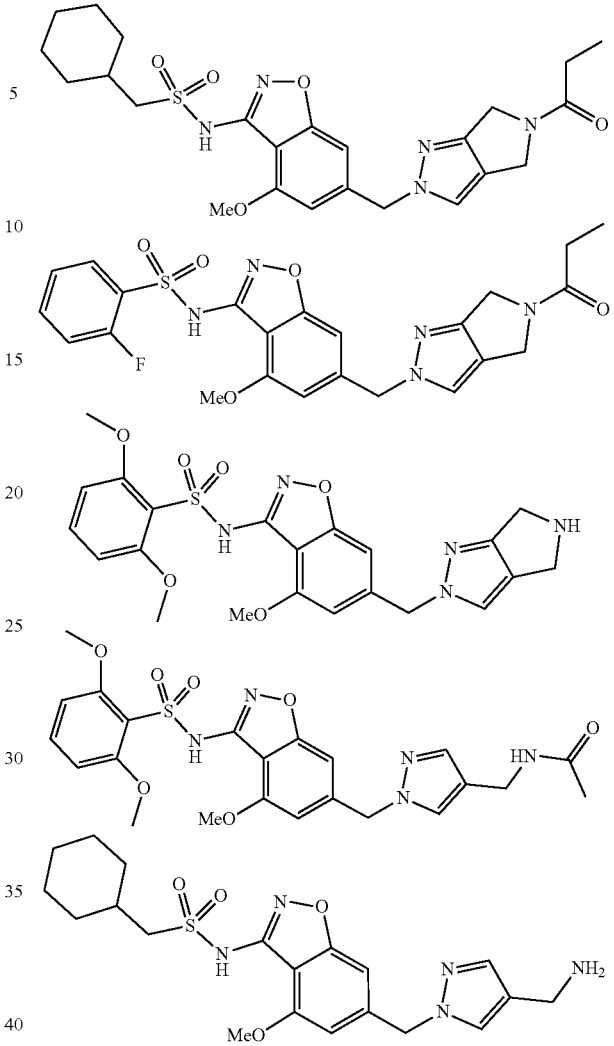

or a regioisomer, stereoisomer, a mixture of stereoisomers, and/or a pharmaceutically acceptable salt thereof.

55. A pharmaceutical composition comprising a compound of claim 1 or claim 28, or a stereoisomer, a mixture of stereoisomers, and/or a pharmaceutically acceptable salt thereof; and a pharmaceutically acceptable carrier.

* * * * *

SEQUENCE LISTING

```
Sequence total quantity: 5
SEQ ID NO: 1           moltype = AA  length = 20
FEATURE                Location/Qualifiers
source                 1..20
                       mol_type = protein
                       organism = Homo sapiens
SEQUENCE: 1
ESTEDYNVAC ILTLPPYQRR                                           20

SEQ ID NO: 2           moltype = AA  length = 20
FEATURE                Location/Qualifiers
source                 1..20
                       mol_type = protein
                       organism = Homo sapiens
SEQUENCE: 2
ESPDGNNVAC ILTLPPYQRR                                           20

SEQ ID NO: 3           moltype = AA  length = 20
```

```
                        -continued

FEATURE             Location/Qualifiers
source              1..20
                    mol_type = protein
                    organism = Homo sapiens
SEQUENCE: 3
NSFLNYNVSC ILTMPQYMRQ                                       20

SEQ ID NO: 4        moltype = AA  length = 20
FEATURE             Location/Qualifiers
source              1..20
                    mol_type = protein
                    organism = Homo sapiens
SEQUENCE: 4
HCQQKYNVSC IMILPQYQRK                                       20

SEQ ID NO: 5        moltype = AA  length = 20
FEATURE             Location/Qualifiers
source              1..20
                    mol_type = protein
                    organism = Homo sapiens
SEQUENCE: 5
LCQQKYNVSC IMIMPQHQRQ                                       20
```